US011965157B2

(12) United States Patent
Gole et al.

(10) Patent No.: US 11,965,157 B2
(45) Date of Patent: Apr. 23, 2024

(54) COMPOSITIONS AND METHODS FOR LIBRARY CONSTRUCTION AND SEQUENCE ANALYSIS

(71) Applicant: Singlera Genomics, Inc., La Jolla, CA (US)

(72) Inventors: Jeffrey A Gole, San Diego, CA (US); Athurva Gore, San Diego, CA (US); Rui Liu, Shanghai (CN)

(73) Assignee: Singlera Genomics, Inc., La Jolla, CA (US)

(*) Notice: Subject to any disclaimer, the term of this patent is extended or adjusted under 35 U.S.C. 154(b) by 207 days.

(21) Appl. No.: 16/605,203

(22) PCT Filed: Apr. 18, 2018

(86) PCT No.: PCT/US2018/028191
§ 371 (c)(1),
(2) Date: Oct. 14, 2019

(87) PCT Pub. No.: WO2018/195217
PCT Pub. Date: Oct. 25, 2018

(65) Prior Publication Data
US 2020/0123538 A1 Apr. 23, 2020

Related U.S. Application Data

(60) Provisional application No. 62/657,544, filed on Apr. 13, 2018, provisional application No. 62/487,423, filed on Apr. 19, 2017.

(51) Int. Cl.
*C12N 15/10* (2006.01)
*C12Q 1/6806* (2018.01)
*C12Q 1/6874* (2018.01)

(52) U.S. Cl.
CPC ....... *C12N 15/1093* (2013.01); *C12Q 1/6806* (2013.01); *C12Q 1/6874* (2013.01)

(58) Field of Classification Search
CPC . C12N 15/1093; C12Q 1/6806; C12Q 1/6874
See application file for complete search history.

(56) References Cited

U.S. PATENT DOCUMENTS

| | | | |
|---|---|---|---|
| 7,749,702 B2 | 7/2010 | Lofton-Day et al. | |
| 9,695,478 B2 | 7/2017 | Lofton-Day et al. | |
| 10,590,468 B2 | 3/2020 | Pedersen et al. | |
| 10,731,215 B2 | 8/2020 | Ballhause et al. | |
| 2007/0092833 A1 | 4/2007 | Gore | |
| 2007/0128624 A1 | 6/2007 | Gormley et al. | |
| 2007/0243546 A1 | 10/2007 | Cao et al. | |
| 2008/0261217 A1 | 10/2008 | Melnikov et al. | |
| 2013/0065233 A1 | 3/2013 | Jia et al. | |
| 2014/0093873 A1 | 4/2014 | Tynan et al. | |
| 2014/0100792 A1 | 4/2014 | Declu et al. | |
| 2015/0141275 A1 | 5/2015 | Molloy et al. | |
| 2015/0275314 A1 | 10/2015 | Ahlquist et al. | |
| 2015/0354001 A1 | 12/2015 | Porath et al. | |
| 2015/0368694 A1 | 12/2015 | Pan et al. | |
| 2016/0032357 A1 | 2/2016 | Barany et al. | |
| 2016/0034640 A1 | 2/2016 | Zhao et al. | |
| 2016/0186267 A1* | 6/2016 | So et al. | C12Q 1/6886 |
| 2016/0265042 A1* | 9/2016 | Schroeder et al. | C12Q 1/6858 |
| 2017/0101674 A1 | 4/2017 | So et al. | |
| 2017/0191135 A1 | 7/2017 | Pedersen et al. | |
| 2019/0284608 A1 | 9/2019 | An et al. | |
| 2019/0316210 A1 | 10/2019 | Lofton-Day et al. | |
| 2020/0048697 A1 | 2/2020 | Liu | |
| 2020/0048720 A1 | 2/2020 | Ahlquist et al. | |
| 2020/0308656 A1 | 10/2020 | Lewin et al. | |

FOREIGN PATENT DOCUMENTS

| | | |
|---|---|---|
| EP | 3168309 A1 | 5/2017 |
| WO | 2005/040399 A2 | 5/2005 |
| WO | 2007052006 A1 | 10/2007 |
| WO | 2011/109529 A1 | 9/2011 |
| WO | 2016/115530 A1 | 7/2016 |
| WO | 2016114970 A1 | 7/2016 |
| WO | 2016115530 A1 | 7/2016 |

(Continued)

OTHER PUBLICATIONS

Chen et al., "Non-invassive early detection of cancer four years before conventional diagnosis using a blood test," Nature Communications, (2020)11:3475, 10 pages dio.org/10.1038/s41467-020-17316-z.
Extended European Search Report for European patent application EP18788271.7, dated Dec. 18, 2020, 8 pages.
Communication pursuant to Rules 70(2) and 70a(2) EPC for European patent application EP18786969.8, dated Dec. 21, 2020, 1 page.
Extended European Search Report for European patent application EP18786969.8, dated Nov. 26, 2020, 8 pages.
International Search Report for international patent application PCT/US 18/028185 (WO2018195211), dated Jul. 11, 2018, 4 pages.
International Preliminary Report on Patentability for international patent application PCT/US 18/028185 (WO2018195211), dated Oct. 22, 2019, 7 pages.

(Continued)

*Primary Examiner* — Christopher M Gross

(57) ABSTRACT

The present disclosure relates to methods for constructing polynucleotide libraries and/or polynucleotide sequencing. Related kits and devices are also disclosed. The present disclosure also relates to compositions, kits, devices, and methods for conducting genetic and genomic analysis, for example, by polynucleotide sequencing. In particular aspects, provided herein are compositions, kits, and methods for constructing libraries with improved ligation efficiency and conversion rate during sequencing. In certain embodiments, the compositions, kits, and methods herein are useful for analyzing polynucleotide fragments, such as circulating polynucleotide fragments in the body of a subject, including circulating tumor DNA.

17 Claims, 71 Drawing Sheets

Specification includes a Sequence Listing.

(56) References Cited

FOREIGN PATENT DOCUMENTS

| WO | 2016/172442 A1 | 10/2016 |
|---|---|---|
| WO | 2017/037656 A1 | 3/2017 |

OTHER PUBLICATIONS

Written Opinion of the International Searching Authority for international patent application PCT/US 18/028185 (WO2018195211), dated Jul. 1, 2018, 6 pages.
International Search Report for international patent application PCT/US18/028191 (WO2018195217), dated Oct. 1, 2018, 5 pages.
Written Opinion of the International Searching Authority for international patent application PCT/US18/028191 (WO2018195217), dated Oct. 1, 2018, 7 pages.
International Preliminary Report on Patenability for international patent application PCT/US18/28191 (WO2018195217), dated Oct. 22, 2019, 8 pages.
Melnikov et al., "MSRE-PCR for analysis of gene-specific DNA methylation," Nucleic Acids Research, 2005, vol. 33, No. 10, e93 doi:10.1093/nar/gni092.
Communication pursuant to Rules 70(2) and 70a(2) EPC for European patent application EP18788271.7, dated Jan. 25, 2021, 1 page.
Lowe, T et al., "A computer program for selection of oligonucleotide primers polymerase chain reactions", Nucleic Acids Research, vol. 18(7), p. 1757-1761, 1990.
First Examination Report, Australian Patent Application No. 2018256387.
English Translation of Notice of Official Action for Korean patent application KR10-2019-7033449, dated Jan. 19, 2023, 8 pages.
Allowed Claims for Korean patent application KR10-2019-7033449, dated Sep. 19, 2023, 4 pages.
Examination Submission for Canadian patent application CA3060555, dated Sep. 26, 2022, 7 pages.
Acknowledgment of Request for Examination for Canadian patent application CA3060555, dated Nov. 28, 2022, 1 page.
Response to the Communication pursuant to Rules 70(2) and 70a(2) EPC for European patent application EP18 788 271.7, dated Jul. 27, 2021, 14 pages.
Office Action for European patent application EP18 788 271.7, dated Nov. 30, 2021, 8 pages.
Response to Communication Pursuant to Article 94(3) EPC for European patent application EP18 788 271.7, dated May 31, 2022, 21 pages.
Office Action for European patent application EP18 788 271.7, dated Apr. 12, 2023, 4 pages.
Claims (marked-up) for European patent application EP18 788 271.7, dated Oct. 12, 2023, 3 pages.
Claims for European patent application EP18 788 271.7, dated Oct. 12, 2023, 3 pages.
Reply to Examination Report for European patent application EP18 788 271.7, dated Oct. 12, 2023, 4 pages.
Gansauge MT et al., "Single-stranded DNA library preparation for the sequencing of ancient or damaged DNA", Nat Protoc, vol. 8, No. 4, p. 737-748, Mar. 14, 2013.
Gansauge MT et al., "Single-stranded DNA library preparation from highly degraded DNA using T4 DNA ligase", Nucleic Acids Res, vol. 45, No. 10, p. 1-10, Jan. 24, 2017.
Direction to request examination for patent application for Australia patent application AU2018256387, dated Jan. 25, 2022, 1 page.
Request Examination eSummary for patent application for Australia patent application AU2018256387, dated Feb. 26, 2022, 2 pages.
Request Examination eReceipt for patent application for Australia patent application AU2018256387, dated Feb. 26, 2022, 1 page.
Filing Receipt for Examination for Taiwanese patent application TW107113306, dated Apr. 19, 2021, 1 page.
Search Report in English for Taiwanese patent application TW107113306, dated Jul. 5, 2022, 1 page.
English Translation of the Novelty and Invention Step Rejections for Taiwanese patent application TW107113306, dated Jul. 8, 2022, 3 pages.
English Translation of the replacement claims for Taiwanese patent application TW107113306, dated Oct. 7, 2022, 3 pages.
Amended Claims for Japanese patent application JP2020-507488, dated Apr. 2, 2021, 4 pages.
Amended Claims for Japanese patent application JP2020-507488, dated Jun. 14, 2022, 5 pages.
English Translation of Penultimate Official Action for Japanese patent application JP2020-507488, dated Jul. 8, 2022, 4 pages.
Amended Claims for Japanese patent application JP2020-507488, dated Oct. 7, 2022, 3 pages.
Restriction Requirement for U.S. Appl. No. 16/605,201, dated Mar. 26, 2021, 8 pages.
Response to Restriction Requirement for U.S. Appl. No. 16/605,201, dated May 24, 2021, 12 pages.
Non-Final Office Action for U.S. Appl. No. 16/605,201, dated Jun. 18, 2021, 27 pages.
Response to Non-Final Office Action for U.S. Appl. No. 16/605,201, dated Jun. 18, 2021, 13 pages.
Final Office Action for U.S. Appl. No. 16/605,201, dated Apr. 5, 2022, 18 pages.
Response to Final Office Action for U.S. Appl. No. 16/605,201, dated Apr. 5, 2022, 24 pages.
Non-Final Office Action for U.S. Appl. No. 16/605,201, dated Jan. 4, 2023, 12 pages.
Response to Office Action for U.S. Appl. No. 16/605,201, dated Jan. 4, 2023, 25 pages.
Final Office Action for U.S. Appl. No. 16/605,201, dated Aug. 28, 2023, 25 pages.
Examination Submission for Canadian patent application CA3060553, dated Sep. 23, 2022, 7 pages.
Acknowledgment of Request for Examination for Canadian patent application CA3060553, dated Nov. 23, 2022, 1 page.
Pending Claims for Chinese patent application CN201880040413, dated Aug. 31, 2023, 6 pages.
Description (marked up) for European patent application EP18 786 969.8, dated Jun. 25, 2021, 9 pages.
Response the Communication pursuant to Rules 70(2) and 70a (2) EPC for European patent application EP18 786 969.8, dated Jun. 25, 2021, 3 pages.
Claims (marked up) for European patent application EP18 786 969.8, dated Jun. 25, 2021, 4 pages.
Claims for European patent application EP18 786 969.8, dated Jun. 25, 2021, 4 pages.
Communication pursuant to Article 94(3) EPC for European patent application EP18 786 969.8, dated Jan. 26, 2022, 4 pages.
Claims (marked up) for European patent application EP18 786 969.8, dated Jul. 26, 4 pages.
Claims for European patent application EP18 786 969.8, dated Jul. 26, 2021, 4 pages.
Reply to examination report for European patent application EP18 786 969.8, dated Jul. 27, 6 pages.
Communication pursuant to Article 94(3) EPC for European patent application EP18 786 969.8, dated Mar. 9, 2023, 4 pages.
Claims (marked up) for European patent application EP18 786 969.8, dated Sep. 14, 2023, 4 pages.
Claims for European patent application EP18 786 969.8, dated Sep. 14, 4 pages.
Reply to examination report for European patent application EP18 786 969.8, dated Sep. 14, 2023, 8 pages.

* cited by examiner

|  | The Present Method | Hybridization Capture |
|---|---|---|
| Experimental Time | < 1 day | 3 days |
| Minimal MAF | 0.1% | 0.1% |
| DNA required | 20 ng | 30 ng |
| Ligation efficiency | ~90% | ~20% |
| On target rate | >60% | ~50% |
| Uniformity | ~0.8 | ~0.7 |
| Enrichment Factor | >40,000x | ~2,000x |
| Conversion Rate | 40-80% | ~20% |

| Target Specific Primer | Volume Ratio | Sequence |
|---|---|---|
| SEQ ID NO:308 | 1 | GACTGGAGTTCAGACGTGTGCTCTTCCGATCTAAAAAAGTTCGCCACCCTTGCCGTTTC |
| SEQ ID NO:309 | 1 | GACTGGAGTTCAGACGTGTGCTCTTCCGATCTAAAATGCATAACAACAAAGAATATGAATATGGA |
| SEQ ID NO:310 | 1 | GACTGGAGTTCAGACGTGTGCTCTTCCGATCTAAACCCAAACTTTATAAGATCCTGGCT |
| SEQ ID NO:311 | 1 | GACTGGAGTTCAGACGTGTGCTCTTCCGATCTAAACCTCTCTTTCTTCCACCTTTCTCC |
| SEQ ID NO:312 | 1 | GACTGGAGTTCAGACGTGTGCTCTTCCGATCTAAACTCTACGTCTCCTCCGACCACTGT |
| SEQ ID NO:313 | 1 | GACTGGAGTTCAGACGTGTGCTCTTCCGATCTAAATACCCCTCCATCAACTTCTTCAA |
| SEQ ID NO:314 | 1 | GACTGGAGTTCAGACGTGTGCTCTTCCGATCTAAATCCATCCCACACCCTGTTCACTC |
| SEQ ID NO:315 | 1 | GACTGGAGTTCAGACGTGTGCTCTTCCGATCTAACACAGGGCCAAAGACTAAGTGACAT |
| SEQ ID NO:316 | 1 | GACTGGAGTTCAGACGTGTGCTCTTCCGATCTAACACATACAAGTTGGAAATTTCTGGG |
| SEQ ID NO:317 | 1 | GACTGGAGTTCAGACGTGTGCTCTTCCGATCTAACACATCAAGGTTGGAATGAGCTGGA |
| SEQ ID NO:318 | 1 | GACTGGAGTTCAGACGTGTGCTCTTCCGATCTAACATGCCTTTCACGTTCCTTTCCCC |
| SEQ ID NO:319 | 1 | GACTGGAGTTCAGACGTGTGCTCTTCCGATCTAACTCCTTCCCGTTTTTCAGCCACC |
| SEQ ID NO:320 | 1 | GACTGGAGTTCAGACGTGTGCTCTTCCGATCTAACTCTACACAGAAAGGGCCCAAATTC |
| SEQ ID NO:321 | 1 | GACTGGAGTTCAGACGTGTGCTCTTCCGATCTAACTCTCTTTGACTGCAGAATCCAACT |
| SEQ ID NO:322 | 1 | GACTGGAGTTCAGACGTGTGCTCTTCCGATCTAACTGGAAAAAACTGTTTGGGACC |
| SEQ ID NO:323 | 1 | GACTGGAGTTCAGACGTGTGCTCTTCCGATCTAACTGGAAAAAACTGTTTGGGACCTCC |
| SEQ ID NO:324 | 1 | GACTGGAGTTCAGACGTGTGCTCTTCCGATCTAAGAAAGCCCTCCCCAGTCCTCATGTA |
| SEQ ID NO:325 | 1 | GACTGGAGTTCAGACGTGTGCTCTTCCGATCTAAGAATCAGAACAATGCCTCCACGACC |
| SEQ ID NO:326 | 1 | GACTGGAGTTCAGACGTGTGCTCTTCCGATCTAAGATCACATCACATGAATGGAATAGTTTAA |

FIG. 7B

| Target Specific Primer | Volume Ratio | Sequence |
|---|---|---|
| SEQ ID NO:327 | 1 | GACTGGAGTTCAGACGTGTGCTCTTCCGATCTAAGATTCAGGCAATGTTTGTTAGTATTAGT |
| SEQ ID NO:328 | 1 | GACTGGAGTTCAGACGTGTGCTCTTCCGATCTAAGATTTACCTCTATTGTTGGATCATATTCG |
| SEQ ID NO:329 | 1 | GACTGGAGTTCAGACGTGTGCTCTTCCGATCTAAGCAACCTTTTTCTCTTTCTCTTTAGA |
| SEQ ID NO:330 | 1 | GACTGGAGTTCAGACGTGTGCTCTTCCGATCTAAGCACCTGATCCTAGTACCTTCCCTG |
| SEQ ID NO:331 | 1 | GACTGGAGTTCAGACGTGTGCTCTTCCGATCTAAGCAGCCACACCCCATTCTTGAG |
| SEQ ID NO:332 | 1 | GACTGGAGTTCAGACGTGTGCTCTTCCGATCTAAGCAACACACCACAGATGTCTTCAG |
| SEQ ID NO:333 | 1 | GACTGGAGTTCAGACGTGTGCTCTTCCGATCTAAGCCCTCCAACATCCTAGTCAACTCC |
| SEQ ID NO:334 | 1 | GACTGGAGTTCAGACGTGTGCTCTTCCGATCTAAGGACCAAGGAGCAGAGGAGGC |
| SEQ ID NO:335 | 1 | GACTGGAGTTCAGACGTGTGCTCTTCCGATCTAAGGGCCTCTTCATGCGG |
| SEQ ID NO:336 | 1 | GACTGGAGTTCAGACGTGTGCTCTTCCGATCTAAGTAATTTTGCCCAGTTCAGGATCCA |
| SEQ ID NO:337 | 1 | GACTGGAGTTCAGACGTGTGCTCTTCCGATCTAAGTAGTCTGATCCACTGAAGCTGAAT |
| SEQ ID NO:338 | 1 | GACTGGAGTTCAGACGTGTGCTCTTCCGATCTAAGTTCGCCACCCTTGCCGTTTCTTT |
| SEQ ID NO:339 | 1 | GACTGGAGTTCAGACGTGTGCTCTTCCGATCTAATAATAGGAAATCACAGCTAAGGGGC |
| SEQ ID NO:340 | 1 | GACTGGAGTTCAGACGTGTGCTCTTCCGATCTAATACATTCTTCATACCAGGACCAGAG |
| SEQ ID NO:341 | 1 | GACTGGAGTTCAGACGTGTGCTCTTCCGATCTAATCACCAAAAAAGTTCGCCACCCTTG |
| SEQ ID NO:342 | 1 | GACTGGAGTTCAGACGTGTGCTCTTCCGATCTAATCAGAACAATGCCTCCACGACCATC |
| SEQ ID NO:343 | 1 | GACTGGAGTTCAGACGTGTGCTCTTCCGATCTAATGCATGTTTCCAATTTTAGCGAGTG |
| SEQ ID NO:344 | 1 | GACTGGAGTTCAGACGTGTGCTCTTCCGATCTAATGTAGGAGTGGTCATAAGGCTGGTA |
| SEQ ID NO:345 | 1 | GACTGGAGTTCAGACGTGTGCTCTTCCGATCTAATTCTACCTTGTAGCCTCCAATGCGA |

FIG. 7C

| Target Specific Primer | Volume Ratio | Sequence |
|---|---|---|
| SEQ ID NO:346 | 1 | GACTGGAGTTCAGACGTGTGCTCTTCCGATCTACAAAGTGGTTCTGGATTAGCTGGATT |
| SEQ ID NO:347 | 1 | GACTGGAGTTCAGACGTGTGCTCTTCCGATCTACAAATGGAAAATACAACTACGAGAGAAA |
| SEQ ID NO:348 | 1 | GACTGGAGTTCAGACGTGTGCTCTTCCGATCTACAACCCTCCTGCCATCATATTGAACA |
| SEQ ID NO:349 | 1 | GACTGGAGTTCAGACGTGTGCTCTTCCGATCTACAACCTCCGTCATGTGCTGTGA |
| SEQ ID NO:350 | 1 | GACTGGAGTTCAGACGTGTGCTCTTCCGATCTACAACTACGAGAGAAAAAATGACTTGCT |
| SEQ ID NO:351 | 1 | GACTGGAGTTCAGACGTGTGCTCTTCCGATCTACAACTTAACCTGTTTCTCCTCCCTCT |
| SEQ ID NO:352 | 1 | GACTGGAGTTCAGACGTGTGCTCTTCCGATCTACAACTTACCATGTTCAATGATTTCAACT |
| SEQ ID NO:353 | 1 | GACTGGAGTTCAGACGTGTGCTCTTCCGATCTACAAGGGTATGGGTTTGTCACTGAGA |
| SEQ ID NO:354 | 1 | GACTGGAGTTCAGACGTGTGCTCTTCCGATCTACACAAATGGAAAATACAACTACGAGAG |
| SEQ ID NO:355 | 1 | GACTGGAGTTCAGACGTGTGCTCTTCCGATCTACACAGTGGAAGAGGTAGATATTGGGG |
| SEQ ID NO:356 | 1 | GACTGGAGTTCAGACGTGTGCTCTTCCGATCTACACATCCCCCAAAGCCAACAAAGAAA |
| SEQ ID NO:357 | 1 | GACTGGAGTTCAGACGTGTGCTCTTCCGATCTACACATTCTTAGAGCATAGTAAGCAGT |
| SEQ ID NO:358 | 1 | GACTGGAGTTCAGACGTGTGCTCTTCCGATCTACACGAGACAAATGTAGGAAAAACCA |
| SEQ ID NO:359 | 1 | GACTGGAGTTCAGACGTGTGCTCTTCCGATCTACACTCTAGTATCTGGAAAAATGGCTTTG |
| SEQ ID NO:360 | 1 | GACTGGAGTTCAGACGTGTGCTCTTCCGATCTACACTCTCTGCTGGCTAGTCAAAAAAG |
| SEQ ID NO:361 | 1 | GACTGGAGTTCAGACGTGTGCTCTTCCGATCTACACTTACCTCATTGTCTGACTCCACG |
| SEQ ID NO:362 | 1 | GACTGGAGTTCAGACGTGTGCTCTTCCGATCTACAGAAAGGACTATAATGACAGTTAACCC |
| SEQ ID NO:363 | 1 | GACTGGAGTTCAGACGTGTGCTCTTCCGATCTACAGAATATTGTTGCTATGGTGATCTTTT |
| SEQ ID NO:364 | 1 | GACTGGAGTTCAGACGTGTGCTCTTCCGATCTACAGACTAGCTAGAGACAATGAATTAAGGG |

FIG. 7D

| Target Specific Primer | Volume Ratio | Sequence |
|---|---|---|
| SEQ ID NO:365 | 1 | GACTGGAGTTCAGACGTGTGCTCTTCCGATCTACAGCAAAACACCAAAAGACCAGACGT |
| SEQ ID NO:366 | 1 | GACTGGAGTTCAGACGTGTGCTCTTCCGATCTACAGCACCCTAGAACCAAATCCAGCAG |
| SEQ ID NO:367 | 1 | GACTGGAGTTCAGACGTGTGCTCTTCCGATCTACAGGCGAGGAGTAGCTGTGC |
| SEQ ID NO:368 | 1 | GACTGGAGTTCAGACGTGTGCTCTTCCGATCTACAGGGCCAAAGACTAAGTGACATAAA |
| SEQ ID NO:369 | 1 | GACTGGAGTTCAGACGTGTGCTCTTCCGATCTACAGTGAGTGCAGTTGTTTACCATGAT |
| SEQ ID NO:370 | 1 | GACTGGAGTTCAGACGTGTGCTCTTCCGATCTACAGTGGAAGAGGTAGATATTGGGGAAG |
| SEQ ID NO:371 | 1 | GACTGGAGTTCAGACGTGTGCTCTTCCGATCTACATACAAGTTGGAAATTTCTGGGCCA |
| SEQ ID NO:372 | 1 | GACTGGAGTTCAGACGTGTGCTCTTCCGATCTACATACTTGGACTTGGTGATAGACATGT |
| SEQ ID NO:373 | 1 | GACTGGAGTTCAGACGTGTGCTCTTCCGATCTACATAGAGTTTTAATGCATTGTCTCATCTT |
| SEQ ID NO:374 | 1 | GACTGGAGTTCAGACGTGTGCTCTTCCGATCTACATAGAGTTTTAATGCATTGTCTCATCTTTTT |
| SEQ ID NO:375 | 1 | GACTGGAGTTCAGACGTGTGCTCTTCCGATCTACATCAAGTTCAACAGTTCAGGCCAG |
| SEQ ID NO:376 | 1 | GACTGGAGTTCAGACGTGTGCTCTTCCGATCTACATCGGGGCAAATTTTTAAAGGCACA |
| SEQ ID NO:377 | 1 | GACTGGAGTTCAGACGTGTGCTCTTCCGATCTACATGCCATCATTCTAGGAAGCTCACC |
| SEQ ID NO:378 | 1 | GACTGGAGTTCAGACGTGTGCTCTTCCGATCTACATTAGGCAGTGACTCGATGAAGGCA |
| SEQ ID NO:379 | 1 | GACTGGAGTTCAGACGTGTGCTCTTCCGATCTACATTCATAGACAGTAAAACAGAAAGGAC |
| SEQ ID NO:380 | 1 | GACTGGAGTTCAGACGTGTGCTCTTCCGATCTACATTCTTCATACCAGGACCAGAGGAA |
| SEQ ID NO:381 | 1 | GACTGGAGTTCAGACGTGTGCTCTTCCGATCTACATTCTTCATACCAGGACCAGAGGAA |
| SEQ ID NO:382 | 1 | GACTGGAGTTCAGACGTGTGCTCTTCCGATCTACCAAATTAAATTACTCACCTATCTCCCA |
| SEQ ID NO:383 | 1 | GACTGGAGTTCAGACGTGTGCTCTTCCGATCTACCAAGCTATATCTGAACAAAAATTCCGT |

FIG. 7E

| Target Specific Primer | Volume Ratio | Sequence |
|---|---|---|
| SEQ ID NO:384 | 1 | GACTGGAGTTCAGACGTGTGCTCTTCCGATCTACCACACCTGTCATGTAGCAGCTTT |
| SEQ ID NO:385 | 1 | GACTGGAGTTCAGACGTGTGCTCTTCCGATCTACCACATTACATACTTACCATGCCACT |
| SEQ ID NO:386 | 1 | GACTGGAGTTCAGACGTGTGCTCTTCCGATCTACCACATTACATACTTACCATGCCACTTTCC |
| SEQ ID NO:387 | 1 | GACTGGAGTTCAGACGTGTGCTCTTCCGATCTACCAGGTAGAGGGAGTACAGAGTGACC |
| SEQ ID NO:388 | 1 | GACTGGAGTTCAGACGTGTGCTCTTCCGATCTACCATATACCCAGTGCCTTGTGTGGT |
| SEQ ID NO:389 | 1 | GACTGGAGTTCAGACGTGTGCTCTTCCGATCTACCATCTCACAATTGCCAGTTAACGTCT |
| SEQ ID NO:390 | 1 | GACTGGAGTTCAGACGTGTGCTCTTCCGATCTACCATCTCACAATTGCCAGTTAACGTCT |
| SEQ ID NO:391 | 1 | GACTGGAGTTCAGACGTGTGCTCTTCCGATCTACCATCTCACAATTGCCAGTTAACGTCT |
| SEQ ID NO:392 | 1 | GACTGGAGTTCAGACGTGTGCTCTTCCGATCTACCATGTTCAATGATTTCAACTAAACTTCT |
| SEQ ID NO:393 | 1 | GACTGGAGTTCAGACGTGTGCTCTTCCGATCTACCCACTGAAAAGCACTTCCTGAAATA |
| SEQ ID NO:394 | 1 | GACTGGAGTTCAGACGTGTGCTCTTCCGATCTACCCTAGCCTTAGATAAAACTGAGCAAGAGG |
| SEQ ID NO:395 | 1 | GACTGGAGTTCAGACGTGTGCTCTTCCGATCTACCCTTGTCTCTGTGTTCTTGTC |
| SEQ ID NO:396 | 1 | GACTGGAGTTCAGACGTGTGCTCTTCCGATCTACCCTTGTCTCTGTGTTCTTGTC |
| SEQ ID NO:397 | 1 | GACTGGAGTTCAGACGTGTGCTCTTCCGATCTACCTAAGCACACAGAGTAATATAGCAG |
| SEQ ID NO:398 | 1 | GACTGGAGTTCAGACGTGTGCTCTTCCGATCTACCTAAGCACACAGAGTAATATAGCAGAGC |
| SEQ ID NO:399 | 1 | GACTGGAGTTCAGACGTGTGCTCTTCCGATCTACCTAGTATTCTGCTCTGAAGGGGGAAA |
| SEQ ID NO:400 | 1 | GACTGGAGTTCAGACGTGTGCTCTTCCGATCTACCTCTATTGTTGGATCATATTCGTCC |
| SEQ ID NO:401 | 1 | GACTGGAGTTCAGACGTGTGCTCTTCCGATCTACCTCTATTGTTGGATCATATTCGTCC |
| SEQ ID NO:402 | 1 | GACTGGAGTTCAGACGTGTGCTCTTCCGATCTACCTGGAATTTGGATGTGATTGGAAAGTGG |

FIG. 7F

| Target Specific Primer | Volume Ratio | Sequence |
|---|---|---|
| SEQ ID NO:403 | 1 | GACTGGAGTTCAGACGTGTGCTCTTCCGATCTACCTGTCTTGTCTTTGCTGATGTTTCA |
| SEQ ID NO:404 | 1 | GACTGGAGTTCAGACGTGTGCTCTTCCGATCTACCTGTCTTGTCTTTGCTGATGTTTCA |
| SEQ ID NO:405 | 1 | GACTGGAGTTCAGACGTGTGCTCTTCCGATCTACCTGTCTTGTCTTTGCTGATGTTTCAATA |
| SEQ ID NO:406 | 1 | GACTGGAGTTCAGACGTGTGCTCTTCCGATCTACCTTCTTTCTAACCTTTTCTTATGTGCT |
| SEQ ID NO:407 | 1 | GACTGGAGTTCAGACGTGTGCTCTTCCGATCTACGACTGATTCAAAGCTGGTCATTTAGA |
| SEQ ID NO:408 | 1 | GACTGGAGTTCAGACGTGTGCTCTTCCGATCTACGAGACAAATGTAGGAAAAACCAGAA |
| SEQ ID NO:409 | 1 | GACTGGAGTTCAGACGTGTGCTCTTCCGATCTACGCATTTATGTTTTCTCTTCTTAGACCA |
| SEQ ID NO:410 | 1 | GACTGGAGTTCAGACGTGTGCTCTTCCGATCTACGCATTTATGTTTTCTCTTCTTAGACCATCC |
| SEQ ID NO:411 | 1 | GACTGGAGTTCAGACGTGTGCTCTTCCGATCTACGCTCTTCTCACTCATATCCTCCTCT |
| SEQ ID NO:412 | 1 | GACTGGAGTTCAGACGTGTGCTCTTCCGATCTACGGCCAGATCCAGTGAAAAACAAGC |
| SEQ ID NO:413 | 1 | GACTGGAGTTCAGACGTGTGCTCTTCCGATCTACGTCTTCCTTCTCTCTCTGTCATAGGG |
| SEQ ID NO:414 | 1 | GACTGGAGTTCAGACGTGTGCTCTTCCGATCTACGTCTTCCTTCTCTCTCTGTCATAGGG |
| SEQ ID NO:415 | 1 | GACTGGAGTTCAGACGTGTGCTCTTCCGATCTACGTGATTCATTTATTTGTTCAAAGCAGG |
| SEQ ID NO:416 | 1 | GACTGGAGTTCAGACGTGTGCTCTTCCGATCTACTAAACTTCTAAGATGTGGCAAGATGG |
| SEQ ID NO:417 | 1 | GACTGGAGTTCAGACGTGTGCTCTTCCGATCTACTAAGTAGTCTGATCCACTGAAGCTG |
| SEQ ID NO:418 | 1 | GACTGGAGTTCAGACGTGTGCTCTTCCGATCTACTACGAGAGAAAAAATGACTTGCTTAA |
| SEQ ID NO:419 | 1 | GACTGGAGTTCAGACGTGTGCTCTTCCGATCTACTAGCTAGAGACAATGAATTAAGGGAAA |
| SEQ ID NO:420 | 1 | GACTGGAGTTCAGACGTGTGCTCTTCCGATCTACTAGGCGTGGGATGTTTTTGCAGATG |
| SEQ ID NO:421 | 1 | GACTGGAGTTCAGACGTGTGCTCTTCCGATCTACTATCTCCCTGGGTGTAGCTTTTTAA |

FIG. 7G

| Target Specific Primer | Volume Ratio | Sequence |
|---|---|---|
| SEQ ID NO:422 | 1 | GACTGGAGTTCAGACGTGTGCTCTTCCGATCTACTATTCAGTCCTGCCTTCCTGCCC |
| SEQ ID NO:423 | 1 | GACTGGAGTTCAGACGTGTGCTCTTCCGATCTACTCAAATGTCTTACTGCTCTACAAGG |
| SEQ ID NO:424 | 1 | GACTGGAGTTCAGACGTGTGCTCTTCCGATCTACTCTCTGCTGGCTAGTCAAAAAGAGA |
| SEQ ID NO:425 | 1 | GACTGGAGTTCAGACGTGTGCTCTTCCGATCTACTCTCTGGTGGTAGAATGAAAATAGA |
| SEQ ID NO:426 | 1 | GACTGGAGTTCAGACGTGTGCTCTTCCGATCTACTCTGTCAAAAATTGTTTCTGGGGCCA |
| SEQ ID NO:427 | 1 | GACTGGAGTTCAGACGTGTGCTCTTCCGATCTACTCTGTCCTGCGTCATCATCTTTGTC |
| SEQ ID NO:428 | 1 | GACTGGAGTTCAGACGTGTGCTCTTCCGATCTACTCTTTATTTGTCCCCTTGCCTCCCT |
| SEQ ID NO:429 | 1 | GACTGGAGTTCAGACGTGTGCTCTTCCGATCTACTGAAGCCACTTGTTTAATCTGTAGA |
| SEQ ID NO:430 | 1 | GACTGGAGTTCAGACGTGTGCTCTTCCGATCTACTGAGCACTGAATCTATAAAGCATGT |
| SEQ ID NO:431 | 1 | GACTGGAGTTCAGACGTGTGCTCTTCCGATCTACTGCCAATGGACTGTTTTACAATGCC |
| SEQ ID NO:432 | 1 | GACTGGAGTTCAGACGTGTGCTCTTCCGATCTACTGTAAAGCTGGAAAGGGACGAACTG |
| SEQ ID NO:433 | 1 | GACTGGAGTTCAGACGTGTGCTCTTCCGATCTACTGTGTTGTGGAGTGCAAGTGAAAGC |
| SEQ ID NO:434 | 1 | GACTGGAGTTCAGACGTGTGCTCTTCCGATCTACTTAACCTGTTTCTCCTCCCTCTACC |
| SEQ ID NO:435 | 1 | GACTGGAGTTCAGACGTGTGCTCTTCCGATCTACTTACCCACTGAAAAGCACTTCCTGA |
| SEQ ID NO:436 | 1 | GACTGGAGTTCAGACGTGTGCTCTTCCGATCTACTTACCTGTCTTGTCTTTGCTGATGT |
| SEQ ID NO:437 | 1 | GACTGGAGTTCAGACGTGTGCTCTTCCGATCTACTTACCTGTCTTGTCTTTGCTGATGT |
| SEQ ID NO:438 | 1 | GACTGGAGTTCAGACGTGTGCTCTTCCGATCTACTTCCCAGTGTGATTGCAGGTTC |
| SEQ ID NO:439 | 1 | GACTGGAGTTCAGACGTGTGCTCTTCCGATCTACTTCCTGTAATTTTTCAAGGCTTCAG |
| SEQ ID NO:440 | 1 | GACTGGAGTTCAGACGTGTGCTCTTCCGATCTACTTCTTTGGGTTGACTTCTCTGGTGA |

FIG. 7H

| Target Specific Primer | Volume Ratio | Sequence |
|---|---|---|
| SEQ ID NO:441 | 1 | GACTGGAGTTCAGACGTGTGCTCTTCCGATCTACTTGTCCCAAAGCAGAAGTAAAACCA |
| SEQ ID NO:442 | 1 | GACTGGAGTTCAGACGTGTGCTCTTCCGATCTACTTTATAAGATCCTGGCTATCCTGTGG |
| SEQ ID NO:443 | 1 | GACTGGAGTTCAGACGTGTGCTCTTCCGATCTAGAAAAGTTTGCTGAGCTGGGTAG |
| SEQ ID NO:444 | 1 | GACTGGAGTTCAGACGTGTGCTCTTCCGATCTAGAAAAGGGGACATGCTAGGGACAACA |
| SEQ ID NO:445 | 1 | GACTGGAGTTCAGACGTGTGCTCTTCCGATCTAGAACACTCTGCTGGCTAGTCAAAA |
| SEQ ID NO:446 | 1 | GACTGGAGTTCAGACGTGTGCTCTTCCGATCTAGAACACTTACCTCATTGTCTGACTCC |
| SEQ ID NO:447 | 1 | GACTGGAGTTCAGACGTGTGCTCTTCCGATCTAGAAGCAACATCTCCGAAAGCCAACAA |
| SEQ ID NO:448 | 1 | GACTGGAGTTCAGACGTGTGCTCTTCCGATCTAGAAGCAAGAAAATACCCCTCCATCA |
| SEQ ID NO:449 | 1 | GACTGGAGTTCAGACGTGTGCTCTTCCGATCTAGAAGGAGGAGAGACACCATCAGAAGG |
| SEQ ID NO:450 | 1 | GACTGGAGTTCAGACGTGTGCTCTTCCGATCTAGAATGTGTCAGCCTCAAAGAAAGCT |
| SEQ ID NO:451 | 1 | GACTGGAGTTCAGACGTGTGCTCTTCCGATCTAGACACTAAACTCATCTGGGCCAC |
| SEQ ID NO:452 | 1 | GACTGGAGTTCAGACGTGTGCTCTTCCGATCTAGACACTAAACTCATCTGGGCCAC |
| SEQ ID NO:453 | 1 | GACTGGAGTTCAGACGTGTGCTCTTCCGATCTAGACAGAAGGAGGAGAGACACCATCAG |
| SEQ ID NO:454 | 1 | GACTGGAGTTCAGACGTGTGCTCTTCCGATCTAGACAGTTGTTTGTTCAGTTGGGAGCG |
| SEQ ID NO:455 | 1 | GACTGGAGTTCAGACGTGTGCTCTTCCGATCTAGACAGTTGTTTGTTCAGTTGGGAGCG |
| SEQ ID NO:456 | 1 | GACTGGAGTTCAGACGTGTGCTCTTCCGATCTAGACCTAGTATTCTGCTCTGAAGGGGG |
| SEQ ID NO:457 | 1 | GACTGGAGTTCAGACGTGTGCTCTTCCGATCTAGACGACTGATTCAAAGCTGGTCATTT |
| SEQ ID NO:458 | 1 | GACTGGAGTTCAGACGTGTGCTCTTCCGATCTAGACGACTGATTCAAAGCTGGTCATTT |
| SEQ ID NO:459 | 1 | GACTGGAGTTCAGACGTGTGCTCTTCCGATCTAGACTGCTGTGAGGGTTTTTTGATGTT |

FIG. 7I

| Target Specific Primer | Volume Ratio | Sequence |
|---|---|---|
| SEQ ID NO:460 | 1 | GACTGGAGTTCAGACGTGTGCTCTTCCGATCTAGACTTGAAGGCGTATACAGGAACAAT |
| SEQ ID NO:461 | 1 | GACTGGAGTTCAGACGTGTGCTCTTCCGATCTAGAGAGGGAGTGAAGTGAATGTTGCTG |
| SEQ ID NO:462 | 1 | GACTGGAGTTCAGACGTGTGCTCTTCCGATCTAGAGATCCCATCCTGCCAAAGTTTGTG |
| SEQ ID NO:463 | 1 | GACTGGAGTTCAGACGTGTGCTCTTCCGATCTAGAGCAATCAGTGAGGAATCAGAGGCC |
| SEQ ID NO:464 | 1 | GACTGGAGTTCAGACGTGTGCTCTTCCGATCTAGAGCAATCAGTGAGGAATCAGAGGCC |
| SEQ ID NO:465 | 1 | GACTGGAGTTCAGACGTGTGCTCTTCCGATCTAGAGCATAGTAAGCAGTAGGGAGTAACA |
| SEQ ID NO:466 | 1 | GACTGGAGTTCAGACGTGTGCTCTTCCGATCTAGAGCCAAGGGTGTGAGTGAACG |
| SEQ ID NO:467 | 1 | GACTGGAGTTCAGACGTGTGCTCTTCCGATCTAGAGCGTGCAGATAATGACAAGGAATA |
| SEQ ID NO:468 | 1 | GACTGGAGTTCAGACGTGTGCTCTTCCGATCTAGAGTCATGTTAGTCTGGTTCCTCC |
| SEQ ID NO:469 | 1 | GACTGGAGTTCAGACGTGTGCTCTTCCGATCTAGATATTCCCATTATTATAGAGATGATTGTTGAAT |
| SEQ ID NO:470 | 1 | GACTGGAGTTCAGACGTGTGCTCTTCCGATCTAGATGATCCGACAAGTGAGAGACAGGA |
| SEQ ID NO:471 | 1 | GACTGGAGTTCAGACGTGTGCTCTTCCGATCTAGATGTTAACTATGCAAAGAGACATTT |
| SEQ ID NO:472 | 1 | GACTGGAGTTCAGACGTGTGCTCTTCCGATCTAGCAAACTTCTGTACACAACTAACTAGA |
| SEQ ID NO:473 | 1 | GACTGGAGTTCAGACGTGTGCTCTTCCGATCTAGCAAGAAAATACCCCCTCCATCAACT |
| SEQ ID NO:474 | 1 | GACTGGAGTTCAGACGTGTGCTCTTCCGATCTAGCAAGTATGATGAGCAAGCTTTCTC |
| SEQ ID NO:475 | 1 | GACTGGAGTTCAGACGTGTGCTCTTCCGATCTAGCACTACCTAAGGACCGGGATTATGT |
| SEQ ID NO:476 | 1 | GACTGGAGTTCAGACGTGTGCTCTTCCGATCTAGCACTCTGACATATGGCCATTTCTGT |
| SEQ ID NO:477 | 1 | GACTGGAGTTCAGACGTGTGCTCTTCCGATCTAGCAGTAGGGAGTAACAAAATAACACT |
| SEQ ID NO:478 | 1 | GACTGGAGTTCAGACGTGTGCTCTTCCGATCTAGCCAGTACCTTCCTCTTCTTCTACAT |

FIG. 7J

| Target Specific Primer | Volume Ratio | Sequence |
|---|---|---|
| SEQ ID NO:479 | 1 | GACTGGAGTTCAGACGTGTGCTCTTCCGATCTAGCCCATCCCTGACTGTGAGAT |
| SEQ ID NO:480 | 1 | GACTGGAGTTCAGACGTGTGCTCTTCCGATCTAGCCCATCCCTGACTGTGAGATCAA |
| SEQ ID NO:481 | 1 | GACTGGAGTTCAGACGTGTGCTCTTCCGATCTAGCCCATCCCTGACTGTGAGATCAA |
| SEQ ID NO:482 | 1 | GACTGGAGTTCAGACGTGTGCTCTTCCGATCTAGCCTCCAGTTCAGCAAGGGGTCATA |
| SEQ ID NO:483 | 1 | GACTGGAGTTCAGACGTGTGCTCTTCCGATCTAGCCTCTTACCTGGAATTTGGATGTGA |
| SEQ ID NO:484 | 1 | GACTGGAGTTCAGACGTGTGCTCTTCCGATCTAGCGCTACTAGAAACATGATAGAGGTG |
| SEQ ID NO:485 | 1 | GACTGGAGTTCAGACGTGTGCTCTTCCGATCTAGCTAAAGGTGAAGATATATTCCTCCAA |
| SEQ ID NO:486 | 1 | GACTGGAGTTCAGACGTGTGCTCTTCCGATCTAGCTACCTGACCGACGTTGACC |
| SEQ ID NO:487 | 1 | GACTGGAGTTCAGACGTGTGCTCTTCCGATCTAGCTATATCTGAACAAAAATTCCGTGGT |
| SEQ ID NO:488 | 1 | GACTGGAGTTCAGACGTGTGCTCTTCCGATCTAGCTGACACCACGATACTTGACAATGA |
| SEQ ID NO:489 | 1 | GACTGGAGTTCAGACGTGTGCTCTTCCGATCTAGCTTAATAAAAACCCCGCAGAGAGA |
| SEQ ID NO:490 | 1 | GACTGGAGTTCAGACGTGTGCTCTTCCGATCTAGCTTAATTCTACCTTGTAGCCTCCAA |
| SEQ ID NO:491 | 1 | GACTGGAGTTCAGACGTGTGCTCTTCCGATCTAGCTTACCATGGACCCTGACAAATGTG |
| SEQ ID NO:492 | 1 | GACTGGAGTTCAGACGTGTGCTCTTCCGATCTAGCTTCTTCACGCTCCTTCCCTATCC |
| SEQ ID NO:493 | 1 | GACTGGAGTTCAGACGTGTGCTCTTCCGATCTAGGAAAACTACAATGGAGAAAGAAGACTA |
| SEQ ID NO:494 | 1 | GACTGGAGTTCAGACGTGTGCTCTTCCGATCTAGGAGATAAGTGATGGAGATGTGATAATTT |
| SEQ ID NO:495 | 1 | GACTGGAGTTCAGACGTGTGCTCTTCCGATCTAGGAGTACTTCTTTGGGTTGACTTCTC |
| SEQ ID NO:496 | 1 | GACTGGAGTTCAGACGTGTGCTCTTCCGATCTAGGCCATCTTCCATCTTCTCACACTGG |
| SEQ ID NO:497 | 1 | GACTGGAGTTCAGACGTGTGCTCTTCCGATCTAGGCCTTCGTCCTCCTTCCTCACTC |

FIG. 7K

| Target Specific Primer | Volume Ratio | Sequence |
|---|---|---|
| SEQ ID NO:498 | 1 | GACTGGAGTTCAGACGTGTGCTCTTCCGATCTAGGCGTGGGATGTTTTTGCAGATGATG |
| SEQ ID NO:499 | 1 | GACTGGAGTTCAGACGTGTGCTCTTCCGATCTAGGGAGTGAAGTGAATGTTGCTGAGGT |
| SEQ ID NO:500 | 1 | GACTGGAGTTCAGACGTGTGCTCTTCCGATCTAGGGGACATGCTAGGGACAACACGATT |
| SEQ ID NO:501 | 1 | GACTGGAGTTCAGACGTGTGCTCTTCCGATCTAGGTGTGTCTTTAATTGAAGCATGATTT |
| SEQ ID NO:502 | 1 | GACTGGAGTTCAGACGTGTGCTCTTCCGATCTAGGTTCACTGCATATTCTCCCCACAGA |
| SEQ ID NO:503 | 1 | GACTGGAGTTCAGACGTGTGCTCTTCCGATCTAGGTTTCATGGACTCAGTTACTACCTG |
| SEQ ID NO:504 | 1 | GACTGGAGTTCAGACGTGTGCTCTTCCGATCTAGTACTTACCCACTGAAAAGCACTTCC |
| SEQ ID NO:505 | 1 | GACTGGAGTTCAGACGTGTGCTCTTCCGATCTAGTCACACTCATCAGCACCAGGTCTTG |
| SEQ ID NO:506 | 1 | GACTGGAGTTCAGACGTGTGCTCTTCCGATCTAGTCCCAACCATGTCAAAATTACAGAC |
| SEQ ID NO:507 | 1 | GACTGGAGTTCAGACGTGTGCTCTTCCGATCTAGTCCCAACCATGTCAAAATTACAGAC |
| SEQ ID NO:508 | 1 | GACTGGAGTTCAGACGTGTGCTCTTCCGATCTAGTCCCCAGCTACTCTCAAAATCAGCA |
| SEQ ID NO:509 | 1 | GACTGGAGTTCAGACGTGTGCTCTTCCGATCTAGTCCTCCACACTTCTCCATTCTTC |
| SEQ ID NO:510 | 1 | GACTGGAGTTCAGACGTGTGCTCTTCCGATCTAGTCTATGTGATCAAGAAATCGATAGCA |
| SEQ ID NO:511 | 1 | GACTGGAGTTCAGACGTGTGCTCTTCCGATCTAGTCTTTCTTTGAAGCAGCAAGTATGA |
| SEQ ID NO:512 | 1 | GACTGGAGTTCAGACGTGTGCTCTTCCGATCTAGTGAACGTTGTTGGACTCTACTGTGT |
| SEQ ID NO:513 | 1 | GACTGGAGTTCAGACGTGTGCTCTTCCGATCTAGTGGTGGTATACGATATGGGTTTTGT |
| SEQ ID NO:514 | 1 | GACTGGAGTTCAGACGTGTGCTCTTCCGATCTAGTGGTTCTGGATTAGCTGGATTGTCA |
| SEQ ID NO:515 | 1 | GACTGGAGTTCAGACGTGTGCTCTTCCGATCTAGTGTTACTCAAGAAGCAGAAAGGGAA |
| SEQ ID NO:516 | 1 | GACTGGAGTTCAGACGTGTGCTCTTCCGATCTAGTGTTACTCAAGAAGCAGAAAGGGAA |

FIG. 7L

| Target Specific Primer | Volume Ratio | Sequence |
| --- | --- | --- |
| SEQ ID NO:517 | 1 | GACTGGAGTTCAGACGTGTGCTCTTCCGATCTAGTTAACTCTCTGGTGGTAGAATGAAA |
| SEQ ID NO:518 | 1 | GACTGGAGTTCAGACGTGTGCTCTTCCGATCTAGTTCCCTCAGCCGTTACCTGTGT |
| SEQ ID NO:519 | 1 | GACTGGAGTTCAGACGTGTGCTCTTCCGATCTAGTTGAAAATACATAGAGTTTTAATGCATTGTC |
| SEQ ID NO:520 | 1 | GACTGGAGTTCAGACGTGTGCTCTTCCGATCTAGTTGCTAAGAACCGGTCACTGAAAAT |
| SEQ ID NO:521 | 1 | GACTGGAGTTCAGACGTGTGCTCTTCCGATCTAGTTTTCCTCCTACTCACCATCCTGT |
| SEQ ID NO:522 | 1 | GACTGGAGTTCAGACGTGTGCTCTTCCGATCTATAAAAGCTCTTCCTGTTTCAGTCCCC |
| SEQ ID NO:523 | 1 | GACTGGAGTTCAGACGTGTGCTCTTCCGATCTATACACAAAGAAAGCCCTCCCCAGTCC |
| SEQ ID NO:524 | 1 | GACTGGAGTTCAGACGTGTGCTCTTCCGATCTATATACCCAGTGCCTTGTGTGGTGACT |
| SEQ ID NO:525 | 1 | GACTGGAGTTCAGACGTGTGCTCTTCCGATCTATATGCTCCACTAACAACCCTCCTGCC |
| SEQ ID NO:526 | 1 | GACTGGAGTTCAGACGTGTGCTCTTCCGATCTATATGGAGAAGTTAGACATGTCAACCT |
| SEQ ID NO:527 | 1 | GACTGGAGTTCAGACGTGTGCTCTTCCGATCTATATGGCCATTTCTGTTTTCCTGTAGC |
| SEQ ID NO:528 | 1 | GACTGGAGTTCAGACGTGTGCTCTTCCGATCTATATTGGCCTGTCTGCTCTTCCCACCA |
| SEQ ID NO:529 | 1 | GACTGGAGTTCAGACGTGTGCTCTTCCGATCTATATTTGAGTCTATCGAGTGTGTGCAT |
| SEQ ID NO:530 | 1 | GACTGGAGTTCAGACGTGTGCTCTTCCGATCTATCAAAGACGACTGATTCAAAGCTGG |
| SEQ ID NO:531 | 1 | GACTGGAGTTCAGACGTGTGCTCTTCCGATCTATCAAGTTCAACAGTTCAGGCCAGTGC |
| SEQ ID NO:532 | 1 | GACTGGAGTTCAGACGTGTGCTCTTCCGATCTATCACTCCACATTTCAGCAACAGCAGC |
| SEQ ID NO:533 | 1 | GACTGGAGTTCAGACGTGTGCTCTTCCGATCTATCATATTGGCCTGTCTGCTCTTCCCA |
| SEQ ID NO:534 | 1 | GACTGGAGTTCAGACGTGTGCTCTTCCGATCTATCCACTCAATCTTCTACTTTAAAATGACTT |
| SEQ ID NO:535 | 1 | GACTGGAGTTCAGACGTGTGCTCTTCCGATCTATCGCGGGCTTGGTTCTGATGTTTGTA |

FIG. 7M

| Target Specific Primer | Volume Ratio | Sequence |
|---|---|---|
| SEQ ID NO:536 | 1 | GACTGGAGTTCAGACGTGTGCTCTTCCGATCTATCTCCCTTCTACCGGCAGATCCC |
| SEQ ID NO:537 | 1 | GACTGGAGTTCAGACGTGTGCTCTTCCGATCTATCTCCCTTCTACCGGCAGATCCCTTT |
| SEQ ID NO:538 | 1 | GACTGGAGTTCAGACGTGTGCTCTTCCGATCTATCTGATGCTGAGGAAGTGGATTTTGC |
| SEQ ID NO:539 | 1 | GACTGGAGTTCAGACGTGTGCTCTTCCGATCTATCTGGAGATCAAACCCGCAATCCG |
| SEQ ID NO:540 | 1 | GACTGGAGTTCAGACGTGTGCTCTTCCGATCTATCTGGAGCATGGGACTGTCTCTGGTA |
| SEQ ID NO:541 | 1 | GACTGGAGTTCAGACGTGTGCTCTTCCGATCTATGAACATGACCCTGAATTCGGATGCA |
| SEQ ID NO:542 | 1 | GACTGGAGTTCAGACGTGTGCTCTTCCGATCTATGACTGAGACAATAATTATTAAAAGGTGATCT |
| SEQ ID NO:543 | 1 | GACTGGAGTTCAGACGTGTGCTCTTCCGATCTATGAGTTCTGGGCACTGGGTCAAAGTC |
| SEQ ID NO:544 | 1 | GACTGGAGTTCAGACGTGTGCTCTTCCGATCTATGCAGAGCTTCTTCCCATGATGATC |
| SEQ ID NO:545 | 1 | GACTGGAGTTCAGACGTGTGCTCTTCCGATCTATGCGCTTGACATCAGTTTGCCAGTTG |
| SEQ ID NO:546 | 1 | GACTGGAGTTCAGACGTGTGCTCTTCCGATCTATGCGCTTGACATCAGTTTGCCAGTTG |
| SEQ ID NO:547 | 1 | GACTGGAGTTCAGACGTGTGCTCTTCCGATCTATGCTCTGCTTCTGTACTGCCAG |
| SEQ ID NO:548 | 1 | GACTGGAGTTCAGACGTGTGCTCTTCCGATCTATGGAACTGATGTCTGGACGCTCATTG |
| SEQ ID NO:549 | 1 | GACTGGAGTTCAGACGTGTGCTCTTCCGATCTATGGAAGAAATCGGTAAGAGGTGGGCC |
| SEQ ID NO:550 | 1 | GACTGGAGTTCAGACGTGTGCTCTTCCGATCTATGGAAGGTGCGTTCGATGACAGTG |
| SEQ ID NO:551 | 1 | GACTGGAGTTCAGACGTGTGCTCTTCCGATCTATGGACATGAAGCAGGCTGATAC |
| SEQ ID NO:552 | 1 | GACTGGAGTTCAGACGTGTGCTCTTCCGATCTATGGACATGAAGCAGGCTGATACTAC |
| SEQ ID NO:553 | 1 | GACTGGAGTTCAGACGTGTGCTCTTCCGATCTATGGACCATTTAACACAGAAGAGAGT |
| SEQ ID NO:554 | 1 | GACTGGAGTTCAGACGTGTGCTCTTCCGATCTATGGCAGTCAAACCTTCTCTCTTATGT |

FIG. 7N

| Target Specific Primer | Volume Ratio | Sequence |
|---|---|---|
| SEQ ID NO:555 | 1 | GACTGGAGTTCAGACGTGTGCTCTTCCGATCTATGGCTGTGGTTTGTGATGGTTGGGAG |
| SEQ ID NO:556 | 1 | GACTGGAGTTCAGACGTGTGCTCTTCCGATCTATGGGAGAACTCTGAGTGGCCACCTC |
| SEQ ID NO:557 | 1 | GACTGGAGTTCAGACGTGTGCTCTTCCGATCTATGGTGAATGACGGCGTGGAGGAC |
| SEQ ID NO:558 | 1 | GACTGGAGTTCAGACGTGTGCTCTTCCGATCTATGTATTGGTCTCTCATGGCACTGTA |
| SEQ ID NO:559 | 1 | GACTGGAGTTCAGACGTGTGCTCTTCCGATCTATGTCTTACTGCTCTACAAGGGCTTTA |
| SEQ ID NO:560 | 1 | GACTGGAGTTCAGACGTGTGCTCTTCCGATCTATGTTATTTGAGCTAGAACCAGTGCCA |
| SEQ ID NO:561 | 1 | GACTGGAGTTCAGACGTGTGCTCTTCCGATCTATTACATGTGGAGTGAACGTTGTTGGA |
| SEQ ID NO:562 | 1 | GACTGGAGTTCAGACGTGTGCTCTTCCGATCTATTAGTGATGGATTTGATGAATTGGTGAT |
| SEQ ID NO:563 | 1 | GACTGGAGTTCAGACGTGTGCTCTTCCGATCTATTCTGCTCTGAAGGGGGAAATGTGAG |
| SEQ ID NO:564 | 1 | GACTGGAGTTCAGACGTGTGCTCTTCCGATCTATTCTGTGTGTAAAGCCCAGCCCCC |
| SEQ ID NO:565 | 1 | GACTGGAGTTCAGACGTGTGCTCTTCCGATCTATTGAAATTCACTTACACCGGGCCCTC |
| SEQ ID NO:566 | 1 | GACTGGAGTTCAGACGTGTGCTCTTCCGATCTATTGTGAAGATCTGTGACTTTGGCCTG |
| SEQ ID NO:567 | 1 | GACTGGAGTTCAGACGTGTGCTCTTCCGATCTATTTATTTCAGTGTTACTTACCTGTCTTGT |
| SEQ ID NO:568 | 1 | GACTGGAGTTCAGACGTGTGCTCTTCCGATCTATTTCAACTAAACTTCTAAGATGTGGCA |
| SEQ ID NO:569 | 1 | GACTGGAGTTCAGACGTGTGCTCTTCCGATCTATTTGAGGGGAGTCTGGGAATGAACA |
| SEQ ID NO:570 | 1 | GACTGGAGTTCAGACGTGTGCTCTTCCGATCTATTTTTTATGGCAGTCAAACCTTCTCT |
| SEQ ID NO:571 | 1 | GACTGGAGTTCAGACGTGTGCTCTTCCGATCTCAAAACGCAGCCCAGGACGAGTATG |
| SEQ ID NO:572 | 1 | GACTGGAGTTCAGACGTGTGCTCTTCCGATCTCAAACCAGACCTCAGGCGGCTCATAG |
| SEQ ID NO:573 | 1 | GACTGGAGTTCAGACGTGTGCTCTTCCGATCTCAAACTAGCCCTCAATCCCTGACCCTG |

FIG. 7O

| Target Specific Primer | Volume Ratio | Sequence |
|---|---|---|
| SEQ ID NO:574 | 1 | GACTGGAGTTCAGACGTGTGCTCTTCCGATCTCAAACTAGCCCTCAATCCCTGACCCTG |
| SEQ ID NO:575 | 1 | GACTGGAGTTCAGACGTGTGCTCTTCCGATCTCAAAGACGACTGATTCAAAGCTGGTCA |
| SEQ ID NO:576 | 1 | GACTGGAGTTCAGACGTGTGCTCTTCCGATCTCAAAGCAGCCTCTCTTAACCCCCTTCC |
| SEQ ID NO:577 | 1 | GACTGGAGTTCAGACGTGTGCTCTTCCGATCTCAAAGTCTGTGGCCTTGTACTGCAGA |
| SEQ ID NO:578 | 1 | GACTGGAGTTCAGACGTGTGCTCTTCCGATCTCAAAGTTTGGGAAGGCTGGAAGGGAC |
| SEQ ID NO:579 | 1 | GACTGGAGTTCAGACGTGTGCTCTTCCGATCTCAAATGTCTTACTGCTCTACAAGGGCT |
| SEQ ID NO:580 | 1 | GACTGGAGTTCAGACGTGTGCTCTTCCGATCTCAAATTGTTGCCATTTCAGGGTTTCT |
| SEQ ID NO:581 | 1 | GACTGGAGTTCAGACGTGTGCTCTTCCGATCTCAACACACCACAGATGTCTTCAGGCTT |
| SEQ ID NO:582 | 1 | GACTGGAGTTCAGACGTGTGCTCTTCCGATCTCAACCAGCCCTGTCGTCTCTCCAG |
| SEQ ID NO:583 | 1 | GACTGGAGTTCAGACGTGTGCTCTTCCGATCTCAACCCAATAGACCCACCCCAATCTCC |
| SEQ ID NO:584 | 1 | GACTGGAGTTCAGACGTGTGCTCTTCCGATCTCAACGGGTTCCTTCCTTCGAGAGCTTC |
| SEQ ID NO:585 | 1 | GACTGGAGTTCAGACGTGTGCTCTTCCGATCTCAACTTGGAGGCCTTGCAGAAGAA |
| SEQ ID NO:586 | 1 | GACTGGAGTTCAGACGTGTGCTCTTCCGATCTCAAGAGATCTGATGCTGAGGAAGTGGA |
| SEQ ID NO:587 | 1 | GACTGGAGTTCAGACGTGTGCTCTTCCGATCTCAAGCCTCACACCACCCCCAC |
| SEQ ID NO:588 | 1 | GACTGGAGTTCAGACGTGTGCTCTTCCGATCTCAAGGAGATAAGTGATGGAGATGTGATAA |
| SEQ ID NO:589 | 1 | GACTGGAGTTCAGACGTGTGCTCTTCCGATCTCAAGGGCTAGGATGGGGACTCTTG |
| SEQ ID NO:590 | 1 | GACTGGAGTTCAGACGTGTGCTCTTCCGATCTCAAGGGTGTGAGTGAACGGTGAGC |
| SEQ ID NO:591 | 1 | GACTGGAGTTCAGACGTGTGCTCTTCCGATCTCAAGGTGGAAAGAGGAAGATGAGAAC |
| SEQ ID NO:592 | 1 | GACTGGAGTTCAGACGTGTGCTCTTCCGATCTCAATAGACCCACCCCAATCTCCCCAGA |

FIG. 7P

| Target Specific Primer | Volume Ratio | Sequence |
|---|---|---|
| SEQ ID NO:593 | 1 | GACTGGAGTTCAGACGTGTGCTCTTCCGATCTCAATCAAACTGCAGAGTATTTGGGCGA |
| SEQ ID NO:594 | 1 | GACTGGAGTTCAGACGTGTGCTCTTCCGATCTCAATCCTCGGCCTCTAGTGTGCAGA |
| SEQ ID NO:595 | 1 | GACTGGAGTTCAGACGTGTGCTCTTCCGATCTCACAAAATGGTTCTGGATCAGCTGGA |
| SEQ ID NO:596 | 1 | GACTGGAGTTCAGACGTGTGCTCTTCCGATCTCACAAGCCACCCATCTCCTCAGCTG |
| SEQ ID NO:597 | 1 | GACTGGAGTTCAGACGTGTGCTCTTCCGATCTCACAAGGGGCTAGGATGGGGACTC |
| SEQ ID NO:598 | 1 | GACTGGAGTTCAGACGTGTGCTCTTCCGATCTCACACCACCCCACCCACAGATC |
| SEQ ID NO:599 | 1 | GACTGGAGTTCAGACGTGTGCTCTTCCGATCTCACAGAGAAGTTGTTGAGGGGAGCCT |
| SEQ ID NO:600 | 1 | GACTGGAGTTCAGACGTGTGCTCTTCCGATCTCACAGATGTTCCCGGGGCTGC |
| SEQ ID NO:601 | 1 | GACTGGAGTTCAGACGTGTGCTCTTCCGATCTCACAGCCCACGTACCGCTCCTC |
| SEQ ID NO:602 | 1 | GACTGGAGTTCAGACGTGTGCTCTTCCGATCTCACAGCTGGAAGGACAAGCC |
| SEQ ID NO:603 | 1 | GACTGGAGTTCAGACGTGTGCTCTTCCGATCTCACCAGCCGCGAAACCTGAGAAG |
| SEQ ID NO:604 | 1 | GACTGGAGTTCAGACGTGTGCTCTTCCGATCTCACCAGGACATGCACAGCTACATCG |
| SEQ ID NO:605 | 1 | GACTGGAGTTCAGACGTGTGCTCTTCCGATCTCACCCAAATGTGCAGAAAGACCT |
| SEQ ID NO:606 | 1 | GACTGGAGTTCAGACGTGTGCTCTTCCGATCTCACCCCCACCCACAGATCCACT |
| SEQ ID NO:607 | 1 | GACTGGAGTTCAGACGTGTGCTCTTCCGATCTCACCCCTTCCCCAGTGCATCCA |
| SEQ ID NO:608 | 1 | GACTGGAGTTCAGACGTGTGCTCTTCCGATCTCACCCTGCCATGCTACCTAGATACCTT |
| SEQ ID NO:609 | 1 | GACTGGAGTTCAGACGTGTGCTCTTCCGATCTCACCCTGTTCACTCCTTTGCTGATTGG |
| SEQ ID NO:610 | 1 | GACTGGAGTTCAGACGTGTGCTCTTCCGATCTCACCGCTTCTTGTCCTGCTTGCTTAC |
| SEQ ID NO:611 | 1 | GACTGGAGTTCAGACGTGTGCTCTTCCGATCTCACCTGATCCTAGTACCTTCCCTGCAA |

FIG. 7Q

| Target Specific Primer | Volume Ratio | Sequence |
|---|---|---|
| SEQ ID NO: 612 | 1 | GACTGGAGTTCAGACGTGTGCTCTTCCGATCTCACGCTCCATTATCCAGCCCCAAAG |
| SEQ ID NO: 613 | 1 | GACTGGAGTTCAGACGTGTGCTCTTCCGATCTCACGTGTTGAAGTCCTCGTTGTCTTGT |
| SEQ ID NO: 614 | 1 | GACTGGAGTTCAGACGTGTGCTCTTCCGATCTCACGTGTTGAAGTCCTCGTTGTCTTGT |
| SEQ ID NO: 615 | 1 | GACTGGAGTTCAGACGTGTGCTCTTCCGATCTCACTCAGATCTCGTCAGCCATGGAGT |
| SEQ ID NO: 616 | 1 | GACTGGAGTTCAGACGTGTGCTCTTCCGATCTCACTCGGATAAGATGCTGAGGAGGGG |
| SEQ ID NO: 617 | 1 | GACTGGAGTTCAGACGTGTGCTCTTCCGATCTCACTGACCCACCACCCCCTCAC |
| SEQ ID NO: 618 | 1 | GACTGGAGTTCAGACGTGTGCTCTTCCGATCTCACTGCCGCTTCCCCACCAG |
| SEQ ID NO: 619 | 1 | GACTGGAGTTCAGACGTGTGCTCTTCCGATCTCACTGCCTCATCTCTCACCATCCCAAG |
| SEQ ID NO: 620 | 1 | GACTGGAGTTCAGACGTGTGCTCTTCCGATCTCACTGCTACCACAAGTTTGCCCACAA |
| SEQ ID NO: 621 | 1 | GACTGGAGTTCAGACGTGTGCTCTTCCGATCTCACTTTGACTCACCGGTGGATGAAGTG |
| SEQ ID NO: 622 | 1 | GACTGGAGTTCAGACGTGTGCTCTTCCGATCTCAGAAAAGCGGCTGTTAGTCACTGG |
| SEQ ID NO: 623 | 1 | GACTGGAGTTCAGACGTGTGCTCTTCCGATCTCAGAAGATGACAGGGGCCAGGAG |
| SEQ ID NO: 624 | 1 | GACTGGAGTTCAGACGTGTGCTCTTCCGATCTCAGACATTGTGCAAGCAGGTCCCTC |
| SEQ ID NO: 625 | 1 | GACTGGAGTTCAGACGTGTGCTCTTCCGATCTCAGACGCATTTCCACAGCTACACCATA |
| SEQ ID NO: 626 | 1 | GACTGGAGTTCAGACGTGTGCTCTTCCGATCTCAGACTGATGGCCAACTCCCCTTC |
| SEQ ID NO: 627 | 1 | GACTGGAGTTCAGACGTGTGCTCTTCCGATCTCAGAGAGCAACAAACCACTGGAAT |
| SEQ ID NO: 628 | 1 | GACTGGAGTTCAGACGTGTGCTCTTCCGATCTCAGAGAGCAACAAACCACTGGAATATA |
| SEQ ID NO: 629 | 1 | GACTGGAGTTCAGACGTGTGCTCTTCCGATCTCAGAGCCCAGTCCCCTCAGG |
| SEQ ID NO: 630 | 1 | GACTGGAGTTCAGACGTGTGCTCTTCCGATCTCAGAGGGGAGTTGGGGTGAGGG |

FIG. 7R

| Target Specific Primer | Volume Ratio | Sequence |
|---|---|---|
| SEQ ID NO: 631 | 1 | GACTGGAGTTCAGACGTGTGCTCTTCCGATCTCAGAGTAGGGGCTGGCTGGATGAG |
| SEQ ID NO: 632 | 1 | GACTGGAGTTCAGACGTGTGCTCTTCCGATCTCAGATCTGTATTTATTTCAGTGTTACTTACCT |
| SEQ ID NO: 633 | 1 | GACTGGAGTTCAGACGTGTGCTCTTCCGATCTCAGATGCTTTGAATGAGTGTTAGAAC |
| SEQ ID NO: 634 | 1 | GACTGGAGTTCAGACGTGTGCTCTTCCGATCTCAGCATTGTTGGGGGACACGAGC |
| SEQ ID NO: 635 | 1 | GACTGGAGTTCAGACGTGTGCTCTTCCGATCTCAGCCACACATGCCATCATTCTAGGA |
| SEQ ID NO: 636 | 1 | GACTGGAGTTCAGACGTGTGCTCTTCCGATCTCAGCCACGGGTAATAATTTTTGTCCTT |
| SEQ ID NO: 637 | 1 | GACTGGAGTTCAGACGTGTGCTCTTCCGATCTCAGCCGATGTCAGTCTGGTGTGG |
| SEQ ID NO: 638 | 1 | GACTGGAGTTCAGACGTGTGCTCTTCCGATCTCAGCCGGTTCTCTGCACATTGGAA |
| SEQ ID NO: 639 | 1 | GACTGGAGTTCAGACGTGTGCTCTTCCGATCTCAGCCTACAGAGTCCGCAAGCCAAG |
| SEQ ID NO: 640 | 1 | GACTGGAGTTCAGACGTGTGCTCTTCCGATCTCAGCCTCTCTTAACCCCCTTCCCTAG |
| SEQ ID NO: 641 | 1 | GACTGGAGTTCAGACGTGTGCTCTTCCGATCTCAGGCACAGCTTTTCCTCCATGAG |
| SEQ ID NO: 642 | 1 | GACTGGAGTTCAGACGTGTGCTCTTCCGATCTCAGGCACAGCTTTTCCTCCATGAGTAC |
| SEQ ID NO: 643 | 1 | GACTGGAGTTCAGACGTGTGCTCTTCCGATCTCAGGCATCCTCAGCTACGGGGT |
| SEQ ID NO: 644 | 1 | GACTGGAGTTCAGACGTGTGCTCTTCCGATCTCAGGCCCTGGTAGCTCATCATC |
| SEQ ID NO: 645 | 1 | GACTGGAGTTCAGACGTGTGCTCTTCCGATCTCAGGCCTCTCTGTCTGAACTTGGG |
| SEQ ID NO: 646 | 1 | GACTGGAGTTCAGACGTGTGCTCTTCCGATCTCAGGGAGCAGCGAGGCCTTCAC |
| SEQ ID NO: 647 | 1 | GACTGGAGTTCAGACGTGTGCTCTTCCGATCTCAGGGCATGAACTACTTGGAGGACC |
| SEQ ID NO: 648 | 1 | GACTGGAGTTCAGACGTGTGCTCTTCCGATCTCAGGGGTACTTAGATGGGGATGGCTG |
| SEQ ID NO: 649 | 1 | GACTGGAGTTCAGACGTGTGCTCTTCCGATCTCAGGTCTCCGTGGATGCCTTCAAG |

FIG. 7S

| Target Specific Primer | Volume Ratio | Sequence |
|---|---|---|
| SEQ ID NO:650 | 1 | GACTGGAGTTCAGACGTGTGCTCTTCCGATCTCAGGTTCCACACACAGGCGTCC |
| SEQ ID NO:651 | 1 | GACTGGAGTTCAGACGTGTGCTCTTCCGATCTCAGGTTCTTTGGGGGCAGAGGG |
| SEQ ID NO:652 | 1 | GACTGGAGTTCAGACGTGTGCTCTTCCGATCTCAGTATAGAGCGTGCAGATAATGACAA |
| SEQ ID NO:653 | 1 | GACTGGAGTTCAGACGTGTGCTCTTCCGATCTCAGTCGCCTCAGTAAAGCCACCTCAC |
| SEQ ID NO:654 | 1 | GACTGGAGTTCAGACGTGTGCTCTTCCGATCTCAGTGGGGCAGACTCTCTCCTCC |
| SEQ ID NO:655 | 1 | GACTGGAGTTCAGACGTGTGCTCTTCCGATCTCAGTGGGGCAGACTCTCTCCTCC |
| SEQ ID NO:656 | 1 | GACTGGAGTTCAGACGTGTGCTCTTCCGATCTCAGTTGTTTGTTCAGTTGGGAGCGGAG |
| SEQ ID NO:657 | 1 | GACTGGAGTTCAGACGTGTGCTCTTCCGATCTCAGTTGTTTGTTCAGTTGGGAGCGGAG |
| SEQ ID NO:658 | 1 | GACTGGAGTTCAGACGTGTGCTCTTCCGATCTCATACGTCTTGGTTCACTCATCCGGGA |
| SEQ ID NO:659 | 1 | GACTGGAGTTCAGACGTGTGCTCTTCCGATCTCATCAGCACCACCACCACCAGC |
| SEQ ID NO:660 | 1 | GACTGGAGTTCAGACGTGTGCTCTTCCGATCTCATCCACTGCTACCACAAGTTTGCCC |
| SEQ ID NO:661 | 1 | GACTGGAGTTCAGACGTGTGCTCTTCCGATCTCATCCAGTGCCAGAACCCGCTCTTC |
| SEQ ID NO:662 | 1 | GACTGGAGTTCAGACGTGTGCTCTTCCGATCTCATCGTCTTTGCAGGCCTCTCT |
| SEQ ID NO:663 | 1 | GACTGGAGTTCAGACGTGTGCTCTTCCGATCTCATCTGCCTCACCTCCACCGTG |
| SEQ ID NO:664 | 1 | GACTGGAGTTCAGACGTGTGCTCTTCCGATCTCATCTTCCATCTTCTCACACTGGGGGT |
| SEQ ID NO:665 | 1 | GACTGGAGTTCAGACGTGTGCTCTTCCGATCTCATGAACTCCACATTTGCCTTGGGACC |
| SEQ ID NO:666 | 1 | GACTGGAGTTCAGACGTGTGCTCTTCCGATCTCATGCCTGGCTCCCTAATTTTATAGTT |
| SEQ ID NO:667 | 1 | GACTGGAGTTCAGACGTGTGCTCTTCCGATCTCATGCGCTTGACATCAGTTTGCCAG |
| SEQ ID NO:668 | 1 | GACTGGAGTTCAGACGTGTGCTCTTCCGATCTCATGCTGCAGGGAGGGGC |

FIG. 7T

| Target Specific Primer | Volume Ratio | Sequence |
|---|---|---|
| SEQ ID NO:669 | 1 | GACTGGAGTTCAGACGTGTGCTCTTCCGATCTCATGGAACCAGACAGAAAAGCGGCT |
| SEQ ID NO:670 | 1 | GACTGGAGTTCAGACGTGTGCTCTTCCGATCTCATGGACCCTGACAAATGTGCTGTTCT |
| SEQ ID NO:671 | 1 | GACTGGAGTTCAGACGTGTGCTCTTCCGATCTCATGTCTGGCACTGCTTTCCA |
| SEQ ID NO:672 | 1 | GACTGGAGTTCAGACGTGTGCTCTTCCGATCTCATTCTTGAGGGGCTGAGGTGGAAGAG |
| SEQ ID NO:673 | 1 | GACTGGAGTTCAGACGTGTGCTCTTCCGATCTCATTGGCATGGGGAAATATAAACTTGT |
| SEQ ID NO:674 | 1 | GACTGGAGTTCAGACGTGTGCTCTTCCGATCTCATTGGGGAGGTAGAGGGCACAC |
| SEQ ID NO:675 | 1 | GACTGGAGTTCAGACGTGTGCTCTTCCGATCTCATTGTTGGGGGACACGAGCCTG |
| SEQ ID NO:676 | 1 | GACTGGAGTTCAGACGTGTGCTCTTCCGATCTCATTTCCATCTCCCCTCCCTTTACCCT |
| SEQ ID NO:677 | 1 | GACTGGAGTTCAGACGTGTGCTCTTCCGATCTCATTTCTTCCTTTTCCATGCAGTGTGT |
| SEQ ID NO:678 | 1 | GACTGGAGTTCAGACGTGTGCTCTTCCGATCTCATTTGGATGCCTTATTGCGACAGATC |
| SEQ ID NO:679 | 1 | GACTGGAGTTCAGACGTGTGCTCTTCCGATCTCCAAAGCAGCCTCTCTTAACCCCCT |
| SEQ ID NO:680 | 1 | GACTGGAGTTCAGACGTGTGCTCTTCCGATCTCCAATGGAAAAGAAATGCTGCAGAAACA |
| SEQ ID NO:681 | 1 | GACTGGAGTTCAGACGTGTGCTCTTCCGATCTCCAATTCAGGACCCACACGACGG |
| SEQ ID NO:682 | 1 | GACTGGAGTTCAGACGTGTGCTCTTCCGATCTCCACACACCACCCCTCTGCTGG |
| SEQ ID NO:683 | 1 | GACTGGAGTTCAGACGTGTGCTCTTCCGATCTCCACACTTCTCCATTCTTCACAAGGGTATG |
| SEQ ID NO:684 | 1 | GACTGGAGTTCAGACGTGTGCTCTTCCGATCTCCACATTTCAGCAACAGCAGCATCTATA |
| SEQ ID NO:685 | 1 | GACTGGAGTTCAGACGTGTGCTCTTCCGATCTCCACATTTCAGCAACAGCAGCATCTATAAGA |
| SEQ ID NO:686 | 1 | GACTGGAGTTCAGACGTGTGCTCTTCCGATCTCCACCAAGCAGCCCATCCCTG |
| SEQ ID NO:687 | 1 | GACTGGAGTTCAGACGTGTGCTCTTCCGATCTCCACGATGCCCAGTCAATCTTGTGTAA |

FIG. 7U

| Target Specific Primer | Volume Ratio | Sequence |
|---|---|---|
| SEQ ID NO:688 | 1 | GACTGGAGTTCAGACGTGTGCTCTTCCGATCTCCACGATGCCCAGTCAATCTTGTGTAATTT |
| SEQ ID NO:689 | 1 | GACTGGAGTTCAGACGTGTGCTCTTCCGATCTCCACTAACAACCCTCCTGCCATCATATT |
| SEQ ID NO:690 | 1 | GACTGGAGTTCAGACGTGTGCTCTTCCGATCTCCACTCAATCTTCTACTTTAAAATGACTTAGG |
| SEQ ID NO:691 | 1 | GACTGGAGTTCAGACGTGTGCTCTTCCGATCTCCACTCAATCTTCTACTTTAAAATGACTTAGGAAA |
| SEQ ID NO:692 | 1 | GACTGGAGTTCAGACGTGTGCTCTTCCGATCTCCACTCATGCTCTACAACCCCACCAC |
| SEQ ID NO:693 | 1 | GACTGGAGTTCAGACGTGTGCTCTTCCGATCTCCACTCTTGCTCCTTCCATCCTTGCTC |
| SEQ ID NO:694 | 1 | GACTGGAGTTCAGACGTGTGCTCTTCCGATCTCCACTGACAACCACCCTTAACCCCTC |
| SEQ ID NO:695 | 1 | GACTGGAGTTCAGACGTGTGCTCTTCCGATCTCCACTGCTGGCTGATCTATGTCCCTG |
| SEQ ID NO:696 | 1 | GACTGGAGTTCAGACGTGTGCTCTTCCGATCTCCACTTCTACGACTTCTTCAACCAGGC |
| SEQ ID NO:697 | 1 | GACTGGAGTTCAGACGTGTGCTCTTCCGATCTCCAGAAGGTCTACATGGGTGCT |
| SEQ ID NO:698 | 1 | GACTGGAGTTCAGACGTGTGCTCTTCCGATCTCCAGAAGGTCTACATGGGTGCTTCC |
| SEQ ID NO:699 | 1 | GACTGGAGTTCAGACGTGTGCTCTTCCGATCTCCAGAAGGTCTACATGGGTGCTTCC |
| SEQ ID NO:700 | 1 | GACTGGAGTTCAGACGTGTGCTCTTCCGATCTCCAGAAGGTCTACATGGGTGCTTCC |
| SEQ ID NO:701 | 1 | GACTGGAGTTCAGACGTGTGCTCTTCCGATCTCCAGACCTAACTCTTGAATGACCCTGT |
| SEQ ID NO:702 | 1 | GACTGGAGTTCAGACGTGTGCTCTTCCGATCTCCAGACCTAAGAGCAATCAGTGAGGAATCA |
| SEQ ID NO:703 | 1 | GACTGGAGTTCAGACGTGTGCTCTTCCGATCTCCAGCCAGACCCAGCCAGTATTATTTC |
| SEQ ID NO:704 | 1 | GACTGGAGTTCAGACGTGTGCTCTTCCGATCTCCAGCGTGTCCTCTCTCCTCCATAG |
| SEQ ID NO:705 | 1 | GACTGGAGTTCAGACGTGTGCTCTTCCGATCTCCAGCGTGTCCTCTCTCCTCCATAG |
| SEQ ID NO:706 | 1 | GACTGGAGTTCAGACGTGTGCTCTTCCGATCTCCAGCTGCTCACCATCGCTATCTGA |

FIG. 7V

| Target Specific Primer | Volume Ratio | Sequence |
|---|---|---|
| SEQ ID NO:707 | 1 | GACTGGAGTTCAGACGTGTGCTCTTCCGATCTCCAGCTGCTCACCATCGCTATCTGA |
| SEQ ID NO:708 | 1 | GACTGGAGTTCAGACGTGTGCTCTTCCGATCTCCAGCTGGGTGAACTTTGAGGCC |
| SEQ ID NO:709 | 1 | GACTGGAGTTCAGACGTGTGCTCTTCCGATCTCCAGGAGCTAATAAAAATAACTTCTTTCTCTGG |
| SEQ ID NO:710 | 1 | GACTGGAGTTCAGACGTGTGCTCTTCCGATCTCCAGGGAGCAGCGAGGCCTT |
| SEQ ID NO:711 | 1 | GACTGGAGTTCAGACGTGTGCTCTTCCGATCTCCAGGGAGGGAGGCCAGCTG |
| SEQ ID NO:712 | 1 | GACTGGAGTTCAGACGTGTGCTCTTCCGATCTCCAGGGGTCCAAGTTAGGTTAGGTGAT |
| SEQ ID NO:713 | 1 | GACTGGAGTTCAGACGTGTGCTCTTCCGATCTCCAGGTCCACGGGCAGAC |
| SEQ ID NO:714 | 1 | GACTGGAGTTCAGACGTGTGCTCTTCCGATCTCCAGTGTTTCTTTTAAATACCTGTTAAGTTTGT |
| SEQ ID NO:715 | 1 | GACTGGAGTTCAGACGTGTGCTCTTCCGATCTCCAGTTGGTTACATACTTGGACTTGGTGAT |
| SEQ ID NO:716 | 1 | GACTGGAGTTCAGACGTGTGCTCTTCCGATCTCCATAAAGACAGAAGGAGGAGAGACACCA |
| SEQ ID NO:717 | 1 | GACTGGAGTTCAGACGTGTGCTCTTCCGATCTCCATAAAGGCTTTAACACAGAATCAAAAG |
| SEQ ID NO:718 | 1 | GACTGGAGTTCAGACGTGTGCTCTTCCGATCTCCATCATGCTGAGGTGCCACA |
| SEQ ID NO:719 | 1 | GACTGGAGTTCAGACGTGTGCTCTTCCGATCTCCATCCCAAGGTGCCTATCAAGTGGA |
| SEQ ID NO:720 | 1 | GACTGGAGTTCAGACGTGTGCTCTTCCGATCTCCATCCCCAGTGACTGTGTGTTGATCA |
| SEQ ID NO:721 | 1 | GACTGGAGTTCAGACGTGTGCTCTTCCGATCTCCATCCCCGTGTCCCTCCTAAGC |
| SEQ ID NO:722 | 1 | GACTGGAGTTCAGACGTGTGCTCTTCCGATCTCCATCTCCCCTCCCTTTACCCTTTCTT |
| SEQ ID NO:723 | 1 | GACTGGAGTTCAGACGTGTGCTCTTCCGATCTCCATCTGTCCTGGGCATGTCTCTG |
| SEQ ID NO:724 | 1 | GACTGGAGTTCAGACGTGTGCTCTTCCGATCTCCATCTTCTCTTTAGGGTCGGATTCCA |
| SEQ ID NO:725 | 1 | GACTGGAGTTCAGACGTGTGCTCTTCCGATCTCCATGAGTTCTGGGCACTGGGTCAAA |

FIG. 7W

| Target Specific Primer | Volume Ratio | Sequence |
| --- | --- | --- |
| SEQ ID NO:726 | 1 | GACTGGAGTTCAGACGTGTGCTCTTCCGATCTCCATGGGAGAACTCTGAGTGGCCAC |
| SEQ ID NO:727 | 1 | GACTGGAGTTCAGACGTGTGCTCTTCCGATCTCCATTATCTTCAGCTTTCTCCCACTGT |
| SEQ ID NO:728 | 1 | GACTGGAGTTCAGACGTGTGCTCTTCCGATCTCCATTCCAGGGGATGAGCTACCT |
| SEQ ID NO:729 | 1 | GACTGGAGTTCAGACGTGTGCTCTTCCGATCTCCATTCTTGAGGGGCTGAGGTGGAA |
| SEQ ID NO:730 | 1 | GACTGGAGTTCAGACGTGTGCTCTTCCGATCTCCATTTTAGACCTTGAGTTCTTGAGTTC |
| SEQ ID NO:731 | 1 | GACTGGAGTTCAGACGTGTGCTCTTCCGATCTCCATTTTGAAAGTGCCGGCCCG |
| SEQ ID NO:732 | 1 | GACTGGAGTTCAGACGTGTGCTCTTCCGATCTCCCAAACTAGCCCTCAATCCCTGACC |
| SEQ ID NO:733 | 1 | GACTGGAGTTCAGACGTGTGCTCTTCCGATCTCCCAAATATTCTCCAGGCGTTTCTTCCA |
| SEQ ID NO:734 | 1 | GACTGGAGTTCAGACGTGTGCTCTTCCGATCTCCCAATCTACCTGTGTCAGTTCCCTCC |
| SEQ ID NO:735 | 1 | GACTGGAGTTCAGACGTGTGCTCTTCCGATCTCCCACAGATGTTCCCGGGGC |
| SEQ ID NO:736 | 1 | GACTGGAGTTCAGACGTGTGCTCTTCCGATCTCCCACCACAGCTAGAACTTATCAAACCC |
| SEQ ID NO:737 | 1 | GACTGGAGTTCAGACGTGTGCTCTTCCGATCTCCCACGCTCTTCTCACTCATATCCTCC |
| SEQ ID NO:738 | 1 | GACTGGAGTTCAGACGTGTGCTCTTCCGATCTCCCACGCTCTTCTCACTCATATCCTCC |
| SEQ ID NO:739 | 1 | GACTGGAGTTCAGACGTGTGCTCTTCCGATCTCCCACGTACCGCTCCTCAGGA |
| SEQ ID NO:740 | 1 | GACTGGAGTTCAGACGTGTGCTCTTCCGATCTCCCAGAACTAACAGGTTAAGTGCTCCCA |
| SEQ ID NO:741 | 1 | GACTGGAGTTCAGACGTGTGCTCTTCCGATCTCCCAGAGCCCAGTCCCCCTC |
| SEQ ID NO:742 | 1 | GACTGGAGTTCAGACGTGTGCTCTTCCGATCTCCCAGCTGCTCACCATCGCTATC |
| SEQ ID NO:743 | 1 | GACTGGAGTTCAGACGTGTGCTCTTCCGATCTCCCATCCCCAGTGACTGTGTGTTGA |
| SEQ ID NO:744 | 1 | GACTGGAGTTCAGACGTGTGCTCTTCCGATCTCCCATTATTATAGAGATGATTGTTGAATTTTCC |

FIG. 7X

| Target Specific Primer | Volume Ratio | Sequence |
|---|---|---|
| SEQ ID NO:745 | 1 | GACTGGAGTTCAGACGTGTGCTCTTCCGATCTCCCATTATTATAGAGATGATTGTTGAATTTTCCTTT |
| SEQ ID NO:746 | 1 | GACTGGAGTTCAGACGTGTGCTCTTCCGATCTCCCCAGCTACTCTCAAAATCAGCATCC |
| SEQ ID NO:747 | 1 | GACTGGAGTTCAGACGTGTGCTCTTCCGATCTCCCCATTAAATGAGGTTTTACTGTTGT |
| SEQ ID NO:748 | 1 | GACTGGAGTTCAGACGTGTGCTCTTCCGATCTCCCGTTCCATCATAGCATGCAAGGG |
| SEQ ID NO:749 | 1 | GACTGGAGTTCAGACGTGTGCTCTTCCGATCTCCCTAATCACCACCCCACCCAATTCC |
| SEQ ID NO:750 | 1 | GACTGGAGTTCAGACGTGTGCTCTTCCGATCTCCCTATCCTGGCTGTGTCCTG |
| SEQ ID NO:751 | 1 | GACTGGAGTTCAGACGTGTGCTCTTCCGATCTCCCTCCCAGCTGCCTTCCA |
| SEQ ID NO:752 | 1 | GACTGGAGTTCAGACGTGTGCTCTTCCGATCTCCCTCCCCTCGAAATGAAGCTACAACA |
| SEQ ID NO:753 | 1 | GACTGGAGTTCAGACGTGTGCTCTTCCGATCTCCCTCGGGTCCCTGCTCTG |
| SEQ ID NO:754 | 1 | GACTGGAGTTCAGACGTGTGCTCTTCCGATCTCCCTGACAAATGTGCTGTTCTTCTTGGT |
| SEQ ID NO:755 | 1 | GACTGGAGTTCAGACGTGTGCTCTTCCGATCTCCCTGATAGTTGCTAAGAACCGGTCAC |
| SEQ ID NO:756 | 1 | GACTGGAGTTCAGACGTGTGCTCTTCCGATCTCCCTGCAAAGACAAATGGTGAGTACGT |
| SEQ ID NO:757 | 1 | GACTGGAGTTCAGACGTGTGCTCTTCCGATCTCCCTGTTCACTCCTTTGCTGATTGGTTT |
| SEQ ID NO:758 | 1 | GACTGGAGTTCAGACGTGTGCTCTTCCGATCTCCCTTGCCTCCCTTTCCAATGGACTAT |
| SEQ ID NO:759 | 1 | GACTGGAGTTCAGACGTGTGCTCTTCCGATCTCCCTTTGAACTTGCTCCCTCAGGCTAC |
| SEQ ID NO:760 | 1 | GACTGGAGTTCAGACGTGTGCTCTTCCGATCTCCGAAGTGTAAGCCCAACTACAGAAATGG |
| SEQ ID NO:761 | 1 | GACTGGAGTTCAGACGTGTGCTCTTCCGATCTCCGACAAGTGAGAGACAGGATCAGGTC |
| SEQ ID NO:762 | 1 | GACTGGAGTTCAGACGTGTGCTCTTCCGATCTCCGCAGTTCCATTCTCCCGCAG |
| SEQ ID NO:763 | 1 | GACTGGAGTTCAGACGTGTGCTCTTCCGATCTCCGGGGATTAAAGCTGGCTATGG |

FIG. 7Y

| Target Specific Primer | Volume Ratio | Sequence |
|---|---|---|
| SEQ ID NO:764 | 1 | GACTGGAGTTCAGACGTGTGCTCTTCCGATCTCCGGTAGTTGCCCTTCTCGAACATGT |
| SEQ ID NO:765 | 1 | GACTGGAGTTCAGACGTGTGCTCTTCCGATCTCCGGTGTAGGAGCTGCTGGTG |
| SEQ ID NO:766 | 1 | GACTGGAGTTCAGACGTGTGCTCTTCCGATCTCCGTGTCCCTCCTAAGCGCTGG |
| SEQ ID NO:767 | 1 | GACTGGAGTTCAGACGTGTGCTCTTCCGATCTCCTACACTGCACCCCTCTCCTCC |
| SEQ ID NO:768 | 1 | GACTGGAGTTCAGACGTGTGCTCTTCCGATCTCCTAGACTTGGGTGAGGCAGGG |
| SEQ ID NO:769 | 1 | GACTGGAGTTCAGACGTGTGCTCTTCCGATCTCCTATAGCTCCTGAGTATTGGTGTTCC |
| SEQ ID NO:770 | 1 | GACTGGAGTTCAGACGTGTGCTCTTCCGATCTCCTATCTCCCAGGCCTAAAATATACCCA |
| SEQ ID NO:771 | 1 | GACTGGAGTTCAGACGTGTGCTCTTCCGATCTCCTCACAGCAGGGTCTTCTCTG |
| SEQ ID NO:772 | 1 | GACTGGAGTTCAGACGTGTGCTCTTCCGATCTCCTCACCTGTCTACGTTCCCTCACT |
| SEQ ID NO:773 | 1 | GACTGGAGTTCAGACGTGTGCTCTTCCGATCTCCTCAGGATCCATTTCTGCCCAGTG |
| SEQ ID NO:774 | 1 | GACTGGAGTTCAGACGTGTGCTCTTCCGATCTCCTCCAGTTCAGCAAGGGGTCATAGAC |
| SEQ ID NO:775 | 1 | GACTGGAGTTCAGACGTGTGCTCTTCCGATCTCCTCCCCGGTGCGCATGTACT |
| SEQ ID NO:776 | 1 | GACTGGAGTTCAGACGTGTGCTCTTCCGATCTCCTCCCTGGTCAGAGTTCAAGTA |
| SEQ ID NO:777 | 1 | GACTGGAGTTCAGACGTGTGCTCTTCCGATCTCCTCGGGTCCCTGCTCTGTCA |
| SEQ ID NO:778 | 1 | GACTGGAGTTCAGACGTGTGCTCTTCCGATCTCCTCTCTGTCTGAACTTGGGCAA |
| SEQ ID NO:779 | 1 | GACTGGAGTTCAGACGTGTGCTCTTCCGATCTCCTCTCTTTCTTCCACCTTTCTCCAGC |
| SEQ ID NO:780 | 1 | GACTGGAGTTCAGACGTGTGCTCTTCCGATCTCCTCTCTTTCTTCCACCTTTCTCCAGC |
| SEQ ID NO:781 | 1 | GACTGGAGTTCAGACGTGTGCTCTTCCGATCTCCTCTGGCATTCTGGGAGCTTCATC |
| SEQ ID NO:782 | 1 | GACTGGAGTTCAGACGTGTGCTCTTCCGATCTCCTCTGGTCAAGGTCACATTCTT |

FIG. 7Z

| Target Specific Primer | Volume Ratio | Sequence |
|---|---|---|
| SEQ ID NO:783 | 1 | GACTGGAGTTCAGACGTGTGCTCTTCCGATCTCCTGAGCCTGTTTTGTGTCTACTGTTCT |
| SEQ ID NO:784 | 1 | GACTGGAGTTCAGACGTGTGCTCTTCCGATCTCCTGAGTCATTTCTTCCTTTTCCATGCA |
| SEQ ID NO:785 | 1 | GACTGGAGTTCAGACGTGTGCTCTTCCGATCTCCTGGAAGTTTAGGTCAAAGAGGCTGC |
| SEQ ID NO:786 | 1 | GACTGGAGTTCAGACGTGTGCTCTTCCGATCTCCTGGATCATGGCAGGCTTTGG |
| SEQ ID NO:787 | 1 | GACTGGAGTTCAGACGTGTGCTCTTCCGATCTCCTGGCCTTCTCCTTTACCCCTCC |
| SEQ ID NO:788 | 1 | GACTGGAGTTCAGACGTGTGCTCTTCCGATCTCCTGGGGTGACGGATGCC |
| SEQ ID NO:789 | 1 | GACTGGAGTTCAGACGTGTGCTCTTCCGATCTCCTGGTAGCTCATCATCTGGGACA |
| SEQ ID NO:790 | 1 | GACTGGAGTTCAGACGTGTGCTCTTCCGATCTCCTGGTAGGTTTTCTGGGAAGGGACA |
| SEQ ID NO:791 | 1 | GACTGGAGTTCAGACGTGTGCTCTTCCGATCTCCTGGTATGGTCATGGAAGGGG |
| SEQ ID NO:792 | 1 | GACTGGAGTTCAGACGTGTGCTCTTCCGATCTCCTGTGCTTCAACTAAATTTAACTGTCA |
| SEQ ID NO:793 | 1 | GACTGGAGTTCAGACGTGTGCTCTTCCGATCTCCTGTGGATTTTTAGGCCCTTGTATTTGT |
| SEQ ID NO:794 | 1 | GACTGGAGTTCAGACGTGTGCTCTTCCGATCTCCTGTGTGGTGATATCAAAGTAGAGT |
| SEQ ID NO:795 | 1 | GACTGGAGTTCAGACGTGTGCTCTTCCGATCTCCTTAGTCTTTCTTTGAAGCAGCAAGT |
| SEQ ID NO:796 | 1 | GACTGGAGTTCAGACGTGTGCTCTTCCGATCTCCTTATTACTTGGGAGACTTGTCTGAACA |
| SEQ ID NO:797 | 1 | GACTGGAGTTCAGACGTGTGCTCTTCCGATCTCCTTCCCTGCAAAGACAAATGGTGAGT |
| SEQ ID NO:798 | 1 | GACTGGAGTTCAGACGTGTGCTCTTCCGATCTCCTTCGCCTGTCCTCATGTATTGGTCT |
| SEQ ID NO:799 | 1 | GACTGGAGTTCAGACGTGTGCTCTTCCGATCTCCTTCTAGTAATTTGGGAATGCCTGGT |
| SEQ ID NO:800 | 1 | GACTGGAGTTCAGACGTGTGCTCTTCCGATCTCCTTGGGTATTTTTATGGGAGGCAGAA |
| SEQ ID NO:801 | 1 | GACTGGAGTTCAGACGTGTGCTCTTCCGATCTCCTTGGTGACCGCTCTGCATCTAGTG |

FIG. 7AA

| Target Specific Primer | Volume Ratio | Sequence |
|---|---|---|
| SEQ ID NO:802 | 1 | GACTGGAGTTCAGACGTGTGCTCTTCCGATCTCCTTTCCGAATGCCAAACACCTTCATG |
| SEQ ID NO:803 | 1 | GACTGGAGTTCAGACGTGTGCTCTTCCGATCTCCTTTCTGTAGGCTGGATGAAAATTC |
| SEQ ID NO:804 | 1 | GACTGGAGTTCAGACGTGTGCTCTTCCGATCTCCTTTCTGTAGGCTGGATGAAAATTC |
| SEQ ID NO:805 | 1 | GACTGGAGTTCAGACGTGTGCTCTTCCGATCTCCTTTCTTTGCAGGGGTGGCTATGTAG |
| SEQ ID NO:806 | 1 | GACTGGAGTTCAGACGTGTGCTCTTCCGATCTCCTTTGTCCCTCCCACCCCAAACTAG |
| SEQ ID NO:807 | 1 | GACTGGAGTTCAGACGTGTGCTCTTCCGATCTCGAAAGACCCTAGCCTTAGATAAAACT |
| SEQ ID NO:808 | 1 | GACTGGAGTTCAGACGTGTGCTCTTCCGATCTCGAAATGAAGCTACAACATCACCACGG |
| SEQ ID NO:809 | 1 | GACTGGAGTTCAGACGTGTGCTCTTCCGATCTCGAATGAGGGTGATGTTTTTCCGCGG |
| SEQ ID NO:810 | 1 | GACTGGAGTTCAGACGTGTGCTCTTCCGATCTCGAATGCAGTTTTTCCTCCTACTCACCA |
| SEQ ID NO:811 | 1 | GACTGGAGTTCAGACGTGTGCTCTTCCGATCTCGACTCGTGCTATTTTTCCTCACAGCT |
| SEQ ID NO:812 | 1 | GACTGGAGTTCAGACGTGTGCTCTTCCGATCTCGACTTTGTGACCTTCGGCTTTTTCAA |
| SEQ ID NO:813 | 1 | GACTGGAGTTCAGACGTGTGCTCTTCCGATCTCGAGGGGGGCGTCAGGAAC |
| SEQ ID NO:814 | 1 | GACTGGAGTTCAGACGTGTGCTCTTCCGATCTCGAGTGAGCTGCGAGACCTGC |
| SEQ ID NO:815 | 1 | GACTGGAGTTCAGACGTGTGCTCTTCCGATCTCGATCTGGGACTGCATGCTGGTG |
| SEQ ID NO:816 | 1 | GACTGGAGTTCAGACGTGTGCTCTTCCGATCTCGCAGGAAGTGGAAGGAGCTGTTG |
| SEQ ID NO:817 | 1 | GACTGGAGTTCAGACGTGTGCTCTTCCGATCTCGCAGTGCTAACCAAGTTCTTTC |
| SEQ ID NO:818 | 1 | GACTGGAGTTCAGACGTGTGCTCTTCCGATCTCGCAGTGCTAACCAAGTTCTTTCTTT |
| SEQ ID NO:819 | 1 | GACTGGAGTTCAGACGTGTGCTCTTCCGATCTCGCCCATGTCTTTGCAGCCGAG |
| SEQ ID NO:820 | 1 | GACTGGAGTTCAGACGTGTGCTCTTCCGATCTCGCCGGTAGTTGCCCTTC |

FIG. 7AB

| Target Specific Primer | Volume Ratio | Sequence |
|---|---|---|
| SEQ ID NO:821 | 1 | GACTGGAGTTCAGACGTGTGCTCTTCCGATCTCGCCGGTAGTTGCCCTTCTCG |
| SEQ ID NO:822 | 1 | GACTGGAGTTCAGACGTGTGCTCTTCCGATCTCGCTGGTTTGGGTGCTGTGTCC |
| SEQ ID NO:823 | 1 | GACTGGAGTTCAGACGTGTGCTCTTCCGATCTCGCTTCTTGTCCTGCTTGCTTACCTC |
| SEQ ID NO:824 | 1 | GACTGGAGTTCAGACGTGTGCTCTTCCGATCTCGGAAGCAACCCACAGATGTTCC |
| SEQ ID NO:825 | 1 | GACTGGAGTTCAGACGTGTGCTCTTCCGATCTCGGACATCAGCAAAGACCTGGAGAAG |
| SEQ ID NO:826 | 1 | GACTGGAGTTCAGACGTGTGCTCTTCCGATCTCGGCTGCTGGACATTGACGAGAC |
| SEQ ID NO:827 | 1 | GACTGGAGTTCAGACGTGTGCTCTTCCGATCTCGGGAGCGCGAGGAGGAGC |
| SEQ ID NO:828 | 1 | GACTGGAGTTCAGACGTGTGCTCTTCCGATCTCGGGATGGGGCCACACTTACTCTG |
| SEQ ID NO:829 | 1 | GACTGGAGTTCAGACGTGTGCTCTTCCGATCTCGGGCTCATCACCACGCTCCATTA |
| SEQ ID NO:830 | 1 | GACTGGAGTTCAGACGTGTGCTCTTCCGATCTCGGGCTTGGTTCTGATGTTTGTAGTGT |
| SEQ ID NO:831 | 1 | GACTGGAGTTCAGACGTGTGCTCTTCCGATCTCGGGTATGGCAGCAGGTATATCTCAGG |
| SEQ ID NO:832 | 1 | GACTGGAGTTCAGACGTGTGCTCTTCCGATCTCGGGTCTCTCGGAGGAAGGACTTGA |
| SEQ ID NO:833 | 1 | GACTGGAGTTCAGACGTGTGCTCTTCCGATCTCGTCAGCCTGAACATAACATCCTTGGG |
| SEQ ID NO:834 | 1 | GACTGGAGTTCAGACGTGTGCTCTTCCGATCTCGTCCACAAAATGATTCTGAATTAGCTGT |
| SEQ ID NO:835 | 1 | GACTGGAGTTCAGACGTGTGCTCTTCCGATCTCGTCCTCTCGTTTCCTTACATGCAGG |
| SEQ ID NO:836 | 1 | GACTGGAGTTCAGACGTGTGCTCTTCCGATCTCGTCGTGGAGAACAAGTTTGGCAGC |
| SEQ ID NO:837 | 1 | GACTGGAGTTCAGACGTGTGCTCTTCCGATCTCGTCTCCTCCGGCCCCTCG |
| SEQ ID NO:838 | 1 | GACTGGAGTTCAGACGTGTGCTCTTCCGATCTCGTCTCTGGATGGAACTGATGTCTGG |
| SEQ ID NO:839 | 1 | GACTGGAGTTCAGACGTGTGCTCTTCCGATCTCGTTCTTTTCCACGTGCTTGATCCACT |

FIG. 7AC

| Target Specific Primer | Volume Ratio | Sequence |
|---|---|---|
| SEQ ID NO:840 | 1 | GACTGGAGTTCAGACGTGTGCTCTTCCGATCTCTAAGTGCTGGGATTACTGGTGTGAGC |
| SEQ ID NO:841 | 1 | GACTGGAGTTCAGACGTGTGCTCTTCCGATCTCTACACTGCACCCCTCTCCTCCCAG |
| SEQ ID NO:842 | 1 | GACTGGAGTTCAGACGTGTGCTCTTCCGATCTCTAGACTTGGGTGAGGCAGGGGTG |
| SEQ ID NO:843 | 1 | GACTGGAGTTCAGACGTGTGCTCTTCCGATCTCTATGTGCTCAGTTCCCTCCTCTATGC |
| SEQ ID NO:844 | 1 | GACTGGAGTTCAGACGTGTGCTCTTCCGATCTCTCAAAAGCCTCCAGTCGCCTCAGTA |
| SEQ ID NO:845 | 1 | GACTGGAGTTCAGACGTGTGCTCTTCCGATCTCTCAACGCCCATGTCTTTGCAGCC |
| SEQ ID NO:846 | 1 | GACTGGAGTTCAGACGTGTGCTCTTCCGATCTCTCAACGCCCATGTCTTTGCAGCC |
| SEQ ID NO:847 | 1 | GACTGGAGTTCAGACGTGTGCTCTTCCGATCTCTCACACCACCCCCACCCACAG |
| SEQ ID NO:848 | 1 | GACTGGAGTTCAGACGTGTGCTCTTCCGATCTCTCACCGCAGTTCCATTCTCCCG |
| SEQ ID NO:849 | 1 | GACTGGAGTTCAGACGTGTGCTCTTCCGATCTCTCACCTCCACCGTGCAGCTC |
| SEQ ID NO:850 | 1 | GACTGGAGTTCAGACGTGTGCTCTTCCGATCTCTCACCTGGGGCCACATTTGAACATTG |
| SEQ ID NO:851 | 1 | GACTGGAGTTCAGACGTGTGCTCTTCCGATCTCTCACCTGTCTACGTTCCCTCACTGTA |
| SEQ ID NO:852 | 1 | GACTGGAGTTCAGACGTGTGCTCTTCCGATCTCTCAGATCTCGTCAGCCATGGAGTACC |
| SEQ ID NO:853 | 1 | GACTGGAGTTCAGACGTGTGCTCTTCCGATCTCTCAGGGGGCAGCATTGTTGGG |
| SEQ ID NO:854 | 1 | GACTGGAGTTCAGACGTGTGCTCTTCCGATCTCTCATCACCACGCTCCATTATCCAGC |
| SEQ ID NO:855 | 1 | GACTGGAGTTCAGACGTGTGCTCTTCCGATCTCTCATGCTCTACAACCCCACCACGTAC |
| SEQ ID NO:856 | 1 | GACTGGAGTTCAGACGTGTGCTCTTCCGATCTCTCCACTAACAACCCTCCTGCCATCAT |
| SEQ ID NO:857 | 1 | GACTGGAGTTCAGACGTGTGCTCTTCCGATCTCTCCACTTTTGCACAGCCAAGAACACT |
| SEQ ID NO:858 | 1 | GACTGGAGTTCAGACGTGTGCTCTTCCGATCTCTCCAGTCTCCCTCCTGTTTGCACA |

FIG. 7AD

| Target Specific Primer | Volume Ratio | Sequence |
|---|---|---|
| SEQ ID NO:859 | 1 | GACTGGAGTTCAGACGTGTGCTCTTCCGATCTCTCCCACCCCAAACTAGCCCTCAATC |
| SEQ ID NO:860 | 1 | GACTGGAGTTCAGACGTGTGCTCTTCCGATCTCTCCCAGGCCTAAAATATACCCAACCA |
| SEQ ID NO:861 | 1 | GACTGGAGTTCAGACGTGTGCTCTTCCGATCTCTCCCATACCCTCTCAGCGTACCCTTG |
| SEQ ID NO:862 | 1 | GACTGGAGTTCAGACGTGTGCTCTTCCGATCTCTCCCCGAGTGAGCTGCGAGAC |
| SEQ ID NO:863 | 1 | GACTGGAGTTCAGACGTGTGCTCTTCCGATCTCTCCTCCACCTCCTCCTCCATTGG |
| SEQ ID NO:864 | 1 | GACTGGAGTTCAGACGTGTGCTCTTCCGATCTCTCCTTCCATCCTTGCTCCTGTCCTTG |
| SEQ ID NO:865 | 1 | GACTGGAGTTCAGACGTGTGCTCTTCCGATCTCTCGGGTCCCTGCTCTGTCACTG |
| SEQ ID NO:866 | 1 | GACTGGAGTTCAGACGTGTGCTCTTCCGATCTCTCGTGTTGTCTCTCCTCCTGTCAGTG |
| SEQ ID NO:867 | 1 | GACTGGAGTTCAGACGTGTGCTCTTCCGATCTCTCTCTCCTCCCCACTGCTGCTG |
| SEQ ID NO:868 | 1 | GACTGGAGTTCAGACGTGTGCTCTTCCGATCTCTCTCTGTTTTAAGATCTGGGCAGTGA |
| SEQ ID NO:869 | 1 | GACTGGAGTTCAGACGTGTGCTCTTCCGATCTCTCTCTTAACCCCCTTCCCTAGCTGTG |
| SEQ ID NO:870 | 1 | GACTGGAGTTCAGACGTGTGCTCTTCCGATCTCTCTGCCTCAATAAGCCAACCATGTCT |
| SEQ ID NO:871 | 1 | GACTGGAGTTCAGACGTGTGCTCTTCCGATCTCTCTGGCTACTGGTGATGCTGTCC |
| SEQ ID NO:872 | 1 | GACTGGAGTTCAGACGTGTGCTCTTCCGATCTCTCTGGCTACTGGTGATGCTGTCCAAG |
| SEQ ID NO:873 | 1 | GACTGGAGTTCAGACGTGTGCTCTTCCGATCTCTCTTCTTCAGGGGGCCATGGTCTTC |
| SEQ ID NO:874 | 1 | GACTGGAGTTCAGACGTGTGCTCTTCCGATCTCTCTTGCTCCTTCCATCCTTGCTCCTG |
| SEQ ID NO:875 | 1 | GACTGGAGTTCAGACGTGTGCTCTTCCGATCTCTGAAAGCTGTACCATACCTGTCTG |
| SEQ ID NO:876 | 1 | GACTGGAGTTCAGACGTGTGCTCTTCCGATCTCTGAAAGTCCCTCTGCTGGTCTGGC |
| SEQ ID NO:877 | 1 | GACTGGAGTTCAGACGTGTGCTCTTCCGATCTCTGAAGATAATGACTCACCTGGGGCCA |

FIG. 7AE

| Target Specific Primer | Volume Ratio | Sequence |
|---|---|---|
| SEQ ID NO:878 | 1 | GACTGGAGTTCAGACGTGTGCTCTTCCGATCTCTGACAACCACCCTTAACCCCTCCTC |
| SEQ ID NO:879 | 1 | GACTGGAGTTCAGACGTGTGCTCTTCCGATCTCTGACGTGCCTCTCCCTCCCTC |
| SEQ ID NO:880 | 1 | GACTGGAGTTCAGACGTGTGCTCTTCCGATCTCTGAGCCTGCCGAGATTCCACAGTG |
| SEQ ID NO:881 | 1 | GACTGGAGTTCAGACGTGTGCTCTTCCGATCTCTGAGCGTCATCTGCCCCCAC |
| SEQ ID NO:882 | 1 | GACTGGAGTTCAGACGTGTGCTCTTCCGATCTCTGAGGTTCTGAGCCCCCTTCCG |
| SEQ ID NO:883 | 1 | GACTGGAGTTCAGACGTGTGCTCTTCCGATCTCTGAGTCCTGGCGCTGTGTCCTTTC |
| SEQ ID NO:884 | 1 | GACTGGAGTTCAGACGTGTGCTCTTCCGATCTCTGATGGCTGGTGTGGTTTGGTTTGTG |
| SEQ ID NO:885 | 1 | GACTGGAGTTCAGACGTGTGCTCTTCCGATCTCTGCAACCCCCACAGGCCC |
| SEQ ID NO:886 | 1 | GACTGGAGTTCAGACGTGTGCTCTTCCGATCTCTGCCCAGCCTCGACTCGGTTTC |
| SEQ ID NO:887 | 1 | GACTGGAGTTCAGACGTGTGCTCTTCCGATCTCTGCCCTAATCACCACCCCACCC |
| SEQ ID NO:888 | 1 | GACTGGAGTTCAGACGTGTGCTCTTCCGATCTCTGCGAGGGGGCGTCAG |
| SEQ ID NO:889 | 1 | GACTGGAGTTCAGACGTGTGCTCTTCCGATCTCTGCTGTACATGGCCACTCAGATCTCG |
| SEQ ID NO:890 | 1 | GACTGGAGTTCAGACGTGTGCTCTTCCGATCTCTGGAAAAATGGCTTTGAATCTTTGGC |
| SEQ ID NO:891 | 1 | GACTGGAGTTCAGACGTGTGCTCTTCCGATCTCTGGAGGATGTGCGGCTCGTA |
| SEQ ID NO:892 | 1 | GACTGGAGTTCAGACGTGTGCTCTTCCGATCTCTGGATGGAACTGATGTCTGGACGCTC |
| SEQ ID NO:893 | 1 | GACTGGAGTTCAGACGTGTGCTCTTCCGATCTCTGGATGGGGTGAGTTTGAGGGAGG |
| SEQ ID NO:894 | 1 | GACTGGAGTTCAGACGTGTGCTCTTCCGATCTCTGGATGGTCAGCGCACTC |
| SEQ ID NO:895 | 1 | GACTGGAGTTCAGACGTGTGCTCTTCCGATCTCTGGATGGTCAGCGCACTCTTG |
| SEQ ID NO:896 | 1 | GACTGGAGTTCAGACGTGTGCTCTTCCGATCTCTGGCCTTCTCCTTTACCCCTCCTTC |

FIG. 7AF

| Target Specific Primer | Volume Ratio | Sequence |
|---|---|---|
| SEQ ID NO:897 | 1 | GACTGGAGTTCAGACGTGTGCTCTTCCGATCTCTGGCTAGCTGTGGGGTGGAGAG |
| SEQ ID NO:898 | 1 | GACTGGAGTTCAGACGTGTGCTCTTCCGATCTCTGGCTGTGTCCTGGGCTCG |
| SEQ ID NO:899 | 1 | GACTGGAGTTCAGACGTGTGCTCTTCCGATCTCTGGGGCTCGGGTTGGCTCTAAAG |
| SEQ ID NO:900 | 1 | GACTGGAGTTCAGACGTGTGCTCTTCCGATCTCTGGGTAGCAAACTTCTGTACACA |
| SEQ ID NO:901 | 1 | GACTGGAGTTCAGACGTGTGCTCTTCCGATCTCTGGGTAGCAAACTTCTGTACACAACT |
| SEQ ID NO:902 | 1 | GACTGGAGTTCAGACGTGTGCTCTTCCGATCTCTGGGTGCTGATACTTCTCTCCATCCT |
| SEQ ID NO:903 | 1 | GACTGGAGTTCAGACGTGTGCTCTTCCGATCTCTGGTGTGGTTTGGTTTGTGGTCCTC |
| SEQ ID NO:904 | 1 | GACTGGAGTTCAGACGTGTGCTCTTCCGATCTCTGTATCAGTCTGTCCAGCACTTCCAT |
| SEQ ID NO:905 | 1 | GACTGGAGTTCAGACGTGTGCTCTTCCGATCTCTGTCATGTAGCAGCTTTCAGGGGC |
| SEQ ID NO:906 | 1 | GACTGGAGTTCAGACGTGTGCTCTTCCGATCTCTGTCCTCTTCTCCTTCATCGTCTCGG |
| SEQ ID NO:907 | 1 | GACTGGAGTTCAGACGTGTGCTCTTCCGATCTCTGTGATAGGAAGCTGTGGAGTGATG |
| SEQ ID NO:908 | 1 | GACTGGAGTTCAGACGTGTGCTCTTCCGATCTCTGTGCTGCGAGGGGGGC |
| SEQ ID NO:909 | 1 | GACTGGAGTTCAGACGTGTGCTCTTCCGATCTCTGTGTCCCTGTCCTGCCCCC |
| SEQ ID NO:910 | 1 | GACTGGAGTTCAGACGTGTGCTCTTCCGATCTCTGTGTGCTCAGGGGCCT |
| SEQ ID NO:911 | 1 | GACTGGAGTTCAGACGTGTGCTCTTCCGATCTCTGTGTGTTGATCAGGCGCCCAG |
| SEQ ID NO:912 | 1 | GACTGGAGTTCAGACGTGTGCTCTTCCGATCTCTTACTCATTGGGTGGCCGGGC |
| SEQ ID NO:913 | 1 | GACTGGAGTTCAGACGTGTGCTCTTCCGATCTCTTCACGCTCCTTCCCTATCCCTTCTG |
| SEQ ID NO:914 | 1 | GACTGGAGTTCAGACGTGTGCTCTTCCGATCTCTTCCCAGTGTGATTGCAGGTTCCAC |
| SEQ ID NO:915 | 1 | GACTGGAGTTCAGACGTGTGCTCTTCCGATCTCTTCCCCACCAGCTTTCCTAATTG |

FIG. 7AG

| Target Specific Primer | Volume Ratio | Sequence |
|---|---|---|
| SEQ ID NO:916 | 1 | GACTGGAGTTCAGACGTGTGCTCTTCCGATCTCTTCCCTCCCCTCGAAATGAAGCTACA |
| SEQ ID NO:917 | 1 | GACTGGAGTTCAGACGTGTGCTCTTCCGATCTCTTCTCCAGGACCACGGACTGCAC |
| SEQ ID NO:918 | 1 | GACTGGAGTTCAGACGTGTGCTCTTCCGATCTCTTCTGTCAAAGTGGGGGTTCGGAGA |
| SEQ ID NO:919 | 1 | GACTGGAGTTCAGACGTGTGCTCTTCCGATCTCTTCTTCATCGCGGGCTTGGTTCTG |
| SEQ ID NO:920 | 1 | GACTGGAGTTCAGACGTGTGCTCTTCCGATCTCTTCTTGTCCTGCTTGCTTACCTCGCT |
| SEQ ID NO:921 | 1 | GACTGGAGTTCAGACGTGTGCTCTTCCGATCTCTTGAATGACCCTGTTAATCCGTTCGT |
| SEQ ID NO:922 | 1 | GACTGGAGTTCAGACGTGTGCTCTTCCGATCTCTTGAGGTCTCCCCCCGCCATG |
| SEQ ID NO:923 | 1 | GACTGGAGTTCAGACGTGTGCTCTTCCGATCTCTTGCAGTCGTCAGCCTGAACATAACA |
| SEQ ID NO:924 | 1 | GACTGGAGTTCAGACGTGTGCTCTTCCGATCTCTTGTGTGGTGACTGGCATCTGGTAGG |
| SEQ ID NO:925 | 1 | GACTGGAGTTCAGACGTGTGCTCTTCCGATCTCTTTATTTGTCCCCTTGCCTCCCTTTC |
| SEQ ID NO:926 | 1 | GACTGGAGTTCAGACGTGTGCTCTTCCGATCTCTTTCCCTCTGCCCTTTTCAAGCCTCT |
| SEQ ID NO:927 | 1 | GACTGGAGTTCAGACGTGTGCTCTTCCGATCTCTTTGTGACCTTCGGCTTTTTCAACCC |
| SEQ ID NO:928 | 1 | GACTGGAGTTCAGACGTGTGCTCTTCCGATCTCTTTTCCTCCTCTTCTCCTGGCCTGAG |
| SEQ ID NO:929 | 1 | GACTGGAGTTCAGACGTGTGCTCTTCCGATCTCTTTTCTCAATGATGCTTGGCTCTGGA |
| SEQ ID NO:930 | 1 | GACTGGAGTTCAGACGTGTGCTCTTCCGATCTGAAAATACATAGAGTTTTAATGCATTGTCTCA |
| SEQ ID NO:931 | 1 | GACTGGAGTTCAGACGTGTGCTCTTCCGATCTGAAAGATCACATCACATGAATGGAATAGT |
| SEQ ID NO:932 | 1 | GACTGGAGTTCAGACGTGTGCTCTTCCGATCTGAAAGCCTCACCTGTCTACGTTCCCTC |
| SEQ ID NO:933 | 1 | GACTGGAGTTCAGACGTGTGCTCTTCCGATCTGAAATGGATGTTCAGGTAGGAGAGACA |
| SEQ ID NO:934 | 1 | GACTGGAGTTCAGACGTGTGCTCTTCCGATCTGAACCTGGAAGCTGTCTCCACCCA |

FIG. 7AH

| Target Specific Primer | Volume Ratio | Sequence |
|---|---|---|
| SEQ ID NO:935 | 1 | GACTGGAGTTCAGACGTGTGCTCTTCCGATCTGAACGCCTCCCCGAGTGAGCTG |
| SEQ ID NO:936 | 1 | GACTGGAGTTCAGACGTGTGCTCTTCCGATCTGAACGTGCTGGTCAAGAGTCCCAAC |
| SEQ ID NO:937 | 1 | GACTGGAGTTCAGACGTGTGCTCTTCCGATCTGAACGTGCTGGTCAAGAGTCCCAAC |
| SEQ ID NO:938 | 1 | GACTGGAGTTCAGACGTGTGCTCTTCCGATCTGAAGATCCCCTGCCCTCCCCAG |
| SEQ ID NO:939 | 1 | GACTGGAGTTCAGACGTGTGCTCTTCCGATCTGAAGGGACAGAAGATGACAGGGGCC |
| SEQ ID NO:940 | 1 | GACTGGAGTTCAGACGTGTGCTCTTCCGATCTGAAGGTGAAGGTGCTTGGATCTGGC |
| SEQ ID NO:941 | 1 | GACTGGAGTTCAGACGTGTGCTCTTCCGATCTGAAGTCCTCGTTGTCTTGTTGGCAGGG |
| SEQ ID NO:942 | 1 | GACTGGAGTTCAGACGTGTGCTCTTCCGATCTGAAGTCCTCGTTGTCTTGTTGGCAGGG |
| SEQ ID NO:943 | 1 | GACTGGAGTTCAGACGTGTGCTCTTCCGATCTGAAGTGCCCTTGGTTCGGACAGAC |
| SEQ ID NO:944 | 1 | GACTGGAGTTCAGACGTGTGCTCTTCCGATCTGAATGCGGGCGATCTGGGACTG |
| SEQ ID NO:945 | 1 | GACTGGAGTTCAGACGTGTGCTCTTCCGATCTGAATTTTCTGAACTATTTATGGACAACAGTC |
| SEQ ID NO:946 | 1 | GACTGGAGTTCAGACGTGTGCTCTTCCGATCTGACAAACTCTACGTCTCCTCCGACCAC |
| SEQ ID NO:947 | 1 | GACTGGAGTTCAGACGTGTGCTCTTCCGATCTGACAAGAGGATGGCTAGGCGAGGAG |
| SEQ ID NO:948 | 1 | GACTGGAGTTCAGACGTGTGCTCTTCCGATCTGACAAGCAGCCACACCCCATTCTT |
| SEQ ID NO:949 | 1 | GACTGGAGTTCAGACGTGTGCTCTTCCGATCTGACACTCTAGTATCTGGAAAAATGGCT |
| SEQ ID NO:950 | 1 | GACTGGAGTTCAGACGTGTGCTCTTCCGATCTGACAGAAGATGACAGGGGCCAGGAG |
| SEQ ID NO:951 | 1 | GACTGGAGTTCAGACGTGTGCTCTTCCGATCTGACAGTAACTTGGGCTTTCTGACGGGA |
| SEQ ID NO:952 | 1 | GACTGGAGTTCAGACGTGTGCTCTTCCGATCTGACATCTGGAGCATGGGACTGTCTCTG |
| SEQ ID NO:953 | 1 | GACTGGAGTTCAGACGTGTGCTCTTCCGATCTGACCCACTCTGTCTCCGCA |

FIG. 7AI

| Target Specific Primer | Volume Ratio | Sequence |
| --- | --- | --- |
| SEQ ID NO:954 | 1 | GACTGGAGTTCAGACGTGTGCTCTTCCGATCTGACCCTAGCCTTAGATAAAACTGAGCA |
| SEQ ID NO:955 | 1 | GACTGGAGTTCAGACGTGTGCTCTTCCGATCTGACGAGGCGGGCAGTGTGTATG |
| SEQ ID NO:956 | 1 | GACTGGAGTTCAGACGTGTGCTCTTCCGATCTGACTCTGTCCTGCGTCATCATCTTTGT |
| SEQ ID NO:957 | 1 | GACTGGAGTTCAGACGTGTGCTCTTCCGATCTGACTGTGATGAGGTGCCGTTCCCAT |
| SEQ ID NO:958 | 1 | GACTGGAGTTCAGACGTGTGCTCTTCCGATCTGACTTCCCTTTCCGAATGCCAAACACC |
| SEQ ID NO:959 | 1 | GACTGGAGTTCAGACGTGTGCTCTTCCGATCTGAGACCACCACCCTAACCCCAGTCAG |
| SEQ ID NO:960 | 1 | GACTGGAGTTCAGACGTGTGCTCTTCCGATCTGAGCCAAGGGTGTGAGTGAACGGTG |
| SEQ ID NO:961 | 1 | GACTGGAGTTCAGACGTGTGCTCTTCCGATCTGAGCCACGATGCCCAGTCAATCTTG |
| SEQ ID NO:962 | 1 | GACTGGAGTTCAGACGTGTGCTCTTCCGATCTGAGCTGCCATCTCACCAAACTGCA |
| SEQ ID NO:963 | 1 | GACTGGAGTTCAGACGTGTGCTCTTCCGATCTGAGGATGGCAGCGACGTGGG |
| SEQ ID NO:964 | 1 | GACTGGAGTTCAGACGTGTGCTCTTCCGATCTGAGGCAGGGCTGTGTCCACC |
| SEQ ID NO:965 | 1 | GACTGGAGTTCAGACGTGTGCTCTTCCGATCTGAGGCTGGGTGGAGTGGTGTCTAG |
| SEQ ID NO:966 | 1 | GACTGGAGTTCAGACGTGTGCTCTTCCGATCTGAGGGCCCAGGAGAGTTGCGG |
| SEQ ID NO:967 | 1 | GACTGGAGTTCAGACGTGTGCTCTTCCGATCTGAGGGAAAAATATGACAAAGAAAGCTAT |
| SEQ ID NO:968 | 1 | GACTGGAGTTCAGACGTGTGCTCTTCCGATCTGAGGGGAGTCTGGGAATGAACACTAA |
| SEQ ID NO:969 | 1 | GACTGGAGTTCAGACGTGTGCTCTTCCGATCTGAGGTCTCGATGTAGGGGATGCCG |
| SEQ ID NO:970 | 1 | GACTGGAGTTCAGACGTGTGCTCTTCCGATCTGAGGTCTCGATGTAGGGGATGCCGTAG |
| SEQ ID NO:971 | 1 | GACTGGAGTTCAGACGTGTGCTCTTCCGATCTGAGTACAGAGTGACCGCCTCAAGTGAC |
| SEQ ID NO:972 | 1 | GACTGGAGTTCAGACGTGTGCTCTTCCGATCTGAGTGGGTTTATATTAAAAAGTTGGTCTACT |

FIG. 7AJ

| Target Specific Primer | Volume Ratio | Sequence |
|---|---|---|
| SEQ ID NO:973 | 1 | GACTGGAGTTCAGACGTGTGCTCTTCCGATCTGAGTTCCTCAAAAGAGAAATCACGCAT |
| SEQ ID NO:974 | 1 | GACTGGAGTTCAGACGTGTGCTCTTCCGATCTGAGTTTACCAAATGTACTCAAGGCATAA |
| SEQ ID NO:975 | 1 | GACTGGAGTTCAGACGTGTGCTCTTCCGATCTGATCATGTCTCGGCTCAAGGACCCAAA |
| SEQ ID NO:976 | 1 | GACTGGAGTTCAGACGTGTGCTCTTCCGATCTGATCCACTTCCTTGCCCTGCTCAG |
| SEQ ID NO:977 | 1 | GACTGGAGTTCAGACGTGTGCTCTTCCGATCTGATCTCCTTGGTGACCGCTCTGCAT |
| SEQ ID NO:978 | 1 | GACTGGAGTTCAGACGTGTGCTCTTCCGATCTGATCTTGTAGGGGATGTTGAGGCTGCC |
| SEQ ID NO:979 | 1 | GACTGGAGTTCAGACGTGTGCTCTTCCGATCTGATCTTTGTTCCTTCCATTCTTATAGAGC |
| SEQ ID NO:980 | 1 | GACTGGAGTTCAGACGTGTGCTCTTCCGATCTGATGGCCAACTCCCCTTCACACCTG |
| SEQ ID NO:981 | 1 | GACTGGAGTTCAGACGTGTGCTCTTCCGATCTGATGGGGCCACACTTACTCTGCAC |
| SEQ ID NO:982 | 1 | GACTGGAGTTCAGACGTGTGCTCTTCCGATCTGATGTTTTCCGCGGCACCTCCTTC |
| SEQ ID NO:983 | 1 | GACTGGAGTTCAGACGTGTGCTCTTCCGATCTGATTTACCTTTCCTCTGTGTTGGC |
| SEQ ID NO:984 | 1 | GACTGGAGTTCAGACGTGTGCTCTTCCGATCTGATTTACCTTTCCTCTGTGTTGGCGGA |
| SEQ ID NO:985 | 1 | GACTGGAGTTCAGACGTGTGCTCTTCCGATCTGCAAAACAGCACAGTGAAAGCCAGC |
| SEQ ID NO:986 | 1 | GACTGGAGTTCAGACGTGTGCTCTTCCGATCTGCAAACAAACCTGGCTAAACGTCGGT |
| SEQ ID NO:987 | 1 | GACTGGAGTTCAGACGTGTGCTCTTCCGATCTGCAAACACAGGGCCAAAGACTAAGTGA |
| SEQ ID NO:988 | 1 | GACTGGAGTTCAGACGTGTGCTCTTCCGATCTGCAAAGAATCAGAACAATGCCTCCACG |
| SEQ ID NO:989 | 1 | GACTGGAGTTCAGACGTGTGCTCTTCCGATCTGCAAAGACAAATGGTGAGTACGTGCAT |
| SEQ ID NO:990 | 1 | GACTGGAGTTCAGACGTGTGCTCTTCCGATCTGCAAAGACAAATGGTGAGTACGTGCAT |
| SEQ ID NO:991 | 1 | GACTGGAGTTCAGACGTGTGCTCTTCCGATCTGCAAATACACAAAGAAAGCCCTCCCCA |

FIG. 7AK

| Target Specific Primer | Volume Ratio | Sequence |
|---|---|---|
| SEQ ID NO:992 | 1 | GACTGGAGTTCAGACGTGTGCTCTTCCGATCTGCAACACCCAGCCCTCGGT |
| SEQ ID NO:993 | 1 | GACTGGAGTTCAGACGTGTGCTCTTCCGATCTGCAACACCCAGCCCTCGGTAAG |
| SEQ ID NO:994 | 1 | GACTGGAGTTCAGACGTGTGCTCTTCCGATCTGCAACATCAGAGCTGGATCTAGAAATGG |
| SEQ ID NO:995 | 1 | GACTGGAGTTCAGACGTGTGCTCTTCCGATCTGCAAGAAAATACCCCCTCCATCAACTTCT |
| SEQ ID NO:996 | 1 | GACTGGAGTTCAGACGTGTGCTCTTCCGATCTGCACACAGATACAGATGTTTTGGAAGCA |
| SEQ ID NO:997 | 1 | GACTGGAGTTCAGACGTGTGCTCTTCCGATCTGCACAGCTTTTCCTCCATGAGTACGTA |
| SEQ ID NO:998 | 1 | GACTGGAGTTCAGACGTGTGCTCTTCCGATCTGCACAGCTTTTCCTCCATGAGTACGTATTT |
| SEQ ID NO:999 | 1 | GACTGGAGTTCAGACGTGTGCTCTTCCGATCTGCACTCTGACATATGGCCATTTCTGTTTT |
| SEQ ID NO:1000 | 1 | GACTGGAGTTCAGACGTGTGCTCTTCCGATCTGCAGAAAGACTTGAAGGCGTATACAGGAAC |
| SEQ ID NO:1001 | 1 | GACTGGAGTTCAGACGTGTGCTCTTCCGATCTGCAGAGCTAGCTACTACTGGATTTTT |
| SEQ ID NO:1002 | 1 | GACTGGAGTTCAGACGTGTGCTCTTCCGATCTGCAGAGCTAGCTACTACTGGATTTTTGCA |
| SEQ ID NO:1003 | 1 | GACTGGAGTTCAGACGTGTGCTCTTCCGATCTGCAGCATCTCAGGGCCAAAAATTTAAT |
| SEQ ID NO:1004 | 1 | GACTGGAGTTCAGACGTGTGCTCTTCCGATCTGCAGCATCTCAGGGCCAAAAATTTAATCAG |
| SEQ ID NO:1005 | 1 | GACTGGAGTTCAGACGTGTGCTCTTCCGATCTGCAGCCAGAAATATCCTCCTTACTCATGG |
| SEQ ID NO:1006 | 1 | GACTGGAGTTCAGACGTGTGCTCTTCCGATCTGCAGCCTACAGAGTCCGCAAGC |
| SEQ ID NO:1007 | 1 | GACTGGAGTTCAGACGTGTGCTCTTCCGATCTGCAGGTACCGTGCGACATC |
| SEQ ID NO:1008 | 1 | GACTGGAGTTCAGACGTGTGCTCTTCCGATCTGCAGTCGTCAGCCTGAACATAACATCC |
| SEQ ID NO:1009 | 1 | GACTGGAGTTCAGACGTGTGCTCTTCCGATCTGCATAATTGAGAGAAAAACTGATATATTAAATGACA |
| SEQ ID NO:1010 | 1 | GACTGGAGTTCAGACGTGTGCTCTTCCGATCTGCATAGTAAGCAGTAGGGAGTAACAAAA |

FIG. 7AL

| Target Specific Primer | Volume Ratio | Sequence |
|---|---|---|
| SEQ ID NO:1011 | 1 | GACTGGAGTTCAGACGTGTGCTCTTCCGATCTGCATGGTGAGGGCTGAGGT |
| SEQ ID NO:1012 | 1 | GACTGGAGTTCAGACGTGTGCTCTTCCGATCTGCATGGTGAGGGCTGAGGTGAC |
| SEQ ID NO:1013 | 1 | GACTGGAGTTCAGACGTGTGCTCTTCCGATCTGCATGGTGAGGGCTGAGGTGAC |
| SEQ ID NO:1014 | 1 | GACTGGAGTTCAGACGTGTGCTCTTCCGATCTGCATGTAACTTCCTGTAATTTTTCAAGGC |
| SEQ ID NO:1015 | 1 | GACTGGAGTTCAGACGTGTGCTCTTCCGATCTGCATGTATGTTGGCCTCCTTTGCTGC |
| SEQ ID NO:1016 | 1 | GACTGGAGTTCAGACGTGTGCTCTTCCGATCTGCATGTGGGAGCTAGAAGTGACGT |
| SEQ ID NO:1017 | 1 | GACTGGAGTTCAGACGTGTGCTCTTCCGATCTGCATGTGGGAGCTAGAAGTGACGTCTA |
| SEQ ID NO:1018 | 1 | GACTGGAGTTCAGACGTGTGCTCTTCCGATCTGCCAAGCCTCACACCACCCC |
| SEQ ID NO:1019 | 1 | GACTGGAGTTCAGACGTGTGCTCTTCCGATCTGCCACACACCACCCCTCTGC |
| SEQ ID NO:1020 | 1 | GACTGGAGTTCAGACGTGTGCTCTTCCGATCTGCCACACATGCCATCATTCTAGGAAGC |
| SEQ ID NO:1021 | 1 | GACTGGAGTTCAGACGTGTGCTCTTCCGATCTGCCACCCTGCCATGCTACCTAGATAC |
| SEQ ID NO:1022 | 1 | GACTGGAGTTCAGACGTGTGCTCTTCCGATCTGCCACGGGTAATAATTTTTGTCCTTTC |
| SEQ ID NO:1023 | 1 | GACTGGAGTTCAGACGTGTGCTCTTCCGATCTGCCACGGGTAATAATTTTTGTCCTTTCT |
| SEQ ID NO:1024 | 1 | GACTGGAGTTCAGACGTGTGCTCTTCCGATCTGCCACGGGTAATAATTTTTGTCCTTTCTGT |
| SEQ ID NO:1025 | 1 | GACTGGAGTTCAGACGTGTGCTCTTCCGATCTGCCACTGACAACCACCCTTAACCC |
| SEQ ID NO:1026 | 1 | GACTGGAGTTCAGACGTGTGCTCTTCCGATCTGCCACTGCCGCTTCCCCAC |
| SEQ ID NO:1027 | 1 | GACTGGAGTTCAGACGTGTGCTCTTCCGATCTGCCACTTCTTACCTTCACAGCCACTTG |
| SEQ ID NO:1028 | 1 | GACTGGAGTTCAGACGTGTGCTCTTCCGATCTGCCAGAAATATCCTCCTTACTCATGGTCG |
| SEQ ID NO:1029 | 1 | GACTGGAGTTCAGACGTGTGCTCTTCCGATCTGCCAGACCCAGCCAGTATTATTTCATT |

FIG. 7AM

| Target Specific Primer | Volume Ratio | Sequence |
|---|---|---|
| SEQ ID NO:1030 | 1 | GACTGGAGTTCAGACGTGTGCTCTTCCGATCTGCCAGACCTAAGAGCAATCAGTGAGGA |
| SEQ ID NO:1031 | 1 | GACTGGAGTTCAGACGTGTGCTCTTCCGATCTGCCAGATCCAGTGAAAAACAAGCTCTCAT |
| SEQ ID NO:1032 | 1 | GACTGGAGTTCAGACGTGTGCTCTTCCGATCTGCCAGTACCTTCCTCTTCTTCTACATCAC |
| SEQ ID NO:1033 | 1 | GACTGGAGTTCAGACGTGTGCTCTTCCGATCTGCCAGTTAACGTCTTCCTTCTCTCTGT |
| SEQ ID NO:1034 | 1 | GACTGGAGTTCAGACGTGTGCTCTTCCGATCTGCCAGTTAACGTCTTCCTTCTCTCTGT |
| SEQ ID NO:1035 | 1 | GACTGGAGTTCAGACGTGTGCTCTTCCGATCTGCCATCTTATTCCAGACGCATTTCCACA |
| SEQ ID NO:1036 | 1 | GACTGGAGTTCAGACGTGTGCTCTTCCGATCTGCCCACCAAGCAGCCCATCC |
| SEQ ID NO:1037 | 1 | GACTGGAGTTCAGACGTGTGCTCTTCCGATCTGCCCACGCTCTTCTCACTCATATCC |
| SEQ ID NO:1038 | 1 | GACTGGAGTTCAGACGTGTGCTCTTCCGATCTGCCCACTCTTGCTCCTTCCATCCTTG |
| SEQ ID NO:1039 | 1 | GACTGGAGTTCAGACGTGTGCTCTTCCGATCTGCCCATGATAGCCGTCTTTAACAAGC |
| SEQ ID NO:1040 | 1 | GACTGGAGTTCAGACGTGTGCTCTTCCGATCTGCCCATGATAGCCGTCTTTAACAAGC |
| SEQ ID NO:1041 | 1 | GACTGGAGTTCAGACGTGTGCTCTTCCGATCTGCCCCAGAACTAACAGGTTAAGTGCTC |
| SEQ ID NO:1042 | 1 | GACTGGAGTTCAGACGTGTGCTCTTCCGATCTGCCCCGTTCCATCATAGCATGCAA |
| SEQ ID NO:1043 | 1 | GACTGGAGTTCAGACGTGTGCTCTTCCGATCTGCCCGAAGTGTAAGCCCAACTACAGAA |
| SEQ ID NO:1044 | 1 | GACTGGAGTTCAGACGTGTGCTCTTCCGATCTGCCCTAATCACCACCCCACCCAAT |
| SEQ ID NO:1045 | 1 | GACTGGAGTTCAGACGTGTGCTCTTCCGATCTGCCCTGCAGTGAATTTTGAAGATTGC |
| SEQ ID NO:1046 | 1 | GACTGGAGTTCAGACGTGTGCTCTTCCGATCTGCCGCCGCTGAGCCACTG |
| SEQ ID NO:1047 | 1 | GACTGGAGTTCAGACGTGTGCTCTTCCGATCTGCCGGTAGTTGCCCTTCTCGAAC |
| SEQ ID NO:1048 | 1 | GACTGGAGTTCAGACGTGTGCTCTTCCGATCTGCCGTCTTTAACAAGCTCTTTCTTTCT |

FIG. 7AN

| Target Specific Primer | Volume Ratio | Sequence |
|---|---|---|
| SEQ ID NO:1049 | 1 | GACTGGAGTTCAGACGTGTGCTCTTCCGATCTGCCTCAAAGAAAAGCTGCGTGATGATG |
| SEQ ID NO:1050 | 1 | GACTGGAGTTCAGACGTGTGCTCTTCCGATCTGCCTCAACGCCCATGTCTTTGCA |
| SEQ ID NO:1051 | 1 | GACTGGAGTTCAGACGTGTGCTCTTCCGATCTGCCTCAACGCCCATGTCTTTGCA |
| SEQ ID NO:1052 | 1 | GACTGGAGTTCAGACGTGTGCTCTTCCGATCTGCCTCAGTAAAGCCACCTCACGAACT |
| SEQ ID NO:1053 | 1 | GACTGGAGTTCAGACGTGTGCTCTTCCGATCTGCCTCCACTTTTGCACAGCCAAGAAC |
| SEQ ID NO:1054 | 1 | GACTGGAGTTCAGACGTGTGCTCTTCCGATCTGCCTCCCAAAATGTTAGGATTACAGGTGTG |
| SEQ ID NO:1055 | 1 | GACTGGAGTTCAGACGTGTGCTCTTCCGATCTGCCTCTTACCTGGAATTTGGATGTGATTGG |
| SEQ ID NO:1056 | 1 | GACTGGAGTTCAGACGTGTGCTCTTCCGATCTGCCTGCCTCCACTTCAACCACAG |
| SEQ ID NO:1057 | 1 | GACTGGAGTTCAGACGTGTGCTCTTCCGATCTGCCTGGGGAGCTGGGGACTC |
| SEQ ID NO:1058 | 1 | GACTGGAGTTCAGACGTGTGCTCTTCCGATCTGCCTTCGCCTGTCCTCATGTATTGG |
| SEQ ID NO:1059 | 1 | GACTGGAGTTCAGACGTGTGCTCTTCCGATCTGCCTTCTCCTTTACCCCTCCTTCCTAG |
| SEQ ID NO:1060 | 1 | GACTGGAGTTCAGACGTGTGCTCTTCCGATCTGCCTTGGTGTGCATTCTTCTCTCTT |
| SEQ ID NO:1061 | 1 | GACTGGAGTTCAGACGTGTGCTCTTCCGATCTGCCTTTCTTCCCTCCCCTCGAAATGAA |
| SEQ ID NO:1062 | 1 | GACTGGAGTTCAGACGTGTGCTCTTCCGATCTGCGACAGATCCGGAATATTGTAGAGAAGC |
| SEQ ID NO:1063 | 1 | GACTGGAGTTCAGACGTGTGCTCTTCCGATCTGCGACATGTCTTTCCCCACAATCATACT |
| SEQ ID NO:1064 | 1 | GACTGGAGTTCAGACGTGTGCTCTTCCGATCTGCGATGGCCCAGCTCCTCAG |
| SEQ ID NO:1065 | 1 | GACTGGAGTTCAGACGTGTGCTCTTCCGATCTGCGCATCTCCCTCAGGTAGTTCAGG |
| SEQ ID NO:1066 | 1 | GACTGGAGTTCAGACGTGTGCTCTTCCGATCTGCGCTACTAGAAACATGATAGAGGTGACA |
| SEQ ID NO:1067 | 1 | GACTGGAGTTCAGACGTGTGCTCTTCCGATCTGCGGAAGAATGTGTCAGCCTCAAA |

FIG. 7AO

| Target Specific Primer | Volume Ratio | Sequence |
|---|---|---|
| SEQ ID NO:1068 | 1 | GACTGGAGTTCAGACGTGTGCTCTTCCGATCTGCGGGTCTCTCGGAGGAAGGAC |
| SEQ ID NO:1069 | 1 | GACTGGAGTTCAGACGTGTGCTCTTCCGATCTGCGTCGTGGAGAACAAGTTTGGC |
| SEQ ID NO:1070 | 1 | GACTGGAGTTCAGACGTGTGCTCTTCCGATCTGCGTGGTAGGGCATTTAAGTATTGGTT |
| SEQ ID NO:1071 | 1 | GACTGGAGTTCAGACGTGTGCTCTTCCGATCTGCGTGGTAGGGCATTTAAGTATTGGTTGAT |
| SEQ ID NO:1072 | 1 | GACTGGAGTTCAGACGTGTGCTCTTCCGATCTGCTAACCAAGTTCTTTCTTTTGCACAGGG |
| SEQ ID NO:1073 | 1 | GACTGGAGTTCAGACGTGTGCTCTTCCGATCTGCTCAGATGACAGCCGGTTCTCT |
| SEQ ID NO:1074 | 1 | GACTGGAGTTCAGACGTGTGCTCTTCCGATCTGCTCCCAGGCTGTTTATTTGAAGAGAC |
| SEQ ID NO:1075 | 1 | GACTGGAGTTCAGACGTGTGCTCTTCCGATCTGCTCCTTCCATCCTTGCTCCTGTCC |
| SEQ ID NO:1076 | 1 | GACTGGAGTTCAGACGTGTGCTCTTCCGATCTGCTCCTTCCCTATCCCTTCTGCTCTC |
| SEQ ID NO:1077 | 1 | GACTGGAGTTCAGACGTGTGCTCTTCCGATCTGCTCTTCCTGTTTCAGTCCCCATTAAA |
| SEQ ID NO:1078 | 1 | GACTGGAGTTCAGACGTGTGCTCTTCCGATCTGCTGACACCACGATACTTGACAATGAAAT |
| SEQ ID NO:1079 | 1 | GACTGGAGTTCAGACGTGTGCTCTTCCGATCTGCTGAGGAAGGTGAAGGTGCTTGGA |
| SEQ ID NO:1080 | 1 | GACTGGAGTTCAGACGTGTGCTCTTCCGATCTGCTGCTGGAATTGGTGTTGATGACC |
| SEQ ID NO:1081 | 1 | GACTGGAGTTCAGACGTGTGCTCTTCCGATCTGCTGGCTGATCTATGTCCCTGAAGCAG |
| SEQ ID NO:1082 | 1 | GACTGGAGTTCAGACGTGTGCTCTTCCGATCTGCTGGGCATCACTGTAAACCTTGCA |
| SEQ ID NO:1083 | 1 | GACTGGAGTTCAGACGTGTGCTCTTCCGATCTGCTGGTTTGGGAAGAGTGGGCTA |
| SEQ ID NO:1084 | 1 | GACTGGAGTTCAGACGTGTGCTCTTCCGATCTGCTGTCCTCTTCTCCTTCATCGTCT |
| SEQ ID NO:1085 | 1 | GACTGGAGTTCAGACGTGTGCTCTTCCGATCTGCTGTGGAGTGATGAGCTGCCAT |
| SEQ ID NO:1086 | 1 | GACTGGAGTTCAGACGTGTGCTCTTCCGATCTGCTGTGTCCACCCCCTTACTCATTGG |

FIG. 7AP

| Target Specific Primer | Volume Ratio | Sequence |
|---|---|---|
| SEQ ID NO:1087 | 1 | GACTGGAGTTCAGACGTGTGCTCTTCCGATCTGCTTGACATCAGTTTGCCAGTTGTGCT |
| SEQ ID NO:1088 | 1 | GACTGGAGTTCAGACGTGTGCTCTTCCGATCTGCTTGACATCAGTTTGCCAGTTGTGCT |
| SEQ ID NO:1089 | 1 | GACTGGAGTTCAGACGTGTGCTCTTCCGATCTGCTTGTAAGTGCCCGAAGTGTAAGC |
| SEQ ID NO:1090 | 1 | GACTGGAGTTCAGACGTGTGCTCTTCCGATCTGCTTTTCCTCCATGAGTACGTATTTTGA |
| SEQ ID NO:1091 | 1 | GACTGGAGTTCAGACGTGTGCTCTTCCGATCTGGAAAAACTGTGTTGTGGAGTGCAAGT |
| SEQ ID NO:1092 | 1 | GACTGGAGTTCAGACGTGTGCTCTTCCGATCTGGAAAACACATCCCCCAAAGCCAACAA |
| SEQ ID NO:1093 | 1 | GACTGGAGTTCAGACGTGTGCTCTTCCGATCTGGAACCAGGAGCTAATAAAAATAACTTCT |
| SEQ ID NO:1094 | 1 | GACTGGAGTTCAGACGTGTGCTCTTCCGATCTGGAACTGCTTTGACTCCAGGTATTCC |
| SEQ ID NO:1095 | 1 | GACTGGAGTTCAGACGTGTGCTCTTCCGATCTGGAACTTACTCTCCAGGCTTAACACAG |
| SEQ ID NO:1096 | 1 | GACTGGAGTTCAGACGTGTGCTCTTCCGATCTGGAAGATCATCTGCTGGCCGTGTG |
| SEQ ID NO:1097 | 1 | GACTGGAGTTCAGACGTGTGCTCTTCCGATCTGGAAGCACACAGATCAGCGACAGGAT |
| SEQ ID NO:1098 | 1 | GACTGGAGTTCAGACGTGTGCTCTTCCGATCTGGAAGCACACAGATCAGCGACAGGAT |
| SEQ ID NO:1099 | 1 | GACTGGAGTTCAGACGTGTGCTCTTCCGATCTGGAAGCCCTCATGTCTGAACTCAAAGT |
| SEQ ID NO:1100 | 1 | GACTGGAGTTCAGACGTGTGCTCTTCCGATCTGGAAGTTTAGGTCAAAGAGGCTGCTTGG |
| SEQ ID NO:1101 | 1 | GACTGGAGTTCAGACGTGTGCTCTTCCGATCTGGAATAGGCCTTGGTGTGCATTCTTCT |
| SEQ ID NO:1102 | 1 | GACTGGAGTTCAGACGTGTGCTCTTCCGATCTGGAATTTGGATGTGATTGGAAAGTGGGGT |
| SEQ ID NO:1103 | 1 | GACTGGAGTTCAGACGTGTGCTCTTCCGATCTGGACATGCTAGGGACAACACGATTTCC |
| SEQ ID NO:1104 | 1 | GACTGGAGTTCAGACGTGTGCTCTTCCGATCTGGACCCTGACAAATGTGCTGTTCTTCT |
| SEQ ID NO:1105 | 1 | GACTGGAGTTCAGACGTGTGCTCTTCCGATCTGGACCGACCGTGATCAGATTAGGG |

FIG. 7AQ

| Target Specific Primer | Volume Ratio | Sequence |
|---|---|---|
| SEQ ID NO:1106 | 1 | GACTGGAGTTCAGACGTGTGCTCTTCCGATCTGGACTAGGCGTGGGATGTTTTTGCAG |
| SEQ ID NO:1107 | 1 | GACTGGAGTTCAGACGTGTGCTCTTCCGATCTGGACTTCCTCTTCTGCCCTCCCAG |
| SEQ ID NO:1108 | 1 | GACTGGAGTTCAGACGTGTGCTCTTCCGATCTGGAGAAAAGGGGACATGCTAGGGACA |
| SEQ ID NO:1109 | 1 | GACTGGAGTTCAGACGTGTGCTCTTCCGATCTGGAGAACAAGTTTGGCAGCATCCGG |
| SEQ ID NO:1110 | 1 | GACTGGAGTTCAGACGTGTGCTCTTCCGATCTGGAGACCAGGTAGAGGGAGTACAGAGT |
| SEQ ID NO:1111 | 1 | GACTGGAGTTCAGACGTGTGCTCTTCCGATCTGGAGACGTTGGAATGCGGGGAC |
| SEQ ID NO:1112 | 1 | GACTGGAGTTCAGACGTGTGCTCTTCCGATCTGGAGAGACATTTAAGGTTCCTTCAAGC |
| SEQ ID NO:1113 | 1 | GACTGGAGTTCAGACGTGTGCTCTTCCGATCTGGAGTACTTCTTTGGGTTGACTTCTCTGG |
| SEQ ID NO:1114 | 1 | GACTGGAGTTCAGACGTGTGCTCTTCCGATCTGGAGTGGTCATAAGGCTGGTATAATGT |
| SEQ ID NO:1115 | 1 | GACTGGAGTTCAGACGTGTGCTCTTCCGATCTGGAGTTCCTCTTCCTTCCCCTTCTAG |
| SEQ ID NO:1116 | 1 | GACTGGAGTTCAGACGTGTGCTCTTCCGATCTGGATGAGTTTTGTGAAAGGCTGGGGAC |
| SEQ ID NO:1117 | 1 | GACTGGAGTTCAGACGTGTGCTCTTCCGATCTGGATTCAAAGTCAGTCCCCAGCTACTC |
| SEQ ID NO:1118 | 1 | GACTGGAGTTCAGACGTGTGCTCTTCCGATCTGGATTGCAGATTGGGCCTTGGGG |
| SEQ ID NO:1119 | 1 | GACTGGAGTTCAGACGTGTGCTCTTCCGATCTGGCAAAGGTGGGCTTGTTGGAAGAAC |
| SEQ ID NO:1120 | 1 | GACTGGAGTTCAGACGTGTGCTCTTCCGATCTGGCAACAGCTCTTACCTTGTCTTTCTTCC |
| SEQ ID NO:1121 | 1 | GACTGGAGTTCAGACGTGTGCTCTTCCGATCTGGCAATTCATTTCCAATCAAACCCACAGAC |
| SEQ ID NO:1122 | 1 | GACTGGAGTTCAGACGTGTGCTCTTCCGATCTGGCACATTCCATTCTTACCAAACTCTAAATTT |
| SEQ ID NO:1123 | 1 | GACTGGAGTTCAGACGTGTGCTCTTCCGATCTGGCAGACTCTCTCTCCCCACTG |
| SEQ ID NO:1124 | 1 | GACTGGAGTTCAGACGTGTGCTCTTCCGATCTGGCAGACTCTCTCTCCCCACTG |

FIG. 7AR

| Target Specific Primer | Volume Ratio | Sequence |
|---|---|---|
| SEQ ID NO:1125 | 1 | GACTGGAGTTCAGACGTGTGCTCTTCCGATCTGGCATCAATGTCCTTATTACTTGGGAG |
| SEQ ID NO:1126 | 1 | GACTGGAGTTCAGACGTGTGCTCTTCCGATCTGGCATCAATGTCCTTATTACTTGGGAGACT |
| SEQ ID NO:1127 | 1 | GACTGGAGTTCAGACGTGTGCTCTTCCGATCTGGCATTCTGGGAGCTTCATCTGGACC |
| SEQ ID NO:1128 | 1 | GACTGGAGTTCAGACGTGTGCTCTTCCGATCTGGCCAGATCCAGTGAAAAACAAGCTCT |
| SEQ ID NO:1129 | 1 | GACTGGAGTTCAGACGTGTGCTCTTCCGATCTGGCCAGATCCAGTGAAAAACAAGCTCT |
| SEQ ID NO:1130 | 1 | GACTGGAGTTCAGACGTGTGCTCTTCCGATCTGGCCGAAGTCTGACCCTTTTTGTC |
| SEQ ID NO:1131 | 1 | GACTGGAGTTCAGACGTGTGCTCTTCCGATCTGGCCTCCCAAAATGTTAGGATTACAGGT |
| SEQ ID NO:1132 | 1 | GACTGGAGTTCAGACGTGTGCTCTTCCGATCTGGCCTCGATCTTGTAGGGGATGTTGAG |
| SEQ ID NO:1133 | 1 | GACTGGAGTTCAGACGTGTGCTCTTCCGATCTGGCCTGCCTCCACTTCAACCA |
| SEQ ID NO:1134 | 1 | GACTGGAGTTCAGACGTGTGCTCTTCCGATCTGGCGATCTGGGACTGCATGCTG |
| SEQ ID NO:1135 | 1 | GACTGGAGTTCAGACGTGTGCTCTTCCGATCTGGCTCATCACCACGCTCCATTATCC |
| SEQ ID NO:1136 | 1 | GACTGGAGTTCAGACGTGTGCTCTTCCGATCTGGCTGCTGGACATTGACGAGACAGA |
| SEQ ID NO:1137 | 1 | GACTGGAGTTCAGACGTGTGCTCTTCCGATCTGGCTGTGTCCACCCCCTTACTCAT |
| SEQ ID NO:1138 | 1 | GACTGGAGTTCAGACGTGTGCTCTTCCGATCTGGGAAGCAGGATCTCAGGTCTCTCAAA |
| SEQ ID NO:1139 | 1 | GACTGGAGTTCAGACGTGTGCTCTTCCGATCTGGGAATGCCTGGTTTATTTGGGACTCC |
| SEQ ID NO:1140 | 1 | GACTGGAGTTCAGACGTGTGCTCTTCCGATCTGGGACGTGCACAACCTCGACTA |
| SEQ ID NO:1141 | 1 | GACTGGAGTTCAGACGTGTGCTCTTCCGATCTGGGACGTGCACAACCTCGACTACTA |
| SEQ ID NO:1142 | 1 | GACTGGAGTTCAGACGTGTGCTCTTCCGATCTGGGACTAGGCGTGGATGTTTTTG |
| SEQ ID NO:1143 | 1 | GACTGGAGTTCAGACGTGTGCTCTTCCGATCTGGGAGTTGGGGTGAGGGTGTCT |

FIG. 7AS

| Target Specific Primer | Volume Ratio | Sequence |
|---|---|---|
| SEQ ID NO:1144 | 1 | GACTGGAGTTCAGACGTGTGCTCTTCCGATCTGGGCAAATGAGTCACCCGCTATGT |
| SEQ ID NO:1145 | 1 | GACTGGAGTTCAGACGTGTGCTCTTCCGATCTGGGCAGCATTGTTGGGGACAC |
| SEQ ID NO:1146 | 1 | GACTGGAGTTCAGACGTGTGCTCTTCCGATCTGGGCGGGTCTCTCGGAGGAAG |
| SEQ ID NO:1147 | 1 | GACTGGAGTTCAGACGTGTGCTCTTCCGATCTGGGCTCGGGTTGGCTCTAAAGTAGT |
| SEQ ID NO:1148 | 1 | GACTGGAGTTCAGACGTGTGCTCTTCCGATCTGGGCTTGAACATACTAAATGCTCCAGTACT |
| SEQ ID NO:1149 | 1 | GACTGGAGTTCAGACGTGTGCTCTTCCGATCTGGGCTTTCTCGGTTCTCTGATTCCTGG |
| SEQ ID NO:1150 | 1 | GACTGGAGTTCAGACGTGTGCTCTTCCGATCTGGGCTTTTGTTTTCTTCCCTTTAGATGC |
| SEQ ID NO:1151 | 1 | GACTGGAGTTCAGACGTGTGCTCTTCCGATCTGGGCTTTTGTTTTCTTCCCTTTAGATGC |
| SEQ ID NO:1152 | 1 | GACTGGAGTTCAGACGTGTGCTCTTCCGATCTGGGCTTTTGTTTTCTTCCCTTTAGATGCTCT |
| SEQ ID NO:1153 | 1 | GACTGGAGTTCAGACGTGTGCTCTTCCGATCTGGGCTTTTGTTTTCTTCCCTTTAGATGCTCT |
| SEQ ID NO:1154 | 1 | GACTGGAGTTCAGACGTGTGCTCTTCCGATCTGGGGAAGCAGGATCTCAGGTCTCTC |
| SEQ ID NO:1155 | 1 | GACTGGAGTTCAGACGTGTGCTCTTCCGATCTGGGGACGATGGGGCAAGTGATG |
| SEQ ID NO:1156 | 1 | GACTGGAGTTCAGACGTGTGCTCTTCCGATCTGGGGATCCTGTCGGTGAGCACT |
| SEQ ID NO:1157 | 1 | GACTGGAGTTCAGACGTGTGCTCTTCCGATCTGGGGATGTGATGAGAGGTGGATGGG |
| SEQ ID NO:1158 | 1 | GACTGGAGTTCAGACGTGTGCTCTTCCGATCTGGGGCAAATTTTTAAAGGCACAAGAGGC |
| SEQ ID NO:1159 | 1 | GACTGGAGTTCAGACGTGTGCTCTTCCGATCTGGGGCTGGGCATCACTGTAAACCTT |
| SEQ ID NO:1160 | 1 | GACTGGAGTTCAGACGTGTGCTCTTCCGATCTGGGGCTTTCTCGGTTCTCTGATTCC |
| SEQ ID NO:1161 | 1 | GACTGGAGTTCAGACGTGTGCTCTTCCGATCTGGGGGCTTTCTCGGTTCTCTGAT |
| SEQ ID NO:1162 | 1 | GACTGGAGTTCAGACGTGTGCTCTTCCGATCTGGGGTGGCTATGTAGAGAAGTTGTCCT |

FIG. 7AT

| Target Specific Primer | Volume Ratio | Sequence |
|---|---|---|
| SEQ ID NO:1163 | 1 | GACTGGAGTTCAGACGTGTGCTCTTCCGATCTGGGGTGGTCTTTGGGATCCTCATCAAG |
| SEQ ID NO:1164 | 1 | GACTGGAGTTCAGACGTGTGCTCTTCCGATCTGGGTGGGGGGCTCTCACTGTC |
| SEQ ID NO:1165 | 1 | GACTGGAGTTCAGACGTGTGCTCTTCCGATCTGGGTTGTAGTCGGTCATGATGGTCGAG |
| SEQ ID NO:1166 | 1 | GACTGGAGTTCAGACGTGTGCTCTTCCGATCTGGTAACCATTTATTTGTTCTCTCCAGA |
| SEQ ID NO:1167 | 1 | GACTGGAGTTCAGACGTGTGCTCTTCCGATCTGGTACTGCCCTATTGCCCCTGG |
| SEQ ID NO:1168 | 1 | GACTGGAGTTCAGACGTGTGCTCTTCCGATCTGGTACTTAGATGGGGGATGGCTGTTGT |
| SEQ ID NO:1169 | 1 | GACTGGAGTTCAGACGTGTGCTCTTCCGATCTGGTAGAGATGGCGGTTGGGAGGTATC |
| SEQ ID NO:1170 | 1 | GACTGGAGTTCAGACGTGTGCTCTTCCGATCTGGTATTCGATGATCCCTGTGGTGG |
| SEQ ID NO:1171 | 1 | GACTGGAGTTCAGACGTGTGCTCTTCCGATCTGGTCAAAATTAGAACAGTAGATGCTTAGT |
| SEQ ID NO:1172 | 1 | GACTGGAGTTCAGACGTGTGCTCTTCCGATCTGGTCAAGAGTCCCAACCATGTCAAAATTACA |
| SEQ ID NO:1173 | 1 | GACTGGAGTTCAGACGTGTGCTCTTCCGATCTGGTCTCACTCACCCGCGGAC |
| SEQ ID NO:1174 | 1 | GACTGGAGTTCAGACGTGTGCTCTTCCGATCTGGTCTCTCGGAGGAAGGACTTGAGGT |
| SEQ ID NO:1175 | 1 | GACTGGAGTTCAGACGTGTGCTCTTCCGATCTGGTGACCGAGGACAACGTGATGAAG |
| SEQ ID NO:1176 | 1 | GACTGGAGTTCAGACGTGTGCTCTTCCGATCTGGTGAGAAAGTTAAAATTCCCGTCGCT |
| SEQ ID NO:1177 | 1 | GACTGGAGTTCAGACGTGTGCTCTTCCGATCTGGTGAGCACTGAGGGAATGAAAGT |
| SEQ ID NO:1178 | 1 | GACTGGAGTTCAGACGTGTGCTCTTCCGATCTGGTGCGCATGTACTGGTCCCG |
| SEQ ID NO:1179 | 1 | GACTGGAGTTCAGACGTGTGCTCTTCCGATCTGGTGGCTATGTAGAGAAGTTGTCCTGGA |
| SEQ ID NO:1180 | 1 | GACTGGAGTTCAGACGTGTGCTCTTCCGATCTGGTGGCTTTTGTTTGTTTGTTTTGTTTTAAGG |
| SEQ ID NO:1181 | 1 | GACTGGAGTTCAGACGTGTGCTCTTCCGATCTGGTGTGTCTTTAATTGAAGCATGATTTAAA |

FIG. 7AU

| Target Specific Primer | Volume Ratio | Sequence |
|---|---|---|
| SEQ ID NO:1182 | 1 | GACTGGAGTTCAGACGTGTGCTCTTCCGATCTGGTTCCTTCAAGCTGCCCTATTGTTAC |
| SEQ ID NO:1183 | 1 | GACTGGAGTTCAGACGTGTGCTCTTCCGATCTGGTTCTTTGGGGGCAGAGGGGAG |
| SEQ ID NO:1184 | 1 | GACTGGAGTTCAGACGTGTGCTCTTCCGATCTGGTTGACTGGGCAGAGTGACGATGAG |
| SEQ ID NO:1185 | 1 | GACTGGAGTTCAGACGTGTGCTCTTCCGATCTGGTTGTCCGGAGCCTAGTCA |
| SEQ ID NO:1186 | 1 | GACTGGAGTTCAGACGTGTGCTCTTCCGATCTGGTTGTCCGGAGCCTAGTCAAGC |
| SEQ ID NO:1187 | 1 | GACTGGAGTTCAGACGTGTGCTCTTCCGATCTGTAAAGCTGGAAAGGGACGAACTGGTG |
| SEQ ID NO:1188 | 1 | GACTGGAGTTCAGACGTGTGCTCTTCCGATCTGTAACGTCCTGTCCTGCCCCTGTC |
| SEQ ID NO:1189 | 1 | GACTGGAGTTCAGACGTGTGCTCTTCCGATCTGTAACGTCCTGTCCTGCCCCTGTC |
| SEQ ID NO:1190 | 1 | GACTGGAGTTCAGACGTGTGCTCTTCCGATCTGTACTTACCTCACTTGCCCAGCGTGTC |
| SEQ ID NO:1191 | 1 | GACTGGAGTTCAGACGTGTGCTCTTCCGATCTGTAGAGGGAGTACAGAGTGACCGCCTC |
| SEQ ID NO:1192 | 1 | GACTGGAGTTCAGACGTGTGCTCTTCCGATCTGTCAACCACCCACATGTCATCAAA |
| SEQ ID NO:1193 | 1 | GACTGGAGTTCAGACGTGTGCTCTTCCGATCTGTCAAGTACTTACCCACTGAAAAGCAC |
| SEQ ID NO:1194 | 1 | GACTGGAGTTCAGACGTGTGCTCTTCCGATCTGTCAGTCCCCAGCTACTCTCAAAATCA |
| SEQ ID NO:1195 | 1 | GACTGGAGTTCAGACGTGTGCTCTTCCGATCTGTCCATGTGCCCCTCCTTCTGG |
| SEQ ID NO:1196 | 1 | GACTGGAGTTCAGACGTGTGCTCTTCCGATCTGTCCCAACCATGACAAGATTTTCCCTT |
| SEQ ID NO:1197 | 1 | GACTGGAGTTCAGACGTGTGCTCTTCCGATCTGTCCCTTACTTGTTCAGCTCCTTG |
| SEQ ID NO:1198 | 1 | GACTGGAGTTCAGACGTGTGCTCTTCCGATCTGTCCTCAAAAGACTTGGTGTTGTTGAT |
| SEQ ID NO:1199 | 1 | GACTGGAGTTCAGACGTGTGCTCTTCCGATCTGTCCTCCACACTTCTCCATTCTTCACA |
| SEQ ID NO:1200 | 1 | GACTGGAGTTCAGACGTGTGCTCTTCCGATCTGTCCTGAGCCTGCCGAGATTCCAC |

FIG. 7AV

| Target Specific Primer | Volume Ratio | Sequence |
|---|---|---|
| SEQ ID NO:1201 | 1 | GACTGGAGTTCAGACGTGTGCTCTTCCGATCTGTCCTGAGCCTGTTTTGTGTCTACTGT |
| SEQ ID NO:1202 | 1 | GACTGGAGTTCAGACGTGTGCTCTTCCGATCTGTCCTGGGATTGCAGATTGGGCC |
| SEQ ID NO:1203 | 1 | GACTGGAGTTCAGACGTGTGCTCTTCCGATCTGTCTCCAACCCATTCTGCCCAG |
| SEQ ID NO:1204 | 1 | GACTGGAGTTCAGACGTGTGCTCTTCCGATCTGTCTCCTCCACCGCTTCTTGTCCTG |
| SEQ ID NO:1205 | 1 | GACTGGAGTTCAGACGTGTGCTCTTCCGATCTGTCTGCCGCAAATTCCGAGACGAAG |
| SEQ ID NO:1206 | 1 | GACTGGAGTTCAGACGTGTGCTCTTCCGATCTGTGACTATCTCCCTGGGTGTAGCT |
| SEQ ID NO:1207 | 1 | GACTGGAGTTCAGACGTGTGCTCTTCCGATCTGTGACTATCTCCCTGGGTGTAGCTTTT |
| SEQ ID NO:1208 | 1 | GACTGGAGTTCAGACGTGTGCTCTTCCGATCTGTGAGTGGGTTTATATTAAAAGTTGGT |
| SEQ ID NO:1209 | 1 | GACTGGAGTTCAGACGTGTGCTCTTCCGATCTGTGAGCCACGATGCCCAGTCAATC |
| SEQ ID NO:1210 | 1 | GACTGGAGTTCAGACGTGTGCTCTTCCGATCTGTGAGCCACTTCTTACCTTCACAGC |
| SEQ ID NO:1211 | 1 | GACTGGAGTTCAGACGTGTGCTCTTCCGATCTGTGAGCGAGTCCCACAGTGAGGA |
| SEQ ID NO:1212 | 1 | GACTGGAGTTCAGACGTGTGCTCTTCCGATCTGTGATCCTCCTGCCTTGGCCTCTATTA |
| SEQ ID NO:1213 | 1 | GACTGGAGTTCAGACGTGTGCTCTTCCGATCTGTGATCTGGCTCGTCTGTGTGTCA |
| SEQ ID NO:1214 | 1 | GACTGGAGTTCAGACGTGTGCTCTTCCGATCTGTGATGGATTTGATGAATTGGTGATAAGA |
| SEQ ID NO:1215 | 1 | GACTGGAGTTCAGACGTGTGCTCTTCCGATCTGTGATTGCAGGTTCCACACACAGGC |
| SEQ ID NO:1216 | 1 | GACTGGAGTTCAGACGTGTGCTCTTCCGATCTGTGCAACGGGTTCTTCCTTCGAGAG |
| SEQ ID NO:1217 | 1 | GACTGGAGTTCAGACGTGTGCTCTTCCGATCTGTGCACGAAGGGCCAGGGTATGTG |
| SEQ ID NO:1218 | 1 | GACTGGAGTTCAGACGTGTGCTCTTCCGATCTGTGCCTCTCCCTCCCTCCAGG |
| SEQ ID NO:1219 | 1 | GACTGGAGTTCAGACGTGTGCTCTTCCGATCTGTGCTATTTTCCTCACAGCTCGTTCA |

FIG. 7AW

| Target Specific Primer | Volume Ratio | Sequence |
|---|---|---|
| SEQ ID NO:1220 | 1 | GACTGGAGTTCAGACGTGTGCTCTTCCGATCTGTGCTCCAGACCCCTCACCTG |
| SEQ ID NO:1221 | 1 | GACTGGAGTTCAGACGTGTGCTCTTCCGATCTGTGCTGCTGTACATGGCCACTCAGATC |
| SEQ ID NO:1222 | 1 | GACTGGAGTTCAGACGTGTGCTCTTCCGATCTGTGCTGTGTCCCTGTCCTGCC |
| SEQ ID NO:1223 | 1 | GACTGGAGTTCAGACGTGTGCTCTTCCGATCTGTGGAGCCTCTTACACCCAGT |
| SEQ ID NO:1224 | 1 | GACTGGAGTTCAGACGTGTGCTCTTCCGATCTGTGGAGCCTCTTACACCCAGT |
| SEQ ID NO:1225 | 1 | GACTGGAGTTCAGACGTGTGCTCTTCCGATCTGTGGCGCATCTCCCTCAGGTAGTTC |
| SEQ ID NO:1226 | 1 | GACTGGAGTTCAGACGTGTGCTCTTCCGATCTGTGGCTCCAGTCTCCCTCCTGTTTG |
| SEQ ID NO:1227 | 1 | GACTGGAGTTCAGACGTGTGCTCTTCCGATCTGTGGGGAAGCAGGATCTCAGGTC |
| SEQ ID NO:1228 | 1 | GACTGGAGTTCAGACGTGTGCTCTTCCGATCTGTGGGGGCTCTCACTGTCTCC |
| SEQ ID NO:1229 | 1 | GACTGGAGTTCAGACGTGTGCTCTTCCGATCTGTGGGGGCTTTCTCGGTTCTCT |
| SEQ ID NO:1230 | 1 | GACTGGAGTTCAGACGTGTGCTCTTCCGATCTGTGGGTGGTCAGCTGCAACATGG |
| SEQ ID NO:1231 | 1 | GACTGGAGTTCAGACGTGTGCTCTTCCGATCTGTGTACTTACCTCACTTGCCCAGCGT |
| SEQ ID NO:1232 | 1 | GACTGGAGTTCAGACGTGTGCTCTTCCGATCTGTGTCTTCCCACCTACAGTAACAAAG |
| SEQ ID NO:1233 | 1 | GACTGGAGTTCAGACGTGTGCTCTTCCGATCTGTGTGAGTGAATGTGTGCCAGGGGTA |
| SEQ ID NO:1234 | 1 | GACTGGAGTTCAGACGTGTGCTCTTCCGATCTGTGTGGATGGAGGGGCACTGAAGTC |
| SEQ ID NO:1235 | 1 | GACTGGAGTTCAGACGTGTGCTCTTCCGATCTGTGTGTGGCGCTGAGTGTACTTACCTC |
| SEQ ID NO:1236 | 1 | GACTGGAGTTCAGACGTGTGCTCTTCCGATCTGTGTTGATCAGGCGCCCAGTCAC |
| SEQ ID NO:1237 | 1 | GACTGGAGTTCAGACGTGTGCTCTTCCGATCTGTGTTGTGGAGTGCAAGTGAAAGCCTT |
| SEQ ID NO:1238 | 1 | GACTGGAGTTCAGACGTGTGCTCTTCCGATCTGTTATCACTCCACATTTCAGCAACAGC |

FIG. 7AX

| Target Specific Primer | Volume Ratio | Sequence |
|---|---|---|
| SEQ ID NO:1239 | 1 | GACTGGAGTTCAGACGTGTGCTCTTCCGATCTGTTCCCTCAGCCGTTACCTGTGTGTG |
| SEQ ID NO:1240 | 1 | GACTGGAGTTCAGACGTGTGCTCTTCCGATCTGTTCGCCAGCCATAAGTCCTCGAC |
| SEQ ID NO:1241 | 1 | GACTGGAGTTCAGACGTGTGCTCTTCCGATCTGTTCGGACAGACAACCCCAAGAGCTG |
| SEQ ID NO:1242 | 1 | GACTGGAGTTCAGACGTGTGCTCTTCCGATCTGTTCTGGGCACTGGGTCAAAGTCTCC |
| SEQ ID NO:1243 | 1 | GACTGGAGTTCAGACGTGTGCTCTTCCGATCTGTTCTTTGGGGGCAGAGGGGAGTTG |
| SEQ ID NO:1244 | 1 | GACTGGAGTTCAGACGTGTGCTCTTCCGATCTGTTGACCGCATCGCCACCTTG |
| SEQ ID NO:1245 | 1 | GACTGGAGTTCAGACGTGTGCTCTTCCGATCTGTTGGGGTTGTAGTCGGTCATGATG |
| SEQ ID NO:1246 | 1 | GACTGGAGTTCAGACGTGTGCTCTTCCGATCTGTTGTCCGGAGCCTAGTCAAGCCTG |
| SEQ ID NO:1247 | 1 | GACTGGAGTTCAGACGTGTGCTCTTCCGATCTGTTTGTGATGGTTGGGAGGCTGTGTG |
| SEQ ID NO:1248 | 1 | GACTGGAGTTCAGACGTGTGCTCTTCCGATCTGTTTTCCTCCAAATACTGACAGCCACA |
| SEQ ID NO:1249 | 1 | GACTGGAGTTCAGACGTGTGCTCTTCCGATCTTAACCCACCTTCTGTCCCACCCCTTC |
| SEQ ID NO:1250 | 1 | GACTGGAGTTCAGACGTGTGCTCTTCCGATCTTAACCTTTTCTTATGTGCTTTTAGGGC |
| SEQ ID NO:1251 | 1 | GACTGGAGTTCAGACGTGTGCTCTTCCGATCTTAACTCAGCAGCATCTCAGGGCCAAAA |
| SEQ ID NO:1252 | 1 | GACTGGAGTTCAGACGTGTGCTCTTCCGATCTTAAGTCCTGAGCCTGTTTTGTGTCTAC |
| SEQ ID NO:1253 | 1 | GACTGGAGTTCAGACGTGTGCTCTTCCGATCTTAATGACTCACCTGGGGCCACATTTGA |
| SEQ ID NO:1254 | 1 | GACTGGAGTTCAGACGTGTGCTCTTCCGATCTTAATTTGCCCAGTTCAGGATCCAGCC |
| SEQ ID NO:1255 | 1 | GACTGGAGTTCAGACGTGTGCTCTTCCGATCTTACACACGCAAAATACTCCTTCAGC |
| SEQ ID NO:1256 | 1 | GACTGGAGTTCAGACGTGTGCTCTTCCGATCTTACCAAATGTACTCAAGGCATAAAAGC |
| SEQ ID NO:1257 | 1 | GACTGGAGTTCAGACGTGTGCTCTTCCGATCTTACCACAGTTGCACAATATCCTTTTGA |

FIG. 7AY

| Target Specific Primer | Volume Ratio | Sequence |
|---|---|---|
| SEQ ID NO:1258 | 1 | GACTGGAGTTCAGACGTGTGCTCTTCCGATCTTACCTCAGTTTGCCCCCATGTCCCTTA |
| SEQ ID NO:1259 | 1 | GACTGGAGTTCAGACGTGTGCTCTTCCGATCTTACCTCAGTTTGCCCCCATGTCCCTTA |
| SEQ ID NO:1260 | 1 | GACTGGAGTTCAGACGTGTGCTCTTCCGATCTTACCTTCAGCTGCCACTTCTACGACTT |
| SEQ ID NO:1261 | 1 | GACTGGAGTTCAGACGTGTGCTCTTCCGATCTTACTGGAGAAAAGGGGACATGCTAGGG |
| SEQ ID NO:1262 | 1 | GACTGGAGTTCAGACGTGTGCTCTTCCGATCTTACTTACGCGCCACAGAGAAGTTGTTG |
| SEQ ID NO:1263 | 1 | GACTGGAGTTCAGACGTGTGCTCTTCCGATCTTAGAAACCGAGGTATGAAATTCGCTGG |
| SEQ ID NO:1264 | 1 | GACTGGAGTTCAGACGTGTGCTCTTCCGATCTTAGAAGTGACGTCTAGGGGTGGGGG |
| SEQ ID NO:1265 | 1 | GACTGGAGTTCAGACGTGTGCTCTTCCGATCTTAGCAAGGTGAAGTAAGACTCAAATGT |
| SEQ ID NO:1266 | 1 | GACTGGAGTTCAGACGTGTGCTCTTCCGATCTTAGTAGGGGAAGATCATCTGCTGG |
| SEQ ID NO:1267 | 1 | GACTGGAGTTCAGACGTGTGCTCTTCCGATCTTAGTAGGGGAAGATCATCTGCTGGCCG |
| SEQ ID NO:1268 | 1 | GACTGGAGTTCAGACGTGTGCTCTTCCGATCTTATAGAGCGTGCAGATAATGACAAGGA |
| SEQ ID NO:1269 | 1 | GACTGGAGTTCAGACGTGTGCTCTTCCGATCTTATCTGTATCAAAGAATGGTCCTGCAC |
| SEQ ID NO:1270 | 1 | GACTGGAGTTCAGACGTGTGCTCTTCCGATCTTATCTGTATCAAAGAATGGTCCTGCAC |
| SEQ ID NO:1271 | 1 | GACTGGAGTTCAGACGTGTGCTCTTCCGATCTTATTTGTCCCCTTGCCTCCCTTTCCAA |
| SEQ ID NO:1272 | 1 | GACTGGAGTTCAGACGTGTGCTCTTCCGATCTTCAAACTCCTGGCCTCTTGTGATCCTC |
| SEQ ID NO:1273 | 1 | GACTGGAGTTCAGACGTGTGCTCTTCCGATCTTCAAAGTCAGTCCCCAGCTACTCTCAA |
| SEQ ID NO:1274 | 1 | GACTGGAGTTCAGACGTGTGCTCTTCCGATCTTCAACTAAACTTCTAAGATGTGGCAAGA |
| SEQ ID NO:1275 | 1 | GACTGGAGTTCAGACGTGTGCTCTTCCGATCTTCAAGGAGATAAGTGATGGAGATGTGA |
| SEQ ID NO:1276 | 1 | GACTGGAGTTCAGACGTGTGCTCTTCCGATCTTCAATTTGAGGGGGAGTCTGGGAATGA |

FIG. 7AZ

| Target Specific Primer | Volume Ratio | Sequence |
|---|---|---|
| SEQ ID NO:1277 | 1 | GACTGGAGTTCAGACGTGTGCTCTTCCGATCTTCACAGACATCCTTGCACATCTCTAGC |
| SEQ ID NO:1278 | 1 | GACTGGAGTTCAGACGTGTGCTCTTCCGATCTTCACATGAATGGAATAGTTTAATAGTTTGGA |
| SEQ ID NO:1279 | 1 | GACTGGAGTTCAGACGTGTGCTCTTCCGATCTTCACTCATATCCTCCTCTTTCTGCCCA |
| SEQ ID NO:1280 | 1 | GACTGGAGTTCAGACGTGTGCTCTTCCGATCTTCACTCATATCCTCCTCTTTCTGCCCA |
| SEQ ID NO:1281 | 1 | GACTGGAGTTCAGACGTGTGCTCTTCCGATCTTCAGCAGCATCTCAGGGCCAAAAATTT |
| SEQ ID NO:1282 | 1 | GACTGGAGTTCAGACGTGTGCTCTTCCGATCTTCAGCCACGGGTAATAATTTTTGTCCT |
| SEQ ID NO:1283 | 1 | GACTGGAGTTCAGACGTGTGCTCTTCCGATCTTCAGCTGCCACTTCTACGACTTCTTCA |
| SEQ ID NO:1284 | 1 | GACTGGAGTTCAGACGTGTGCTCTTCCGATCTTCAGGAAAACTACAATGGAGAAAGAAGA |
| SEQ ID NO:1285 | 1 | GACTGGAGTTCAGACGTGTGCTCTTCCGATCTTCAGGTAGGAGAGACATTTAAGGTTCC |
| SEQ ID NO:1286 | 1 | GACTGGAGTTCAGACGTGTGCTCTTCCGATCTTCAGTAACTCTACACAGAAAGGGCCCA |
| SEQ ID NO:1287 | 1 | GACTGGAGTTCAGACGTGTGCTCTTCCGATCTTCAGTCCAGACATGTAGCTCCTGTGC |
| SEQ ID NO:1288 | 1 | GACTGGAGTTCAGACGTGTGCTCTTCCGATCTTCAGTCCAGACATGTAGCTCCTGTGC |
| SEQ ID NO:1289 | 1 | GACTGGAGTTCAGACGTGTGCTCTTCCGATCTTCAGTGTTACTTACCTGTCTTGTCTTT |
| SEQ ID NO:1290 | 1 | GACTGGAGTTCAGACGTGTGCTCTTCCGATCTTCATAGATAAAAGCTAAGTTGCCCCAG |
| SEQ ID NO:1291 | 1 | GACTGGAGTTCAGACGTGTGCTCTTCCGATCTTCATATTCGTCCACAAAATGATTCTGAA |
| SEQ ID NO:1292 | 1 | GACTGGAGTTCAGACGTGTGCTCTTCCGATCTTCATGATTCGTCATAGTTGTTGCAAGC |
| SEQ ID NO:1293 | 1 | GACTGGAGTTCAGACGTGTGCTCTTCCGATCTTCATGGGAATTTAAAGGAGCTGGAAAGA |
| SEQ ID NO:1294 | 1 | GACTGGAGTTCAGACGTGTGCTCTTCCGATCTTCATGTACTGGTCCCTCATTGCACTGT |
| SEQ ID NO:1295 | 1 | GACTGGAGTTCAGACGTGTGCTCTTCCGATCTTCATTATCTGAGGAGCCGGTCACC |

FIG. 7BA

| Target Specific Primer | Volume Ratio | Sequence |
|---|---|---|
| SEQ ID NO:1296 | 1 | GACTGGAGTTCAGACGTGTGCTCTTCCGATCTTCATTCTTGAGGAGGAAGTAGCGTGGC |
| SEQ ID NO:1297 | 1 | GACTGGAGTTCAGACGTGTGCTCTTCCGATCTTCCAATCAAACCCACAGACTTACCTAAT |
| SEQ ID NO:1298 | 1 | GACTGGAGTTCAGACGTGTGCTCTTCCGATCTTCCAATGGAAAAGAAATGCTGCAGAA |
| SEQ ID NO:1299 | 1 | GACTGGAGTTCAGACGTGTGCTCTTCCGATCTTCCACTGAAGCTGAATATTAATGGCCA |
| SEQ ID NO:1300 | 1 | GACTGGAGTTCAGACGTGTGCTCTTCCGATCTTCCAGTGAAAAACAAGCTCTCATGTCT |
| SEQ ID NO:1301 | 1 | GACTGGAGTTCAGACGTGTGCTCTTCCGATCTTCCAGTGTTTCTTTTAAATACCTGTTAAGT |
| SEQ ID NO:1302 | 1 | GACTGGAGTTCAGACGTGTGCTCTTCCGATCTTCCATAAAGACAGAAGGAGGAGAGACA |
| SEQ ID NO:1303 | 1 | GACTGGAGTTCAGACGTGTGCTCTTCCGATCTTCCCAAGTTTTCTCCCAAATCCCATTT |
| SEQ ID NO:1304 | 1 | GACTGGAGTTCAGACGTGTGCTCTTCCGATCTTCCCATTTCTCTTTCAGGTGACATTGA |
| SEQ ID NO:1305 | 1 | GACTGGAGTTCAGACGTGTGCTCTTCCGATCTTCCCCACAATCATACTGCTGACATACA |
| SEQ ID NO:1306 | 1 | GACTGGAGTTCAGACGTGTGCTCTTCCGATCTTCCTCATTTGGATAGGCTTGTAAGTGC |
| SEQ ID NO:1307 | 1 | GACTGGAGTTCAGACGTGTGCTCTTCCGATCTTCCTCATTTGGATAGGCTTGTAAGTGC |
| SEQ ID NO:1308 | 1 | GACTGGAGTTCAGACGTGTGCTCTTCCGATCTTCCTCTCTCAACTCCAACAGGAAATCA |
| SEQ ID NO:1309 | 1 | GACTGGAGTTCAGACGTGTGCTCTTCCGATCTTCCTGTAATTTTTCAAGGCTTCAGTCT |
| SEQ ID NO:1310 | 1 | GACTGGAGTTCAGACGTGTGCTCTTCCGATCTTCCTGTGGATTTTTAGGCCCTTGTATT |
| SEQ ID NO:1311 | 1 | GACTGGAGTTCAGACGTGTGCTCTTCCGATCTTCCTGTTTCAGTCCCCATTAAATGAGG |
| SEQ ID NO:1312 | 1 | GACTGGAGTTCAGACGTGTGCTCTTCCGATCTTCCTTACTCATGGTCGGATCACAAAGA |
| SEQ ID NO:1313 | 1 | GACTGGAGTTCAGACGTGTGCTCTTCCGATCTTCCTTTTGAAGACCATAACCCACCACA |
| SEQ ID NO:1314 | 1 | GACTGGAGTTCAGACGTGTGCTCTTCCGATCTTCGTCCACAAAATGATTCTGAATTAGC |

FIG. 7BB

| Target Specific Primer | Volume Ratio | Sequence |
|---|---|---|
| SEQ ID NO:1315 | 1 | GACTGGAGTTCAGACGTGTGCTCTTCCGATCTTCTAACTCTCTTTGACTGCAGAATCCA |
| SEQ ID NO:1316 | 1 | GACTGGAGTTCAGACGTGTGCTCTTCCGATCTTCTAATGACTGAGACAATAATTATTAAAAGGTGA |
| SEQ ID NO:1317 | 1 | GACTGGAGTTCAGACGTGTGCTCTTCCGATCTTCTACACAGAAAGGGCCCAAATTCACC |
| SEQ ID NO:1318 | 1 | GACTGGAGTTCAGACGTGTGCTCTTCCGATCTTCTACGACTTCTTCAACCAGGCTGAGT |
| SEQ ID NO:1319 | 1 | GACTGGAGTTCAGACGTGTGCTCTTCCGATCTTCTAGGTGAGAGGCAGTGGTCAGG |
| SEQ ID NO:1320 | 1 | GACTGGAGTTCAGACGTGTGCTCTTCCGATCTTCTCAATGATGCTTGGCTCTGGAATGC |
| SEQ ID NO:1321 | 1 | GACTGGAGTTCAGACGTGTGCTCTTCCGATCTTCTCCCTGGGTGTAGCTTTTTAAAAAT |
| SEQ ID NO:1322 | 1 | GACTGGAGTTCAGACGTGTGCTCTTCCGATCTTCTCCGGAGCAAACCCCTATGTCCAC |
| SEQ ID NO:1323 | 1 | GACTGGAGTTCAGACGTGTGCTCTTCCGATCTTCTCTCTCCTTTTCCTCCTCTTCTCCT |
| SEQ ID NO:1324 | 1 | GACTGGAGTTCAGACGTGTGCTCTTCCGATCTTCTCTCTCTTGATTCTGACTCTGGCAA |
| SEQ ID NO:1325 | 1 | GACTGGAGTTCAGACGTGTGCTCTTCCGATCTTCTCTGAAATCAACGTAGAAGTACTCA |
| SEQ ID NO:1326 | 1 | GACTGGAGTTCAGACGTGTGCTCTTCCGATCTTCTCTTGCAGTCGTCAGCCTGAACATA |
| SEQ ID NO:1327 | 1 | GACTGGAGTTCAGACGTGTGCTCTTCCGATCTTCTGAATTAGCTGTATCGTCAAGGCAC |
| SEQ ID NO:1328 | 1 | GACTGGAGTTCAGACGTGTGCTCTTCCGATCTTCTGGAAAAGAGTAATTCACACAAGCT |
| SEQ ID NO:1329 | 1 | GACTGGAGTTCAGACGTGTGCTCTTCCGATCTTCTGTATTTATTTCAGTGTTACTTACCTGTC |
| SEQ ID NO:1330 | 1 | GACTGGAGTTCAGACGTGTGCTCTTCCGATCTTCTGTGAGTGGATTTGTTTTGTGGGC |
| SEQ ID NO:1331 | 1 | GACTGGAGTTCAGACGTGTGCTCTTCCGATCTTCTGTGGCCTTGTACTGCAGAGACAA |
| SEQ ID NO:1332 | 1 | GACTGGAGTTCAGACGTGTGCTCTTCCGATCTTCTTAGAGCATAGTAAGCAGTAGGGAGT |
| SEQ ID NO:1333 | 1 | GACTGGAGTTCAGACGTGTGCTCTTCCGATCTTCTTATTCCAGACGCATTTCCACAGCT |

FIG. 7BC

| Target Specific Primer | Volume Ratio | Sequence |
|---|---|---|
| SEQ ID NO:1334 | 1 | GACTGGAGTTCAGACGTGTGCTCTTCCGATCTTCTTCAGCTTTCTCCCACTGTATTGAA |
| SEQ ID NO:1335 | 1 | GACTGGAGTTCAGACGTGTGCTCTTCCGATCTTCTTCCCATGATGATCTGTCCCTCACA |
| SEQ ID NO:1336 | 1 | GACTGGAGTTCAGACGTGTGCTCTTCCGATCTTCTTCCCATGATGATCTGTCCCTCACA |
| SEQ ID NO:1337 | 1 | GACTGGAGTTCAGACGTGTGCTCTTCCGATCTTCTTCTCTTTAGGGTCGGATTCCAGTT |
| SEQ ID NO:1338 | 1 | GACTGGAGTTCAGACGTGTGCTCTTCCGATCTTCTTCTGGGTGCTGATACTTCTCTCCA |
| SEQ ID NO:1339 | 1 | GACTGGAGTTCAGACGTGTGCTCTTCCGATCTTCTTGCCAGAGACATGTATGATAAAGA |
| SEQ ID NO:1340 | 1 | GACTGGAGTTCAGACGTGTGCTCTTCCGATCTTCTTGGACCCATGACTCAACCTCAGTA |
| SEQ ID NO:1341 | 1 | GACTGGAGTTCAGACGTGTGCTCTTCCGATCTTCTTTCATCCCTTCCTCCCTCTTTCTT |
| SEQ ID NO:1342 | 1 | GACTGGAGTTCAGACGTGTGCTCTTCCGATCTTCTTTCATCCCTTCCTCCCTCTTTCTT |
| SEQ ID NO:1343 | 1 | GACTGGAGTTCAGACGTGTGCTCTTCCGATCTTCTTTCCCCACAATCATACTGCTGACA |
| SEQ ID NO:1344 | 1 | GACTGGAGTTCAGACGTGTGCTCTTCCGATCTTCTTTGCAGGGGTGGCTATGTAGAGAA |
| SEQ ID NO:1345 | 1 | GACTGGAGTTCAGACGTGTGCTCTTCCGATCTTCTTTTGAAAACAATGGTGACTACATGG |
| SEQ ID NO:1346 | 1 | GACTGGAGTTCAGACGTGTGCTCTTCCGATCTTCTTTTTACCACAGTTGCACAATATCCT |
| SEQ ID NO:1347 | 1 | GACTGGAGTTCAGACGTGTGCTCTTCCGATCTTGAAAGAGACGGAGCTGAGGAAGG |
| SEQ ID NO:1348 | 1 | GACTGGAGTTCAGACGTGTGCTCTTCCGATCTTGAAAGCTTAATTCTACCTTGTAGCCT |
| SEQ ID NO:1349 | 1 | GACTGGAGTTCAGACGTGTGCTCTTCCGATCTTGAAGACCATAACCCACCACAGCTAGA |
| SEQ ID NO:1350 | 1 | GACTGGAGTTCAGACGTGTGCTCTTCCGATCTTGAAGTCAGAAGGGGGTGCCTTTC |
| SEQ ID NO:1351 | 1 | GACTGGAGTTCAGACGTGTGCTCTTCCGATCTTGACAGTTTGACAGTTAAAGGCATTTCC |
| SEQ ID NO:1352 | 1 | GACTGGAGTTCAGACGTGTGCTCTTCCGATCTTGACATATGGCCATTTCTGTTTTCCTGT |

FIG. 7BD

| Target Specific Primer | Volume Ratio | Sequence |
|---|---|---|
| SEQ ID NO:1353 | 1 | GACTGGAGTTCAGACGTGTGCTCTTCCGATCTTGACATCAGTTTGCCAGTTGTGCTTTT |
| SEQ ID NO:1354 | 1 | GACTGGAGTTCAGACGTGTGCTCTTCCGATCTTGACATCAGTTTGCCAGTTGTGCTTTT |
| SEQ ID NO:1355 | 1 | GACTGGAGTTCAGACGTGTGCTCTTCCGATCTTGACCTTCGGCTTTTTCAACCCTTTTTA |
| SEQ ID NO:1356 | 1 | GACTGGAGTTCAGACGTGTGCTCTTCCGATCTTGAGAGGTGGATGGGTAGTAGTATGGA |
| SEQ ID NO:1357 | 1 | GACTGGAGTTCAGACGTGTGCTCTTCCGATCTTGAGCACTGAATCTATAAAGCATGTAAC |
| SEQ ID NO:1358 | 1 | GACTGGAGTTCAGACGTGTGCTCTTCCGATCTTGAGCATTTGAAGTTTTTATTAGTGATGGA |
| SEQ ID NO:1359 | 1 | GACTGGAGTTCAGACGTGTGCTCTTCCGATCTTGAGCCACTTCTTACCTTCACAGCCAC |
| SEQ ID NO:1360 | 1 | GACTGGAGTTCAGACGTGTGCTCTTCCGATCTTGAGTCTATCGAGTGTGTGCATATGTGT |
| SEQ ID NO:1361 | 1 | GACTGGAGTTCAGACGTGTGCTCTTCCGATCTTGAGTGCAGTTGTTTACCATGATAACG |
| SEQ ID NO:1362 | 1 | GACTGGAGTTCAGACGTGTGCTCTTCCGATCTTGATACCCCAGCTCAGATCTTCTCCCC |
| SEQ ID NO:1363 | 1 | GACTGGAGTTCAGACGTGTGCTCTTCCGATCTTGATAGTTGCTAAGAACCGGTCACTGA |
| SEQ ID NO:1364 | 1 | GACTGGAGTTCAGACGTGTGCTCTTCCGATCTTGATGCGAACAGTGAATATTTCCTTTGA |
| SEQ ID NO:1365 | 1 | GACTGGAGTTCAGACGTGTGCTCTTCCGATCTTGATGCTGAGGAAGTGGATTTTGCAGG |
| SEQ ID NO:1366 | 1 | GACTGGAGTTCAGACGTGTGCTCTTCCGATCTTGATGGATTTGATGAATTGGTGATAAGATTA |
| SEQ ID NO:1367 | 1 | GACTGGAGTTCAGACGTGTGCTCTTCCGATCTTGATGTCTATGAAGTGTTGTGGTTCCT |
| SEQ ID NO:1368 | 1 | GACTGGAGTTCAGACGTGTGCTCTTCCGATCTTGATTCGTCATAGTTGTTGCAAGCCGA |
| SEQ ID NO:1369 | 1 | GACTGGAGTTCAGACGTGTGCTCTTCCGATCTTGCAAGGTTTACACATTTTAATCCCA |
| SEQ ID NO:1370 | 1 | GACTGGAGTTCAGACGTGTGCTCTTCCGATCTTGCACCGCGACCTGGCAG |
| SEQ ID NO:1371 | 1 | GACTGGAGTTCAGACGTGTGCTCTTCCGATCTTGCAGAAAGACTTGAAGGCGTATACAGG |

FIG. 7BE

| Target Specific Primer | Volume Ratio | Sequence |
|---|---|---|
| SEQ ID NO:1372 | 1 | GACTGGAGTTCAGACGTGTGCTCTTCCGATCTTGCAGAAGTCCAGGCTGAAAAGGC |
| SEQ ID NO:1373 | 1 | GACTGGAGTTCAGACGTGTGCTCTTCCGATCTTGCAGTTTTTCCTCCTACTCACCATCC |
| SEQ ID NO:1374 | 1 | GACTGGAGTTCAGACGTGTGCTCTTCCGATCTTGCATAACAACAAAGAATATGAATATGGATCA |
| SEQ ID NO:1375 | 1 | GACTGGAGTTCAGACGTGTGCTCTTCCGATCTTGCCAACATGACTTACTTGATCCCCATAA |
| SEQ ID NO:1376 | 1 | GACTGGAGTTCAGACGTGTGCTCTTCCGATCTTGCCAGTTAACGTCTTCCTTCTCTCTC |
| SEQ ID NO:1377 | 1 | GACTGGAGTTCAGACGTGTGCTCTTCCGATCTTGCCAGTTAACGTCTTCCTTCTCTCTC |
| SEQ ID NO:1378 | 1 | GACTGGAGTTCAGACGTGTGCTCTTCCGATCTTGCCAGTTAACGTCTTCCTTCTCTCTC |
| SEQ ID NO:1379 | 1 | GACTGGAGTTCAGACGTGTGCTCTTCCGATCTTGCCATCATTCTAGGAAGCTCACCATT |
| SEQ ID NO:1380 | 1 | GACTGGAGTTCAGACGTGTGCTCTTCCGATCTTGCCATGCTACCTAGATACCTTTCCCT |
| SEQ ID NO:1381 | 1 | GACTGGAGTTCAGACGTGTGCTCTTCCGATCTTGCCCCAAGAATCCTAGTAGAATGTT |
| SEQ ID NO:1382 | 1 | GACTGGAGTTCAGACGTGTGCTCTTCCGATCTTGCCTCAATAAGCCAACCATGTCTTTCA |
| SEQ ID NO:1383 | 1 | GACTGGAGTTCAGACGTGTGCTCTTCCGATCTTGCCTCTGGTGCCCCCCG |
| SEQ ID NO:1384 | 1 | GACTGGAGTTCAGACGTGTGCTCTTCCGATCTTGCCTGGCTCCCTAATTTTATAGTTTTT |
| SEQ ID NO:1385 | 1 | GACTGGAGTTCAGACGTGTGCTCTTCCGATCTTGCGAACAGTGAATATTTCCTTTGATGA |
| SEQ ID NO:1386 | 1 | GACTGGAGTTCAGACGTGTGCTCTTCCGATCTTGCGACAGATCCGGAATATTGTAGAGA |
| SEQ ID NO:1387 | 1 | GACTGGAGTTCAGACGTGTGCTCTTCCGATCTTGCGGCTCGTACACAGGGAC |
| SEQ ID NO:1388 | 1 | GACTGGAGTTCAGACGTGTGCTCTTCCGATCTTGCTAACCAAGTTCTTTCTTTTGCACA |
| SEQ ID NO:1389 | 1 | GACTGGAGTTCAGACGTGTGCTCTTCCGATCTTGCTAAGAACCGGTCACTGAAAATGAA |
| SEQ ID NO:1390 | 1 | GACTGGAGTTCAGACGTGTGCTCTTCCGATCTTGCTCCCAGGCTGTTTATTTGAAGAGA |

FIG. 7BF

| Target Specific Primer | Volume Ratio | Sequence |
|---|---|---|
| SEQ ID NO:1391 | 1 | GACTGGAGTTCAGACGTGTGCTCTTCCGATCTTGCTGGATTGAAATTCACTTACACCGG |
| SEQ ID NO:1392 | 1 | GACTGGAGTTCAGACGTGTGCTCTTCCGATCTTGCTGTCAGAGTTCAACGTCCTGA |
| SEQ ID NO:1393 | 1 | GACTGGAGTTCAGACGTGTGCTCTTCCGATCTTGCTGTGAGGGTTTTTTGATGTTACCA |
| SEQ ID NO:1394 | 1 | GACTGGAGTTCAGACGTGTGCTCTTCCGATCTTGCTTTTCTAACTCTCTTTGACTGCAG |
| SEQ ID NO:1395 | 1 | GACTGGAGTTCAGACGTGTGCTCTTCCGATCTTGCTTTTCTAACTCTCTTTGACTGCAGAAT |
| SEQ ID NO:1396 | 1 | GACTGGAGTTCAGACGTGTGCTCTTCCGATCTTGGAAAGAGTAATTCACACAAGCTCACC |
| SEQ ID NO:1397 | 1 | GACTGGAGTTCAGACGTGTGCTCTTCCGATCTTGGAACTAGGTCAGCTGAAGATCCTGT |
| SEQ ID NO:1398 | 1 | GACTGGAGTTCAGACGTGTGCTCTTCCGATCTTGGAAGCCAAGCCCAGTTCTGG |
| SEQ ID NO:1399 | 1 | GACTGGAGTTCAGACGTGTGCTCTTCCGATCTTGGAAGTCTATGTGATCAAGAAATCGA |
| SEQ ID NO:1400 | 1 | GACTGGAGTTCAGACGTGTGCTCTTCCGATCTTGGAATCCAGTGTTTCTTTTAAATACCTGT |
| SEQ ID NO:1401 | 1 | GACTGGAGTTCAGACGTGTGCTCTTCCGATCTTGGACCCATGACTCAACCTCAGTATTT |
| SEQ ID NO:1402 | 1 | GACTGGAGTTCAGACGTGTGCTCTTCCGATCTTGGACGATTTCACCCAGACCCATGAA |
| SEQ ID NO:1403 | 1 | GACTGGAGTTCAGACGTGTGCTCTTCCGATCTTGGAGAAAAATGTGATTGCCTGGGTGT |
| SEQ ID NO:1404 | 1 | GACTGGAGTTCAGACGTGTGCTCTTCCGATCTTGGAGAAGTTAGACATGTCAACCTTTT |
| SEQ ID NO:1405 | 1 | GACTGGAGTTCAGACGTGTGCTCTTCCGATCTTGGAGTCTGGATGGAAGGACAAAAGA |
| SEQ ID NO:1406 | 1 | GACTGGAGTTCAGACGTGTGCTCTTCCGATCTTGGATCATATTGGCCTGTCTGCTCTTC |
| SEQ ID NO:1407 | 1 | GACTGGAGTTCAGACGTGTGCTCTTCCGATCTTGGATGTGATTGGAAAGTGGGGTAAAA |
| SEQ ID NO:1408 | 1 | GACTGGAGTTCAGACGTGTGCTCTTCCGATCTTGGATTGAAATTCACTTACACCGGGCC |
| SEQ ID NO:1409 | 1 | GACTGGAGTTCAGACGTGTGCTCTTCCGATCTTGGATTTGATGAATTGGTGATAAGATTAACA |

FIG. 7BG

| Target Specific Primer | Volume Ratio | Sequence |
|---|---|---|
| SEQ ID NO:1410 | 1 | GACTGGAGTTCAGACGTGTGCTCTTCCGATCTTGGCAAACAATACCAAATTTACTTCATGT |
| SEQ ID NO:1411 | 1 | GACTGGAGTTCAGACGTGTGCTCTTCCGATCTTGGCAATTCATTTCCAATCAAACCCACA |
| SEQ ID NO:1412 | 1 | GACTGGAGTTCAGACGTGTGCTCTTCCGATCTTGGCACATCAAGGGAGGGTTC |
| SEQ ID NO:1413 | 1 | GACTGGAGTTCAGACGTGTGCTCTTCCGATCTTGGCACATTCCATTCTTACCAAACTCTAAA |
| SEQ ID NO:1414 | 1 | GACTGGAGTTCAGACGTGTGCTCTTCCGATCTTGGCACATTCCATTCTTACCAAACTCTAAA |
| SEQ ID NO:1415 | 1 | GACTGGAGTTCAGACGTGTGCTCTTCCGATCTTGGCAGTCAAACCTTCTCTCTTATGTATA |
| SEQ ID NO:1416 | 1 | GACTGGAGTTCAGACGTGTGCTCTTCCGATCTTGGCAGTCAAACCTTCTCTCTTATGTATAT |
| SEQ ID NO:1417 | 1 | GACTGGAGTTCAGACGTGTGCTCTTCCGATCTTGGCATGGGGAAATATAAACTTGTTTGA |
| SEQ ID NO:1418 | 1 | GACTGGAGTTCAGACGTGTGCTCTTCCGATCTTGGCCATGGAACCAGACAGAAAAGC |
| SEQ ID NO:1419 | 1 | GACTGGAGTTCAGACGTGTGCTCTTCCGATCTTGGCCATTTCTGTTTTCCTGTAGCAAA |
| SEQ ID NO:1420 | 1 | GACTGGAGTTCAGACGTGTGCTCTTCCGATCTTGGCTTGATCCTGAGTCATTTCTTCCT |
| SEQ ID NO:1421 | 1 | GACTGGAGTTCAGACGTGTGCTCTTCCGATCTTGGGAAAAGTGGTGGTATACGATATGGGT |
| SEQ ID NO:1422 | 1 | GACTGGAGTTCAGACGTGTGCTCTTCCGATCTTGGGAAGGGACAGAAGATGACAGGG |
| SEQ ID NO:1423 | 1 | GACTGGAGTTCAGACGTGTGCTCTTCCGATCTTGGGAATTTAAAGGAGCTGGAAAGAGTGC |
| SEQ ID NO:1424 | 1 | GACTGGAGTTCAGACGTGTGCTCTTCCGATCTTGGGATGTTTTGCAGATGATGGGCTC |
| SEQ ID NO:1425 | 1 | GACTGGAGTTCAGACGTGTGCTCTTCCGATCTTGGGCCCCAGAACTAACAGGTTAAGTG |
| SEQ ID NO:1426 | 1 | GACTGGAGTTCAGACGTGTGCTCTTCCGATCTTGGGTAAAGATGATCCGACAAGTGAGA |
| SEQ ID NO:1427 | 1 | GACTGGAGTTCAGACGTGTGCTCTTCCGATCTTGGGTAGCAAACTTCTGTACACAACTAAC |
| SEQ ID NO:1428 | 1 | GACTGGAGTTCAGACGTGTGCTCTTCCGATCTTGGTATTTTGGTTCTAGATCTTTGTTCC |

FIG. 7BH

| Target Specific Primer | Volume Ratio | Sequence |
|---|---|---|
| SEQ ID NO:1429 | 1 | GACTGGAGTTCAGACGTGTGCTCTTCCGATCTTGGTGGCTTTTTGTTTGTTTGTTTTGT |
| SEQ ID NO:1430 | 1 | GACTGGAGTTCAGACGTGTGCTCTTCCGATCTTGGTGGCTTTTTGTTTGTTTGTTTTGTTTT |
| SEQ ID NO:1431 | 1 | GACTGGAGTTCAGACGTGTGCTCTTCCGATCTTGGTTACATACTTGGACTTGGTGATAGA |
| SEQ ID NO:1432 | 1 | GACTGGAGTTCAGACGTGTGCTCTTCCGATCTTGGTTCAGAGTTCTATAGATTCTAGTGCA |
| SEQ ID NO:1433 | 1 | GACTGGAGTTCAGACGTGTGCTCTTCCGATCTTGGTTCTAGATCTTTGTTCCTTCCATTC |
| SEQ ID NO:1434 | 1 | GACTGGAGTTCAGACGTGTGCTCTTCCGATCTTGGTTGATATTATTCTTCTTGTGCCTGGG |
| SEQ ID NO:1435 | 1 | GACTGGAGTTCAGACGTGTGCTCTTCCGATCTTGGTTGTGTTTGGTTTTGTGGGAGTCT |
| SEQ ID NO:1436 | 1 | GACTGGAGTTCAGACGTGTGCTCTTCCGATCTTGGTTTGTTTTGGTTGTGTTTGGTTTT |
| SEQ ID NO:1437 | 1 | GACTGGAGTTCAGACGTGTGCTCTTCCGATCTTGTAAGTCAAAGGGGTATTCGATGATCC |
| SEQ ID NO:1438 | 1 | GACTGGAGTTCAGACGTGTGCTCTTCCGATCTTGTAATCAGACGACACAGGAAGCAGAT |
| SEQ ID NO:1439 | 1 | GACTGGAGTTCAGACGTGTGCTCTTCCGATCTTGTACCAACCTCACCAACATTACAGAG |
| SEQ ID NO:1440 | 1 | GACTGGAGTTCAGACGTGTGCTCTTCCGATCTTGTACCAACCTCACCAACATTACAGAG |
| SEQ ID NO:1441 | 1 | GACTGGAGTTCAGACGTGTGCTCTTCCGATCTTGTAGAGGTTAATATCCGCAAATGACT |
| SEQ ID NO:1442 | 1 | GACTGGAGTTCAGACGTGTGCTCTTCCGATCTTGTAGGAGTGGTCATAAGGCTGGTATAA |
| SEQ ID NO:1443 | 1 | GACTGGAGTTCAGACGTGTGCTCTTCCGATCTTGTATTATATAGGGCAGAGTCATGTTAGTC |
| SEQ ID NO:1444 | 1 | GACTGGAGTTCAGACGTGTGCTCTTCCGATCTTGTATTCACAGAGACTTGGCAGCCA |
| SEQ ID NO:1445 | 1 | GACTGGAGTTCAGACGTGTGCTCTTCCGATCTTGTATTTAACCATGCAGATCCTCAGTT |
| SEQ ID NO:1446 | 1 | GACTGGAGTTCAGACGTGTGCTCTTCCGATCTTGTCAAAAATTGTTTCTGGGGCCATCC |
| SEQ ID NO:1447 | 1 | GACTGGAGTTCAGACGTGTGCTCTTCCGATCTTGTCAAGCCCTCCAACATCCTAGTCAA |

FIG. 7BI

| Target Specific Primer | Volume Ratio | Sequence |
|---|---|---|
| SEQ ID NO:1448 | 1 | GACTGGAGTTCAGACGTGTGCTCTTCCGATCTTGTCACAGCACCCTAGAACCAAATCCA |
| SEQ ID NO:1449 | 1 | GACTGGAGTTCAGACGTGTGCTCTTCCGATCTTGTCACCCACATCAAGATTCAGAACAC |
| SEQ ID NO:1450 | 1 | GACTGGAGTTCAGACGTGTGCTCTTCCGATCTTGTCAGTCTGCCCTTCTGTCAAAGTGG |
| SEQ ID NO:1451 | 1 | GACTGGAGTTCAGACGTGTGCTCTTCCGATCTTGTCCAGTCACTGTGCTGCTTCA |
| SEQ ID NO:1452 | 1 | GACTGGAGTTCAGACGTGTGCTCTTCCGATCTTGTCCTGCGTCATCATCTTTGTCATCG |
| SEQ ID NO:1453 | 1 | GACTGGAGTTCAGACGTGTGCTCTTCCGATCTTGTCCTTATTACTTGGGAGACTTGTCT |
| SEQ ID NO:1454 | 1 | GACTGGAGTTCAGACGTGTGCTCTTCCGATCTTGTCTATGAAGTGTTGTGGTTCCTTAA |
| SEQ ID NO:1455 | 1 | GACTGGAGTTCAGACGTGTGCTCTTCCGATCTTGTCTCACTGCCTCATCTCTCACCATC |
| SEQ ID NO:1456 | 1 | GACTGGAGTTCAGACGTGTGCTCTTCCGATCTTGTCTCATCCCAAATATTCTCCAGGCGT |
| SEQ ID NO:1457 | 1 | GACTGGAGTTCAGACGTGTGCTCTTCCGATCTTGTGACCTTCGGCTTTTTCAACCCTTT |
| SEQ ID NO:1458 | 1 | GACTGGAGTTCAGACGTGTGCTCTTCCGATCTTGTGAGTGGGATTTGTTTTGTGGGCTAC |
| SEQ ID NO:1459 | 1 | GACTGGAGTTCAGACGTGTGCTCTTCCGATCTTGTGATGAGAGGTGGATGGGTAGTAGT |
| SEQ ID NO:1460 | 1 | GACTGGAGTTCAGACGTGTGCTCTTCCGATCTTGTGCATTATTGTGATGATTCTGACCT |
| SEQ ID NO:1461 | 1 | GACTGGAGTTCAGACGTGTGCTCTTCCGATCTTGTGCATTATTGTGATGATTCTGACCTACA |
| SEQ ID NO:1462 | 1 | GACTGGAGTTCAGACGTGTGCTCTTCCGATCTTGTGGCTACATGTTCCTGATCTCCTTA |
| SEQ ID NO:1463 | 1 | GACTGGAGTTCAGACGTGTGCTCTTCCGATCTTGTGGGTATTTCAGAGAGGGATTAAGT |
| SEQ ID NO:1464 | 1 | GACTGGAGTTCAGACGTGTGCTCTTCCGATCTTGTGGGTATTTCAGAGAGGGATTAAGTAAT |
| SEQ ID NO:1465 | 1 | GACTGGAGTTCAGACGTGTGCTCTTCCGATCTTGTTAATGGTGGCTTTTTGTTTGTTTGT |
| SEQ ID NO:1466 | 1 | GACTGGAGTTCAGACGTGTGCTCTTCCGATCTTGTTACTTACCTGTCTTGTCTTTGCTG |

FIG. 7BJ

| Target Specific Primer | Volume Ratio | Sequence |
|---|---|---|
| SEQ ID NO:1467 | 1 | GACTGGAGTTCAGACGTGTGCTCTTCCGATCTTGTTCCTCAAAGTTTTCCTCTAGCAGA |
| SEQ ID NO:1468 | 1 | GACTGGAGTTCAGACGTGTGCTCTTCCGATCTTGTTAACTTTGTGTCGCTACCTCAGT |
| SEQ ID NO:1469 | 1 | GACTGGAGTTCAGACGTGTGCTCTTCCGATCTTGTTTATTTTGTTCTCCCACACAGAC |
| SEQ ID NO:1470 | 1 | GACTGGAGTTCAGACGTGTGCTCTTCCGATCTTGTTTCTGTCATCCAAATACTCCACACG |
| SEQ ID NO:1471 | 1 | GACTGGAGTTCAGACGTGTGCTCTTCCGATCTTGTTTTAGAAAGATCACATCACATGAATGG |
| SEQ ID NO:1472 | 1 | GACTGGAGTTCAGACGTGTGCTCTTCCGATCTTGTTTTGAAATGTGTTTTATAATTTAGACTAGTGA |
| SEQ ID NO:1473 | 1 | GACTGGAGTTCAGACGTGTGCTCTTCCGATCTTGTTTTGGTTGTGTTTGGTTTTGTGGG |
| SEQ ID NO:1474 | 1 | GACTGGAGTTCAGACGTGTGCTCTTCCGATCTTTACCATGGACCCTGACAAATGTGCTG |
| SEQ ID NO:1475 | 1 | GACTGGAGTTCAGACGTGTGCTCTTCCGATCTTTACGCGCCACAGAGAAGTTGTTGAGG |
| SEQ ID NO:1476 | 1 | GACTGGAGTTCAGACGTGTGCTCTTCCGATCTTTAGACTAGTGAATATTTTCTTTGTTTTTAAGGA |
| SEQ ID NO:1477 | 1 | GACTGGAGTTCAGACGTGTGCTCTTCCGATCTTTAGATGGGGATGGCTGTTGTTAACC |
| SEQ ID NO:1478 | 1 | GACTGGAGTTCAGACGTGTGCTCTTCCGATCTTTATAGCTGATTTGATGGAGTTGGACA |
| SEQ ID NO:1479 | 1 | GACTGGAGTTCAGACGTGTGCTCTTCCGATCTTTATTTGTTTCTCCCACACAGACACT |
| SEQ ID NO:1480 | 1 | GACTGGAGTTCAGACGTGTGCTCTTCCGATCTTTCACCCAGACCCATGAATACCACGTG |
| SEQ ID NO:1481 | 1 | GACTGGAGTTCAGACGTGTGCTCTTCCGATCTTTCAGGGGCCATGGTCTTCGAGTT |
| SEQ ID NO:1482 | 1 | GACTGGAGTTCAGACGTGTGCTCTTCCGATCTTTCATCCCTTCCTCCCTCTTTCTTTCA |
| SEQ ID NO:1483 | 1 | GACTGGAGTTCAGACGTGTGCTCTTCCGATCTTTCATCCCTTCCTCCCTCTTTCTTTCA |
| SEQ ID NO:1484 | 1 | GACTGGAGTTCAGACGTGTGCTCTTCCGATCTTTCATGGAATTTAAAGGAGCTGGAA |
| SEQ ID NO:1485 | 1 | GACTGGAGTTCAGACGTGTGCTCTTCCGATCTTTCCCACAGCAAAACACCAAAAGACCA |

FIG. 7BK

| Target Specific Primer | Volume Ratio | Sequence |
|---|---|---|
| SEQ ID NO:1486 | 1 | GACTGGAGTTCAGACGTGTGCTCTTCCGATCTTTCCCTTTCCGAATGCCAAACACCTTC |
| SEQ ID NO:1487 | 1 | GACTGGAGTTCAGACGTGTGCTCTTCCGATCTTTCCGACTTCCCTTTCCGAATGCCAAA |
| SEQ ID NO:1488 | 1 | GACTGGAGTTCAGACGTGTGCTCTTCCGATCTTTCCTGCAGAAAGACTTGAAGGCGTAT |
| SEQ ID NO:1489 | 1 | GACTGGAGTTCAGACGTGTGCTCTTCCGATCTTTCTGCCCTTTGAACTTGCTCCCTCAG |
| SEQ ID NO:1490 | 1 | GACTGGAGTTCAGACGTGTGCTCTTCCGATCTTTCTTCCCATGATGATCTGTCCCTC |
| SEQ ID NO:1491 | 1 | GACTGGAGTTCAGACGTGTGCTCTTCCGATCTTTCTTTAAATCTGTTTTGGGGCTTGA |
| SEQ ID NO:1492 | 1 | GACTGGAGTTCAGACGTGTGCTCTTCCGATCTTTGAAAACAATGGTGACTACATGGACA |
| SEQ ID NO:1493 | 1 | GACTGGAGTTCAGACGTGTGCTCTTCCGATCTTTGAGGGCTGAGGTGGAAGAGACAG |
| SEQ ID NO:1494 | 1 | GACTGGAGTTCAGACGTGTGCTCTTCCGATCTTTGATGGCAAACACACACAGGAAGC |
| SEQ ID NO:1495 | 1 | GACTGGAGTTCAGACGTGTGCTCTTCCGATCTTTGATGGGAAAAAGTGGTGGTATACGA |
| SEQ ID NO:1496 | 1 | GACTGGAGTTCAGACGTGTGCTCTTCCGATCTTTGCAGGGGTGGCTATGTAGAGAAGTT |
| SEQ ID NO:1497 | 1 | GACTGGAGTTCAGACGTGTGCTCTTCCGATCTTTGCCAACATGACTTACTTGATCCCCA |
| SEQ ID NO:1498 | 1 | GACTGGAGTTCAGACGTGTGCTCTTCCGATCTTTGCCTGTCTAAAGAACACTTACCTCA |
| SEQ ID NO:1499 | 1 | GACTGGAGTTCAGACGTGTGCTCTTCCGATCTTTGGGGCTTGAACATACTAAATGCTC |
| SEQ ID NO:1500 | 1 | GACTGGAGTTCAGACGTGTGCTCTTCCGATCTTTGGGGTTGTAGTCGGTCATGATGGTC |
| SEQ ID NO:1501 | 1 | GACTGGAGTTCAGACGTGTGCTCTTCCGATCTTTGTAAGTGCCCGAAGTGTAAGCCCAA |
| SEQ ID NO:1502 | 1 | GACTGGAGTTCAGACGTGTGCTCTTCCGATCTTTGTACTGCAGAGACAAGAGGATGGC |
| SEQ ID NO:1503 | 1 | GACTGGAGTTCAGACGTGTGCTCTTCCGATCTTTGTAGTCGGTCATGATGGTCGAGGTG |
| SEQ ID NO:1504 | 1 | GACTGGAGTTCAGACGTGTGCTCTTCCGATCTTTGTCGTCGATTCTTGTGTGCTGTCTT |

FIG. 7BL

| Target Specific Primer | Volume Ratio | Sequence |
|---|---|---|
| SEQ ID NO:1505 | 1 | GACTGGAGTTCAGACGTGTGCTCTTCCGATCTTTGTTCCTTCCATTCTTATAGAGCTCA |
| SEQ ID NO:1506 | 1 | GACTGGAGTTCAGACGTGTGCTCTTCCGATCTTTGTTTGTTTCTTTTTTCTCCAGTTGG |
| SEQ ID NO:1507 | 1 | GACTGGAGTTCAGACGTGTGCTCTTCCGATCTTTTAAATCTGTTTTGGGGGCTTGAACA |
| SEQ ID NO:1508 | 1 | GACTGGAGTTCAGACGTGTGCTCTTCCGATCTTTTAACACATCAAGGTTGGAATGAGCT |
| SEQ ID NO:1509 | 1 | GACTGGAGTTCAGACGTGTGCTCTTCCGATCTTTTAGAAAGATCACATCACATGAATGGAAT |
| SEQ ID NO:1510 | 1 | GACTGGAGTTCAGACGTGTGCTCTTCCGATCTTTTAGACCTTGAGTTCTTGAGTTCCTC |
| SEQ ID NO:1511 | 1 | GACTGGAGTTCAGACGTGTGCTCTTCCGATCTTTTCCAATCAAACCCACAGACTTACCT |
| SEQ ID NO:1512 | 1 | GACTGGAGTTCAGACGTGTGCTCTTCCGATCTTTTCCCAAAGTACAAACGAGATGCCT |
| SEQ ID NO:1513 | 1 | GACTGGAGTTCAGACGTGTGCTCTTCCGATCTTTTCCTCTGTGTTGGCGGATACCCTTC |
| SEQ ID NO:1514 | 1 | GACTGGAGTTCAGACGTGTGCTCTTCCGATCTTTTCCTTAGTCTTTCTTTGAAGCAGCA |
| SEQ ID NO:1515 | 1 | GACTGGAGTTCAGACGTGTGCTCTTCCGATCTTTTCTTCTTCTCATCGCGGGCTTGGTT |
| SEQ ID NO:1516 | 1 | GACTGGAGTTCAGACGTGTGCTCTTCCGATCTTTTGAACTTGCTCCCTCAGGCTACTCA |
| SEQ ID NO:1517 | 1 | GACTGGAGTTCAGACGTGTGCTCTTCCGATCTTTTGACAGTTTGACAGTTAAAGGCATT |
| SEQ ID NO:1518 | 1 | GACTGGAGTTCAGACGTGTGCTCTTCCGATCTTTTGACTCACCGGTGGATGAAGTGGTT |
| SEQ ID NO:1519 | 1 | GACTGGAGTTCAGACGTGTGCTCTTCCGATCTTTTGAGTCTATCGAGTGTGTGCATATG |
| SEQ ID NO:1520 | 1 | GACTGGAGTTCAGACGTGTGCTCTTCCGATCTTTTGGGAATGCCTGGTTTATTTGGGAC |
| SEQ ID NO:1521 | 1 | GACTGGAGTTCAGACGTGTGCTCTTCCGATCTTTTGGTTCTAGATCTTTGTTCCTTCCA |
| SEQ ID NO:1522 | 1 | GACTGGAGTTCAGACGTGTGCTCTTCCGATCTTTTGTTAATGGTGCTTTTTGTTTGTT |
| SEQ ID NO:1523 | 1 | GACTGGAGTTCAGACGTGTGCTCTTCCGATCTTTTGTTTCTCCCACACAGACACTATTG |

FIG. 7BM

| Target Specific Primer | Volume Ratio | Sequence |
| --- | --- | --- |
| SEQ ID NO:1524 | 1 | GACTGGAGTTCAGACGTGTGCTCTTCCGATCTTTTTATGGCAGTCAAACCTTCTCTCTT |
| SEQ ID NO:1525 | 1 | GACTGGAGTTCAGACGTGTGCTCTTCCGATCTTTTTCTCTTCCCTGCAGATGTCAAGCC |
| SEQ ID NO:1526 | 1 | GACTGGAGTTCAGACGTGTGCTCTTCCGATCTTTTTCTCTTGCAGTCGTCAGCCTGAAC |
| SEQ ID NO:1527 | 1 | GACTGGAGTTCAGACGTGTGCTCTTCCGATCTTTTTGAAGACCATAACCCACCACAGCT |
| SEQ ID NO:1528 | 1 | GACTGGAGTTCAGACGTGTGCTCTTCCGATCTTTTTTAGCAAGGTGAAGTAAGACTCAAA |
| SEQ ID NO:1529 | 1 | GACTGGAGTTCAGACGTGTGCTCTTCCGATCTTTTTTTAGCAAGGTGAAGTAAGACTCAA |

SEQUENCE LISTING

<160> NUMBER OF SEQ ID NOS: 1529

<210> SEQ ID NO 1
<211> LENGTH: 32
<212> TYPE: DNA
<213> ORGANISM: Artificial
<220> FEATURE:
<223> OTHER INFORMATION: Synthetic sequences

<400> SEQUENCE: 1
agatcggaag agcgtcgtgt agggaaagag tg        32

<210> SEQ ID NO 2
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(14)
<223> OTHER INFORMATION: n is a, c, g, or t

<400> SEQUENCE: 2
gannnnnnnn nnnnagatcg aagagcgtc gtgtagggaa agagtg        46

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
cactctttcc ctacacgacg c        21

<210> SEQ ID NO 4

```
<211> LENGTH: 57
<212> TYPE: DNA
<213> ORGANISM: Homo Sapiens

<400> SEQUENCE: 4
gactggagtt cagacgtgtg ctcttccgat ctaaaacatc ccacgcctag tccctgg      57

<210> SEQ ID NO 5
<211> LENGTH: 54
<212> TYPE: DNA
<213> ORGANISM: Homo Sapiens

<400> SEQUENCE: 5
gactggagtt cagacgtgtg ctcttccgat ctaaacaggt ttccagtgcc agct         54

<210> SEQ ID NO 6
<211> LENGTH: 65
<212> TYPE: DNA
<213> ORGANISM: Homo Sapiens

<400> SEQUENCE: 6
gactggagtt cagacgtgtg ctcttccgat ctaaacccat agaaggggta tttgttggat   60
tattt                                                               65

<210> SEQ ID NO 7
<211> LENGTH: 58
<212> TYPE: DNA
<213> ORGANISM: Homo Sapiens

<400> SEQUENCE: 7
gactggagtt cagacgtgtg ctcttccgat ctaaagccac ctccttactt tgcctcct     58

<210> SEQ ID NO 8
<211> LENGTH: 59
<212> TYPE: DNA
<213> ORGANISM: Homo Sapiens

<400> SEQUENCE: 8
gactggagtt cagacgtgtg ctcttccgat ctaacagatt gtgaacagcc ttggaagcc    59

<210> SEQ ID NO 9
<211> LENGTH: 59
<212> TYPE: DNA
<213> ORGANISM: Homo Sapiens

<400> SEQUENCE: 9
gactggagtt cagacgtgtg ctcttccgat ctaacatgca gaagtccagg ctgaaaagg    59

<210> SEQ ID NO 10
<211> LENGTH: 63
<212> TYPE: DNA
<213> ORGANISM: Homo Sapiens

<400> SEQUENCE: 10
gactggagtt cagacgtgtg ctcttccgat ctaaccatca tgatgtgtta cccagaatgt   60
ttt                                                                 63

<210> SEQ ID NO 11
<211> LENGTH: 57
<212> TYPE: DNA
<213> ORGANISM: Homo Sapiens

<400> SEQUENCE: 11
```

```
gactggagtt cagacgtgtg ctcttccgat ctaaccgtag ttcacatgca ctcctgt        57
```

<210> SEQ ID NO 12
<211> LENGTH: 59
<212> TYPE: DNA
<213> ORGANISM: Homo Sapiens

<400> SEQUENCE: 12

```
gactggagtt cagacgtgtg ctcttccgat ctaactaaca ggttaagtgc tcccagggg     59
```

<210> SEQ ID NO 13
<211> LENGTH: 59
<212> TYPE: DNA
<213> ORGANISM: Homo Sapiens

<400> SEQUENCE: 13

```
gactggagtt cagacgtgtg ctcttccgat ctaactttgt gtcgctacct cagtttgcc    59
```

<210> SEQ ID NO 14
<211> LENGTH: 59
<212> TYPE: DNA
<213> ORGANISM: Homo Sapiens

<400> SEQUENCE: 14

```
gactggagtt cagacgtgtg ctcttccgat ctaagagtaa ttcacacaag ctcacctga    59
```

<210> SEQ ID NO 15
<211> LENGTH: 59
<212> TYPE: DNA
<213> ORGANISM: Homo Sapiens

<400> SEQUENCE: 15

```
gactggagtt cagacgtgtg ctcttccgat ctaagcagga tctcaggtct ctcaaaggg    59
```

<210> SEQ ID NO 16
<211> LENGTH: 59
<212> TYPE: DNA
<213> ORGANISM: Homo Sapiens

<400> SEQUENCE: 16

```
gactggagtt cagacgtgtg ctcttccgat ctaaggcaaa cacatccacc caaagactc    59
```

<210> SEQ ID NO 17
<211> LENGTH: 58
<212> TYPE: DNA
<213> ORGANISM: Homo Sapiens

<400> SEQUENCE: 17

```
gactggagtt cagacgtgtg ctcttccgat ctaagtgaat tgcagtcctt ccctctg     58
```

<210> SEQ ID NO 18
<211> LENGTH: 59
<212> TYPE: DNA
<213> ORGANISM: Homo Sapiens

<400> SEQUENCE: 18

```
gactggagtt cagacgtgtg ctcttccgat ctaatctatt gtgggctctg ggaatcctg   59
```

<210> SEQ ID NO 19
<211> LENGTH: 67
<212> TYPE: DNA
<213> ORGANISM: Homo Sapiens -continued

<400> SEQUENCE: 19
gactggagtt cagacgtgtg ctcttccgat ctaattctta agtaatacta accttgaacc     60
gactggt                                                              67

<210> SEQ ID NO 20
<211> LENGTH: 59
<212> TYPE: DNA
<213> ORGANISM: Homo Sapiens

<400> SEQUENCE: 20
gactggagtt cagacgtgtg ctcttccgat ctacaagagc agaaagtcag tcccatgga     59

<210> SEQ ID NO 21
<211> LENGTH: 59
<212> TYPE: DNA
<213> ORGANISM: Homo Sapiens

<400> SEQUENCE: 21
gactggagtt cagacgtgtg ctcttccgat ctacaagttg gaaatttctg ggccatgaa     59

<210> SEQ ID NO 22
<211> LENGTH: 59
<212> TYPE: DNA
<213> ORGANISM: Homo Sapiens

<400> SEQUENCE: 22
gactggagtt cagacgtgtg ctcttccgat ctacacagaa agggcccaaa ttcaccaat     59

<210> SEQ ID NO 23
<211> LENGTH: 59
<212> TYPE: DNA
<213> ORGANISM: Homo Sapiens

<400> SEQUENCE: 23
gactggagtt cagacgtgtg ctcttccgat ctacagaaga cctcacatgc cacaaagaa     59

<210> SEQ ID NO 24
<211> LENGTH: 59
<212> TYPE: DNA
<213> ORGANISM: Homo Sapiens

<400> SEQUENCE: 24
gactggagtt cagacgtgtg ctcttccgat ctacatgtgg agtgaacgtt gttggactc     59

<210> SEQ ID NO 25
<211> LENGTH: 62
<212> TYPE: DNA
<213> ORGANISM: Homo Sapiens

<400> SEQUENCE: 25
gactggagtt cagacgtgtg ctcttccgat ctaccaactc cataaactaa acagaaagcg     60
gt                                                                   62

<210> SEQ ID NO 26
<211> LENGTH: 59
<212> TYPE: DNA
<213> ORGANISM: Homo Sapiens

<400> SEQUENCE: 26
gactggagtt cagacgtgtg ctcttccgat ctaccgggat tatgtctctt gtttgggga     59

```
<210> SEQ ID NO 27
<211> LENGTH: 58
<212> TYPE: DNA
<213> ORGANISM: Homo Sapiens

<400> SEQUENCE: 27
gactggagtt cagacgtgtg ctcttccgat ctacggaata taagctggtg gtggtggg      58

<210> SEQ ID NO 28
<211> LENGTH: 59
<212> TYPE: DNA
<213> ORGANISM: Homo Sapiens

<400> SEQUENCE: 28
gactggagtt cagacgtgtg ctcttccgat ctacgggaga aaatagcacc tcacttcca     59

<210> SEQ ID NO 29
<211> LENGTH: 59
<212> TYPE: DNA
<213> ORGANISM: Homo Sapiens

<400> SEQUENCE: 29
gactggagtt cagacgtgtg ctcttccgat ctactaggtc agctgaagat cctgtgagc     59

<210> SEQ ID NO 30
<211> LENGTH: 59
<212> TYPE: DNA
<213> ORGANISM: Homo Sapiens

<400> SEQUENCE: 30
gactggagtt cagacgtgtg ctcttccgat ctactccaca cgcaaatttc cttccactc     59

<210> SEQ ID NO 31
<211> LENGTH: 59
<212> TYPE: DNA
<213> ORGANISM: Homo Sapiens

<400> SEQUENCE: 31
gactggagtt cagacgtgtg ctcttccgat ctactgctgg ctgatctatg tccctgaag     59

<210> SEQ ID NO 32
<211> LENGTH: 61
<212> TYPE: DNA
<213> ORGANISM: Homo Sapiens

<400> SEQUENCE: 32
gactggagtt cagacgtgtg ctcttccgat ctactggttt ccaacaggtt cttgctggtg    60
t                                                                    61

<210> SEQ ID NO 33
<211> LENGTH: 59
<212> TYPE: DNA
<213> ORGANISM: Homo Sapiens

<400> SEQUENCE: 33
gactggagtt cagacgtgtg ctcttccgat ctacttactg cagctgtttt cacctctgt     59

<210> SEQ ID NO 34
<211> LENGTH: 56
<212> TYPE: DNA
<213> ORGANISM: Homo Sapiens

<400> SEQUENCE: 34
```
gactggagtt cagacgtgtg ctcttccgat ctagaaaaag tttgctgagc tgggta    56

<210> SEQ ID NO 35
<211> LENGTH: 60
<212> TYPE: DNA
<213> ORGANISM: Homo Sapiens

<400> SEQUENCE: 35
gactggagtt cagacgtgtg ctcttccgat ctagaaggtg tgtctttaat tgaagcatga    60

<210> SEQ ID NO 36
<211> LENGTH: 59
<212> TYPE: DNA
<213> ORGANISM: Homo Sapiens

<400> SEQUENCE: 36
gactggagtt cagacgtgtg ctcttccgat ctagacaata aaggcagct tggacacgg    59

<210> SEQ ID NO 37
<211> LENGTH: 59
<212> TYPE: DNA
<213> ORGANISM: Homo Sapiens

<400> SEQUENCE: 37
gactggagtt cagacgtgtg ctcttccgat ctagaccata acccaccaca gctagaact    59

<210> SEQ ID NO 38
<211> LENGTH: 62
<212> TYPE: DNA
<213> ORGANISM: Homo Sapiens

<400> SEQUENCE: 38
gactggagtt cagacgtgtg ctcttccgat ctagacccaa cacaacttcc ttatgatcac    60
aa    62

<210> SEQ ID NO 39
<211> LENGTH: 57
<212> TYPE: DNA
<213> ORGANISM: Homo Sapiens

<400> SEQUENCE: 39
gactggagtt cagacgtgtg ctcttccgat ctagagtgcc agctgatgaa gacggag    57

<210> SEQ ID NO 40
<211> LENGTH: 59
<212> TYPE: DNA
<213> ORGANISM: Homo Sapiens

<400> SEQUENCE: 40
gactggagtt cagacgtgtg ctcttccgat ctagataatg actcacctgg ggccacatt    59

<210> SEQ ID NO 41
<211> LENGTH: 59
<212> TYPE: DNA
<213> ORGANISM: Homo Sapiens

<400> SEQUENCE: 41
gactggagtt cagacgtgtg ctcttccgat ctagattgtc gtcgattctt gtgtgctgt    59

<210> SEQ ID NO 42
<211> LENGTH: 59
<212> TYPE: DNA
<213> ORGANISM: Homo Sapiens

```
<400> SEQUENCE: 42
gactggagtt cagacgtgtg ctcttccgat ctagcaagtt cttcatcagc tgtactcct      59

<210> SEQ ID NO 43
<211> LENGTH: 62
<212> TYPE: DNA
<213> ORGANISM: Homo Sapiens

<400> SEQUENCE: 43
gactggagtt cagacgtgtg ctcttccgat ctagcactta cctgtgactc catagaaaat      60
ct                                                                    62

<210> SEQ ID NO 44
<211> LENGTH: 58
<212> TYPE: DNA
<213> ORGANISM: Homo Sapiens

<400> SEQUENCE: 44
gactggagtt cagacgtgtg ctcttccgat ctagccacaa aacttacaga tgcagcag        58

<210> SEQ ID NO 45
<211> LENGTH: 59
<212> TYPE: DNA
<213> ORGANISM: Homo Sapiens

<400> SEQUENCE: 45
gactggagtt cagacgtgtg ctcttccgat ctagccagcc cgaagtctgt aattttgac      59

<210> SEQ ID NO 46
<211> LENGTH: 59
<212> TYPE: DNA
<213> ORGANISM: Homo Sapiens

<400> SEQUENCE: 46
gactggagtt cagacgtgtg ctcttccgat ctagccctca tgtctgaact caaagtcct      59

<210> SEQ ID NO 47
<211> LENGTH: 59
<212> TYPE: DNA
<213> ORGANISM: Homo Sapiens

<400> SEQUENCE: 47
gactggagtt cagacgtgtg ctcttccgat ctagctgatt tgatggagtt ggacatggc      59

<210> SEQ ID NO 48
<211> LENGTH: 59
<212> TYPE: DNA
<213> ORGANISM: Homo Sapiens

<400> SEQUENCE: 48
gactggagtt cagacgtgtg ctcttccgat ctaggaaatc aaagaacctg tggccaaac      59

<210> SEQ ID NO 49
<211> LENGTH: 59
<212> TYPE: DNA
<213> ORGANISM: Homo Sapiens

<400> SEQUENCE: 49
gactggagtt cagacgtgtg ctcttccgat ctaggatctt ttcttcacgg ttgcctact      59

<210> SEQ ID NO 50
```

<211> LENGTH: 57
<212> TYPE: DNA
<213> ORGANISM: Homo Sapiens

<400> SEQUENCE: 50
gactggagtt cagacgtgtg ctcttccgat ctaggatgaa caggaagaag cccaccc    57

<210> SEQ ID NO 51
<211> LENGTH: 59
<212> TYPE: DNA
<213> ORGANISM: Homo Sapiens

<400> SEQUENCE: 51
gactggagtt cagacgtgtg ctcttccgat ctagggaggt caaataagca gcaggagaa    59

<210> SEQ ID NO 52
<211> LENGTH: 57
<212> TYPE: DNA
<213> ORGANISM: Homo Sapiens

<400> SEQUENCE: 52
gactggagtt cagacgtgtg ctcttccgat ctaggtcact gatggaggag gtcttgc    57

<210> SEQ ID NO 53
<211> LENGTH: 62
<212> TYPE: DNA
<213> ORGANISM: Homo Sapiens

<400> SEQUENCE: 53
gactggagtt cagacgtgtg ctcttccgat ctagtactta cccactgaaa agcacttcct    60
ga    62

<210> SEQ ID NO 54
<211> LENGTH: 58
<212> TYPE: DNA
<213> ORGANISM: Homo Sapiens

<400> SEQUENCE: 54
gactggagtt cagacgtgtg ctcttccgat ctagtcaagg ttgctgattt tggtcttg    58

<210> SEQ ID NO 55
<211> LENGTH: 59
<212> TYPE: DNA
<213> ORGANISM: Homo Sapiens

<400> SEQUENCE: 55
gactggagtt cagacgtgtg ctcttccgat ctagtccctg atagttgcta agaaccggt    59

<210> SEQ ID NO 56
<211> LENGTH: 59
<212> TYPE: DNA
<213> ORGANISM: Homo Sapiens

<400> SEQUENCE: 56
gactggagtt cagacgtgtg ctcttccgat ctagtcctca tgtactggtc cctcattgc    59

<210> SEQ ID NO 57
<211> LENGTH: 59
<212> TYPE: DNA
<213> ORGANISM: Homo Sapiens

<400> SEQUENCE: 57
gactggagtt cagacgtgtg ctcttccgat ctagtctctc tgcctcaata agccaacca    59

<210> SEQ ID NO 58
<211> LENGTH: 59
<212> TYPE: DNA
<213> ORGANISM: Homo Sapiens

<400> SEQUENCE: 58
gactggagtt cagacgtgtg ctcttccgat ctagttgtct cactgcctca tctctcacc      59

<210> SEQ ID NO 59
<211> LENGTH: 59
<212> TYPE: DNA
<213> ORGANISM: Homo Sapiens

<400> SEQUENCE: 59
gactggagtt cagacgtgtg ctcttccgat ctatcagtct gtccagcact tccattggg      59

<210> SEQ ID NO 60
<211> LENGTH: 59
<212> TYPE: DNA
<213> ORGANISM: Homo Sapiens

<400> SEQUENCE: 60
gactggagtt cagacgtgtg ctcttccgat ctatccatga actccacatt tgccttggg      59

<210> SEQ ID NO 61
<211> LENGTH: 59
<212> TYPE: DNA
<213> ORGANISM: Homo Sapiens

<400> SEQUENCE: 61
gactggagtt cagacgtgtg ctcttccgat ctatctcctt ggtgaccgct ctgcatcta      59

<210> SEQ ID NO 62
<211> LENGTH: 59
<212> TYPE: DNA
<213> ORGANISM: Homo Sapiens

<400> SEQUENCE: 62
gactggagtt cagacgtgtg ctcttccgat ctattccaga cgcatttcca cagctacac      59

<210> SEQ ID NO 63
<211> LENGTH: 59
<212> TYPE: DNA
<213> ORGANISM: Homo Sapiens

<400> SEQUENCE: 63
gactggagtt cagacgtgtg ctcttccgat ctcaaaacag cacagtgaaa gccagccac      59

<210> SEQ ID NO 64
<211> LENGTH: 59
<212> TYPE: DNA
<213> ORGANISM: Homo Sapiens

<400> SEQUENCE: 64
gactggagtt cagacgtgtg ctcttccgat ctcaaaagcc tccagtcgcc tcagtaaag      59

<210> SEQ ID NO 65
<211> LENGTH: 64
<212> TYPE: DNA
<213> ORGANISM: Homo Sapiens

<400> SEQUENCE: 65

```
gactggagtt cagacgtgtg ctcttccgat ctcaaacttt ataagatcct ggctatcctg    60
tgga                                                                 64

<210> SEQ ID NO 66
<211> LENGTH: 64
<212> TYPE: DNA
<213> ORGANISM: Homo Sapiens

<400> SEQUENCE: 66
gactggagtt cagacgtgtg ctcttccgat ctcaacaagt gttagctcct attatcctgt    60
ccct                                                                 64

<210> SEQ ID NO 67
<211> LENGTH: 62
<212> TYPE: DNA
<213> ORGANISM: Homo Sapiens

<400> SEQUENCE: 67
gactggagtt cagacgtgtg ctcttccgat ctcaacggat gggagattga agatttctgt    60
tg                                                                   62

<210> SEQ ID NO 68
<211> LENGTH: 59
<212> TYPE: DNA
<213> ORGANISM: Homo Sapiens

<400> SEQUENCE: 68
gactggagtt cagacgtgtg ctcttccgat ctcaacttgg aggccttgca gaagaagct     59

<210> SEQ ID NO 69
<211> LENGTH: 63
<212> TYPE: DNA
<213> ORGANISM: Homo Sapiens

<400> SEQUENCE: 69
gactggagtt cagacgtgtg ctcttccgat ctcaaggggg actgtagatg ggtgaaaaga    60
gca                                                                  63

<210> SEQ ID NO 70
<211> LENGTH: 59
<212> TYPE: DNA
<213> ORGANISM: Homo Sapiens

<400> SEQUENCE: 70
gactggagtt cagacgtgtg ctcttccgat ctcactcacc aatcatgatg ccggagaaa     59

<210> SEQ ID NO 71
<211> LENGTH: 56
<212> TYPE: DNA
<213> ORGANISM: Homo Sapiens

<400> SEQUENCE: 71
gactggagtt cagacgtgtg ctcttccgat ctcagaaggt tgcacttgtc cacgca        56

<210> SEQ ID NO 72
<211> LENGTH: 58
<212> TYPE: DNA
<213> ORGANISM: Homo Sapiens

<400> SEQUENCE: 72
gactggagtt cagacgtgtg ctcttccgat ctcagacagc agcaccgaga cgatgaag      58
```

<210> SEQ ID NO 73
<211> LENGTH: 56
<212> TYPE: DNA
<213> ORGANISM: Homo Sapiens

<400> SEQUENCE: 73
gactggagtt cagacgtgtg ctcttccgat ctcagactct ctcctcccca ctgctg      56

<210> SEQ ID NO 74
<211> LENGTH: 59
<212> TYPE: DNA
<213> ORGANISM: Homo Sapiens

<400> SEQUENCE: 74
gactggagtt cagacgtgtg ctcttccgat ctcagactct ggcctacgtg tttgtttcc   59

<210> SEQ ID NO 75
<211> LENGTH: 59
<212> TYPE: DNA
<213> ORGANISM: Homo Sapiens

<400> SEQUENCE: 75
gactggagtt cagacgtgtg ctcttccgat ctcagcgaca tgtctttccc cacaatcat   59

<210> SEQ ID NO 76
<211> LENGTH: 59
<212> TYPE: DNA
<213> ORGANISM: Homo Sapiens

<400> SEQUENCE: 76
gactggagtt cagacgtgtg ctcttccgat ctcagctttg cacctgtttt gttgtgtac   59

<210> SEQ ID NO 77
<211> LENGTH: 57
<212> TYPE: DNA
<213> ORGANISM: Homo Sapiens

<400> SEQUENCE: 77
gactggagtt cagacgtgtg ctcttccgat ctcaggccct ggtagctcat catctgg     57

<210> SEQ ID NO 78
<211> LENGTH: 59
<212> TYPE: DNA
<213> ORGANISM: Homo Sapiens

<400> SEQUENCE: 78
gactggagtt cagacgtgtg ctcttccgat ctcaggtctc cgtggatgcc ttcaagatc   59

<210> SEQ ID NO 79
<211> LENGTH: 59
<212> TYPE: DNA
<213> ORGANISM: Homo Sapiens

<400> SEQUENCE: 79
gactggagtt cagacgtgtg ctcttccgat ctcagtctct ggatcccaca cctttacca   59

<210> SEQ ID NO 80
<211> LENGTH: 59
<212> TYPE: DNA
<213> ORGANISM: Homo Sapiens

<400> SEQUENCE: 80

```
gactggagtt cagacgtgtg ctcttccgat ctcagtttct tcttctcatc gcgggcttg      59
```

<210> SEQ ID NO 81
<211> LENGTH: 58
<212> TYPE: DNA
<213> ORGANISM: Homo Sapiens

<400> SEQUENCE: 81

```
gactggagtt cagacgtgtg ctcttccgat ctcataccct ctcagcgtac ccttgtcc       58
```

<210> SEQ ID NO 82
<211> LENGTH: 71
<212> TYPE: DNA
<213> ORGANISM: Homo Sapiens

<400> SEQUENCE: 82

```
gactggagtt cagacgtgtg ctcttccgat ctcatatagt tatcaccata aaattgtcat    60
agctagacat g                                                          71
```

<210> SEQ ID NO 83
<211> LENGTH: 59
<212> TYPE: DNA
<213> ORGANISM: Homo Sapiens

<400> SEQUENCE: 83

```
gactggagtt cagacgtgtg ctcttccgat ctcatcgtgt acttccggat cttctgctg      59
```

<210> SEQ ID NO 84
<211> LENGTH: 59
<212> TYPE: DNA
<213> ORGANISM: Homo Sapiens

<400> SEQUENCE: 84

```
gactggagtt cagacgtgtg ctcttccgat ctcatgcctt tcacgttcct ttccccaaa      59
```

<210> SEQ ID NO 85
<211> LENGTH: 59
<212> TYPE: DNA
<213> ORGANISM: Homo Sapiens

<400> SEQUENCE: 85

```
gactggagtt cagacgtgtg ctcttccgat ctcattctgg gagcttcatc tggacctgg      59
```

<210> SEQ ID NO 86
<211> LENGTH: 59
<212> TYPE: DNA
<213> ORGANISM: Homo Sapiens

<400> SEQUENCE: 86

```
gactggagtt cagacgtgtg ctcttccgat ctccaattgg catgctcttc aatcactga      59
```

<210> SEQ ID NO 87
<211> LENGTH: 59
<212> TYPE: DNA
<213> ORGANISM: Homo Sapiens

<400> SEQUENCE: 87

```
gactggagtt cagacgtgtg ctcttccgat ctccacacct gtcatgtagc agctttcag     59
```

<210> SEQ ID NO 88
<211> LENGTH: 58
<212> TYPE: DNA
<213> ORGANISM: Homo Sapiens

<400> SEQUENCE: 88
gactggagtt cagacgtgtg ctcttccgat ctccacacga cgggaagaca agttcatg      58

<210> SEQ ID NO 89
<211> LENGTH: 59
<212> TYPE: DNA
<213> ORGANISM: Homo Sapiens

<400> SEQUENCE: 89
gactggagtt cagacgtgtg ctcttccgat ctccacactt ctccattctt cacaagggt     59

<210> SEQ ID NO 90
<211> LENGTH: 59
<212> TYPE: DNA
<213> ORGANISM: Homo Sapiens

<400> SEQUENCE: 90
gactggagtt cagacgtgtg ctcttccgat ctccacatgc tcccaggctg tttatttga     59

<210> SEQ ID NO 91
<211> LENGTH: 56
<212> TYPE: DNA
<213> ORGANISM: Homo Sapiens

<400> SEQUENCE: 91
gactggagtt cagacgtgtg ctcttccgat ctccacttct ccaggaccac ggactg        56

<210> SEQ ID NO 92
<211> LENGTH: 55
<212> TYPE: DNA
<213> ORGANISM: Homo Sapiens

<400> SEQUENCE: 92
gactggagtt cagacgtgtg ctcttccgat ctccaggaga gttgcgggga ttgac         55

<210> SEQ ID NO 93
<211> LENGTH: 53
<212> TYPE: DNA
<213> ORGANISM: Homo Sapiens

<400> SEQUENCE: 93
gactggagtt cagacgtgtg ctcttccgat ctccagggaa tgtggggcca gac           53

<210> SEQ ID NO 94
<211> LENGTH: 59
<212> TYPE: DNA
<213> ORGANISM: Homo Sapiens

<400> SEQUENCE: 94
gactggagtt cagacgtgtg ctcttccgat ctccagttgg ttacatactt ggacttggt     59

<210> SEQ ID NO 95
<211> LENGTH: 59
<212> TYPE: DNA
<213> ORGANISM: Homo Sapiens

<400> SEQUENCE: 95
gactggagtt cagacgtgtg ctcttccgat ctccatagct gacaccacga tacttgaca     59

<210> SEQ ID NO 96
<211> LENGTH: 59
<212> TYPE: DNA

<213> ORGANISM: Homo Sapiens

<400> SEQUENCE: 96
gactggagtt cagacgtgtg ctcttccgat ctccatgtaa caaaccttca cgtcctgca    59

<210> SEQ ID NO 97
<211> LENGTH: 64
<212> TYPE: DNA
<213> ORGANISM: Homo Sapiens

<400> SEQUENCE: 97
gactggagtt cagacgtgtg ctcttccgat ctccattggc atggggaaat ataaacttgt    60
ttga    64

<210> SEQ ID NO 98
<211> LENGTH: 60
<212> TYPE: DNA
<213> ORGANISM: Homo Sapiens

<400> SEQUENCE: 98
gactggagtt cagacgtgtg ctcttccgat ctcccagttt aagatttgcc cagactcagc    60

<210> SEQ ID NO 99
<211> LENGTH: 59
<212> TYPE: DNA
<213> ORGANISM: Homo Sapiens

<400> SEQUENCE: 99
gactggagtt cagacgtgtg ctcttccgat ctcccatcct gccaaagttt gtgattcca    59

<210> SEQ ID NO 100
<211> LENGTH: 55
<212> TYPE: DNA
<213> ORGANISM: Homo Sapiens

<400> SEQUENCE: 100
gactggagtt cagacgtgtg ctcttccgat ctcccatgtc tttgcagccg aggag    55

<210> SEQ ID NO 101
<211> LENGTH: 55
<212> TYPE: DNA
<213> ORGANISM: Homo Sapiens

<400> SEQUENCE: 101
gactggagtt cagacgtgtg ctcttccgat ctcccctcct tctggccacc atgcg    55

<210> SEQ ID NO 102
<211> LENGTH: 59
<212> TYPE: DNA
<213> ORGANISM: Homo Sapiens

<400> SEQUENCE: 102
gactggagtt cagacgtgtg ctcttccgat ctccctgtaa atttctcatg ggcagctcc    59

<210> SEQ ID NO 103
<211> LENGTH: 58
<212> TYPE: DNA
<213> ORGANISM: Homo Sapiens

<400> SEQUENCE: 103
gactggagtt cagacgtgtg ctcttccgat ctcccttgaa gcactacaca ggccactt    58

```
<210> SEQ ID NO 104
<211> LENGTH: 59
<212> TYPE: DNA
<213> ORGANISM: Homo Sapiens

<400> SEQUENCE: 104
gactggagtt cagacgtgtg ctcttccgat ctccggaaga tgatgttctc caggtcgaa      59

<210> SEQ ID NO 105
<211> LENGTH: 59
<212> TYPE: DNA
<213> ORGANISM: Homo Sapiens

<400> SEQUENCE: 105
gactggagtt cagacgtgtg ctcttccgat ctccgtagta ggggaagatc atctgctgg      59

<210> SEQ ID NO 106
<211> LENGTH: 60
<212> TYPE: DNA
<213> ORGANISM: Homo Sapiens

<400> SEQUENCE: 106
gactggagtt cagacgtgtg ctcttccgat ctcctcaaaa gacttggtgt tgttgatggc     60

<210> SEQ ID NO 107
<211> LENGTH: 56
<212> TYPE: DNA
<213> ORGANISM: Homo Sapiens

<400> SEQUENCE: 107
gactggagtt cagacgtgtg ctcttccgat ctcctcatgg cagggctcta ggatga         56

<210> SEQ ID NO 108
<211> LENGTH: 58
<212> TYPE: DNA
<213> ORGANISM: Homo Sapiens

<400> SEQUENCE: 108
gactggagtt cagacgtgtg ctcttccgat ctcctctggt caaggtcaca ttcttcca       58

<210> SEQ ID NO 109
<211> LENGTH: 59
<212> TYPE: DNA
<213> ORGANISM: Homo Sapiens

<400> SEQUENCE: 109
gactggagtt cagacgtgtg ctcttccgat ctcctgcgtc atcatctttg tcatcgtgt      59

<210> SEQ ID NO 110
<211> LENGTH: 59
<212> TYPE: DNA
<213> ORGANISM: Homo Sapiens

<400> SEQUENCE: 110
gactggagtt cagacgtgtg ctcttccgat ctcctgtgcc cttagctgt gatttccta       59

<210> SEQ ID NO 111
<211> LENGTH: 63
<212> TYPE: DNA
<213> ORGANISM: Homo Sapiens

<400> SEQUENCE: 111
gactggagtt cagacgtgtg ctcttccgat ctcctgtgct tcaactaaat ttaactgtca     60
```

-continued

```
gca                                                             63

<210> SEQ ID NO 112
<211> LENGTH: 57
<212> TYPE: DNA
<213> ORGANISM: Homo Sapiens

<400> SEQUENCE: 112
gactggagtt cagacgtgtg ctcttccgat ctccttcgtc ctccttcctc actctgc   57

<210> SEQ ID NO 113
<211> LENGTH: 57
<212> TYPE: DNA
<213> ORGANISM: Homo Sapiens

<400> SEQUENCE: 113
gactggagtt cagacgtgtg ctcttccgat ctcgatgtag ctgtgcatgt cctggtg   57

<210> SEQ ID NO 114
<211> LENGTH: 61
<212> TYPE: DNA
<213> ORGANISM: Homo Sapiens

<400> SEQUENCE: 114
gactggagtt cagacgtgtg ctcttccgat ctcgcagtgc taaccaagtt ctttcttttg 60
c                                                               61

<210> SEQ ID NO 115
<211> LENGTH: 59
<212> TYPE: DNA
<213> ORGANISM: Homo Sapiens

<400> SEQUENCE: 115
gactggagtt cagacgtgtg ctcttccgat ctcgccagtc tgtatcacat ccacctcat  59

<210> SEQ ID NO 116
<211> LENGTH: 59
<212> TYPE: DNA
<213> ORGANISM: Homo Sapiens

<400> SEQUENCE: 116
gactggagtt cagacgtgtg ctcttccgat ctcggacgca acagagaaag acttgtcag  59

<210> SEQ ID NO 117
<211> LENGTH: 57
<212> TYPE: DNA
<213> ORGANISM: Homo Sapiens

<400> SEQUENCE: 117
gactggagtt cagacgtgtg ctcttccgat ctcggagcaa accctatgt ccacaag    57

<210> SEQ ID NO 118
<211> LENGTH: 62
<212> TYPE: DNA
<213> ORGANISM: Homo Sapiens

<400> SEQUENCE: 118
gactggagtt cagacgtgtg ctcttccgat ctcgtcactc tggattgtgt acactctgtc 60
aa                                                              62

<210> SEQ ID NO 119
<211> LENGTH: 56
```

```
<212> TYPE: DNA
<213> ORGANISM: Homo Sapiens

<400> SEQUENCE: 119
gactggagtt cagacgtgtg ctcttccgat ctcgtgagcg cttcgagatg ttccga        56

<210> SEQ ID NO 120
<211> LENGTH: 59
<212> TYPE: DNA
<213> ORGANISM: Homo Sapiens

<400> SEQUENCE: 120
gactggagtt cagacgtgtg ctcttccgat ctctaaagga aatcacgctg tcccctgtg    59

<210> SEQ ID NO 121
<211> LENGTH: 58
<212> TYPE: DNA
<213> ORGANISM: Homo Sapiens

<400> SEQUENCE: 121
gactggagtt cagacgtgtg ctcttccgat ctctaacccc agtcagctcc agagtcac     58

<210> SEQ ID NO 122
<211> LENGTH: 65
<212> TYPE: DNA
<213> ORGANISM: Homo Sapiens

<400> SEQUENCE: 122
gactggagtt cagacgtgtg ctcttccgat ctctaactct ctttgactgc agaatccaac   60
tgtaa                                                                65

<210> SEQ ID NO 123
<211> LENGTH: 59
<212> TYPE: DNA
<213> ORGANISM: Homo Sapiens

<400> SEQUENCE: 123
gactggagtt cagacgtgtg ctcttccgat ctctaatcac caccccaccc aattccagg    59

<210> SEQ ID NO 124
<211> LENGTH: 58
<212> TYPE: DNA
<213> ORGANISM: Homo Sapiens

<400> SEQUENCE: 124
gactggagtt cagacgtgtg ctcttccgat ctctacgaca agtgggagat ggaacgca     58

<210> SEQ ID NO 125
<211> LENGTH: 58
<212> TYPE: DNA
<213> ORGANISM: Homo Sapiens

<400> SEQUENCE: 125
gactggagtt cagacgtgtg ctcttccgat ctctaggtga gaggcagtgg tcagggtc     58

<210> SEQ ID NO 126
<211> LENGTH: 58
<212> TYPE: DNA
<213> ORGANISM: Homo Sapiens

<400> SEQUENCE: 126
gactggagtt cagacgtgtg ctcttccgat ctctcaacga gtgcttcatc aaggtgcc     58
```

<210> SEQ ID NO 127
<211> LENGTH: 59
<212> TYPE: DNA
<213> ORGANISM: Homo Sapiens

<400> SEQUENCE: 127
gactggagtt cagacgtgtg ctcttccgat ctctccacat ttcagcaaca gcagcatct    59

<210> SEQ ID NO 128
<211> LENGTH: 59
<212> TYPE: DNA
<213> ORGANISM: Homo Sapiens

<400> SEQUENCE: 128
gactggagtt cagacgtgtg ctcttccgat ctctcgatct tgtaggggat gttgaggct    59

<210> SEQ ID NO 129
<211> LENGTH: 59
<212> TYPE: DNA
<213> ORGANISM: Homo Sapiens

<400> SEQUENCE: 129
gactggagtt cagacgtgtg ctcttccgat ctctctacaa ccccaccacg taccagatg    59

<210> SEQ ID NO 130
<211> LENGTH: 59
<212> TYPE: DNA
<213> ORGANISM: Homo Sapiens

<400> SEQUENCE: 130
gactggagtt cagacgtgtg ctcttccgat ctctctcctt ttcctcctct tctcctggc    59

<210> SEQ ID NO 131
<211> LENGTH: 59
<212> TYPE: DNA
<213> ORGANISM: Homo Sapiens

<400> SEQUENCE: 131
gactggagtt cagacgtgtg ctcttccgat ctctctctca atggcttctg tcctgtgga    59

<210> SEQ ID NO 132
<211> LENGTH: 69
<212> TYPE: DNA
<213> ORGANISM: Homo Sapiens

<400> SEQUENCE: 132
gactggagtt cagacgtgtg ctcttccgat ctctctggaa tccagtgttt cttttaaata    60
cctgttaag                                                            69

<210> SEQ ID NO 133
<211> LENGTH: 59
<212> TYPE: DNA
<213> ORGANISM: Homo Sapiens

<400> SEQUENCE: 133
gactggagtt cagacgtgtg ctcttccgat ctctctggca ttctgggagc ttcatctgg    59

<210> SEQ ID NO 134
<211> LENGTH: 57
<212> TYPE: DNA
<213> ORGANISM: Homo Sapiens

<400> SEQUENCE: 134
gactggagtt cagacgtgtg ctcttccgat ctctgagcct gttctttcca agggtgc    57

<210> SEQ ID NO 135
<211> LENGTH: 59
<212> TYPE: DNA
<213> ORGANISM: Homo Sapiens

<400> SEQUENCE: 135
gactggagtt cagacgtgtg ctcttccgat ctctgaggga atgaaagtgg gatcaggga   59

<210> SEQ ID NO 136
<211> LENGTH: 59
<212> TYPE: DNA
<213> ORGANISM: Homo Sapiens

<400> SEQUENCE: 136
gactggagtt cagacgtgtg ctcttccgat ctctgataag gttaagggcc ccaacggta   59

<210> SEQ ID NO 137
<211> LENGTH: 59
<212> TYPE: DNA
<213> ORGANISM: Homo Sapiens

<400> SEQUENCE: 137
gactggagtt cagacgtgtg ctcttccgat ctctggaagt cgatcacctg cctcactat   59

<210> SEQ ID NO 138
<211> LENGTH: 58
<212> TYPE: DNA
<213> ORGANISM: Homo Sapiens

<400> SEQUENCE: 138
gactggagtt cagacgtgtg ctcttccgat ctctggatgc tgcacaggtg tacaatcc    58

<210> SEQ ID NO 139
<211> LENGTH: 58
<212> TYPE: DNA
<213> ORGANISM: Homo Sapiens

<400> SEQUENCE: 139
gactggagtt cagacgtgtg ctcttccgat ctctggtgct catttagtcc tggggcag    58

<210> SEQ ID NO 140
<211> LENGTH: 58
<212> TYPE: DNA
<213> ORGANISM: Homo Sapiens

<400> SEQUENCE: 140
gactggagtt cagacgtgtg ctcttccgat ctctggtttg gggaagagtg ggctagtg    58

<210> SEQ ID NO 141
<211> LENGTH: 65
<212> TYPE: DNA
<213> ORGANISM: Homo Sapiens

<400> SEQUENCE: 141
gactggagtt cagacgtgtg ctcttccgat ctctgtagac taccgagcta cttttccaga   60
aggta    65

<210> SEQ ID NO 142
<211> LENGTH: 56
<212> TYPE: DNA

```
<213> ORGANISM: Homo Sapiens

<400> SEQUENCE: 142
gactggagtt cagacgtgtg ctcttccgat ctctgtgccg agtatcctgg agcctc       56

<210> SEQ ID NO 143
<211> LENGTH: 59
<212> TYPE: DNA
<213> ORGANISM: Homo Sapiens

<400> SEQUENCE: 143
gactggagtt cagacgtgtg ctcttccgat ctctgtgtga ctatctccct gggtgtagc    59

<210> SEQ ID NO 144
<211> LENGTH: 57
<212> TYPE: DNA
<213> ORGANISM: Homo Sapiens

<400> SEQUENCE: 144
gactggagtt cagacgtgtg ctcttccgat ctcttccaca ctctgaggcg gaacatg      57

<210> SEQ ID NO 145
<211> LENGTH: 59
<212> TYPE: DNA
<213> ORGANISM: Homo Sapiens

<400> SEQUENCE: 145
gactggagtt cagacgtgtg ctcttccgat ctcttcccag agacattgct gccagaaac    59

<210> SEQ ID NO 146
<211> LENGTH: 59
<212> TYPE: DNA
<213> ORGANISM: Homo Sapiens

<400> SEQUENCE: 146
gactggagtt cagacgtgtg ctcttccgat ctcttcttca cgctccttcc ctatcccctt   59

<210> SEQ ID NO 147
<211> LENGTH: 59
<212> TYPE: DNA
<213> ORGANISM: Homo Sapiens

<400> SEQUENCE: 147
gactggagtt cagacgtgtg ctcttccgat ctcttgtcct gcttgcttac ctcgcttag    59

<210> SEQ ID NO 148
<211> LENGTH: 63
<212> TYPE: DNA
<213> ORGANISM: Homo Sapiens

<400> SEQUENCE: 148
gactggagtt cagacgtgtg ctcttccgat ctctttatct gtatcaaaga atggtcctgc   60
acc                                                                63

<210> SEQ ID NO 149
<211> LENGTH: 59
<212> TYPE: DNA
<213> ORGANISM: Homo Sapiens

<400> SEQUENCE: 149
gactggagtt cagacgtgtg ctcttccgat ctctttctcg gttctctgat tcctggcag    59
```

```
<210> SEQ ID NO 150
<211> LENGTH: 58
<212> TYPE: DNA
<213> ORGANISM: Homo Sapiens

<400> SEQUENCE: 150
gactggagtt cagacgtgtg ctcttccgat ctgaaatgtg agcccttgag atctgcgg         58

<210> SEQ ID NO 151
<211> LENGTH: 59
<212> TYPE: DNA
<213> ORGANISM: Homo Sapiens

<400> SEQUENCE: 151
gactggagtt cagacgtgtg ctcttccgat ctgaacaatg cctccacgac catcatcag       59

<210> SEQ ID NO 152
<211> LENGTH: 54
<212> TYPE: DNA
<213> ORGANISM: Homo Sapiens

<400> SEQUENCE: 152
gactggagtt cagacgtgtg ctcttccgat ctgaagaccc aagctgcctg accc            54

<210> SEQ ID NO 153
<211> LENGTH: 56
<212> TYPE: DNA
<213> ORGANISM: Homo Sapiens

<400> SEQUENCE: 153
gactggagtt cagacgtgtg ctcttccgat ctgaagcaac ccacagatgt tcccgg          56

<210> SEQ ID NO 154
<211> LENGTH: 57
<212> TYPE: DNA
<213> ORGANISM: Homo Sapiens

<400> SEQUENCE: 154
gactggagtt cagacgtgtg ctcttccgat ctgaagcccc tttctttgtt cagcccc         57

<210> SEQ ID NO 155
<211> LENGTH: 59
<212> TYPE: DNA
<213> ORGANISM: Homo Sapiens

<400> SEQUENCE: 155
gactggagtt cagacgtgtg ctcttccgat ctgaagtgcc cttggttcgg acagacaac      59

<210> SEQ ID NO 156
<211> LENGTH: 59
<212> TYPE: DNA
<213> ORGANISM: Homo Sapiens

<400> SEQUENCE: 156
gactggagtt cagacgtgtg ctcttccgat ctgaatctcc tcccaactca acttcccag     59

<210> SEQ ID NO 157
<211> LENGTH: 63
<212> TYPE: DNA
<213> ORGANISM: Homo Sapiens

<400> SEQUENCE: 157
gactggagtt cagacgtgtg ctcttccgat ctgacaccta gctgtgatcc tgaaactgaa    60
``` ttt                                                                                        63

<210> SEQ ID NO 158
<211> LENGTH: 59
<212> TYPE: DNA
<213> ORGANISM: Homo Sapiens

<400> SEQUENCE: 158
gactggagtt cagacgtgtg ctcttccgat ctgacccaaa caaaagcgat ctcctccag        59

<210> SEQ ID NO 159
<211> LENGTH: 59
<212> TYPE: DNA
<213> ORGANISM: Homo Sapiens

<400> SEQUENCE: 159
gactggagtt cagacgtgtg ctcttccgat ctgactcacc ggtggatgaa gtggttttc        59

<210> SEQ ID NO 160
<211> LENGTH: 59
<212> TYPE: DNA
<213> ORGANISM: Homo Sapiens

<400> SEQUENCE: 160
gactggagtt cagacgtgtg ctcttccgat ctgacttctc ctccacaaat ccagagctg        59

<210> SEQ ID NO 161
<211> LENGTH: 58
<212> TYPE: DNA
<213> ORGANISM: Homo Sapiens

<400> SEQUENCE: 161
gactggagtt cagacgtgtg ctcttccgat ctgagccttt ccctctgccc ttttcaag         58

<210> SEQ ID NO 162
<211> LENGTH: 54
<212> TYPE: DNA
<213> ORGANISM: Homo Sapiens

<400> SEQUENCE: 162
gactggagtt cagacgtgtg ctcttccgat ctgagctccc caccccctga tcag             54

<210> SEQ ID NO 163
<211> LENGTH: 59
<212> TYPE: DNA
<213> ORGANISM: Homo Sapiens

<400> SEQUENCE: 163
gactggagtt cagacgtgtg ctcttccgat ctgaggaggc catcttccat cttctcaca        59

<210> SEQ ID NO 164
<211> LENGTH: 59
<212> TYPE: DNA
<213> ORGANISM: Homo Sapiens

<400> SEQUENCE: 164
gactggagtt cagacgtgtg ctcttccgat ctgagtcttc ccacaagttc gctctttgg        59

<210> SEQ ID NO 165
<211> LENGTH: 59
<212> TYPE: DNA
<213> ORGANISM: Homo Sapiens

<400> SEQUENCE: 165

```
gactggagtt cagacgtgtg ctcttccgat ctgagtgggc attgtatgga aactgaggc    59
```

<210> SEQ ID NO 166
<211> LENGTH: 59
<212> TYPE: DNA
<213> ORGANISM: Homo Sapiens

<400> SEQUENCE: 166

```
gactggagtt cagacgtgtg ctcttccgat ctgatacggc caggcattga agtctcatg    59
```

<210> SEQ ID NO 167
<211> LENGTH: 66
<212> TYPE: DNA
<213> ORGANISM: Homo Sapiens

<400> SEQUENCE: 167

```
gactggagtt cagacgtgtg ctcttccgat ctgatagttt ctgaaggaat gctatggtat    60
gaaaca                                                               66
```

<210> SEQ ID NO 168
<211> LENGTH: 59
<212> TYPE: DNA
<213> ORGANISM: Homo Sapiens

<400> SEQUENCE: 168

```
gactggagtt cagacgtgtg ctcttccgat ctgatccagc cagacccagc cagtattat    59
```

<210> SEQ ID NO 169
<211> LENGTH: 57
<212> TYPE: DNA
<213> ORGANISM: Homo Sapiens

<400> SEQUENCE: 169

```
gactggagtt cagacgtgtg ctcttccgat ctgatcttga aggcatccac ggagacc      57
```

<210> SEQ ID NO 170
<211> LENGTH: 62
<212> TYPE: DNA
<213> ORGANISM: Homo Sapiens

<400> SEQUENCE: 170

```
gactggagtt cagacgtgtg ctcttccgat ctgcaaagga gaagacaaga ggagacagag    60
tc                                                                   62
```

<210> SEQ ID NO 171
<211> LENGTH: 54
<212> TYPE: DNA
<213> ORGANISM: Homo Sapiens

<400> SEQUENCE: 171

```
gactggagtt cagacgtgtg ctcttccgat ctgcaacacc cagccctcgg taag          54
```

<210> SEQ ID NO 172
<211> LENGTH: 59
<212> TYPE: DNA
<213> ORGANISM: Homo Sapiens

<400> SEQUENCE: 172

```
gactggagtt cagacgtgtg ctcttccgat ctgcagcaac ggacatgagt ttgttttcc    59
```

<210> SEQ ID NO 173

```
<211> LENGTH: 58
<212> TYPE: DNA
<213> ORGANISM: Homo Sapiens

<400> SEQUENCE: 173
gactggagtt cagacgtgtg ctcttccgat ctgcagcacc gagacgatga aggagaag      58

<210> SEQ ID NO 174
<211> LENGTH: 59
<212> TYPE: DNA
<213> ORGANISM: Homo Sapiens

<400> SEQUENCE: 174
gactggagtt cagacgtgtg ctcttccgat ctgcaggacc cgacaaaacc taaagatgg     59

<210> SEQ ID NO 175
<211> LENGTH: 59
<212> TYPE: DNA
<213> ORGANISM: Homo Sapiens

<400> SEQUENCE: 175
gactggagtt cagacgtgtg ctcttccgat ctgcccatcc ctgactgtga gatcaagaa     59

<210> SEQ ID NO 176
<211> LENGTH: 59
<212> TYPE: DNA
<213> ORGANISM: Homo Sapiens

<400> SEQUENCE: 176
gactggagtt cagacgtgtg ctcttccgat ctgccccaat tgcaggtaaa acagtcaag     59

<210> SEQ ID NO 177
<211> LENGTH: 59
<212> TYPE: DNA
<213> ORGANISM: Homo Sapiens

<400> SEQUENCE: 177
gactggagtt cagacgtgtg ctcttccgat ctgcccgtat ttactgccgt tcttttcca     59

<210> SEQ ID NO 178
<211> LENGTH: 58
<212> TYPE: DNA
<213> ORGANISM: Homo Sapiens

<400> SEQUENCE: 178
gactggagtt cagacgtgtg ctcttccgat ctgcctccca gcaatttcct cccttgtt      58

<210> SEQ ID NO 179
<211> LENGTH: 54
<212> TYPE: DNA
<213> ORGANISM: Homo Sapiens

<400> SEQUENCE: 179
gactggagtt cagacgtgtg ctcttccgat ctgcctgtgt tctgccccca tttc           54

<210> SEQ ID NO 180
<211> LENGTH: 59
<212> TYPE: DNA
<213> ORGANISM: Homo Sapiens

<400> SEQUENCE: 180
gactggagtt cagacgtgtg ctcttccgat ctgcggaaga atgtgtcagc ctcaaagaa     59
```

```
<210> SEQ ID NO 181
<211> LENGTH: 53
<212> TYPE: DNA
<213> ORGANISM: Homo Sapiens

<400> SEQUENCE: 181
gactggagtt cagacgtgtg ctcttccgat ctgcgtgcct gccaatggtg atg          53

<210> SEQ ID NO 182
<211> LENGTH: 56
<212> TYPE: DNA
<213> ORGANISM: Homo Sapiens

<400> SEQUENCE: 182
gactggagtt cagacgtgtg ctcttccgat ctgctaaggg gcacagggta ggtagt       56

<210> SEQ ID NO 183
<211> LENGTH: 77
<212> TYPE: DNA
<213> ORGANISM: Homo Sapiens

<400> SEQUENCE: 183
gactggagtt cagacgtgtg ctcttccgat ctgctaatgt taagaatgta ctgatattta   60
ttactgaacc tttaggt                                                  77

<210> SEQ ID NO 184
<211> LENGTH: 71
<212> TYPE: DNA
<213> ORGANISM: Homo Sapiens

<400> SEQUENCE: 184
gactggagtt cagacgtgtg ctcttccgat ctgctattta agattacgaa ggtattggtt   60
tagacagaaa t                                                        71

<210> SEQ ID NO 185
<211> LENGTH: 58
<212> TYPE: DNA
<213> ORGANISM: Homo Sapiens

<400> SEQUENCE: 185
gactggagtt cagacgtgtg ctcttccgat ctgctcgggt tggctctaaa gtagtcct     58

<210> SEQ ID NO 186
<211> LENGTH: 59
<212> TYPE: DNA
<213> ORGANISM: Homo Sapiens

<400> SEQUENCE: 186
gactggagtt cagacgtgtg ctcttccgat ctgctgccac ttctacgact tcttcaacc    59

<210> SEQ ID NO 187
<211> LENGTH: 59
<212> TYPE: DNA
<213> ORGANISM: Homo Sapiens

<400> SEQUENCE: 187
gactggagtt cagacgtgtg ctcttccgat ctgctggaaa gggacgaact ggtgtaatg    59

<210> SEQ ID NO 188
<211> LENGTH: 64
<212> TYPE: DNA
<213> ORGANISM: Homo Sapiens
```

<400> SEQUENCE: 188
gactggagtt cagacgtgtg ctcttccgat ctgcttgcaa aaatccagta gtagctagct    60
ctgc                                                                 64

<210> SEQ ID NO 189
<211> LENGTH: 59
<212> TYPE: DNA
<213> ORGANISM: Homo Sapiens

<400> SEQUENCE: 189
gactggagtt cagacgtgtg ctcttccgat ctgcttggat catattggcc tgtctgctc     59

<210> SEQ ID NO 190
<211> LENGTH: 65
<212> TYPE: DNA
<213> ORGANISM: Homo Sapiens

<400> SEQUENCE: 190
gactggagtt cagacgtgtg ctcttccgat ctggaaatag gtttcatgga ctcagttact    60
acctg                                                                65

<210> SEQ ID NO 191
<211> LENGTH: 56
<212> TYPE: DNA
<213> ORGANISM: Homo Sapiens

<400> SEQUENCE: 191
gactggagtt cagacgtgtg ctcttccgat ctggaagcca agcccagttc tggaag        56

<210> SEQ ID NO 192
<211> LENGTH: 59
<212> TYPE: DNA
<213> ORGANISM: Homo Sapiens

<400> SEQUENCE: 192
gactggagtt cagacgtgtg ctcttccgat ctggacagtt gatacaaaac aagcccacg     59

<210> SEQ ID NO 193
<211> LENGTH: 59
<212> TYPE: DNA
<213> ORGANISM: Homo Sapiens

<400> SEQUENCE: 193
gactggagtt cagacgtgtg ctcttccgat ctggagcaga tcaaacgggt gaaggactc     59

<210> SEQ ID NO 194
<211> LENGTH: 60
<212> TYPE: DNA
<213> ORGANISM: Homo Sapiens

<400> SEQUENCE: 194
gactggagtt cagacgtgtg ctcttccgat ctggagtcca ggaaatgata tcacataagt    60

<210> SEQ ID NO 195
<211> LENGTH: 59
<212> TYPE: DNA
<213> ORGANISM: Homo Sapiens

<400> SEQUENCE: 195
gactggagtt cagacgtgtg ctcttccgat ctggatactt acgcgccaca gagaagttg     59

```
<210> SEQ ID NO 196
<211> LENGTH: 62
<212> TYPE: DNA
<213> ORGANISM: Homo Sapiens

<400> SEQUENCE: 196
gactggagtt cagacgtgtg ctcttccgat ctggatatat tccagtggtt tgttgctctc    60
tg                                                                  62

<210> SEQ ID NO 197
<211> LENGTH: 58
<212> TYPE: DNA
<213> ORGANISM: Homo Sapiens

<400> SEQUENCE: 197
gactggagtt cagacgtgtg ctcttccgat ctggatgcct tattgcgaca gatccgga     58

<210> SEQ ID NO 198
<211> LENGTH: 59
<212> TYPE: DNA
<213> ORGANISM: Homo Sapiens

<400> SEQUENCE: 198
gactggagtt cagacgtgtg ctcttccgat ctggatgttc tggaaggcaa actccatgg   59

<210> SEQ ID NO 199
<211> LENGTH: 59
<212> TYPE: DNA
<213> ORGANISM: Homo Sapiens

<400> SEQUENCE: 199
gactggagtt cagacgtgtg ctcttccgat ctggcctctg attcctcact gattgctct   59

<210> SEQ ID NO 200
<211> LENGTH: 66
<212> TYPE: DNA
<213> ORGANISM: Homo Sapiens

<400> SEQUENCE: 200
gactggagtt cagacgtgtg ctcttccgat ctggcctgct gaaaatgact gaatataaac   60
ttgtgg                                                              66

<210> SEQ ID NO 201
<211> LENGTH: 59
<212> TYPE: DNA
<213> ORGANISM: Homo Sapiens

<400> SEQUENCE: 201
gactggagtt cagacgtgtg ctcttccgat ctggctggat cctgaactgg gcaaaatta   59

<210> SEQ ID NO 202
<211> LENGTH: 59
<212> TYPE: DNA
<213> ORGANISM: Homo Sapiens

<400> SEQUENCE: 202
gactggagtt cagacgtgtg ctcttccgat ctggcttcac agacatcctt gcacatctc   59

<210> SEQ ID NO 203
<211> LENGTH: 59
<212> TYPE: DNA
<213> ORGANISM: Homo Sapiens
```

<400> SEQUENCE: 203
gactggagtt cagacgtgtg ctcttccgat ctgggcttga acatactaaa tgctccagt    59

<210> SEQ ID NO 204
<211> LENGTH: 61
<212> TYPE: DNA
<213> ORGANISM: Homo Sapiens

<400> SEQUENCE: 204
gactggagtt cagacgtgtg ctcttccgat ctgggttcag caaatcttct aatccatgag    60
g    61

<210> SEQ ID NO 205
<211> LENGTH: 59
<212> TYPE: DNA
<213> ORGANISM: Homo Sapiens

<400> SEQUENCE: 205
gactggagtt cagacgtgtg ctcttccgat ctggtactct gtctcgtcaa tgtccagca    59

<210> SEQ ID NO 206
<211> LENGTH: 59
<212> TYPE: DNA
<213> ORGANISM: Homo Sapiens

<400> SEQUENCE: 206
gactggagtt cagacgtgtg ctcttccgat ctggtagatt ccagttcttg tgtgcgtgc    59

<210> SEQ ID NO 207
<211> LENGTH: 57
<212> TYPE: DNA
<213> ORGANISM: Homo Sapiens

<400> SEQUENCE: 207
gactggagtt cagacgtgtg ctcttccgat ctggtccctc ccacagttgc ttcaagt    57

<210> SEQ ID NO 208
<211> LENGTH: 58
<212> TYPE: DNA
<213> ORGANISM: Homo Sapiens

<400> SEQUENCE: 208
gactggagtt cagacgtgtg ctcttccgat ctggtgggaa gaacagccta gacttggg    58

<210> SEQ ID NO 209
<211> LENGTH: 59
<212> TYPE: DNA
<213> ORGANISM: Homo Sapiens

<400> SEQUENCE: 209
gactggagtt cagacgtgtg ctcttccgat ctggttccag gcttgctgta attacccag    59

<210> SEQ ID NO 210
<211> LENGTH: 59
<212> TYPE: DNA
<213> ORGANISM: Homo Sapiens

<400> SEQUENCE: 210
gactggagtt cagacgtgtg ctcttccgat ctgtaatccc caacccaata gacccaccc    59

<210> SEQ ID NO 211
<211> LENGTH: 57

```
<212> TYPE: DNA
<213> ORGANISM: Homo Sapiens

<400> SEQUENCE: 211
gactggagtt cagacgtgtg ctcttccgat ctgtcagagt tcaagtactg ggggcca      57

<210> SEQ ID NO 212
<211> LENGTH: 59
<212> TYPE: DNA
<213> ORGANISM: Homo Sapiens

<400> SEQUENCE: 212
gactggagtt cagacgtgtg ctcttccgat ctgtcagcag agaaccaagc cctcctaag    59

<210> SEQ ID NO 213
<211> LENGTH: 62
<212> TYPE: DNA
<213> ORGANISM: Homo Sapiens

<400> SEQUENCE: 213
gactggagtt cagacgtgtg ctcttccgat ctgtcctgag cctgttttgt gtctactgtt   60
tc                                                                  62

<210> SEQ ID NO 214
<211> LENGTH: 58
<212> TYPE: DNA
<213> ORGANISM: Homo Sapiens

<400> SEQUENCE: 214
gactggagtt cagacgtgtg ctcttccgat ctgtcctggg attgcagatt gggccttg     58

<210> SEQ ID NO 215
<211> LENGTH: 57
<212> TYPE: DNA
<213> ORGANISM: Homo Sapiens

<400> SEQUENCE: 215
gactggagtt cagacgtgtg ctcttccgat ctgtctccca taccctctca gcgtacc      57

<210> SEQ ID NO 216
<211> LENGTH: 57
<212> TYPE: DNA
<213> ORGANISM: Homo Sapiens

<400> SEQUENCE: 216
gactggagtt cagacgtgtg ctcttccgat ctgtgaagga ccaaggagca gaggagg      57

<210> SEQ ID NO 217
<211> LENGTH: 59
<212> TYPE: DNA
<213> ORGANISM: Homo Sapiens

<400> SEQUENCE: 217
gactggagtt cagacgtgtg ctcttccgat ctgtgaccga ggacaacgtg atgaagatc    59

<210> SEQ ID NO 218
<211> LENGTH: 59
<212> TYPE: DNA
<213> ORGANISM: Homo Sapiens

<400> SEQUENCE: 218
gactggagtt cagacgtgtg ctcttccgat ctgtgagcag gtggaagtag gaggtcttg    59
```

```
<210> SEQ ID NO 219
<211> LENGTH: 59
<212> TYPE: DNA
<213> ORGANISM: Homo Sapiens

<400> SEQUENCE: 219
gactggagtt cagacgtgtg ctcttccgat ctgtgatagg aagctgtgga gtgatgagc      59

<210> SEQ ID NO 220
<211> LENGTH: 59
<212> TYPE: DNA
<213> ORGANISM: Homo Sapiens

<400> SEQUENCE: 220
gactggagtt cagacgtgtg ctcttccgat ctgtgcaatt cagaccccaa cagtacgaa      59

<210> SEQ ID NO 221
<211> LENGTH: 68
<212> TYPE: DNA
<213> ORGANISM: Homo Sapiens

<400> SEQUENCE: 221
gactggagtt cagacgtgtg ctcttccgat ctgttcagag tagtagctgc aaataatcta     60
gggtttgg                                                              68

<210> SEQ ID NO 222
<211> LENGTH: 54
<212> TYPE: DNA
<213> ORGANISM: Homo Sapiens

<400> SEQUENCE: 222
gactggagtt cagacgtgtg ctcttccgat ctgttcatcg ggacttggca gcca           54

<210> SEQ ID NO 223
<211> LENGTH: 57
<212> TYPE: DNA
<213> ORGANISM: Homo Sapiens

<400> SEQUENCE: 223
gactggagtt cagacgtgtg ctcttccgat ctgttgggac cacactgagt tctctgt        57

<210> SEQ ID NO 224
<211> LENGTH: 55
<212> TYPE: DNA
<213> ORGANISM: Homo Sapiens

<400> SEQUENCE: 224
gactggagtt cagacgtgtg ctcttccgat ctgttggtgc gggagtgaat aggcc          55

<210> SEQ ID NO 225
<211> LENGTH: 58
<212> TYPE: DNA
<213> ORGANISM: Homo Sapiens

<400> SEQUENCE: 225
gactggagtt cagacgtgtg ctcttccgat ctgtttactt gaaggcctcc ggaatgcg       58

<210> SEQ ID NO 226
<211> LENGTH: 59
<212> TYPE: DNA
<213> ORGANISM: Homo Sapiens

<400> SEQUENCE: 226
```

```
gactggagtt cagacgtgtg ctcttccgat cttacctttc ctctgtgttg gcggatacc    59
```

<210> SEQ ID NO 227
<211> LENGTH: 59
<212> TYPE: DNA
<213> ORGANISM: Homo Sapiens

<400> SEQUENCE: 227

```
gactggagtt cagacgtgtg ctcttccgat cttaggcctt ggtgtgcatt cttctctct    59
```

<210> SEQ ID NO 228
<211> LENGTH: 57
<212> TYPE: DNA
<213> ORGANISM: Homo Sapiens

<400> SEQUENCE: 228

```
gactggagtt cagacgtgtg ctcttccgat cttagtcggt catgatggtc gaggtgc      57
```

<210> SEQ ID NO 229
<211> LENGTH: 59
<212> TYPE: DNA
<213> ORGANISM: Homo Sapiens

<400> SEQUENCE: 229

```
gactggagtt cagacgtgtg ctcttccgat cttcaaactg cagagtattt gggcgaatg    59
```

<210> SEQ ID NO 230
<211> LENGTH: 59
<212> TYPE: DNA
<213> ORGANISM: Homo Sapiens

<400> SEQUENCE: 230

```
gactggagtt cagacgtgtg ctcttccgat cttcaaggtt ggaatgagct ggataaggc    59
```

<210> SEQ ID NO 231
<211> LENGTH: 62
<212> TYPE: DNA
<213> ORGANISM: Homo Sapiens

<400> SEQUENCE: 231

```
gactggagtt cagacgtgtg ctcttccgat cttcacattt ctttgaccat ttgttttgct   60
gt                                                                  62
```

<210> SEQ ID NO 232
<211> LENGTH: 59
<212> TYPE: DNA
<213> ORGANISM: Homo Sapiens

<400> SEQUENCE: 232

```
gactggagtt cagacgtgtg ctcttccgat cttcccaaag cagaagtaaa accagatgc    59
```

<210> SEQ ID NO 233
<211> LENGTH: 59
<212> TYPE: DNA
<213> ORGANISM: Homo Sapiens

<400> SEQUENCE: 233

```
gactggagtt cagacgtgtg ctcttccgat cttcccttac acacacgcaa aatactcct    59
```

<210> SEQ ID NO 234
<211> LENGTH: 59
<212> TYPE: DNA

<213> ORGANISM: Homo Sapiens

<400> SEQUENCE: 234
gactggagtt cagacgtgtg ctcttccgat cttcctcccc tgtcatcctc acactttc    59

<210> SEQ ID NO 235
<211> LENGTH: 59
<212> TYPE: DNA
<213> ORGANISM: Homo Sapiens

<400> SEQUENCE: 235
gactggagtt cagacgtgtg ctcttccgat cttcgtcata gttgttgcaa gccgaagag    59

<210> SEQ ID NO 236
<211> LENGTH: 58
<212> TYPE: DNA
<213> ORGANISM: Homo Sapiens

<400> SEQUENCE: 236
gactggagtt cagacgtgtg ctcttccgat cttcgtggag aacaagtttg gcagcatc    58

<210> SEQ ID NO 237
<211> LENGTH: 59
<212> TYPE: DNA
<213> ORGANISM: Homo Sapiens

<400> SEQUENCE: 237
gactggagtt cagacgtgtg ctcttccgat cttctacctt gtagcctcca atgcgatgc    59

<210> SEQ ID NO 238
<211> LENGTH: 59
<212> TYPE: DNA
<213> ORGANISM: Homo Sapiens

<400> SEQUENCE: 238
gactggagtt cagacgtgtg ctcttccgat cttctcaact aaaagcttct gtctgcaag    59

<210> SEQ ID NO 239
<211> LENGTH: 59
<212> TYPE: DNA
<213> ORGANISM: Homo Sapiens

<400> SEQUENCE: 239
gactggagtt cagacgtgtg ctcttccgat cttctcccca ataataatca gccacccc    59

<210> SEQ ID NO 240
<211> LENGTH: 59
<212> TYPE: DNA
<213> ORGANISM: Homo Sapiens

<400> SEQUENCE: 240
gactggagtt cagacgtgtg ctcttccgat cttctctgga tggaactgat gtctggacg    59

<210> SEQ ID NO 241
<211> LENGTH: 59
<212> TYPE: DNA
<213> ORGANISM: Homo Sapiens

<400> SEQUENCE: 241
gactggagtt cagacgtgtg ctcttccgat cttctgcagc aaattcaacc accagaaca    59

<210> SEQ ID NO 242
<211> LENGTH: 66

```
<212> TYPE: DNA
<213> ORGANISM: Homo Sapiens

<400> SEQUENCE: 242
gactggagtt cagacgtgtg ctcttccgat cttgagcatt tgaagttttt attagtgatg    60
gatttg                                                                66

<210> SEQ ID NO 243
<211> LENGTH: 59
<212> TYPE: DNA
<213> ORGANISM: Homo Sapiens

<400> SEQUENCE: 243
gactggagtt cagacgtgtg ctcttccgat cttgagtctg aagtgagaac tccgtgtgg     59

<210> SEQ ID NO 244
<211> LENGTH: 60
<212> TYPE: DNA
<213> ORGANISM: Homo Sapiens

<400> SEQUENCE: 244
gactggagtt cagacgtgtg ctcttccgat cttgataacg acacaacaca aaatagccgt    60

<210> SEQ ID NO 245
<211> LENGTH: 57
<212> TYPE: DNA
<213> ORGANISM: Homo Sapiens

<400> SEQUENCE: 245
gactggagtt cagacgtgtg ctcttccgat cttgcaagaa cccagacctc gagtttg       57

<210> SEQ ID NO 246
<211> LENGTH: 58
<212> TYPE: DNA
<213> ORGANISM: Homo Sapiens

<400> SEQUENCE: 246
gactggagtt cagacgtgtg ctcttccgat cttgcataca ttcgaaagac cctagcct      58

<210> SEQ ID NO 247
<211> LENGTH: 59
<212> TYPE: DNA
<213> ORGANISM: Homo Sapiens

<400> SEQUENCE: 247
gactggagtt cagacgtgtg ctcttccgat cttgcccgtg atgttccatg taatactgg     59

<210> SEQ ID NO 248
<211> LENGTH: 60
<212> TYPE: DNA
<213> ORGANISM: Homo Sapiens

<400> SEQUENCE: 248
gactggagtt cagacgtgtg ctcttccgat cttgccttct agaacagtag acacaaaaca    60

<210> SEQ ID NO 249
<211> LENGTH: 59
<212> TYPE: DNA
<213> ORGANISM: Homo Sapiens

<400> SEQUENCE: 249
gactggagtt cagacgtgtg ctcttccgat cttgctagga aagaggcaag gaaaggtga     59
```

<210> SEQ ID NO 250
<211> LENGTH: 59
<212> TYPE: DNA
<213> ORGANISM: Homo Sapiens

<400> SEQUENCE: 250
gactggagtt cagacgtgtg ctcttccgat cttgctcttt tcacccatct acagtcccc      59

<210> SEQ ID NO 251
<211> LENGTH: 59
<212> TYPE: DNA
<213> ORGANISM: Homo Sapiens

<400> SEQUENCE: 251
gactggagtt cagacgtgtg ctcttccgat cttgctgagg aagtggattt tgcaggttg      59

<210> SEQ ID NO 252
<211> LENGTH: 74
<212> TYPE: DNA
<213> ORGANISM: Homo Sapiens

<400> SEQUENCE: 252
gactggagtt cagacgtgtg ctcttccgat cttggaatat atccactcaa tcttctactt      60
taaaatgact tagg                                                       74

<210> SEQ ID NO 253
<211> LENGTH: 60
<212> TYPE: DNA
<213> ORGANISM: Homo Sapiens

<400> SEQUENCE: 253
gactggagtt cagacgtgtg ctcttccgat cttggacatg aagcaggctg atactacaca     60

<210> SEQ ID NO 254
<211> LENGTH: 59
<212> TYPE: DNA
<213> ORGANISM: Homo Sapiens

<400> SEQUENCE: 254
gactggagtt cagacgtgtg ctcttccgat cttggcacat tccattctta ccaaactct      59

<210> SEQ ID NO 255
<211> LENGTH: 55
<212> TYPE: DNA
<213> ORGANISM: Homo Sapiens

<400> SEQUENCE: 255
gactggagtt cagacgtgtg ctcttccgat cttggcagtt cccatctcag gctgg          55

<210> SEQ ID NO 256
<211> LENGTH: 59
<212> TYPE: DNA
<213> ORGANISM: Homo Sapiens

<400> SEQUENCE: 256
gactggagtt cagacgtgtg ctcttccgat cttggccccg cctctgaata tttctttaa      59

<210> SEQ ID NO 257
<211> LENGTH: 59
<212> TYPE: DNA
<213> ORGANISM: Homo Sapiens

<400> SEQUENCE: 257
gactggagtt cagacgtgtg ctcttccgat cttgggctac aagaactacc gataccgtg    59

<210> SEQ ID NO 258
<211> LENGTH: 59
<212> TYPE: DNA
<213> ORGANISM: Homo Sapiens

<400> SEQUENCE: 258
gactggagtt cagacgtgtg ctcttccgat cttgtacatg gccactcaga tctcgtcag    59

<210> SEQ ID NO 259
<211> LENGTH: 60
<212> TYPE: DNA
<213> ORGANISM: Homo Sapiens

<400> SEQUENCE: 259
gactggagtt cagacgtgtg ctcttccgat cttgtcacca cattacatac ttaccatgcc    60

<210> SEQ ID NO 260
<211> LENGTH: 59
<212> TYPE: DNA
<213> ORGANISM: Homo Sapiens

<400> SEQUENCE: 260
gactggagtt cagacgtgtg ctcttccgat cttgtcagtg gggaacaaga agtggagaa    59

<210> SEQ ID NO 261
<211> LENGTH: 58
<212> TYPE: DNA
<213> ORGANISM: Homo Sapiens

<400> SEQUENCE: 261
gactggagtt cagacgtgtg ctcttccgat cttgtccatc agcctccagt tcagcaag     58

<210> SEQ ID NO 262
<211> LENGTH: 59
<212> TYPE: DNA
<213> ORGANISM: Homo Sapiens

<400> SEQUENCE: 262
gactggagtt cagacgtgtg ctcttccgat cttgtctgaa cacttcttcc aggtccaag    59

<210> SEQ ID NO 263
<211> LENGTH: 59
<212> TYPE: DNA
<213> ORGANISM: Homo Sapiens

<400> SEQUENCE: 263
gactggagtt cagacgtgtg ctcttccgat cttgtgattt attctttcaa cagccacgg    59

<210> SEQ ID NO 264
<211> LENGTH: 59
<212> TYPE: DNA
<213> ORGANISM: Homo Sapiens

<400> SEQUENCE: 264
gactggagtt cagacgtgtg ctcttccgat cttgtgctca gttccctcct ctatgcaat    59

<210> SEQ ID NO 265
<211> LENGTH: 59
<212> TYPE: DNA
<213> ORGANISM: Homo Sapiens -continued

<400> SEQUENCE: 265
gactggagtt cagacgtgtg ctcttccgat cttgtggttg gtcagaaaga taagccagt    59

<210> SEQ ID NO 266
<211> LENGTH: 60
<212> TYPE: DNA
<213> ORGANISM: Homo Sapiens

<400> SEQUENCE: 266
gactggagtt cagacgtgtg ctcttccgat cttgtgtcac attataaaga ttcaggcaat    60

<210> SEQ ID NO 267
<211> LENGTH: 59
<212> TYPE: DNA
<213> ORGANISM: Homo Sapiens

<400> SEQUENCE: 267
gactggagtt cagacgtgtg ctcttccgat ctttatcact gtctgtctct cctgcagcc    59

<210> SEQ ID NO 268
<211> LENGTH: 59
<212> TYPE: DNA
<213> ORGANISM: Homo Sapiens

<400> SEQUENCE: 268
gactggagtt cagacgtgtg ctcttccgat ctttatttga gctagaacca gtgccaggc    59

<210> SEQ ID NO 269
<211> LENGTH: 59
<212> TYPE: DNA
<213> ORGANISM: Homo Sapiens

<400> SEQUENCE: 269
gactggagtt cagacgtgtg ctcttccgat cttttccccaa tctacctgtg tcagttccc    59

<210> SEQ ID NO 270
<211> LENGTH: 59
<212> TYPE: DNA
<213> ORGANISM: Homo Sapiens

<400> SEQUENCE: 270
gactggagtt cagacgtgtg ctcttccgat ctttctacct gcagtaaaac gatgtttgc    59

<210> SEQ ID NO 271
<211> LENGTH: 59
<212> TYPE: DNA
<213> ORGANISM: Homo Sapiens

<400> SEQUENCE: 271
gactggagtt cagacgtgtg ctcttccgat ctttctccag gcgtttcttc catccttcc    59

<210> SEQ ID NO 272
<211> LENGTH: 59
<212> TYPE: DNA
<213> ORGANISM: Homo Sapiens

<400> SEQUENCE: 272
gactggagtt cagacgtgtg ctcttccgat ctttctctct ggcaggtcat gatgatggg    59

<210> SEQ ID NO 273
<211> LENGTH: 59
<212> TYPE: DNA
<213> ORGANISM: Homo Sapiens

```
<400> SEQUENCE: 273
gactggagtt cagacgtgtg ctcttccgat cttcttcat accaggacca gaggaaacc        59

<210> SEQ ID NO 274
<211> LENGTH: 59
<212> TYPE: DNA
<213> ORGANISM: Homo Sapiens

<400> SEQUENCE: 274
gactggagtt cagacgtgtg ctcttccgat cttcttcct tttccatgca gtgtgtcca        59

<210> SEQ ID NO 275
<211> LENGTH: 64
<212> TYPE: DNA
<213> ORGANISM: Homo Sapiens

<400> SEQUENCE: 275
gactggagtt cagacgtgtg ctcttccgat cttttaaaca tgcattgata acacccctac      60
tgct                                                                   64

<210> SEQ ID NO 276
<211> LENGTH: 63
<212> TYPE: DNA
<213> ORGANISM: Homo Sapiens

<400> SEQUENCE: 276
gactggagtt cagacgtgtg ctcttccgat cttttctaat cacataggca ggaaatctca      60
gtg                                                                    63

<210> SEQ ID NO 277
<211> LENGTH: 59
<212> TYPE: DNA
<213> ORGANISM: Homo Sapiens

<400> SEQUENCE: 277
gactggagtt cagacgtgtg ctcttccgat cttttcttcc ctccctcga aatgaagct        59

<210> SEQ ID NO 278
<211> LENGTH: 61
<212> TYPE: DNA
<213> ORGANISM: Homo Sapiens

<400> SEQUENCE: 278
gactggagtt cagacgtgtg ctcttccgat cttttgtttc tcccacacag acactattgt      60
g                                                                      61

<210> SEQ ID NO 279
<211> LENGTH: 59
<212> TYPE: DNA
<213> ORGANISM: Homo Sapiens

<400> SEQUENCE: 279
gactggagtt cagacgtgtg ctcttccgat cttttttgtgt gagtgaatgt gtgccaggg      59

<210> SEQ ID NO 280
<211> LENGTH: 59
<212> TYPE: DNA
<213> ORGANISM: Homo Sapiens

<400> SEQUENCE: 280
```
gactggagtt cagacgtgtg ctcttccgat ctaaagctct tcctgtttca gtccccatt    59

<210> SEQ ID NO 281
<211> LENGTH: 60
<212> TYPE: DNA
<213> ORGANISM: Homo Sapiens

<400> SEQUENCE: 281
gactggagtt cagacgtgtg ctcttccgat ctacctttc ttatgtgctt ttagggccca    60

<210> SEQ ID NO 282
<211> LENGTH: 59
<212> TYPE: DNA
<213> ORGANISM: Homo Sapiens

<400> SEQUENCE: 282
gactggagtt cagacgtgtg ctcttccgat ctagcttctt cccatgatga tctgtccct    59

<210> SEQ ID NO 283
<211> LENGTH: 59
<212> TYPE: DNA
<213> ORGANISM: Homo Sapiens

<400> SEQUENCE: 283
gactggagtt cagacgtgtg ctcttccgat ctagtggctg tgaaggtaag aagtggctc    59

<210> SEQ ID NO 284
<211> LENGTH: 59
<212> TYPE: DNA
<213> ORGANISM: Homo Sapiens

<400> SEQUENCE: 284
gactggagtt cagacgtgtg ctcttccgat ctcatcgctg tagaacgcac catagaagc    59

<210> SEQ ID NO 285
<211> LENGTH: 56
<212> TYPE: DNA
<213> ORGANISM: Homo Sapiens

<400> SEQUENCE: 285
gactggagtt cagacgtgtg ctcttccgat ctcattctgc tggtcgtggt cttggg    56

<210> SEQ ID NO 286
<211> LENGTH: 59
<212> TYPE: DNA
<213> ORGANISM: Homo Sapiens

<400> SEQUENCE: 286
gactggagtt cagacgtgtg ctcttccgat ctccaagaga gcaacaccca cacttacac    59

<210> SEQ ID NO 287
<211> LENGTH: 57
<212> TYPE: DNA
<213> ORGANISM: Homo Sapiens

<400> SEQUENCE: 287
gactggagtt cagacgtgtg ctcttccgat ctcctggtat ggtcatggaa ggggctt    57

<210> SEQ ID NO 288
<211> LENGTH: 59
<212> TYPE: DNA
<213> ORGANISM: Homo Sapiens

<400> SEQUENCE: 288
gactggagtt cagacgtgtg ctcttccgat ctctgaggaa ggtgaaggtg cttggatct    59

<210> SEQ ID NO 289
<211> LENGTH: 59
<212> TYPE: DNA
<213> ORGANISM: Homo Sapiens

<400> SEQUENCE: 289
gactggagtt cagacgtgtg ctcttccgat ctgggatgtg atgagaggtg gatgggtag    59

<210> SEQ ID NO 290
<211> LENGTH: 59
<212> TYPE: DNA
<213> ORGANISM: Homo Sapiens

<400> SEQUENCE: 290
gactggagtt cagacgtgtg ctcttccgat ctggtcaaga gtcccaacca tgtcaaaat    59

<210> SEQ ID NO 291
<211> LENGTH: 60
<212> TYPE: DNA
<213> ORGANISM: Homo Sapiens

<400> SEQUENCE: 291
gactggagtt cagacgtgtg ctcttccgat ctggttcttc tgatacgatc tgtgacctgt    60

<210> SEQ ID NO 292
<211> LENGTH: 57
<212> TYPE: DNA
<213> ORGANISM: Homo Sapiens

<400> SEQUENCE: 292
gactggagtt cagacgtgtg ctcttccgat ctgtatgcga cacttacagc tgcccag    57

<210> SEQ ID NO 293
<211> LENGTH: 59
<212> TYPE: DNA
<213> ORGANISM: Homo Sapiens

<400> SEQUENCE: 293
gactggagtt cagacgtgtg ctcttccgat ctgtttctga tgtaccaacc tcaccaaca    59

<210> SEQ ID NO 294
<211> LENGTH: 59
<212> TYPE: DNA
<213> ORGANISM: Homo Sapiens

<400> SEQUENCE: 294
gactggagtt cagacgtgtg ctcttccgat cttaagtgcc cgaagtgtaa gcccaacta    59

<210> SEQ ID NO 295
<211> LENGTH: 59
<212> TYPE: DNA
<213> ORGANISM: Homo Sapiens

<400> SEQUENCE: 295
gactggagtt cagacgtgtg ctcttccgat cttccttcct cttcctacag tactcccct    59

<210> SEQ ID NO 296
<211> LENGTH: 59
<212> TYPE: DNA
<213> ORGANISM: Homo Sapiens

```
<400> SEQUENCE: 296
gactggagtt cagacgtgtg ctcttccgat cttcgcctgt cctcatgtat tggtctctc      59

<210> SEQ ID NO 297
<211> LENGTH: 59
<212> TYPE: DNA
<213> ORGANISM: Homo Sapiens

<400> SEQUENCE: 297
gactggagtt cagacgtgtg ctcttccgat cttctagtaa ctcagcagca tctcagggc      59

<210> SEQ ID NO 298
<211> LENGTH: 59
<212> TYPE: DNA
<213> ORGANISM: Homo Sapiens

<400> SEQUENCE: 298
gactggagtt cagacgtgtg ctcttccgat cttgaagcaa tttaggtatg aaagccagc      59

<210> SEQ ID NO 299
<211> LENGTH: 60
<212> TYPE: DNA
<213> ORGANISM: Homo Sapiens

<400> SEQUENCE: 299
gactggagtt cagacgtgtg ctcttccgat cttggcagcc agaaatatcc tccttactca     60

<210> SEQ ID NO 300
<211> LENGTH: 59
<212> TYPE: DNA
<213> ORGANISM: Homo Sapiens

<400> SEQUENCE: 300
gactggagtt cagacgtgtg ctcttccgat cttgttccat cctctgctgt cacctcttg      59

<210> SEQ ID NO 301
<211> LENGTH: 59
<212> TYPE: DNA
<213> ORGANISM: Homo Sapiens

<400> SEQUENCE: 301
gactggagtt cagacgtgtg ctcttccgat cttgttttct tccctttaga tgctctgct      59

<210> SEQ ID NO 302
<211> LENGTH: 59
<212> TYPE: DNA
<213> ORGANISM: Homo Sapiens

<400> SEQUENCE: 302
gactggagtt cagacgtgtg ctcttccgat cttttaacca tgcagatcct cagtttgtg      59

<210> SEQ ID NO 303
<211> LENGTH: 58
<212> TYPE: DNA
<213> ORGANISM: Homo Sapiens

<400> SEQUENCE: 303
gactggagtt cagacgtgtg ctcttccgat ctacccttgt ctctgtgttc ttgtcccc       58

<210> SEQ ID NO 304
<211> LENGTH: 59
<212> TYPE: DNA
<213> ORGANISM: Homo Sapiens
```

<400> SEQUENCE: 304
gactggagtt cagacgtgtg ctcttccgat ctagccaata ttgtctttgt gttcccgga    59

<210> SEQ ID NO 305
<211> LENGTH: 59
<212> TYPE: DNA
<213> ORGANISM: Homo Sapiens

<400> SEQUENCE: 305
gactggagtt cagacgtgtg ctcttccgat ctctcatatc ctcctctttc tgcccaggg    59

<210> SEQ ID NO 306
<211> LENGTH: 59
<212> TYPE: DNA
<213> ORGANISM: Homo Sapiens

<400> SEQUENCE: 306
gactggagtt cagacgtgtg ctcttccgat ctgttgaagt cctcgttgtc ttgttggca    59

<210> SEQ ID NO 307
<211> LENGTH: 59
<212> TYPE: DNA
<213> ORGANISM: Homo Sapiens

<400> SEQUENCE: 307
gactggagtt cagacgtgtg ctcttccgat ctgcaccatc tcacaattgc cagttaacg    59

<210> SEQ ID NO 308
<211> LENGTH: 59
<212> TYPE: DNA
<213> ORGANISM: Homo Sapiens

<400> SEQUENCE: 308
gactggagtt cagacgtgtg ctcttccgat ctaaaaaagt tcgccaccct tgccgtttc    59

<210> SEQ ID NO 309
<211> LENGTH: 65
<212> TYPE: DNA
<213> ORGANISM: Homo Sapiens

<400> SEQUENCE: 309
gactggagtt cagacgtgtg ctcttccgat ctaaaatgca taacaacaaa gaatatgaat    60
atgga    65

<210> SEQ ID NO 310
<211> LENGTH: 59
<212> TYPE: DNA
<213> ORGANISM: Homo Sapiens

<400> SEQUENCE: 310
gactggagtt cagacgtgtg ctcttccgat ctaaacccaa actttataag atcctggct    59

<210> SEQ ID NO 311
<211> LENGTH: 59
<212> TYPE: DNA
<213> ORGANISM: Homo Sapiens

<400> SEQUENCE: 311
gactggagtt cagacgtgtg ctcttccgat ctaaacctct ctttcttcca cctttctcc    59

<210> SEQ ID NO 312

<210> SEQ ID NO 312
<211> LENGTH: 59
<212> TYPE: DNA
<213> ORGANISM: Homo Sapiens

<400> SEQUENCE: 312
gactggagtt cagacgtgtg ctcttccgat ctaaactcta cgtctcctcc gaccactgt    59

<210> SEQ ID NO 313
<211> LENGTH: 59
<212> TYPE: DNA
<213> ORGANISM: Homo Sapiens

<400> SEQUENCE: 313
gactggagtt cagacgtgtg ctcttccgat ctaaataccc cctccatcaa cttcttcaa    59

<210> SEQ ID NO 314
<211> LENGTH: 59
<212> TYPE: DNA
<213> ORGANISM: Homo Sapiens

<400> SEQUENCE: 314
gactggagtt cagacgtgtg ctcttccgat ctaaatccat ccccacaccc tgttcactc    59

<210> SEQ ID NO 315
<211> LENGTH: 59
<212> TYPE: DNA
<213> ORGANISM: Homo Sapiens

<400> SEQUENCE: 315
gactggagtt cagacgtgtg ctcttccgat ctaacacagg gccaaagact aagtgacat    59

<210> SEQ ID NO 316
<211> LENGTH: 59
<212> TYPE: DNA
<213> ORGANISM: Homo Sapiens

<400> SEQUENCE: 316
gactggagtt cagacgtgtg ctcttccgat ctaacacata caagttggaa atttctggg    59

<210> SEQ ID NO 317
<211> LENGTH: 59
<212> TYPE: DNA
<213> ORGANISM: Homo Sapiens

<400> SEQUENCE: 317
gactggagtt cagacgtgtg ctcttccgat ctaacacatc aaggttggaa tgagctgga    59

<210> SEQ ID NO 318
<211> LENGTH: 58
<212> TYPE: DNA
<213> ORGANISM: Homo Sapiens

<400> SEQUENCE: 318
gactggagtt cagacgtgtg ctcttccgat ctaacatgcc tttcacgttc ctttcccc     58

<210> SEQ ID NO 319
<211> LENGTH: 57
<212> TYPE: DNA
<213> ORGANISM: Homo Sapiens

<400> SEQUENCE: 319
gactggagtt cagacgtgtg ctcttccgat ctaactcctt cccgttttc agccacc       57

```
<210> SEQ ID NO 320
<211> LENGTH: 59
<212> TYPE: DNA
<213> ORGANISM: Homo Sapiens

<400> SEQUENCE: 320
gactggagtt cagacgtgtg ctcttccgat ctaactctac acagaaaggg cccaaattc      59

<210> SEQ ID NO 321
<211> LENGTH: 59
<212> TYPE: DNA
<213> ORGANISM: Homo Sapiens

<400> SEQUENCE: 321
gactggagtt cagacgtgtg ctcttccgat ctaactctct ttgactgcag aatccaact      59

<210> SEQ ID NO 322
<211> LENGTH: 56
<212> TYPE: DNA
<213> ORGANISM: Homo Sapiens

<400> SEQUENCE: 322
gactggagtt cagacgtgtg ctcttccgat ctaactggaa aaaactgttt gggacc         56

<210> SEQ ID NO 323
<211> LENGTH: 59
<212> TYPE: DNA
<213> ORGANISM: Homo Sapiens

<400> SEQUENCE: 323
gactggagtt cagacgtgtg ctcttccgat ctaactggaa aaaactgttt gggacctcc      59

<210> SEQ ID NO 324
<211> LENGTH: 59
<212> TYPE: DNA
<213> ORGANISM: Homo Sapiens

<400> SEQUENCE: 324
gactggagtt cagacgtgtg ctcttccgat ctaagaaagc cctccccagt cctcatgta      59

<210> SEQ ID NO 325
<211> LENGTH: 59
<212> TYPE: DNA
<213> ORGANISM: Homo Sapiens

<400> SEQUENCE: 325
gactggagtt cagacgtgtg ctcttccgat ctaagaatca gaacaatgcc tccacgacc      59

<210> SEQ ID NO 326
<211> LENGTH: 63
<212> TYPE: DNA
<213> ORGANISM: Homo Sapiens

<400> SEQUENCE: 326
gactggagtt cagacgtgtg ctcttccgat ctaagatcac atcacatgaa tggaatagtt     60
taa                                                                   63

<210> SEQ ID NO 327
<211> LENGTH: 62
<212> TYPE: DNA
<213> ORGANISM: Homo Sapiens

<400> SEQUENCE: 327
```

-continued

```
gactggagtt cagacgtgtg ctcttccgat ctaagattca ggcaatgttt gttagtatta    60
gt                                                                  62
```

<210> SEQ ID NO 328
<211> LENGTH: 63
<212> TYPE: DNA
<213> ORGANISM: Homo Sapiens

<400> SEQUENCE: 328

```
gactggagtt cagacgtgtg ctcttccgat ctaagattta cctctattgt tggatcatat    60
tcg                                                                 63
```

<210> SEQ ID NO 329
<211> LENGTH: 61
<212> TYPE: DNA
<213> ORGANISM: Homo Sapiens

<400> SEQUENCE: 329

```
gactggagtt cagacgtgtg ctcttccgat ctaagcaacc ttttttctct ttctctttag    60
a                                                                   61
```

<210> SEQ ID NO 330
<211> LENGTH: 59
<212> TYPE: DNA
<213> ORGANISM: Homo Sapiens

<400> SEQUENCE: 330

```
gactggagtt cagacgtgtg ctcttccgat ctaagcacct gatcctagta ccttccctg     59
```

<210> SEQ ID NO 331
<211> LENGTH: 56
<212> TYPE: DNA
<213> ORGANISM: Homo Sapiens

<400> SEQUENCE: 331

```
gactggagtt cagacgtgtg ctcttccgat ctaagcagcc acacccatt cttgag          56
```

<210> SEQ ID NO 332
<211> LENGTH: 59
<212> TYPE: DNA
<213> ORGANISM: Homo Sapiens

<400> SEQUENCE: 332

```
gactggagtt cagacgtgtg ctcttccgat ctaagccaac acaccacaga tgtcttcag     59
```

<210> SEQ ID NO 333
<211> LENGTH: 59
<212> TYPE: DNA
<213> ORGANISM: Homo Sapiens

<400> SEQUENCE: 333

```
gactggagtt cagacgtgtg ctcttccgat ctaagccctc aacatccta gtcaactcc      59
```

<210> SEQ ID NO 334
<211> LENGTH: 55
<212> TYPE: DNA
<213> ORGANISM: Homo Sapiens

<400> SEQUENCE: 334

```
gactggagtt cagacgtgtg ctcttccgat ctaaggacca aggagcagag gaggc          55
```

```
<210> SEQ ID NO 335
<211> LENGTH: 50
<212> TYPE: DNA
<213> ORGANISM: Homo Sapiens

<400> SEQUENCE: 335
gactggagtt cagacgtgtg ctcttccgat ctaagggcct cttcatgcgg          50

<210> SEQ ID NO 336
<211> LENGTH: 59
<212> TYPE: DNA
<213> ORGANISM: Homo Sapiens

<400> SEQUENCE: 336
gactggagtt cagacgtgtg ctcttccgat ctaagtaatt ttgcccagtt caggatcca  59

<210> SEQ ID NO 337
<211> LENGTH: 59
<212> TYPE: DNA
<213> ORGANISM: Homo Sapiens

<400> SEQUENCE: 337
gactggagtt cagacgtgtg ctcttccgat ctaagtagtc tgatccactg aagctgaat  59

<210> SEQ ID NO 338
<211> LENGTH: 58
<212> TYPE: DNA
<213> ORGANISM: Homo Sapiens

<400> SEQUENCE: 338
gactggagtt cagacgtgtg ctcttccgat ctaagttcgc caccttgcc gtttcttt    58

<210> SEQ ID NO 339
<211> LENGTH: 59
<212> TYPE: DNA
<213> ORGANISM: Homo Sapiens

<400> SEQUENCE: 339
gactggagtt cagacgtgtg ctcttccgat ctaataatag gaaatcacag ctaaggggc  59

<210> SEQ ID NO 340
<211> LENGTH: 59
<212> TYPE: DNA
<213> ORGANISM: Homo Sapiens

<400> SEQUENCE: 340
gactggagtt cagacgtgtg ctcttccgat ctaatacatt cttcatacca ggaccagag  59

<210> SEQ ID NO 341
<211> LENGTH: 59
<212> TYPE: DNA
<213> ORGANISM: Homo Sapiens

<400> SEQUENCE: 341
gactggagtt cagacgtgtg ctcttccgat ctaatcacca aaaaagttcg ccacccttg  59

<210> SEQ ID NO 342
<211> LENGTH: 59
<212> TYPE: DNA
<213> ORGANISM: Homo Sapiens

<400> SEQUENCE: 342
gactggagtt cagacgtgtg ctcttccgat ctaatcagaa caatgcctcc acgaccatc  59
```

<210> SEQ ID NO 343
<211> LENGTH: 59
<212> TYPE: DNA
<213> ORGANISM: Homo Sapiens

<400> SEQUENCE: 343
gactggagtt cagacgtgtg ctcttccgat ctaatgcatg tttccaattt tagcgagtg    59

<210> SEQ ID NO 344
<211> LENGTH: 59
<212> TYPE: DNA
<213> ORGANISM: Homo Sapiens

<400> SEQUENCE: 344
gactggagtt cagacgtgtg ctcttccgat ctaatgtagg agtggtcata aggctggta    59

<210> SEQ ID NO 345
<211> LENGTH: 59
<212> TYPE: DNA
<213> ORGANISM: Homo Sapiens

<400> SEQUENCE: 345
gactggagtt cagacgtgtg ctcttccgat ctaattctac cttgtagcct ccaatgcga    59

<210> SEQ ID NO 346
<211> LENGTH: 59
<212> TYPE: DNA
<213> ORGANISM: Homo Sapiens

<400> SEQUENCE: 346
gactggagtt cagacgtgtg ctcttccgat ctacaaagtg gttctggatt agctggatt    59

<210> SEQ ID NO 347
<211> LENGTH: 61
<212> TYPE: DNA
<213> ORGANISM: Homo Sapiens

<400> SEQUENCE: 347
gactggagtt cagacgtgtg ctcttccgat ctacaaatgg aaaatacaac tacgagagaa    60
a                                                                    61

<210> SEQ ID NO 348
<211> LENGTH: 59
<212> TYPE: DNA
<213> ORGANISM: Homo Sapiens

<400> SEQUENCE: 348
gactggagtt cagacgtgtg ctcttccgat ctacaaccct cctgccatca tattgaaca    59

<210> SEQ ID NO 349
<211> LENGTH: 55
<212> TYPE: DNA
<213> ORGANISM: Homo Sapiens

<400> SEQUENCE: 349
gactggagtt cagacgtgtg ctcttccgat ctacaacctc cgtcatgtgc tgtga    55

<210> SEQ ID NO 350
<211> LENGTH: 60
<212> TYPE: DNA
<213> ORGANISM: Homo Sapiens

<400> SEQUENCE: 350

```
gactggagtt cagacgtgtg ctcttccgat ctacaactac gagagaaaaa atgacttgct    60

<210> SEQ ID NO 351
<211> LENGTH: 59
<212> TYPE: DNA
<213> ORGANISM: Homo Sapiens

<400> SEQUENCE: 351
gactggagtt cagacgtgtg ctcttccgat ctacaactta acctgtttct cctccctct    59

<210> SEQ ID NO 352
<211> LENGTH: 61
<212> TYPE: DNA
<213> ORGANISM: Homo Sapiens

<400> SEQUENCE: 352
gactggagtt cagacgtgtg ctcttccgat ctacaactta ccatgttcaa tgatttcaac    60
t                                                                   61

<210> SEQ ID NO 353
<211> LENGTH: 58
<212> TYPE: DNA
<213> ORGANISM: Homo Sapiens

<400> SEQUENCE: 353
gactggagtt cagacgtgtg ctcttccgat ctacaagggt atgggtttgt cactgaga     58

<210> SEQ ID NO 354
<211> LENGTH: 60
<212> TYPE: DNA
<213> ORGANISM: Homo Sapiens

<400> SEQUENCE: 354
gactggagtt cagacgtgtg ctcttccgat ctacacaaat ggaaaataca actacgagag    60

<210> SEQ ID NO 355
<211> LENGTH: 59
<212> TYPE: DNA
<213> ORGANISM: Homo Sapiens

<400> SEQUENCE: 355
gactggagtt cagacgtgtg ctcttccgat ctacacagtg aagaggtag atattgggg      59

<210> SEQ ID NO 356
<211> LENGTH: 59
<212> TYPE: DNA
<213> ORGANISM: Homo Sapiens

<400> SEQUENCE: 356
gactggagtt cagacgtgtg ctcttccgat ctacacatcc cccaaagcca acaaagaaa    59

<210> SEQ ID NO 357
<211> LENGTH: 59
<212> TYPE: DNA
<213> ORGANISM: Homo Sapiens

<400> SEQUENCE: 357
gactggagtt cagacgtgtg ctcttccgat ctacacattc ttagagcata gtaagcagt    59

<210> SEQ ID NO 358
<211> LENGTH: 59
<212> TYPE: DNA
```

```
<213> ORGANISM: Homo Sapiens

<400> SEQUENCE: 358
gactggagtt cagacgtgtg ctcttccgat ctacacgaga caaatgtagg aaaaaacca      59

<210> SEQ ID NO 359
<211> LENGTH: 61
<212> TYPE: DNA
<213> ORGANISM: Homo Sapiens

<400> SEQUENCE: 359
gactggagtt cagacgtgtg ctcttccgat ctacactcta gtatctggaa aaatggcttt     60
g                                                                    61

<210> SEQ ID NO 360
<211> LENGTH: 59
<212> TYPE: DNA
<213> ORGANISM: Homo Sapiens

<400> SEQUENCE: 360
gactggagtt cagacgtgtg ctcttccgat ctacactctc tgctggctag tcaaaaaag     59

<210> SEQ ID NO 361
<211> LENGTH: 59
<212> TYPE: DNA
<213> ORGANISM: Homo Sapiens

<400> SEQUENCE: 361
gactggagtt cagacgtgtg ctcttccgat ctacacttac ctcattgtct gactccacg     59

<210> SEQ ID NO 362
<211> LENGTH: 61
<212> TYPE: DNA
<213> ORGANISM: Homo Sapiens

<400> SEQUENCE: 362
gactggagtt cagacgtgtg ctcttccgat ctacagaaag gactataatg acagttaacc    60
c                                                                    61

<210> SEQ ID NO 363
<211> LENGTH: 61
<212> TYPE: DNA
<213> ORGANISM: Homo Sapiens

<400> SEQUENCE: 363
gactggagtt cagacgtgtg ctcttccgat ctacagaata ttgttgctat ggtgatcttt    60
t                                                                    61

<210> SEQ ID NO 364
<211> LENGTH: 62
<212> TYPE: DNA
<213> ORGANISM: Homo Sapiens

<400> SEQUENCE: 364
gactggagtt cagacgtgtg ctcttccgat ctacagacta gctagagaca atgaattaag    60
gg                                                                   62

<210> SEQ ID NO 365
<211> LENGTH: 59
<212> TYPE: DNA
<213> ORGANISM: Homo Sapiens
```

-continued

<400> SEQUENCE: 365
gactggagtt cagacgtgtg ctcttccgat ctacagcaaa acaccaaaag accagacgt    59

<210> SEQ ID NO 366
<211> LENGTH: 59
<212> TYPE: DNA
<213> ORGANISM: Homo Sapiens

<400> SEQUENCE: 366
gactggagtt cagacgtgtg ctcttccgat ctacagcacc ctagaaccaa atccagcag    59

<210> SEQ ID NO 367
<211> LENGTH: 53
<212> TYPE: DNA
<213> ORGANISM: Homo Sapiens

<400> SEQUENCE: 367
gactggagtt cagacgtgtg ctcttccgat ctacaggcga ggagtagctg tgc          53

<210> SEQ ID NO 368
<211> LENGTH: 59
<212> TYPE: DNA
<213> ORGANISM: Homo Sapiens

<400> SEQUENCE: 368
gactggagtt cagacgtgtg ctcttccgat ctacagggcc aaagactaag tgacataaa    59

<210> SEQ ID NO 369
<211> LENGTH: 59
<212> TYPE: DNA
<213> ORGANISM: Homo Sapiens

<400> SEQUENCE: 369
gactggagtt cagacgtgtg ctcttccgat ctacagtgag tgcagttgtt taccatgat    59

<210> SEQ ID NO 370
<211> LENGTH: 60
<212> TYPE: DNA
<213> ORGANISM: Homo Sapiens

<400> SEQUENCE: 370
gactggagtt cagacgtgtg ctcttccgat ctacagtgga agaggtagat attggggaag   60

<210> SEQ ID NO 371
<211> LENGTH: 59
<212> TYPE: DNA
<213> ORGANISM: Homo Sapiens

<400> SEQUENCE: 371
gactggagtt cagacgtgtg ctcttccgat ctacatacaa gttggaaatt tctgggcca    59

<210> SEQ ID NO 372
<211> LENGTH: 60
<212> TYPE: DNA
<213> ORGANISM: Homo Sapiens

<400> SEQUENCE: 372
gactggagtt cagacgtgtg ctcttccgat ctacatactt ggacttggtg atagacatgt   60

<210> SEQ ID NO 373
<211> LENGTH: 62
<212> TYPE: DNA

<210> SEQ ID NO 373
<211> LENGTH: 62
<212> TYPE: DNA
<213> ORGANISM: Homo Sapiens

<400> SEQUENCE: 373
gactggagtt cagacgtgtg ctcttccgat ctacatagag ttttaatgca ttgtctcatc    60
tt                                                                  62

<210> SEQ ID NO 374
<211> LENGTH: 65
<212> TYPE: DNA
<213> ORGANISM: Homo Sapiens

<400> SEQUENCE: 374
gactggagtt cagacgtgtg ctcttccgat ctacatagag ttttaatgca ttgtctcatc    60
ttttt                                                               65

<210> SEQ ID NO 375
<211> LENGTH: 58
<212> TYPE: DNA
<213> ORGANISM: Homo Sapiens

<400> SEQUENCE: 375
gactggagtt cagacgtgtg ctcttccgat ctacatcaag ttcaacagtt caggccag      58

<210> SEQ ID NO 376
<211> LENGTH: 59
<212> TYPE: DNA
<213> ORGANISM: Homo Sapiens

<400> SEQUENCE: 376
gactggagtt cagacgtgtg ctcttccgat ctacatcggg gcaaatttttt aaaggcaca    59

<210> SEQ ID NO 377
<211> LENGTH: 59
<212> TYPE: DNA
<213> ORGANISM: Homo Sapiens

<400> SEQUENCE: 377
gactggagtt cagacgtgtg ctcttccgat ctacatgcca tcattctagg aagctcacc     59

<210> SEQ ID NO 378
<211> LENGTH: 59
<212> TYPE: DNA
<213> ORGANISM: Homo Sapiens

<400> SEQUENCE: 378
gactggagtt cagacgtgtg ctcttccgat ctacattagg cagtgactcg atgaaggca     59

<210> SEQ ID NO 379
<211> LENGTH: 61
<212> TYPE: DNA
<213> ORGANISM: Homo Sapiens

<400> SEQUENCE: 379
gactggagtt cagacgtgtg ctcttccgat ctacattcat agacagtaaa acagaaagga    60
c                                                                   61

<210> SEQ ID NO 380
<211> LENGTH: 59
<212> TYPE: DNA
<213> ORGANISM: Homo Sapiens

<400> SEQUENCE: 380

```
gactggagtt cagacgtgtg ctcttccgat ctacattctt cataccagga ccagaggaa      59
```

<210> SEQ ID NO 381
<211> LENGTH: 59
<212> TYPE: DNA
<213> ORGANISM: Homo Sapiens

<400> SEQUENCE: 381

```
gactggagtt cagacgtgtg ctcttccgat ctacattctt cataccagga ccagaggaa      59
```

<210> SEQ ID NO 382
<211> LENGTH: 61
<212> TYPE: DNA
<213> ORGANISM: Homo Sapiens

<400> SEQUENCE: 382

```
gactggagtt cagacgtgtg ctcttccgat ctaccaaatt aaattactca cctatctccc     60
a                                                                     61
```

<210> SEQ ID NO 383
<211> LENGTH: 61
<212> TYPE: DNA
<213> ORGANISM: Homo Sapiens

<400> SEQUENCE: 383

```
gactggagtt cagacgtgtg ctcttccgat ctaccaagct atatctgaac aaaaattccg     60
t                                                                     61
```

<210> SEQ ID NO 384
<211> LENGTH: 57
<212> TYPE: DNA
<213> ORGANISM: Homo Sapiens

<400> SEQUENCE: 384

```
gactggagtt cagacgtgtg ctcttccgat ctaccacacc tgtcatgtag cagcttt        57
```

<210> SEQ ID NO 385
<211> LENGTH: 59
<212> TYPE: DNA
<213> ORGANISM: Homo Sapiens

<400> SEQUENCE: 385

```
gactggagtt cagacgtgtg ctcttccgat ctaccacatt acatacttac catgccact      59
```

<210> SEQ ID NO 386
<211> LENGTH: 63
<212> TYPE: DNA
<213> ORGANISM: Homo Sapiens

<400> SEQUENCE: 386

```
gactggagtt cagacgtgtg ctcttccgat ctaccacatt acatacttac catgccactt     60
tcc                                                                   63
```

<210> SEQ ID NO 387
<211> LENGTH: 59
<212> TYPE: DNA
<213> ORGANISM: Homo Sapiens

<400> SEQUENCE: 387

```
gactggagtt cagacgtgtg ctcttccgat ctaccaggta gagggagtac agagtgacc      59
```

<210> SEQ ID NO 388
<211> LENGTH: 58
<212> TYPE: DNA
<213> ORGANISM: Homo Sapiens

<400> SEQUENCE: 388
gactggagtt cagacgtgtg ctcttccgat ctaccatata cccagtgcct tgtgtggt      58

<210> SEQ ID NO 389
<211> LENGTH: 60
<212> TYPE: DNA
<213> ORGANISM: Homo Sapiens

<400> SEQUENCE: 389
gactggagtt cagacgtgtg ctcttccgat ctaccatctc acaattgcca gttaacgtct    60

<210> SEQ ID NO 390
<211> LENGTH: 60
<212> TYPE: DNA
<213> ORGANISM: Homo Sapiens

<400> SEQUENCE: 390
gactggagtt cagacgtgtg ctcttccgat ctaccatctc acaattgcca gttaacgtct    60

<210> SEQ ID NO 391
<211> LENGTH: 60
<212> TYPE: DNA
<213> ORGANISM: Homo Sapiens

<400> SEQUENCE: 391
gactggagtt cagacgtgtg ctcttccgat ctaccatctc acaattgcca gttaacgtct    60

<210> SEQ ID NO 392
<211> LENGTH: 62
<212> TYPE: DNA
<213> ORGANISM: Homo Sapiens

<400> SEQUENCE: 392
gactggagtt cagacgtgtg ctcttccgat ctaccatgtt caatgatttc aactaaactt    60
ct                                                                   62

<210> SEQ ID NO 393
<211> LENGTH: 59
<212> TYPE: DNA
<213> ORGANISM: Homo Sapiens

<400> SEQUENCE: 393
gactggagtt cagacgtgtg ctcttccgat ctacccactg aaaagcactt cctgaaata     59

<210> SEQ ID NO 394
<211> LENGTH: 63
<212> TYPE: DNA
<213> ORGANISM: Homo Sapiens

<400> SEQUENCE: 394
gactggagtt cagacgtgtg ctcttccgat ctaccctagc cttagataaa actgagcaag    60
agg                                                                  63

<210> SEQ ID NO 395
<211> LENGTH: 55
<212> TYPE: DNA
<213> ORGANISM: Homo Sapiens

<400> SEQUENCE: 395
gactggagtt cagacgtgtg ctcttccgat ctacccttgt ctctgtgttc ttgtc    55

<210> SEQ ID NO 396
<211> LENGTH: 55
<212> TYPE: DNA
<213> ORGANISM: Homo Sapiens

<400> SEQUENCE: 396
gactggagtt cagacgtgtg ctcttccgat ctacccttgt ctctgtgttc ttgtc    55

<210> SEQ ID NO 397
<211> LENGTH: 59
<212> TYPE: DNA
<213> ORGANISM: Homo Sapiens

<400> SEQUENCE: 397
gactggagtt cagacgtgtg ctcttccgat ctacctaagc acacagagta atatagcag    59

<210> SEQ ID NO 398
<211> LENGTH: 62
<212> TYPE: DNA
<213> ORGANISM: Homo Sapiens

<400> SEQUENCE: 398
gactggagtt cagacgtgtg ctcttccgat ctacctaagc acacagagta atatagcaga    60
gc    62

<210> SEQ ID NO 399
<211> LENGTH: 60
<212> TYPE: DNA
<213> ORGANISM: Homo Sapiens

<400> SEQUENCE: 399
gactggagtt cagacgtgtg ctcttccgat ctacctagta ttctgctctg aaggggaaa    60

<210> SEQ ID NO 400
<211> LENGTH: 59
<212> TYPE: DNA
<213> ORGANISM: Homo Sapiens

<400> SEQUENCE: 400
gactggagtt cagacgtgtg ctcttccgat ctacctctat tgttggatca tattcgtcc    59

<210> SEQ ID NO 401
<211> LENGTH: 59
<212> TYPE: DNA
<213> ORGANISM: Homo Sapiens

<400> SEQUENCE: 401
gactggagtt cagacgtgtg ctcttccgat ctacctctat tgttggatca tattcgtcc    59

<210> SEQ ID NO 402
<211> LENGTH: 62
<212> TYPE: DNA
<213> ORGANISM: Homo Sapiens

<400> SEQUENCE: 402
gactggagtt cagacgtgtg ctcttccgat ctacctggaa tttggatgtg attggaaagt    60
gg    62

<210> SEQ ID NO 403
<211> LENGTH: 59
<212> TYPE: DNA
<213> ORGANISM: Homo Sapiens

<400> SEQUENCE: 403
gactggagtt cagacgtgtg ctcttccgat ctacctgtct tgtctttgct gatgtttca    59

<210> SEQ ID NO 404
<211> LENGTH: 59
<212> TYPE: DNA
<213> ORGANISM: Homo Sapiens

<400> SEQUENCE: 404
gactggagtt cagacgtgtg ctcttccgat ctacctgtct tgtctttgct gatgtttca    59

<210> SEQ ID NO 405
<211> LENGTH: 62
<212> TYPE: DNA
<213> ORGANISM: Homo Sapiens

<400> SEQUENCE: 405
gactggagtt cagacgtgtg ctcttccgat ctacctgtct tgtctttgct gatgtttcaa    60
ta    62

<210> SEQ ID NO 406
<211> LENGTH: 61
<212> TYPE: DNA
<213> ORGANISM: Homo Sapiens

<400> SEQUENCE: 406
gactggagtt cagacgtgtg ctcttccgat ctaccttctt tctaaccttt tcttatgtgc    60
t    61

<210> SEQ ID NO 407
<211> LENGTH: 60
<212> TYPE: DNA
<213> ORGANISM: Homo Sapiens

<400> SEQUENCE: 407
gactggagtt cagacgtgtg ctcttccgat ctacgactga ttcaaagctg gtcatttaga    60

<210> SEQ ID NO 408
<211> LENGTH: 60
<212> TYPE: DNA
<213> ORGANISM: Homo Sapiens

<400> SEQUENCE: 408
gactggagtt cagacgtgtg ctcttccgat ctacgagaca aatgtaggaa aaaccagaa    60

<210> SEQ ID NO 409
<211> LENGTH: 61
<212> TYPE: DNA
<213> ORGANISM: Homo Sapiens

<400> SEQUENCE: 409
gactggagtt cagacgtgtg ctcttccgat ctacgcattt atgttttctc ttcttagacc    60
a    61

<210> SEQ ID NO 410
<211> LENGTH: 64

```
<212> TYPE: DNA
<213> ORGANISM: Homo Sapiens

<400> SEQUENCE: 410
gactggagtt cagacgtgtg ctcttccgat ctacgcattt atgttttctc ttcttagacc    60
atcc                                                                 64

<210> SEQ ID NO 411
<211> LENGTH: 59
<212> TYPE: DNA
<213> ORGANISM: Homo Sapiens

<400> SEQUENCE: 411
gactggagtt cagacgtgtg ctcttccgat ctacgctctt ctcactcata tcctcctct     59

<210> SEQ ID NO 412
<211> LENGTH: 58
<212> TYPE: DNA
<213> ORGANISM: Homo Sapiens

<400> SEQUENCE: 412
gactggagtt cagacgtgtg ctcttccgat ctacggccag atccagtgaa aaacaagc      58

<210> SEQ ID NO 413
<211> LENGTH: 60
<212> TYPE: DNA
<213> ORGANISM: Homo Sapiens

<400> SEQUENCE: 413
gactggagtt cagacgtgtg ctcttccgat ctacgtcttc cttctctctc tgtcataggg    60

<210> SEQ ID NO 414
<211> LENGTH: 60
<212> TYPE: DNA
<213> ORGANISM: Homo Sapiens

<400> SEQUENCE: 414
gactggagtt cagacgtgtg ctcttccgat ctacgtcttc cttctctctc tgtcataggg    60

<210> SEQ ID NO 415
<211> LENGTH: 61
<212> TYPE: DNA
<213> ORGANISM: Homo Sapiens

<400> SEQUENCE: 415
gactggagtt cagacgtgtg ctcttccgat ctacgtgatt catttatttg ttcaaagcag    60
g                                                                    61

<210> SEQ ID NO 416
<211> LENGTH: 60
<212> TYPE: DNA
<213> ORGANISM: Homo Sapiens

<400> SEQUENCE: 416
gactggagtt cagacgtgtg ctcttccgat ctactaaact tctaagatgt ggcaagatgg    60

<210> SEQ ID NO 417
<211> LENGTH: 59
<212> TYPE: DNA
<213> ORGANISM: Homo Sapiens

<400> SEQUENCE: 417
```

-continued

```
gactggagtt cagacgtgtg ctcttccgat ctactaagta gtctgatcca ctgaagctg      59
```

<210> SEQ ID NO 418
<211> LENGTH: 60
<212> TYPE: DNA
<213> ORGANISM: Homo Sapiens

<400> SEQUENCE: 418

```
gactggagtt cagacgtgtg ctcttccgat ctactacgag agaaaaaatg acttgcttaa     60
```

<210> SEQ ID NO 419
<211> LENGTH: 61
<212> TYPE: DNA
<213> ORGANISM: Homo Sapiens

<400> SEQUENCE: 419

```
gactggagtt cagacgtgtg ctcttccgat ctactagcta gagacaatga attaagggaa     60
a                                                                    61
```

<210> SEQ ID NO 420
<211> LENGTH: 59
<212> TYPE: DNA
<213> ORGANISM: Homo Sapiens

<400> SEQUENCE: 420

```
gactggagtt cagacgtgtg ctcttccgat ctactaggcg tgggatgttt ttgcagatg      59
```

<210> SEQ ID NO 421
<211> LENGTH: 59
<212> TYPE: DNA
<213> ORGANISM: Homo Sapiens

<400> SEQUENCE: 421

```
gactggagtt cagacgtgtg ctcttccgat ctactatctc cctgggtgta gcttttttaa    59
```

<210> SEQ ID NO 422
<211> LENGTH: 57
<212> TYPE: DNA
<213> ORGANISM: Homo Sapiens

<400> SEQUENCE: 422

```
gactggagtt cagacgtgtg ctcttccgat ctactattca gtcctgcctt cctgccc        57
```

<210> SEQ ID NO 423
<211> LENGTH: 59
<212> TYPE: DNA
<213> ORGANISM: Homo Sapiens

<400> SEQUENCE: 423

```
gactggagtt cagacgtgtg ctcttccgat ctactcaaat gtcttactgc tctacaagg      59
```

<210> SEQ ID NO 424
<211> LENGTH: 60
<212> TYPE: DNA
<213> ORGANISM: Homo Sapiens

<400> SEQUENCE: 424

```
gactggagtt cagacgtgtg ctcttccgat ctactctctg ctggctagtc aaaaaagaga     60
```

<210> SEQ ID NO 425
<211> LENGTH: 60
<212> TYPE: DNA
<213> ORGANISM: Homo Sapiens -continued

<400> SEQUENCE: 425
gactggagtt cagacgtgtg ctcttccgat ctactctctg gtggtagaat gaaaaataga    60

<210> SEQ ID NO 426
<211> LENGTH: 60
<212> TYPE: DNA
<213> ORGANISM: Homo Sapiens

<400> SEQUENCE: 426
gactggagtt cagacgtgtg ctcttccgat ctactctgtc aaaaattgtt tctggggcca    60

<210> SEQ ID NO 427
<211> LENGTH: 59
<212> TYPE: DNA
<213> ORGANISM: Homo Sapiens

<400> SEQUENCE: 427
gactggagtt cagacgtgtg ctcttccgat ctactctgtc ctgcgtcatc atctttgtc    59

<210> SEQ ID NO 428
<211> LENGTH: 59
<212> TYPE: DNA
<213> ORGANISM: Homo Sapiens

<400> SEQUENCE: 428
gactggagtt cagacgtgtg ctcttccgat ctactcttta tttgtcccct tgcctccct    59

<210> SEQ ID NO 429
<211> LENGTH: 59
<212> TYPE: DNA
<213> ORGANISM: Homo Sapiens

<400> SEQUENCE: 429
gactggagtt cagacgtgtg ctcttccgat ctactgaagc cacttgttta atctgtaga    59

<210> SEQ ID NO 430
<211> LENGTH: 59
<212> TYPE: DNA
<213> ORGANISM: Homo Sapiens

<400> SEQUENCE: 430
gactggagtt cagacgtgtg ctcttccgat ctactgagca ctgaatctat aaagcatgt    59

<210> SEQ ID NO 431
<211> LENGTH: 59
<212> TYPE: DNA
<213> ORGANISM: Homo Sapiens

<400> SEQUENCE: 431
gactggagtt cagacgtgtg ctcttccgat ctactgccaa tggactgttt tacaatgcc    59

<210> SEQ ID NO 432
<211> LENGTH: 59
<212> TYPE: DNA
<213> ORGANISM: Homo Sapiens

<400> SEQUENCE: 432
gactggagtt cagacgtgtg ctcttccgat ctactgtaaa gctggaaagg gacgaactg    59

<210> SEQ ID NO 433
<211> LENGTH: 59
<212> TYPE: DNA

<213> ORGANISM: Homo Sapiens

<400> SEQUENCE: 433
gactggagtt cagacgtgtg ctcttccgat ctactgtgtt gtggagtgca agtgaaagc     59

<210> SEQ ID NO 434
<211> LENGTH: 59
<212> TYPE: DNA
<213> ORGANISM: Homo Sapiens

<400> SEQUENCE: 434
gactggagtt cagacgtgtg ctcttccgat ctacttaacc tgtttctcct ccctctacc     59

<210> SEQ ID NO 435
<211> LENGTH: 59
<212> TYPE: DNA
<213> ORGANISM: Homo Sapiens

<400> SEQUENCE: 435
gactggagtt cagacgtgtg ctcttccgat ctacttaccc actgaaaagc acttcctga     59

<210> SEQ ID NO 436
<211> LENGTH: 59
<212> TYPE: DNA
<213> ORGANISM: Homo Sapiens

<400> SEQUENCE: 436
gactggagtt cagacgtgtg ctcttccgat ctacttacct gtcttgtctt tgctgatgt     59

<210> SEQ ID NO 437
<211> LENGTH: 59
<212> TYPE: DNA
<213> ORGANISM: Homo Sapiens

<400> SEQUENCE: 437
gactggagtt cagacgtgtg ctcttccgat ctacttacct gtcttgtctt tgctgatgt     59

<210> SEQ ID NO 438
<211> LENGTH: 56
<212> TYPE: DNA
<213> ORGANISM: Homo Sapiens

<400> SEQUENCE: 438
gactggagtt cagacgtgtg ctcttccgat ctacttccca gtgtgattgc aggttc        56

<210> SEQ ID NO 439
<211> LENGTH: 59
<212> TYPE: DNA
<213> ORGANISM: Homo Sapiens

<400> SEQUENCE: 439
gactggagtt cagacgtgtg ctcttccgat ctacttcctg taatttttca aggcttcag     59

<210> SEQ ID NO 440
<211> LENGTH: 59
<212> TYPE: DNA
<213> ORGANISM: Homo Sapiens

<400> SEQUENCE: 440
gactggagtt cagacgtgtg ctcttccgat ctacttcttt gggttgactt ctctggtga     59

<210> SEQ ID NO 441
<211> LENGTH: 59

<212> TYPE: DNA
<213> ORGANISM: Homo Sapiens

<400> SEQUENCE: 441
gactggagtt cagacgtgtg ctcttccgat ctacttgtcc caaagcagaa gtaaaacca     59

<210> SEQ ID NO 442
<211> LENGTH: 60
<212> TYPE: DNA
<213> ORGANISM: Homo Sapiens

<400> SEQUENCE: 442
gactggagtt cagacgtgtg ctcttccgat ctactttata agatcctggc tatcctgtgg    60

<210> SEQ ID NO 443
<211> LENGTH: 57
<212> TYPE: DNA
<213> ORGANISM: Homo Sapiens

<400> SEQUENCE: 443
gactggagtt cagacgtgtg ctcttccgat ctagaaaaag tttgctgagc tgggtag       57

<210> SEQ ID NO 444
<211> LENGTH: 59
<212> TYPE: DNA
<213> ORGANISM: Homo Sapiens

<400> SEQUENCE: 444
gactggagtt cagacgtgtg ctcttccgat ctagaaaagg ggacatgcta gggacaaca     59

<210> SEQ ID NO 445
<211> LENGTH: 59
<212> TYPE: DNA
<213> ORGANISM: Homo Sapiens

<400> SEQUENCE: 445
gactggagtt cagacgtgtg ctcttccgat ctagaacact ctctgctggc tagtcaaaa     59

<210> SEQ ID NO 446
<211> LENGTH: 59
<212> TYPE: DNA
<213> ORGANISM: Homo Sapiens

<400> SEQUENCE: 446
gactggagtt cagacgtgtg ctcttccgat ctagaacact tacctcattg tctgactcc     59

<210> SEQ ID NO 447
<211> LENGTH: 59
<212> TYPE: DNA
<213> ORGANISM: Homo Sapiens

<400> SEQUENCE: 447
gactggagtt cagacgtgtg ctcttccgat ctagaagcaa catctccgaa agccaacaa     59

<210> SEQ ID NO 448
<211> LENGTH: 59
<212> TYPE: DNA
<213> ORGANISM: Homo Sapiens

<400> SEQUENCE: 448
gactggagtt cagacgtgtg ctcttccgat ctagaagcaa gaaaataccc cctccatca     59

<210> SEQ ID NO 449

```
<211> LENGTH: 59
<212> TYPE: DNA
<213> ORGANISM: Homo Sapiens

<400> SEQUENCE: 449
gactggagtt cagacgtgtg ctcttccgat ctagaaggag gagagacacc atcagaagg    59

<210> SEQ ID NO 450
<211> LENGTH: 59
<212> TYPE: DNA
<213> ORGANISM: Homo Sapiens

<400> SEQUENCE: 450
gactggagtt cagacgtgtg ctcttccgat ctagaatgtg tcagcctcaa agaaaagct    59

<210> SEQ ID NO 451
<211> LENGTH: 56
<212> TYPE: DNA
<213> ORGANISM: Homo Sapiens

<400> SEQUENCE: 451
gactggagtt cagacgtgtg ctcttccgat ctagacacta aactcatctg ggccac       56

<210> SEQ ID NO 452
<211> LENGTH: 56
<212> TYPE: DNA
<213> ORGANISM: Homo Sapiens

<400> SEQUENCE: 452
gactggagtt cagacgtgtg ctcttccgat ctagacacta aactcatctg ggccac       56

<210> SEQ ID NO 453
<211> LENGTH: 59
<212> TYPE: DNA
<213> ORGANISM: Homo Sapiens

<400> SEQUENCE: 453
gactggagtt cagacgtgtg ctcttccgat ctagacagaa ggaggagaga caccatcag    59

<210> SEQ ID NO 454
<211> LENGTH: 59
<212> TYPE: DNA
<213> ORGANISM: Homo Sapiens

<400> SEQUENCE: 454
gactggagtt cagacgtgtg ctcttccgat ctagacagtt gtttgttcag ttgggagcg    59

<210> SEQ ID NO 455
<211> LENGTH: 59
<212> TYPE: DNA
<213> ORGANISM: Homo Sapiens

<400> SEQUENCE: 455
gactggagtt cagacgtgtg ctcttccgat ctagacagtt gtttgttcag ttgggagcg    59

<210> SEQ ID NO 456
<211> LENGTH: 59
<212> TYPE: DNA
<213> ORGANISM: Homo Sapiens

<400> SEQUENCE: 456
gactggagtt cagacgtgtg ctcttccgat ctagacctag tattctgctc tgaaggggg    59
```

```
<210> SEQ ID NO 457
<211> LENGTH: 59
<212> TYPE: DNA
<213> ORGANISM: Homo Sapiens

<400> SEQUENCE: 457
gactggagtt cagacgtgtg ctcttccgat ctagacgact gattcaaagc tggtcattt      59

<210> SEQ ID NO 458
<211> LENGTH: 59
<212> TYPE: DNA
<213> ORGANISM: Homo Sapiens

<400> SEQUENCE: 458
gactggagtt cagacgtgtg ctcttccgat ctagacgact gattcaaagc tggtcattt      59

<210> SEQ ID NO 459
<211> LENGTH: 59
<212> TYPE: DNA
<213> ORGANISM: Homo Sapiens

<400> SEQUENCE: 459
gactggagtt cagacgtgtg ctcttccgat ctagactgct gtgagggttt tttgatgtt      59

<210> SEQ ID NO 460
<211> LENGTH: 59
<212> TYPE: DNA
<213> ORGANISM: Homo Sapiens

<400> SEQUENCE: 460
gactggagtt cagacgtgtg ctcttccgat ctagacttga aggcgtatac aggaacaat      59

<210> SEQ ID NO 461
<211> LENGTH: 59
<212> TYPE: DNA
<213> ORGANISM: Homo Sapiens

<400> SEQUENCE: 461
gactggagtt cagacgtgtg ctcttccgat ctagagaggg agtgaagtga atgttgctg      59

<210> SEQ ID NO 462
<211> LENGTH: 59
<212> TYPE: DNA
<213> ORGANISM: Homo Sapiens

<400> SEQUENCE: 462
gactggagtt cagacgtgtg ctcttccgat ctagagatcc catcctgcca aagtttgtg      59

<210> SEQ ID NO 463
<211> LENGTH: 59
<212> TYPE: DNA
<213> ORGANISM: Homo Sapiens

<400> SEQUENCE: 463
gactggagtt cagacgtgtg ctcttccgat ctagagcaat cagtgaggaa tcagaggcc      59

<210> SEQ ID NO 464
<211> LENGTH: 59
<212> TYPE: DNA
<213> ORGANISM: Homo Sapiens

<400> SEQUENCE: 464
gactggagtt cagacgtgtg ctcttccgat ctagagcaat cagtgaggaa tcagaggcc      59
```

<210> SEQ ID NO 465
<211> LENGTH: 60
<212> TYPE: DNA
<213> ORGANISM: Homo Sapiens

<400> SEQUENCE: 465
gactggagtt cagacgtgtg ctcttccgat ctagagcata gtaagcagta gggagtaaca    60

<210> SEQ ID NO 466
<211> LENGTH: 55
<212> TYPE: DNA
<213> ORGANISM: Homo Sapiens

<400> SEQUENCE: 466
gactggagtt cagacgtgtg ctcttccgat ctagagccaa gggtgtgagt gaacg    55

<210> SEQ ID NO 467
<211> LENGTH: 59
<212> TYPE: DNA
<213> ORGANISM: Homo Sapiens

<400> SEQUENCE: 467
gactggagtt cagacgtgtg ctcttccgat ctagagcgtg cagataatga caaggaata    59

<210> SEQ ID NO 468
<211> LENGTH: 57
<212> TYPE: DNA
<213> ORGANISM: Homo Sapiens

<400> SEQUENCE: 468
gactggagtt cagacgtgtg ctcttccgat ctagagtcat gttagtctgg ttcctcc    57

<210> SEQ ID NO 469
<211> LENGTH: 67
<212> TYPE: DNA
<213> ORGANISM: Homo Sapiens

<400> SEQUENCE: 469
gactggagtt cagacgtgtg ctcttccgat ctagatattc ccattattat agagatgatt    60
gttgaat    67

<210> SEQ ID NO 470
<211> LENGTH: 59
<212> TYPE: DNA
<213> ORGANISM: Homo Sapiens

<400> SEQUENCE: 470
gactggagtt cagacgtgtg ctcttccgat ctagatgatc cgacaagtga gagacagga    59

<210> SEQ ID NO 471
<211> LENGTH: 60
<212> TYPE: DNA
<213> ORGANISM: Homo Sapiens

<400> SEQUENCE: 471
gactggagtt cagacgtgtg ctcttccgat ctagatgttg aactatgcaa agagacattt    60

<210> SEQ ID NO 472
<211> LENGTH: 60
<212> TYPE: DNA
<213> ORGANISM: Homo Sapiens

<400> SEQUENCE: 472
gactggagtt cagacgtgtg ctcttccgat ctagcaaact tctgtacaca actaactaga    60

<210> SEQ ID NO 473
<211> LENGTH: 59
<212> TYPE: DNA
<213> ORGANISM: Homo Sapiens

<400> SEQUENCE: 473
gactggagtt cagacgtgtg ctcttccgat ctagcaagaa ataccccct ccatcaact    59

<210> SEQ ID NO 474
<211> LENGTH: 58
<212> TYPE: DNA
<213> ORGANISM: Homo Sapiens

<400> SEQUENCE: 474
gactggagtt cagacgtgtg ctcttccgat ctagcaagta tgatgagcaa gctttctc    58

<210> SEQ ID NO 475
<211> LENGTH: 59
<212> TYPE: DNA
<213> ORGANISM: Homo Sapiens

<400> SEQUENCE: 475
gactggagtt cagacgtgtg ctcttccgat ctagcactac ctaaggaccg ggattatgt    59

<210> SEQ ID NO 476
<211> LENGTH: 59
<212> TYPE: DNA
<213> ORGANISM: Homo Sapiens

<400> SEQUENCE: 476
gactggagtt cagacgtgtg ctcttccgat ctagcactct gacatatggc catttctgt    59

<210> SEQ ID NO 477
<211> LENGTH: 59
<212> TYPE: DNA
<213> ORGANISM: Homo Sapiens

<400> SEQUENCE: 477
gactggagtt cagacgtgtg ctcttccgat ctagcagtag ggagtaacaa ataacact    59

<210> SEQ ID NO 478
<211> LENGTH: 59
<212> TYPE: DNA
<213> ORGANISM: Homo Sapiens

<400> SEQUENCE: 478
gactggagtt cagacgtgtg ctcttccgat ctagccagta ccttcctctt cttctacat    59

<210> SEQ ID NO 479
<211> LENGTH: 54
<212> TYPE: DNA
<213> ORGANISM: Homo Sapiens

<400> SEQUENCE: 479
gactggagtt cagacgtgtg ctcttccgat ctagcccatc cctgactgtg agat    54

<210> SEQ ID NO 480
<211> LENGTH: 57
<212> TYPE: DNA
<213> ORGANISM: Homo Sapiens

<400> SEQUENCE: 480
gactggagtt cagacgtgtg ctcttccgat ctagcccatc cctgactgtg agatcaa    57

<210> SEQ ID NO 481
<211> LENGTH: 57
<212> TYPE: DNA
<213> ORGANISM: Homo Sapiens

<400> SEQUENCE: 481
gactggagtt cagacgtgtg ctcttccgat ctagcccatc cctgactgtg agatcaa    57

<210> SEQ ID NO 482
<211> LENGTH: 58
<212> TYPE: DNA
<213> ORGANISM: Homo Sapiens

<400> SEQUENCE: 482
gactggagtt cagacgtgtg ctcttccgat ctagcctcca gttcagcaag gggtcata   58

<210> SEQ ID NO 483
<211> LENGTH: 59
<212> TYPE: DNA
<213> ORGANISM: Homo Sapiens

<400> SEQUENCE: 483
gactggagtt cagacgtgtg ctcttccgat ctagcctctt acctggaatt tggatgtga  59

<210> SEQ ID NO 484
<211> LENGTH: 59
<212> TYPE: DNA
<213> ORGANISM: Homo Sapiens

<400> SEQUENCE: 484
gactggagtt cagacgtgtg ctcttccgat ctagcgctac tagaaacatg atagaggtg  59

<210> SEQ ID NO 485
<211> LENGTH: 60
<212> TYPE: DNA
<213> ORGANISM: Homo Sapiens

<400> SEQUENCE: 485
gactggagtt cagacgtgtg ctcttccgat ctagctaaag gtgaagatat attcctccaa 60

<210> SEQ ID NO 486
<211> LENGTH: 54
<212> TYPE: DNA
<213> ORGANISM: Homo Sapiens

<400> SEQUENCE: 486
gactggagtt cagacgtgtg ctcttccgat ctagctacct gaccgacgtt gacc       54

<210> SEQ ID NO 487
<211> LENGTH: 60
<212> TYPE: DNA
<213> ORGANISM: Homo Sapiens

<400> SEQUENCE: 487
gactggagtt cagacgtgtg ctcttccgat ctagctatat ctgaacaaaa attccgtggt 60

<210> SEQ ID NO 488
<211> LENGTH: 59
<212> TYPE: DNA
<213> ORGANISM: Homo Sapiens

```
<400> SEQUENCE: 488
gactggagtt cagacgtgtg ctcttccgat ctagctgaca ccacgatact tgacaatga      59

<210> SEQ ID NO 489
<211> LENGTH: 59
<212> TYPE: DNA
<213> ORGANISM: Homo Sapiens

<400> SEQUENCE: 489
gactggagtt cagacgtgtg ctcttccgat ctagcttaat aaaaaacccc gcagagaga      59

<210> SEQ ID NO 490
<211> LENGTH: 59
<212> TYPE: DNA
<213> ORGANISM: Homo Sapiens

<400> SEQUENCE: 490
gactggagtt cagacgtgtg ctcttccgat ctagcttaat tctaccttgt agcctccaa      59

<210> SEQ ID NO 491
<211> LENGTH: 59
<212> TYPE: DNA
<213> ORGANISM: Homo Sapiens

<400> SEQUENCE: 491
gactggagtt cagacgtgtg ctcttccgat ctagcttacc atggaccctg acaaatgtg      59

<210> SEQ ID NO 492
<211> LENGTH: 58
<212> TYPE: DNA
<213> ORGANISM: Homo Sapiens

<400> SEQUENCE: 492
gactggagtt cagacgtgtg ctcttccgat ctagcttctt cacgctcctt ccctatcc       58

<210> SEQ ID NO 493
<211> LENGTH: 61
<212> TYPE: DNA
<213> ORGANISM: Homo Sapiens

<400> SEQUENCE: 493
gactggagtt cagacgtgtg ctcttccgat ctaggaaaac tacaatggag aaagaagact     60
a                                                                     61

<210> SEQ ID NO 494
<211> LENGTH: 62
<212> TYPE: DNA
<213> ORGANISM: Homo Sapiens

<400> SEQUENCE: 494
gactggagtt cagacgtgtg ctcttccgat ctaggagata agtgatggag atgtgataat     60
tt                                                                    62

<210> SEQ ID NO 495
<211> LENGTH: 59
<212> TYPE: DNA
<213> ORGANISM: Homo Sapiens

<400> SEQUENCE: 495
gactggagtt cagacgtgtg ctcttccgat ctaggagtac ttctttgggt tgacttctc      59
```

<210> SEQ ID NO 496
<211> LENGTH: 59
<212> TYPE: DNA
<213> ORGANISM: Homo Sapiens

<400> SEQUENCE: 496
gactggagtt cagacgtgtg ctcttccgat ctaggccatc ttccatcttc tcacactgg      59

<210> SEQ ID NO 497
<211> LENGTH: 57
<212> TYPE: DNA
<213> ORGANISM: Homo Sapiens

<400> SEQUENCE: 497
gactggagtt cagacgtgtg ctcttccgat ctaggccttc gtcctccttc ctcactc        57

<210> SEQ ID NO 498
<211> LENGTH: 59
<212> TYPE: DNA
<213> ORGANISM: Homo Sapiens

<400> SEQUENCE: 498
gactggagtt cagacgtgtg ctcttccgat ctaggcgtgg gatgttttt g cagatgatg     59

<210> SEQ ID NO 499
<211> LENGTH: 59
<212> TYPE: DNA
<213> ORGANISM: Homo Sapiens

<400> SEQUENCE: 499
gactggagtt cagacgtgtg ctcttccgat ctagggagtg aagtgaatgt tgctgaggt      59

<210> SEQ ID NO 500
<211> LENGTH: 59
<212> TYPE: DNA
<213> ORGANISM: Homo Sapiens

<400> SEQUENCE: 500
gactggagtt cagacgtgtg ctcttccgat ctaggggaca tgctagggac aacacgatt      59

<210> SEQ ID NO 501
<211> LENGTH: 60
<212> TYPE: DNA
<213> ORGANISM: Homo Sapiens

<400> SEQUENCE: 501
gactggagtt cagacgtgtg ctcttccgat ctaggtgtgt ctttaattga agcatgattt     60

<210> SEQ ID NO 502
<211> LENGTH: 59
<212> TYPE: DNA
<213> ORGANISM: Homo Sapiens

<400> SEQUENCE: 502
gactggagtt cagacgtgtg ctcttccgat ctaggttcac tgcatattct ccccacaga     59

<210> SEQ ID NO 503
<211> LENGTH: 59
<212> TYPE: DNA
<213> ORGANISM: Homo Sapiens

<400> SEQUENCE: 503
gactggagtt cagacgtgtg ctcttccgat ctaggtttca tggactcagt tactacctg     59

<210> SEQ ID NO 504
<211> LENGTH: 59
<212> TYPE: DNA
<213> ORGANISM: Homo Sapiens

<400> SEQUENCE: 504
gactggagtt cagacgtgtg ctcttccgat ctagtactta cccactgaaa agcacttcc    59

<210> SEQ ID NO 505
<211> LENGTH: 59
<212> TYPE: DNA
<213> ORGANISM: Homo Sapiens

<400> SEQUENCE: 505
gactggagtt cagacgtgtg ctcttccgat ctagtcacac tcatcagcac caggtcttg    59

<210> SEQ ID NO 506
<211> LENGTH: 59
<212> TYPE: DNA
<213> ORGANISM: Homo Sapiens

<400> SEQUENCE: 506
gactggagtt cagacgtgtg ctcttccgat ctagtcccaa ccatgtcaaa attacagac    59

<210> SEQ ID NO 507
<211> LENGTH: 59
<212> TYPE: DNA
<213> ORGANISM: Homo Sapiens

<400> SEQUENCE: 507
gactggagtt cagacgtgtg ctcttccgat ctagtcccaa ccatgtcaaa attacagac    59

<210> SEQ ID NO 508
<211> LENGTH: 59
<212> TYPE: DNA
<213> ORGANISM: Homo Sapiens

<400> SEQUENCE: 508
gactggagtt cagacgtgtg ctcttccgat ctagtccccca gctactctca aaatcagca   59

<210> SEQ ID NO 509
<211> LENGTH: 57
<212> TYPE: DNA
<213> ORGANISM: Homo Sapiens

<400> SEQUENCE: 509
gactggagtt cagacgtgtg ctcttccgat ctagtcctcc acacttctcc attcttc      57

<210> SEQ ID NO 510
<211> LENGTH: 60
<212> TYPE: DNA
<213> ORGANISM: Homo Sapiens

<400> SEQUENCE: 510
gactggagtt cagacgtgtg ctcttccgat ctagtctatg tgatcaagaa atcgatagca   60

<210> SEQ ID NO 511
<211> LENGTH: 59
<212> TYPE: DNA
<213> ORGANISM: Homo Sapiens

<400> SEQUENCE: 511
gactggagtt cagacgtgtg ctcttccgat ctagtctttc tttgaagcag caagtatga        59

<210> SEQ ID NO 512
<211> LENGTH: 59
<212> TYPE: DNA
<213> ORGANISM: Homo Sapiens

<400> SEQUENCE: 512
gactggagtt cagacgtgtg ctcttccgat ctagtgaacg ttgttggact ctactgtgt        59

<210> SEQ ID NO 513
<211> LENGTH: 59
<212> TYPE: DNA
<213> ORGANISM: Homo Sapiens

<400> SEQUENCE: 513
gactggagtt cagacgtgtg ctcttccgat ctagtggtgg tatacgatat gggttttgt        59

<210> SEQ ID NO 514
<211> LENGTH: 59
<212> TYPE: DNA
<213> ORGANISM: Homo Sapiens

<400> SEQUENCE: 514
gactggagtt cagacgtgtg ctcttccgat ctagtggttc tggattagct ggattgtca        59

<210> SEQ ID NO 515
<211> LENGTH: 59
<212> TYPE: DNA
<213> ORGANISM: Homo Sapiens

<400> SEQUENCE: 515
gactggagtt cagacgtgtg ctcttccgat ctagtgttac tcaagaagca gaaagggaa        59

<210> SEQ ID NO 516
<211> LENGTH: 59
<212> TYPE: DNA
<213> ORGANISM: Homo Sapiens

<400> SEQUENCE: 516
gactggagtt cagacgtgtg ctcttccgat ctagtgttac tcaagaagca gaaagggaa        59

<210> SEQ ID NO 517
<211> LENGTH: 59
<212> TYPE: DNA
<213> ORGANISM: Homo Sapiens

<400> SEQUENCE: 517
gactggagtt cagacgtgtg ctcttccgat ctagttaact ctctggtggt agaatgaaa        59

<210> SEQ ID NO 518
<211> LENGTH: 56
<212> TYPE: DNA
<213> ORGANISM: Homo Sapiens

<400> SEQUENCE: 518
gactggagtt cagacgtgtg ctcttccgat ctagttccct cagccgttac ctgtgt        56

<210> SEQ ID NO 519
<211> LENGTH: 65
<212> TYPE: DNA
<213> ORGANISM: Homo Sapiens

<400> SEQUENCE: 519

```
gactggagtt cagacgtgtg ctcttccgat ctagttgaaa atacatagag ttttaatgca    60
ttgtc                                                                65

<210> SEQ ID NO 520
<211> LENGTH: 59
<212> TYPE: DNA
<213> ORGANISM: Homo Sapiens

<400> SEQUENCE: 520
gactggagtt cagacgtgtg ctcttccgat ctagttgcta agaaccggtc actgaaaat    59

<210> SEQ ID NO 521
<211> LENGTH: 59
<212> TYPE: DNA
<213> ORGANISM: Homo Sapiens

<400> SEQUENCE: 521
gactggagtt cagacgtgtg ctcttccgat ctagtttttc ctcctactca ccatcctgt    59

<210> SEQ ID NO 522
<211> LENGTH: 59
<212> TYPE: DNA
<213> ORGANISM: Homo Sapiens

<400> SEQUENCE: 522
gactggagtt cagacgtgtg ctcttccgat ctataaaagc tcttcctgtt tcagtcccc    59

<210> SEQ ID NO 523
<211> LENGTH: 59
<212> TYPE: DNA
<213> ORGANISM: Homo Sapiens

<400> SEQUENCE: 523
gactggagtt cagacgtgtg ctcttccgat ctatacacaa agaaagccct ccccagtcc    59

<210> SEQ ID NO 524
<211> LENGTH: 59
<212> TYPE: DNA
<213> ORGANISM: Homo Sapiens

<400> SEQUENCE: 524
gactggagtt cagacgtgtg ctcttccgat ctatataccc agtgccttgt gtggtgact    59

<210> SEQ ID NO 525
<211> LENGTH: 59
<212> TYPE: DNA
<213> ORGANISM: Homo Sapiens

<400> SEQUENCE: 525
gactggagtt cagacgtgtg ctcttccgat ctatatgctc cactaacaac cctcctgcc    59

<210> SEQ ID NO 526
<211> LENGTH: 59
<212> TYPE: DNA
<213> ORGANISM: Homo Sapiens

<400> SEQUENCE: 526
gactggagtt cagacgtgtg ctcttccgat ctatatggag aagttagaca tgtcaacct    59

<210> SEQ ID NO 527
<211> LENGTH: 59
<212> TYPE: DNA
```

<213> ORGANISM: Homo Sapiens

<400> SEQUENCE: 527
gactggagtt cagacgtgtg ctcttccgat ctatatggcc atttctgttt tcctgtagc       59

<210> SEQ ID NO 528
<211> LENGTH: 59
<212> TYPE: DNA
<213> ORGANISM: Homo Sapiens

<400> SEQUENCE: 528
gactggagtt cagacgtgtg ctcttccgat ctatattggc ctgtctgctc ttcccacca       59

<210> SEQ ID NO 529
<211> LENGTH: 59
<212> TYPE: DNA
<213> ORGANISM: Homo Sapiens

<400> SEQUENCE: 529
gactggagtt cagacgtgtg ctcttccgat ctatatttga gtctatcgag tgtgtgcat       59

<210> SEQ ID NO 530
<211> LENGTH: 58
<212> TYPE: DNA
<213> ORGANISM: Homo Sapiens

<400> SEQUENCE: 530
gactggagtt cagacgtgtg ctcttccgat ctatcaaaga cgactgattc aaagctgg        58

<210> SEQ ID NO 531
<211> LENGTH: 59
<212> TYPE: DNA
<213> ORGANISM: Homo Sapiens

<400> SEQUENCE: 531
gactggagtt cagacgtgtg ctcttccgat ctatcaagtt caacagttca ggccagtgc       59

<210> SEQ ID NO 532
<211> LENGTH: 59
<212> TYPE: DNA
<213> ORGANISM: Homo Sapiens

<400> SEQUENCE: 532
gactggagtt cagacgtgtg ctcttccgat ctatcactcc acatttcagc aacagcagc       59

<210> SEQ ID NO 533
<211> LENGTH: 59
<212> TYPE: DNA
<213> ORGANISM: Homo Sapiens

<400> SEQUENCE: 533
gactggagtt cagacgtgtg ctcttccgat ctatcatatt ggcctgtctg ctcttccca       59

<210> SEQ ID NO 534
<211> LENGTH: 63
<212> TYPE: DNA
<213> ORGANISM: Homo Sapiens

<400> SEQUENCE: 534
gactggagtt cagacgtgtg ctcttccgat ctatccactc aatcttctac tttaaaatga      60
ctt                                                                    63

```
<210> SEQ ID NO 535
<211> LENGTH: 59
<212> TYPE: DNA
<213> ORGANISM: Homo Sapiens

<400> SEQUENCE: 535
gactggagtt cagacgtgtg ctcttccgat ctatcgcggg cttggttctg atgtttgta      59

<210> SEQ ID NO 536
<211> LENGTH: 56
<212> TYPE: DNA
<213> ORGANISM: Homo Sapiens

<400> SEQUENCE: 536
gactggagtt cagacgtgtg ctcttccgat ctatctccct tctaccggca gatccc         56

<210> SEQ ID NO 537
<211> LENGTH: 59
<212> TYPE: DNA
<213> ORGANISM: Homo Sapiens

<400> SEQUENCE: 537
gactggagtt cagacgtgtg ctcttccgat ctatctccct tctaccggca gatcccttt      59

<210> SEQ ID NO 538
<211> LENGTH: 59
<212> TYPE: DNA
<213> ORGANISM: Homo Sapiens

<400> SEQUENCE: 538
gactggagtt cagacgtgtg ctcttccgat ctatctgatg ctgaggaagt ggattttgc      59

<210> SEQ ID NO 539
<211> LENGTH: 57
<212> TYPE: DNA
<213> ORGANISM: Homo Sapiens

<400> SEQUENCE: 539
gactggagtt cagacgtgtg ctcttccgat ctatctggag atcaaacccg caatccg        57

<210> SEQ ID NO 540
<211> LENGTH: 59
<212> TYPE: DNA
<213> ORGANISM: Homo Sapiens

<400> SEQUENCE: 540
gactggagtt cagacgtgtg ctcttccgat ctatctggag catgggactg tctctggta      59

<210> SEQ ID NO 541
<211> LENGTH: 59
<212> TYPE: DNA
<213> ORGANISM: Homo Sapiens

<400> SEQUENCE: 541
gactggagtt cagacgtgtg ctcttccgat ctatgaacat gaccctgaat tcggatgca      59

<210> SEQ ID NO 542
<211> LENGTH: 65
<212> TYPE: DNA
<213> ORGANISM: Homo Sapiens

<400> SEQUENCE: 542
gactggagtt cagacgtgtg ctcttccgat ctatgactga gacaataatt attaaaaggt     60
``` gatct                                                              65

<210> SEQ ID NO 543
<211> LENGTH: 59
<212> TYPE: DNA
<213> ORGANISM: Homo Sapiens

<400> SEQUENCE: 543
gactggagtt cagacgtgtg ctcttccgat ctatgagttc tgggcactgg gtcaaagtc    59

<210> SEQ ID NO 544
<211> LENGTH: 58
<212> TYPE: DNA
<213> ORGANISM: Homo Sapiens

<400> SEQUENCE: 544
gactggagtt cagacgtgtg ctcttccgat ctatgcagag cttcttccca tgatgatc     58

<210> SEQ ID NO 545
<211> LENGTH: 59
<212> TYPE: DNA
<213> ORGANISM: Homo Sapiens

<400> SEQUENCE: 545
gactggagtt cagacgtgtg ctcttccgat ctatgcgctt gacatcagtt tgccagttg    59

<210> SEQ ID NO 546
<211> LENGTH: 59
<212> TYPE: DNA
<213> ORGANISM: Homo Sapiens

<400> SEQUENCE: 546
gactggagtt cagacgtgtg ctcttccgat ctatgcgctt gacatcagtt tgccagttg    59

<210> SEQ ID NO 547
<211> LENGTH: 55
<212> TYPE: DNA
<213> ORGANISM: Homo Sapiens

<400> SEQUENCE: 547
gactggagtt cagacgtgtg ctcttccgat ctatgctctg cttctgtact gccag         55

<210> SEQ ID NO 548
<211> LENGTH: 59
<212> TYPE: DNA
<213> ORGANISM: Homo Sapiens

<400> SEQUENCE: 548
gactggagtt cagacgtgtg ctcttccgat ctatggaact gatgtctgga cgctcattg    59

<210> SEQ ID NO 549
<211> LENGTH: 59
<212> TYPE: DNA
<213> ORGANISM: Homo Sapiens

<400> SEQUENCE: 549
gactggagtt cagacgtgtg ctcttccgat ctatggaaga aatcggtaag aggtgggcc    59

<210> SEQ ID NO 550
<211> LENGTH: 57
<212> TYPE: DNA
<213> ORGANISM: Homo Sapiens

<400> SEQUENCE: 550
gactggagtt cagacgtgtg ctcttccgat ctatggaagg tgcgttcgat gacagtg        57

<210> SEQ ID NO 551
<211> LENGTH: 55
<212> TYPE: DNA
<213> ORGANISM: Homo Sapiens

<400> SEQUENCE: 551
gactggagtt cagacgtgtg ctcttccgat ctatggacat gaagcaggct gatac          55

<210> SEQ ID NO 552
<211> LENGTH: 58
<212> TYPE: DNA
<213> ORGANISM: Homo Sapiens

<400> SEQUENCE: 552
gactggagtt cagacgtgtg ctcttccgat ctatggacat gaagcaggct gatactac       58

<210> SEQ ID NO 553
<211> LENGTH: 58
<212> TYPE: DNA
<213> ORGANISM: Homo Sapiens

<400> SEQUENCE: 553
gactggagtt cagacgtgtg ctcttccgat ctatggacca tttaacacag aagagagt       58

<210> SEQ ID NO 554
<211> LENGTH: 59
<212> TYPE: DNA
<213> ORGANISM: Homo Sapiens

<400> SEQUENCE: 554
gactggagtt cagacgtgtg ctcttccgat ctatggcagt caaaccttct ctcttatgt      59

<210> SEQ ID NO 555
<211> LENGTH: 59
<212> TYPE: DNA
<213> ORGANISM: Homo Sapiens

<400> SEQUENCE: 555
gactggagtt cagacgtgtg ctcttccgat ctatggctgt ggtttgtgat ggttgggag      59

<210> SEQ ID NO 556
<211> LENGTH: 58
<212> TYPE: DNA
<213> ORGANISM: Homo Sapiens

<400> SEQUENCE: 556
gactggagtt cagacgtgtg ctcttccgat ctatgggaga actctgagtg gccacctc       58

<210> SEQ ID NO 557
<211> LENGTH: 56
<212> TYPE: DNA
<213> ORGANISM: Homo Sapiens

<400> SEQUENCE: 557
gactggagtt cagacgtgtg ctcttccgat ctatggtgaa tgacggcgtg gaggac         56

<210> SEQ ID NO 558
<211> LENGTH: 58
<212> TYPE: DNA
<213> ORGANISM: Homo Sapiens

<400> SEQUENCE: 558
gactggagtt cagacgtgtg ctcttccgat ctatgtattg gtctctcatg gcactgta         58

<210> SEQ ID NO 559
<211> LENGTH: 59
<212> TYPE: DNA
<213> ORGANISM: Homo Sapiens

<400> SEQUENCE: 559
gactggagtt cagacgtgtg ctcttccgat ctatgtctta ctgctctaca agggcttta        59

<210> SEQ ID NO 560
<211> LENGTH: 59
<212> TYPE: DNA
<213> ORGANISM: Homo Sapiens

<400> SEQUENCE: 560
gactggagtt cagacgtgtg ctcttccgat ctatgttatt tgagctagaa ccagtgcca        59

<210> SEQ ID NO 561
<211> LENGTH: 59
<212> TYPE: DNA
<213> ORGANISM: Homo Sapiens

<400> SEQUENCE: 561
gactggagtt cagacgtgtg ctcttccgat ctattacatg tggagtgaac gttgttgga        59

<210> SEQ ID NO 562
<211> LENGTH: 61
<212> TYPE: DNA
<213> ORGANISM: Homo Sapiens

<400> SEQUENCE: 562
gactggagtt cagacgtgtg ctcttccgat ctattagtga tggatttgat gaattggtga       60
t                                                                      61

<210> SEQ ID NO 563
<211> LENGTH: 59
<212> TYPE: DNA
<213> ORGANISM: Homo Sapiens

<400> SEQUENCE: 563
gactggagtt cagacgtgtg ctcttccgat ctattctgct ctgaaggggg aaatgtgag        59

<210> SEQ ID NO 564
<211> LENGTH: 57
<212> TYPE: DNA
<213> ORGANISM: Homo Sapiens

<400> SEQUENCE: 564
gactggagtt cagacgtgtg ctcttccgat ctattctgtg tgtaaagccc agccccc          57

<210> SEQ ID NO 565
<211> LENGTH: 59
<212> TYPE: DNA
<213> ORGANISM: Homo Sapiens

<400> SEQUENCE: 565
gactggagtt cagacgtgtg ctcttccgat ctattgaaat tcacttacac cgggccctc        59

<210> SEQ ID NO 566
<211> LENGTH: 59

```
<212> TYPE: DNA
<213> ORGANISM: Homo Sapiens

<400> SEQUENCE: 566
gactggagtt cagacgtgtg ctcttccgat ctattgtgaa gatctgtgac tttggcctg       59

<210> SEQ ID NO 567
<211> LENGTH: 62
<212> TYPE: DNA
<213> ORGANISM: Homo Sapiens

<400> SEQUENCE: 567
gactggagtt cagacgtgtg ctcttccgat ctatttattt cagtgttact tacctgtctt     60
gt                                                                    62

<210> SEQ ID NO 568
<211> LENGTH: 60
<212> TYPE: DNA
<213> ORGANISM: Homo Sapiens

<400> SEQUENCE: 568
gactggagtt cagacgtgtg ctcttccgat ctatttcaac taaacttcta agatgtggca     60

<210> SEQ ID NO 569
<211> LENGTH: 59
<212> TYPE: DNA
<213> ORGANISM: Homo Sapiens

<400> SEQUENCE: 569
gactggagtt cagacgtgtg ctcttccgat ctatttgagg gggagtctgg gaatgaaca      59

<210> SEQ ID NO 570
<211> LENGTH: 59
<212> TYPE: DNA
<213> ORGANISM: Homo Sapiens

<400> SEQUENCE: 570
gactggagtt cagacgtgtg ctcttccgat ctattttttta tggcagtcaa accttctct     59

<210> SEQ ID NO 571
<211> LENGTH: 57
<212> TYPE: DNA
<213> ORGANISM: Homo Sapiens

<400> SEQUENCE: 571
gactggagtt cagacgtgtg ctcttccgat ctcaaaacgc agcccaggac gagtatg        57

<210> SEQ ID NO 572
<211> LENGTH: 58
<212> TYPE: DNA
<213> ORGANISM: Homo Sapiens

<400> SEQUENCE: 572
gactggagtt cagacgtgtg ctcttccgat ctcaaaccag acctcaggcg gctcatag       58

<210> SEQ ID NO 573
<211> LENGTH: 59
<212> TYPE: DNA
<213> ORGANISM: Homo Sapiens

<400> SEQUENCE: 573
gactggagtt cagacgtgtg ctcttccgat ctcaaaactag ccctcaatcc ctgaccctg     59
```

```
<210> SEQ ID NO 574
<211> LENGTH: 59
<212> TYPE: DNA
<213> ORGANISM: Homo Sapiens

<400> SEQUENCE: 574
gactggagtt cagacgtgtg ctcttccgat ctcaaactag ccctcaatcc ctgaccctg      59

<210> SEQ ID NO 575
<211> LENGTH: 59
<212> TYPE: DNA
<213> ORGANISM: Homo Sapiens

<400> SEQUENCE: 575
gactggagtt cagacgtgtg ctcttccgat ctcaaagacg actgattcaa agctggtca      59

<210> SEQ ID NO 576
<211> LENGTH: 59
<212> TYPE: DNA
<213> ORGANISM: Homo Sapiens

<400> SEQUENCE: 576
gactggagtt cagacgtgtg ctcttccgat ctcaaagcag cctctcttaa cccccttcc      59

<210> SEQ ID NO 577
<211> LENGTH: 58
<212> TYPE: DNA
<213> ORGANISM: Homo Sapiens

<400> SEQUENCE: 577
gactggagtt cagacgtgtg ctcttccgat ctcaaagtct gtggccttgt actgcaga       58

<210> SEQ ID NO 578
<211> LENGTH: 58
<212> TYPE: DNA
<213> ORGANISM: Homo Sapiens

<400> SEQUENCE: 578
gactggagtt cagacgtgtg ctcttccgat ctcaaagttt gggaaggctg aagggac        58

<210> SEQ ID NO 579
<211> LENGTH: 59
<212> TYPE: DNA
<213> ORGANISM: Homo Sapiens

<400> SEQUENCE: 579
gactggagtt cagacgtgtg ctcttccgat ctcaaatgtc ttactgctct acagggct       59

<210> SEQ ID NO 580
<211> LENGTH: 58
<212> TYPE: DNA
<213> ORGANISM: Homo Sapiens

<400> SEQUENCE: 580
gactggagtt cagacgtgtg ctcttccgat ctcaaattgt tgccatttca gggtttct       58

<210> SEQ ID NO 581
<211> LENGTH: 59
<212> TYPE: DNA
<213> ORGANISM: Homo Sapiens

<400> SEQUENCE: 581
gactggagtt cagacgtgtg ctcttccgat ctcaacacac cacagatgtc ttcaggctt      59
```

<210> SEQ ID NO 582
<211> LENGTH: 56
<212> TYPE: DNA
<213> ORGANISM: Homo Sapiens

<400> SEQUENCE: 582
gactggagtt cagacgtgtg ctcttccgat ctcaaccagc cctgtcgtct ctccag      56

<210> SEQ ID NO 583
<211> LENGTH: 59
<212> TYPE: DNA
<213> ORGANISM: Homo Sapiens

<400> SEQUENCE: 583
gactggagtt cagacgtgtg ctcttccgat ctcaacccaa tagacccacc ccaatctcc   59

<210> SEQ ID NO 584
<211> LENGTH: 59
<212> TYPE: DNA
<213> ORGANISM: Homo Sapiens

<400> SEQUENCE: 584
gactggagtt cagacgtgtg ctcttccgat ctcaacgggt tccttccttc gagagcttc   59

<210> SEQ ID NO 585
<211> LENGTH: 56
<212> TYPE: DNA
<213> ORGANISM: Homo Sapiens

<400> SEQUENCE: 585
gactggagtt cagacgtgtg ctcttccgat ctcaacttgg aggccttgca gaagaa      56

<210> SEQ ID NO 586
<211> LENGTH: 59
<212> TYPE: DNA
<213> ORGANISM: Homo Sapiens

<400> SEQUENCE: 586
gactggagtt cagacgtgtg ctcttccgat ctcaagagat ctgatgctga ggaagtgga   59

<210> SEQ ID NO 587
<211> LENGTH: 53
<212> TYPE: DNA
<213> ORGANISM: Homo Sapiens

<400> SEQUENCE: 587
gactggagtt cagacgtgtg ctcttccgat ctcaagcctc acaccacccc cac         53

<210> SEQ ID NO 588
<211> LENGTH: 61
<212> TYPE: DNA
<213> ORGANISM: Homo Sapiens

<400> SEQUENCE: 588
gactggagtt cagacgtgtg ctcttccgat ctcaaggaga taagtgatgg agatgtgata  60
a                                                                  61

<210> SEQ ID NO 589
<211> LENGTH: 57
<212> TYPE: DNA
<213> ORGANISM: Homo Sapiens

<400> SEQUENCE: 589
gactggagtt cagacgtgtg ctcttccgat ctcaaggggc taggatgggg actcttg      57

<210> SEQ ID NO 590
<211> LENGTH: 56
<212> TYPE: DNA
<213> ORGANISM: Homo Sapiens

<400> SEQUENCE: 590
gactggagtt cagacgtgtg ctcttccgat ctcaagggtg tgagtgaacg gtgagc      56

<210> SEQ ID NO 591
<211> LENGTH: 58
<212> TYPE: DNA
<213> ORGANISM: Homo Sapiens

<400> SEQUENCE: 591
gactggagtt cagacgtgtg ctcttccgat ctcaaggtgg aaagaggaag atgagaac    58

<210> SEQ ID NO 592
<211> LENGTH: 59
<212> TYPE: DNA
<213> ORGANISM: Homo Sapiens

<400> SEQUENCE: 592
gactggagtt cagacgtgtg ctcttccgat ctcaatagac ccaccccaat ctccccaga   59

<210> SEQ ID NO 593
<211> LENGTH: 59
<212> TYPE: DNA
<213> ORGANISM: Homo Sapiens

<400> SEQUENCE: 593
gactggagtt cagacgtgtg ctcttccgat ctcaatcaaa ctgcagagta tttgggcga   59

<210> SEQ ID NO 594
<211> LENGTH: 57
<212> TYPE: DNA
<213> ORGANISM: Homo Sapiens

<400> SEQUENCE: 594
gactggagtt cagacgtgtg ctcttccgat ctcaatcctc ggcctctagt gtgcaga     57

<210> SEQ ID NO 595
<211> LENGTH: 58
<212> TYPE: DNA
<213> ORGANISM: Homo Sapiens

<400> SEQUENCE: 595
gactggagtt cagacgtgtg ctcttccgat ctcacaaaat ggttctggat cagctgga    58

<210> SEQ ID NO 596
<211> LENGTH: 57
<212> TYPE: DNA
<213> ORGANISM: Homo Sapiens

<400> SEQUENCE: 596
gactggagtt cagacgtgtg ctcttccgat ctcacaagcc acccatctcc tcagctg     57

<210> SEQ ID NO 597
<211> LENGTH: 56
<212> TYPE: DNA
<213> ORGANISM: Homo Sapiens -continued

<400> SEQUENCE: 597
gactggagtt cagacgtgtg ctcttccgat ctcacaaggg gctaggatgg ggactc    56

<210> SEQ ID NO 598
<211> LENGTH: 55
<212> TYPE: DNA
<213> ORGANISM: Homo Sapiens

<400> SEQUENCE: 598
gactggagtt cagacgtgtg ctcttccgat ctcacaccac ccccacccac agatc    55

<210> SEQ ID NO 599
<211> LENGTH: 58
<212> TYPE: DNA
<213> ORGANISM: Homo Sapiens

<400> SEQUENCE: 599
gactggagtt cagacgtgtg ctcttccgat ctcacagaga agttgttgag gggagcct    58

<210> SEQ ID NO 600
<211> LENGTH: 53
<212> TYPE: DNA
<213> ORGANISM: Homo Sapiens

<400> SEQUENCE: 600
gactggagtt cagacgtgtg ctcttccgat ctcacagatg ttcccggggc tgc    53

<210> SEQ ID NO 601
<211> LENGTH: 54
<212> TYPE: DNA
<213> ORGANISM: Homo Sapiens

<400> SEQUENCE: 601
gactggagtt cagacgtgtg ctcttccgat ctcacagccc acgtaccgct cctc    54

<210> SEQ ID NO 602
<211> LENGTH: 52
<212> TYPE: DNA
<213> ORGANISM: Homo Sapiens

<400> SEQUENCE: 602
gactggagtt cagacgtgtg ctcttccgat ctcacagctg gaaggacaag cc    52

<210> SEQ ID NO 603
<211> LENGTH: 55
<212> TYPE: DNA
<213> ORGANISM: Homo Sapiens

<400> SEQUENCE: 603
gactggagtt cagacgtgtg ctcttccgat ctcaccagcc gcgaaacctg agaag    55

<210> SEQ ID NO 604
<211> LENGTH: 57
<212> TYPE: DNA
<213> ORGANISM: Homo Sapiens

<400> SEQUENCE: 604
gactggagtt cagacgtgtg ctcttccgat ctcaccagga catgcacagc tacatcg    57

<210> SEQ ID NO 605
<211> LENGTH: 55
<212> TYPE: DNA

<213> ORGANISM: Homo Sapiens

<400> SEQUENCE: 605
gactggagtt cagacgtgtg ctcttccgat ctcacccaaa tgtgcagaaa gacct    55

<210> SEQ ID NO 606
<211> LENGTH: 54
<212> TYPE: DNA
<213> ORGANISM: Homo Sapiens

<400> SEQUENCE: 606
gactggagtt cagacgtgtg ctcttccgat ctcaccccca cccacagatc cact    54

<210> SEQ ID NO 607
<211> LENGTH: 54
<212> TYPE: DNA
<213> ORGANISM: Homo Sapiens

<400> SEQUENCE: 607
gactggagtt cagacgtgtg ctcttccgat ctcacccctt ccccagtgca tcca    54

<210> SEQ ID NO 608
<211> LENGTH: 59
<212> TYPE: DNA
<213> ORGANISM: Homo Sapiens

<400> SEQUENCE: 608
gactggagtt cagacgtgtg ctcttccgat ctcaccctgc catgctacct agatacctt    59

<210> SEQ ID NO 609
<211> LENGTH: 59
<212> TYPE: DNA
<213> ORGANISM: Homo Sapiens

<400> SEQUENCE: 609
gactggagtt cagacgtgtg ctcttccgat ctcaccctgt tcactccttt gctgattgg    59

<210> SEQ ID NO 610
<211> LENGTH: 58
<212> TYPE: DNA
<213> ORGANISM: Homo Sapiens

<400> SEQUENCE: 610
gactggagtt cagacgtgtg ctcttccgat ctcaccgctt cttgtcctgc ttgcttac    58

<210> SEQ ID NO 611
<211> LENGTH: 59
<212> TYPE: DNA
<213> ORGANISM: Homo Sapiens

<400> SEQUENCE: 611
gactggagtt cagacgtgtg ctcttccgat ctcacctgat cctagtacct tccctgcaa    59

<210> SEQ ID NO 612
<211> LENGTH: 57
<212> TYPE: DNA
<213> ORGANISM: Homo Sapiens

<400> SEQUENCE: 612
gactggagtt cagacgtgtg ctcttccgat ctcacgctcc attatccagc cccaaag    57

<210> SEQ ID NO 613
<211> LENGTH: 59

<212> TYPE: DNA
<213> ORGANISM: Homo Sapiens

<400> SEQUENCE: 613
gactggagtt cagacgtgtg ctcttccgat ctcacgtgtt gaagtcctcg ttgtcttgt    59

<210> SEQ ID NO 614
<211> LENGTH: 59
<212> TYPE: DNA
<213> ORGANISM: Homo Sapiens

<400> SEQUENCE: 614
gactggagtt cagacgtgtg ctcttccgat ctcacgtgtt gaagtcctcg ttgtcttgt    59

<210> SEQ ID NO 615
<211> LENGTH: 58
<212> TYPE: DNA
<213> ORGANISM: Homo Sapiens

<400> SEQUENCE: 615
gactggagtt cagacgtgtg ctcttccgat ctcactcaga tctcgtcagc catggagt     58

<210> SEQ ID NO 616
<211> LENGTH: 58
<212> TYPE: DNA
<213> ORGANISM: Homo Sapiens

<400> SEQUENCE: 616
gactggagtt cagacgtgtg ctcttccgat ctcactcgga taagatgctg aggagggg     58

<210> SEQ ID NO 617
<211> LENGTH: 54
<212> TYPE: DNA
<213> ORGANISM: Homo Sapiens

<400> SEQUENCE: 617
gactggagtt cagacgtgtg ctcttccgat ctcactgacc caccaccccc tcac         54

<210> SEQ ID NO 618
<211> LENGTH: 52
<212> TYPE: DNA
<213> ORGANISM: Homo Sapiens

<400> SEQUENCE: 618
gactggagtt cagacgtgtg ctcttccgat ctcactgccg cttccccacc ag           52

<210> SEQ ID NO 619
<211> LENGTH: 59
<212> TYPE: DNA
<213> ORGANISM: Homo Sapiens

<400> SEQUENCE: 619
gactggagtt cagacgtgtg ctcttccgat ctcactgcct catctctcac catcccaag    59

<210> SEQ ID NO 620
<211> LENGTH: 58
<212> TYPE: DNA
<213> ORGANISM: Homo Sapiens

<400> SEQUENCE: 620
gactggagtt cagacgtgtg ctcttccgat ctcactgcta ccacaagttt gcccacaa     58

<210> SEQ ID NO 621

```
<211> LENGTH: 59
<212> TYPE: DNA
<213> ORGANISM: Homo Sapiens

<400> SEQUENCE: 621
gactggagtt cagacgtgtg ctcttccgat ctcactttga ctcaccggtg gatgaagtg      59

<210> SEQ ID NO 622
<211> LENGTH: 57
<212> TYPE: DNA
<213> ORGANISM: Homo Sapiens

<400> SEQUENCE: 622
gactggagtt cagacgtgtg ctcttccgat ctcagaaaag cggctgttag tcactgg        57

<210> SEQ ID NO 623
<211> LENGTH: 55
<212> TYPE: DNA
<213> ORGANISM: Homo Sapiens

<400> SEQUENCE: 623
gactggagtt cagacgtgtg ctcttccgat ctcagaagat gacaggggcc aggag          55

<210> SEQ ID NO 624
<211> LENGTH: 57
<212> TYPE: DNA
<213> ORGANISM: Homo Sapiens

<400> SEQUENCE: 624
gactggagtt cagacgtgtg ctcttccgat ctcagacatt gtgcaagcag gtccctc        57

<210> SEQ ID NO 625
<211> LENGTH: 59
<212> TYPE: DNA
<213> ORGANISM: Homo Sapiens

<400> SEQUENCE: 625
gactggagtt cagacgtgtg ctcttccgat ctcagacgca tttccacagc tacaccata     59

<210> SEQ ID NO 626
<211> LENGTH: 56
<212> TYPE: DNA
<213> ORGANISM: Homo Sapiens

<400> SEQUENCE: 626
gactggagtt cagacgtgtg ctcttccgat ctcagactga tggccaactc cccttc         56

<210> SEQ ID NO 627
<211> LENGTH: 56
<212> TYPE: DNA
<213> ORGANISM: Homo Sapiens

<400> SEQUENCE: 627
gactggagtt cagacgtgtg ctcttccgat ctcagagagc aacaaaccac tggaat         56

<210> SEQ ID NO 628
<211> LENGTH: 59
<212> TYPE: DNA
<213> ORGANISM: Homo Sapiens

<400> SEQUENCE: 628
gactggagtt cagacgtgtg ctcttccgat ctcagagagc aacaaaccac tggaatata     59
```

```
<210> SEQ ID NO 629
<211> LENGTH: 53
<212> TYPE: DNA
<213> ORGANISM: Homo Sapiens

<400> SEQUENCE: 629
gactggagtt cagacgtgtg ctcttccgat ctcagagccc agtcccctc agg            53

<210> SEQ ID NO 630
<211> LENGTH: 54
<212> TYPE: DNA
<213> ORGANISM: Homo Sapiens

<400> SEQUENCE: 630
gactggagtt cagacgtgtg ctcttccgat ctcagagggg agttggggtg aggg           54

<210> SEQ ID NO 631
<211> LENGTH: 56
<212> TYPE: DNA
<213> ORGANISM: Homo Sapiens

<400> SEQUENCE: 631
gactggagtt cagacgtgtg ctcttccgat ctcagagtag gggctggctg gatgag         56

<210> SEQ ID NO 632
<211> LENGTH: 64
<212> TYPE: DNA
<213> ORGANISM: Homo Sapiens

<400> SEQUENCE: 632
gactggagtt cagacgtgtg ctcttccgat ctcagatctg tatttatttc agtgttactt     60
acct                                                                  64

<210> SEQ ID NO 633
<211> LENGTH: 59
<212> TYPE: DNA
<213> ORGANISM: Homo Sapiens

<400> SEQUENCE: 633
gactggagtt cagacgtgtg ctcttccgat ctcagatgct ttggaatgag tgttagaac      59

<210> SEQ ID NO 634
<211> LENGTH: 55
<212> TYPE: DNA
<213> ORGANISM: Homo Sapiens

<400> SEQUENCE: 634
gactggagtt cagacgtgtg ctcttccgat ctcagcattg ttgggggaca cgagc          55

<210> SEQ ID NO 635
<211> LENGTH: 58
<212> TYPE: DNA
<213> ORGANISM: Homo Sapiens

<400> SEQUENCE: 635
gactggagtt cagacgtgtg ctcttccgat ctcagccaca catgccatca ttctagga       58

<210> SEQ ID NO 636
<211> LENGTH: 59
<212> TYPE: DNA
<213> ORGANISM: Homo Sapiens

<400> SEQUENCE: 636
```

```
gactggagtt cagacgtgtg ctcttccgat ctcagccacg ggtaataatt tttgtccctt         59
```

<210> SEQ ID NO 637
<211> LENGTH: 55
<212> TYPE: DNA
<213> ORGANISM: Homo Sapiens

<400> SEQUENCE: 637

```
gactggagtt cagacgtgtg ctcttccgat ctcagccgat gtcagtctgg tgtgg             55
```

<210> SEQ ID NO 638
<211> LENGTH: 56
<212> TYPE: DNA
<213> ORGANISM: Homo Sapiens

<400> SEQUENCE: 638

```
gactggagtt cagacgtgtg ctcttccgat ctcagccggt tctctgcaca ttggaa            56
```

<210> SEQ ID NO 639
<211> LENGTH: 57
<212> TYPE: DNA
<213> ORGANISM: Homo Sapiens

<400> SEQUENCE: 639

```
gactggagtt cagacgtgtg ctcttccgat ctcagcctac agagtccgca agccaag           57
```

<210> SEQ ID NO 640
<211> LENGTH: 58
<212> TYPE: DNA
<213> ORGANISM: Homo Sapiens

<400> SEQUENCE: 640

```
gactggagtt cagacgtgtg ctcttccgat ctcagcctct cttaaccccc ttccctag          58
```

<210> SEQ ID NO 641
<211> LENGTH: 56
<212> TYPE: DNA
<213> ORGANISM: Homo Sapiens

<400> SEQUENCE: 641

```
gactggagtt cagacgtgtg ctcttccgat ctcaggcaca gcttttcctc catgag            56
```

<210> SEQ ID NO 642
<211> LENGTH: 59
<212> TYPE: DNA
<213> ORGANISM: Homo Sapiens

<400> SEQUENCE: 642

```
gactggagtt cagacgtgtg ctcttccgat ctcaggcaca gcttttcctc catgagtac         59
```

<210> SEQ ID NO 643
<211> LENGTH: 54
<212> TYPE: DNA
<213> ORGANISM: Homo Sapiens

<400> SEQUENCE: 643

```
gactggagtt cagacgtgtg ctcttccgat ctcaggcatc ctcagctacg ggt               54
```

<210> SEQ ID NO 644
<211> LENGTH: 54
<212> TYPE: DNA
<213> ORGANISM: Homo Sapiens

<400> SEQUENCE: 644

-continued

```
gactggagtt cagacgtgtg ctcttccgat ctcaggccct ggtagctcat catc        54
```

<210> SEQ ID NO 645
<211> LENGTH: 56
<212> TYPE: DNA
<213> ORGANISM: Homo Sapiens

<400> SEQUENCE: 645

```
gactggagtt cagacgtgtg ctcttccgat ctcaggcctc tctgtctgaa cttggg       56
```

<210> SEQ ID NO 646
<211> LENGTH: 54
<212> TYPE: DNA
<213> ORGANISM: Homo Sapiens

<400> SEQUENCE: 646

```
gactggagtt cagacgtgtg ctcttccgat ctcagggagc agcgaggcct tcac         54
```

<210> SEQ ID NO 647
<211> LENGTH: 57
<212> TYPE: DNA
<213> ORGANISM: Homo Sapiens

<400> SEQUENCE: 647

```
gactggagtt cagacgtgtg ctcttccgat ctcagggcat gaactacttg gaggacc      57
```

<210> SEQ ID NO 648
<211> LENGTH: 59
<212> TYPE: DNA
<213> ORGANISM: Homo Sapiens

<400> SEQUENCE: 648

```
gactggagtt cagacgtgtg ctcttccgat ctcaggggta cttagatggg ggatggctg    59
```

<210> SEQ ID NO 649
<211> LENGTH: 56
<212> TYPE: DNA
<213> ORGANISM: Homo Sapiens

<400> SEQUENCE: 649

```
gactggagtt cagacgtgtg ctcttccgat ctcaggtctc cgtggatgcc ttcaag       56
```

<210> SEQ ID NO 650
<211> LENGTH: 54
<212> TYPE: DNA
<213> ORGANISM: Homo Sapiens

<400> SEQUENCE: 650

```
gactggagtt cagacgtgtg ctcttccgat ctcaggttcc acacacaggc gtcc         54
```

<210> SEQ ID NO 651
<211> LENGTH: 54
<212> TYPE: DNA
<213> ORGANISM: Homo Sapiens

<400> SEQUENCE: 651

```
gactggagtt cagacgtgtg ctcttccgat ctcaggttct tgggggcag aggg          54
```

<210> SEQ ID NO 652
<211> LENGTH: 59
<212> TYPE: DNA
<213> ORGANISM: Homo Sapiens

```
<400> SEQUENCE: 652
gactggagtt cagacgtgtg ctcttccgat ctcagtatag agcgtgcaga taatgacaa      59

<210> SEQ ID NO 653
<211> LENGTH: 58
<212> TYPE: DNA
<213> ORGANISM: Homo Sapiens

<400> SEQUENCE: 653
gactggagtt cagacgtgtg ctcttccgat ctcagtcgcc tcagtaaagc cacctcac       58

<210> SEQ ID NO 654
<211> LENGTH: 55
<212> TYPE: DNA
<213> ORGANISM: Homo Sapiens

<400> SEQUENCE: 654
gactggagtt cagacgtgtg ctcttccgat ctcagtgggg cagactctct cctcc          55

<210> SEQ ID NO 655
<211> LENGTH: 55
<212> TYPE: DNA
<213> ORGANISM: Homo Sapiens

<400> SEQUENCE: 655
gactggagtt cagacgtgtg ctcttccgat ctcagtgggg cagactctct cctcc          55

<210> SEQ ID NO 656
<211> LENGTH: 59
<212> TYPE: DNA
<213> ORGANISM: Homo Sapiens

<400> SEQUENCE: 656
gactggagtt cagacgtgtg ctcttccgat ctcagttgtt tgttcagttg ggagcggag      59

<210> SEQ ID NO 657
<211> LENGTH: 59
<212> TYPE: DNA
<213> ORGANISM: Homo Sapiens

<400> SEQUENCE: 657
gactggagtt cagacgtgtg ctcttccgat ctcagttgtt tgttcagttg ggagcggag      59

<210> SEQ ID NO 658
<211> LENGTH: 59
<212> TYPE: DNA
<213> ORGANISM: Homo Sapiens

<400> SEQUENCE: 658
gactggagtt cagacgtgtg ctcttccgat ctcatacgtc ttggttcact catccggga     59

<210> SEQ ID NO 659
<211> LENGTH: 54
<212> TYPE: DNA
<213> ORGANISM: Homo Sapiens

<400> SEQUENCE: 659
gactggagtt cagacgtgtg ctcttccgat ctcatcagca ccaccaccac cagc           54

<210> SEQ ID NO 660
<211> LENGTH: 58
<212> TYPE: DNA
<213> ORGANISM: Homo Sapiens
```

<400> SEQUENCE: 660
gactggagtt cagacgtgtg ctcttccgat ctcatccact gctaccacaa gtttgccc    58

<210> SEQ ID NO 661
<211> LENGTH: 57
<212> TYPE: DNA
<213> ORGANISM: Homo Sapiens

<400> SEQUENCE: 661
gactggagtt cagacgtgtg ctcttccgat ctcatccagt gccagaaccc gctcttc    57

<210> SEQ ID NO 662
<211> LENGTH: 54
<212> TYPE: DNA
<213> ORGANISM: Homo Sapiens

<400> SEQUENCE: 662
gactggagtt cagacgtgtg ctcttccgat ctcatcgtct ttgcaggcct ctct    54

<210> SEQ ID NO 663
<211> LENGTH: 54
<212> TYPE: DNA
<213> ORGANISM: Homo Sapiens

<400> SEQUENCE: 663
gactggagtt cagacgtgtg ctcttccgat ctcatctgcc tcacctccac cgtg    54

<210> SEQ ID NO 664
<211> LENGTH: 59
<212> TYPE: DNA
<213> ORGANISM: Homo Sapiens

<400> SEQUENCE: 664
gactggagtt cagacgtgtg ctcttccgat ctcatcttcc atcttctcac actgggggt    59

<210> SEQ ID NO 665
<211> LENGTH: 59
<212> TYPE: DNA
<213> ORGANISM: Homo Sapiens

<400> SEQUENCE: 665
gactggagtt cagacgtgtg ctcttccgat ctcatgaact ccacatttgc cttgggacc    59

<210> SEQ ID NO 666
<211> LENGTH: 59
<212> TYPE: DNA
<213> ORGANISM: Homo Sapiens

<400> SEQUENCE: 666
gactggagtt cagacgtgtg ctcttccgat ctcatgcctg gctccctaat tttatagtt    59

<210> SEQ ID NO 667
<211> LENGTH: 57
<212> TYPE: DNA
<213> ORGANISM: Homo Sapiens

<400> SEQUENCE: 667
gactggagtt cagacgtgtg ctcttccgat ctcatgcgct tgacatcagt ttgccag    57

<210> SEQ ID NO 668
<211> LENGTH: 51
<212> TYPE: DNA

```
<213> ORGANISM: Homo Sapiens

<400> SEQUENCE: 668
gactggagtt cagacgtgtg ctcttccgat ctcatgctgc agggaggggg c          51

<210> SEQ ID NO 669
<211> LENGTH: 57
<212> TYPE: DNA
<213> ORGANISM: Homo Sapiens

<400> SEQUENCE: 669
gactggagtt cagacgtgtg ctcttccgat ctcatggaac cagacagaaa agcggct    57

<210> SEQ ID NO 670
<211> LENGTH: 59
<212> TYPE: DNA
<213> ORGANISM: Homo Sapiens

<400> SEQUENCE: 670
gactggagtt cagacgtgtg ctcttccgat ctcatggacc ctgacaaatg tgctgttct  59

<210> SEQ ID NO 671
<211> LENGTH: 53
<212> TYPE: DNA
<213> ORGANISM: Homo Sapiens

<400> SEQUENCE: 671
gactggagtt cagacgtgtg ctcttccgat ctcatgtctg gcactgcttt cca        53

<210> SEQ ID NO 672
<211> LENGTH: 59
<212> TYPE: DNA
<213> ORGANISM: Homo Sapiens

<400> SEQUENCE: 672
gactggagtt cagacgtgtg ctcttccgat ctcattcttg aggggctgag gtggaagag  59

<210> SEQ ID NO 673
<211> LENGTH: 59
<212> TYPE: DNA
<213> ORGANISM: Homo Sapiens

<400> SEQUENCE: 673
gactggagtt cagacgtgtg ctcttccgat ctcattggca tggggaaata taaacttgt  59

<210> SEQ ID NO 674
<211> LENGTH: 55
<212> TYPE: DNA
<213> ORGANISM: Homo Sapiens

<400> SEQUENCE: 674
gactggagtt cagacgtgtg ctcttccgat ctcattgggg aggtagaggg cacac      55

<210> SEQ ID NO 675
<211> LENGTH: 55
<212> TYPE: DNA
<213> ORGANISM: Homo Sapiens

<400> SEQUENCE: 675
gactggagtt cagacgtgtg ctcttccgat ctcattgttg ggggacacga gcctg      55

<210> SEQ ID NO 676
<211> LENGTH: 59
```

```
<212> TYPE: DNA
<213> ORGANISM: Homo Sapiens

<400> SEQUENCE: 676
gactggagtt cagacgtgtg ctcttccgat ctcatttcca tctcccctcc ctttaccct      59

<210> SEQ ID NO 677
<211> LENGTH: 59
<212> TYPE: DNA
<213> ORGANISM: Homo Sapiens

<400> SEQUENCE: 677
gactggagtt cagacgtgtg ctcttccgat ctcatttctt cctttccat gcagtgtgt      59

<210> SEQ ID NO 678
<211> LENGTH: 59
<212> TYPE: DNA
<213> ORGANISM: Homo Sapiens

<400> SEQUENCE: 678
gactggagtt cagacgtgtg ctcttccgat ctcatttgga tgccttattg cgacagatc      59

<210> SEQ ID NO 679
<211> LENGTH: 57
<212> TYPE: DNA
<213> ORGANISM: Homo Sapiens

<400> SEQUENCE: 679
gactggagtt cagacgtgtg ctcttccgat ctccaaagca gcctctctta accccct        57

<210> SEQ ID NO 680
<211> LENGTH: 60
<212> TYPE: DNA
<213> ORGANISM: Homo Sapiens

<400> SEQUENCE: 680
gactggagtt cagacgtgtg ctcttccgat ctccaatgga aagaaatgc tgcagaaaca      60

<210> SEQ ID NO 681
<211> LENGTH: 55
<212> TYPE: DNA
<213> ORGANISM: Homo Sapiens

<400> SEQUENCE: 681
gactggagtt cagacgtgtg ctcttccgat ctccaattca ggacccacac gacgg          55

<210> SEQ ID NO 682
<211> LENGTH: 54
<212> TYPE: DNA
<213> ORGANISM: Homo Sapiens

<400> SEQUENCE: 682
gactggagtt cagacgtgtg ctcttccgat ctccacacac caccctctg ctgg            54

<210> SEQ ID NO 683
<211> LENGTH: 62
<212> TYPE: DNA
<213> ORGANISM: Homo Sapiens

<400> SEQUENCE: 683
gactggagtt cagacgtgtg ctcttccgat ctccacactt ctccattctt cacaagggta     60
tg                                                                    62
```

<210> SEQ ID NO 684
<211> LENGTH: 60
<212> TYPE: DNA
<213> ORGANISM: Homo Sapiens

<400> SEQUENCE: 684
gactggagtt cagacgtgtg ctcttccgat ctccacattt cagcaacagc agcatctata    60

<210> SEQ ID NO 685
<211> LENGTH: 63
<212> TYPE: DNA
<213> ORGANISM: Homo Sapiens

<400> SEQUENCE: 685
gactggagtt cagacgtgtg ctcttccgat ctccacattt cagcaacagc agcatctata    60
aga                                                                  63

<210> SEQ ID NO 686
<211> LENGTH: 53
<212> TYPE: DNA
<213> ORGANISM: Homo Sapiens

<400> SEQUENCE: 686
gactggagtt cagacgtgtg ctcttccgat ctccaccaag cagcccatcc ctg           53

<210> SEQ ID NO 687
<211> LENGTH: 59
<212> TYPE: DNA
<213> ORGANISM: Homo Sapiens

<400> SEQUENCE: 687
gactggagtt cagacgtgtg ctcttccgat ctccacgatg cccagtcaat cttgtgtaa     59

<210> SEQ ID NO 688
<211> LENGTH: 62
<212> TYPE: DNA
<213> ORGANISM: Homo Sapiens

<400> SEQUENCE: 688
gactggagtt cagacgtgtg ctcttccgat ctccacgatg cccagtcaat cttgtgtaat    60
tt                                                                   62

<210> SEQ ID NO 689
<211> LENGTH: 60
<212> TYPE: DNA
<213> ORGANISM: Homo Sapiens

<400> SEQUENCE: 689
gactggagtt cagacgtgtg ctcttccgat ctccactaac aaccctcctg ccatcatatt    60

<210> SEQ ID NO 690
<211> LENGTH: 64
<212> TYPE: DNA
<213> ORGANISM: Homo Sapiens

<400> SEQUENCE: 690
gactggagtt cagacgtgtg ctcttccgat ctccactcaa tcttctactt taaaatgact    60
tagg                                                                 64

<210> SEQ ID NO 691
<211> LENGTH: 67

```
<212> TYPE: DNA
<213> ORGANISM: Homo Sapiens

<400> SEQUENCE: 691
gactggagtt cagacgtgtg ctcttccgat ctccactcaa tcttctactt taaaatgact    60
taggaaa                                                              67

<210> SEQ ID NO 692
<211> LENGTH: 58
<212> TYPE: DNA
<213> ORGANISM: Homo Sapiens

<400> SEQUENCE: 692
gactggagtt cagacgtgtg ctcttccgat ctccactcat gctctacaac cccaccac      58

<210> SEQ ID NO 693
<211> LENGTH: 59
<212> TYPE: DNA
<213> ORGANISM: Homo Sapiens

<400> SEQUENCE: 693
gactggagtt cagacgtgtg ctcttccgat ctccactctt gctccttcca tccttgctc     59

<210> SEQ ID NO 694
<211> LENGTH: 58
<212> TYPE: DNA
<213> ORGANISM: Homo Sapiens

<400> SEQUENCE: 694
gactggagtt cagacgtgtg ctcttccgat ctccactgac aaccaccctt aaccccct      58

<210> SEQ ID NO 695
<211> LENGTH: 58
<212> TYPE: DNA
<213> ORGANISM: Homo Sapiens

<400> SEQUENCE: 695
gactggagtt cagacgtgtg ctcttccgat ctccactgct ggctgatcta tgtccctg      58

<210> SEQ ID NO 696
<211> LENGTH: 59
<212> TYPE: DNA
<213> ORGANISM: Homo Sapiens

<400> SEQUENCE: 696
gactggagtt cagacgtgtg ctcttccgat ctccacttct acgacttctt caaccaggc     59

<210> SEQ ID NO 697
<211> LENGTH: 54
<212> TYPE: DNA
<213> ORGANISM: Homo Sapiens

<400> SEQUENCE: 697
gactggagtt cagacgtgtg ctcttccgat ctccagaagg tctacatggg tgct          54

<210> SEQ ID NO 698
<211> LENGTH: 57
<212> TYPE: DNA
<213> ORGANISM: Homo Sapiens

<400> SEQUENCE: 698
gactggagtt cagacgtgtg ctcttccgat ctccagaagg tctacatggg tgcttcc       57
```

```
<210> SEQ ID NO 699
<211> LENGTH: 57
<212> TYPE: DNA
<213> ORGANISM: Homo Sapiens

<400> SEQUENCE: 699
gactggagtt cagacgtgtg ctcttccgat ctccagaagg tctacatggg tgcttcc      57

<210> SEQ ID NO 700
<211> LENGTH: 57
<212> TYPE: DNA
<213> ORGANISM: Homo Sapiens

<400> SEQUENCE: 700
gactggagtt cagacgtgtg ctcttccgat ctccagaagg tctacatggg tgcttcc      57

<210> SEQ ID NO 701
<211> LENGTH: 59
<212> TYPE: DNA
<213> ORGANISM: Homo Sapiens

<400> SEQUENCE: 701
gactggagtt cagacgtgtg ctcttccgat ctccagacct aactcttgaa tgaccctgt    59

<210> SEQ ID NO 702
<211> LENGTH: 62
<212> TYPE: DNA
<213> ORGANISM: Homo Sapiens

<400> SEQUENCE: 702
gactggagtt cagacgtgtg ctcttccgat ctccagacct aagagcaatc agtgaggaat   60
ca                                                                 62

<210> SEQ ID NO 703
<211> LENGTH: 59
<212> TYPE: DNA
<213> ORGANISM: Homo Sapiens

<400> SEQUENCE: 703
gactggagtt cagacgtgtg ctcttccgat ctccagccag acccagccag tattatttc    59

<210> SEQ ID NO 704
<211> LENGTH: 57
<212> TYPE: DNA
<213> ORGANISM: Homo Sapiens

<400> SEQUENCE: 704
gactggagtt cagacgtgtg ctcttccgat ctccagcgtg tcctctctcc tccatag      57

<210> SEQ ID NO 705
<211> LENGTH: 57
<212> TYPE: DNA
<213> ORGANISM: Homo Sapiens

<400> SEQUENCE: 705
gactggagtt cagacgtgtg ctcttccgat ctccagcgtg tcctctctcc tccatag      57

<210> SEQ ID NO 706
<211> LENGTH: 57
<212> TYPE: DNA
<213> ORGANISM: Homo Sapiens

<400> SEQUENCE: 706
```

-continued

```
gactggagtt cagacgtgtg ctcttccgat ctccagctgc tcaccatcgc tatctga        57
```

<210> SEQ ID NO 707
<211> LENGTH: 57
<212> TYPE: DNA
<213> ORGANISM: Homo Sapiens

<400> SEQUENCE: 707

```
gactggagtt cagacgtgtg ctcttccgat ctccagctgc tcaccatcgc tatctga        57
```

<210> SEQ ID NO 708
<211> LENGTH: 55
<212> TYPE: DNA
<213> ORGANISM: Homo Sapiens

<400> SEQUENCE: 708

```
gactggagtt cagacgtgtg ctcttccgat ctccagctgg gtgaactttg aggcc          55
```

<210> SEQ ID NO 709
<211> LENGTH: 65
<212> TYPE: DNA
<213> ORGANISM: Homo Sapiens

<400> SEQUENCE: 709

```
gactggagtt cagacgtgtg ctcttccgat ctccaggagc taataaaaat aacttctttc     60
tctgg                                                                 65
```

<210> SEQ ID NO 710
<211> LENGTH: 52
<212> TYPE: DNA
<213> ORGANISM: Homo Sapiens

<400> SEQUENCE: 710

```
gactggagtt cagacgtgtg ctcttccgat ctccagggag cagcgaggcc tt             52
```

<210> SEQ ID NO 711
<211> LENGTH: 52
<212> TYPE: DNA
<213> ORGANISM: Homo Sapiens

<400> SEQUENCE: 711

```
gactggagtt cagacgtgtg ctcttccgat ctccagggag ggaggccagc tg             52
```

<210> SEQ ID NO 712
<211> LENGTH: 59
<212> TYPE: DNA
<213> ORGANISM: Homo Sapiens

<400> SEQUENCE: 712

```
gactggagtt cagacgtgtg ctcttccgat ctccaggggt ccaagttagg ttaggtgat      59
```

<210> SEQ ID NO 713
<211> LENGTH: 50
<212> TYPE: DNA
<213> ORGANISM: Homo Sapiens

<400> SEQUENCE: 713

```
gactggagtt cagacgtgtg ctcttccgat ctccaggtcc acgggcagac                50
```

<210> SEQ ID NO 714
<211> LENGTH: 65
<212> TYPE: DNA

<213> ORGANISM: Homo Sapiens

<400> SEQUENCE: 714
gactggagtt cagacgtgtg ctcttccgat ctccagtgtt tcttttaaat acctgttaag    60
tttgt    65

<210> SEQ ID NO 715
<211> LENGTH: 62
<212> TYPE: DNA
<213> ORGANISM: Homo Sapiens

<400> SEQUENCE: 715
gactggagtt cagacgtgtg ctcttccgat ctccagttgg ttacatactt ggacttggtg    60
at    62

<210> SEQ ID NO 716
<211> LENGTH: 61
<212> TYPE: DNA
<213> ORGANISM: Homo Sapiens

<400> SEQUENCE: 716
gactggagtt cagacgtgtg ctcttccgat ctccataaag acagaaggag gagagacacc    60
a    61

<210> SEQ ID NO 717
<211> LENGTH: 61
<212> TYPE: DNA
<213> ORGANISM: Homo Sapiens

<400> SEQUENCE: 717
gactggagtt cagacgtgtg ctcttccgat ctccataaag gctttaacac agaatcaaaa    60
g    61

<210> SEQ ID NO 718
<211> LENGTH: 53
<212> TYPE: DNA
<213> ORGANISM: Homo Sapiens

<400> SEQUENCE: 718
gactggagtt cagacgtgtg ctcttccgat ctccatcatg ctgaggtgcc aca    53

<210> SEQ ID NO 719
<211> LENGTH: 58
<212> TYPE: DNA
<213> ORGANISM: Homo Sapiens

<400> SEQUENCE: 719
gactggagtt cagacgtgtg ctcttccgat ctccatccca aggtgcctat caagtgga    58

<210> SEQ ID NO 720
<211> LENGTH: 59
<212> TYPE: DNA
<213> ORGANISM: Homo Sapiens

<400> SEQUENCE: 720
gactggagtt cagacgtgtg ctcttccgat ctccatcccc agtgactgtg tgttgatca    59

<210> SEQ ID NO 721
<211> LENGTH: 55
<212> TYPE: DNA
<213> ORGANISM: Homo Sapiens

<400> SEQUENCE: 721
gactggagtt cagacgtgtg ctcttccgat ctccatcccc gtgtccctcc taagc        55

<210> SEQ ID NO 722
<211> LENGTH: 59
<212> TYPE: DNA
<213> ORGANISM: Homo Sapiens

<400> SEQUENCE: 722
gactggagtt cagacgtgtg ctcttccgat ctccatctcc cctcccttta ccctttctt    59

<210> SEQ ID NO 723
<211> LENGTH: 56
<212> TYPE: DNA
<213> ORGANISM: Homo Sapiens

<400> SEQUENCE: 723
gactggagtt cagacgtgtg ctcttccgat ctccatctgt cctgggcatg tctctg       56

<210> SEQ ID NO 724
<211> LENGTH: 59
<212> TYPE: DNA
<213> ORGANISM: Homo Sapiens

<400> SEQUENCE: 724
gactggagtt cagacgtgtg ctcttccgat ctccatcttc tctttagggt cggattcca    59

<210> SEQ ID NO 725
<211> LENGTH: 58
<212> TYPE: DNA
<213> ORGANISM: Homo Sapiens

<400> SEQUENCE: 725
gactggagtt cagacgtgtg ctcttccgat ctccatgagt tctgggcact gggtcaaa     58

<210> SEQ ID NO 726
<211> LENGTH: 57
<212> TYPE: DNA
<213> ORGANISM: Homo Sapiens

<400> SEQUENCE: 726
gactggagtt cagacgtgtg ctcttccgat ctccatggga gaactctgag tggccac      57

<210> SEQ ID NO 727
<211> LENGTH: 59
<212> TYPE: DNA
<213> ORGANISM: Homo Sapiens

<400> SEQUENCE: 727
gactggagtt cagacgtgtg ctcttccgat ctccattatc ttcagctttc tcccactgt    59

<210> SEQ ID NO 728
<211> LENGTH: 55
<212> TYPE: DNA
<213> ORGANISM: Homo Sapiens

<400> SEQUENCE: 728
gactggagtt cagacgtgtg ctcttccgat ctccattcca ggggatgagc tacct        55

<210> SEQ ID NO 729
<211> LENGTH: 57
<212> TYPE: DNA

<213> ORGANISM: Homo Sapiens

<400> SEQUENCE: 729
gactggagtt cagacgtgtg ctcttccgat ctccattctt gaggggctga ggtggaa    57

<210> SEQ ID NO 730
<211> LENGTH: 60
<212> TYPE: DNA
<213> ORGANISM: Homo Sapiens

<400> SEQUENCE: 730
gactggagtt cagacgtgtg ctcttccgat ctccatttta gaccttgagt tcttgagttc    60

<210> SEQ ID NO 731
<211> LENGTH: 54
<212> TYPE: DNA
<213> ORGANISM: Homo Sapiens

<400> SEQUENCE: 731
gactggagtt cagacgtgtg ctcttccgat ctccattttg aaagtgccgg cccg    54

<210> SEQ ID NO 732
<211> LENGTH: 58
<212> TYPE: DNA
<213> ORGANISM: Homo Sapiens

<400> SEQUENCE: 732
gactggagtt cagacgtgtg ctcttccgat ctcccaaact agccctcaat ccctgacc    58

<210> SEQ ID NO 733
<211> LENGTH: 60
<212> TYPE: DNA
<213> ORGANISM: Homo Sapiens

<400> SEQUENCE: 733
gactggagtt cagacgtgtg ctcttccgat ctcccaaata ttctccaggc gtttcttcca    60

<210> SEQ ID NO 734
<211> LENGTH: 59
<212> TYPE: DNA
<213> ORGANISM: Homo Sapiens

<400> SEQUENCE: 734
gactggagtt cagacgtgtg ctcttccgat ctcccaatct acctgtgtca gttccctcc    59

<210> SEQ ID NO 735
<211> LENGTH: 52
<212> TYPE: DNA
<213> ORGANISM: Homo Sapiens

<400> SEQUENCE: 735
gactggagtt cagacgtgtg ctcttccgat ctcccacaga tgttcccggg gc    52

<210> SEQ ID NO 736
<211> LENGTH: 60
<212> TYPE: DNA
<213> ORGANISM: Homo Sapiens

<400> SEQUENCE: 736
gactggagtt cagacgtgtg ctcttccgat ctcccaccac agctagaact tatcaaaccc    60

<210> SEQ ID NO 737
<211> LENGTH: 59

```
<212> TYPE: DNA
<213> ORGANISM: Homo Sapiens

<400> SEQUENCE: 737
gactggagtt cagacgtgtg ctcttccgat ctcccacgct cttctcactc atatcctcc      59

<210> SEQ ID NO 738
<211> LENGTH: 59
<212> TYPE: DNA
<213> ORGANISM: Homo Sapiens

<400> SEQUENCE: 738
gactggagtt cagacgtgtg ctcttccgat ctcccacgct cttctcactc atatcctcc      59

<210> SEQ ID NO 739
<211> LENGTH: 53
<212> TYPE: DNA
<213> ORGANISM: Homo Sapiens

<400> SEQUENCE: 739
gactggagtt cagacgtgtg ctcttccgat ctcccacgta ccgctcctca gga            53

<210> SEQ ID NO 740
<211> LENGTH: 60
<212> TYPE: DNA
<213> ORGANISM: Homo Sapiens

<400> SEQUENCE: 740
gactggagtt cagacgtgtg ctcttccgat ctcccagaac taacaggtta agtgctccca     60

<210> SEQ ID NO 741
<211> LENGTH: 52
<212> TYPE: DNA
<213> ORGANISM: Homo Sapiens

<400> SEQUENCE: 741
gactggagtt cagacgtgtg ctcttccgat ctcccagagc ccagtccccc tc             52

<210> SEQ ID NO 742
<211> LENGTH: 55
<212> TYPE: DNA
<213> ORGANISM: Homo Sapiens

<400> SEQUENCE: 742
gactggagtt cagacgtgtg ctcttccgat ctcccagctg ctcaccatcg ctatc          55

<210> SEQ ID NO 743
<211> LENGTH: 57
<212> TYPE: DNA
<213> ORGANISM: Homo Sapiens

<400> SEQUENCE: 743
gactggagtt cagacgtgtg ctcttccgat ctcccatccc cagtgactgt gtgttga        57

<210> SEQ ID NO 744
<211> LENGTH: 65
<212> TYPE: DNA
<213> ORGANISM: Homo Sapiens

<400> SEQUENCE: 744
gactggagtt cagacgtgtg ctcttccgat ctcccattat tatagagatg attgttgaat     60
tttcc                                                                 65
```

<210> SEQ ID NO 745
<211> LENGTH: 68
<212> TYPE: DNA
<213> ORGANISM: Homo Sapiens

<400> SEQUENCE: 745
gactggagtt cagacgtgtg ctcttccgat ctcccattat tatagagatg attgttgaat    60
tttccttt    68

<210> SEQ ID NO 746
<211> LENGTH: 59
<212> TYPE: DNA
<213> ORGANISM: Homo Sapiens

<400> SEQUENCE: 746
gactggagtt cagacgtgtg ctcttccgat ctccccagct actctcaaaa tcagcatcc    59

<210> SEQ ID NO 747
<211> LENGTH: 59
<212> TYPE: DNA
<213> ORGANISM: Homo Sapiens

<400> SEQUENCE: 747
gactggagtt cagacgtgtg ctcttccgat ctccccatta aatgaggttt tactgttgt    59

<210> SEQ ID NO 748
<211> LENGTH: 57
<212> TYPE: DNA
<213> ORGANISM: Homo Sapiens

<400> SEQUENCE: 748
gactggagtt cagacgtgtg ctcttccgat ctcccgttcc atcatagcat gcaaggg    57

<210> SEQ ID NO 749
<211> LENGTH: 58
<212> TYPE: DNA
<213> ORGANISM: Homo Sapiens

<400> SEQUENCE: 749
gactggagtt cagacgtgtg ctcttccgat ctccctaatc accacccac ccaattcc    58

<210> SEQ ID NO 750
<211> LENGTH: 53
<212> TYPE: DNA
<213> ORGANISM: Homo Sapiens

<400> SEQUENCE: 750
gactggagtt cagacgtgtg ctcttccgat ctccctatcc tggctgtgtc ctg    53

<210> SEQ ID NO 751
<211> LENGTH: 52
<212> TYPE: DNA
<213> ORGANISM: Homo Sapiens

<400> SEQUENCE: 751
gactggagtt cagacgtgtg ctcttccgat ctccctcccc agctgccttc ca    52

<210> SEQ ID NO 752
<211> LENGTH: 59
<212> TYPE: DNA
<213> ORGANISM: Homo Sapiens

<400> SEQUENCE: 752

```
gactggagtt cagacgtgtg ctcttccgat ctccctcccc tcgaaatgaa gctacaaca        59
```

<210> SEQ ID NO 753
<211> LENGTH: 51
<212> TYPE: DNA
<213> ORGANISM: Homo Sapiens

<400> SEQUENCE: 753

```
gactggagtt cagacgtgtg ctcttccgat ctccctcggg tccctgctct g                51
```

<210> SEQ ID NO 754
<211> LENGTH: 60
<212> TYPE: DNA
<213> ORGANISM: Homo Sapiens

<400> SEQUENCE: 754

```
gactggagtt cagacgtgtg ctcttccgat ctccctgaca aatgtgctgt tcttcttggt       60
```

<210> SEQ ID NO 755
<211> LENGTH: 59
<212> TYPE: DNA
<213> ORGANISM: Homo Sapiens

<400> SEQUENCE: 755

```
gactggagtt cagacgtgtg ctcttccgat ctccctgata gttgctaaga accggtcac        59
```

<210> SEQ ID NO 756
<211> LENGTH: 59
<212> TYPE: DNA
<213> ORGANISM: Homo Sapiens

<400> SEQUENCE: 756

```
gactggagtt cagacgtgtg ctcttccgat ctccctgcaa agacaaatgg tgagtacgt        59
```

<210> SEQ ID NO 757
<211> LENGTH: 60
<212> TYPE: DNA
<213> ORGANISM: Homo Sapiens

<400> SEQUENCE: 757

```
gactggagtt cagacgtgtg ctcttccgat ctccctgttc actcctttgc tgattggttt       60
```

<210> SEQ ID NO 758
<211> LENGTH: 59
<212> TYPE: DNA
<213> ORGANISM: Homo Sapiens

<400> SEQUENCE: 758

```
gactggagtt cagacgtgtg ctcttccgat ctcccttgcc tccctttcca atggactat        59
```

<210> SEQ ID NO 759
<211> LENGTH: 59
<212> TYPE: DNA
<213> ORGANISM: Homo Sapiens

<400> SEQUENCE: 759

```
gactggagtt cagacgtgtg ctcttccgat ctcccttga acttgctccc tcaggctac         59
```

<210> SEQ ID NO 760
<211> LENGTH: 61
<212> TYPE: DNA
<213> ORGANISM: Homo Sapiens

```
<400> SEQUENCE: 760
gactggagtt cagacgtgtg ctcttccgat ctccgaagtg taagcccaac tacagaaatg    60
g                                                                    61

<210> SEQ ID NO 761
<211> LENGTH: 59
<212> TYPE: DNA
<213> ORGANISM: Homo Sapiens

<400> SEQUENCE: 761
gactggagtt cagacgtgtg ctcttccgat ctccgacaag tgagagacag gatcaggtc     59

<210> SEQ ID NO 762
<211> LENGTH: 54
<212> TYPE: DNA
<213> ORGANISM: Homo Sapiens

<400> SEQUENCE: 762
gactggagtt cagacgtgtg ctcttccgat ctccgcagtt ccattctccc gcag          54

<210> SEQ ID NO 763
<211> LENGTH: 56
<212> TYPE: DNA
<213> ORGANISM: Homo Sapiens

<400> SEQUENCE: 763
gactggagtt cagacgtgtg ctcttccgat ctccggggga ttaaagctgg ctatgg        56

<210> SEQ ID NO 764
<211> LENGTH: 58
<212> TYPE: DNA
<213> ORGANISM: Homo Sapiens

<400> SEQUENCE: 764
gactggagtt cagacgtgtg ctcttccgat ctccggtagt tgcccttctc gaacatgt      58

<210> SEQ ID NO 765
<211> LENGTH: 53
<212> TYPE: DNA
<213> ORGANISM: Homo Sapiens

<400> SEQUENCE: 765
gactggagtt cagacgtgtg ctcttccgat ctccggtgta ggagctgctg gtg           53

<210> SEQ ID NO 766
<211> LENGTH: 54
<212> TYPE: DNA
<213> ORGANISM: Homo Sapiens

<400> SEQUENCE: 766
gactggagtt cagacgtgtg ctcttccgat ctccgtgtcc ctcctaagcg ctgg          54

<210> SEQ ID NO 767
<211> LENGTH: 55
<212> TYPE: DNA
<213> ORGANISM: Homo Sapiens

<400> SEQUENCE: 767
gactggagtt cagacgtgtg ctcttccgat ctcctacact gcaccctct cctcc          55

<210> SEQ ID NO 768
<211> LENGTH: 54
```

```
<212> TYPE: DNA
<213> ORGANISM: Homo Sapiens

<400> SEQUENCE: 768
gactggagtt cagacgtgtg ctcttccgat ctcctagact tgggtgaggc aggg          54

<210> SEQ ID NO 769
<211> LENGTH: 59
<212> TYPE: DNA
<213> ORGANISM: Homo Sapiens

<400> SEQUENCE: 769
gactggagtt cagacgtgtg ctcttccgat ctcctatagc tcctgagtat tggtgttcc     59

<210> SEQ ID NO 770
<211> LENGTH: 60
<212> TYPE: DNA
<213> ORGANISM: Homo Sapiens

<400> SEQUENCE: 770
gactggagtt cagacgtgtg ctcttccgat ctcctatctc ccaggcctaa aatatacccca   60

<210> SEQ ID NO 771
<211> LENGTH: 54
<212> TYPE: DNA
<213> ORGANISM: Homo Sapiens

<400> SEQUENCE: 771
gactggagtt cagacgtgtg ctcttccgat ctcctcacag cagggtcttc tctg          54

<210> SEQ ID NO 772
<211> LENGTH: 57
<212> TYPE: DNA
<213> ORGANISM: Homo Sapiens

<400> SEQUENCE: 772
gactggagtt cagacgtgtg ctcttccgat ctcctcacct gtctacgttc cctcact       57

<210> SEQ ID NO 773
<211> LENGTH: 57
<212> TYPE: DNA
<213> ORGANISM: Homo Sapiens

<400> SEQUENCE: 773
gactggagtt cagacgtgtg ctcttccgat ctcctcagga tccatttctg cccagtg       57

<210> SEQ ID NO 774
<211> LENGTH: 59
<212> TYPE: DNA
<213> ORGANISM: Homo Sapiens

<400> SEQUENCE: 774
gactggagtt cagacgtgtg ctcttccgat ctcctccagt tcagcaaggg gtcatagac     59

<210> SEQ ID NO 775
<211> LENGTH: 53
<212> TYPE: DNA
<213> ORGANISM: Homo Sapiens

<400> SEQUENCE: 775
gactggagtt cagacgtgtg ctcttccgat ctcctccccg gtgcgcatgt act           53

<210> SEQ ID NO 776
```

```
<211> LENGTH: 55
<212> TYPE: DNA
<213> ORGANISM: Homo Sapiens

<400> SEQUENCE: 776
gactggagtt cagacgtgtg ctcttccgat ctcctccctg gtcagagttc aagta      55

<210> SEQ ID NO 777
<211> LENGTH: 53
<212> TYPE: DNA
<213> ORGANISM: Homo Sapiens

<400> SEQUENCE: 777
gactggagtt cagacgtgtg ctcttccgat ctcctcgggt ccctgctctg tca        53

<210> SEQ ID NO 778
<211> LENGTH: 55
<212> TYPE: DNA
<213> ORGANISM: Homo Sapiens

<400> SEQUENCE: 778
gactggagtt cagacgtgtg ctcttccgat ctcctctctg tctgaacttg ggcaa      55

<210> SEQ ID NO 779
<211> LENGTH: 59
<212> TYPE: DNA
<213> ORGANISM: Homo Sapiens

<400> SEQUENCE: 779
gactggagtt cagacgtgtg ctcttccgat ctcctctctt tcttccacct ttctccagc      59

<210> SEQ ID NO 780
<211> LENGTH: 59
<212> TYPE: DNA
<213> ORGANISM: Homo Sapiens

<400> SEQUENCE: 780
gactggagtt cagacgtgtg ctcttccgat ctcctctctt tcttccacct ttctccagc      59

<210> SEQ ID NO 781
<211> LENGTH: 57
<212> TYPE: DNA
<213> ORGANISM: Homo Sapiens

<400> SEQUENCE: 781
gactggagtt cagacgtgtg ctcttccgat ctcctctggc attctgggag cttcatc      57

<210> SEQ ID NO 782
<211> LENGTH: 55
<212> TYPE: DNA
<213> ORGANISM: Homo Sapiens

<400> SEQUENCE: 782
gactggagtt cagacgtgtg ctcttccgat ctcctctggt caaggtcaca ttctt      55

<210> SEQ ID NO 783
<211> LENGTH: 60
<212> TYPE: DNA
<213> ORGANISM: Homo Sapiens

<400> SEQUENCE: 783
gactggagtt cagacgtgtg ctcttccgat ctcctgagcc tgttttgtgt ctactgttct      60
```

```
<210> SEQ ID NO 784
<211> LENGTH: 60
<212> TYPE: DNA
<213> ORGANISM: Homo Sapiens

<400> SEQUENCE: 784
gactggagtt cagacgtgtg ctcttccgat ctcctgagtc atttcttcct tttccatgca    60

<210> SEQ ID NO 785
<211> LENGTH: 59
<212> TYPE: DNA
<213> ORGANISM: Homo Sapiens

<400> SEQUENCE: 785
gactggagtt cagacgtgtg ctcttccgat ctcctggaag tttaggtcaa agaggctgc     59

<210> SEQ ID NO 786
<211> LENGTH: 54
<212> TYPE: DNA
<213> ORGANISM: Homo Sapiens

<400> SEQUENCE: 786
gactggagtt cagacgtgtg ctcttccgat ctcctggatc atggcaggct ttgg          54

<210> SEQ ID NO 787
<211> LENGTH: 56
<212> TYPE: DNA
<213> ORGANISM: Homo Sapiens

<400> SEQUENCE: 787
gactggagtt cagacgtgtg ctcttccgat ctcctggcct tctcctttac ccctcc        56

<210> SEQ ID NO 788
<211> LENGTH: 50
<212> TYPE: DNA
<213> ORGANISM: Homo Sapiens

<400> SEQUENCE: 788
gactggagtt cagacgtgtg ctcttccgat ctcctggggt gacggatgcc               50

<210> SEQ ID NO 789
<211> LENGTH: 56
<212> TYPE: DNA
<213> ORGANISM: Homo Sapiens

<400> SEQUENCE: 789
gactggagtt cagacgtgtg ctcttccgat ctcctggtag ctcatcatct gggaca        56

<210> SEQ ID NO 790
<211> LENGTH: 58
<212> TYPE: DNA
<213> ORGANISM: Homo Sapiens

<400> SEQUENCE: 790
gactggagtt cagacgtgtg ctcttccgat ctcctggtag gttttctggg aagggaca     58

<210> SEQ ID NO 791
<211> LENGTH: 54
<212> TYPE: DNA
<213> ORGANISM: Homo Sapiens

<400> SEQUENCE: 791
gactggagtt cagacgtgtg ctcttccgat ctcctggtat ggtcatggaa gggg          54
```

<210> SEQ ID NO 792
<211> LENGTH: 60
<212> TYPE: DNA
<213> ORGANISM: Homo Sapiens

<400> SEQUENCE: 792
gactggagtt cagacgtgtg ctcttccgat ctcctgtgct tcaactaaat ttaactgtca    60

<210> SEQ ID NO 793
<211> LENGTH: 61
<212> TYPE: DNA
<213> ORGANISM: Homo Sapiens

<400> SEQUENCE: 793
gactggagtt cagacgtgtg ctcttccgat ctcctgtgga tttttaggcc cttgtatttg    60
t                                                                   61

<210> SEQ ID NO 794
<211> LENGTH: 60
<212> TYPE: DNA
<213> ORGANISM: Homo Sapiens

<400> SEQUENCE: 794
gactggagtt cagacgtgtg ctcttccgat ctcctgtgtg tggtgatatc aaagtagagt    60

<210> SEQ ID NO 795
<211> LENGTH: 59
<212> TYPE: DNA
<213> ORGANISM: Homo Sapiens

<400> SEQUENCE: 795
gactggagtt cagacgtgtg ctcttccgat ctccttagtc tttctttgaa gcagcaagt     59

<210> SEQ ID NO 796
<211> LENGTH: 61
<212> TYPE: DNA
<213> ORGANISM: Homo Sapiens

<400> SEQUENCE: 796
gactggagtt cagacgtgtg ctcttccgat ctccttatta cttgggagac ttgtctgaac    60
a                                                                   61

<210> SEQ ID NO 797
<211> LENGTH: 59
<212> TYPE: DNA
<213> ORGANISM: Homo Sapiens

<400> SEQUENCE: 797
gactggagtt cagacgtgtg ctcttccgat ctccttccct gcaaagacaa atggtgagt     59

<210> SEQ ID NO 798
<211> LENGTH: 59
<212> TYPE: DNA
<213> ORGANISM: Homo Sapiens

<400> SEQUENCE: 798
gactggagtt cagacgtgtg ctcttccgat ctccttcgcc tgtcctcatg tattggtct     59

<210> SEQ ID NO 799
<211> LENGTH: 59
<212> TYPE: DNA
<213> ORGANISM: Homo Sapiens

```
<400> SEQUENCE: 799
gactggagtt cagacgtgtg ctcttccgat ctccttctag taatttggga atgcctggt      59

<210> SEQ ID NO 800
<211> LENGTH: 59
<212> TYPE: DNA
<213> ORGANISM: Homo Sapiens

<400> SEQUENCE: 800
gactggagtt cagacgtgtg ctcttccgat ctccttgggt atttttatgg gaggcagaa      59

<210> SEQ ID NO 801
<211> LENGTH: 58
<212> TYPE: DNA
<213> ORGANISM: Homo Sapiens

<400> SEQUENCE: 801
gactggagtt cagacgtgtg ctcttccgat ctccttggtg accgctctgc atctagtg       58

<210> SEQ ID NO 802
<211> LENGTH: 59
<212> TYPE: DNA
<213> ORGANISM: Homo Sapiens

<400> SEQUENCE: 802
gactggagtt cagacgtgtg ctcttccgat ctcctttccg aatgccaaac accttcatg      59

<210> SEQ ID NO 803
<211> LENGTH: 59
<212> TYPE: DNA
<213> ORGANISM: Homo Sapiens

<400> SEQUENCE: 803
gactggagtt cagacgtgtg ctcttccgat ctcctttctg taggctggat gaaaaattc      59

<210> SEQ ID NO 804
<211> LENGTH: 59
<212> TYPE: DNA
<213> ORGANISM: Homo Sapiens

<400> SEQUENCE: 804
gactggagtt cagacgtgtg ctcttccgat ctcctttctg taggctggat gaaaaattc      59

<210> SEQ ID NO 805
<211> LENGTH: 59
<212> TYPE: DNA
<213> ORGANISM: Homo Sapiens

<400> SEQUENCE: 805
gactggagtt cagacgtgtg ctcttccgat ctcctttctt tgcaggggtg gctatgtag      59

<210> SEQ ID NO 806
<211> LENGTH: 58
<212> TYPE: DNA
<213> ORGANISM: Homo Sapiens

<400> SEQUENCE: 806
gactggagtt cagacgtgtg ctcttccgat ctcctttgtc cctcccaccc caaactag       58

<210> SEQ ID NO 807
<211> LENGTH: 59
<212> TYPE: DNA
```

```
<213> ORGANISM: Homo Sapiens

<400> SEQUENCE: 807
gactggagtt cagacgtgtg ctcttccgat ctcgaaagac cctagcctta gataaaact    59

<210> SEQ ID NO 808
<211> LENGTH: 59
<212> TYPE: DNA
<213> ORGANISM: Homo Sapiens

<400> SEQUENCE: 808
gactggagtt cagacgtgtg ctcttccgat ctcgaaatga agctacaaca tcaccacgg    59

<210> SEQ ID NO 809
<211> LENGTH: 58
<212> TYPE: DNA
<213> ORGANISM: Homo Sapiens

<400> SEQUENCE: 809
gactggagtt cagacgtgtg ctcttccgat ctcgaatgag ggtgatgttt ttccgcgg     58

<210> SEQ ID NO 810
<211> LENGTH: 60
<212> TYPE: DNA
<213> ORGANISM: Homo Sapiens

<400> SEQUENCE: 810
gactggagtt cagacgtgtg ctcttccgat ctcgaatgca gttttcctc ctactcacca    60

<210> SEQ ID NO 811
<211> LENGTH: 59
<212> TYPE: DNA
<213> ORGANISM: Homo Sapiens

<400> SEQUENCE: 811
gactggagtt cagacgtgtg ctcttccgat ctcgactcgt gctatttttc ctcacagct    59

<210> SEQ ID NO 812
<211> LENGTH: 59
<212> TYPE: DNA
<213> ORGANISM: Homo Sapiens

<400> SEQUENCE: 812
gactggagtt cagacgtgtg ctcttccgat ctcgactttg tgaccttcgg cttttttcaa   59

<210> SEQ ID NO 813
<211> LENGTH: 51
<212> TYPE: DNA
<213> ORGANISM: Homo Sapiens

<400> SEQUENCE: 813
gactggagtt cagacgtgtg ctcttccgat ctcgaggggg gcgtcaggaa c             51

<210> SEQ ID NO 814
<211> LENGTH: 53
<212> TYPE: DNA
<213> ORGANISM: Homo Sapiens

<400> SEQUENCE: 814
gactggagtt cagacgtgtg ctcttccgat ctcgagtgag ctgcgagacc tgc           53

<210> SEQ ID NO 815
<211> LENGTH: 55
```

```
<212> TYPE: DNA
<213> ORGANISM: Homo Sapiens

<400> SEQUENCE: 815
gactggagtt cagacgtgtg ctcttccgat ctcgatctgg gactgcatgc tggtg          55

<210> SEQ ID NO 816
<211> LENGTH: 56
<212> TYPE: DNA
<213> ORGANISM: Homo Sapiens

<400> SEQUENCE: 816
gactggagtt cagacgtgtg ctcttccgat ctcgcaggaa gtggaaggag ctgttg         56

<210> SEQ ID NO 817
<211> LENGTH: 55
<212> TYPE: DNA
<213> ORGANISM: Homo Sapiens

<400> SEQUENCE: 817
gactggagtt cagacgtgtg ctcttccgat ctcgcagtgc taaccaagtt ctttc          55

<210> SEQ ID NO 818
<211> LENGTH: 58
<212> TYPE: DNA
<213> ORGANISM: Homo Sapiens

<400> SEQUENCE: 818
gactggagtt cagacgtgtg ctcttccgat ctcgcagtgc taaccaagtt ctttcttt      58

<210> SEQ ID NO 819
<211> LENGTH: 54
<212> TYPE: DNA
<213> ORGANISM: Homo Sapiens

<400> SEQUENCE: 819
gactggagtt cagacgtgtg ctcttccgat ctcgcccatg tctttgcagc cgag           54

<210> SEQ ID NO 820
<211> LENGTH: 50
<212> TYPE: DNA
<213> ORGANISM: Homo Sapiens

<400> SEQUENCE: 820
gactggagtt cagacgtgtg ctcttccgat ctcgccggta gttgcccttc                50

<210> SEQ ID NO 821
<211> LENGTH: 53
<212> TYPE: DNA
<213> ORGANISM: Homo Sapiens

<400> SEQUENCE: 821
gactggagtt cagacgtgtg ctcttccgat ctcgccggta gttgcccttc tcg            53

<210> SEQ ID NO 822
<211> LENGTH: 54
<212> TYPE: DNA
<213> ORGANISM: Homo Sapiens

<400> SEQUENCE: 822
gactggagtt cagacgtgtg ctcttccgat ctcgctggtt tgggtgctgt gtcc           54

<210> SEQ ID NO 823
```

```
<211> LENGTH: 58
<212> TYPE: DNA
<213> ORGANISM: Homo Sapiens

<400> SEQUENCE: 823
gactggagtt cagacgtgtg ctcttccgat ctcgcttctt gtcctgcttg cttacctc     58

<210> SEQ ID NO 824
<211> LENGTH: 55
<212> TYPE: DNA
<213> ORGANISM: Homo Sapiens

<400> SEQUENCE: 824
gactggagtt cagacgtgtg ctcttccgat ctcggaagca acccacagat gttcc        55

<210> SEQ ID NO 825
<211> LENGTH: 58
<212> TYPE: DNA
<213> ORGANISM: Homo Sapiens

<400> SEQUENCE: 825
gactggagtt cagacgtgtg ctcttccgat ctcggacatc agcaaagacc tggagaag     58

<210> SEQ ID NO 826
<211> LENGTH: 55
<212> TYPE: DNA
<213> ORGANISM: Homo Sapiens

<400> SEQUENCE: 826
gactggagtt cagacgtgtg ctcttccgat ctcggctgct ggacattgac gagac        55

<210> SEQ ID NO 827
<211> LENGTH: 51
<212> TYPE: DNA
<213> ORGANISM: Homo Sapiens

<400> SEQUENCE: 827
gactggagtt cagacgtgtg ctcttccgat ctcgggagcg cgaggaggag c            51

<210> SEQ ID NO 828
<211> LENGTH: 56
<212> TYPE: DNA
<213> ORGANISM: Homo Sapiens

<400> SEQUENCE: 828
gactggagtt cagacgtgtg ctcttccgat ctcgggatgg ggccacactt actctg       56

<210> SEQ ID NO 829
<211> LENGTH: 56
<212> TYPE: DNA
<213> ORGANISM: Homo Sapiens

<400> SEQUENCE: 829
gactggagtt cagacgtgtg ctcttccgat ctcgggctca tcaccacgct ccatta       56

<210> SEQ ID NO 830
<211> LENGTH: 59
<212> TYPE: DNA
<213> ORGANISM: Homo Sapiens

<400> SEQUENCE: 830
gactggagtt cagacgtgtg ctcttccgat ctcgggcttg gttctgatgt ttgtagtgt    59
```

```
<210> SEQ ID NO 831
<211> LENGTH: 59
<212> TYPE: DNA
<213> ORGANISM: Homo Sapiens

<400> SEQUENCE: 831
gactggagtt cagacgtgtg ctcttccgat ctcgggtatg gcagcaggta tatctcagg      59

<210> SEQ ID NO 832
<211> LENGTH: 57
<212> TYPE: DNA
<213> ORGANISM: Homo Sapiens

<400> SEQUENCE: 832
gactggagtt cagacgtgtg ctcttccgat ctcgggtctc tcggaggaag gacttga        57

<210> SEQ ID NO 833
<211> LENGTH: 59
<212> TYPE: DNA
<213> ORGANISM: Homo Sapiens

<400> SEQUENCE: 833
gactggagtt cagacgtgtg ctcttccgat ctcgtcagcc tgaacataac atccttggg      59

<210> SEQ ID NO 834
<211> LENGTH: 61
<212> TYPE: DNA
<213> ORGANISM: Homo Sapiens

<400> SEQUENCE: 834
gactggagtt cagacgtgtg ctcttccgat ctcgtccaca aaatgattct gaattagctg     60
t                                                                     61

<210> SEQ ID NO 835
<211> LENGTH: 58
<212> TYPE: DNA
<213> ORGANISM: Homo Sapiens

<400> SEQUENCE: 835
gactggagtt cagacgtgtg ctcttccgat ctcgtcctct cgtttcctta catgcagg       58

<210> SEQ ID NO 836
<211> LENGTH: 57
<212> TYPE: DNA
<213> ORGANISM: Homo Sapiens

<400> SEQUENCE: 836
gactggagtt cagacgtgtg ctcttccgat ctcgtcgtgg agaacaagtt tggcagc        57

<210> SEQ ID NO 837
<211> LENGTH: 51
<212> TYPE: DNA
<213> ORGANISM: Homo Sapiens

<400> SEQUENCE: 837
gactggagtt cagacgtgtg ctcttccgat ctcgtctcct ccggcccctc g              51

<210> SEQ ID NO 838
<211> LENGTH: 58
<212> TYPE: DNA
<213> ORGANISM: Homo Sapiens

<400> SEQUENCE: 838
```

-continued gactggagtt cagacgtgtg ctcttccgat ctcgtctctg gatggaactg atgtctgg    58

<210> SEQ ID NO 839
<211> LENGTH: 59
<212> TYPE: DNA
<213> ORGANISM: Homo Sapiens

<400> SEQUENCE: 839
gactggagtt cagacgtgtg ctcttccgat ctcgttcttt tccacgtgct tgatccact    59

<210> SEQ ID NO 840
<211> LENGTH: 59
<212> TYPE: DNA
<213> ORGANISM: Homo Sapiens

<400> SEQUENCE: 840
gactggagtt cagacgtgtg ctcttccgat ctctaagtgc tgggattact ggtgtgagc    59

<210> SEQ ID NO 841
<211> LENGTH: 57
<212> TYPE: DNA
<213> ORGANISM: Homo Sapiens

<400> SEQUENCE: 841
gactggagtt cagacgtgtg ctcttccgat ctctacactg caccoctctc ctcccag    57

<210> SEQ ID NO 842
<211> LENGTH: 56
<212> TYPE: DNA
<213> ORGANISM: Homo Sapiens

<400> SEQUENCE: 842
gactggagtt cagacgtgtg ctcttccgat ctctagactt gggtgaggca ggggtg    56

<210> SEQ ID NO 843
<211> LENGTH: 59
<212> TYPE: DNA
<213> ORGANISM: Homo Sapiens

<400> SEQUENCE: 843
gactggagtt cagacgtgtg ctcttccgat ctctatgtgc tcagttccct cctctatgc    59

<210> SEQ ID NO 844
<211> LENGTH: 58
<212> TYPE: DNA
<213> ORGANISM: Homo Sapiens

<400> SEQUENCE: 844
gactggagtt cagacgtgtg ctcttccgat ctctcaaaag cctccagtcg cctcagta    58

<210> SEQ ID NO 845
<211> LENGTH: 56
<212> TYPE: DNA
<213> ORGANISM: Homo Sapiens

<400> SEQUENCE: 845
gactggagtt cagacgtgtg ctcttccgat ctctcaacgc ccatgtcttt gcagcc    56

<210> SEQ ID NO 846
<211> LENGTH: 56
<212> TYPE: DNA
<213> ORGANISM: Homo Sapiens

<400> SEQUENCE: 846
gactggagtt cagacgtgtg ctcttccgat ctctcaacgc ccatgtcttt gcagcc   56

<210> SEQ ID NO 847
<211> LENGTH: 54
<212> TYPE: DNA
<213> ORGANISM: Homo Sapiens

<400> SEQUENCE: 847
gactggagtt cagacgtgtg ctcttccgat ctctcacacc accccaccc acag   54

<210> SEQ ID NO 848
<211> LENGTH: 55
<212> TYPE: DNA
<213> ORGANISM: Homo Sapiens

<400> SEQUENCE: 848
gactggagtt cagacgtgtg ctcttccgat ctctcaccgc agttccattc tcccg   55

<210> SEQ ID NO 849
<211> LENGTH: 53
<212> TYPE: DNA
<213> ORGANISM: Homo Sapiens

<400> SEQUENCE: 849
gactggagtt cagacgtgtg ctcttccgat ctctcacctc caccgtgcag ctc   53

<210> SEQ ID NO 850
<211> LENGTH: 59
<212> TYPE: DNA
<213> ORGANISM: Homo Sapiens

<400> SEQUENCE: 850
gactggagtt cagacgtgtg ctcttccgat ctctcacctg gggccacatt tgaacattg   59

<210> SEQ ID NO 851
<211> LENGTH: 59
<212> TYPE: DNA
<213> ORGANISM: Homo Sapiens

<400> SEQUENCE: 851
gactggagtt cagacgtgtg ctcttccgat ctctcacctg tctacgttcc ctcactgta   59

<210> SEQ ID NO 852
<211> LENGTH: 59
<212> TYPE: DNA
<213> ORGANISM: Homo Sapiens

<400> SEQUENCE: 852
gactggagtt cagacgtgtg ctcttccgat ctctcagatc tcgtcagcca tggagtacc   59

<210> SEQ ID NO 853
<211> LENGTH: 54
<212> TYPE: DNA
<213> ORGANISM: Homo Sapiens

<400> SEQUENCE: 853
gactggagtt cagacgtgtg ctcttccgat ctctcagggg gcagcattgt tggg   54

<210> SEQ ID NO 854
<211> LENGTH: 58
<212> TYPE: DNA
<213> ORGANISM: Homo Sapiens

```
<400> SEQUENCE: 854
gactggagtt cagacgtgtg ctcttccgat ctctcatcac cacgctccat tatccagc        58

<210> SEQ ID NO 855
<211> LENGTH: 59
<212> TYPE: DNA
<213> ORGANISM: Homo Sapiens

<400> SEQUENCE: 855
gactggagtt cagacgtgtg ctcttccgat ctctcatgct ctacaacccc accacgtac       59

<210> SEQ ID NO 856
<211> LENGTH: 59
<212> TYPE: DNA
<213> ORGANISM: Homo Sapiens

<400> SEQUENCE: 856
gactggagtt cagacgtgtg ctcttccgat ctctccacta acaaccctcc tgccatcat       59

<210> SEQ ID NO 857
<211> LENGTH: 59
<212> TYPE: DNA
<213> ORGANISM: Homo Sapiens

<400> SEQUENCE: 857
gactggagtt cagacgtgtg ctcttccgat ctctccactt ttgcacagcc aagaacact       59

<210> SEQ ID NO 858
<211> LENGTH: 57
<212> TYPE: DNA
<213> ORGANISM: Homo Sapiens

<400> SEQUENCE: 858
gactggagtt cagacgtgtg ctcttccgat ctctccagtc tccctcctgt ttgcaca         57

<210> SEQ ID NO 859
<211> LENGTH: 58
<212> TYPE: DNA
<213> ORGANISM: Homo Sapiens

<400> SEQUENCE: 859
gactggagtt cagacgtgtg ctcttccgat ctctcccacc ccaaactagc cctcaatc        58

<210> SEQ ID NO 860
<211> LENGTH: 59
<212> TYPE: DNA
<213> ORGANISM: Homo Sapiens

<400> SEQUENCE: 860
gactggagtt cagacgtgtg ctcttccgat ctctcccagg cctaaaatat acccaacca       59

<210> SEQ ID NO 861
<211> LENGTH: 59
<212> TYPE: DNA
<213> ORGANISM: Homo Sapiens

<400> SEQUENCE: 861
gactggagtt cagacgtgtg ctcttccgat ctctcccata ccctctcagc gtacccttg       59

<210> SEQ ID NO 862
<211> LENGTH: 54
<212> TYPE: DNA
<213> ORGANISM: Homo Sapiens
```

```
<400> SEQUENCE: 862
gactggagtt cagacgtgtg ctcttccgat ctctccccga gtgagctgcg agac        54

<210> SEQ ID NO 863
<211> LENGTH: 56
<212> TYPE: DNA
<213> ORGANISM: Homo Sapiens

<400> SEQUENCE: 863
gactggagtt cagacgtgtg ctcttccgat ctctcctcca cctcctcctc cattgg      56

<210> SEQ ID NO 864
<211> LENGTH: 59
<212> TYPE: DNA
<213> ORGANISM: Homo Sapiens

<400> SEQUENCE: 864
gactggagtt cagacgtgtg ctcttccgat ctctccttcc atccttgctc ctgtccttg   59

<210> SEQ ID NO 865
<211> LENGTH: 55
<212> TYPE: DNA
<213> ORGANISM: Homo Sapiens

<400> SEQUENCE: 865
gactggagtt cagacgtgtg ctcttccgat ctctcgggtc cctgctctgt cactg       55

<210> SEQ ID NO 866
<211> LENGTH: 59
<212> TYPE: DNA
<213> ORGANISM: Homo Sapiens

<400> SEQUENCE: 866
gactggagtt cagacgtgtg ctcttccgat ctctcgtgtt gtctctcctc ctgtcagtg   59

<210> SEQ ID NO 867
<211> LENGTH: 55
<212> TYPE: DNA
<213> ORGANISM: Homo Sapiens

<400> SEQUENCE: 867
gactggagtt cagacgtgtg ctcttccgat ctctctctcc tccccactgc tgctg       55

<210> SEQ ID NO 868
<211> LENGTH: 59
<212> TYPE: DNA
<213> ORGANISM: Homo Sapiens

<400> SEQUENCE: 868
gactggagtt cagacgtgtg ctcttccgat ctctctctgt tttaagatct gggcagtga   59

<210> SEQ ID NO 869
<211> LENGTH: 59
<212> TYPE: DNA
<213> ORGANISM: Homo Sapiens

<400> SEQUENCE: 869
gactggagtt cagacgtgtg ctcttccgat ctctctctta accccttcc ctagctgtg    59

<210> SEQ ID NO 870
<211> LENGTH: 59
<212> TYPE: DNA
```

```
<213> ORGANISM: Homo Sapiens

<400> SEQUENCE: 870
gactggagtt cagacgtgtg ctcttccgat ctctctgcct caataagcca accatgtct     59

<210> SEQ ID NO 871
<211> LENGTH: 56
<212> TYPE: DNA
<213> ORGANISM: Homo Sapiens

<400> SEQUENCE: 871
gactggagtt cagacgtgtg ctcttccgat ctctctggct actggtgatg ctgtcc        56

<210> SEQ ID NO 872
<211> LENGTH: 59
<212> TYPE: DNA
<213> ORGANISM: Homo Sapiens

<400> SEQUENCE: 872
gactggagtt cagacgtgtg ctcttccgat ctctctggct actggtgatg ctgtccaag     59

<210> SEQ ID NO 873
<211> LENGTH: 58
<212> TYPE: DNA
<213> ORGANISM: Homo Sapiens

<400> SEQUENCE: 873
gactggagtt cagacgtgtg ctcttccgat ctctcttctt caggggggcca tggtcttc     58

<210> SEQ ID NO 874
<211> LENGTH: 59
<212> TYPE: DNA
<213> ORGANISM: Homo Sapiens

<400> SEQUENCE: 874
gactggagtt cagacgtgtg ctcttccgat ctctcttgct ccttccatcc ttgctcctg     59

<210> SEQ ID NO 875
<211> LENGTH: 57
<212> TYPE: DNA
<213> ORGANISM: Homo Sapiens

<400> SEQUENCE: 875
gactggagtt cagacgtgtg ctcttccgat ctctgaaagc tgtaccatac ctgtctg       57

<210> SEQ ID NO 876
<211> LENGTH: 57
<212> TYPE: DNA
<213> ORGANISM: Homo Sapiens

<400> SEQUENCE: 876
gactggagtt cagacgtgtg ctcttccgat ctctgaaagt ccctctgctg gtctggc       57

<210> SEQ ID NO 877
<211> LENGTH: 59
<212> TYPE: DNA
<213> ORGANISM: Homo Sapiens

<400> SEQUENCE: 877
gactggagtt cagacgtgtg ctcttccgat ctctgaagat aatgactcac ctggggcca     59

<210> SEQ ID NO 878
<211> LENGTH: 58
```

```
<212> TYPE: DNA
<213> ORGANISM: Homo Sapiens

<400> SEQUENCE: 878
gactggagtt cagacgtgtg ctcttccgat ctctgacaac caccttaac ccctcctc      58

<210> SEQ ID NO 879
<211> LENGTH: 54
<212> TYPE: DNA
<213> ORGANISM: Homo Sapiens

<400> SEQUENCE: 879
gactggagtt cagacgtgtg ctcttccgat ctctgacgtg cctctccctc cctc         54

<210> SEQ ID NO 880
<211> LENGTH: 57
<212> TYPE: DNA
<213> ORGANISM: Homo Sapiens

<400> SEQUENCE: 880
gactggagtt cagacgtgtg ctcttccgat ctctgagcct gccgagattc cacagtg      57

<210> SEQ ID NO 881
<211> LENGTH: 53
<212> TYPE: DNA
<213> ORGANISM: Homo Sapiens

<400> SEQUENCE: 881
gactggagtt cagacgtgtg ctcttccgat ctctgagcgt catctgcccc cac          53

<210> SEQ ID NO 882
<211> LENGTH: 55
<212> TYPE: DNA
<213> ORGANISM: Homo Sapiens

<400> SEQUENCE: 882
gactggagtt cagacgtgtg ctcttccgat ctctgaggtt ctgagccccc ttccg        55

<210> SEQ ID NO 883
<211> LENGTH: 57
<212> TYPE: DNA
<213> ORGANISM: Homo Sapiens

<400> SEQUENCE: 883
gactggagtt cagacgtgtg ctcttccgat ctctgagtcc tggcgctgtg tcctttc      57

<210> SEQ ID NO 884
<211> LENGTH: 59
<212> TYPE: DNA
<213> ORGANISM: Homo Sapiens

<400> SEQUENCE: 884
gactggagtt cagacgtgtg ctcttccgat ctctgatggc tggtgtggtt tggtttgtg    59

<210> SEQ ID NO 885
<211> LENGTH: 51
<212> TYPE: DNA
<213> ORGANISM: Homo Sapiens

<400> SEQUENCE: 885
gactggagtt cagacgtgtg ctcttccgat ctctgcaacc cccacaggcc c            51

<210> SEQ ID NO 886
```

```
<211> LENGTH: 55
<212> TYPE: DNA
<213> ORGANISM: Homo Sapiens

<400> SEQUENCE: 886
gactggagtt cagacgtgtg ctcttccgat ctctgcccag cctcgactcg gtttc      55

<210> SEQ ID NO 887
<211> LENGTH: 55
<212> TYPE: DNA
<213> ORGANISM: Homo Sapiens

<400> SEQUENCE: 887
gactggagtt cagacgtgtg ctcttccgat ctctgcccta atcaccaccc caccc      55

<210> SEQ ID NO 888
<211> LENGTH: 50
<212> TYPE: DNA
<213> ORGANISM: Homo Sapiens

<400> SEQUENCE: 888
gactggagtt cagacgtgtg ctcttccgat ctctgcgagg ggggcgtcag            50

<210> SEQ ID NO 889
<211> LENGTH: 59
<212> TYPE: DNA
<213> ORGANISM: Homo Sapiens

<400> SEQUENCE: 889
gactggagtt cagacgtgtg ctcttccgat ctctgctgta catggccact cagatctcg  59

<210> SEQ ID NO 890
<211> LENGTH: 59
<212> TYPE: DNA
<213> ORGANISM: Homo Sapiens

<400> SEQUENCE: 890
gactggagtt cagacgtgtg ctcttccgat ctctggaaaa atggctttga atctttggc  59

<210> SEQ ID NO 891
<211> LENGTH: 53
<212> TYPE: DNA
<213> ORGANISM: Homo Sapiens

<400> SEQUENCE: 891
gactggagtt cagacgtgtg ctcttccgat ctctggagga tgtgcggctc gta        53

<210> SEQ ID NO 892
<211> LENGTH: 59
<212> TYPE: DNA
<213> ORGANISM: Homo Sapiens

<400> SEQUENCE: 892
gactggagtt cagacgtgtg ctcttccgat ctctggatgg aactgatgtc tggacgctc  59

<210> SEQ ID NO 893
<211> LENGTH: 57
<212> TYPE: DNA
<213> ORGANISM: Homo Sapiens

<400> SEQUENCE: 893
gactggagtt cagacgtgtg ctcttccgat ctctggatgg ggtgagtttg agggagg    57
```

```
<210> SEQ ID NO 894
<211> LENGTH: 51
<212> TYPE: DNA
<213> ORGANISM: Homo Sapiens

<400> SEQUENCE: 894
gactggagtt cagacgtgtg ctcttccgat ctctggatgg tcagcgcact c          51

<210> SEQ ID NO 895
<211> LENGTH: 54
<212> TYPE: DNA
<213> ORGANISM: Homo Sapiens

<400> SEQUENCE: 895
gactggagtt cagacgtgtg ctcttccgat ctctggatgg tcagcgcact cttg       54

<210> SEQ ID NO 896
<211> LENGTH: 58
<212> TYPE: DNA
<213> ORGANISM: Homo Sapiens

<400> SEQUENCE: 896
gactggagtt cagacgtgtg ctcttccgat ctctggcctt ctcctttacc cctccttc   58

<210> SEQ ID NO 897
<211> LENGTH: 55
<212> TYPE: DNA
<213> ORGANISM: Homo Sapiens

<400> SEQUENCE: 897
gactggagtt cagacgtgtg ctcttccgat ctctggctag ctgtggggtg gagag      55

<210> SEQ ID NO 898
<211> LENGTH: 52
<212> TYPE: DNA
<213> ORGANISM: Homo Sapiens

<400> SEQUENCE: 898
gactggagtt cagacgtgtg ctcttccgat ctctggctgt gtcctgggct cg         52

<210> SEQ ID NO 899
<211> LENGTH: 56
<212> TYPE: DNA
<213> ORGANISM: Homo Sapiens

<400> SEQUENCE: 899
gactggagtt cagacgtgtg ctcttccgat ctctggggct cgggttggct ctaaag     56

<210> SEQ ID NO 900
<211> LENGTH: 56
<212> TYPE: DNA
<213> ORGANISM: Homo Sapiens

<400> SEQUENCE: 900
gactggagtt cagacgtgtg ctcttccgat ctctgggtag caaacttctg tacaca     56

<210> SEQ ID NO 901
<211> LENGTH: 59
<212> TYPE: DNA
<213> ORGANISM: Homo Sapiens

<400> SEQUENCE: 901
gactggagtt cagacgtgtg ctcttccgat ctctgggtag caaacttctg tacacaact  59
```

-continued

<210> SEQ ID NO 902
<211> LENGTH: 59
<212> TYPE: DNA
<213> ORGANISM: Homo Sapiens

<400> SEQUENCE: 902
gactggagtt cagacgtgtg ctcttccgat ctctgggtgc tgatacttct ctccatcct      59

<210> SEQ ID NO 903
<211> LENGTH: 58
<212> TYPE: DNA
<213> ORGANISM: Homo Sapiens

<400> SEQUENCE: 903
gactggagtt cagacgtgtg ctcttccgat ctctggtgtg gtttggtttg tggtcctc       58

<210> SEQ ID NO 904
<211> LENGTH: 59
<212> TYPE: DNA
<213> ORGANISM: Homo Sapiens

<400> SEQUENCE: 904
gactggagtt cagacgtgtg ctcttccgat ctctgtatca gtctgtccag cacttccat      59

<210> SEQ ID NO 905
<211> LENGTH: 57
<212> TYPE: DNA
<213> ORGANISM: Homo Sapiens

<400> SEQUENCE: 905
gactggagtt cagacgtgtg ctcttccgat ctctgtcatg tagcagcttt caggggc        57

<210> SEQ ID NO 906
<211> LENGTH: 59
<212> TYPE: DNA
<213> ORGANISM: Homo Sapiens

<400> SEQUENCE: 906
gactggagtt cagacgtgtg ctcttccgat ctctgtcctc ttctccttca tcgtctcgg      59

<210> SEQ ID NO 907
<211> LENGTH: 58
<212> TYPE: DNA
<213> ORGANISM: Homo Sapiens

<400> SEQUENCE: 907
gactggagtt cagacgtgtg ctcttccgat ctctgtgata ggaagctgtg gagtgatg       58

<210> SEQ ID NO 908
<211> LENGTH: 50
<212> TYPE: DNA
<213> ORGANISM: Homo Sapiens

<400> SEQUENCE: 908
gactggagtt cagacgtgtg ctcttccgat ctctgtgctg cgaggggggc                50

<210> SEQ ID NO 909
<211> LENGTH: 53
<212> TYPE: DNA
<213> ORGANISM: Homo Sapiens

<400> SEQUENCE: 909
gactggagtt cagacgtgtg ctcttccgat ctctgtgtcc ctgtcctgcc ccc            53

<210> SEQ ID NO 910
<211> LENGTH: 51
<212> TYPE: DNA
<213> ORGANISM: Homo Sapiens

<400> SEQUENCE: 910
gactggagtt cagacgtgtg ctcttccgat ctctgtgtgc tcagggggcc t    51

<210> SEQ ID NO 911
<211> LENGTH: 55
<212> TYPE: DNA
<213> ORGANISM: Homo Sapiens

<400> SEQUENCE: 911
gactggagtt cagacgtgtg ctcttccgat ctctgtgtgt tgatcaggcg cccag    55

<210> SEQ ID NO 912
<211> LENGTH: 54
<212> TYPE: DNA
<213> ORGANISM: Homo Sapiens

<400> SEQUENCE: 912
gactggagtt cagacgtgtg ctcttccgat ctcttactca ttgggtggcc gggc    54

<210> SEQ ID NO 913
<211> LENGTH: 59
<212> TYPE: DNA
<213> ORGANISM: Homo Sapiens

<400> SEQUENCE: 913
gactggagtt cagacgtgtg ctcttccgat ctcttcacgc tccttcccta tcccttctg    59

<210> SEQ ID NO 914
<211> LENGTH: 58
<212> TYPE: DNA
<213> ORGANISM: Homo Sapiens

<400> SEQUENCE: 914
gactggagtt cagacgtgtg ctcttccgat ctcttcccag tgtgattgca ggttccac    58

<210> SEQ ID NO 915
<211> LENGTH: 56
<212> TYPE: DNA
<213> ORGANISM: Homo Sapiens

<400> SEQUENCE: 915
gactggagtt cagacgtgtg ctcttccgat ctcttcccca ccagctttcc taattg    56

<210> SEQ ID NO 916
<211> LENGTH: 59
<212> TYPE: DNA
<213> ORGANISM: Homo Sapiens

<400> SEQUENCE: 916
gactggagtt cagacgtgtg ctcttccgat ctcttccctc ccctcgaaat gaagctaca    59

<210> SEQ ID NO 917
<211> LENGTH: 56
<212> TYPE: DNA
<213> ORGANISM: Homo Sapiens

<400> SEQUENCE: 917

```
gactggagtt cagacgtgtg ctcttccgat ctcttctcca ggaccacgga ctgcac        56
```

<210> SEQ ID NO 918
<211> LENGTH: 58
<212> TYPE: DNA
<213> ORGANISM: Homo Sapiens

<400> SEQUENCE: 918

```
gactggagtt cagacgtgtg ctcttccgat ctcttctgtc aaagtggggg ttcggaga       58
```

<210> SEQ ID NO 919
<211> LENGTH: 59
<212> TYPE: DNA
<213> ORGANISM: Homo Sapiens

<400> SEQUENCE: 919

```
gactggagtt cagacgtgtg ctcttccgat ctcttcttct catcgcgggc ttggttctg      59
```

<210> SEQ ID NO 920
<211> LENGTH: 59
<212> TYPE: DNA
<213> ORGANISM: Homo Sapiens

<400> SEQUENCE: 920

```
gactggagtt cagacgtgtg ctcttccgat ctcttcttgt cctgcttgct tacctcgct      59
```

<210> SEQ ID NO 921
<211> LENGTH: 59
<212> TYPE: DNA
<213> ORGANISM: Homo Sapiens

<400> SEQUENCE: 921

```
gactggagtt cagacgtgtg ctcttccgat ctcttgaatg accctgttaa tccgttcgt      59
```

<210> SEQ ID NO 922
<211> LENGTH: 54
<212> TYPE: DNA
<213> ORGANISM: Homo Sapiens

<400> SEQUENCE: 922

```
gactggagtt cagacgtgtg ctcttccgat ctcttgaggt ctcccccgc catg             54
```

<210> SEQ ID NO 923
<211> LENGTH: 59
<212> TYPE: DNA
<213> ORGANISM: Homo Sapiens

<400> SEQUENCE: 923

```
gactggagtt cagacgtgtg ctcttccgat ctcttgcagt cgtcagcctg aacataaca      59
```

<210> SEQ ID NO 924
<211> LENGTH: 59
<212> TYPE: DNA
<213> ORGANISM: Homo Sapiens

<400> SEQUENCE: 924

```
gactggagtt cagacgtgtg ctcttccgat ctcttgtgtg gtgactggca tctggtagg      59
```

<210> SEQ ID NO 925
<211> LENGTH: 59
<212> TYPE: DNA
<213> ORGANISM: Homo Sapiens

<400> SEQUENCE: 925

```
gactggagtt cagacgtgtg ctcttccgat ctctttattt gtcccctttgc ctcccttttc          59
```

<210> SEQ ID NO 926
<211> LENGTH: 59
<212> TYPE: DNA
<213> ORGANISM: Homo Sapiens

<400> SEQUENCE: 926

```
gactggagtt cagacgtgtg ctcttccgat ctctttccct ctgcccttttt caagcctct          59
```

<210> SEQ ID NO 927
<211> LENGTH: 59
<212> TYPE: DNA
<213> ORGANISM: Homo Sapiens

<400> SEQUENCE: 927

```
gactggagtt cagacgtgtg ctcttccgat ctctttgtga ccttcggctt tttcaaccc          59
```

<210> SEQ ID NO 928
<211> LENGTH: 59
<212> TYPE: DNA
<213> ORGANISM: Homo Sapiens

<400> SEQUENCE: 928

```
gactggagtt cagacgtgtg ctcttccgat ctcttttcct cctcttctcc tggcctgag          59
```

<210> SEQ ID NO 929
<211> LENGTH: 59
<212> TYPE: DNA
<213> ORGANISM: Homo Sapiens

<400> SEQUENCE: 929

```
gactggagtt cagacgtgtg ctcttccgat ctcttttctc aatgatgctt ggctctgga          59
```

<210> SEQ ID NO 930
<211> LENGTH: 64
<212> TYPE: DNA
<213> ORGANISM: Homo Sapiens

<400> SEQUENCE: 930

```
gactggagtt cagacgtgtg ctcttccgat ctgaaaatac atagagtttt aatgcattgt          60
ctca                                                                      64
```

<210> SEQ ID NO 931
<211> LENGTH: 61
<212> TYPE: DNA
<213> ORGANISM: Homo Sapiens

<400> SEQUENCE: 931

```
gactggagtt cagacgtgtg ctcttccgat ctgaaagatc acatcacatg aatggaatag          60
t                                                                         61
```

<210> SEQ ID NO 932
<211> LENGTH: 59
<212> TYPE: DNA
<213> ORGANISM: Homo Sapiens

<400> SEQUENCE: 932

```
gactggagtt cagacgtgtg ctcttccgat ctgaaagcct cacctgtcta cgttccctc          59
```

<210> SEQ ID NO 933

-continued

<210> SEQ ID NO 933
<211> LENGTH: 59
<212> TYPE: DNA
<213> ORGANISM: Homo Sapiens

<400> SEQUENCE: 933
gactggagtt cagacgtgtg ctcttccgat ctgaaatgga tgttcaggta ggagagaca    59

<210> SEQ ID NO 934
<211> LENGTH: 56
<212> TYPE: DNA
<213> ORGANISM: Homo Sapiens

<400> SEQUENCE: 934
gactggagtt cagacgtgtg ctcttccgat ctgaacctgg aagctgtctc caccca       56

<210> SEQ ID NO 935
<211> LENGTH: 54
<212> TYPE: DNA
<213> ORGANISM: Homo Sapiens

<400> SEQUENCE: 935
gactggagtt cagacgtgtg ctcttccgat ctgaacgcct ccccgagtga gctg         54

<210> SEQ ID NO 936
<211> LENGTH: 57
<212> TYPE: DNA
<213> ORGANISM: Homo Sapiens

<400> SEQUENCE: 936
gactggagtt cagacgtgtg ctcttccgat ctgaacgtgc tggtcaagag tcccaac      57

<210> SEQ ID NO 937
<211> LENGTH: 57
<212> TYPE: DNA
<213> ORGANISM: Homo Sapiens

<400> SEQUENCE: 937
gactggagtt cagacgtgtg ctcttccgat ctgaacgtgc tggtcaagag tcccaac      57

<210> SEQ ID NO 938
<211> LENGTH: 54
<212> TYPE: DNA
<213> ORGANISM: Homo Sapiens

<400> SEQUENCE: 938
gactggagtt cagacgtgtg ctcttccgat ctgaagatcc cctgccctcc ccag         54

<210> SEQ ID NO 939
<211> LENGTH: 57
<212> TYPE: DNA
<213> ORGANISM: Homo Sapiens

<400> SEQUENCE: 939
gactggagtt cagacgtgtg ctcttccgat ctgaagggac agaagatgac aggggcc      57

<210> SEQ ID NO 940
<211> LENGTH: 57
<212> TYPE: DNA
<213> ORGANISM: Homo Sapiens

<400> SEQUENCE: 940
gactggagtt cagacgtgtg ctcttccgat ctgaaggtga aggtgcttgg atctggc      57

```
<210> SEQ ID NO 941
<211> LENGTH: 59
<212> TYPE: DNA
<213> ORGANISM: Homo Sapiens

<400> SEQUENCE: 941
gactggagtt cagacgtgtg ctcttccgat ctgaagtcct cgttgtcttg ttggcaggg      59

<210> SEQ ID NO 942
<211> LENGTH: 59
<212> TYPE: DNA
<213> ORGANISM: Homo Sapiens

<400> SEQUENCE: 942
gactggagtt cagacgtgtg ctcttccgat ctgaagtcct cgttgtcttg ttggcaggg      59

<210> SEQ ID NO 943
<211> LENGTH: 56
<212> TYPE: DNA
<213> ORGANISM: Homo Sapiens

<400> SEQUENCE: 943
gactggagtt cagacgtgtg ctcttccgat ctgaagtgcc cttggttcgg acagac         56

<210> SEQ ID NO 944
<211> LENGTH: 54
<212> TYPE: DNA
<213> ORGANISM: Homo Sapiens

<400> SEQUENCE: 944
gactggagtt cagacgtgtg ctcttccgat ctgaatgcgg gcgatctggg actg           54

<210> SEQ ID NO 945
<211> LENGTH: 63
<212> TYPE: DNA
<213> ORGANISM: Homo Sapiens

<400> SEQUENCE: 945
gactggagtt cagacgtgtg ctcttccgat ctgaattttc tgaactattt atggacaaca     60
gtc                                                                   63

<210> SEQ ID NO 946
<211> LENGTH: 59
<212> TYPE: DNA
<213> ORGANISM: Homo Sapiens

<400> SEQUENCE: 946
gactggagtt cagacgtgtg ctcttccgat ctgacaaact ctacgtctcc tccgaccac      59

<210> SEQ ID NO 947
<211> LENGTH: 57
<212> TYPE: DNA
<213> ORGANISM: Homo Sapiens

<400> SEQUENCE: 947
gactggagtt cagacgtgtg ctcttccgat ctgacaagag gatggctagg cgaggag        57

<210> SEQ ID NO 948
<211> LENGTH: 56
<212> TYPE: DNA
<213> ORGANISM: Homo Sapiens

<400> SEQUENCE: 948
```

```
gactggagtt cagacgtgtg ctcttccgat ctgacaagca gccacacccc attctt        56
```

<210> SEQ ID NO 949
<211> LENGTH: 59
<212> TYPE: DNA
<213> ORGANISM: Homo Sapiens

<400> SEQUENCE: 949

```
gactggagtt cagacgtgtg ctcttccgat ctgacactct agtatctgga aaaatggct     59
```

<210> SEQ ID NO 950
<211> LENGTH: 57
<212> TYPE: DNA
<213> ORGANISM: Homo Sapiens

<400> SEQUENCE: 950

```
gactggagtt cagacgtgtg ctcttccgat ctgacagaag atgacagggg ccaggag       57
```

<210> SEQ ID NO 951
<211> LENGTH: 59
<212> TYPE: DNA
<213> ORGANISM: Homo Sapiens

<400> SEQUENCE: 951

```
gactggagtt cagacgtgtg ctcttccgat ctgacagtaa cttgggcttt ctgacggga    59
```

<210> SEQ ID NO 952
<211> LENGTH: 59
<212> TYPE: DNA
<213> ORGANISM: Homo Sapiens

<400> SEQUENCE: 952

```
gactggagtt cagacgtgtg ctcttccgat ctgacatctg gagcatggga ctgtctctg    59
```

<210> SEQ ID NO 953
<211> LENGTH: 51
<212> TYPE: DNA
<213> ORGANISM: Homo Sapiens

<400> SEQUENCE: 953

```
gactggagtt cagacgtgtg ctcttccgat ctgacccact ctgtctccgc a            51
```

<210> SEQ ID NO 954
<211> LENGTH: 59
<212> TYPE: DNA
<213> ORGANISM: Homo Sapiens

<400> SEQUENCE: 954

```
gactggagtt cagacgtgtg ctcttccgat ctgaccctag ccttagataa aactgagca    59
```

<210> SEQ ID NO 955
<211> LENGTH: 54
<212> TYPE: DNA
<213> ORGANISM: Homo Sapiens

<400> SEQUENCE: 955

```
gactggagtt cagacgtgtg ctcttccgat ctgacgaggc gggcagtgtg tatg         54
```

<210> SEQ ID NO 956
<211> LENGTH: 59
<212> TYPE: DNA
<213> ORGANISM: Homo Sapiens

<400> SEQUENCE: 956
gactggagtt cagacgtgtg ctcttccgat ctgactctgt cctgcgtcat catctttgt    59

<210> SEQ ID NO 957
<211> LENGTH: 57
<212> TYPE: DNA
<213> ORGANISM: Homo Sapiens

<400> SEQUENCE: 957
gactggagtt cagacgtgtg ctcttccgat ctgactgtga tgaggtgccg ttcccat    57

<210> SEQ ID NO 958
<211> LENGTH: 59
<212> TYPE: DNA
<213> ORGANISM: Homo Sapiens

<400> SEQUENCE: 958
gactggagtt cagacgtgtg ctcttccgat ctgacttccc tttccgaatg ccaaacacc    59

<210> SEQ ID NO 959
<211> LENGTH: 58
<212> TYPE: DNA
<213> ORGANISM: Homo Sapiens

<400> SEQUENCE: 959
gactggagtt cagacgtgtg ctcttccgat ctgagaccac caccctaacc ccagtcag    58

<210> SEQ ID NO 960
<211> LENGTH: 57
<212> TYPE: DNA
<213> ORGANISM: Homo Sapiens

<400> SEQUENCE: 960
gactggagtt cagacgtgtg ctcttccgat ctgagccaag ggtgtgagtg aacggtg    57

<210> SEQ ID NO 961
<211> LENGTH: 57
<212> TYPE: DNA
<213> ORGANISM: Homo Sapiens

<400> SEQUENCE: 961
gactggagtt cagacgtgtg ctcttccgat ctgagccacg atgcccagtc aatcttg    57

<210> SEQ ID NO 962
<211> LENGTH: 56
<212> TYPE: DNA
<213> ORGANISM: Homo Sapiens

<400> SEQUENCE: 962
gactggagtt cagacgtgtg ctcttccgat ctgagctgcc atctcaccaa actgca    56

<210> SEQ ID NO 963
<211> LENGTH: 52
<212> TYPE: DNA
<213> ORGANISM: Homo Sapiens

<400> SEQUENCE: 963
gactggagtt cagacgtgtg ctcttccgat ctgaggatgg cagcgacgtg gg    52

<210> SEQ ID NO 964
<211> LENGTH: 52
<212> TYPE: DNA
<213> ORGANISM: Homo Sapiens

<400> SEQUENCE: 964
gactggagtt cagacgtgtg ctcttccgat ctgaggcagg gctgtgtcca cc    52

<210> SEQ ID NO 965
<211> LENGTH: 56
<212> TYPE: DNA
<213> ORGANISM: Homo Sapiens

<400> SEQUENCE: 965
gactggagtt cagacgtgtg ctcttccgat ctgaggctgg gtggagtggt gtctag    56

<210> SEQ ID NO 966
<211> LENGTH: 53
<212> TYPE: DNA
<213> ORGANISM: Homo Sapiens

<400> SEQUENCE: 966
gactggagtt cagacgtgtg ctcttccgat ctgagggccc aggagagttg cgg    53

<210> SEQ ID NO 967
<211> LENGTH: 61
<212> TYPE: DNA
<213> ORGANISM: Homo Sapiens

<400> SEQUENCE: 967
gactggagtt cagacgtgtg ctcttccgat ctgaggggaa aaatatgaca agaaagcta    60 t    61

<210> SEQ ID NO 968
<211> LENGTH: 59
<212> TYPE: DNA
<213> ORGANISM: Homo Sapiens

<400> SEQUENCE: 968
gactggagtt cagacgtgtg ctcttccgat ctgaggggga gtctgggaat gaacactaa    59

<210> SEQ ID NO 969
<211> LENGTH: 56
<212> TYPE: DNA
<213> ORGANISM: Homo Sapiens

<400> SEQUENCE: 969
gactggagtt cagacgtgtg ctcttccgat ctgaggtctc gatgtagggg atgccg    56

<210> SEQ ID NO 970
<211> LENGTH: 59
<212> TYPE: DNA
<213> ORGANISM: Homo Sapiens

<400> SEQUENCE: 970
gactggagtt cagacgtgtg ctcttccgat ctgaggtctc gatgtagggg atgccgtag    59

<210> SEQ ID NO 971
<211> LENGTH: 59
<212> TYPE: DNA
<213> ORGANISM: Homo Sapiens

<400> SEQUENCE: 971
gactggagtt cagacgtgtg ctcttccgat ctgagtacag agtgaccgcc tcaagtgac    59

<210> SEQ ID NO 972
<211> LENGTH: 63

```
<212> TYPE: DNA
<213> ORGANISM: Homo Sapiens

<400> SEQUENCE: 972
gactggagtt cagacgtgtg ctcttccgat ctgagtgggt ttatattaaa aagttggtct     60
act                                                                  63

<210> SEQ ID NO 973
<211> LENGTH: 59
<212> TYPE: DNA
<213> ORGANISM: Homo Sapiens

<400> SEQUENCE: 973
gactggagtt cagacgtgtg ctcttccgat ctgagttcct caaaagagaa atcacgcat      59

<210> SEQ ID NO 974
<211> LENGTH: 60
<212> TYPE: DNA
<213> ORGANISM: Homo Sapiens

<400> SEQUENCE: 974
gactggagtt cagacgtgtg ctcttccgat ctgagtttac caaatgtact caaggcataa    60

<210> SEQ ID NO 975
<211> LENGTH: 59
<212> TYPE: DNA
<213> ORGANISM: Homo Sapiens

<400> SEQUENCE: 975
gactggagtt cagacgtgtg ctcttccgat ctgatcatgt ctcggctcaa ggacccaaa     59

<210> SEQ ID NO 976
<211> LENGTH: 56
<212> TYPE: DNA
<213> ORGANISM: Homo Sapiens

<400> SEQUENCE: 976
gactggagtt cagacgtgtg ctcttccgat ctgatccact tccttgccct gctcag         56

<210> SEQ ID NO 977
<211> LENGTH: 57
<212> TYPE: DNA
<213> ORGANISM: Homo Sapiens

<400> SEQUENCE: 977
gactggagtt cagacgtgtg ctcttccgat ctgatctcct tggtgaccgc tctgcat        57

<210> SEQ ID NO 978
<211> LENGTH: 59
<212> TYPE: DNA
<213> ORGANISM: Homo Sapiens

<400> SEQUENCE: 978
gactggagtt cagacgtgtg ctcttccgat ctgatcttgt aggggatgtt gaggctgcc     59

<210> SEQ ID NO 979
<211> LENGTH: 61
<212> TYPE: DNA
<213> ORGANISM: Homo Sapiens

<400> SEQUENCE: 979
gactggagtt cagacgtgtg ctcttccgat ctgatctttg ttccttccat tcttatagag    60
```

-continued c                                                              61

<210> SEQ ID NO 980
<211> LENGTH: 57
<212> TYPE: DNA
<213> ORGANISM: Homo Sapiens

<400> SEQUENCE: 980
gactggagtt cagacgtgtg ctcttccgat ctgatggcca actccccttc acacctg      57

<210> SEQ ID NO 981
<211> LENGTH: 56
<212> TYPE: DNA
<213> ORGANISM: Homo Sapiens

<400> SEQUENCE: 981
gactggagtt cagacgtgtg ctcttccgat ctgatggggc cacacttact ctgcac       56

<210> SEQ ID NO 982
<211> LENGTH: 57
<212> TYPE: DNA
<213> ORGANISM: Homo Sapiens

<400> SEQUENCE: 982
gactggagtt cagacgtgtg ctcttccgat ctgatgttttt tccgcggcac ctccttc     57

<210> SEQ ID NO 983
<211> LENGTH: 56
<212> TYPE: DNA
<213> ORGANISM: Homo Sapiens

<400> SEQUENCE: 983
gactggagtt cagacgtgtg ctcttccgat ctgatttacc tttcctctgt gttggc       56

<210> SEQ ID NO 984
<211> LENGTH: 59
<212> TYPE: DNA
<213> ORGANISM: Homo Sapiens

<400> SEQUENCE: 984
gactggagtt cagacgtgtg ctcttccgat ctgatttacc tttcctctgt gttggcgga   59

<210> SEQ ID NO 985
<211> LENGTH: 57
<212> TYPE: DNA
<213> ORGANISM: Homo Sapiens

<400> SEQUENCE: 985
gactggagtt cagacgtgtg ctcttccgat ctgcaaaaca gcacagtgaa agccagc      57

<210> SEQ ID NO 986
<211> LENGTH: 58
<212> TYPE: DNA
<213> ORGANISM: Homo Sapiens

<400> SEQUENCE: 986
gactggagtt cagacgtgtg ctcttccgat ctgcaaacaa acctggctaa acgtcggt     58

<210> SEQ ID NO 987
<211> LENGTH: 59
<212> TYPE: DNA
<213> ORGANISM: Homo Sapiens

<400> SEQUENCE: 987

```
gactggagtt cagacgtgtg ctcttccgat ctgcaaacac agggccaaag actaagtga      59

<210> SEQ ID NO 988
<211> LENGTH: 59
<212> TYPE: DNA
<213> ORGANISM: Homo Sapiens

<400> SEQUENCE: 988
gactggagtt cagacgtgtg ctcttccgat ctgcaaagaa tcagaacaat gcctccacg      59

<210> SEQ ID NO 989
<211> LENGTH: 59
<212> TYPE: DNA
<213> ORGANISM: Homo Sapiens

<400> SEQUENCE: 989
gactggagtt cagacgtgtg ctcttccgat ctgcaaagac aaatggtgag tacgtgcat      59

<210> SEQ ID NO 990
<211> LENGTH: 59
<212> TYPE: DNA
<213> ORGANISM: Homo Sapiens

<400> SEQUENCE: 990
gactggagtt cagacgtgtg ctcttccgat ctgcaaagac aaatggtgag tacgtgcat      59

<210> SEQ ID NO 991
<211> LENGTH: 59
<212> TYPE: DNA
<213> ORGANISM: Homo Sapiens

<400> SEQUENCE: 991
gactggagtt cagacgtgtg ctcttccgat ctgcaaatac acaaagaaag ccctcccca      59

<210> SEQ ID NO 992
<211> LENGTH: 51
<212> TYPE: DNA
<213> ORGANISM: Homo Sapiens

<400> SEQUENCE: 992
gactggagtt cagacgtgtg ctcttccgat ctgcaacacc cagccctcgg t              51

<210> SEQ ID NO 993
<211> LENGTH: 54
<212> TYPE: DNA
<213> ORGANISM: Homo Sapiens

<400> SEQUENCE: 993
gactggagtt cagacgtgtg ctcttccgat ctgcaacacc cagccctcgg taag           54

<210> SEQ ID NO 994
<211> LENGTH: 60
<212> TYPE: DNA
<213> ORGANISM: Homo Sapiens

<400> SEQUENCE: 994
gactggagtt cagacgtgtg ctcttccgat ctgcaacatc agagctggat ctagaaatgg     60

<210> SEQ ID NO 995
<211> LENGTH: 61
<212> TYPE: DNA
<213> ORGANISM: Homo Sapiens
```

```
<400> SEQUENCE: 995
gactggagtt cagacgtgtg ctcttccgat ctgcaagaaa atacccctc catcaacttc    60
t                                                                  61

<210> SEQ ID NO 996
<211> LENGTH: 60
<212> TYPE: DNA
<213> ORGANISM: Homo Sapiens

<400> SEQUENCE: 996
gactggagtt cagacgtgtg ctcttccgat ctgcacacag atacagatgt tttggaagca    60

<210> SEQ ID NO 997
<211> LENGTH: 59
<212> TYPE: DNA
<213> ORGANISM: Homo Sapiens

<400> SEQUENCE: 997
gactggagtt cagacgtgtg ctcttccgat ctgcacagct tttcctccat gagtacgta    59

<210> SEQ ID NO 998
<211> LENGTH: 62
<212> TYPE: DNA
<213> ORGANISM: Homo Sapiens

<400> SEQUENCE: 998
gactggagtt cagacgtgtg ctcttccgat ctgcacagct tttcctccat gagtacgtat    60
tt                                                                 62

<210> SEQ ID NO 999
<211> LENGTH: 61
<212> TYPE: DNA
<213> ORGANISM: Homo Sapiens

<400> SEQUENCE: 999
gactggagtt cagacgtgtg ctcttccgat ctgcactctg acatatggcc atttctgttt    60
t                                                                  61

<210> SEQ ID NO 1000
<211> LENGTH: 62
<212> TYPE: DNA
<213> ORGANISM: Homo Sapiens

<400> SEQUENCE: 1000
gactggagtt cagacgtgtg ctcttccgat ctgcagaaag acttgaaggc gtatacagga    60
ac                                                                 62

<210> SEQ ID NO 1001
<211> LENGTH: 58
<212> TYPE: DNA
<213> ORGANISM: Homo Sapiens

<400> SEQUENCE: 1001
gactggagtt cagacgtgtg ctcttccgat ctgcagagct agctactact ggattttt     58

<210> SEQ ID NO 1002
<211> LENGTH: 61
<212> TYPE: DNA
<213> ORGANISM: Homo Sapiens

<400> SEQUENCE: 1002
```

```
gactggagtt cagacgtgtg ctcttccgat ctgcagagct agctactact ggattttgc    60 a                                                                   61

<210> SEQ ID NO 1003
<211> LENGTH: 59
<212> TYPE: DNA
<213> ORGANISM: Homo Sapiens

<400> SEQUENCE: 1003
gactggagtt cagacgtgtg ctcttccgat ctgcagcatc tcagggccaa aaatttaat     59

<210> SEQ ID NO 1004
<211> LENGTH: 62
<212> TYPE: DNA
<213> ORGANISM: Homo Sapiens

<400> SEQUENCE: 1004
gactggagtt cagacgtgtg ctcttccgat ctgcagcatc tcagggccaa aaatttaatc    60
ag                                                                  62

<210> SEQ ID NO 1005
<211> LENGTH: 61
<212> TYPE: DNA
<213> ORGANISM: Homo Sapiens

<400> SEQUENCE: 1005
gactggagtt cagacgtgtg ctcttccgat ctgcagccag aaatatcctc cttactcatg    60
g                                                                   61

<210> SEQ ID NO 1006
<211> LENGTH: 54
<212> TYPE: DNA
<213> ORGANISM: Homo Sapiens

<400> SEQUENCE: 1006
gactggagtt cagacgtgtg ctcttccgat ctgcagccta cagagtccgc aagc          54

<210> SEQ ID NO 1007
<211> LENGTH: 51
<212> TYPE: DNA
<213> ORGANISM: Homo Sapiens

<400> SEQUENCE: 1007
gactggagtt cagacgtgtg ctcttccgat ctgcaggtac cgtgcgacat c              51

<210> SEQ ID NO 1008
<211> LENGTH: 59
<212> TYPE: DNA
<213> ORGANISM: Homo Sapiens

<400> SEQUENCE: 1008
gactggagtt cagacgtgtg ctcttccgat ctgcagtcgt cagcctgaac ataacatcc     59

<210> SEQ ID NO 1009
<211> LENGTH: 68
<212> TYPE: DNA
<213> ORGANISM: Homo Sapiens

<400> SEQUENCE: 1009
gactggagtt cagacgtgtg ctcttccgat ctgcataatt gagagaaaaa ctgatatatt    60
```

-continued aaatgaca                                                                68

<210> SEQ ID NO 1010
<211> LENGTH: 60
<212> TYPE: DNA
<213> ORGANISM: Homo Sapiens

<400> SEQUENCE: 1010
gactggagtt cagacgtgtg ctcttccgat ctgcatagta agcagtaggg agtaacaaaa    60

<210> SEQ ID NO 1011
<211> LENGTH: 51
<212> TYPE: DNA
<213> ORGANISM: Homo Sapiens

<400> SEQUENCE: 1011
gactggagtt cagacgtgtg ctcttccgat ctgcatggtg agggctgagg t              51

<210> SEQ ID NO 1012
<211> LENGTH: 54
<212> TYPE: DNA
<213> ORGANISM: Homo Sapiens

<400> SEQUENCE: 1012
gactggagtt cagacgtgtg ctcttccgat ctgcatggtg agggctgagg tgac           54

<210> SEQ ID NO 1013
<211> LENGTH: 54
<212> TYPE: DNA
<213> ORGANISM: Homo Sapiens

<400> SEQUENCE: 1013
gactggagtt cagacgtgtg ctcttccgat ctgcatggtg agggctgagg tgac           54

<210> SEQ ID NO 1014
<211> LENGTH: 61
<212> TYPE: DNA
<213> ORGANISM: Homo Sapiens

<400> SEQUENCE: 1014
gactggagtt cagacgtgtg ctcttccgat ctgcatgtaa cttcctgtaa tttttcaagg    60
c                                                                    61

<210> SEQ ID NO 1015
<211> LENGTH: 58
<212> TYPE: DNA
<213> ORGANISM: Homo Sapiens

<400> SEQUENCE: 1015
gactggagtt cagacgtgtg ctcttccgat ctgcatgtat gttggcctcc tttgctgc      58

<210> SEQ ID NO 1016
<211> LENGTH: 56
<212> TYPE: DNA
<213> ORGANISM: Homo Sapiens

<400> SEQUENCE: 1016
gactggagtt cagacgtgtg ctcttccgat ctgcatgtgg gagctagaag tgacgt        56

<210> SEQ ID NO 1017
<211> LENGTH: 59
<212> TYPE: DNA
<213> ORGANISM: Homo Sapiens

```
<400> SEQUENCE: 1017
gactggagtt cagacgtgtg ctcttccgat ctgcatgtgg gagctagaag tgacgtcta        59

<210> SEQ ID NO 1018
<211> LENGTH: 52
<212> TYPE: DNA
<213> ORGANISM: Homo Sapiens

<400> SEQUENCE: 1018
gactggagtt cagacgtgtg ctcttccgat ctgccaagcc tcacaccacc cc              52

<210> SEQ ID NO 1019
<211> LENGTH: 52
<212> TYPE: DNA
<213> ORGANISM: Homo Sapiens

<400> SEQUENCE: 1019
gactggagtt cagacgtgtg ctcttccgat ctgccacaca ccaccctct gc               52

<210> SEQ ID NO 1020
<211> LENGTH: 59
<212> TYPE: DNA
<213> ORGANISM: Homo Sapiens

<400> SEQUENCE: 1020
gactggagtt cagacgtgtg ctcttccgat ctgccacaca tgccatcatt ctaggaagc       59

<210> SEQ ID NO 1021
<211> LENGTH: 58
<212> TYPE: DNA
<213> ORGANISM: Homo Sapiens

<400> SEQUENCE: 1021
gactggagtt cagacgtgtg ctcttccgat ctgccaccct gccatgctac ctagatac        58

<210> SEQ ID NO 1022
<211> LENGTH: 59
<212> TYPE: DNA
<213> ORGANISM: Homo Sapiens

<400> SEQUENCE: 1022
gactggagtt cagacgtgtg ctcttccgat ctgccacggg taataatttt tgtcctttc       59

<210> SEQ ID NO 1023
<211> LENGTH: 60
<212> TYPE: DNA
<213> ORGANISM: Homo Sapiens

<400> SEQUENCE: 1023
gactggagtt cagacgtgtg ctcttccgat ctgccacggg taataatttt tgtcctttct      60

<210> SEQ ID NO 1024
<211> LENGTH: 62
<212> TYPE: DNA
<213> ORGANISM: Homo Sapiens

<400> SEQUENCE: 1024
gactggagtt cagacgtgtg ctcttccgat ctgccacggg taataatttt tgtcctttct      60
gt                                                                    62

<210> SEQ ID NO 1025
```

```
<211> LENGTH: 56
<212> TYPE: DNA
<213> ORGANISM: Homo Sapiens

<400> SEQUENCE: 1025
gactggagtt cagacgtgtg ctcttccgat ctgccactga caaccaccct taaccc        56

<210> SEQ ID NO 1026
<211> LENGTH: 51
<212> TYPE: DNA
<213> ORGANISM: Homo Sapiens

<400> SEQUENCE: 1026
gactggagtt cagacgtgtg ctcttccgat ctgccactgc cgcttcccca c             51

<210> SEQ ID NO 1027
<211> LENGTH: 59
<212> TYPE: DNA
<213> ORGANISM: Homo Sapiens

<400> SEQUENCE: 1027
gactggagtt cagacgtgtg ctcttccgat ctgccacttc ttaccttcac agccacttg     59

<210> SEQ ID NO 1028
<211> LENGTH: 61
<212> TYPE: DNA
<213> ORGANISM: Homo Sapiens

<400> SEQUENCE: 1028
gactggagtt cagacgtgtg ctcttccgat ctgccagaaa tatcctcctt actcatggtc    60
g                                                                    61

<210> SEQ ID NO 1029
<211> LENGTH: 59
<212> TYPE: DNA
<213> ORGANISM: Homo Sapiens

<400> SEQUENCE: 1029
gactggagtt cagacgtgtg ctcttccgat ctgccagacc cagccagtat tatttcatt     59

<210> SEQ ID NO 1030
<211> LENGTH: 59
<212> TYPE: DNA
<213> ORGANISM: Homo Sapiens

<400> SEQUENCE: 1030
gactggagtt cagacgtgtg ctcttccgat ctgccagacc taagagcaat cagtgagga     59

<210> SEQ ID NO 1031
<211> LENGTH: 61
<212> TYPE: DNA
<213> ORGANISM: Homo Sapiens

<400> SEQUENCE: 1031
gactggagtt cagacgtgtg ctcttccgat ctgccagatc cagtgaaaaa caagctctca    60
t                                                                    61

<210> SEQ ID NO 1032
<211> LENGTH: 61
<212> TYPE: DNA
<213> ORGANISM: Homo Sapiens

<400> SEQUENCE: 1032
```

```
gactggagtt cagacgtgtg ctcttccgat ctgccagtac cttcctcttc ttctacatca    60
c                                                                   61

<210> SEQ ID NO 1033
<211> LENGTH: 61
<212> TYPE: DNA
<213> ORGANISM: Homo Sapiens

<400> SEQUENCE: 1033
gactggagtt cagacgtgtg ctcttccgat ctgccagtta acgtcttcct tctctctctg    60
t                                                                   61

<210> SEQ ID NO 1034
<211> LENGTH: 61
<212> TYPE: DNA
<213> ORGANISM: Homo Sapiens

<400> SEQUENCE: 1034
gactggagtt cagacgtgtg ctcttccgat ctgccagtta acgtcttcct tctctctctg    60
t                                                                   61

<210> SEQ ID NO 1035
<211> LENGTH: 60
<212> TYPE: DNA
<213> ORGANISM: Homo Sapiens

<400> SEQUENCE: 1035
gactggagtt cagacgtgtg ctcttccgat ctgccatctt attccagacg catttccaca    60

<210> SEQ ID NO 1036
<211> LENGTH: 52
<212> TYPE: DNA
<213> ORGANISM: Homo Sapiens

<400> SEQUENCE: 1036
gactggagtt cagacgtgtg ctcttccgat ctgcccacca agcagcccat cc            52

<210> SEQ ID NO 1037
<211> LENGTH: 57
<212> TYPE: DNA
<213> ORGANISM: Homo Sapiens

<400> SEQUENCE: 1037
gactggagtt cagacgtgtg ctcttccgat ctgcccacgc tcttctcact catatcc       57

<210> SEQ ID NO 1038
<211> LENGTH: 58
<212> TYPE: DNA
<213> ORGANISM: Homo Sapiens

<400> SEQUENCE: 1038
gactggagtt cagacgtgtg ctcttccgat ctgcccactc ttgctccttc catccttg      58

<210> SEQ ID NO 1039
<211> LENGTH: 58
<212> TYPE: DNA
<213> ORGANISM: Homo Sapiens

<400> SEQUENCE: 1039
gactggagtt cagacgtgtg ctcttccgat ctgcccatga tagccgtctt taacaagc      58
```

<210> SEQ ID NO 1040
<211> LENGTH: 58
<212> TYPE: DNA
<213> ORGANISM: Homo Sapiens

<400> SEQUENCE: 1040
gactggagtt cagacgtgtg ctcttccgat ctgcccatga tagccgtctt taacaagc        58

<210> SEQ ID NO 1041
<211> LENGTH: 59
<212> TYPE: DNA
<213> ORGANISM: Homo Sapiens

<400> SEQUENCE: 1041
gactggagtt cagacgtgtg ctcttccgat ctgccccaga actaacaggt taagtgctc       59

<210> SEQ ID NO 1042
<211> LENGTH: 56
<212> TYPE: DNA
<213> ORGANISM: Homo Sapiens

<400> SEQUENCE: 1042
gactggagtt cagacgtgtg ctcttccgat ctgccccgtt ccatcatagc atgcaa          56

<210> SEQ ID NO 1043
<211> LENGTH: 59
<212> TYPE: DNA
<213> ORGANISM: Homo Sapiens

<400> SEQUENCE: 1043
gactggagtt cagacgtgtg ctcttccgat ctgcccgaag tgtaagccca actacagaa       59

<210> SEQ ID NO 1044
<211> LENGTH: 56
<212> TYPE: DNA
<213> ORGANISM: Homo Sapiens

<400> SEQUENCE: 1044
gactggagtt cagacgtgtg ctcttccgat ctgccctaat caccacccca cccaat          56

<210> SEQ ID NO 1045
<211> LENGTH: 58
<212> TYPE: DNA
<213> ORGANISM: Homo Sapiens

<400> SEQUENCE: 1045
gactggagtt cagacgtgtg ctcttccgat ctgccctgca gtgaattttg aagattgc        58

<210> SEQ ID NO 1046
<211> LENGTH: 50
<212> TYPE: DNA
<213> ORGANISM: Homo Sapiens

<400> SEQUENCE: 1046
gactggagtt cagacgtgtg ctcttccgat ctgccgccgc tgagccactg                 50

<210> SEQ ID NO 1047
<211> LENGTH: 55
<212> TYPE: DNA
<213> ORGANISM: Homo Sapiens

<400> SEQUENCE: 1047
gactggagtt cagacgtgtg ctcttccgat ctgccggtag ttgcccttct cgaac           55

<210> SEQ ID NO 1048
<211> LENGTH: 59
<212> TYPE: DNA
<213> ORGANISM: Homo Sapiens

<400> SEQUENCE: 1048
gactggagtt cagacgtgtg ctcttccgat ctgccgtctt taacaagctc tttctttct    59

<210> SEQ ID NO 1049
<211> LENGTH: 59
<212> TYPE: DNA
<213> ORGANISM: Homo Sapiens

<400> SEQUENCE: 1049
gactggagtt cagacgtgtg ctcttccgat ctgcctcaaa gaaaagctgc gtgatgatg    59

<210> SEQ ID NO 1050
<211> LENGTH: 55
<212> TYPE: DNA
<213> ORGANISM: Homo Sapiens

<400> SEQUENCE: 1050
gactggagtt cagacgtgtg ctcttccgat ctgcctcaac gcccatgtct ttgca        55

<210> SEQ ID NO 1051
<211> LENGTH: 55
<212> TYPE: DNA
<213> ORGANISM: Homo Sapiens

<400> SEQUENCE: 1051
gactggagtt cagacgtgtg ctcttccgat ctgcctcaac gcccatgtct ttgca        55

<210> SEQ ID NO 1052
<211> LENGTH: 58
<212> TYPE: DNA
<213> ORGANISM: Homo Sapiens

<400> SEQUENCE: 1052
gactggagtt cagacgtgtg ctcttccgat ctgcctcagt aaagccacct cacgaact     58

<210> SEQ ID NO 1053
<211> LENGTH: 58
<212> TYPE: DNA
<213> ORGANISM: Homo Sapiens

<400> SEQUENCE: 1053
gactggagtt cagacgtgtg ctcttccgat ctgcctccac ttttgcacag ccaagaac     58

<210> SEQ ID NO 1054
<211> LENGTH: 62
<212> TYPE: DNA
<213> ORGANISM: Homo Sapiens

<400> SEQUENCE: 1054
gactggagtt cagacgtgtg ctcttccgat ctgcctccca aaatgttagg attacaggtg   60
tg                                                                  62

<210> SEQ ID NO 1055
<211> LENGTH: 62
<212> TYPE: DNA
<213> ORGANISM: Homo Sapiens

<400> SEQUENCE: 1055
gactggagtt cagacgtgtg ctcttccgat ctgcctctta cctggaattt ggatgtgatt    60
gg    62

<210> SEQ ID NO 1056
<211> LENGTH: 55
<212> TYPE: DNA
<213> ORGANISM: Homo Sapiens

<400> SEQUENCE: 1056
gactggagtt cagacgtgtg ctcttccgat ctgcctgcct ccacttcaac cacag    55

<210> SEQ ID NO 1057
<211> LENGTH: 52
<212> TYPE: DNA
<213> ORGANISM: Homo Sapiens

<400> SEQUENCE: 1057
gactggagtt cagacgtgtg ctcttccgat ctgcctgggg agctggggac tc    52

<210> SEQ ID NO 1058
<211> LENGTH: 57
<212> TYPE: DNA
<213> ORGANISM: Homo Sapiens

<400> SEQUENCE: 1058
gactggagtt cagacgtgtg ctcttccgat ctgccttcgc ctgtcctcat gtattgg    57

<210> SEQ ID NO 1059
<211> LENGTH: 59
<212> TYPE: DNA
<213> ORGANISM: Homo Sapiens

<400> SEQUENCE: 1059
gactggagtt cagacgtgtg ctcttccgat ctgccttctc ctttacccct ccttcctag    59

<210> SEQ ID NO 1060
<211> LENGTH: 59
<212> TYPE: DNA
<213> ORGANISM: Homo Sapiens

<400> SEQUENCE: 1060
gactggagtt cagacgtgtg ctcttccgat ctgccttggt gtgcattctt ctctctctt    59

<210> SEQ ID NO 1061
<211> LENGTH: 59
<212> TYPE: DNA
<213> ORGANISM: Homo Sapiens

<400> SEQUENCE: 1061
gactggagtt cagacgtgtg ctcttccgat ctgcctttct tccctcccct cgaaatgaa    59

<210> SEQ ID NO 1062
<211> LENGTH: 61
<212> TYPE: DNA
<213> ORGANISM: Homo Sapiens

<400> SEQUENCE: 1062
gactggagtt cagacgtgtg ctcttccgat ctgcgacaga tccggaatat tgtagagaag    60
c    61

```
<210> SEQ ID NO 1063
<211> LENGTH: 60
<212> TYPE: DNA
<213> ORGANISM: Homo Sapiens

<400> SEQUENCE: 1063
gactggagtt cagacgtgtg ctcttccgat ctgcgacatg tctttcccca caatcatact    60

<210> SEQ ID NO 1064
<211> LENGTH: 52
<212> TYPE: DNA
<213> ORGANISM: Homo Sapiens

<400> SEQUENCE: 1064
gactggagtt cagacgtgtg ctcttccgat ctgcgatggc ccagctcctc ag            52

<210> SEQ ID NO 1065
<211> LENGTH: 57
<212> TYPE: DNA
<213> ORGANISM: Homo Sapiens

<400> SEQUENCE: 1065
gactggagtt cagacgtgtg ctcttccgat ctgcgcatct ccctcaggta gttcagg       57

<210> SEQ ID NO 1066
<211> LENGTH: 61
<212> TYPE: DNA
<213> ORGANISM: Homo Sapiens

<400> SEQUENCE: 1066
gactggagtt cagacgtgtg ctcttccgat ctgcgctact agaaacatga tagaggtgac    60
a                                                                    61

<210> SEQ ID NO 1067
<211> LENGTH: 56
<212> TYPE: DNA
<213> ORGANISM: Homo Sapiens

<400> SEQUENCE: 1067
gactggagtt cagacgtgtg ctcttccgat ctgcggaaga atgtgtcagc ctcaaa        56

<210> SEQ ID NO 1068
<211> LENGTH: 54
<212> TYPE: DNA
<213> ORGANISM: Homo Sapiens

<400> SEQUENCE: 1068
gactggagtt cagacgtgtg ctcttccgat ctgcgggtct ctcggaggaa ggac          54

<210> SEQ ID NO 1069
<211> LENGTH: 55
<212> TYPE: DNA
<213> ORGANISM: Homo Sapiens

<400> SEQUENCE: 1069
gactggagtt cagacgtgtg ctcttccgat ctgcgtcgtg gagaacaagt ttggc         55

<210> SEQ ID NO 1070
<211> LENGTH: 59
<212> TYPE: DNA
<213> ORGANISM: Homo Sapiens

<400> SEQUENCE: 1070
```

```
gactggagtt cagacgtgtg ctcttccgat ctgcgtggta gggcatttaa gtattggtt       59
```

<210> SEQ ID NO 1071
<211> LENGTH: 62
<212> TYPE: DNA
<213> ORGANISM: Homo Sapiens

<400> SEQUENCE: 1071

```
gactggagtt cagacgtgtg ctcttccgat ctgcgtggta gggcatttaa gtattggttg       60
at                                                                      62
```

<210> SEQ ID NO 1072
<211> LENGTH: 61
<212> TYPE: DNA
<213> ORGANISM: Homo Sapiens

<400> SEQUENCE: 1072

```
gactggagtt cagacgtgtg ctcttccgat ctgctaacca agttctttct tttgcacagg       60
g                                                                       61
```

<210> SEQ ID NO 1073
<211> LENGTH: 55
<212> TYPE: DNA
<213> ORGANISM: Homo Sapiens

<400> SEQUENCE: 1073

```
gactggagtt cagacgtgtg ctcttccgat ctgctcagat gacagccggt tctct           55
```

<210> SEQ ID NO 1074
<211> LENGTH: 61
<212> TYPE: DNA
<213> ORGANISM: Homo Sapiens

<400> SEQUENCE: 1074

```
gactggagtt cagacgtgtg ctcttccgat ctgctcccag gctgtttatt tgaagagaga       60
c                                                                       61
```

<210> SEQ ID NO 1075
<211> LENGTH: 57
<212> TYPE: DNA
<213> ORGANISM: Homo Sapiens

<400> SEQUENCE: 1075

```
gactggagtt cagacgtgtg ctcttccgat ctgctccttc catccttgct cctgtcc         57
```

<210> SEQ ID NO 1076
<211> LENGTH: 58
<212> TYPE: DNA
<213> ORGANISM: Homo Sapiens

<400> SEQUENCE: 1076

```
gactggagtt cagacgtgtg ctcttccgat ctgctccttc cctatccctt ctgctctc        58
```

<210> SEQ ID NO 1077
<211> LENGTH: 59
<212> TYPE: DNA
<213> ORGANISM: Homo Sapiens

<400> SEQUENCE: 1077

```
gactggagtt cagacgtgtg ctcttccgat ctgctcttcc tgtttcagtc cccattaaa       59
```

```
<210> SEQ ID NO 1078
<211> LENGTH: 61
<212> TYPE: DNA
<213> ORGANISM: Homo Sapiens

<400> SEQUENCE: 1078
gactggagtt cagacgtgtg ctcttccgat ctgctgacac cacgatactt gacaatgaaa    60
t                                                                   61

<210> SEQ ID NO 1079
<211> LENGTH: 57
<212> TYPE: DNA
<213> ORGANISM: Homo Sapiens

<400> SEQUENCE: 1079
gactggagtt cagacgtgtg ctcttccgat ctgctgagga aggtgaaggt gcttgga       57

<210> SEQ ID NO 1080
<211> LENGTH: 57
<212> TYPE: DNA
<213> ORGANISM: Homo Sapiens

<400> SEQUENCE: 1080
gactggagtt cagacgtgtg ctcttccgat ctgctgctgg aattggtgtt gatgacc       57

<210> SEQ ID NO 1081
<211> LENGTH: 59
<212> TYPE: DNA
<213> ORGANISM: Homo Sapiens

<400> SEQUENCE: 1081
gactggagtt cagacgtgtg ctcttccgat ctgctggctg atctatgtcc ctgaagcag     59

<210> SEQ ID NO 1082
<211> LENGTH: 57
<212> TYPE: DNA
<213> ORGANISM: Homo Sapiens

<400> SEQUENCE: 1082
gactggagtt cagacgtgtg ctcttccgat ctgctgggca tcactgtaaa ccttgca       57

<210> SEQ ID NO 1083
<211> LENGTH: 56
<212> TYPE: DNA
<213> ORGANISM: Homo Sapiens

<400> SEQUENCE: 1083
gactggagtt cagacgtgtg ctcttccgat ctgctggttt ggggaagagt gggcta        56

<210> SEQ ID NO 1084
<211> LENGTH: 57
<212> TYPE: DNA
<213> ORGANISM: Homo Sapiens

<400> SEQUENCE: 1084
gactggagtt cagacgtgtg ctcttccgat ctgctgtcct cttctccttc atcgtct       57

<210> SEQ ID NO 1085
<211> LENGTH: 55
<212> TYPE: DNA
<213> ORGANISM: Homo Sapiens

<400> SEQUENCE: 1085
```
gactggagtt cagacgtgtg ctcttccgat ctgctgtgga gtgatgagct gccat       55

<210> SEQ ID NO 1086
<211> LENGTH: 58
<212> TYPE: DNA
<213> ORGANISM: Homo Sapiens

<400> SEQUENCE: 1086
gactggagtt cagacgtgtg ctcttccgat ctgctgtgtc cacccccttac tcattgg    58

<210> SEQ ID NO 1087
<211> LENGTH: 59
<212> TYPE: DNA
<213> ORGANISM: Homo Sapiens

<400> SEQUENCE: 1087
gactggagtt cagacgtgtg ctcttccgat ctgcttgaca tcagtttgcc agttgtgct   59

<210> SEQ ID NO 1088
<211> LENGTH: 59
<212> TYPE: DNA
<213> ORGANISM: Homo Sapiens

<400> SEQUENCE: 1088
gactggagtt cagacgtgtg ctcttccgat ctgcttgaca tcagtttgcc agttgtgct   59

<210> SEQ ID NO 1089
<211> LENGTH: 57
<212> TYPE: DNA
<213> ORGANISM: Homo Sapiens

<400> SEQUENCE: 1089
gactggagtt cagacgtgtg ctcttccgat ctgcttgtaa gtgcccgaag tgtaagc     57

<210> SEQ ID NO 1090
<211> LENGTH: 60
<212> TYPE: DNA
<213> ORGANISM: Homo Sapiens

<400> SEQUENCE: 1090
gactggagtt cagacgtgtg ctcttccgat ctgcttttcc tccatgagta cgtattttga  60

<210> SEQ ID NO 1091
<211> LENGTH: 59
<212> TYPE: DNA
<213> ORGANISM: Homo Sapiens

<400> SEQUENCE: 1091
gactggagtt cagacgtgtg ctcttccgat ctggaaaaac tgtgttgtgg agtgcaagt   59

<210> SEQ ID NO 1092
<211> LENGTH: 59
<212> TYPE: DNA
<213> ORGANISM: Homo Sapiens

<400> SEQUENCE: 1092
gactggagtt cagacgtgtg ctcttccgat ctggaaaaca catcccccaa agccaacaa   59

<210> SEQ ID NO 1093
<211> LENGTH: 61
<212> TYPE: DNA
<213> ORGANISM: Homo Sapiens

<400> SEQUENCE: 1093
gactggagtt cagacgtgtg ctcttccgat ctggaaccag gagctaataa aaataacttc    60
t                                                                   61

<210> SEQ ID NO 1094
<211> LENGTH: 58
<212> TYPE: DNA
<213> ORGANISM: Homo Sapiens

<400> SEQUENCE: 1094
gactggagtt cagacgtgtg ctcttccgat ctggaactgc tttgactcca ggtattcc     58

<210> SEQ ID NO 1095
<211> LENGTH: 59
<212> TYPE: DNA
<213> ORGANISM: Homo Sapiens

<400> SEQUENCE: 1095
gactggagtt cagacgtgtg ctcttccgat ctggaactta ctctccaggc ttaacacag    59

<210> SEQ ID NO 1096
<211> LENGTH: 56
<212> TYPE: DNA
<213> ORGANISM: Homo Sapiens

<400> SEQUENCE: 1096
gactggagtt cagacgtgtg ctcttccgat ctggaagatc atctgctggc cgtgtg       56

<210> SEQ ID NO 1097
<211> LENGTH: 58
<212> TYPE: DNA
<213> ORGANISM: Homo Sapiens

<400> SEQUENCE: 1097
gactggagtt cagacgtgtg ctcttccgat ctggaagcac acagatcagc gacaggat     58

<210> SEQ ID NO 1098
<211> LENGTH: 58
<212> TYPE: DNA
<213> ORGANISM: Homo Sapiens

<400> SEQUENCE: 1098
gactggagtt cagacgtgtg ctcttccgat ctggaagcac acagatcagc gacaggat     58

<210> SEQ ID NO 1099
<211> LENGTH: 59
<212> TYPE: DNA
<213> ORGANISM: Homo Sapiens

<400> SEQUENCE: 1099
gactggagtt cagacgtgtg ctcttccgat ctggaagccc tcatgtctga actcaaagt    59

<210> SEQ ID NO 1100
<211> LENGTH: 60
<212> TYPE: DNA
<213> ORGANISM: Homo Sapiens

<400> SEQUENCE: 1100
gactggagtt cagacgtgtg ctcttccgat ctggaagttt aggtcaaaga ggctgcttgg   60

<210> SEQ ID NO 1101
<211> LENGTH: 59
<212> TYPE: DNA

<213> ORGANISM: Homo Sapiens

<400> SEQUENCE: 1101
gactggagtt cagacgtgtg ctcttccgat ctggaatagg ccttggtgtg cattcttct    59

<210> SEQ ID NO 1102
<211> LENGTH: 61
<212> TYPE: DNA
<213> ORGANISM: Homo Sapiens

<400> SEQUENCE: 1102
gactggagtt cagacgtgtg ctcttccgat ctggaatttg gatgtgattg gaaagtgggg    60
t    61

<210> SEQ ID NO 1103
<211> LENGTH: 59
<212> TYPE: DNA
<213> ORGANISM: Homo Sapiens

<400> SEQUENCE: 1103
gactggagtt cagacgtgtg ctcttccgat ctggacatgc tagggacaac acgatttcc    59

<210> SEQ ID NO 1104
<211> LENGTH: 59
<212> TYPE: DNA
<213> ORGANISM: Homo Sapiens

<400> SEQUENCE: 1104
gactggagtt cagacgtgtg ctcttccgat ctggaccctg acaaatgtgc tgttcttct    59

<210> SEQ ID NO 1105
<211> LENGTH: 56
<212> TYPE: DNA
<213> ORGANISM: Homo Sapiens

<400> SEQUENCE: 1105
gactggagtt cagacgtgtg ctcttccgat ctggaccgac cgtgatcaga ttaggg    56

<210> SEQ ID NO 1106
<211> LENGTH: 58
<212> TYPE: DNA
<213> ORGANISM: Homo Sapiens

<400> SEQUENCE: 1106
gactggagtt cagacgtgtg ctcttccgat ctggactagg cgtgggatgt ttttgcag    58

<210> SEQ ID NO 1107
<211> LENGTH: 56
<212> TYPE: DNA
<213> ORGANISM: Homo Sapiens

<400> SEQUENCE: 1107
gactggagtt cagacgtgtg ctcttccgat ctggacttcc tcttctgccc tcccag    56

<210> SEQ ID NO 1108
<211> LENGTH: 58
<212> TYPE: DNA
<213> ORGANISM: Homo Sapiens

<400> SEQUENCE: 1108
gactggagtt cagacgtgtg ctcttccgat ctggagaaaa ggggacatgc tagggaca    58

<210> SEQ ID NO 1109
<211> LENGTH: 57
<212> TYPE: DNA
<213> ORGANISM: Homo Sapiens

<400> SEQUENCE: 1109
gactggagtt cagacgtgtg ctcttccgat ctggagaaca agtttggcag catccgg        57

<210> SEQ ID NO 1110
<211> LENGTH: 59
<212> TYPE: DNA
<213> ORGANISM: Homo Sapiens

<400> SEQUENCE: 1110
gactggagtt cagacgtgtg ctcttccgat ctggagacca ggtagaggga gtacagagt      59

<210> SEQ ID NO 1111
<211> LENGTH: 54
<212> TYPE: DNA
<213> ORGANISM: Homo Sapiens

<400> SEQUENCE: 1111
gactggagtt cagacgtgtg ctcttccgat ctggagacgt tggaatgcgg ggac           54

<210> SEQ ID NO 1112
<211> LENGTH: 59
<212> TYPE: DNA
<213> ORGANISM: Homo Sapiens

<400> SEQUENCE: 1112
gactggagtt cagacgtgtg ctcttccgat ctggagagac atttaaggtt ccttcaagc      59

<210> SEQ ID NO 1113
<211> LENGTH: 61
<212> TYPE: DNA
<213> ORGANISM: Homo Sapiens

<400> SEQUENCE: 1113
gactggagtt cagacgtgtg ctcttccgat ctggagtact tctttgggtt gacttctctg     60
g                                                                      61

<210> SEQ ID NO 1114
<211> LENGTH: 59
<212> TYPE: DNA
<213> ORGANISM: Homo Sapiens

<400> SEQUENCE: 1114
gactggagtt cagacgtgtg ctcttccgat ctggagtggt cataaggctg gtataatgt      59

<210> SEQ ID NO 1115
<211> LENGTH: 58
<212> TYPE: DNA
<213> ORGANISM: Homo Sapiens

<400> SEQUENCE: 1115
gactggagtt cagacgtgtg ctcttccgat ctggagttcc tcttccttcc ccttctag       58

<210> SEQ ID NO 1116
<211> LENGTH: 59
<212> TYPE: DNA
<213> ORGANISM: Homo Sapiens

<400> SEQUENCE: 1116

-continued gactggagtt cagacgtgtg ctcttccgat ctggatgagt tttgtgaaag gctggggac    59

<210> SEQ ID NO 1117
<211> LENGTH: 59
<212> TYPE: DNA
<213> ORGANISM: Homo Sapiens

<400> SEQUENCE: 1117
gactggagtt cagacgtgtg ctcttccgat ctggattcaa agtcagtccc cagctactc    59

<210> SEQ ID NO 1118
<211> LENGTH: 55
<212> TYPE: DNA
<213> ORGANISM: Homo Sapiens

<400> SEQUENCE: 1118
gactggagtt cagacgtgtg ctcttccgat ctggattgca gattgggcct tgggg        55

<210> SEQ ID NO 1119
<211> LENGTH: 58
<212> TYPE: DNA
<213> ORGANISM: Homo Sapiens

<400> SEQUENCE: 1119
gactggagtt cagacgtgtg ctcttccgat ctggcaaagg tgggcttgtt ggaagaac     58

<210> SEQ ID NO 1120
<211> LENGTH: 61
<212> TYPE: DNA
<213> ORGANISM: Homo Sapiens

<400> SEQUENCE: 1120
gactggagtt cagacgtgtg ctcttccgat ctggcaacag ctcttacctt gtctttcttc    60
c                                                                   61

<210> SEQ ID NO 1121
<211> LENGTH: 62
<212> TYPE: DNA
<213> ORGANISM: Homo Sapiens

<400> SEQUENCE: 1121
gactggagtt cagacgtgtg ctcttccgat ctggcaattc atttccaatc aaacccacag    60
ac                                                                  62

<210> SEQ ID NO 1122
<211> LENGTH: 64
<212> TYPE: DNA
<213> ORGANISM: Homo Sapiens

<400> SEQUENCE: 1122
gactggagtt cagacgtgtg ctcttccgat ctggcacatt ccattcttac caaactctaa    60
attt                                                                64

<210> SEQ ID NO 1123
<211> LENGTH: 55
<212> TYPE: DNA
<213> ORGANISM: Homo Sapiens

<400> SEQUENCE: 1123
gactggagtt cagacgtgtg ctcttccgat ctggcagact ctctcctccc cactg         55

```
<210> SEQ ID NO 1124
<211> LENGTH: 55
<212> TYPE: DNA
<213> ORGANISM: Homo Sapiens

<400> SEQUENCE: 1124
gactggagtt cagacgtgtg ctcttccgat ctggcagact ctctcctccc cactg        55

<210> SEQ ID NO 1125
<211> LENGTH: 59
<212> TYPE: DNA
<213> ORGANISM: Homo Sapiens

<400> SEQUENCE: 1125
gactggagtt cagacgtgtg ctcttccgat ctggcatcaa tgtccttatt acttgggag    59

<210> SEQ ID NO 1126
<211> LENGTH: 62
<212> TYPE: DNA
<213> ORGANISM: Homo Sapiens

<400> SEQUENCE: 1126
gactggagtt cagacgtgtg ctcttccgat ctggcatcaa tgtccttatt acttgggaga   60
ct                                                                  62

<210> SEQ ID NO 1127
<211> LENGTH: 58
<212> TYPE: DNA
<213> ORGANISM: Homo Sapiens

<400> SEQUENCE: 1127
gactggagtt cagacgtgtg ctcttccgat ctggcattct gggagcttca tctggacc     58

<210> SEQ ID NO 1128
<211> LENGTH: 59
<212> TYPE: DNA
<213> ORGANISM: Homo Sapiens

<400> SEQUENCE: 1128
gactggagtt cagacgtgtg ctcttccgat ctggccagat ccagtgaaaa acaagctct    59

<210> SEQ ID NO 1129
<211> LENGTH: 59
<212> TYPE: DNA
<213> ORGANISM: Homo Sapiens

<400> SEQUENCE: 1129
gactggagtt cagacgtgtg ctcttccgat ctggccagat ccagtgaaaa acaagctct    59

<210> SEQ ID NO 1130
<211> LENGTH: 56
<212> TYPE: DNA
<213> ORGANISM: Homo Sapiens

<400> SEQUENCE: 1130
gactggagtt cagacgtgtg ctcttccgat ctggccgaag tctgaccctt tttgtc        56

<210> SEQ ID NO 1131
<211> LENGTH: 60
<212> TYPE: DNA
<213> ORGANISM: Homo Sapiens

<400> SEQUENCE: 1131
```

```
gactggagtt cagacgtgtg ctcttccgat ctggcctccc aaaatgttag gattacaggt    60
```

<210> SEQ ID NO 1132
<211> LENGTH: 59
<212> TYPE: DNA
<213> ORGANISM: Homo Sapiens

<400> SEQUENCE: 1132

```
gactggagtt cagacgtgtg ctcttccgat ctggcctcga tcttgtaggg gatgttgag     59
```

<210> SEQ ID NO 1133
<211> LENGTH: 53
<212> TYPE: DNA
<213> ORGANISM: Homo Sapiens

<400> SEQUENCE: 1133

```
gactggagtt cagacgtgtg ctcttccgat ctggcctgcc tccacttcaa cca            53
```

<210> SEQ ID NO 1134
<211> LENGTH: 54
<212> TYPE: DNA
<213> ORGANISM: Homo Sapiens

<400> SEQUENCE: 1134

```
gactggagtt cagacgtgtg ctcttccgat ctggcgatct gggactgcat gctg           54
```

<210> SEQ ID NO 1135
<211> LENGTH: 57
<212> TYPE: DNA
<213> ORGANISM: Homo Sapiens

<400> SEQUENCE: 1135

```
gactggagtt cagacgtgtg ctcttccgat ctggctcatc accacgctcc attatcc        57
```

<210> SEQ ID NO 1136
<211> LENGTH: 57
<212> TYPE: DNA
<213> ORGANISM: Homo Sapiens

<400> SEQUENCE: 1136

```
gactggagtt cagacgtgtg ctcttccgat ctggctgctg gacattgacg agacaga       57
```

<210> SEQ ID NO 1137
<211> LENGTH: 56
<212> TYPE: DNA
<213> ORGANISM: Homo Sapiens

<400> SEQUENCE: 1137

```
gactggagtt cagacgtgtg ctcttccgat ctggctgtgt ccacccctt actcat          56
```

<210> SEQ ID NO 1138
<211> LENGTH: 59
<212> TYPE: DNA
<213> ORGANISM: Homo Sapiens

<400> SEQUENCE: 1138

```
gactggagtt cagacgtgtg ctcttccgat ctgggaagca ggatctcagg tctctcaaa     59
```

<210> SEQ ID NO 1139
<211> LENGTH: 59
<212> TYPE: DNA
<213> ORGANISM: Homo Sapiens

<400> SEQUENCE: 1139

```
gactggagtt cagacgtgtg ctcttccgat ctgggaatgc ctggtttatt tgggactcc      59
```

<210> SEQ ID NO 1140
<211> LENGTH: 54
<212> TYPE: DNA
<213> ORGANISM: Homo Sapiens

<400> SEQUENCE: 1140

```
gactggagtt cagacgtgtg ctcttccgat ctgggacgtg cacaacctcg acta            54
```

<210> SEQ ID NO 1141
<211> LENGTH: 57
<212> TYPE: DNA
<213> ORGANISM: Homo Sapiens

<400> SEQUENCE: 1141

```
gactggagtt cagacgtgtg ctcttccgat ctgggacgtg cacaacctcg actacta         57
```

<210> SEQ ID NO 1142
<211> LENGTH: 56
<212> TYPE: DNA
<213> ORGANISM: Homo Sapiens

<400> SEQUENCE: 1142

```
gactggagtt cagacgtgtg ctcttccgat ctgggactag gcgtgggatg tttttg          56
```

<210> SEQ ID NO 1143
<211> LENGTH: 54
<212> TYPE: DNA
<213> ORGANISM: Homo Sapiens

<400> SEQUENCE: 1143

```
gactggagtt cagacgtgtg ctcttccgat ctgggagttg gggtgagggt gtct            54
```

<210> SEQ ID NO 1144
<211> LENGTH: 56
<212> TYPE: DNA
<213> ORGANISM: Homo Sapiens

<400> SEQUENCE: 1144

```
gactggagtt cagacgtgtg ctcttccgat ctgggcaaat gagtcacccg ctatgt          56
```

<210> SEQ ID NO 1145
<211> LENGTH: 54
<212> TYPE: DNA
<213> ORGANISM: Homo Sapiens

<400> SEQUENCE: 1145

```
gactggagtt cagacgtgtg ctcttccgat ctgggcagca ttgttggggg acac            54
```

<210> SEQ ID NO 1146
<211> LENGTH: 53
<212> TYPE: DNA
<213> ORGANISM: Homo Sapiens

<400> SEQUENCE: 1146

```
gactggagtt cagacgtgtg ctcttccgat ctgggcgggt ctctcggagg aag             53
```

<210> SEQ ID NO 1147
<211> LENGTH: 57
<212> TYPE: DNA
<213> ORGANISM: Homo Sapiens

<400> SEQUENCE: 1147
gactggagtt cagacgtgtg ctcttccgat ctgggctcgg gttggctcta aagtagt    57

<210> SEQ ID NO 1148
<211> LENGTH: 62
<212> TYPE: DNA
<213> ORGANISM: Homo Sapiens

<400> SEQUENCE: 1148
gactggagtt cagacgtgtg ctcttccgat ctgggcttga acatactaaa tgctccagta    60
ct    62

<210> SEQ ID NO 1149
<211> LENGTH: 59
<212> TYPE: DNA
<213> ORGANISM: Homo Sapiens

<400> SEQUENCE: 1149
gactggagtt cagacgtgtg ctcttccgat ctgggctttc tcggttctct gattcctgg    59

<210> SEQ ID NO 1150
<211> LENGTH: 60
<212> TYPE: DNA
<213> ORGANISM: Homo Sapiens

<400> SEQUENCE: 1150
gactggagtt cagacgtgtg ctcttccgat ctgggctttt gttttcttcc ctttagatgc    60

<210> SEQ ID NO 1151
<211> LENGTH: 60
<212> TYPE: DNA
<213> ORGANISM: Homo Sapiens

<400> SEQUENCE: 1151
gactggagtt cagacgtgtg ctcttccgat ctgggctttt gttttcttcc ctttagatgc    60

<210> SEQ ID NO 1152
<211> LENGTH: 63
<212> TYPE: DNA
<213> ORGANISM: Homo Sapiens

<400> SEQUENCE: 1152
gactggagtt cagacgtgtg ctcttccgat ctgggctttt gttttcttcc ctttagatgc    60
tct    63

<210> SEQ ID NO 1153
<211> LENGTH: 63
<212> TYPE: DNA
<213> ORGANISM: Homo Sapiens

<400> SEQUENCE: 1153
gactggagtt cagacgtgtg ctcttccgat ctgggctttt gttttcttcc ctttagatgc    60
tct    63

<210> SEQ ID NO 1154
<211> LENGTH: 57
<212> TYPE: DNA
<213> ORGANISM: Homo Sapiens

<400> SEQUENCE: 1154
gactggagtt cagacgtgtg ctcttccgat ctggggaagc aggatctcag gtctctc    57

<210> SEQ ID NO 1155
<211> LENGTH: 54
<212> TYPE: DNA
<213> ORGANISM: Homo Sapiens

<400> SEQUENCE: 1155
gactggagtt cagacgtgtg ctcttccgat ctggggacga tggggcaagt gatg         54

<210> SEQ ID NO 1156
<211> LENGTH: 54
<212> TYPE: DNA
<213> ORGANISM: Homo Sapiens

<400> SEQUENCE: 1156
gactggagtt cagacgtgtg ctcttccgat ctggggatcc tgtcggtgag cact         54

<210> SEQ ID NO 1157
<211> LENGTH: 57
<212> TYPE: DNA
<213> ORGANISM: Homo Sapiens

<400> SEQUENCE: 1157
gactggagtt cagacgtgtg ctcttccgat ctggggatgt gatgagaggt ggatggg      57

<210> SEQ ID NO 1158
<211> LENGTH: 60
<212> TYPE: DNA
<213> ORGANISM: Homo Sapiens

<400> SEQUENCE: 1158
gactggagtt cagacgtgtg ctcttccgat ctggggcaaa tttttaaagg cacaagaggc   60

<210> SEQ ID NO 1159
<211> LENGTH: 57
<212> TYPE: DNA
<213> ORGANISM: Homo Sapiens

<400> SEQUENCE: 1159
gactggagtt cagacgtgtg ctcttccgat ctggggctgg gcatcactgt aaacctt      57

<210> SEQ ID NO 1160
<211> LENGTH: 58
<212> TYPE: DNA
<213> ORGANISM: Homo Sapiens

<400> SEQUENCE: 1160
gactggagtt cagacgtgtg ctcttccgat ctgggggctt tctcggttct ctgattcc     58

<210> SEQ ID NO 1161
<211> LENGTH: 56
<212> TYPE: DNA
<213> ORGANISM: Homo Sapiens

<400> SEQUENCE: 1161
gactggagtt cagacgtgtg ctcttccgat ctgggggggct ttctcggttc tctgat      56

<210> SEQ ID NO 1162
<211> LENGTH: 59
<212> TYPE: DNA
<213> ORGANISM: Homo Sapiens

<400> SEQUENCE: 1162

```
gactggagtt cagacgtgtg ctcttccgat ctggggtggc tatgtagaga agttgtcct      59
```

<210> SEQ ID NO 1163
<211> LENGTH: 59
<212> TYPE: DNA
<213> ORGANISM: Homo Sapiens

<400> SEQUENCE: 1163

```
gactggagtt cagacgtgtg ctcttccgat ctggggtggt ctttgggatc ctcatcaag      59
```

<210> SEQ ID NO 1164
<211> LENGTH: 53
<212> TYPE: DNA
<213> ORGANISM: Homo Sapiens

<400> SEQUENCE: 1164

```
gactggagtt cagacgtgtg ctcttccgat ctgggtgggg ggctctcact gtc            53
```

<210> SEQ ID NO 1165
<211> LENGTH: 59
<212> TYPE: DNA
<213> ORGANISM: Homo Sapiens

<400> SEQUENCE: 1165

```
gactggagtt cagacgtgtg ctcttccgat ctgggttgta gtcggtcatg atggtcgag      59
```

<210> SEQ ID NO 1166
<211> LENGTH: 61
<212> TYPE: DNA
<213> ORGANISM: Homo Sapiens

<400> SEQUENCE: 1166

```
gactggagtt cagacgtgtg ctcttccgat ctggtaacca tttatttgtt ctctctccag      60
a                                                                      61
```

<210> SEQ ID NO 1167
<211> LENGTH: 54
<212> TYPE: DNA
<213> ORGANISM: Homo Sapiens

<400> SEQUENCE: 1167

```
gactggagtt cagacgtgtg ctcttccgat ctggtactgc cctattgccc ctgg            54
```

<210> SEQ ID NO 1168
<211> LENGTH: 59
<212> TYPE: DNA
<213> ORGANISM: Homo Sapiens

<400> SEQUENCE: 1168

```
gactggagtt cagacgtgtg ctcttccgat ctggtactta gatgggggat ggctgttgt      59
```

<210> SEQ ID NO 1169
<211> LENGTH: 58
<212> TYPE: DNA
<213> ORGANISM: Homo Sapiens

<400> SEQUENCE: 1169

```
gactggagtt cagacgtgtg ctcttccgat ctggtagaga tggcggttgg gaggtatc        58
```

<210> SEQ ID NO 1170
<211> LENGTH: 56
<212> TYPE: DNA
<213> ORGANISM: Homo Sapiens

<400> SEQUENCE: 1170
gactggagtt cagacgtgtg ctcttccgat ctggtattcg atgatccctg tggtgg        56

<210> SEQ ID NO 1171
<211> LENGTH: 61
<212> TYPE: DNA
<213> ORGANISM: Homo Sapiens

<400> SEQUENCE: 1171
gactggagtt cagacgtgtg ctcttccgat ctggtcaaaa ttagaacagt agatgcttag    60
t                                                                    61

<210> SEQ ID NO 1172
<211> LENGTH: 63
<212> TYPE: DNA
<213> ORGANISM: Homo Sapiens

<400> SEQUENCE: 1172
gactggagtt cagacgtgtg ctcttccgat ctggtcaaga gtcccaacca tgtcaaaatt    60
aca                                                                  63

<210> SEQ ID NO 1173
<211> LENGTH: 52
<212> TYPE: DNA
<213> ORGANISM: Homo Sapiens

<400> SEQUENCE: 1173
gactggagtt cagacgtgtg ctcttccgat ctggtctcac tcacccgcgg ac            52

<210> SEQ ID NO 1174
<211> LENGTH: 58
<212> TYPE: DNA
<213> ORGANISM: Homo Sapiens

<400> SEQUENCE: 1174
gactggagtt cagacgtgtg ctcttccgat ctggtctctc ggaggaagga cttgaggt      58

<210> SEQ ID NO 1175
<211> LENGTH: 57
<212> TYPE: DNA
<213> ORGANISM: Homo Sapiens

<400> SEQUENCE: 1175
gactggagtt cagacgtgtg ctcttccgat ctggtgaccg aggacaacgt gatgaag       57

<210> SEQ ID NO 1176
<211> LENGTH: 59
<212> TYPE: DNA
<213> ORGANISM: Homo Sapiens

<400> SEQUENCE: 1176
gactggagtt cagacgtgtg ctcttccgat ctggtgagaa agttaaaatt cccgtcgct     59

<210> SEQ ID NO 1177
<211> LENGTH: 56
<212> TYPE: DNA
<213> ORGANISM: Homo Sapiens

<400> SEQUENCE: 1177
gactggagtt cagacgtgtg ctcttccgat ctggtgagca ctgagggaat gaaagt        56

<210> SEQ ID NO 1178
<211> LENGTH: 53
<212> TYPE: DNA
<213> ORGANISM: Homo Sapiens

<400> SEQUENCE: 1178
gactggagtt cagacgtgtg ctcttccgat ctggtgcgca tgtactggtc ccg        53

<210> SEQ ID NO 1179
<211> LENGTH: 60
<212> TYPE: DNA
<213> ORGANISM: Homo Sapiens

<400> SEQUENCE: 1179
gactggagtt cagacgtgtg ctcttccgat ctggtggcta tgtagagaag ttgtcctgga    60

<210> SEQ ID NO 1180
<211> LENGTH: 65
<212> TYPE: DNA
<213> ORGANISM: Homo Sapiens

<400> SEQUENCE: 1180
gactggagtt cagacgtgtg ctcttccgat ctggtggctt tttgtttgtt tgttttgttt    60
taagg                                                              65

<210> SEQ ID NO 1181
<211> LENGTH: 62
<212> TYPE: DNA
<213> ORGANISM: Homo Sapiens

<400> SEQUENCE: 1181
gactggagtt cagacgtgtg ctcttccgat ctggtgtgtc tttaattgaa gcatgattta    60
aa                                                                 62

<210> SEQ ID NO 1182
<211> LENGTH: 59
<212> TYPE: DNA
<213> ORGANISM: Homo Sapiens

<400> SEQUENCE: 1182
gactggagtt cagacgtgtg ctcttccgat ctggttcctt caagctgccc tattgttac     59

<210> SEQ ID NO 1183
<211> LENGTH: 55
<212> TYPE: DNA
<213> ORGANISM: Homo Sapiens

<400> SEQUENCE: 1183
gactggagtt cagacgtgtg ctcttccgat ctggttcttt gggggcagag gggag         55

<210> SEQ ID NO 1184
<211> LENGTH: 58
<212> TYPE: DNA
<213> ORGANISM: Homo Sapiens

<400> SEQUENCE: 1184
gactggagtt cagacgtgtg ctcttccgat ctggttgact gggcagagtg acgatgag      58

<210> SEQ ID NO 1185
<211> LENGTH: 52
<212> TYPE: DNA
<213> ORGANISM: Homo Sapiens -continued

<400> SEQUENCE: 1185
gactggagtt cagacgtgtg ctcttccgat ctggttgtcc ggagcctagt ca            52

<210> SEQ ID NO 1186
<211> LENGTH: 55
<212> TYPE: DNA
<213> ORGANISM: Homo Sapiens

<400> SEQUENCE: 1186
gactggagtt cagacgtgtg ctcttccgat ctggttgtcc ggagcctagt caagc         55

<210> SEQ ID NO 1187
<211> LENGTH: 59
<212> TYPE: DNA
<213> ORGANISM: Homo Sapiens

<400> SEQUENCE: 1187
gactggagtt cagacgtgtg ctcttccgat ctgtaaagct ggaaagggac gaactggtg     59

<210> SEQ ID NO 1188
<211> LENGTH: 56
<212> TYPE: DNA
<213> ORGANISM: Homo Sapiens

<400> SEQUENCE: 1188
gactggagtt cagacgtgtg ctcttccgat ctgtaacgtc ctgtcctgcc cctgtc        56

<210> SEQ ID NO 1189
<211> LENGTH: 56
<212> TYPE: DNA
<213> ORGANISM: Homo Sapiens

<400> SEQUENCE: 1189
gactggagtt cagacgtgtg ctcttccgat ctgtaacgtc ctgtcctgcc cctgtc        56

<210> SEQ ID NO 1190
<211> LENGTH: 59
<212> TYPE: DNA
<213> ORGANISM: Homo Sapiens

<400> SEQUENCE: 1190
gactggagtt cagacgtgtg ctcttccgat ctgtacttac tcacttgcc cagcgtgtc      59

<210> SEQ ID NO 1191
<211> LENGTH: 59
<212> TYPE: DNA
<213> ORGANISM: Homo Sapiens

<400> SEQUENCE: 1191
gactggagtt cagacgtgtg ctcttccgat ctgtagaggg agtacagagt gaccgcctc     59

<210> SEQ ID NO 1192
<211> LENGTH: 56
<212> TYPE: DNA
<213> ORGANISM: Homo Sapiens

<400> SEQUENCE: 1192
gactggagtt cagacgtgtg ctcttccgat ctgtcaacca cccacatgtc atcaaa        56

<210> SEQ ID NO 1193
<211> LENGTH: 59
<212> TYPE: DNA

```
<213> ORGANISM: Homo Sapiens

<400> SEQUENCE: 1193
gactggagtt cagacgtgtg ctcttccgat ctgtcaagta cttacccact gaaaagcac      59

<210> SEQ ID NO 1194
<211> LENGTH: 59
<212> TYPE: DNA
<213> ORGANISM: Homo Sapiens

<400> SEQUENCE: 1194
gactggagtt cagacgtgtg ctcttccgat ctgtcagtcc ccagctactc tcaaaatca      59

<210> SEQ ID NO 1195
<211> LENGTH: 54
<212> TYPE: DNA
<213> ORGANISM: Homo Sapiens

<400> SEQUENCE: 1195
gactggagtt cagacgtgtg ctcttccgat ctgtccatgt gccctcctt ctgg            54

<210> SEQ ID NO 1196
<211> LENGTH: 59
<212> TYPE: DNA
<213> ORGANISM: Homo Sapiens

<400> SEQUENCE: 1196
gactggagtt cagacgtgtg ctcttccgat ctgtcccaac catgacaaga ttttccctt      59

<210> SEQ ID NO 1197
<211> LENGTH: 56
<212> TYPE: DNA
<213> ORGANISM: Homo Sapiens

<400> SEQUENCE: 1197
gactggagtt cagacgtgtg ctcttccgat ctgtccctta cttgttcagc tccttg         56

<210> SEQ ID NO 1198
<211> LENGTH: 59
<212> TYPE: DNA
<213> ORGANISM: Homo Sapiens

<400> SEQUENCE: 1198
gactggagtt cagacgtgtg ctcttccgat ctgtcctcaa aagacttggt gttgttgat      59

<210> SEQ ID NO 1199
<211> LENGTH: 59
<212> TYPE: DNA
<213> ORGANISM: Homo Sapiens

<400> SEQUENCE: 1199
gactggagtt cagacgtgtg ctcttccgat ctgtcctcca cacttctcca ttcttcaca     59

<210> SEQ ID NO 1200
<211> LENGTH: 56
<212> TYPE: DNA
<213> ORGANISM: Homo Sapiens

<400> SEQUENCE: 1200
gactggagtt cagacgtgtg ctcttccgat ctgtcctgag cctgccgaga ttccac         56

<210> SEQ ID NO 1201
<211> LENGTH: 59
```

```
<212> TYPE: DNA
<213> ORGANISM: Homo Sapiens

<400> SEQUENCE: 1201
gactggagtt cagacgtgtg ctcttccgat ctgtcctgag cctgttttgt gtctactgt      59

<210> SEQ ID NO 1202
<211> LENGTH: 55
<212> TYPE: DNA
<213> ORGANISM: Homo Sapiens

<400> SEQUENCE: 1202
gactggagtt cagacgtgtg ctcttccgat ctgtcctggg attgcagatt gggcc          55

<210> SEQ ID NO 1203
<211> LENGTH: 54
<212> TYPE: DNA
<213> ORGANISM: Homo Sapiens

<400> SEQUENCE: 1203
gactggagtt cagacgtgtg ctcttccgat ctgtctccaa cccattctgc ccag           54

<210> SEQ ID NO 1204
<211> LENGTH: 57
<212> TYPE: DNA
<213> ORGANISM: Homo Sapiens

<400> SEQUENCE: 1204
gactggagtt cagacgtgtg ctcttccgat ctgtctcctc caccgcttct tgtcctg        57

<210> SEQ ID NO 1205
<211> LENGTH: 57
<212> TYPE: DNA
<213> ORGANISM: Homo Sapiens

<400> SEQUENCE: 1205
gactggagtt cagacgtgtg ctcttccgat ctgtctgccg caaattccga gacgaag        57

<210> SEQ ID NO 1206
<211> LENGTH: 56
<212> TYPE: DNA
<213> ORGANISM: Homo Sapiens

<400> SEQUENCE: 1206
gactggagtt cagacgtgtg ctcttccgat ctgtgactat ctccctgggt gtagct         56

<210> SEQ ID NO 1207
<211> LENGTH: 59
<212> TYPE: DNA
<213> ORGANISM: Homo Sapiens

<400> SEQUENCE: 1207
gactggagtt cagacgtgtg ctcttccgat ctgtgactat ctccctgggt gtagctttt      59

<210> SEQ ID NO 1208
<211> LENGTH: 62
<212> TYPE: DNA
<213> ORGANISM: Homo Sapiens

<400> SEQUENCE: 1208
gactggagtt cagacgtgtg ctcttccgat ctgtgagagt gggtttatat taaaaagttg     60
gt                                                                    62
```

<210> SEQ ID NO 1209
<211> LENGTH: 56
<212> TYPE: DNA
<213> ORGANISM: Homo Sapiens

<400> SEQUENCE: 1209
gactggagtt cagacgtgtg ctcttccgat ctgtgagcca cgatgcccag tcaatc      56

<210> SEQ ID NO 1210
<211> LENGTH: 57
<212> TYPE: DNA
<213> ORGANISM: Homo Sapiens

<400> SEQUENCE: 1210
gactggagtt cagacgtgtg ctcttccgat ctgtgagcca cttcttacct tcacagc     57

<210> SEQ ID NO 1211
<211> LENGTH: 55
<212> TYPE: DNA
<213> ORGANISM: Homo Sapiens

<400> SEQUENCE: 1211
gactggagtt cagacgtgtg ctcttccgat ctgtgagcga gtcccacagt gagga       55

<210> SEQ ID NO 1212
<211> LENGTH: 59
<212> TYPE: DNA
<213> ORGANISM: Homo Sapiens

<400> SEQUENCE: 1212
gactggagtt cagacgtgtg ctcttccgat ctgtgatcct cctgccttgg cctctatta  59

<210> SEQ ID NO 1213
<211> LENGTH: 58
<212> TYPE: DNA
<213> ORGANISM: Homo Sapiens

<400> SEQUENCE: 1213
gactggagtt cagacgtgtg ctcttccgat ctgtgatctg gctcgtctgt gtgtgtca   58

<210> SEQ ID NO 1214
<211> LENGTH: 61
<212> TYPE: DNA
<213> ORGANISM: Homo Sapiens

<400> SEQUENCE: 1214
gactggagtt cagacgtgtg ctcttccgat ctgtgatgga tttgatgaat tggtgataag  60
a                                                                  61

<210> SEQ ID NO 1215
<211> LENGTH: 57
<212> TYPE: DNA
<213> ORGANISM: Homo Sapiens

<400> SEQUENCE: 1215
gactggagtt cagacgtgtg ctcttccgat ctgtgattgc aggttccaca cacaggc     57

<210> SEQ ID NO 1216
<211> LENGTH: 58
<212> TYPE: DNA
<213> ORGANISM: Homo Sapiens

<400> SEQUENCE: 1216

```
gactggagtt cagacgtgtg ctcttccgat ctgtgcaacg ggttccttcc ttcgagag        58
```

<210> SEQ ID NO 1217
<211> LENGTH: 56
<212> TYPE: DNA
<213> ORGANISM: Homo Sapiens

<400> SEQUENCE: 1217

```
gactggagtt cagacgtgtg ctcttccgat ctgtgcacga agggccaggg tatgtg          56
```

<210> SEQ ID NO 1218
<211> LENGTH: 53
<212> TYPE: DNA
<213> ORGANISM: Homo Sapiens

<400> SEQUENCE: 1218

```
gactggagtt cagacgtgtg ctcttccgat ctgtgcctct ccctccctcc agg             53
```

<210> SEQ ID NO 1219
<211> LENGTH: 59
<212> TYPE: DNA
<213> ORGANISM: Homo Sapiens

<400> SEQUENCE: 1219

```
gactggagtt cagacgtgtg ctcttccgat ctgtgctatt tttcctcaca gctcgttca      59
```

<210> SEQ ID NO 1220
<211> LENGTH: 53
<212> TYPE: DNA
<213> ORGANISM: Homo Sapiens

<400> SEQUENCE: 1220

```
gactggagtt cagacgtgtg ctcttccgat ctgtgctcca gacccctcac ctg             53
```

<210> SEQ ID NO 1221
<211> LENGTH: 59
<212> TYPE: DNA
<213> ORGANISM: Homo Sapiens

<400> SEQUENCE: 1221

```
gactggagtt cagacgtgtg ctcttccgat ctgtgctgct gtacatggcc actcagatc      59
```

<210> SEQ ID NO 1222
<211> LENGTH: 53
<212> TYPE: DNA
<213> ORGANISM: Homo Sapiens

<400> SEQUENCE: 1222

```
gactggagtt cagacgtgtg ctcttccgat ctgtgctgtg tccctgtcct gcc             53
```

<210> SEQ ID NO 1223
<211> LENGTH: 53
<212> TYPE: DNA
<213> ORGANISM: Homo Sapiens

<400> SEQUENCE: 1223

```
gactggagtt cagacgtgtg ctcttccgat ctgtggagcc tcttacaccc agt             53
```

<210> SEQ ID NO 1224
<211> LENGTH: 53
<212> TYPE: DNA
<213> ORGANISM: Homo Sapiens

```
<400> SEQUENCE: 1224
gactggagtt cagacgtgtg ctcttccgat ctgtggagcc tcttacaccc agt          53

<210> SEQ ID NO 1225
<211> LENGTH: 57
<212> TYPE: DNA
<213> ORGANISM: Homo Sapiens

<400> SEQUENCE: 1225
gactggagtt cagacgtgtg ctcttccgat ctgtggcgca tctccctcag gtagttc      57

<210> SEQ ID NO 1226
<211> LENGTH: 57
<212> TYPE: DNA
<213> ORGANISM: Homo Sapiens

<400> SEQUENCE: 1226
gactggagtt cagacgtgtg ctcttccgat ctgtggctcc agtctccctc ctgtttg      57

<210> SEQ ID NO 1227
<211> LENGTH: 56
<212> TYPE: DNA
<213> ORGANISM: Homo Sapiens

<400> SEQUENCE: 1227
gactggagtt cagacgtgtg ctcttccgat ctgtgggga agcaggatct caggtc        56

<210> SEQ ID NO 1228
<211> LENGTH: 54
<212> TYPE: DNA
<213> ORGANISM: Homo Sapiens

<400> SEQUENCE: 1228
gactggagtt cagacgtgtg ctcttccgat ctgtggggg ctctcactgt ctcc          54

<210> SEQ ID NO 1229
<211> LENGTH: 55
<212> TYPE: DNA
<213> ORGANISM: Homo Sapiens

<400> SEQUENCE: 1229
gactggagtt cagacgtgtg ctcttccgat ctgtgggggg ctttctcggt tctct        55

<210> SEQ ID NO 1230
<211> LENGTH: 55
<212> TYPE: DNA
<213> ORGANISM: Homo Sapiens

<400> SEQUENCE: 1230
gactggagtt cagacgtgtg ctcttccgat ctgtgggtgg tcagctgcaa catgg        55

<210> SEQ ID NO 1231
<211> LENGTH: 58
<212> TYPE: DNA
<213> ORGANISM: Homo Sapiens

<400> SEQUENCE: 1231
gactggagtt cagacgtgtg ctcttccgat ctgtgtactt acctcacttg cccagcgt     58

<210> SEQ ID NO 1232
<211> LENGTH: 58
<212> TYPE: DNA
<213> ORGANISM: Homo Sapiens
```

```
<400> SEQUENCE: 1232
gactggagtt cagacgtgtg ctcttccgat ctgtgtcttc ccacctacag taacaaag        58

<210> SEQ ID NO 1233
<211> LENGTH: 58
<212> TYPE: DNA
<213> ORGANISM: Homo Sapiens

<400> SEQUENCE: 1233
gactggagtt cagacgtgtg ctcttccgat ctgtgtgagt gaatgtgtgc caggggta        58

<210> SEQ ID NO 1234
<211> LENGTH: 57
<212> TYPE: DNA
<213> ORGANISM: Homo Sapiens

<400> SEQUENCE: 1234
gactggagtt cagacgtgtg ctcttccgat ctgtgtggat ggaggggcac tgaagtc         57

<210> SEQ ID NO 1235
<211> LENGTH: 59
<212> TYPE: DNA
<213> ORGANISM: Homo Sapiens

<400> SEQUENCE: 1235
gactggagtt cagacgtgtg ctcttccgat ctgtgtgtgg cgctgagtgt acttacctc       59

<210> SEQ ID NO 1236
<211> LENGTH: 55
<212> TYPE: DNA
<213> ORGANISM: Homo Sapiens

<400> SEQUENCE: 1236
gactggagtt cagacgtgtg ctcttccgat ctgtgttgat caggcgccca gtcac          55

<210> SEQ ID NO 1237
<211> LENGTH: 59
<212> TYPE: DNA
<213> ORGANISM: Homo Sapiens

<400> SEQUENCE: 1237
gactggagtt cagacgtgtg ctcttccgat ctgtgttgtg gagtgcaagt gaaagcctt       59

<210> SEQ ID NO 1238
<211> LENGTH: 59
<212> TYPE: DNA
<213> ORGANISM: Homo Sapiens

<400> SEQUENCE: 1238
gactggagtt cagacgtgtg ctcttccgat ctgttatcac tccacatttc agcaacagc       59

<210> SEQ ID NO 1239
<211> LENGTH: 58
<212> TYPE: DNA
<213> ORGANISM: Homo Sapiens

<400> SEQUENCE: 1239
gactggagtt cagacgtgtg ctcttccgat ctgttccctc agccgttacc tgtgtgtg        58

<210> SEQ ID NO 1240
<211> LENGTH: 56
<212> TYPE: DNA
```

-continued

<213> ORGANISM: Homo Sapiens

<400> SEQUENCE: 1240
gactggagtt cagacgtgtg ctcttccgat ctgttcgcca gccataagtc ctcgac        56

<210> SEQ ID NO 1241
<211> LENGTH: 58
<212> TYPE: DNA
<213> ORGANISM: Homo Sapiens

<400> SEQUENCE: 1241
gactggagtt cagacgtgtg ctcttccgat ctgttcggac agacaacccc aagagctg      58

<210> SEQ ID NO 1242
<211> LENGTH: 58
<212> TYPE: DNA
<213> ORGANISM: Homo Sapiens

<400> SEQUENCE: 1242
gactggagtt cagacgtgtg ctcttccgat ctgttctggg cactgggtca aagtctcc      58

<210> SEQ ID NO 1243
<211> LENGTH: 57
<212> TYPE: DNA
<213> ORGANISM: Homo Sapiens

<400> SEQUENCE: 1243
gactggagtt cagacgtgtg ctcttccgat ctgttctttg ggggcagagg ggagttg       57

<210> SEQ ID NO 1244
<211> LENGTH: 53
<212> TYPE: DNA
<213> ORGANISM: Homo Sapiens

<400> SEQUENCE: 1244
gactggagtt cagacgtgtg ctcttccgat ctgttgaccg catcgccacc ttg           53

<210> SEQ ID NO 1245
<211> LENGTH: 57
<212> TYPE: DNA
<213> ORGANISM: Homo Sapiens

<400> SEQUENCE: 1245
gactggagtt cagacgtgtg ctcttccgat ctgttggggt tgtagtcggt catgatg       57

<210> SEQ ID NO 1246
<211> LENGTH: 57
<212> TYPE: DNA
<213> ORGANISM: Homo Sapiens

<400> SEQUENCE: 1246
gactggagtt cagacgtgtg ctcttccgat ctgttgtccg gagcctagtc aagcctg       57

<210> SEQ ID NO 1247
<211> LENGTH: 58
<212> TYPE: DNA
<213> ORGANISM: Homo Sapiens

<400> SEQUENCE: 1247
gactggagtt cagacgtgtg ctcttccgat ctgtttgtga tggttgggag gctgtgtg      58

<210> SEQ ID NO 1248
<211> LENGTH: 59

```
<212> TYPE: DNA
<213> ORGANISM: Homo Sapiens

<400> SEQUENCE: 1248
gactggagtt cagacgtgtg ctcttccgat ctgttttcct ccaaatactg acagccaca      59

<210> SEQ ID NO 1249
<211> LENGTH: 58
<212> TYPE: DNA
<213> ORGANISM: Homo Sapiens

<400> SEQUENCE: 1249
gactggagtt cagacgtgtg ctcttccgat cttaacccac cttctgtccc acccttc        58

<210> SEQ ID NO 1250
<211> LENGTH: 59
<212> TYPE: DNA
<213> ORGANISM: Homo Sapiens

<400> SEQUENCE: 1250
gactggagtt cagacgtgtg ctcttccgat cttaacctttt cttatgtgc ttttagggc      59

<210> SEQ ID NO 1251
<211> LENGTH: 59
<212> TYPE: DNA
<213> ORGANISM: Homo Sapiens

<400> SEQUENCE: 1251
gactggagtt cagacgtgtg ctcttccgat cttaactcag cagcatctca gggccaaaa     59

<210> SEQ ID NO 1252
<211> LENGTH: 59
<212> TYPE: DNA
<213> ORGANISM: Homo Sapiens

<400> SEQUENCE: 1252
gactggagtt cagacgtgtg ctcttccgat cttaagtcct gagcctgttt tgtgtctac     59

<210> SEQ ID NO 1253
<211> LENGTH: 59
<212> TYPE: DNA
<213> ORGANISM: Homo Sapiens

<400> SEQUENCE: 1253
gactggagtt cagacgtgtg ctcttccgat cttaatgact cacctggggc cacatttga     59

<210> SEQ ID NO 1254
<211> LENGTH: 59
<212> TYPE: DNA
<213> ORGANISM: Homo Sapiens

<400> SEQUENCE: 1254
gactggagtt cagacgtgtg ctcttccgat cttaattttg cccagttcag gatccagcc     59

<210> SEQ ID NO 1255
<211> LENGTH: 59
<212> TYPE: DNA
<213> ORGANISM: Homo Sapiens

<400> SEQUENCE: 1255
gactggagtt cagacgtgtg ctcttccgat cttacacaca cgcaaaatac tccttcagc     59

<210> SEQ ID NO 1256
```

```
<211> LENGTH: 59
<212> TYPE: DNA
<213> ORGANISM: Homo Sapiens

<400> SEQUENCE: 1256
gactggagtt cagacgtgtg ctcttccgat cttaccaaat gtactcaagg cataaaagc      59

<210> SEQ ID NO 1257
<211> LENGTH: 59
<212> TYPE: DNA
<213> ORGANISM: Homo Sapiens

<400> SEQUENCE: 1257
gactggagtt cagacgtgtg ctcttccgat cttaccacag ttgcacaata tccttttga      59

<210> SEQ ID NO 1258
<211> LENGTH: 59
<212> TYPE: DNA
<213> ORGANISM: Homo Sapiens

<400> SEQUENCE: 1258
gactggagtt cagacgtgtg ctcttccgat cttacctcag tttgccccca tgtccctta      59

<210> SEQ ID NO 1259
<211> LENGTH: 59
<212> TYPE: DNA
<213> ORGANISM: Homo Sapiens

<400> SEQUENCE: 1259
gactggagtt cagacgtgtg ctcttccgat cttacctcag tttgccccca tgtccctta      59

<210> SEQ ID NO 1260
<211> LENGTH: 59
<212> TYPE: DNA
<213> ORGANISM: Homo Sapiens

<400> SEQUENCE: 1260
gactggagtt cagacgtgtg ctcttccgat cttaccttca gctgccactt ctacgactt      59

<210> SEQ ID NO 1261
<211> LENGTH: 59
<212> TYPE: DNA
<213> ORGANISM: Homo Sapiens

<400> SEQUENCE: 1261
gactggagtt cagacgtgtg ctcttccgat cttactggag aaaagggac atgctaggg      59

<210> SEQ ID NO 1262
<211> LENGTH: 59
<212> TYPE: DNA
<213> ORGANISM: Homo Sapiens

<400> SEQUENCE: 1262
gactggagtt cagacgtgtg ctcttccgat cttacttacg cgccacagag aagttgttg      59

<210> SEQ ID NO 1263
<211> LENGTH: 59
<212> TYPE: DNA
<213> ORGANISM: Homo Sapiens

<400> SEQUENCE: 1263
gactggagtt cagacgtgtg ctcttccgat cttagaaacc gaggtatgaa attcgctgg      59
```

```
<210> SEQ ID NO 1264
<211> LENGTH: 57
<212> TYPE: DNA
<213> ORGANISM: Homo Sapiens

<400> SEQUENCE: 1264
gactggagtt cagacgtgtg ctcttccgat cttagaagtg acgtctaggg gtggggg      57

<210> SEQ ID NO 1265
<211> LENGTH: 59
<212> TYPE: DNA
<213> ORGANISM: Homo Sapiens

<400> SEQUENCE: 1265
gactggagtt cagacgtgtg ctcttccgat cttagcaagg tgaagtaaga ctcaaatgt    59

<210> SEQ ID NO 1266
<211> LENGTH: 56
<212> TYPE: DNA
<213> ORGANISM: Homo Sapiens

<400> SEQUENCE: 1266
gactggagtt cagacgtgtg ctcttccgat cttagtaggg gaagatcatc tgctgg       56

<210> SEQ ID NO 1267
<211> LENGTH: 59
<212> TYPE: DNA
<213> ORGANISM: Homo Sapiens

<400> SEQUENCE: 1267
gactggagtt cagacgtgtg ctcttccgat cttagtaggg gaagatcatc tgctggccg    59

<210> SEQ ID NO 1268
<211> LENGTH: 59
<212> TYPE: DNA
<213> ORGANISM: Homo Sapiens

<400> SEQUENCE: 1268
gactggagtt cagacgtgtg ctcttccgat cttatagagc gtgcagataa tgacaagga    59

<210> SEQ ID NO 1269
<211> LENGTH: 59
<212> TYPE: DNA
<213> ORGANISM: Homo Sapiens

<400> SEQUENCE: 1269
gactggagtt cagacgtgtg ctcttccgat cttatctgta tcaaagaatg gtcctgcac    59

<210> SEQ ID NO 1270
<211> LENGTH: 59
<212> TYPE: DNA
<213> ORGANISM: Homo Sapiens

<400> SEQUENCE: 1270
gactggagtt cagacgtgtg ctcttccgat cttatctgta tcaaagaatg gtcctgcac    59

<210> SEQ ID NO 1271
<211> LENGTH: 59
<212> TYPE: DNA
<213> ORGANISM: Homo Sapiens

<400> SEQUENCE: 1271
gactggagtt cagacgtgtg ctcttccgat cttatttgtc cccttgcctc cctttccaa    59
```

<210> SEQ ID NO 1272
<211> LENGTH: 59
<212> TYPE: DNA
<213> ORGANISM: Homo Sapiens

<400> SEQUENCE: 1272
gactggagtt cagacgtgtg ctcttccgat cttcaaactc ctggcctctt gtgatcctc    59

<210> SEQ ID NO 1273
<211> LENGTH: 59
<212> TYPE: DNA
<213> ORGANISM: Homo Sapiens

<400> SEQUENCE: 1273
gactggagtt cagacgtgtg ctcttccgat cttcaaagtc agtccccagc tactctcaa    59

<210> SEQ ID NO 1274
<211> LENGTH: 60
<212> TYPE: DNA
<213> ORGANISM: Homo Sapiens

<400> SEQUENCE: 1274
gactggagtt cagacgtgtg ctcttccgat cttcaactaa acttctaaga tgtggcaaga   60

<210> SEQ ID NO 1275
<211> LENGTH: 59
<212> TYPE: DNA
<213> ORGANISM: Homo Sapiens

<400> SEQUENCE: 1275
gactggagtt cagacgtgtg ctcttccgat cttcaaggag ataagtgatg gagatgtga    59

<210> SEQ ID NO 1276
<211> LENGTH: 59
<212> TYPE: DNA
<213> ORGANISM: Homo Sapiens

<400> SEQUENCE: 1276
gactggagtt cagacgtgtg ctcttccgat cttcaatttg aggggagtc tgggaatga     59

<210> SEQ ID NO 1277
<211> LENGTH: 59
<212> TYPE: DNA
<213> ORGANISM: Homo Sapiens

<400> SEQUENCE: 1277
gactggagtt cagacgtgtg ctcttccgat cttcacagac atccttgcac atctctagc    59

<210> SEQ ID NO 1278
<211> LENGTH: 63
<212> TYPE: DNA
<213> ORGANISM: Homo Sapiens

<400> SEQUENCE: 1278
gactggagtt cagacgtgtg ctcttccgat cttcacatga atggaatagt ttaatagttt   60
gga                                                                63

<210> SEQ ID NO 1279
<211> LENGTH: 59
<212> TYPE: DNA
<213> ORGANISM: Homo Sapiens

<400> SEQUENCE: 1279

```
gactggagtt cagacgtgtg ctcttccgat cttcactcat atcctcctct ttctgccca    59

<210> SEQ ID NO 1280
<211> LENGTH: 59
<212> TYPE: DNA
<213> ORGANISM: Homo Sapiens

<400> SEQUENCE: 1280
gactggagtt cagacgtgtg ctcttccgat cttcactcat atcctcctct ttctgccca    59

<210> SEQ ID NO 1281
<211> LENGTH: 59
<212> TYPE: DNA
<213> ORGANISM: Homo Sapiens

<400> SEQUENCE: 1281
gactggagtt cagacgtgtg ctcttccgat cttcagcagc atctcagggc caaaaattt    59

<210> SEQ ID NO 1282
<211> LENGTH: 59
<212> TYPE: DNA
<213> ORGANISM: Homo Sapiens

<400> SEQUENCE: 1282
gactggagtt cagacgtgtg ctcttccgat cttcagccac gggtaataat ttttgtcct    59

<210> SEQ ID NO 1283
<211> LENGTH: 59
<212> TYPE: DNA
<213> ORGANISM: Homo Sapiens

<400> SEQUENCE: 1283
gactggagtt cagacgtgtg ctcttccgat cttcagctgc cacttctacg acttcttca    59

<210> SEQ ID NO 1284
<211> LENGTH: 60
<212> TYPE: DNA
<213> ORGANISM: Homo Sapiens

<400> SEQUENCE: 1284
gactggagtt cagacgtgtg ctcttccgat cttcaggaaa actacaatgg agaaagaaga    60

<210> SEQ ID NO 1285
<211> LENGTH: 59
<212> TYPE: DNA
<213> ORGANISM: Homo Sapiens

<400> SEQUENCE: 1285
gactggagtt cagacgtgtg ctcttccgat cttcaggtag gagagacatt taaggttcc    59

<210> SEQ ID NO 1286
<211> LENGTH: 59
<212> TYPE: DNA
<213> ORGANISM: Homo Sapiens

<400> SEQUENCE: 1286
gactggagtt cagacgtgtg ctcttccgat cttcagtaac tctacacaga aagggccca    59

<210> SEQ ID NO 1287
<211> LENGTH: 58
<212> TYPE: DNA
<213> ORGANISM: Homo Sapiens
```

```
<400> SEQUENCE: 1287
gactggagtt cagacgtgtg ctcttccgat cttcagtcca gacatgtagc tcctgtgc      58

<210> SEQ ID NO 1288
<211> LENGTH: 58
<212> TYPE: DNA
<213> ORGANISM: Homo Sapiens

<400> SEQUENCE: 1288
gactggagtt cagacgtgtg ctcttccgat cttcagtcca gacatgtagc tcctgtgc      58

<210> SEQ ID NO 1289
<211> LENGTH: 59
<212> TYPE: DNA
<213> ORGANISM: Homo Sapiens

<400> SEQUENCE: 1289
gactggagtt cagacgtgtg ctcttccgat cttcagtgtt acttacctgt cttgtcttt     59

<210> SEQ ID NO 1290
<211> LENGTH: 59
<212> TYPE: DNA
<213> ORGANISM: Homo Sapiens

<400> SEQUENCE: 1290
gactggagtt cagacgtgtg ctcttccgat cttcatagat aaaagctaag ttgccccag     59

<210> SEQ ID NO 1291
<211> LENGTH: 60
<212> TYPE: DNA
<213> ORGANISM: Homo Sapiens

<400> SEQUENCE: 1291
gactggagtt cagacgtgtg ctcttccgat cttcatattc gtccacaaaa tgattctgaa    60

<210> SEQ ID NO 1292
<211> LENGTH: 59
<212> TYPE: DNA
<213> ORGANISM: Homo Sapiens

<400> SEQUENCE: 1292
gactggagtt cagacgtgtg ctcttccgat cttcatgatt cgtcatagtt gttgcaagc     59

<210> SEQ ID NO 1293
<211> LENGTH: 60
<212> TYPE: DNA
<213> ORGANISM: Homo Sapiens

<400> SEQUENCE: 1293
gactggagtt cagacgtgtg ctcttccgat cttcatggga atttaaagga gctggaaaga    60

<210> SEQ ID NO 1294
<211> LENGTH: 59
<212> TYPE: DNA
<213> ORGANISM: Homo Sapiens

<400> SEQUENCE: 1294
gactggagtt cagacgtgtg ctcttccgat cttcatgtac tggtccctca ttgcactgt     59

<210> SEQ ID NO 1295
<211> LENGTH: 56
<212> TYPE: DNA
<213> ORGANISM: Homo Sapiens
```

<400> SEQUENCE: 1295
gactggagtt cagacgtgtg ctcttccgat cttcattatc tgaggagccg gtcacc            56

<210> SEQ ID NO 1296
<211> LENGTH: 59
<212> TYPE: DNA
<213> ORGANISM: Homo Sapiens

<400> SEQUENCE: 1296
gactggagtt cagacgtgtg ctcttccgat cttcattctt gaggaggaag tagcgtggc        59

<210> SEQ ID NO 1297
<211> LENGTH: 60
<212> TYPE: DNA
<213> ORGANISM: Homo Sapiens

<400> SEQUENCE: 1297
gactggagtt cagacgtgtg ctcttccgat cttccaatca aacccacaga cttacctaat      60

<210> SEQ ID NO 1298
<211> LENGTH: 58
<212> TYPE: DNA
<213> ORGANISM: Homo Sapiens

<400> SEQUENCE: 1298
gactggagtt cagacgtgtg ctcttccgat cttccaatgg aaagaaatg ctgcagaa          58

<210> SEQ ID NO 1299
<211> LENGTH: 59
<212> TYPE: DNA
<213> ORGANISM: Homo Sapiens

<400> SEQUENCE: 1299
gactggagtt cagacgtgtg ctcttccgat cttccactga agctgaatat taatggcca       59

<210> SEQ ID NO 1300
<211> LENGTH: 59
<212> TYPE: DNA
<213> ORGANISM: Homo Sapiens

<400> SEQUENCE: 1300
gactggagtt cagacgtgtg ctcttccgat cttccagtga aaaacaagct ctcatgtct       59

<210> SEQ ID NO 1301
<211> LENGTH: 62
<212> TYPE: DNA
<213> ORGANISM: Homo Sapiens

<400> SEQUENCE: 1301
gactggagtt cagacgtgtg ctcttccgat cttccagtgt ttcttttaaa tacctgttaa     60
gt                                                                    62

<210> SEQ ID NO 1302
<211> LENGTH: 59
<212> TYPE: DNA
<213> ORGANISM: Homo Sapiens

<400> SEQUENCE: 1302
gactggagtt cagacgtgtg ctcttccgat cttccataaa gacagaagga ggagagaca      59

<210> SEQ ID NO 1303

```
<211> LENGTH: 59
<212> TYPE: DNA
<213> ORGANISM: Homo Sapiens

<400> SEQUENCE: 1303
gactggagtt cagacgtgtg ctcttccgat ctttcccaagt tttctcccaa atcccattt     59

<210> SEQ ID NO 1304
<211> LENGTH: 59
<212> TYPE: DNA
<213> ORGANISM: Homo Sapiens

<400> SEQUENCE: 1304
gactggagtt cagacgtgtg ctcttccgat cttcccattt ctctttcagg tgacattga     59

<210> SEQ ID NO 1305
<211> LENGTH: 59
<212> TYPE: DNA
<213> ORGANISM: Homo Sapiens

<400> SEQUENCE: 1305
gactggagtt cagacgtgtg ctcttccgat cttccccaca atcatactgc tgacataca     59

<210> SEQ ID NO 1306
<211> LENGTH: 59
<212> TYPE: DNA
<213> ORGANISM: Homo Sapiens

<400> SEQUENCE: 1306
gactggagtt cagacgtgtg ctcttccgat cttcctcatt tggataggct tgtaagtgc     59

<210> SEQ ID NO 1307
<211> LENGTH: 59
<212> TYPE: DNA
<213> ORGANISM: Homo Sapiens

<400> SEQUENCE: 1307
gactggagtt cagacgtgtg ctcttccgat cttcctcatt tggataggct tgtaagtgc     59

<210> SEQ ID NO 1308
<211> LENGTH: 59
<212> TYPE: DNA
<213> ORGANISM: Homo Sapiens

<400> SEQUENCE: 1308
gactggagtt cagacgtgtg ctcttccgat cttcctctct caactccaac aggaaatca     59

<210> SEQ ID NO 1309
<211> LENGTH: 59
<212> TYPE: DNA
<213> ORGANISM: Homo Sapiens

<400> SEQUENCE: 1309
gactggagtt cagacgtgtg ctcttccgat cttcctgtaa ttttttcaagg cttcagtct    59

<210> SEQ ID NO 1310
<211> LENGTH: 59
<212> TYPE: DNA
<213> ORGANISM: Homo Sapiens

<400> SEQUENCE: 1310
gactggagtt cagacgtgtg ctcttccgat cttcctgtgg attttttaggc ccttgtatt    59
```

```
<210> SEQ ID NO 1311
<211> LENGTH: 59
<212> TYPE: DNA
<213> ORGANISM: Homo Sapiens

<400> SEQUENCE: 1311
gactggagtt cagacgtgtg ctcttccgat cttcctgttt cagtccccat taaatgagg    59

<210> SEQ ID NO 1312
<211> LENGTH: 59
<212> TYPE: DNA
<213> ORGANISM: Homo Sapiens

<400> SEQUENCE: 1312
gactggagtt cagacgtgtg ctcttccgat cttccttact catggtcgga tcacaaaga    59

<210> SEQ ID NO 1313
<211> LENGTH: 59
<212> TYPE: DNA
<213> ORGANISM: Homo Sapiens

<400> SEQUENCE: 1313
gactggagtt cagacgtgtg ctcttccgat cttccttttg aagaccataa cccaccaca    59

<210> SEQ ID NO 1314
<211> LENGTH: 59
<212> TYPE: DNA
<213> ORGANISM: Homo Sapiens

<400> SEQUENCE: 1314
gactggagtt cagacgtgtg ctcttccgat cttcgtccac aaaatgattc tgaattagc    59

<210> SEQ ID NO 1315
<211> LENGTH: 59
<212> TYPE: DNA
<213> ORGANISM: Homo Sapiens

<400> SEQUENCE: 1315
gactggagtt cagacgtgtg ctcttccgat cttctaactc tctttgactg cagaatcca    59

<210> SEQ ID NO 1316
<211> LENGTH: 66
<212> TYPE: DNA
<213> ORGANISM: Homo Sapiens

<400> SEQUENCE: 1316
gactggagtt cagacgtgtg ctcttccgat cttctaatga ctgagacaat aattattaaa   60
aggtga                                                              66

<210> SEQ ID NO 1317
<211> LENGTH: 59
<212> TYPE: DNA
<213> ORGANISM: Homo Sapiens

<400> SEQUENCE: 1317
gactggagtt cagacgtgtg ctcttccgat cttctacaca gaaagggccc aaattcacc    59

<210> SEQ ID NO 1318
<211> LENGTH: 59
<212> TYPE: DNA
<213> ORGANISM: Homo Sapiens

<400> SEQUENCE: 1318
```

```
gactggagtt cagacgtgtg ctcttccgat cttctacgac ttcttcaacc aggctgagt        59
```

<210> SEQ ID NO 1319
<211> LENGTH: 56
<212> TYPE: DNA
<213> ORGANISM: Homo Sapiens

<400> SEQUENCE: 1319

```
gactggagtt cagacgtgtg ctcttccgat cttctaggtg agaggcagtg gtcagg           56
```

<210> SEQ ID NO 1320
<211> LENGTH: 59
<212> TYPE: DNA
<213> ORGANISM: Homo Sapiens

<400> SEQUENCE: 1320

```
gactggagtt cagacgtgtg ctcttccgat cttctcaatg atgcttggct ctggaatgc        59
```

<210> SEQ ID NO 1321
<211> LENGTH: 59
<212> TYPE: DNA
<213> ORGANISM: Homo Sapiens

<400> SEQUENCE: 1321

```
gactggagtt cagacgtgtg ctcttccgat cttctccctg ggtgtagctt tttaaaaat        59
```

<210> SEQ ID NO 1322
<211> LENGTH: 58
<212> TYPE: DNA
<213> ORGANISM: Homo Sapiens

<400> SEQUENCE: 1322

```
gactggagtt cagacgtgtg ctcttccgat cttctccgga gcaaacccct atgtccac         58
```

<210> SEQ ID NO 1323
<211> LENGTH: 59
<212> TYPE: DNA
<213> ORGANISM: Homo Sapiens

<400> SEQUENCE: 1323

```
gactggagtt cagacgtgtg ctcttccgat cttctctctc cttttcctcc tcttctcct        59
```

<210> SEQ ID NO 1324
<211> LENGTH: 59
<212> TYPE: DNA
<213> ORGANISM: Homo Sapiens

<400> SEQUENCE: 1324

```
gactggagtt cagacgtgtg ctcttccgat cttctctctc ttgattctga ctctggcaa        59
```

<210> SEQ ID NO 1325
<211> LENGTH: 59
<212> TYPE: DNA
<213> ORGANISM: Homo Sapiens

<400> SEQUENCE: 1325

```
gactggagtt cagacgtgtg ctcttccgat cttctctgaa atcaacgtag aagtactca        59
```

<210> SEQ ID NO 1326
<211> LENGTH: 59
<212> TYPE: DNA
<213> ORGANISM: Homo Sapiens

<400> SEQUENCE: 1326

```
gactggagtt cagacgtgtg ctcttccgat cttctcttgc agtcgtcagc ctgaacata        59
```

\<210\> SEQ ID NO 1327
\<211\> LENGTH: 59
\<212\> TYPE: DNA
\<213\> ORGANISM: Homo Sapiens

\<400\> SEQUENCE: 1327

```
gactggagtt cagacgtgtg ctcttccgat cttctgaatt agctgtatcg tcaaggcac        59
```

\<210\> SEQ ID NO 1328
\<211\> LENGTH: 59
\<212\> TYPE: DNA
\<213\> ORGANISM: Homo Sapiens

\<400\> SEQUENCE: 1328

```
gactggagtt cagacgtgtg ctcttccgat cttctggaaa agagtaattc acacaagct        59
```

\<210\> SEQ ID NO 1329
\<211\> LENGTH: 63
\<212\> TYPE: DNA
\<213\> ORGANISM: Homo Sapiens

\<400\> SEQUENCE: 1329

```
gactggagtt cagacgtgtg ctcttccgat cttctgtatt tatttcagtg ttacttacct       60
gtc                                                                    63
```

\<210\> SEQ ID NO 1330
\<211\> LENGTH: 59
\<212\> TYPE: DNA
\<213\> ORGANISM: Homo Sapiens

\<400\> SEQUENCE: 1330

```
gactggagtt cagacgtgtg ctcttccgat cttctgtgag tgggatttgt tttgtgggc        59
```

\<210\> SEQ ID NO 1331
\<211\> LENGTH: 58
\<212\> TYPE: DNA
\<213\> ORGANISM: Homo Sapiens

\<400\> SEQUENCE: 1331

```
gactggagtt cagacgtgtg ctcttccgat cttctgtggc cttgtactgc agagacaa         58
```

\<210\> SEQ ID NO 1332
\<211\> LENGTH: 60
\<212\> TYPE: DNA
\<213\> ORGANISM: Homo Sapiens

\<400\> SEQUENCE: 1332

```
gactggagtt cagacgtgtg ctcttccgat cttcttagag catagtaagc agtagggagt       60
```

\<210\> SEQ ID NO 1333
\<211\> LENGTH: 59
\<212\> TYPE: DNA
\<213\> ORGANISM: Homo Sapiens

\<400\> SEQUENCE: 1333

```
gactggagtt cagacgtgtg ctcttccgat cttcttattc cagacgcatt tccacagct        59
```

\<210\> SEQ ID NO 1334
\<211\> LENGTH: 59
\<212\> TYPE: DNA

<213> ORGANISM: Homo Sapiens

<400> SEQUENCE: 1334
gactggagtt cagacgtgtg ctcttccgat cttcttcagc tttctcccac tgtattgaa        59

<210> SEQ ID NO 1335
<211> LENGTH: 59
<212> TYPE: DNA
<213> ORGANISM: Homo Sapiens

<400> SEQUENCE: 1335
gactggagtt cagacgtgtg ctcttccgat cttcttccca tgatgatctg tccctcaca        59

<210> SEQ ID NO 1336
<211> LENGTH: 59
<212> TYPE: DNA
<213> ORGANISM: Homo Sapiens

<400> SEQUENCE: 1336
gactggagtt cagacgtgtg ctcttccgat cttcttccca tgatgatctg tccctcaca        59

<210> SEQ ID NO 1337
<211> LENGTH: 59
<212> TYPE: DNA
<213> ORGANISM: Homo Sapiens

<400> SEQUENCE: 1337
gactggagtt cagacgtgtg ctcttccgat cttcttctct ttagggtcgg attccagtt        59

<210> SEQ ID NO 1338
<211> LENGTH: 59
<212> TYPE: DNA
<213> ORGANISM: Homo Sapiens

<400> SEQUENCE: 1338
gactggagtt cagacgtgtg ctcttccgat cttcttctgg gtgctgatac ttctctcca        59

<210> SEQ ID NO 1339
<211> LENGTH: 59
<212> TYPE: DNA
<213> ORGANISM: Homo Sapiens

<400> SEQUENCE: 1339
gactggagtt cagacgtgtg ctcttccgat cttcttgcca gagacatgta tgataaaga        59

<210> SEQ ID NO 1340
<211> LENGTH: 59
<212> TYPE: DNA
<213> ORGANISM: Homo Sapiens

<400> SEQUENCE: 1340
gactggagtt cagacgtgtg ctcttccgat cttcttggac ccatgactca acctcagta        59

<210> SEQ ID NO 1341
<211> LENGTH: 59
<212> TYPE: DNA
<213> ORGANISM: Homo Sapiens

<400> SEQUENCE: 1341
gactggagtt cagacgtgtg ctcttccgat cttctttcat cccttcctcc ctctttctt        59

<210> SEQ ID NO 1342
<211> LENGTH: 59

```
<212> TYPE: DNA
<213> ORGANISM: Homo Sapiens

<400> SEQUENCE: 1342
gactggagtt cagacgtgtg ctcttccgat cttctttcat cccttcctcc ctctttctt      59

<210> SEQ ID NO 1343
<211> LENGTH: 59
<212> TYPE: DNA
<213> ORGANISM: Homo Sapiens

<400> SEQUENCE: 1343
gactggagtt cagacgtgtg ctcttccgat cttctttccc cacaatcata ctgctgaca      59

<210> SEQ ID NO 1344
<211> LENGTH: 59
<212> TYPE: DNA
<213> ORGANISM: Homo Sapiens

<400> SEQUENCE: 1344
gactggagtt cagacgtgtg ctcttccgat cttctttgca ggggtggcta tgtagagaa      59

<210> SEQ ID NO 1345
<211> LENGTH: 60
<212> TYPE: DNA
<213> ORGANISM: Homo Sapiens

<400> SEQUENCE: 1345
gactggagtt cagacgtgtg ctcttccgat cttcttttga aaacaatggt gactacatgg     60

<210> SEQ ID NO 1346
<211> LENGTH: 60
<212> TYPE: DNA
<213> ORGANISM: Homo Sapiens

<400> SEQUENCE: 1346
gactggagtt cagacgtgtg ctcttccgat cttcttttta ccacagttgc acaatatcct     60

<210> SEQ ID NO 1347
<211> LENGTH: 56
<212> TYPE: DNA
<213> ORGANISM: Homo Sapiens

<400> SEQUENCE: 1347
gactggagtt cagacgtgtg ctcttccgat cttgaaagag acggagctga ggaagg         56

<210> SEQ ID NO 1348
<211> LENGTH: 59
<212> TYPE: DNA
<213> ORGANISM: Homo Sapiens

<400> SEQUENCE: 1348
gactggagtt cagacgtgtg ctcttccgat cttgaaagct taattctacc ttgtagcct      59

<210> SEQ ID NO 1349
<211> LENGTH: 59
<212> TYPE: DNA
<213> ORGANISM: Homo Sapiens

<400> SEQUENCE: 1349
gactggagtt cagacgtgtg ctcttccgat cttgaagacc ataacccacc acagctaga      59

<210> SEQ ID NO 1350
```

```
<211> LENGTH: 56
<212> TYPE: DNA
<213> ORGANISM: Homo Sapiens

<400> SEQUENCE: 1350
gactggagtt cagacgtgtg ctcttccgat cttgaagtca gaaggggtg cctttc        56

<210> SEQ ID NO 1351
<211> LENGTH: 60
<212> TYPE: DNA
<213> ORGANISM: Homo Sapiens

<400> SEQUENCE: 1351
gactggagtt cagacgtgtg ctcttccgat cttgacagtt tgacagttaa aggcatttcc   60

<210> SEQ ID NO 1352
<211> LENGTH: 60
<212> TYPE: DNA
<213> ORGANISM: Homo Sapiens

<400> SEQUENCE: 1352
gactggagtt cagacgtgtg ctcttccgat cttgacatat ggccatttct gttttcctgt   60

<210> SEQ ID NO 1353
<211> LENGTH: 59
<212> TYPE: DNA
<213> ORGANISM: Homo Sapiens

<400> SEQUENCE: 1353
gactggagtt cagacgtgtg ctcttccgat cttgacatca gtttgccagt tgtgcttttt   59

<210> SEQ ID NO 1354
<211> LENGTH: 59
<212> TYPE: DNA
<213> ORGANISM: Homo Sapiens

<400> SEQUENCE: 1354
gactggagtt cagacgtgtg ctcttccgat cttgacatca gtttgccagt tgtgcttttt   59

<210> SEQ ID NO 1355
<211> LENGTH: 60
<212> TYPE: DNA
<213> ORGANISM: Homo Sapiens

<400> SEQUENCE: 1355
gactggagtt cagacgtgtg ctcttccgat cttgaccttc ggcttttca accctttta     60

<210> SEQ ID NO 1356
<211> LENGTH: 59
<212> TYPE: DNA
<213> ORGANISM: Homo Sapiens

<400> SEQUENCE: 1356
gactggagtt cagacgtgtg ctcttccgat cttgagaggt ggatgggtag tagtatgga    59

<210> SEQ ID NO 1357
<211> LENGTH: 60
<212> TYPE: DNA
<213> ORGANISM: Homo Sapiens

<400> SEQUENCE: 1357
gactggagtt cagacgtgtg ctcttccgat cttgagcact gaatctataa agcatgtaac   60
```

-continued

<210> SEQ ID NO 1358
<211> LENGTH: 62
<212> TYPE: DNA
<213> ORGANISM: Homo Sapiens

<400> SEQUENCE: 1358
gactggagtt cagacgtgtg ctcttccgat cttgagcatt tgaagttttt attagtgatg    60
ga    62

<210> SEQ ID NO 1359
<211> LENGTH: 59
<212> TYPE: DNA
<213> ORGANISM: Homo Sapiens

<400> SEQUENCE: 1359
gactggagtt cagacgtgtg ctcttccgat cttgagccac ttcttacctt cacagccac    59

<210> SEQ ID NO 1360
<211> LENGTH: 60
<212> TYPE: DNA
<213> ORGANISM: Homo Sapiens

<400> SEQUENCE: 1360
gactggagtt cagacgtgtg ctcttccgat cttgagtcta tcgagtgtgt gcatatgtgt    60

<210> SEQ ID NO 1361
<211> LENGTH: 59
<212> TYPE: DNA
<213> ORGANISM: Homo Sapiens

<400> SEQUENCE: 1361
gactggagtt cagacgtgtg ctcttccgat cttgagtgca gttgtttacc atgataacg    59

<210> SEQ ID NO 1362
<211> LENGTH: 59
<212> TYPE: DNA
<213> ORGANISM: Homo Sapiens

<400> SEQUENCE: 1362
gactggagtt cagacgtgtg ctcttccgat cttgataccc cagctcagat cttctcccc    59

<210> SEQ ID NO 1363
<211> LENGTH: 59
<212> TYPE: DNA
<213> ORGANISM: Homo Sapiens

<400> SEQUENCE: 1363
gactggagtt cagacgtgtg ctcttccgat cttgatagtt gctaagaacc ggtcactga    59

<210> SEQ ID NO 1364
<211> LENGTH: 60
<212> TYPE: DNA
<213> ORGANISM: Homo Sapiens

<400> SEQUENCE: 1364
gactggagtt cagacgtgtg ctcttccgat cttgatgcga acagtgaata tttcctttga    60

<210> SEQ ID NO 1365
<211> LENGTH: 59
<212> TYPE: DNA
<213> ORGANISM: Homo Sapiens

<400> SEQUENCE: 1365

```
gactggagtt cagacgtgtg ctcttccgat cttgatgctg aggaagtgga ttttgcagg      59
```

<210> SEQ ID NO 1366
<211> LENGTH: 63
<212> TYPE: DNA
<213> ORGANISM: Homo Sapiens

<400> SEQUENCE: 1366

```
gactggagtt cagacgtgtg ctcttccgat cttgatggat ttgatgaatt ggtgataaga      60
tta                                                                    63
```

<210> SEQ ID NO 1367
<211> LENGTH: 59
<212> TYPE: DNA
<213> ORGANISM: Homo Sapiens

<400> SEQUENCE: 1367

```
gactggagtt cagacgtgtg ctcttccgat cttgatgtct atgaagtgtt gtggttcct       59
```

<210> SEQ ID NO 1368
<211> LENGTH: 59
<212> TYPE: DNA
<213> ORGANISM: Homo Sapiens

<400> SEQUENCE: 1368

```
gactggagtt cagacgtgtg ctcttccgat cttgattcgt catagttgtt gcaagccga       59
```

<210> SEQ ID NO 1369
<211> LENGTH: 58
<212> TYPE: DNA
<213> ORGANISM: Homo Sapiens

<400> SEQUENCE: 1369

```
gactggagtt cagacgtgtg ctcttccgat cttgcaaggt ttacacattt taatccca        58
```

<210> SEQ ID NO 1370
<211> LENGTH: 50
<212> TYPE: DNA
<213> ORGANISM: Homo Sapiens

<400> SEQUENCE: 1370

```
gactggagtt cagacgtgtg ctcttccgat cttgcaccgc gacctggcag                 50
```

<210> SEQ ID NO 1371
<211> LENGTH: 60
<212> TYPE: DNA
<213> ORGANISM: Homo Sapiens

<400> SEQUENCE: 1371

```
gactggagtt cagacgtgtg ctcttccgat cttgcagaaa gacttgaagg cgtatacagg      60
```

<210> SEQ ID NO 1372
<211> LENGTH: 56
<212> TYPE: DNA
<213> ORGANISM: Homo Sapiens

<400> SEQUENCE: 1372

```
gactggagtt cagacgtgtg ctcttccgat cttgcagaag tccaggctga aaaggc          56
```

<210> SEQ ID NO 1373
<211> LENGTH: 59
<212> TYPE: DNA
<213> ORGANISM: Homo Sapiens

<400> SEQUENCE: 1373
gactggagtt cagacgtgtg ctcttccgat cttgcagttt ttcctcctac tcaccatcc    59

<210> SEQ ID NO 1374
<211> LENGTH: 64
<212> TYPE: DNA
<213> ORGANISM: Homo Sapiens

<400> SEQUENCE: 1374
gactggagtt cagacgtgtg ctcttccgat cttgcataac aacaaagaat atgaatatgg    60
atca                                                                64

<210> SEQ ID NO 1375
<211> LENGTH: 61
<212> TYPE: DNA
<213> ORGANISM: Homo Sapiens

<400> SEQUENCE: 1375
gactggagtt cagacgtgtg ctcttccgat cttgccaaca tgacttactt gatccccata    60
a                                                                   61

<210> SEQ ID NO 1376
<211> LENGTH: 59
<212> TYPE: DNA
<213> ORGANISM: Homo Sapiens

<400> SEQUENCE: 1376
gactggagtt cagacgtgtg ctcttccgat cttgccagtt aacgtcttcc ttctctctc    59

<210> SEQ ID NO 1377
<211> LENGTH: 59
<212> TYPE: DNA
<213> ORGANISM: Homo Sapiens

<400> SEQUENCE: 1377
gactggagtt cagacgtgtg ctcttccgat cttgccagtt aacgtcttcc ttctctctc    59

<210> SEQ ID NO 1378
<211> LENGTH: 59
<212> TYPE: DNA
<213> ORGANISM: Homo Sapiens

<400> SEQUENCE: 1378
gactggagtt cagacgtgtg ctcttccgat cttgccagtt aacgtcttcc ttctctctc    59

<210> SEQ ID NO 1379
<211> LENGTH: 59
<212> TYPE: DNA
<213> ORGANISM: Homo Sapiens

<400> SEQUENCE: 1379
gactggagtt cagacgtgtg ctcttccgat cttgccatca ttctaggaag ctcaccatt    59

<210> SEQ ID NO 1380
<211> LENGTH: 59
<212> TYPE: DNA
<213> ORGANISM: Homo Sapiens

<400> SEQUENCE: 1380
gactggagtt cagacgtgtg ctcttccgat cttgccatgc tacctagata cctttccct    59

```
<210> SEQ ID NO 1381
<211> LENGTH: 59
<212> TYPE: DNA
<213> ORGANISM: Homo Sapiens

<400> SEQUENCE: 1381
gactggagtt cagacgtgtg ctcttccgat cttgccccca agaatcctag tagaatgtt         59

<210> SEQ ID NO 1382
<211> LENGTH: 60
<212> TYPE: DNA
<213> ORGANISM: Homo Sapiens

<400> SEQUENCE: 1382
gactggagtt cagacgtgtg ctcttccgat cttgcctcaa taagccaacc atgtctttca       60

<210> SEQ ID NO 1383
<211> LENGTH: 50
<212> TYPE: DNA
<213> ORGANISM: Homo Sapiens

<400> SEQUENCE: 1383
gactggagtt cagacgtgtg ctcttccgat cttgcctctg gtgcccccg                    50

<210> SEQ ID NO 1384
<211> LENGTH: 60
<212> TYPE: DNA
<213> ORGANISM: Homo Sapiens

<400> SEQUENCE: 1384
gactggagtt cagacgtgtg ctcttccgat cttgcctggc tccctaattt tatagttttt       60

<210> SEQ ID NO 1385
<211> LENGTH: 60
<212> TYPE: DNA
<213> ORGANISM: Homo Sapiens

<400> SEQUENCE: 1385
gactggagtt cagacgtgtg ctcttccgat cttgcgaaca gtgaatattt cctttgatga       60

<210> SEQ ID NO 1386
<211> LENGTH: 59
<212> TYPE: DNA
<213> ORGANISM: Homo Sapiens

<400> SEQUENCE: 1386
gactggagtt cagacgtgtg ctcttccgat cttgcgacag atccggaata ttgtagaga        59

<210> SEQ ID NO 1387
<211> LENGTH: 52
<212> TYPE: DNA
<213> ORGANISM: Homo Sapiens

<400> SEQUENCE: 1387
gactggagtt cagacgtgtg ctcttccgat cttgcggctc gtacacaggg ac               52

<210> SEQ ID NO 1388
<211> LENGTH: 59
<212> TYPE: DNA
<213> ORGANISM: Homo Sapiens

<400> SEQUENCE: 1388
gactggagtt cagacgtgtg ctcttccgat cttgctaacc aagttctttc ttttgcaca        59
```

<210> SEQ ID NO 1389
<211> LENGTH: 59
<212> TYPE: DNA
<213> ORGANISM: Homo Sapiens

<400> SEQUENCE: 1389
gactggagtt cagacgtgtg ctcttccgat cttgctaaga accggtcact gaaaatgaa    59

<210> SEQ ID NO 1390
<211> LENGTH: 59
<212> TYPE: DNA
<213> ORGANISM: Homo Sapiens

<400> SEQUENCE: 1390
gactggagtt cagacgtgtg ctcttccgat cttgctccca ggctgtttat ttgaagaga    59

<210> SEQ ID NO 1391
<211> LENGTH: 59
<212> TYPE: DNA
<213> ORGANISM: Homo Sapiens

<400> SEQUENCE: 1391
gactggagtt cagacgtgtg ctcttccgat cttgctggat tgaaattcac ttacaccgg    59

<210> SEQ ID NO 1392
<211> LENGTH: 56
<212> TYPE: DNA
<213> ORGANISM: Homo Sapiens

<400> SEQUENCE: 1392
gactggagtt cagacgtgtg ctcttccgat cttgctgtca gagttcaacg tcctga        56

<210> SEQ ID NO 1393
<211> LENGTH: 59
<212> TYPE: DNA
<213> ORGANISM: Homo Sapiens

<400> SEQUENCE: 1393
gactggagtt cagacgtgtg ctcttccgat cttgctgtga gggtttttg atgttacca     59

<210> SEQ ID NO 1394
<211> LENGTH: 59
<212> TYPE: DNA
<213> ORGANISM: Homo Sapiens

<400> SEQUENCE: 1394
gactggagtt cagacgtgtg ctcttccgat cttgcttttc taactctctt tgactgcag    59

<210> SEQ ID NO 1395
<211> LENGTH: 62
<212> TYPE: DNA
<213> ORGANISM: Homo Sapiens

<400> SEQUENCE: 1395
gactggagtt cagacgtgtg ctcttccgat cttgcttttc taactctctt tgactgcaga    60
at                                                                   62

<210> SEQ ID NO 1396
<211> LENGTH: 61
<212> TYPE: DNA
<213> ORGANISM: Homo Sapiens -continued

<400> SEQUENCE: 1396
gactggagtt cagacgtgtg ctcttccgat cttggaaaag agtaattcac acaagctcac    60
c                                                                   61

<210> SEQ ID NO 1397
<211> LENGTH: 59
<212> TYPE: DNA
<213> ORGANISM: Homo Sapiens

<400> SEQUENCE: 1397
gactggagtt cagacgtgtg ctcttccgat cttggaacta ggtcagctga agatcctgt     59

<210> SEQ ID NO 1398
<211> LENGTH: 54
<212> TYPE: DNA
<213> ORGANISM: Homo Sapiens

<400> SEQUENCE: 1398
gactggagtt cagacgtgtg ctcttccgat cttggaagcc aagcccagtt ctgg          54

<210> SEQ ID NO 1399
<211> LENGTH: 59
<212> TYPE: DNA
<213> ORGANISM: Homo Sapiens

<400> SEQUENCE: 1399
gactggagtt cagacgtgtg ctcttccgat cttggaagtc tatgtgatca agaaatcga    59

<210> SEQ ID NO 1400
<211> LENGTH: 62
<212> TYPE: DNA
<213> ORGANISM: Homo Sapiens

<400> SEQUENCE: 1400
gactggagtt cagacgtgtg ctcttccgat cttggaatcc agtgtttctt ttaaatacct   60
gt                                                                  62

<210> SEQ ID NO 1401
<211> LENGTH: 59
<212> TYPE: DNA
<213> ORGANISM: Homo Sapiens

<400> SEQUENCE: 1401
gactggagtt cagacgtgtg ctcttccgat cttggaccca tgactcaacc tcagtattt    59

<210> SEQ ID NO 1402
<211> LENGTH: 58
<212> TYPE: DNA
<213> ORGANISM: Homo Sapiens

<400> SEQUENCE: 1402
gactggagtt cagacgtgtg ctcttccgat cttggacgat ttcacccaga cccatgaa     58

<210> SEQ ID NO 1403
<211> LENGTH: 59
<212> TYPE: DNA
<213> ORGANISM: Homo Sapiens

<400> SEQUENCE: 1403
gactggagtt cagacgtgtg ctcttccgat cttggagaaa aatgtgattg cctgggtgt    59

```
<210> SEQ ID NO 1404
<211> LENGTH: 59
<212> TYPE: DNA
<213> ORGANISM: Homo Sapiens

<400> SEQUENCE: 1404
gactggagtt cagacgtgtg ctcttccgat cttggagaag ttagacatgt caaccttttt    59

<210> SEQ ID NO 1405
<211> LENGTH: 59
<212> TYPE: DNA
<213> ORGANISM: Homo Sapiens

<400> SEQUENCE: 1405
gactggagtt cagacgtgtg ctcttccgat cttggagtct ggatggaagg acaaaaaga    59

<210> SEQ ID NO 1406
<211> LENGTH: 59
<212> TYPE: DNA
<213> ORGANISM: Homo Sapiens

<400> SEQUENCE: 1406
gactggagtt cagacgtgtg ctcttccgat cttggatcat attggcctgt ctgctcttc    59

<210> SEQ ID NO 1407
<211> LENGTH: 59
<212> TYPE: DNA
<213> ORGANISM: Homo Sapiens

<400> SEQUENCE: 1407
gactggagtt cagacgtgtg ctcttccgat cttggatgtg attggaaagt ggggtaaaa    59

<210> SEQ ID NO 1408
<211> LENGTH: 59
<212> TYPE: DNA
<213> ORGANISM: Homo Sapiens

<400> SEQUENCE: 1408
gactggagtt cagacgtgtg ctcttccgat cttggattga aattcactta caccgggcc    59

<210> SEQ ID NO 1409
<211> LENGTH: 63
<212> TYPE: DNA
<213> ORGANISM: Homo Sapiens

<400> SEQUENCE: 1409
gactggagtt cagacgtgtg ctcttccgat cttggatttg atgaattggt gataagatta    60
aca                                                                  63

<210> SEQ ID NO 1410
<211> LENGTH: 61
<212> TYPE: DNA
<213> ORGANISM: Homo Sapiens

<400> SEQUENCE: 1410
gactggagtt cagacgtgtg ctcttccgat cttggcaaac aataccaaat ttacttcatg    60
t                                                                    61

<210> SEQ ID NO 1411
<211> LENGTH: 60
<212> TYPE: DNA
<213> ORGANISM: Homo Sapiens
```

```
<400> SEQUENCE: 1411
gactggagtt cagacgtgtg ctcttccgat cttggcaatt catttccaat caaacccaca     60

<210> SEQ ID NO 1412
<211> LENGTH: 53
<212> TYPE: DNA
<213> ORGANISM: Homo Sapiens

<400> SEQUENCE: 1412
gactggagtt cagacgtgtg ctcttccgat cttggcacat caagggaggg ttc            53

<210> SEQ ID NO 1413
<211> LENGTH: 62
<212> TYPE: DNA
<213> ORGANISM: Homo Sapiens

<400> SEQUENCE: 1413
gactggagtt cagacgtgtg ctcttccgat cttggcacat tccattctta ccaaactcta     60
aa                                                                    62

<210> SEQ ID NO 1414
<211> LENGTH: 62
<212> TYPE: DNA
<213> ORGANISM: Homo Sapiens

<400> SEQUENCE: 1414
gactggagtt cagacgtgtg ctcttccgat cttggcacat tccattctta ccaaactcta     60
aa                                                                    62

<210> SEQ ID NO 1415
<211> LENGTH: 61
<212> TYPE: DNA
<213> ORGANISM: Homo Sapiens

<400> SEQUENCE: 1415
gactggagtt cagacgtgtg ctcttccgat cttggcagtc aaaccttctc tcttatgtat     60
a                                                                     61

<210> SEQ ID NO 1416
<211> LENGTH: 64
<212> TYPE: DNA
<213> ORGANISM: Homo Sapiens

<400> SEQUENCE: 1416
gactggagtt cagacgtgtg ctcttccgat cttggcagtc aaaccttctc tcttatgtat     60
atat                                                                  64

<210> SEQ ID NO 1417
<211> LENGTH: 60
<212> TYPE: DNA
<213> ORGANISM: Homo Sapiens

<400> SEQUENCE: 1417
gactggagtt cagacgtgtg ctcttccgat cttggcatgg ggaaatataa acttgtttga     60

<210> SEQ ID NO 1418
<211> LENGTH: 57
<212> TYPE: DNA
<213> ORGANISM: Homo Sapiens

<400> SEQUENCE: 1418
```
gactggagtt cagacgtgtg ctcttccgat cttggccatg gaaccagaca gaaaagc        57

<210> SEQ ID NO 1419
<211> LENGTH: 59
<212> TYPE: DNA
<213> ORGANISM: Homo Sapiens

<400> SEQUENCE: 1419
gactggagtt cagacgtgtg ctcttccgat cttggccatt tctgttttcc tgtagcaaa       59

<210> SEQ ID NO 1420
<211> LENGTH: 59
<212> TYPE: DNA
<213> ORGANISM: Homo Sapiens

<400> SEQUENCE: 1420
gactggagtt cagacgtgtg ctcttccgat cttggcttga tcctgagtca tttcttcct       59

<210> SEQ ID NO 1421
<211> LENGTH: 62
<212> TYPE: DNA
<213> ORGANISM: Homo Sapiens

<400> SEQUENCE: 1421
gactggagtt cagacgtgtg ctcttccgat cttgggaaaa agtggtggta tacgatatgg      60
gt                                                                    62

<210> SEQ ID NO 1422
<211> LENGTH: 57
<212> TYPE: DNA
<213> ORGANISM: Homo Sapiens

<400> SEQUENCE: 1422
gactggagtt cagacgtgtg ctcttccgat cttgggaagg gacagaagat gacaggg         57

<210> SEQ ID NO 1423
<211> LENGTH: 61
<212> TYPE: DNA
<213> ORGANISM: Homo Sapiens

<400> SEQUENCE: 1423
gactggagtt cagacgtgtg ctcttccgat cttgggaatt taaaggagct ggaaagagtg      60
c                                                                     61

<210> SEQ ID NO 1424
<211> LENGTH: 59
<212> TYPE: DNA
<213> ORGANISM: Homo Sapiens

<400> SEQUENCE: 1424
gactggagtt cagacgtgtg ctcttccgat cttgggatgt ttttgcagat gatgggctc       59

<210> SEQ ID NO 1425
<211> LENGTH: 59
<212> TYPE: DNA
<213> ORGANISM: Homo Sapiens

<400> SEQUENCE: 1425
gactggagtt cagacgtgtg ctcttccgat cttgggcccc agaactaaca ggttaagtg       59

<210> SEQ ID NO 1426

```
<211> LENGTH: 59
<212> TYPE: DNA
<213> ORGANISM: Homo Sapiens

<400> SEQUENCE: 1426
gactggagtt cagacgtgtg ctcttccgat cttgggtaaa gatgatccga caagtgaga       59

<210> SEQ ID NO 1427
<211> LENGTH: 61
<212> TYPE: DNA
<213> ORGANISM: Homo Sapiens

<400> SEQUENCE: 1427
gactggagtt cagacgtgtg ctcttccgat cttgggtagc aaacttctgt acacaactaa      60
c                                                                      61

<210> SEQ ID NO 1428
<211> LENGTH: 61
<212> TYPE: DNA
<213> ORGANISM: Homo Sapiens

<400> SEQUENCE: 1428
gactggagtt cagacgtgtg ctcttccgat cttggtattt tggttctag atctttgttc       60 c                                                                      61

<210> SEQ ID NO 1429
<211> LENGTH: 59
<212> TYPE: DNA
<213> ORGANISM: Homo Sapiens

<400> SEQUENCE: 1429
gactggagtt cagacgtgtg ctcttccgat cttggtggct ttttgtttgt ttgttttgt      59

<210> SEQ ID NO 1430
<211> LENGTH: 62
<212> TYPE: DNA
<213> ORGANISM: Homo Sapiens

<400> SEQUENCE: 1430
gactggagtt cagacgtgtg ctcttccgat cttggtggct ttttgtttgt ttgttttgtt     60
tt                                                                     62

<210> SEQ ID NO 1431
<211> LENGTH: 60
<212> TYPE: DNA
<213> ORGANISM: Homo Sapiens

<400> SEQUENCE: 1431
gactggagtt cagacgtgtg ctcttccgat cttggttaca tacttggact tggtgataga     60

<210> SEQ ID NO 1432
<211> LENGTH: 61
<212> TYPE: DNA
<213> ORGANISM: Homo Sapiens

<400> SEQUENCE: 1432
gactggagtt cagacgtgtg ctcttccgat cttggttcag agttctatag attctagtgc     60
a                                                                      61

<210> SEQ ID NO 1433
<211> LENGTH: 60
```

```
<212> TYPE: DNA
<213> ORGANISM: Homo Sapiens

<400> SEQUENCE: 1433
gactggagtt cagacgtgtg ctcttccgat cttggttcta gatctttgtt ccttccattc    60

<210> SEQ ID NO 1434
<211> LENGTH: 61
<212> TYPE: DNA
<213> ORGANISM: Homo Sapiens

<400> SEQUENCE: 1434
gactggagtt cagacgtgtg ctcttccgat cttggttgat attattcttc ttgtgcctgg    60
g                                                                    61

<210> SEQ ID NO 1435
<211> LENGTH: 59
<212> TYPE: DNA
<213> ORGANISM: Homo Sapiens

<400> SEQUENCE: 1435
gactggagtt cagacgtgtg ctcttccgat cttggttgtg tttggttttg tgggagtct     59

<210> SEQ ID NO 1436
<211> LENGTH: 59
<212> TYPE: DNA
<213> ORGANISM: Homo Sapiens

<400> SEQUENCE: 1436
gactggagtt cagacgtgtg ctcttccgat cttggtttgt tttggttgtg tttggtttt     59

<210> SEQ ID NO 1437
<211> LENGTH: 60
<212> TYPE: DNA
<213> ORGANISM: Homo Sapiens

<400> SEQUENCE: 1437
gactggagtt cagacgtgtg ctcttccgat cttgtaagtc aaagggtat tcgatgatcc     60

<210> SEQ ID NO 1438
<211> LENGTH: 59
<212> TYPE: DNA
<213> ORGANISM: Homo Sapiens

<400> SEQUENCE: 1438
gactggagtt cagacgtgtg ctcttccgat cttgtaatca gacgacacag gaagcagat     59

<210> SEQ ID NO 1439
<211> LENGTH: 59
<212> TYPE: DNA
<213> ORGANISM: Homo Sapiens

<400> SEQUENCE: 1439
gactggagtt cagacgtgtg ctcttccgat cttgtaccaa cctcaccaac attacagag     59

<210> SEQ ID NO 1440
<211> LENGTH: 59
<212> TYPE: DNA
<213> ORGANISM: Homo Sapiens

<400> SEQUENCE: 1440
gactggagtt cagacgtgtg ctcttccgat cttgtaccaa cctcaccaac attacagag     59
```

<210> SEQ ID NO 1441
<211> LENGTH: 59
<212> TYPE: DNA
<213> ORGANISM: Homo Sapiens

<400> SEQUENCE: 1441
gactggagtt cagacgtgtg ctcttccgat cttgtagagg ttaatatccg caaatgact        59

<210> SEQ ID NO 1442
<211> LENGTH: 60
<212> TYPE: DNA
<213> ORGANISM: Homo Sapiens

<400> SEQUENCE: 1442
gactggagtt cagacgtgtg ctcttccgat cttgtaggag tggtcataag gctggtataa       60

<210> SEQ ID NO 1443
<211> LENGTH: 62
<212> TYPE: DNA
<213> ORGANISM: Homo Sapiens

<400> SEQUENCE: 1443
gactggagtt cagacgtgtg ctcttccgat cttgtattat atagggcaga gtcatgttag       60
tc                                                                     62

<210> SEQ ID NO 1444
<211> LENGTH: 57
<212> TYPE: DNA
<213> ORGANISM: Homo Sapiens

<400> SEQUENCE: 1444
gactggagtt cagacgtgtg ctcttccgat cttgtattca cagagacttg gcagcca          57

<210> SEQ ID NO 1445
<211> LENGTH: 59
<212> TYPE: DNA
<213> ORGANISM: Homo Sapiens

<400> SEQUENCE: 1445
gactggagtt cagacgtgtg ctcttccgat cttgtattta accatgcaga tcctcagtt        59

<210> SEQ ID NO 1446
<211> LENGTH: 59
<212> TYPE: DNA
<213> ORGANISM: Homo Sapiens

<400> SEQUENCE: 1446
gactggagtt cagacgtgtg ctcttccgat cttgtcaaaa attgtttctg gggccatcc        59

<210> SEQ ID NO 1447
<211> LENGTH: 59
<212> TYPE: DNA
<213> ORGANISM: Homo Sapiens

<400> SEQUENCE: 1447
gactggagtt cagacgtgtg ctcttccgat cttgtcaagc cctccaacat cctagtcaa        59

<210> SEQ ID NO 1448
<211> LENGTH: 59
<212> TYPE: DNA
<213> ORGANISM: Homo Sapiens

<400> SEQUENCE: 1448
gactggagtt cagacgtgtg ctcttccgat cttgtcacag caccctagaa ccaaatcca      59

<210> SEQ ID NO 1449
<211> LENGTH: 59
<212> TYPE: DNA
<213> ORGANISM: Homo Sapiens

<400> SEQUENCE: 1449
gactggagtt cagacgtgtg ctcttccgat cttgtcaccc acatcaagat tcagaacac      59

<210> SEQ ID NO 1450
<211> LENGTH: 59
<212> TYPE: DNA
<213> ORGANISM: Homo Sapiens

<400> SEQUENCE: 1450
gactggagtt cagacgtgtg ctcttccgat cttgtcagtc tgcccttctg tcaaagtgg      59

<210> SEQ ID NO 1451
<211> LENGTH: 55
<212> TYPE: DNA
<213> ORGANISM: Homo Sapiens

<400> SEQUENCE: 1451
gactggagtt cagacgtgtg ctcttccgat cttgtccagt cactgtgctg cttca          55

<210> SEQ ID NO 1452
<211> LENGTH: 59
<212> TYPE: DNA
<213> ORGANISM: Homo Sapiens

<400> SEQUENCE: 1452
gactggagtt cagacgtgtg ctcttccgat cttgtcctgc gtcatcatct ttgtcatcg      59

<210> SEQ ID NO 1453
<211> LENGTH: 59
<212> TYPE: DNA
<213> ORGANISM: Homo Sapiens

<400> SEQUENCE: 1453
gactggagtt cagacgtgtg ctcttccgat cttgtcctta ttacttggga gacttgtct      59

<210> SEQ ID NO 1454
<211> LENGTH: 59
<212> TYPE: DNA
<213> ORGANISM: Homo Sapiens

<400> SEQUENCE: 1454
gactggagtt cagacgtgtg ctcttccgat cttgtctatg aagtgttgtg gttccttaa      59

<210> SEQ ID NO 1455
<211> LENGTH: 59
<212> TYPE: DNA
<213> ORGANISM: Homo Sapiens

<400> SEQUENCE: 1455
gactggagtt cagacgtgtg ctcttccgat cttgtctcac tgcctcatct ctcaccatc      59

<210> SEQ ID NO 1456
<211> LENGTH: 60
<212> TYPE: DNA
<213> ORGANISM: Homo Sapiens

<400> SEQUENCE: 1456
gactggagtt cagacgtgtg ctcttccgat cttgtctcat cccaaatatt ctccaggcgt    60

<210> SEQ ID NO 1457
<211> LENGTH: 59
<212> TYPE: DNA
<213> ORGANISM: Homo Sapiens

<400> SEQUENCE: 1457
gactggagtt cagacgtgtg ctcttccgat cttgtgacct tcggcttttt caacccttt    59

<210> SEQ ID NO 1458
<211> LENGTH: 60
<212> TYPE: DNA
<213> ORGANISM: Homo Sapiens

<400> SEQUENCE: 1458
gactggagtt cagacgtgtg ctcttccgat cttgtgagtg ggatttgttt tgtgggctac    60

<210> SEQ ID NO 1459
<211> LENGTH: 59
<212> TYPE: DNA
<213> ORGANISM: Homo Sapiens

<400> SEQUENCE: 1459
gactggagtt cagacgtgtg ctcttccgat cttgtgatga gaggtggatg ggtagtagt    59

<210> SEQ ID NO 1460
<211> LENGTH: 59
<212> TYPE: DNA
<213> ORGANISM: Homo Sapiens

<400> SEQUENCE: 1460
gactggagtt cagacgtgtg ctcttccgat cttgtgcatt attgtgatga ttctgacct    59

<210> SEQ ID NO 1461
<211> LENGTH: 62
<212> TYPE: DNA
<213> ORGANISM: Homo Sapiens

<400> SEQUENCE: 1461
gactggagtt cagacgtgtg ctcttccgat cttgtgcatt attgtgatga ttctgaccta    60
ca                                                                  62

<210> SEQ ID NO 1462
<211> LENGTH: 59
<212> TYPE: DNA
<213> ORGANISM: Homo Sapiens

<400> SEQUENCE: 1462
gactggagtt cagacgtgtg ctcttccgat cttgtggcta catgttcctg atctcctta    59

<210> SEQ ID NO 1463
<211> LENGTH: 59
<212> TYPE: DNA
<213> ORGANISM: Homo Sapiens

<400> SEQUENCE: 1463
gactggagtt cagacgtgtg ctcttccgat cttgtgggta tttcagagag ggattaagt    59

<210> SEQ ID NO 1464
<211> LENGTH: 62

```
<212> TYPE: DNA
<213> ORGANISM: Homo Sapiens

<400> SEQUENCE: 1464
gactggagtt cagacgtgtg ctcttccgat cttgtgggta tttcagagag ggattaagta    60
at                                                                   62

<210> SEQ ID NO 1465
<211> LENGTH: 60
<212> TYPE: DNA
<213> ORGANISM: Homo Sapiens

<400> SEQUENCE: 1465
gactggagtt cagacgtgtg ctcttccgat cttgttaatg gtggcttttt gtttgtttgt    60

<210> SEQ ID NO 1466
<211> LENGTH: 59
<212> TYPE: DNA
<213> ORGANISM: Homo Sapiens

<400> SEQUENCE: 1466
gactggagtt cagacgtgtg ctcttccgat cttgttactt acctgtcttg tctttgctg     59

<210> SEQ ID NO 1467
<211> LENGTH: 59
<212> TYPE: DNA
<213> ORGANISM: Homo Sapiens

<400> SEQUENCE: 1467
gactggagtt cagacgtgtg ctcttccgat cttgttcctc aaagttttcc tctagcaga     59

<210> SEQ ID NO 1468
<211> LENGTH: 59
<212> TYPE: DNA
<213> ORGANISM: Homo Sapiens

<400> SEQUENCE: 1468
gactggagtt cagacgtgtg ctcttccgat cttgtttaac tttgtgtcgc tacctcagt     59

<210> SEQ ID NO 1469
<211> LENGTH: 59
<212> TYPE: DNA
<213> ORGANISM: Homo Sapiens

<400> SEQUENCE: 1469
gactggagtt cagacgtgtg ctcttccgat cttgtttatt ttgtttctcc cacacagac     59

<210> SEQ ID NO 1470
<211> LENGTH: 60
<212> TYPE: DNA
<213> ORGANISM: Homo Sapiens

<400> SEQUENCE: 1470
gactggagtt cagacgtgtg ctcttccgat cttgtttctg tcatccaaat actccacacg    60

<210> SEQ ID NO 1471
<211> LENGTH: 62
<212> TYPE: DNA
<213> ORGANISM: Homo Sapiens

<400> SEQUENCE: 1471
gactggagtt cagacgtgtg ctcttccgat cttgttttag aaagatcaca tcacatgaat    60
```

-continued

```
gg                                                             62

<210> SEQ ID NO 1472
<211> LENGTH: 67
<212> TYPE: DNA
<213> ORGANISM: Homo Sapiens

<400> SEQUENCE: 1472
gactggagtt cagacgtgtg ctcttccgat cttgttttga aatgtgtttt ataatttaga    60
ctagtga                                                       67

<210> SEQ ID NO 1473
<211> LENGTH: 59
<212> TYPE: DNA
<213> ORGANISM: Homo Sapiens

<400> SEQUENCE: 1473
gactggagtt cagacgtgtg ctcttccgat cttgttttgg ttgtgtttgg ttttgtggg    59

<210> SEQ ID NO 1474
<211> LENGTH: 59
<212> TYPE: DNA
<213> ORGANISM: Homo Sapiens

<400> SEQUENCE: 1474
gactggagtt cagacgtgtg ctcttccgat ctttaccatg gaccctgaca aatgtgctg    59

<210> SEQ ID NO 1475
<211> LENGTH: 59
<212> TYPE: DNA
<213> ORGANISM: Homo Sapiens

<400> SEQUENCE: 1475
gactggagtt cagacgtgtg ctcttccgat ctttacgcgc cacagagaag ttgttgagg    59

<210> SEQ ID NO 1476
<211> LENGTH: 68
<212> TYPE: DNA
<213> ORGANISM: Homo Sapiens

<400> SEQUENCE: 1476
gactggagtt cagacgtgtg ctcttccgat ctttagacta gtgaatattt ttctttgttt    60
tttaagga                                                      68

<210> SEQ ID NO 1477
<211> LENGTH: 59
<212> TYPE: DNA
<213> ORGANISM: Homo Sapiens

<400> SEQUENCE: 1477
gactggagtt cagacgtgtg ctcttccgat ctttagatgg gggatggctg ttgttaacc    59

<210> SEQ ID NO 1478
<211> LENGTH: 59
<212> TYPE: DNA
<213> ORGANISM: Homo Sapiens

<400> SEQUENCE: 1478
gactggagtt cagacgtgtg ctcttccgat ctttatagct gatttgatgg agttggaca    59

<210> SEQ ID NO 1479
<211> LENGTH: 59
```

```
<212> TYPE: DNA
<213> ORGANISM: Homo Sapiens

<400> SEQUENCE: 1479
gactggagtt cagacgtgtg ctcttccgat ctttattttg tttctcccac acagacact      59

<210> SEQ ID NO 1480
<211> LENGTH: 59
<212> TYPE: DNA
<213> ORGANISM: Homo Sapiens

<400> SEQUENCE: 1480
gactggagtt cagacgtgtg ctcttccgat ctttcaccca gacccatgaa taccacgtg      59

<210> SEQ ID NO 1481
<211> LENGTH: 57
<212> TYPE: DNA
<213> ORGANISM: Homo Sapiens

<400> SEQUENCE: 1481
gactggagtt cagacgtgtg ctcttccgat ctttcagggg gccatggtct tcgagtt        57

<210> SEQ ID NO 1482
<211> LENGTH: 59
<212> TYPE: DNA
<213> ORGANISM: Homo Sapiens

<400> SEQUENCE: 1482
gactggagtt cagacgtgtg ctcttccgat ctttcatccc ttcctccctc tttctttca      59

<210> SEQ ID NO 1483
<211> LENGTH: 59
<212> TYPE: DNA
<213> ORGANISM: Homo Sapiens

<400> SEQUENCE: 1483
gactggagtt cagacgtgtg ctcttccgat ctttcatccc ttcctccctc tttctttca      59

<210> SEQ ID NO 1484
<211> LENGTH: 58
<212> TYPE: DNA
<213> ORGANISM: Homo Sapiens

<400> SEQUENCE: 1484
gactggagtt cagacgtgtg ctcttccgat ctttcatggg aatttaaagg agctggaa       58

<210> SEQ ID NO 1485
<211> LENGTH: 59
<212> TYPE: DNA
<213> ORGANISM: Homo Sapiens

<400> SEQUENCE: 1485
gactggagtt cagacgtgtg ctcttccgat ctttcccaca gcaaaacacc aaaagacca      59

<210> SEQ ID NO 1486
<211> LENGTH: 59
<212> TYPE: DNA
<213> ORGANISM: Homo Sapiens

<400> SEQUENCE: 1486
gactggagtt cagacgtgtg ctcttccgat ctttcccttt ccgaatgcca aacaccttc      59

<210> SEQ ID NO 1487
```

```
<211> LENGTH: 59
<212> TYPE: DNA
<213> ORGANISM: Homo Sapiens

<400> SEQUENCE: 1487
gactggagtt cagacgtgtg ctcttccgat ctttccgact tccctttccg aatgccaaa      59

<210> SEQ ID NO 1488
<211> LENGTH: 59
<212> TYPE: DNA
<213> ORGANISM: Homo Sapiens

<400> SEQUENCE: 1488
gactggagtt cagacgtgtg ctcttccgat ctttcctgca gaaagacttg aaggcgtat      59

<210> SEQ ID NO 1489
<211> LENGTH: 59
<212> TYPE: DNA
<213> ORGANISM: Homo Sapiens

<400> SEQUENCE: 1489
gactggagtt cagacgtgtg ctcttccgat ctttctgccc tttgaacttg ctccctcag      59

<210> SEQ ID NO 1490
<211> LENGTH: 57
<212> TYPE: DNA
<213> ORGANISM: Homo Sapiens

<400> SEQUENCE: 1490
gactggagtt cagacgtgtg ctcttccgat ctttcttccc atgatgatct gtccctc        57

<210> SEQ ID NO 1491
<211> LENGTH: 59
<212> TYPE: DNA
<213> ORGANISM: Homo Sapiens

<400> SEQUENCE: 1491
gactggagtt cagacgtgtg ctcttccgat ctttctttaa atctgttttg ggggcttga      59

<210> SEQ ID NO 1492
<211> LENGTH: 59
<212> TYPE: DNA
<213> ORGANISM: Homo Sapiens

<400> SEQUENCE: 1492
gactggagtt cagacgtgtg ctcttccgat ctttgaaaac aatggtgact acatggaca      59

<210> SEQ ID NO 1493
<211> LENGTH: 58
<212> TYPE: DNA
<213> ORGANISM: Homo Sapiens

<400> SEQUENCE: 1493
gactggagtt cagacgtgtg ctcttccgat ctttgagggg ctgaggtgga agagacag       58

<210> SEQ ID NO 1494
<211> LENGTH: 57
<212> TYPE: DNA
<213> ORGANISM: Homo Sapiens

<400> SEQUENCE: 1494
gactggagtt cagacgtgtg ctcttccgat ctttgatggc aaacacacac aggaagc        57
```

```
<210> SEQ ID NO 1495
<211> LENGTH: 59
<212> TYPE: DNA
<213> ORGANISM: Homo Sapiens

<400> SEQUENCE: 1495
gactggagtt cagacgtgtg ctcttccgat ctttgatggg aaaaagtggt ggtatacga      59

<210> SEQ ID NO 1496
<211> LENGTH: 59
<212> TYPE: DNA
<213> ORGANISM: Homo Sapiens

<400> SEQUENCE: 1496
gactggagtt cagacgtgtg ctcttccgat ctttgcaggg gtggctatgt agagaagtt      59

<210> SEQ ID NO 1497
<211> LENGTH: 59
<212> TYPE: DNA
<213> ORGANISM: Homo Sapiens

<400> SEQUENCE: 1497
gactggagtt cagacgtgtg ctcttccgat ctttgccaac atgacttact tgatcccca      59

<210> SEQ ID NO 1498
<211> LENGTH: 59
<212> TYPE: DNA
<213> ORGANISM: Homo Sapiens

<400> SEQUENCE: 1498
gactggagtt cagacgtgtg ctcttccgat ctttgcctgt ctaaagaaca cttacctca      59

<210> SEQ ID NO 1499
<211> LENGTH: 59
<212> TYPE: DNA
<213> ORGANISM: Homo Sapiens

<400> SEQUENCE: 1499
gactggagtt cagacgtgtg ctcttccgat ctttgggggc ttgaacatac taaatgctc      59

<210> SEQ ID NO 1500
<211> LENGTH: 59
<212> TYPE: DNA
<213> ORGANISM: Homo Sapiens

<400> SEQUENCE: 1500
gactggagtt cagacgtgtg ctcttccgat ctttgggggtt gtagtcggtc atgatggtc     59

<210> SEQ ID NO 1501
<211> LENGTH: 59
<212> TYPE: DNA
<213> ORGANISM: Homo Sapiens

<400> SEQUENCE: 1501
gactggagtt cagacgtgtg ctcttccgat ctttgtaagt gcccgaagtg taagcccaa      59

<210> SEQ ID NO 1502
<211> LENGTH: 58
<212> TYPE: DNA
<213> ORGANISM: Homo Sapiens

<400> SEQUENCE: 1502
gactggagtt cagacgtgtg ctcttccgat ctttgtactg cagagacaag aggatggc       58
```

<210> SEQ ID NO 1503
<211> LENGTH: 59
<212> TYPE: DNA
<213> ORGANISM: Homo Sapiens

<400> SEQUENCE: 1503
gactggagtt cagacgtgtg ctcttccgat ctttgtagtc ggtcatgatg gtcgaggtg      59

<210> SEQ ID NO 1504
<211> LENGTH: 59
<212> TYPE: DNA
<213> ORGANISM: Homo Sapiens

<400> SEQUENCE: 1504
gactggagtt cagacgtgtg ctcttccgat ctttgtcgtc gattcttgtg tgctgtctt      59

<210> SEQ ID NO 1505
<211> LENGTH: 59
<212> TYPE: DNA
<213> ORGANISM: Homo Sapiens

<400> SEQUENCE: 1505
gactggagtt cagacgtgtg ctcttccgat ctttgttcct tccattctta tagagctca      59

<210> SEQ ID NO 1506
<211> LENGTH: 59
<212> TYPE: DNA
<213> ORGANISM: Homo Sapiens

<400> SEQUENCE: 1506
gactggagtt cagacgtgtg ctcttccgat ctttgtttgt ttcttttttc tccagttgg      59

<210> SEQ ID NO 1507
<211> LENGTH: 59
<212> TYPE: DNA
<213> ORGANISM: Homo Sapiens

<400> SEQUENCE: 1507
gactggagtt cagacgtgtg ctcttccgat cttttaaatc tgttttgggg gcttgaaca      59

<210> SEQ ID NO 1508
<211> LENGTH: 59
<212> TYPE: DNA
<213> ORGANISM: Homo Sapiens

<400> SEQUENCE: 1508
gactggagtt cagacgtgtg ctcttccgat cttttaacac atcaaggttg gaatgagct      59

<210> SEQ ID NO 1509
<211> LENGTH: 62
<212> TYPE: DNA
<213> ORGANISM: Homo Sapiens

<400> SEQUENCE: 1509
gactggagtt cagacgtgtg ctcttccgat cttttagaaa gatcacatca catgaatgga      60
at                                                                    62

<210> SEQ ID NO 1510
<211> LENGTH: 59
<212> TYPE: DNA
<213> ORGANISM: Homo Sapiens

<400> SEQUENCE: 1510
gactggagtt cagacgtgtg ctcttccgat cttttagacc ttgagttctt gagttcctc    59

<210> SEQ ID NO 1511
<211> LENGTH: 59
<212> TYPE: DNA
<213> ORGANISM: Homo Sapiens

<400> SEQUENCE: 1511
gactggagtt cagacgtgtg ctcttccgat cttttccaat caaacccaca gacttacct    59

<210> SEQ ID NO 1512
<211> LENGTH: 59
<212> TYPE: DNA
<213> ORGANISM: Homo Sapiens

<400> SEQUENCE: 1512
gactggagtt cagacgtgtg ctcttccgat cttttcccca aagtacaaac gagatgcct    59

<210> SEQ ID NO 1513
<211> LENGTH: 59
<212> TYPE: DNA
<213> ORGANISM: Homo Sapiens

<400> SEQUENCE: 1513
gactggagtt cagacgtgtg ctcttccgat cttttcctct gtgttggcgg ataccctc    59

<210> SEQ ID NO 1514
<211> LENGTH: 59
<212> TYPE: DNA
<213> ORGANISM: Homo Sapiens

<400> SEQUENCE: 1514
gactggagtt cagacgtgtg ctcttccgat cttttcctta gtctttcttt gaagcagca    59

<210> SEQ ID NO 1515
<211> LENGTH: 59
<212> TYPE: DNA
<213> ORGANISM: Homo Sapiens

<400> SEQUENCE: 1515
gactggagtt cagacgtgtg ctcttccgat cttttcttct tctcatcgcg ggcttggtt    59

<210> SEQ ID NO 1516
<211> LENGTH: 59
<212> TYPE: DNA
<213> ORGANISM: Homo Sapiens

<400> SEQUENCE: 1516
gactggagtt cagacgtgtg ctcttccgat cttttgaact tgctccctca ggctactca    59

<210> SEQ ID NO 1517
<211> LENGTH: 59
<212> TYPE: DNA
<213> ORGANISM: Homo Sapiens

<400> SEQUENCE: 1517
gactggagtt cagacgtgtg ctcttccgat cttttgacag tttgacagtt aaaggcatt    59

<210> SEQ ID NO 1518
<211> LENGTH: 59
<212> TYPE: DNA
<213> ORGANISM: Homo Sapiens

<400> SEQUENCE: 1518
gactggagtt cagacgtgtg ctcttccgat cttttgactc accgtggat gaagtggtt    59

<210> SEQ ID NO 1519
<211> LENGTH: 59
<212> TYPE: DNA
<213> ORGANISM: Homo Sapiens

<400> SEQUENCE: 1519
gactggagtt cagacgtgtg ctcttccgat cttttgagtc tatcgagtgt gtgcatatg    59

<210> SEQ ID NO 1520
<211> LENGTH: 59
<212> TYPE: DNA
<213> ORGANISM: Homo Sapiens

<400> SEQUENCE: 1520
gactggagtt cagacgtgtg ctcttccgat cttttgggaa tgcctggttt atttgggac    59

<210> SEQ ID NO 1521
<211> LENGTH: 59
<212> TYPE: DNA
<213> ORGANISM: Homo Sapiens

<400> SEQUENCE: 1521
gactggagtt cagacgtgtg ctcttccgat cttttggttc tagatctttg ttccttcca    59

<210> SEQ ID NO 1522
<211> LENGTH: 59
<212> TYPE: DNA
<213> ORGANISM: Homo Sapiens

<400> SEQUENCE: 1522
gactggagtt cagacgtgtg ctcttccgat cttttgttaa tggtggcttt tgtttgtt    59

<210> SEQ ID NO 1523
<211> LENGTH: 59
<212> TYPE: DNA
<213> ORGANISM: Homo Sapiens

<400> SEQUENCE: 1523
gactggagtt cagacgtgtg ctcttccgat cttttgtttc tcccacacag acactattg    59

<210> SEQ ID NO 1524
<211> LENGTH: 59
<212> TYPE: DNA
<213> ORGANISM: Homo Sapiens

<400> SEQUENCE: 1524
gactggagtt cagacgtgtg ctcttccgat ctttttatgg cagtcaaacc ttctctctt    59

<210> SEQ ID NO 1525
<211> LENGTH: 59
<212> TYPE: DNA
<213> ORGANISM: Homo Sapiens

<400> SEQUENCE: 1525
gactggagtt cagacgtgtg ctcttccgat ctttttctct tccctgcaga tgtcaagcc    59

<210> SEQ ID NO 1526
<211> LENGTH: 59
<212> TYPE: DNA
<213> ORGANISM: Homo Sapiens

```
<400> SEQUENCE: 1526
gactggagtt cagacgtgtg ctcttccgat cttttctct tgcagtcgtc agcctgaac      59

<210> SEQ ID NO 1527
<211> LENGTH: 59
<212> TYPE: DNA
<213> ORGANISM: Homo Sapiens

<400> SEQUENCE: 1527
gactggagtt cagacgtgtg ctcttccgat cttttgaag accataaccc accacagct      59

<210> SEQ ID NO 1528
<211> LENGTH: 60
<212> TYPE: DNA
<213> ORGANISM: Homo Sapiens

<400> SEQUENCE: 1528
gactggagtt cagacgtgtg ctcttccgat ctttttagc aaggtgaagt aagactcaaa     60

<210> SEQ ID NO 1529
<211> LENGTH: 60
<212> TYPE: DNA
<213> ORGANISM: Homo Sapiens

<400> SEQUENCE: 1529
gactggagtt cagacgtgtg ctcttccgat cttttttag caaggtgaag taagactcaa     60
```

COMPOSITIONS AND METHODS FOR LIBRARY CONSTRUCTION AND SEQUENCE ANALYSIS

CROSS-REFERENCE TO RELATED APPLICATIONS

This application is a U.S. national phase filing of International Patent Application No. PCT/US2018/028191, entitled "Compositions and methods for library construction and sequence analysis," filed on Apr. 18, 2018, which PCT application claims benefit of priority to U.S. Provisional Application Ser. No. 62/487,423, filed Apr. 19, 2017, and U.S. Provisional Application Ser. No. 62/657,544, filed Apr. 13, 2018. In some aspect, the present disclosure relates to U.S. provisional application Ser. No. 62/487,422, filed on Apr. 19, 2017. The contents of all of the above-described applications are incorporated by reference in their entireties for all purposes.

TECHNICAL FIELD

The present disclosure relates to compositions, kits, devices, and methods for conducting genetic and genomic analysis, for example, by polynucleotide sequencing. In particular aspects, provided herein are compositions, kits, and methods for constructing libraries with improved ligation efficiency and conversion rate during sequencing. In certain embodiments, the compositions, kits, and methods herein are useful for analyzing polynucleotide fragments, such as circulating polynucleotide fragments in the body of a subject, including circulating tumor DNA.

BACKGROUND

In the following discussion, certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Despite several improvements in library construction over the last several years, the process of library construction for next generation sequencing remains inefficient, resulting in many original molecules lost during the various steps. Double stranded ligation efficiency remains low, with ~20-30% of the molecules being properly ligated. Additionally, many molecules are lost during the purification and hybridization capture steps, so that the final conversion rate approximates 10-20%. Sensitivity remains low, when interrogating low allele fraction variants, for example, those found in circulating tumor DNA (ctDNA). This limits the accuracy when calling low allele fraction mutants, since the low efficiency will result in sensitivity loss when looking at libraries with low allele fractions.

There is a need for improved analytical technology to overcome the above issues of art. The present disclosure addresses this and other related needs.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one embodiment, provided herein is a method, comprising ligating a set of adaptors to a library of single-stranded polynucleotides. In one aspect, the ligation is catalyzed by a single-stranded DNA (ssDNA) ligase. In another aspect, each single-stranded polynucleotide is blocked at the 5' end to prevent ligation at the 5' end. In yet another aspect, each adaptor comprises a unique molecular identifier (UMI) sequence that earmarks the single-stranded polynucleotide to which the adaptor is ligated. In one other aspect, each adaptor is blocked at the 3' end to prevent ligation at the 3' end. In one aspect, the 5' end of the adaptor is ligated to the 3' end of the single-stranded polynucleotide by the ssDNA ligase to form a linear ligation product. In any of the preceding embodiments, a library of linear, single-stranded ligation products can be obtained.

In another embodiment, a method comprising ligating a set of adaptors to a library of single-stranded polynucleotides is provided, and in the method, the ligation is catalyzed by a single-stranded DNA (ssDNA) ligase, each single-stranded polynucleotide is blocked at the 5' end to prevent ligation at the 5' end, each adaptor comprises a unique molecular identifier (UMI) sequence that earmarks the single-stranded polynucleotide to which the adaptor is ligated, each adaptor is blocked at the 3' end to prevent ligation at the 3' end, and the 5' end of the adaptor is ligated to the 3' end of the single-stranded polynucleotide by the ssDNA ligase to form a linear ligation product, thereby obtaining a library of linear, single-stranded ligation products.

In any of the preceding embodiments, the method can further comprise before the ligation step, a step of obtaining the library of single-stranded polynucleotides from a sample. In one aspect, the obtaining step comprises denaturing double-stranded polynucleotides from the sample.

In any of the preceding embodiments, the sample can be a biological sample. In some embodiments, the biological sample is obtained directly from a subject without any treatment. In some embodiments, the polynucleotides in the biological sample have not been subject to bisulfite conversion. In other embodiments, the polynucleotides in the biological sample have been subject to partial or complete bisulfite conversion. In certain aspects, the biological sample is from a subject having or suspected of having a disease or condition, such as a cancer or neoplasia.

In any of the preceding embodiments, the single-stranded polynucleotides can be from a sample comprising circulating tumor DNA (ctDNA), such as a blood, serum, plasma, or body fluid sample, or any combination thereof.

In any of the preceding embodiments, the single-stranded polynucleotides can be between about 20 and about 400 nucleic acid residues in length, for example, about 80, about 100, about 120, about 140, about 160, about 180, about 200, about 220, or about 240 nucleic acid residues in length.

In any of the preceding embodiments, the ssDNA ligase can be a *Thermus* bacteriophage RNA ligase such as a bacteriophage TS2126 RNA ligase (e.g., CircLigase™ and CircLigase II™), or an archaebacterium RNA ligase such as *Methanobacterium thermoautotrophicum* RNA ligase 1. In other aspects, the ssDNA ligase is an RNA ligase, such as a T4 RNA ligase, e.g., T4 RNA ligase 1, e.g., New England Biosciences, M0204S, T4 RNA ligase 2, e.g., New England Biosciences. M0239S. T4 RNA ligase 2 truncated, e.g., New England Biosciences. M0242S. T4 RNA ligase 2 truncated KQ, e.g., M0373S, or T4 RNA ligase 2 truncated K227Q, e.g., New England Biosciences, M0351S. In any of the preceding embodiments, the kit can also comprise a thermostable 5' App DNA/RNA ligase, e.g., New England Biosciences. M0319S, or T4 DNA ligase, e.g., New England Biosciences. M0202S.

In any of the preceding embodiments, the blocking of each single-stranded polynucleotide can comprise dephosphorylation to prevent ligation at its 5' end.

In any of the preceding embodiments, the blocking of each adaptor can comprise a carbon spacer, ddCTP, ddATP, ddTTP, ddGTP, hexanediol, triethylene glycol, and/or hexaethylene glycol, to prevent ligation at its 3' end.

In any of the preceding embodiments, each adaptor can comprise a dinucleotide sequence at the 5' end, such as GA (5' to 3'), GG (5' to 3'), AA (5' to 3'), or AG (5' to 3'), which is 5' to the UMI sequence.

In any of the preceding embodiments, the UMI sequence in each adaptor can be between about 6 and about 15 nucleic acid residues in length, for example, the UMI sequence is a 12-mer.

In any of the preceding embodiments, the ligation reaction can be conducted in the presence of a crowding agent. In one aspect, the crowding agent comprises a polyethylene glycol (PEG), such as PEG 4000 or PEG 6000, Dextran, and/or Ficoll.

In any of the preceding embodiments, the method can further comprise converting the library of linear, single-stranded ligation products into a library of linear, double-stranded ligation products. In one aspect, the conversion uses a primer or a set of primers each comprising a sequence that is reverse-complement to the adaptor and/or hybridizable to the adaptor.

In any of the preceding embodiments, the method can further comprise amplifying and/or purifying the library of linear, double-stranded ligation products. In one aspect, the purification is bead-based. In another aspect, the purification is based on size selection, for example, the purification step selectively purifies polynucleotides between about 50 nucleotides and about 1000 nucleotides in lengths, for example, adaptors of about 40 nucleotides in length (and primer dimers and/or primer-adaptor duplexes of about 40 bp) are removed. In another aspect, the purification does not comprise using a specific binding pair (such as biotin/streptavidin), one of which is attached to the linear, double-stranded ligation product and the other is attached to a solid support (such as a bead). In one aspect, the purification is column-based, for example, by using a dsDNA or ssDNA purification column, such as those from Zymo or Qiagen.

In any of the preceding embodiments, the method herein can further comprise amplifying the library of linear, double-stranded ligation products, e.g., by a polymerase chain reaction (PCR), to obtain an amplified library of linear, double-stranded ligation products comprising sequence information of a target sequence. In one aspect, the method comprises using a primer or a set of primers each comprising a sequence that is reverse-complement to the adaptor and/or hybridizable to the adaptor. In another aspect, the method further comprises using a primer hybridizable to the target sequence (e.g., an EGFR gene sequence).

In any of the preceding embodiments, the method herein can comprise amplifying the library of linear, double-stranded ligation products, e.g., by a polymerase chain reaction (PCR), using a primer or a set of primers each comprising a sequence that is reverse-complement to the adaptor and/or hybridizable to the adaptor, a primer hybridizable to the target sequence (e.g., an EGFR gene sequence), thereby obtaining an amplified library of linear, double-stranded ligation products comprising sequence information of the target sequence.

In any of the preceding embodiments, the target-specific primer can comprise any one or more sequences selected from the group consisting of SEQ ID NOs: 4-1529, or a complementary or substantially complementary sequence thereof.

In any of the preceding embodiments, a plurality of primers can be used, each comprising a sequence specific for the target sequence and the primers have the same or different target sequences. In one aspect, the plurality of primers comprise any one or more, e.g., about 10, 20, 50, 100, 150, 200, 250, 300, 400, 500, 600, 700, 800, 900, 1,000, 1,100, 1,200, 1,300, 1,400, 1,500, or all of 1529 of SEQ ID NOs. 4-1529, or a complementary or substantially complementary sequence thereof, or a numerical range or subrange thereof.

In any of the preceding embodiments, the sequence information of the target sequence can comprise a mutation, a single nucleotide polymorphism (SNP), a copy number variation (CNV), or an epigenetic change. In one aspect, the mutation comprises a point mutation, an insertion, a deletion, an inversion, a truncation, a fusion, an amplification, or any combination thereof.

In any of the preceding embodiments, the amplified library of linear, double-stranded ligation products can be a library other than a whole genome library, for example, a semi-targeted genome library.

In any of the preceding embodiments, the method can further comprise purifying the amplified library of linear, double-stranded ligation products. In one aspect, the purification is bead-based in another aspect, the purification is based on size selection, for example, the purification step selectively purifies polynucleotides greater about 150 nucleotides in lengths. In another aspect, the purification does not comprise using a specific binding pair (such as biotin/streptavidin), one of which is attached to the linear, double-stranded ligation product and the other is attached to a solid support (such as a bead). In one aspect, the purification is column-based, for example, by using a dsDNA or ssDNA purification column, such as those from Zymo or Qiagen.

In any of the preceding embodiments, the method can further comprise sequencing the purified amplified library of linear, double-stranded ligation products. In one aspect, the sequencing step comprises attaching a sequencing adapter and/or a sample-specific barcode to each linear, double-stranded ligation product in one particular aspect, the attaching step is performed using a polymerase chain reaction (PCR).

In any of the preceding embodiments, the conversion rate of the sequencing (percentage of single-stranded polynucleotides in the library that give rise to sequencing reads) ma % be at least about 40%, at least about 50%, at least about 60%, at least about 70%, at least about 80%, or at least about 90,%.

In any of the preceding embodiments, the method can be used for the diagnosis and/or prognosis of a disease or condition in a subject, predicting the responsiveness of a subject to a treatment, identifying a pharmacogenetics marker for the disease/condition or treatment, and/or screening a population for a genetic information. In one aspect, the disease or condition is a cancer or neoplasia, and the treatment is a cancer or neoplasia treatment.

In another aspect, disclosed herein is a library of linear, single-stranded ligation products produced by the method of any of proceeding embodiments.

In yet another aspect, disclosed herein is a library of linear, double-stranded ligation products produced by the method of any of proceeding embodiments.

In still another aspect, disclosed herein is an amplified library of linear, double-stranded ligation products produced by the method of any of proceeding embodiments.

In one other aspect, disclosed herein is a sequencing library produced by the method of any of proceeding embodiments.

Disclosed in another aspect herein is a kit for constructing a library of ligation products. In one embodiment, the kit comprises a single-stranded DNA (ssDNA) ligase. In another aspect, the kit comprises a plurality of adaptors. In particular aspects, each adaptor is blocked to prevent ligation at the 3' end while the 5' end of the adaptor is available for ligation to a single-stranded polynucleotide to form a linear, single-stranded ligation product. In further particular aspects, each adaptor comprises a unique molecular identifier (UMI) sequence that earmarks the single-stranded polynucleotide.

In any of the preceding embodiments, the kit for constructing a library of ligation products can comprise a ssDNA ligase and a plurality of adaptors, and each adaptor is blocked to prevent ligation at the 3' end while the 5' end of the adaptor is available for ligation to a single-stranded polynucleotide to form a linear, single-stranded ligation product, and each adaptor comprises a UMI sequence that earmarks the single-stranded polynucleotide.

In any of the preceding embodiments, the kit can further comprise a denaturing reagent for denaturing a double-stranded polynucleotide from a sample to obtain the single-stranded polynucleotide.

In any of the preceding embodiments, the kit can comprise a *Thermus* bacteriophage RNA ligase such as a bacteriophage TS2126 RNA ligase (e.g. CircLigase™ and CircLigase II™), or an archaebacterium RNA ligase such as *Methanobacterium thermoautotrophicum* RNA ligase 1. In any of the preceding embodiments, the kit can comprise an RNA ligase, such as a T4 RNA ligase, e.g., T4 RNA ligase 1, e.g., New England Biosciences, M0204S. T4 RNA ligase 2, e.g., New England Biosciences, M0239S. T4 RNA ligase 2 truncated, e.g., New England Biosciences, M0242S. T4 RNA ligase 2 truncated KQ, e.g., M0373S, or T4 RNA ligase 2 truncated K227Q, e.g., New England Biosciences. M0351 S. In any of the preceding embodiments, the kit can also comprise a thermostable 5' App DNA/RNA ligase, e.g., New England Biosciences, M0319S, or T4 DNA ligase, e.g., New England Biosciences. M0202S.

In any of the preceding embodiments, the kit can further comprise a dephosphorylating reagent for removing a 5' phosphate group of the single-stranded polynucleotide. In any of the preceding embodiments, the blocking of each adaptor can comprise a carbon spacer, ddCTP, ddATP, ddTTP, ddGTP, hexanediol, triethylene glycol, and/or hexaethylene glycol, to prevent ligation at its 3' end. In any of the preceding embodiments of the kit, each adaptor can comprise a dinucleotide sequence at the 5' end, such as GA (5' to 3'), GG (5' to 3'), AA (5' to 3'), or AG (5' to 3'). In any of the preceding embodiments, the UMI sequence in each adaptor can be between about 6 and about 15 nucleic acid residues in length, for example, the UMI sequence is a 12-mer.

In any of the preceding embodiments, the kit can further comprise a crowding agent for the ligation reaction. In one aspect, the crowding agent comprises a polyethylene glycol (PEG), such as PEG 4000 or PEG 6000, Dextran, and/or Ficoll.

In any of the preceding embodiments, the kit can further comprise a primer or a set of primers each comprising a sequence that is reverse-complement to the adaptor and/or hybridizable to the adaptor, for converting the single-stranded polynucleotide to a double-stranded polynucleotide.

In any of the preceding embodiments, the kit can further comprise a reagent for removing primer dimer and/or primer-adaptor duplex.

In any of the preceding embodiments, the kit can further comprise a primer comprising a sequence specific for a target sequence (e.g., an EGFR gene sequence), for obtaining an amplified linear, double-stranded ligation product comprising sequence information of the target sequence. In any of the preceding embodiments, the target-specific primer can comprise any one or more sequences selected from the group consisting of SEQ ID NOs: 4-1529, or a complementary or substantially complementary sequence thereof.

In any of the preceding embodiments, the kit can comprise a plurality of primers, each comprising a sequence specific for the target sequence, wherein the primers have the same or different target sequences. In one aspect, the plurality of primers comprise any one or more, e.g., about 10, 20, 50, 100, 150, 200, 250, 300, 400, 500, 600, 700, 800, 900, 1000, 1,100, 1,200, 1,300, 1,400, 1,500, or all of 1529 of SEQ ID NOs: 4-1529, or a complementary or substantially complementary sequence thereof, or a numerical range or subrange thereof.

In any of the preceding embodiments, the kit can further comprise a sequencing adapter and/or a sample-specific barcode, for sequencing the amplified linear, double-stranded ligation product.

In any of the preceding embodiments, the kit can further comprise separate vials for each component and/or instructions for using the components in one aspect, the instructions comprise obtaining the single-stranded polynucleotide from a sample that comprises circulating tumor DNA (ctDNA), such as a blood, serum, plasma, or body fluid sample, or any combination thereof.

Also disclosed herein is a polynucleotide comprising AGATCGGAAGAGCGTCGTGTAGGGAAAGAGTG (SEQ ID NO: 1) or a portion thereof, e.g., a portion that comprises between about 18 and 22 nucleotide residues.

In one aspect, disclosed herein is a polynucleotide comprising $N_j$ . . . $N_i$AGATICGGAAGAGCGTCGTAGG-GAAAGAGTG or a portion thereof, wherein $N_j$ to $N_i$ is any nucleic acid residue, for example, A, T, C, or G, and i is an integer between about 4 and about 25.

In another aspect, disclosed herein is a polynucleotide comprising GANNNNNNNNNNNAGATCG-GAAGAGCCCGTCGGTAGGGAAAGAGTG (SEQ ID NO: 2) or a portion thereof, e.g, a portion that comprises between about 32 and 36 nucleotide residues, wherein N is any nucleic acid residue, for example, A, T, C, or G.

In one aspect, disclosed herein is a polynucleotide comprising CACTCTTTCCCTACACGACGC (SEQ ID NO: 3) or a portion thereof, e.g., a portion that comprises between about 12 and 20 nucleotide residues.

In one other aspect, disclosed herein is a primer comprising any one or more sequences selected from the group consisting of SEQ ID NOs: 4-1529. In one aspect, disclosed herein is a primer set comprising any one or more, e.g., about 10, 20, 50, 100, 150, 200, 250, 300, 400, 500, 600, 700, 800, 900, 1,000, 1,1000, 1,200, 1,300, 1,400, 1,500, or all of 1529 of SEQ ID NOs: 4-1529, or a complementary or substantially complementary sequence thereof, or a numerical range or subrange thereof. In one aspect, disclosed herein is a primer set comprising any one or more, e.g., about 10, 20, 50, 100, 150, 200, 250, 300, 400, 500, 600, 700, 800, 900, 1,000, 1,100, 1,200, 1,300, 1,400, 1,500, or all of 1529 of SEQ ID NOs: 4-1529, or a complementary or substantially complementary sequence thereof, or a numerical range or subrange thereof, and a primer comprising CACTCTITCCCTACACGACGC (SEQ ID NO: 3) or a portion thereof. In one other aspect, disclosed herein is a kit comprising any one or more, e.g., about 10, 20, 50, 100, 150, 200, 250, 300, 400, 500, 600, 700, 800, 900, 1,000, 1,100, 1,200, 1,300, 1,400, 1,500, or all of 1529 of SEQ ID NOs: 4-1529, or a complementary or substantially complementary sequence thereof, or a numerical range or subrange thereof, a primer comprising CACTcTTTCCCCTACACCGACGC (SEQ ID NO. 3) or a portion thereof, and/or a polynucleotide comprising AGATCGGAAGAGCGTCGTCiTAGG-GAAAGAGTG (SEQ ID NO: 1) or a portion thereof.

BRIEF DESCRIPTION OF THE DRAWINGS

FIG. 5 compares the performance parameters of a method disclosed herein and the conventional hybridization capture method for library construction and sequencing.

FIG. 7 shows additional exemplary primer(s) or primer pool(s).

DETAILED DESCRIPTION

Figure 1:
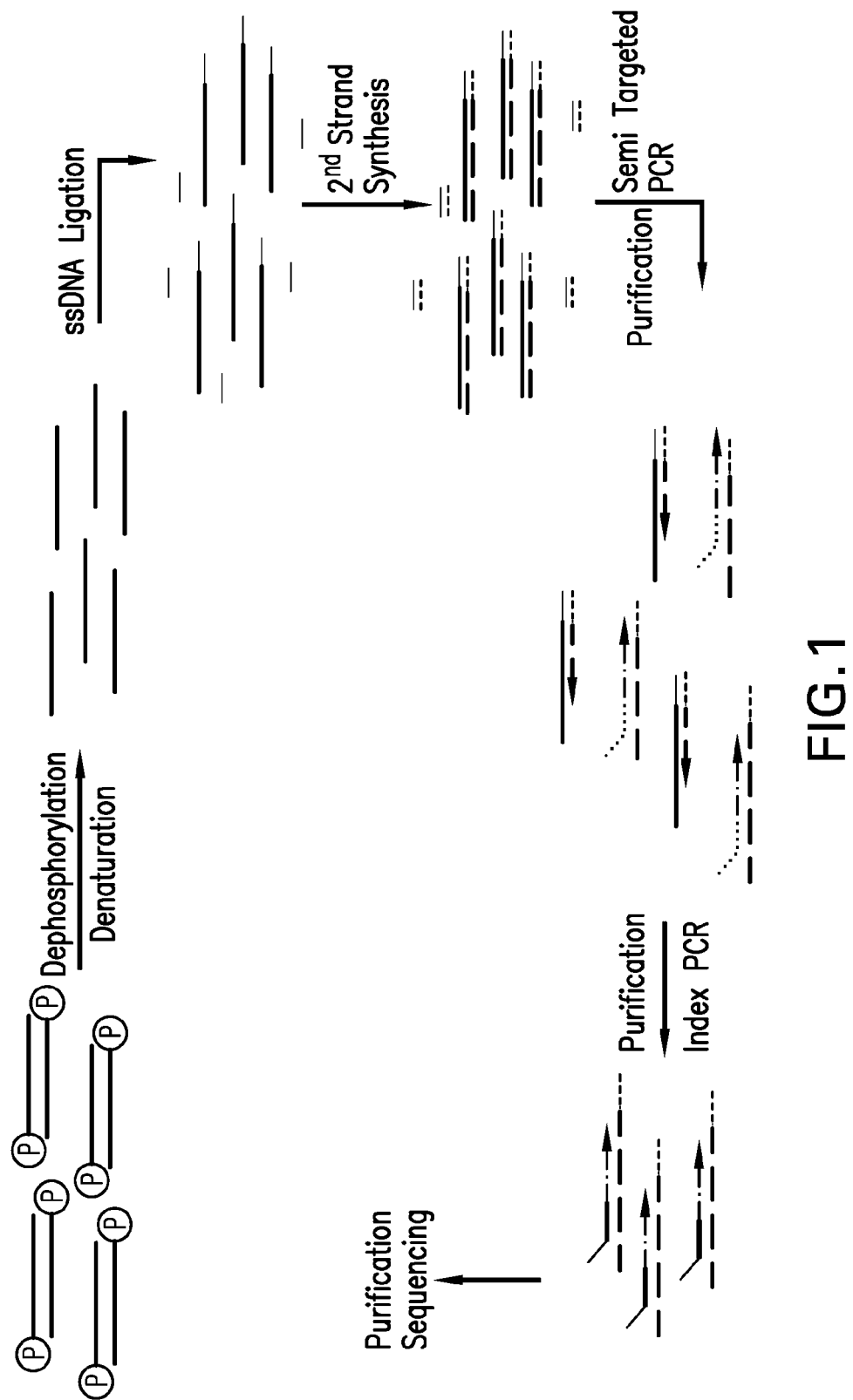
FIG. 1 shows steps for constructing a single-stranded polynucleotide library and performing sequencing analysis using the library, according to one aspect of the present disclosure.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, poly nucleotide synthesis and modification, polymer array synthesis, hybridization and ligation of polynucleotides, detection of hybridization, and nucleotide sequencing. Specific illustrations of suitable techniques can be had by reference to the examples herein. However, other equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003), Boxwtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press: Goeddel ed., *Gene Expression Technology* (1991), Academic Press: A. Bothwell et al., eds., *Methods for Cloning and Analysis of Eukaryotic Genes* (1990), Bartlett Publ.; M. Kriegler, *Gene Transfer and Expression* (1990), Stockton Press, R. Wu et al., eds., *Recombinant DNA Methodology* (1989), Academic Press, M. McPherson et al., *PCR: A Practical Approach* (1991), IRL Press at Oxford University Press. Stryer, *Biochemistry* (4th Ed.) (1995), W H Freeman, New York N Y.; Gait, *Oligonucleotide Synthesis: A Practical Approach* (2002), IRL Press. London; Nelson and Cox, *Lehninger, Principle of Biochemistry* (2)(000) 3rd Ed., W. H. Freeman Pub., New York, N.Y.; Berg, et al., *Biochemistry* (2002) 5th Ed., W. H. Freeman Pub., New York, N.Y., all of which are herein incorporated in their entireties by reference for all purposes.

A. DEFINITIONS

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more." As used herein, the singular forms "a," "an," and "the" include the plural reference unless the context clearly dictates otherwise.

Throughout this disclosure, various aspects of the claimed subject matter are presented in a range format it should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Reference to "about" a value or parameter herein includes (and describes) variations that are directed to that value or parameter per se. For example, description referring to "about X" includes description of "X". Additionally, use of "about" preceding any series of numbers includes "about" each of the recited numbers in that series. For example, description referring to "about X, Y, or Z" is intended to describe "about X, about Y, or about Z."

The term "average" as used herein refers to either a mean or a median, or any value used to approximate the mean or the median, unless the context clearly indicates otherwise.

A "subject" as used herein refers to an organism, or a part or component of the organism, to which the provided compositions, methods, kits, devices, and systems can be administered or applied. For example, the subject can be a mammal or a cell, a tissue, an organ, or a part of the mammal. As used herein, "mammal" refers to any of the mammalian class of species, preferably human (including humans, human subjects, or human patients) Mammals include, but are not limited to, farm animals, sport animals, pets, primates, horses, dogs, cats, and rodents such as mice and rats.

As used herein the term "sample" refers to anything which may contain a target molecule for which analysis is desired, including a biological sample. As used herein, a "biological sample" can refer to any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine, sweat, semen, stool, sputum, tears, mucus, amniotic fluid or the like, an effusion, a bone marrow sample, ascitic fluid, pelvic wash fluid, pleural fluid, spinal fluid, lymph, ocular fluid, extract of nasal, throat or genital swab, cell suspension from digested tissue, or extract of fecal material, and tissue and organ samples from animals and plants and processed samples derived therefrom.

The terms "polynucleotide," "oligonucleotide," "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g, peptide nucleic acids ("PNAs")) and polymorpholino (commercially available from the Anti-Virals, Inc., Corvallis, OR, as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkvlphosphoranmidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g, acridine, psoralen, etc.), those containing chelates (of, e.g, metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

It will be appreciated that, as used herein, the terms "nucleoside" and "nucleotide" include those moieties which contain not only the known purine and pyrimidine bases, but also other heterocyclic bases which have been modified.

Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotide unit" is intended to encompass nucleosides and nucleotides.

The terms "complementary" and "substantially complementary" include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein, for a reference sequence, the reverse complementary sequence is the complementary sequence of the reference sequence in the reverse order. For example, for 5'-ATCG-3', the complementary sequence is 3'-TAGC-5', and the reverse-complementary sequence is 5'-CGAT-3'.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m$=81.5+0.41 (% G C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., *Biochemistry*, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30'C are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency, 0.2×SSPE, 0.1% SDS, 50° C. (also referred to as moderate stringency); and 3) low stringency, 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5/Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA), 20×SSPE (sodium chloride, sodium phosphate, EDTA) contains 3 M sodium chloride, 0.2 M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed, Cold Spring Harbor Press, Plainview, N Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, *Nucleic Acids Res.* 12.203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, for example, a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically. As used herein, ligations are usually carried out enzymatically to form a phosphodiester linkage between a 5' carbon terminal nucleotide of one oligonucleotide with a 3' carbon of another nucleotide.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

"Sequence determination" and the like include determination of information relating to the nucleotide base sequence of a nucleic acid Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid.

The term "Sequencing," "High throughput sequencing," or "next generation sequencing" includes sequence determination using methods that determine many (typically thousands to billions) of nucleic acid sequences in an intrinsically parallel manner, i.e, where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, CT); sequencing by ligation (for example, as commercialized in the SOLiD™ technology, Life Technologies, Inc., Carlsbad, CA); sequencing by synthesis using modified nucleotides (such as commercialized in TruSeq™ and HiSeq™ technology by Illumina, Inc., San Diego, CA, HeliScope™ by Helicos Biosciences Corporation, Cambridge, MA, and PacBio RS by Pacific Biosciences of California, Inc., Menlo Park, CA), sequencing by ion detection technologies (such as Ion Torrent™ technology, Life Technologies, Carlsbad, CA); sequencing of DNA nanoballs (Complete Genomics, Inc., Mountain View, CA); nanopore-based sequencing technologies (for example, as developed by Oxford Nanopore Technologies, LTD, Oxford, UK), and like highly parallelized sequencing methods.

"SNP" or "single nucleotide polymorphism" may include a genetic variation between individuals; e.g., a single nitrogenous base position in the DNA of organisms that is variable. SNPs are found across the genome, much of the genetic variation between individuals is due to variation at SNP loci, and often this genetic variation results in phenotypic variation between individuals. SNPs for use in the present disclosure and their respective alleles may be derived from any number of sources, such as public databases (U.C. Santa Cruz Human Genome Browser Gateway (genome.ucsc.edu/ cgi-bin/hgGateway) or the NCBI dbSNP website (ncbi.nlm.nih.gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it mill be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele." and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleated changes, insertions, deletions, and translocations.

It will be further appreciated that references to DNA herein ma % include genomic DNA, mitochondrial DNA, episomal DNA, and/or derivatives of DNA such as amplicons. RNA transcripts, cDNA. DNA analogs, etc. The polymorphic loci that are screened in an association study may be in a diploid or a haploid state and, ideally, would be from sites across the genome. Sequencing technologies are available for SNP sequencing, such as the BeadArray platform (GOLDENGATE™ assay) (Illumina, Inc., San Diego. CA) (see Fan, et al., *Cold Spring Symp. Quant. Biol*, 68.69-78 (2003)), may be employed.

In some embodiments, the term "methylation state" or "methylation status" refers to the presence or absence of 5-methylcytosine ("5-mC" or "5-mCyt") at one or a plurality of CpG dinucleotides within a DNA sequence, methylation states at one or more particular CpG methylation sites (each having two CpG dinucleotide sequences) within a DNA sequence include "unmethylated," "fully-methylated," and "hemi-methylated." The term "hemimethylation" or "hemimethylation" refers to the methylation state of a double stranded DNA wherein only one strand thereof is methylated. The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample. The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

"Multiplexing" or "multiplex assay" herein may refer to an assay or other analytical method in which the presence and/or amount of multiple targets, e.g., multiple nucleic acid sequences, can be assayed simultaneously by using more than one markers, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

As used herein, "disease or disorder" refers to a pathological condition in an organism resulting from, e.g., infection or genetic defect, and characterized by identifiable symptoms.

B. OVERVIEW OF THE POLYNUCLEOTIDE FRAGMENT ANALYSIS BY LIBRARY CONSTRUCTION AND POLYNUCLEOTIDE SEQUENCING

In one aspect, the target (or template) polynucleotide of the present method is a fragmented polynucleotide, for example, ranging from about 100 residues to about 1000 residues, and in some embodiments, ranging from about 150 residues to about 400 residues.

The target or template DNA can include be regular genomic DNA, chromosomal DNA, extrachromosomal DNA (such as mitochondrial DNA), or a fragment thereof. In other embodiments, the target or template DNA is a processed DNA, for example, one that has undergone enzyme digestion, cross-linking, chemical or physical shearing, bisulfite conversion, and/or degradation.

Bisulfite conversion is a method that uses bisulfite to determine the methylation pattern of DNA. DNA methylation is a biochemical process involving the addition of a methyl group to the cytosine or adenine DNA nucleotides. DNA methylation stably alters the expression of genes in cells as cells divide and differentiate from embryonic stein cells into specific tissues in bisulfite conversion, target nucleic acids are first treated with bisulfite reagents that specifically convert un-methylated cytosines to uracils while having no impact of methylated cytosine. One consequence of bisulfite conversion is that the double-stranded conformation of the original target is disrupted due to loss of sequence complementarity. The target sequences exist as two separate single-stranded DNAs during sample preparation and analytical or diagnostic testing. Target nucleic acid sequences frequently also exist at very low concentrations. This is an especially important consideration for circulating tumor DNA (also referred to as "cell-free tumor DNA," or "ctDNA") due to its often low concentration in circulation and the very low variant allele fraction.

In some embodiments, the nucleic acid molecule of interest disclosed herein is a cell-free DNA, such as cell-free fetal DNA (also referred to as "cfDNA") or ctDNA, cfDNA circulates in the body, such as in the blood, of a pregnant mother, and represents the fetal genome, while ctDNA circulates in the body, such as in the blood, of a cancer patient, and is generally pre-fragmented. In other embodiments, the nucleic acid molecule of interest disclosed herein is an ancient and/or damaged DNA, for example, due to storage under damaging conditions such as in formalin-fixed samples, or partially digested samples.

As cancer cells die, they release DNA into the bloodstream. This DNA, known as circulating tumor DNA (ctDNA), is highly fragmented, with an average length of approximately 150 base pairs. Once the white blood cells are removed, ctDNA generally comprises a very small fraction of the remaining plasma DNA, for example, ctDNA may constitute less than about 10% of the plasma DNA. Generally, this percentage is less than about 1%, for example, less than about 0.5% or less than about 0.01%. Additionally, the total amount of plasma DNA is generally very low, for example, at about 10 ng/mL of plasma.

The variants in the ctDNA can be interrogated using various methods, including next generation sequencing. Due to the low ratio of ctDNA to plasma DNA, it is difficult to call a variant with high confidence due to PCR and sequencing errors. Unique molecular identifiers (UMIs) are generally used to tag original molecules such that any variant seen can be compared to a consensus sequence. This is an effective manner to separate true from false positives. If the variant is matched to a consensus, it is a true positive Otherwise, it is removed from analysis. Furthermore, it is essential that a high percentage of original molecules are turned into sequencing libraries so that the sensitivity remains high, i.e., variants are not missed due to dropout. Thus, ligation efficiency is extremely important during library construction.

In one aspect, provided herein is a technique to vastly improve ligation efficiency while still targeting selected regions of the genome. In one embodiment, polynucleotides to be detected by sequencing, such as ctDNA, are first dephosphorylated to remove 5' phosphates to prevent ligation of ctDNA to itself. The ctDNA is then denatured such that all DNA is single stranded. Circligase™, a single stranded DNA ligase, is used to ligate an adapter to the 3' end of the ctDNA. In one aspect, the adapter contains 2 specific bases on the 5' end to optimize ligation efficiency, followed by a UMI. In one aspect, the 3' end of the adapter contains a carbon spacer to prevent self-ligation of the adapters. In another aspect, the ligation reaction is further optimized using a crowding agent, such as PEG 400). In one aspect, following ligation, molecules are double-stranded using a primer that is reverse complement to the adapter. This allows efficient removal of excess unligated adapters without removed usable DNA by a standard purification.

In one aspect, the DNA is then amplified using a semi-targeted PCR. One primer is reverse complement to the adapter, while the other (e.g., as one primer in a primer pool) anneals to specific, targeted regions of the genome. The specific primers were designed to minimize primer-dimer interactions and off-target annealing. In one aspect, the target-specific primers are further optimized to land in close proximity to specific variants due to the small DNA size. Following another cleanup, a PCR adds the full-length sequencing adapters and barcodes. The final library is then sequenced, for example, on an Illumina machine.

In one aspect, the semi-targeted PCR results in enrichments of >about 40,000 fold of the original molecule set despite having a relatively small target region of ~30,000 bp in one aspect, the overall conversion rates of the present method are at least 60%, implying that at least ~3 times more of the original molecules are converted into sequenceable material when compared to standard library construction and by bridization capture. In other embodiments, the overall conversion rates are between about 60% and about 70%, between about 70%, and about 80%, between about 80% and about 90%, or over 90% in one aspect, the present method thus is able to accurately call genetic or genomic variants, such as SNVs, indels, CNVs, and fusions at extremely low mutant allele fractions, for example, as low as 0.01%. In other aspects, the allele fraction of the genetic or genomic variant is about 0.05%, about 0.1%, about 0.5%, about 1%, or about 2%.

The following sections describe certain steps of the present method in greater detail.

C. SINGLE-STRANDED POLYNUCLEOTIDE LIBRARIES AND METHOD OF CONSTRUCTING THE SAME

Library construction for next generation sequencing, for example, for ctDNA, generally consists of several steps, including end repair, A-tailing, and a double stranded ligation of an adapter molecule. These ligated molecules can then be enriched 1000-2000 times at certain genomic regions using hybridization capture. Despite several improvements in library construction over the last several years, the process remains inefficient, resulting in many original molecules lost during the various steps. Double stranded ligation efficiency remains low, with ~20-30% of the molecules being properly ligated. Additionally, many molecules are lost during the purification and hybridization capture steps, so that the final conversion rate approximates 10-20%. Sensitivity remains low when interrogating low allele fraction variants found in ctDNA. This limits the accuracy % when calling low allele fraction mutants, since the low efficiency will result in sensitivity loss when looking at libraries with low allele fractions.

In addition, the small size of certain polynucleotides, such as ctDNA, prevents the use of tagmentation-based library construction. For example, the polynucleotides are first tagged (e.g., with biotin) to generate a targeted library, and then enriched by capturing the tags (e.g., by streptavidin). This way, the library for the regions of interest can be enriched by about 1000-2000 fold. Finally, a PCR is performed to amplify and index the molecules for sequencing. However, PCR based methods prove difficult to add UMIs to original molecules and result in high error rates.

In one aspect, the compositions, kits, and methods described herein addressed the above problems in some embodiments, the compositions, kits, and methods are useful in sequencing nucleic acid molecules, including but not limited to construction of various libraries, various amplification reactions (such as by PCR and/or primer extension), purification of the constructed libraries, and analysis of sequencing reads.

In certain aspects, a sequencing library can be prepared, for example, from a sample containing fragmented polynucleotides, such as fragment DNA. In one aspect, the sample is obtained a naturally occurring sample, for example, directly from a subject, such as tissue fluid or body fluid, including but not limited to blood, plasma, serum, cerebrospinal fluid, synovial fluid, urine, sweat, semen, sputum, tear, mucus, or amniotic fluid. In other aspects, a sequencing library can be prepared by forming fragments of DNA (for example, by shearing the DNA), and attaching the adapters herein to the DNA fragments. In particular embodiments, the fragmented polynucleotides and the adapters are single-stranded.

The fragments (for example, the ctDNA or fragments formed by fragmenting longer DNA strands) are sometimes referred to as "inserts." as they can be "inserted" or ligated adjacent to an adapter such as a single-stranded adaptor disclosed herein. RNA molecules can also be sequenced, for example by reverse transcribing the RNA molecules to form DNA molecules, which are attached to the adapters.

In one aspect, a method comprising ligating a set of adaptors to a library of single-stranded polynucleotides is provided, and in the method, the ligation is catalyzed by a single-stranded DNA (ssDNA) ligase. As used herein, a ssDNA ligase is capable of ligating ends of ssDNA in the absence of a complementary sequence. For example, CircLigase™ ssDNA Ligase and CircLigase™ II ssDNA Ligase are both thermostable ligases that are typically used to catalyze intramolecular ligation (i.e., circularization) of ssDNA templates having a 5'-phosphate and a 3'-hydroxyl group. In contrast to T4 DNA Ligase and Ampligase™ DNA Ligase, which ligate DNA ends that are annealed adjacent to each other on a complementary DNA sequence, a ssDNA ligase ligates ends of ssDNA in the absence of a complementary sequence. The enzyme is therefore useful for making circular ssDNA molecules from linear ssDNA. Circular ssDNA molecules can be used as substrates for rolling-circle replication or rolling-circle transcription. In addition to its activity on ssDNA, a CircLigase enzyme also has activity in ligating a single-stranded nucleic acid having a 3'-hydroxyl ribonucleotide and a 5'-phosphorylated ribonucleotide or deoxyribonucleotide.

Either CircLigase™ ssDNA Ligase or CircLigase™ II ssDNA Ligase can be used in the present disclosure. The two enzymes are different in that CircLigase I is far less adenylated than CircLigase II and requires ATP for best activity. CircLigase I recircularizes ssDNA in the presence of ATP. CircLigase II is nearly 100% adenylated, therefore it is not necessary to add ATP to the reaction buffer CircLigase II works as a stoichiometric reaction, where the enzyme bonds the 5'-end of an oligo that is adenylated in the enzyme active site, and then ligates the oligo and stops. Since the reaction doesn't contain ATP, CircLigase II works in a 1:1 enzyme-oligo configuration. Once the circularization is complete, the circular ssDNA is released from the active site and the reaction stops. Other suitable ssDNA ligase can also be used. For example, a thermostable 5' App DNA/RNA ligase, e.g., New England Biosciences, M0319S, or T4 DNA ligase, e.g., New England Biosciences. M0202S, or a T4 RNA ligase, e.g., T4 RNA ligase I, e.g., New England Biosciences, M0204S, T4 RNA ligase 2, e.g. New England Biosciences. M0239S, T4 RNA ligase 2 truncated, e.g., New England Biosciences, M0242S. T4 RNA ligase 2 truncated KQ, e.g. M0373S, or T4 RNA ligase 2 truncated K227Q, e.g., New England Biosciences. M0351S, can be used.

In one aspect, each single-stranded polynucleotide is blocked at the 5' end to prevent ligation at the 5' end, each adaptor comprises a unique molecular identifier (UMI) sequence that earmarks the single-stranded polynucleotide to which the adaptor is ligated, each adaptor is blocked at the 3' end to prevent ligation at the 3' end, and the 5' end of the adaptor is ligated to the 3' end of the single-stranded polynucleotide by the ssDNA ligase to form a linear ligation product, thereby obtaining a library of linear, single-stranded ligation products. Template-independent circularization of single-stranded DNA is described in WO2010/094040 A1, the disclosure of which is incorporated herein in its entirety. WO2010/94040 A1, however, only discloses intramolecular ligation (e.g., circularization) of single-stranded polynucleotides.

Thus, the present method uses a ssDNA ligase, such as CircLigase or CircLigase II, in an unconventional manner. Instead of circularization, the present ligation method aims to generate a linear ligation product between the single-stranded target polynucleotide and an adaptor molecule. In one aspect, the present disclosure uses a ssDNA ligase to carry out intramolecular ligate, e.g., for ligating an adaptor to single-stranded polynucleotides. In order to do, in one aspect, the single-stranded polynucleotide is blocked at the 5' end to prevent circularization. This way, intramolecular ligation of the 3' end of an ssDNA to its own 5' end, as well as intermolecular ligation of the 3' end of one ssDNA to the 5' end of another ssDNA within the same library, is prevented. Thus, in one aspect, both circularization of the single-stranded polynucleotide and formation of linear concatemers (containing the single-stranded polynucleotides and/or the adaptors) are prevented during the ligation reaction. As shown in FIG. 1, the blocking of each single-stranded polynucleotide can comprise dephosphorylation at its 5' end to prevent ligation at that end.

In another aspect, each adaptor is blocked at the 3' end to prevent ligation at the 3' end. This way, intramolecular ligation of the 3' end of an adaptor to its own 5' end, as well as intermolecular ligation of the 3' end of one adaptor molecule to the 5' end of another adaptor molecule, is prevented. The blocking of each adaptor can comprise a carbon spacer, ddCTP, ddATP, ddTTP, ddGTP, hexanediol, triethylene glycol (TEG), and/or hexaethylene glycol, to prevent ligation at its 3' end. Thus, in one aspect, both circularization of the single-stranded adaptor and formation of linear concatemers (containing the single-stranded polynucleotides and/or the adaptors) are prevented during the ligation reaction.

The adaptor may comprise one or more copies of one or more spacers, in any suitable combination. For example, Gansauge and Meyer disclosed an adaptor that comprises ten copies of a C3Spacer and a biotinylated TEG spacer. Gansauge and Meyer (2013), "Single-stranded DNA library preparation for the sequencing of ancient or damaged DNA." *Nature Protocols,* 8(4): 737-48, which is incorporated herein by reference in its entirety. This reference, however, requires capturing the ligated ssDNA, via biotin-streptavidin interaction, immediately after ligation. This step may cause a significant loss of the ssDNA molecules in the library. The reference then converts the captured ssDNA to dsDNA while the ssDNA remains captured on a bead.

As shown in FIG. 1, the present disclosure does not require capturing the ligated ssDNA immediately after ligation. Instead, the ligated ssDNA remains in the ligation reaction volume when it is converted into dsDNA.

In one aspect, the ligation efficiency of the ssDNA in the library is high, for example, at least about 40%, at least about 50%, at least about 60%, at least about 70%, at least about 80%, at least about 85%, at least about 90%, at least about 95%, or at least about 99% of the single-stranded polynucleotides in the sample are ligated to an adaptor. In particular embodiments, the ligation efficiency is about 80% b With this vastly improved ligation efficiency, the presently claimed method is still capable of targeting selected regions of the genome, as explained below.

In one aspect, the adaptor has the following structure: /5'Phos/$N_1N_2 \ldots N_i$-UMI-$M_1M_2 \ldots M_j$-Blocker, wherein "5'Phos" represents a 5' phosphate group, "$N_1N_2 \ldots N_i$" represents the sequence 5' to the UMI sequence, "$M_1M_2 \ldots M_j$" represents the sequence 3' to the UMI sequence, and "Blocker" indicates that the 3' end of the adaptor Is blocked to prevent ligation thereto. Both i and j are integers, wherein i can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or greater than 30; and/can be 5, 6, 7, 8, 9, 10, 11, 12, 13, 14, 15, 16, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater than 50. In specific embodiments, i can be 2. In some embodiments, the dinucleotide sequence $N_1N_2$ at the 5' end of $N_1N_2 \ldots N_i$ can be GA (5' to 3'), GG (5' to 3'), AA (5' to 3'), or AG (5' to 3'), in order to enhance the ligation efficiency.

In one aspect, a portion or all of the $M_1M_2 \ldots M_j$ sequence is used in later steps for designing a reverse-complement sequence that is used as a primer to convert the ligated single-stranded polynucleotide into a double-stranded polynucleotide, and/or for the semi-targeted PCR to amplify a selected target sequence (the other primer of the primer pair being the target-specific primer). In one aspect, the $M_1M_2 \ldots M_j$ sequence comprises AGATCG-GAAGAGCCTCGTGTCGTAGGGAAAGAGTG (SEQ ID NO: 1) or a portion thereof that comprises between about 18 and 22 nucleotide residues.

In another aspect, the "Blocker" comprises a carbon spacer, ddCTP, ddATP, ddTTP, ddGTP, hexanediol, triethylene glycol (TEG), and/or hexaethylene glycol, in one or more copies of one or more blocker groups in any suitable combination and order in the 5' to 3' direction.

In one aspect, use of the UMI facilitates the determination, selection, and/or isolation of error-free sequencing reads of a target sequence, and the sequencing reads can be selected with high accuracy and high throughput Such validated, error-free sequencing reads are useful in any technique that requires sequence fidelity, including the construction of larger molecules of known sequence, polymorphism and/or mutation screening, massively parallel sequencing, and quantification methods to preclude bias in the methodologies.

In one aspect, the Unique Molecular Identifier is associated with and uniquely identifies a ligated construct comprising a single-stranded target polynucleotide and an adaptor. In other words, tyro single-stranded target polynucleotides having the same sequence may be ligated to two different adaptors which differ from each other at their UMI sequences; the resultant ligation products are different, and each ligation product (rather than the target polynucleotides having the same sequence) is uniquely identified by the UMI. In another aspect, when the single-stranded ligation products are converted into double-stranded polynucleotides and amplified, amplification errors may be introduced during repeated copying even though very high fidelit, polymerases are available. As a result, even a low error rate can have a significant impact, particularly in the construction of large libraries. Although massively parallel sequencing has advantages in cost and throughput, the accuracy of the reads can be comprised by the limitations of the amplification and/or detection technologies.

By using the UMI, the present method is capable of identifying error-free amplification products and/or sequencing reads, and excluding those with technical errors from analysis. The amplification products and/or sequencing reads having the same UMI can be confirmed as related (identical by descent), and thus sequence differences between molecules with the same UMI can be identified as technical errors rather than real differences in the sequence (e.g., sequence differences between a wild-type sequence and a cancer-related mutant sequence). In other words, since each single-stranded ligation product is unique identifiable by its UMI, all of its descendants (due to amplification and/or sequencing) should have the same target sequence if no technical error is introduced. If, however, an error such as a single-nucleotide insertion is introduced into the target sequence during amplification and/or sequencing, some amplification products and/or sequencing reads identical by descent (e.g. sharing the same UMI) will have the insertion while the others will not. The exact ratio between the products having the insertion and those that do not have the insert will vary, depending on when the error occurs during the amplification and/or sequencing process. In general, when very high fidelity polymerases are used, the products without errors will be in the majority. In another aspect, because amplification products and/or sequencing reads that are identical by descent can be identified, a consensus sequence can be determined using data from multiple molecules, thereby achieving a high accuracy for high throughput sequencing.

In one aspect, the UMI is a degenerate nucleic acid sequence, and the number of nucleotides in the UMI is designed such that the number of potential and actual sequences represented by the UMI sequences is greater than the total number of target single-stranded target polynucleotide in the initial library. In one aspect, UMI sequence diversity (or "uniqueness" with regard to each single UMI sequence) can be provided by using a degenerate collection of sequences randomly generated by synthesizing with a mixture of all four bases at each position. Alternatively, a diverse but pre-defined set of sequences can be synthesized and ligated to the initial single-stranded polynucleotide library. The diversity of the UMI set needs to be sufficient so that molecules that are not related by descent won't be mistaken as such. In one aspect, a "unique" molecular identifier need not be absolutely unique, and may be used on different target single-stranded polynucleotides provided it is clear that they are different and not mistaken for a molecule that is identical by descent. The large number of UMI sequences that can be generated from the random assembly of nucleotides pros ides a high probability that each individual ligation product can be uniquely identified. For example, if the UMI comprises a 12-mer synthesized with a mixture of A. C. G and T at each position, there are $4^{12}$ possible sequences. If the UMI comprises a 20-mer synthesized with a mixture of A. C, G and T at each position, there are $4^{20}$ (about $10^{12}$) possible sequences. The use of such random identifiers allows a large library with single-stranded target polynucleotides that can be individually distinguished from each other.

In particular aspects, the UMI is a 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, or even longer degenerate sequence. In one aspect, the adaptor has the following structure: /5'Phos/GANNNNNNNNNNNNAGATCGGAA GACiGTCCiTGTAGGGAAAGAGTG3SpC3/, wherein "NNNNNNNNNN" represents a 12-mer UMI sequence, and "3SpC3" represents a 3' carbon spacer. The sequence of GANNNNNNNNNNNNAGATCG-GAAGAGCGTCGTGTAGGGAAAGAGTG is SEQ ID NO: 2.

The concentration of DNA can be artificially increased by adding condensing agents such as cobalt hexamine and biogenic polyamines such as spermidine, or by using crowding agents such as polyethylene glycol (PEG) which also increase the effective concentration of enzymes. In one aspect, additives such as cobalt hexamine can produce exclusively intermolecular reaction, resulting in linear ligation products rather than circular products. Thus, in case the 5' ends of the single-stranded target polynucleotides and the 3' ends of the single-stranded adaptor may not be completely blocked to prevent ligation, additives such as cobalt hexamine may be used to enhance intermolecular reaction and further prevent circularization of the single-stranded target polynucleotide and/or the adaptor.

In some embodiments, more than one configurations of the adaptor can be used in the same ligation reaction. For example two configurations of the adaptor may be used:
  Configuration No. 1: /5'Phos/$N_1N_2$ ... $N_i$-$UMI_1$-$M_1M_2$ ... $M_j$-$Blocker_1$, and
  Configuration No. 2: /5'Phos/$P_1P_2$ ... $P_k$-$UMI_2$-$Q_1Q_2$ ... $Q_l$-$Blocker_2$.

$N_1N_2$ ... $N_i$ and $P_1P_2$ ... $P_k$ can be the same or different, $UMI_1$ and $UMI_2$ can be the same or different, $M_1M_2$ ... $M_j$ and $Q_1Q_2$ ... $Q_l$, can be the same or different, and $Blocker_1$ and $Blocker_2$ can be the same or different. In one embodiment, $UMI_1$ is different from $UMI_2$ (for example. $UMI_1$ is a 12-mer degenerate sequence while $UMI_2$ is a 13-mer degenerate sequence), while the other features of the adaptors are the same. In another embodiment, $N_1N_2$ ... $N_i$ is different from $P_1P_2$ ... $P_k$ (for example, one is AG while the other is GA), while the other features of the adaptors are the same. In yet another embodiment. $M_1M_2$ ... $M_j$ is different from $Q_1Q_2$ ... $Q_l$, while the other features of the adaptors are the same. In still another embodiment. $Blocker_1$ and $Blocker_2$ are different, while the other features of the adaptors are the same.

After the ligation reaction, the single-stranded ligation products, without any need for purification (e.g., separation of the ligation products from the excess, unligated adaptor molecules), can be immediately subject to conversion into double-stranded ligation products. In addition, neither the single-stranded target polynucleotide nor the adaptor needs to be captured on a solid support (e.g., by biotin-streptavidin mediated binding to a bead) in order for the subsequent conversion of the ligation product into a double-stranded polynucleotide and/or amplification step. Thus, the present method avoids and/or reduces loss of the already small allele fraction of the mutant in a DNA sample, such as ctDNA, due to the purification or isolation of the single-stranded ligation products. Instead, in one aspect, the single-stranded ligation products remain in the solution which is directed subject to primer extension.

D. CONVERSION OF SINGLE-STRANDED POLYNUCLEOTIDE LIBRARY TO DOUBLE-STRANDED POLYNUCLEOTIDE LIBRARY

In one aspect as shown in FIG. 1, following construction of the library containing the single-stranded ligation products, the method can further comprise converting the library of linear, single-stranded ligation products into a library of linear, double-stranded ligation products. In one aspect, the conversion uses a primer or a set of primers each comprising a sequence that is reverse-complement to the adaptor and/or hybridizable to the adaptor.

For an adaptor having the following structure: /5'Phos/ $N_1N_2$ ... $N_i$-UMI-$M_1M_2$ ... $M_j$-Blocker, the primer can comprise a sequence that is reverse-complement and/or hybridizable to $M_1M_2$ ... $M_j$. In this example, when the primer hybridizes to the ligated product having the structure ssDNA-$N_1N_2$ ... $N_i$-UMI-$M_1M_2$ ... $M_j$-Blocker, the primer extension reaction can convert the ssDNA-$N_1N_2$ ... $N_i$-UMI sequence (and optionally, all or a portion of the $M_1M_2$ ... $M_j$ sequence) into double-stranded polynucleotides. In one specific example, a reverse-complement primer comprises the sequence set forth in SEQ ID NO: 3: CACTCTTTCCC-TACACGACGC (5' to 3').

In some embodiments, the primer may not be a perfect reverse-complement of $M_1M_2$ ... $M_j$ or a portion therefore; nonetheless, the primer is hybridizable to $M_1M_2$ ... $M_j$ (and thus the ssDNA ligated to the adaptor) under stringent conditions.

In any of the preceding embodiments, the method can further comprise amplifying and/or purifying the library of linear, double-stranded ligation products in one aspect, the double-stranded ligation products are purified and size selected to remove unbound adaptor molecules and/or unbound primers, and/or complexes formed between an adaptor and its reverse-complement primer. An suitable methods can be used to remove these fragments which are generally shorter than the desired double-stranded ligation products. For example, using PCR purification column from Qiagen could help to eliminate the smaller fragments from the samples and running the column-purified samples on 2% certified low range ultra agarose gel can help to select the desired fragment size. The beads-based DNA purification including AMPure method is also helpful to remove the smaller fragments. In some embodiments, the desired double-stranded ligation products size is from about 100 bps to about 600 bps, such as from about 100 bps to about 400 bps, from about 150 bps to about 200 bps, from about 200 bps to about 250 bps, and from about 250 bps to about 300 bps. In one embodiment, dsDNA (>150 bps and <400 bps) is purified and collected, for example, by eluting beads suspended in a Tri-EDTA buffer.

In one aspect, the purification is bead-based. In another aspect, the purification is based on size selection, for example, the purification step selectively purifies polynucleotides between about 50 nucleotides and about 1000 nucleotides in lengths, for example adaptors of about 40 nucleotides in length (and primer dimers and/or primer-adaptor duplexes of about 40 bp) are removed. In one aspect, the purification is column-based, for example, by using a dsDNA or ssDNA purification column, such as those from Zymo or Qiagen.

In another aspect, the purification does not comprise using a specific binding pair (such as biotin/streptavidin), one of which is attached to the linear, double-stranded ligation product and the other is attached to a solid support (such as a bead).

In any of the preceding embodiments, the method herein can further comprise amplifying the library of linear, double-stranded ligation products, e.g., by a polymerase chain reaction (PCR), to obtain an amplified library of linear, double-stranded ligation products comprising sequence information of a target sequence. This amplification can be an unbiased amplification, for example, by ligating a universal adaptor pair to the ends of the double-stranded ligation products, and amplifying all the tagged double-stranded ligation products with a universal primer pair. In other embodiments, a semi-targeted amplification is conducted in lieu of or in addition to the unbiased amplification. The semi-targeted amplification can be performed before or after the unbiased amplification E. Semi-targeted amplification of double-stranded polynucleotide library.

In one aspect, as shown in FIG. 1, a semi-targeted amplification of the double-stranded ligation product library comprises using a primer comprising a sequence that is reverse-complement and/or hybridizable to the adaptor, and a primer hybridizable to a target sequence (e.g., an EGFR gene sequence) or primers hybridizable to the same target sequence or multiple target sequences.

For an adaptor having the following structure: /5'Phos/ $N_1N_2 \ldots N_i$-UM-$M_1M_2 \ldots M_j$-Blocker, the primer can comprise a sequence that is reverse-complement and/or hybridizable to $M_1M_2 \ldots M_j$. This way, when the primer hybridizes to one strand of the dsDNA and the target-specific primer hybridizes to the other strand of the dsDNA, the PCR product will contain a target sequence as well as the $N_1N_2 \ldots N_i$-UMI sequence (and optionally, all or a portion of the $M_1M_2 \ldots M_j$ sequence) In one specific example, a reverse-complement primer comprises the sequence set forth in SEQ ID NO: 31 CACTCTTCCTACACGACGC (5' to 3').

In one aspect, a plurality of target-specific primers can be used, each comprising a sequence specific for the same or a different target sequence. In other words, the primers can have the same or different target sequences. In some embodiments, the pool of target-specific primers comprises about 5, about 10, about 25, about 50, about 100, about 150, about 200, about 250, about 300, about 400, about 500, about 60, about 700, about 800, about 900, about 1000, or more than about 100, different primers, such as about $10^4$, about $10^5$, about $10^6$, or more primers. In other embodiments, the pool comprises between about 20 and about 60, between about 60 and about 100, between about 100 and about 140, between about 140 and about 180, between about 180 and about 220, between about 220 and about 260, between about 260 and about 300, between about 300 and about 350, or between about 350 and about 400 different primers. In one aspect, the pool of target-specific primers are used together with one common reverse-complement primer, wherein the common reverse-complement primer forms a primer pair with each individual target-specific primer in the pool to amplify the target sequence in between the primers in a semi-targeted fashion. Thus, in this aspect, the semi-targeted amplification is not a whole genome amplification.

Since ctDNA fragments randomly, in one aspect, the primer position of the target-specific primer may be important. For example, if the primer landing spans a break point, it may result in lower conversion rates. A larger target-specific primer pool and/or using multiple partially overlapping primers for the same target sequence may solve the problem.

In one aspect, the sequence information of the target sequence can comprise a mutation, a single nucleotide polymorphism (SNP), a copy number variation (CNV), or an epigenetic change. In one aspect, the mutation comprises a point mutation, an insertion, a deletion, an inversion, a truncation, a fusion, an amplification, or any combination thereof.

In some embodiments, the amplified library of linear, double-stranded ligation products can be a library other than whole genome library, for example, a semi-targeted genome library.

In some embodiments, the method can further comprise purifying the amplified library of linear, double-stranded ligation products. Any suitable methods can be used to remove smaller fragments including primer dimers. For example, using PCR purification column from Qiagen could help to eliminate the smaller fragments from the samples and running the column-purified samples on 2% certified low range ultra agarose gel can help to select the desired fragment size. The beads-based DNA purification including AMPure method is also helpful to remove the smaller fragments. In some embodiments, the amplification product size is from about 100 bps to about 600 bps, such as from about 100 bps to about 400 bps, from about 150 bps to about 200 bps, from about 200 bps to about 250 bps, and from about 250 bps to about 300 bps. In one embodiment, dsDNA (>150 bps and >400 bps) is purified and collected, for example, by eluting beads suspended in a Tri-EDTA buffer.

In one aspect, the purification is bead-based. In another aspect, the purification is based on size selection, for example, the purification step selectively purifies polynucleotides greater about 150 nucleotides in lengths. In another aspect, the purification does not comprise using a specific binding pair (such as biotin/streptavidin), one of which is attached to the linear, double-stranded ligation product and the other is attached to a solid support (such as a bead). In one aspect, the purification is column-based, for example, by using a dsDNA or ssDNA purification column, such as those from Zymo or Qiagen.

F. CONSTRUCTION OF SEQUENCE LIBRARY AND ANALYSIS OF SEQUENCING READS

In one aspect, the method further comprises sequencing the purified amplified library of linear, double-stranded ligation products. In one aspect, the sequencing step comprises attaching a sequencing adapter and/or a sample-specific barcode to each linear, double-stranded ligation product in one particular aspect, the attaching step is performed using a polymerase chain reaction (PCR).

Figure 2:
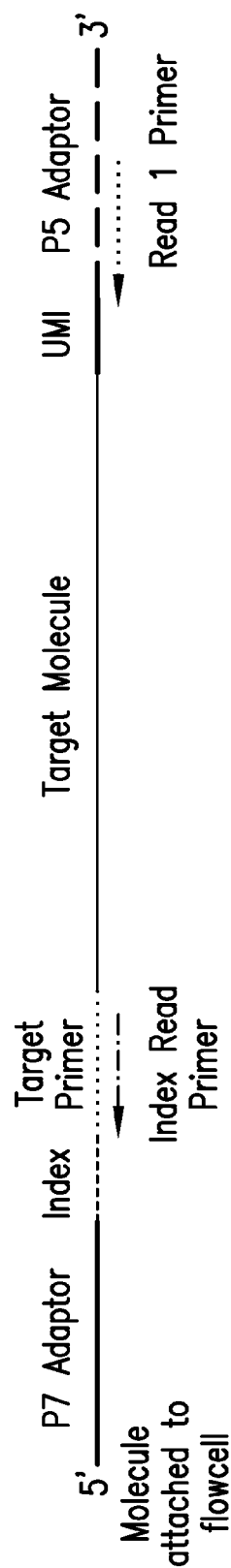
FIG. 2 shows a construct comprising a target molecule for sequencing, according to one aspect of the present disclosure.
Figure 3:
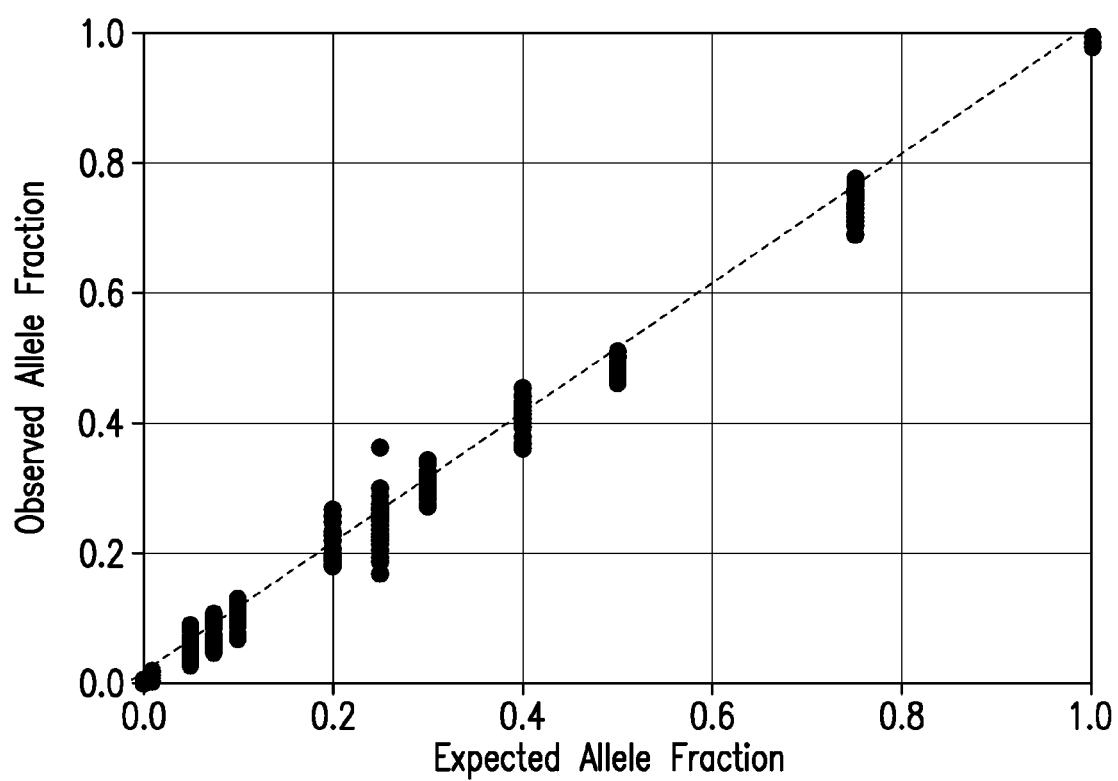
FIG. 3 shows the linear correlation between the expected allele fraction and the observed allele fraction using a method disclosed herein, indicating that the method has great reproducibility.
Figure 4:
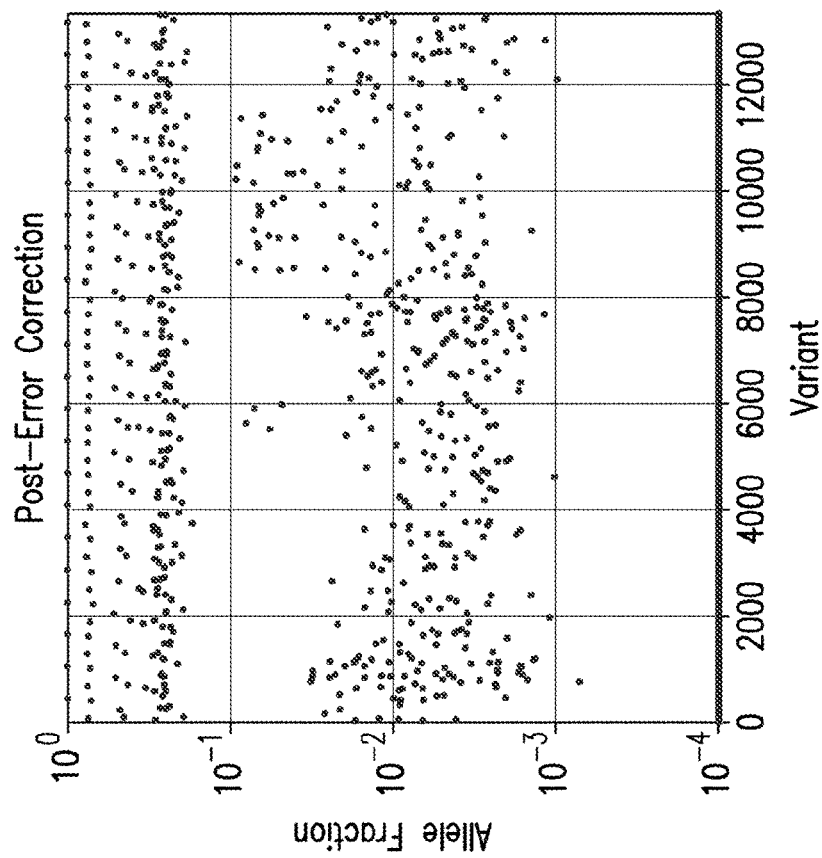
FIG. 4 compares the allele fraction for multiple variants before and after error-correction, using a method disclosed herein.
Figure 4:
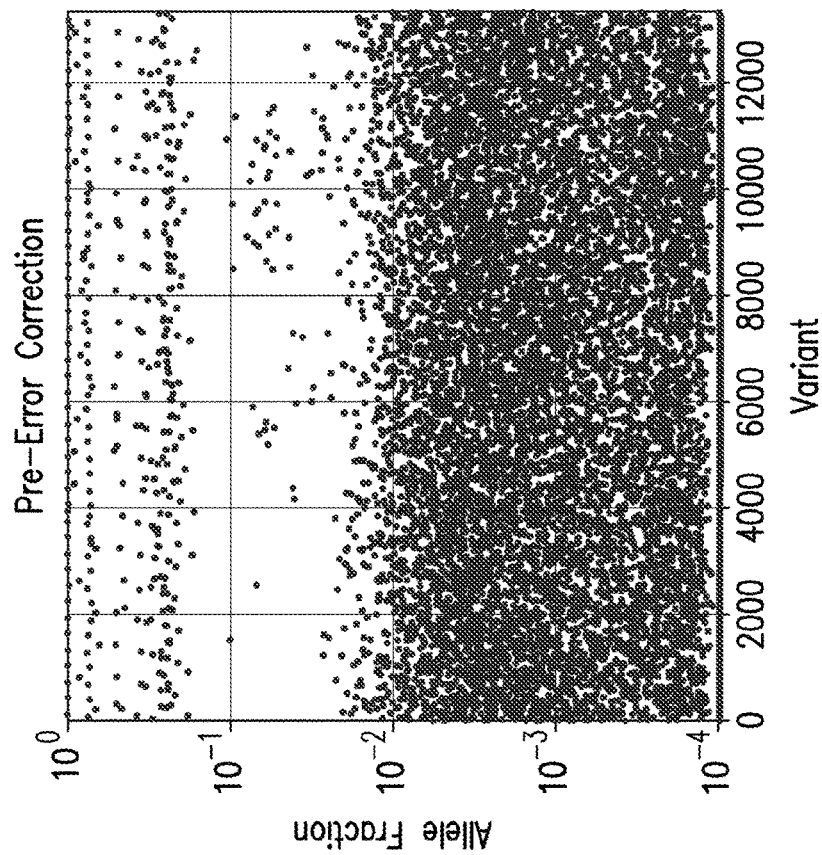

FIG. 2 shows an exemplary configuration of a construct comprising a target molecule for sequencing. For Illumina sequencing, on each end, these constructs have flow cell binding sites. P5 and P7, which allow the library fragment to attach to the flow cell surface. The P5 and P7 regions of single-stranded library fragments anneal to their complementary oligos on the flow cell surface. The flow cell oligos act as primers and a strand complementary to the library fragment is synthesized. Then, the original strand is washed away, leaving behind fragment copies that are covalently bonded to the flowcell surface in a mixture of orientations. Copies of each fragment are then generated by bridge amplification, creating clusters. Then, the P5 region is cleaved, resulting in clusters containing only fragments which are attached by the P7 region. This ensures that all copies are sequenced in the same direction. The sequencing primer anneals to the P5 end of the fragment, and begins the sequencing by synthesis process. Index reads are performed when a sample is barcoded. When Read 1 is finished, everything from Read 1 is removed and an index primer is added, which anneals at the P7 end of the fragment and sequences the barcode. Then, everything is stripped from the template, which forms clusters by bridge amplification as in Read 1. This leaves behind fragment copies that are covalently bonded to the flowcell surface in a mixture of orientations. This time, P7 is cut instead of P5, resulting in clusters containing only fragments which are attached by the P5 region. This ensures that all copies are sequenced in the same direction (opposite Read 1). The sequencing primer anneals to the P7 region and sequences the other end of the template.

Next-generation sequencing platforms, such as MiSeq Illumina Inc., San Diego, CA), can be used for highly multiplexed assay readout. A variety of statistical tools, such as the Proportion test, multiple comparison corrections based on False Discovery Rates (see Benjamini and Hochberg, 1995, *Journal of the Royal Statistical Society Series B (Methodological)* 57, 289-300), and Bonferroni corrections for multiple testing, can be used to analyze assay results. In addition, approaches developed for the analysis of differential expression from RNA-Seq data can be used to reduce variance for each target sequence and increase overall polymer in the analysis. See Smyth, 2004, Stat. Appl. Genet. Mol. Biol. 3, Article 3.

Overall, in some embodiments, the conversion rate of the present method is at least about 40%, at least about 50%, at least about 60%, at least about 70%, at least about 80%, at least about 90%, or at least about 95%. In one aspect, the conversion rate is the percentage of targeted single-stranded polynucleotides in the initial library that give rise to sequencing reads.

In any of the preceding embodiments, the method can be used for the diagnosis and/or prognosis of a disease or condition in a subject, predicting the responsiveness of a subject to a treatment, identifying a pharmacogenetics marker for the disease/condition or treatment, and/or screening a population for a genetic information. In one aspect, the disease or condition is a cancer or neoplasia, and the treatment is a cancer or neoplasia treatment.

Mutant DNA molecules offer unique ad vantages over cancer-associated biomarkers because they are so specific. Though mutations occur in individual normal cells at a low rate (about $10^9$ to $10^{10}$ mutations/bp/generation), such mutations represent such a tiny fraction of the total normal DNA that they are orders of magnitude below the detection limit of certain art methods. Several studies have shown that mutant DNA can be detected in stool, urine, and blood of CRC patients (Osborn and Ahlquist, Stool screening for colorectal cancer: molecular approaches, *Gastroenterology* 2005; 128:192-206).

Based on the sequencing results herein, detection of circulating tumor DNA in the patient can be made, and diagnosis of cancer and predictions regarding tumor recurrence can be made. Based on the predictions, treatment and surveillance decisions can be made. For example, circulating tumor DNA which indicates a future recurrence, can lead to additional or more aggressive therapies as well as additional or more sophisticated imaging and monitoring Circulating DNA refers to DNA that is ectopic to a tumor.

Samples which can be monitored for ctDNA include blood and stool. Blood samples may be for example a fraction of blood, such as serum or plasma. Similarly stool can be fractionated to purify DNA from other components. Tumor samples are used to identify a somatically mutated gene in the tumor that can be used as a marker of tumor in other locations in the body. Thus, as an example, a particular somatic mutation in a tumor can be identified by any standard means known in the art. Typical means include direct sequencing of tumor DNA, using allele-specific probes, allele-specific amplification, primer extension, etc. Once the somatic mutation is identified, it can be used in other compartments of the body to distinguish tumor derived DNA from DNA derived from other cells of the body Somatic mutations are confirmed by determining that they do not occur in normal tissues of the body of the same patient. Types of tumors which can be diagnosed and/or monitored in this fashion are virtually unlimited. Any tumor which sheds cells and/or DNA into the blood or stool or other bodily fluid can be used Such tumors include, in addition to colorectal tumors, tumors of the breast, lung, kidney, liver, pancreas, stomach, brain, head and neck, lymphatics, ovaries, uterus, bone, blood, etc.

In one aspect, the method disclosed herein can be used to construct a library for use in sequencing and/or in determining an epigenetic status/state of one or more regions of the target sequence. DNA methylation was first the discovered epigenetic mark. Epigenetics is the studs of changes in gene expression or cellular phenotype caused by mechanisms other than changes in the underlying DNA sequence. Methylation predominately involves the addition of a methyl group to the carbon-5 position of cytosine residues of the dinucleotide CpG and is associated with repression or inhibition of transcriptional activity.

Bisulfite conversion is the use of bisulfite reagents to treat DNA to determine its pattern of methylation. The treatment of DNA with bisulfite converts cytosine residues to uracil but leaves 5-methylcytosine residues unaffected. Thus, bisulfite treatment introduces specific changes in the DNA sequence that depend on the methylation status of the individual cytosine residues. Various analyses can be performed on the altered sequence to retrieve this information, for example, in order to differentiate between single nucleotide polymorphisms (SNP) resulting from the bisulfite conversion. U.S. Pat. Nos. 7,620,386, 9,365,902, and U.S. Patent Application Publication 2006/0134643, all of which are incorporated herein by reference, exemplify methods known to one of ordinary skill in the art with regard to detecting sequences altered due to bisulfite conversion. Bisulfite conversion can be conducted using any suitable techniques, procedures or reagents. In some embodiments, bisulfite conversion can be conducted using any of the following kits and procedures provided in the kit: EpiMark Bisulfite Conversion Kit, New England Biosciences, E3318S, EZ DNA Methylation Kit, Zymo Research, D5001; MethylCode Bisulfite Conversion Kit, Thermo Fisher Scientific. MECOV50; EZ DNA Methylation Gold Kit, Zymo Research, D5005; EZ DNA Methylation Direct Kit, Zymo Research, D5020; EZ DNA Methylation Lightning Kit, Zymo Research, D5030T; EpiJET Bisulfite Conversion Kit, Thermo Fisher Scientific, K1461; or EpiTect Bisulfite Kit, Qiagen, 59104.

As discussed above, one consequence of bisulfite conversion is that the double-stranded conformation of the original target is disrupted due to loss of sequence complementarity. While this may cause problem for traditional methods for constructing double-stranded libraries, in one aspect the present method is uniquely suited to construct single-stranded libraries from bisulfite conversion sample for sequencing analysis.

In another aspect, the present method can be used in combination with a method for determining a methylation state/status, for example, as described in U.S. Provisional Application No. 62/487,422, entitled "and Methods for Detection of Genomic Variance and DNA Methylation Status," filed Apr. 19, 2017, which is incorporated herein by reference in its entirety for all purposes. In one embodiment, a sample is contacted with a methylation-sensitive restriction enzyme (MSRE) before the dephosphorylation and/or the denaturing step, and methylation profiles are then be analyzed by constructing a single-stranded library by ligation as disclosed herein.

G. KIT FOR LIBRARY CONSTRUCTION AND/OR SEQUENCING

Disclosed in another aspect herein is a kit for constructing a library of ligation products. In one embodiment, the kit comprises a single-stranded DNA (ssDNA) ligase. In another aspect, the kit comprises a plurality of adaptors. In particular aspects, each adaptor is blocked to prevent ligation at the 3' end while the 5' end of the adaptor is available for ligation to a single-stranded polynucleotide to form a linear, single-stranded ligation product. In further particular aspects, each adaptor comprises a unique molecular identifier (UMI) sequence that earmarks the single-stranded polynucleotide.

In one aspect, the kit for constructing a library of ligation products can comprise a ssDNA ligase and a plurality of adaptors, and each adaptor is blocked to prevent ligation at the 3' end while the 5' end of the adaptor is available for ligation to a single-stranded polynucleotide to form a linear, single-stranded ligation product, and each adaptor comprises a UMI sequence that earmarks the single-stranded polynucleotide.

In another aspect, the kit can further comprise a denaturing reagent for denaturing a double-stranded polynucleotide from a sample to obtain the single-stranded polynucleotide.

In still another aspect, the kit can comprise a *Thermus* bacteriophage RNA ligase such as a bacteriophage TS2126 RNA ligase (e.g. CircLigase™ and CircLigase II™), or an archaebacterium RNA ligase such as *Methanobacterium thermoautotrophicum* RNA ligase 1. In any of the preceding embodiments, the kit can comprise an RNA ligase, such as a T4 RNA ligase, e.g., T4 RNA ligase 2, T4 RNA ligase 2 truncated. T4 RNA ligase 2 truncated KQ, or T4 RNA ligase 2 truncated K227Q. The present kit can also comprise other suitable ssDNA ligase, e.g., T4 RNA ligase 1, thermostable 5' App DNA/RNA ligase. T4 RNA ligase 2, truncated T4 RNA ligase 2, e.g., T4 RNA ligase 2 Truncated. T4 RNA ligase2 Truncated K227Q, T4 RNA ligase2 Truncated KQ, or T4 DNA ligase.

In one aspect, the kit can further comprise a crowding agent for the ligation reaction. In one aspect, the crowding agent comprises a polyethylene glycol (PEG), such as PEG 4000 or PEG 6000, Dextran, and/or Ficoll.

In another aspect, the kit can further comprise a set of primers each comprising a sequence that is reverse-complement to the adaptor and/or hybridizable to the adaptor, for converting the single-stranded polynucleotide to a double-stranded polynucleotide.

In one aspect, the kit can further comprise a reagent for removing primer dimer and/or primer-adaptor duplex.

In another aspect, the kit can further comprise a primer comprising a sequence specific for a target sequence (e.g., an EGFR gene sequence), for obtaining an amplified linear, double-stranded ligation product comprising sequence information of the target sequence. In a further aspect, the kit can further comprise a sequencing adapter and/or a sample-specific barcode, for sequencing the amplified linear, double-stranded ligation product.

Diagnostic kits based on the kit components described above are also provided, and they can be used to diagnose a disease or condition in a subject, for example, cancer. In another aspect, the kit can be used to predict individual's response to a drug, therapy, treatment, or a combination thereof. Such test kits can include devices and instructions that a subject can use to obtain a sample, e.g., of ctDNA, without the aid of a health care provider.

For use in the applications described or suggested above, kits or articles of manufacture are also provided Such kits may comprise at least one reagent specific for genotyping a marker for a disease or condition, and may further include instructions for carrying out a method described herein.

In some embodiments, provided herein are compositions and kits comprising primers and primer pairs, which allow the specific amplification of the polynucleotides or of any specific parts thereof, and probes that selectively or specifically hybridize to nucleic acid molecules or to any part thereof for the purpose of detection, either qualitatively or quantitatively. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides in a sample and as a means for detecting cell expressing proteins encoded by the polynucleotides. As will be understood by the skilled artisan, a great mans different primers and probes may be prepared based on the sequences provided herein and used effectively to amplify, clone and/or determine the presence and/or levels of polynucleotides, such as genomic DNAs, mtDNAs, and fragments thereof.

In some embodiments, the kit may additionally comprise reagents for detecting presence of polypeptides Such reagents may be antibodies or other binding molecules that specifically bind to a polypeptide. In some embodiments, such antibodies or binding molecules may be capable of distinguishing a structural variation to the polypeptide as a result of polymorphism, and thus may be used for genotyping. The antibodies or binding molecules may be labeled with a detectable marker, such as, for example, a radioisotope, fluorescent compound, bioluminescent compound, a chemiluminescent compound, metal chelator or enzyme Other reagents for performing binding assays, such as ELISA, may be included in the kit.

In some embodiments, the kits comprise reagents for genotyping at least two, at least three, at least five, at least ten, or more markers. The markers may be a poly nucleotide marker (such as a cancer-associated mutation or SNP) or a polypeptide marker (such as overexpression or a post-translational modification, including hyper- or hypo-phosphorylation, of a protein) or any combination thereof. In some embodiments, the kits may further comprise a surface or substrate (such as a microarray) for capture probes for detecting of amplified nucleic acids.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a biomarker. The kit may also have containers containing nucleotide(s) for amplification of the target nucleic acid sequence and/or a container comprising a reporter-means bound to a reporter molecule, such as an enzymatic, florescent, or radioisotope label.

The kit typically comprises the container(s) described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vi or in vitro use, such as those described above.

The kit can further comprise a set of instructions and materials for preparing a tissue or cell or body fluid sample and preparing nucleic acids (such as ctDNA) from the sample.

H. FURTHER EXEMPLARY EMBODIMENTS

In any of the preceding embodiments, the ssDNA ligase can be a *Thermus* bacteriophage RNA ligase such as a bacteriophage TS2126 RNA ligase (e.g., CircLigase™ and CircLigase II™), or an archaebacterium RNA ligase such as *Methanobacterium thermnoautorophicum* RNA ligase 1. In other aspects, the ssDNA ligase is an RNA ligase, such as a T4 RNA ligase, e.g., T4 RNA ligase 1, e.g., New England Biosciences, M0204S, T4 RNA ligase 2, e.g., New England Biosciences, M0239S, T4 RNA ligase 2 truncated, e.g., New England Biosciences, M0242S, T4 RNA ligase 2 truncated KQ, e.g., M0373S, or T4 RNA ligase 2 truncated K227Q, e.g., New England Biosciences, M0351S. In any of the preceding embodiments, the ssDNA ligase can also be a thermostable 5' App DNA/RNA ligase, e.g., New England Biosciences. M0319S, or T4 DNA ligase, e.g., New England Biosciences, M0202S.

In some embodiments, the present methods comprise ligating a set of adaptors to a library of single-stranded polynucleotides using a single-stranded DNA (ssDNA) ligase. Any suitable ssDNA ligase, including the ones disclosed herein, can be used. The adaptors can be used at any suitable level or concentration, e.g., from about 1 µM to about 100 µM such as about 1 µM, 10 µM, 20 µM, 30 µM, 40 µM, 50 µM, 60 µM, 70 µM, 80 µM, 90 µM, or 100 µM, or any subrange thereof. The adapter can comprise or begin with any suitable sequences or bases. For example, the adapter sequence can begin with all 2 bp combinations of bases.

In some embodiments, the ligation reaction can be conducted in the presence of a crowding agent. In one aspect, the crowding agent comprises a polyethylene glycol (PEG), such as PEG 40(K0, PEG 6000, or PEG 8000, Dextran, and/or Ficoll. The crowding agent, e.g., PEG, can be used at any suitable level or concentration. For example, the crowding agent, e.g., PEG, can be used at a level or concentration from about 0% (w/v) to about 25% (w/v), e.g., at about 0% (w/v), 1% (w/v), 2% (w/v), 3% (w/v), 4% (w/v), 5% (w/v), 6% (w/v), 7% (w/v), 8% (w/v), 9% (w/v), 10% (w/v), 11% (w/v), 12% (w/v), 13% (w/v), 14% (w/v), 15% (w/v), 16% (w/v), 17% (w/v), 18% (w/v), 19% (w/v), 20% (w/v), 21% (w/v), 22% (w/v), 23% (w/v), 24% (w/v), or 25% (w/v), or any subrange thereof.

In some embodiments, the ligation reaction can be conducted for any suitable length of time. For example, the ligation reaction can be conducted for a time from about 2 to about 16 hours. %, e.g., for about 2 hours, 3 hours, 4 hours, 5 hours, 6 hours, 7 hours, 8 hours, 9 hours, 10 hours, 11 hours, 12 hours, 13 hours, 14 hours, 15 hours, or 16 hours, or any subrange thereof.

In some embodiments, the ssDNA ligase in the ligation reaction can be used in any suitable volume. For example, the ssDNA ligase in the ligation reaction can be used at a volume from about 0.5 µl to about 2 µl, %, e.g., at about 0.5 µl, 0.6 µl, 0.7 µl, 0.8 µl, 0.9 µl, 1 µl, 1.1 µl, 1.2 µl, 1.3 µl, 1.4 µl, 1.5 µl, 1.6 µl, 1.7 µl, 1.8 µl, 1.9 µl, or 2 µl, or any subrange thereof.

In some embodiments, the ligation reaction can be conducted in the presence of a ligation enhancer, e.g., betaine. The ligation enhancer, e.g., betaine, can be used at any suitable volume, e.g., from about 0 µl to about 1 µl, e.g., at about 0 µl, 0.1 µl, 0.2 µl, 0.3 µl, 0.4 µl, 0.5 µl, 0.6 µl, 0.7 µl, 0.8 µl, 0.9 µl, 1 µl, or any subrange thereof.

In some embodiments, the ligation reaction can be conducted using a T4 RNA ligase I, e.g., the T4 RNA ligase I from New England Biosciences. M0204S, in the following exemplary reaction mix (20 µl); 1× Reaction Buffer (50 mM Tris-HCl, pH 7.5, 10 mM MgCl2, 1 mM DTT), 25% (wt/vol) PEG 8000, 1 mM hexamine cobalt chloride (optional), 1 µl (10 units) T4 RNA Ligase, and 1 mM ATP. The reaction can be incubated at 25° C. for 16 hours. The reaction can be stopped by adding 40 µl of 10 mM Tris-HCl pH 8.0, 2.5 mM EDTA.

In some embodiments, the ligation reaction can be conducted using a Thermostable 5' App DNA/RNA ligase, e.g., the Thermostable 5' App DNA/RNA ligase from New England Biosciences. M0319S, in the following exemplary reaction mix (20 µl), ssDNA/RNA Substrate 20 pmol (1 pmol/µl), 5' App DNA Oligonucleotide 40 pmol (2 pmol/µl), 10×NEBuffer 1 (2 µl), 50 mM MnCl (for ssDNA ligation only) (2 µl). Thermostable 5' App DNA/RNA Ligase (2 µl (40 pmol)), and Nuclease-free Water (to 20 µl). The reaction can be incubated at 65° C. for 1 hour. The reaction can be stopped by heating at 90° C. for 3 minutes.

In some embodiments, the ligation reaction can be conducted using a T4 RNA ligase 2, e.g., the T4 RNA ligase 2 from New England Biosciences. M0239S, in the following exemplary reaction mix (20 µl) T4 RNA ligase buffer (2 µl), enzyme (1 µl), PEG (10 µl). DNA (1 µl). Adapter (2 µl), and water (4 µl). The reaction can be incubated at 25° C. for 16 hours. The reaction can be stopped by heating at 65° C. for 20 minutes.

In some embodiments, the ligation reaction can be conducted using a T4 RNA ligase 2 Truncated, e.g., the T4 RNA ligase 2 Truncated from New England Biosciences. M0242S, in the following exemplary reaction mix (20 µl).

T4 RNA ligase buffer (2 µl), enzyme (1 µl), PEG (10 µl), DNA (1 µl), Adapter (2 µl), and water (4 µl). The reaction can be incubated at 25° C. for 16 hours. The reaction can be stopped by heating at 65° C. for 20 minutes.

In some embodiments, the ligation reaction can be conducted using a T4 RNA ligase 2 Truncated K227Q, e.g., the T4 RNA ligase 2 Truncated K227Q from New England Biosciences, M0351 S, in the following exemplary reaction mix (20 µl); T4 RNA ligase buffer (2 µl), enzyme (1 µl), PEG (10 µl), DNA (1 µl). Adenylated Adapter (0.72 µl), and water (5.28 µl). The reaction can be incubated at 25° C. for 16 hours. The reaction can be stopped by heating at 65° C. for 20 minutes.

In some embodiments, the ligation reaction can be conducted using a T4 RNA ligase 2 Truncated KQ, e.g., the T4 RNA ligase 2 Truncated KQ from New England Biosciences, M0373S, in the following exemplary reaction mix (20 µl): T4 RNA ligase buffer (2 µl), enzyme (1 µl), PEG (10 µl), DNA (1 µl). Adenylated Adapter (0.72 µl), and water (5.28 µl). The reaction can be incubated at 25° C. for 16 hours. The reaction can be stopped by heating at 65° C. for 20 minutes.

In some embodiments, the ligation reaction can be conducted using a T4 DNA ligase, e.g., the T4 DNA ligase from New England Biosciences, M0202S, in the following exemplary reaction mix (20 µl): T4 RNA ligase buffer (2 µl), enzyme (1 µl), PEG (10 µl), DNA (1 µl). Adenylated Adapter (0.72 µl), and water (5.28 µl). The reaction can be incubated at 16° C. for 16 hours. The reaction can be stopped by heating at 65° C. for 10 minutes.

The second strand synthesis step can be conducted using any suitable enzyme. For example, the second strand synthesis step can be conducted using Bst polymerase, e.g., New England Biosciences. M0275S or Klenow fragment (3'-=5' exo-), e.g., New England Biosciences, M0212S.

In some embodiments, the second strand synthesis step can be conducted using Bst polymerase, e.g., New England Biosciences, M0275S, in the following exemplary reaction mix (10 µl), water (1.5 µl), primer (0.5 µl), dNTP (1 µl), ThermoPol Reaction buffer (5 µl), and Bst (2 µl). The reaction can be incubated at 62° C. for 2 minutes and at 65° C. for 30 minutes. After the reaction, the double stranded DNA molecules can be further purified.

In some embodiments, the second strand synthesis step can be conducted using Klenow fragment (3'->5' exo-), e.g. New England Biosciences, M0212S, in the following exemplary reaction mix (10 µl): water (0.5 µl), primer (0.5 µl), dNTP (1 µl), NEB buffer (2 µl), and exo-(3 µl). The reaction can be incubated at 37° C. for 5 minutes and at 75° C. for 20 minutes. After the reaction, the double stranded DNA molecules can be further purified.

After the second strand synthesis, but before the first or semi-targeted PCR, the double stranded DNA can be purified. The double stranded DNA can be purified using any suitable technique or procedure. For example, the double stranded DNA can be purified using any of the following kits: Zymo clean and concentrator, Zymo research, D4103; Qiaquick, Qiagen, 28104; Zymo ssDNA purification kit, Zymo Research. D7010, Zymo Oligo purification kit, Zymo Research, D4060; and AmpureXP beads, Beckman Coulter, A63882: 1.2×-4× bead ratio.

The first or semi-targeted PCR can be conducted using any suitable enzyme or reaction conditions. For example, the polynucleotides or DNA strands can be annealed at a temperature ranging from about 52° C. to about 72° C., e.g., at about 52° C., 53° C., 54° C., 55° C., 56° C., 57° C., 58° C., 59° C., 60° C., 61° C., 62° C., 63° C., 63° C., 64° C., 65° C., 66° C., 67° C., 68° C. 69° C., 70° C., 71° C., or 72° C., or any subrange thereof. The first or semi-targeted PCR can be conducted for any suitable rounds of cycles. For example, the first or semi-targeted PCR can be conducted for 10-40 cycles, e.g., for 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 cycles. The primer pool can be used at any suitable concentration. For example, the primer pool can be used at a concentration ranging from about 5 nM to about 200 nM, e.g., at about 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 110 nM, 120 nM, 130 nM, 140 nM, 150 nM, 160 nM, 170 nM, 180 nM, 190 nM, or 200 nM, or any subrange thereof.

The first or semi-targeted PCR can be conducted using any suitable temperature cycle conditions. For example, the first or semi-targeted PCR can be conducted using any of the following cycle conditions: 95° C. 3 minutes, (95° C. 15 seconds, 62° C. 30 seconds, 72 C 90 seconds) ×3 or ×5, or 95° C. 15 seconds, 72° C. 90 seconds) ×23 or ×21, 72 C 1 minute, 4° C., forever.

In some embodiments, the first or semi-targeted PCR can be conducted using KAPA SYBR FAST, e.g., KAPA biosciences, KK4600, in the following exemplary reaction mix (50 µl): DNA (2 µl), KAPASYBR (25 µl), Primer Pool (26 nM each) (10 µl), Aprimer (100 µM) (0.4 µl), and water (12.6 µl). The first or semi-targeted PCR can be conducted using any of the following cycle conditions: 95° C. 30 seconds, (95° C. 10 seconds, 50-56° C. 45 seconds, 72° C. 35 seconds) ×40.

In some embodiments, the first or semi-targeted PCR can be conducted using KAPA HiFi, e.g., KAPA Biosciences, KK2601, in the following exemplary reaction mix (50 µl); DNA (15 µl), KAPAHiFi (25 µl), Primer Pool (26 nM each) (10 µl), and Aprimer (100 uM) (0.4 µl). The first or semi-targeted PCR can be conducted using any of the following cycle conditions-95° C. 3 minutes, (98° C. 20 seconds, 53-54° C. 15 seconds, 72° C. 35 seconds)×15, 72° C. 2 minutes, 4° C. forever.

Bisulfite conversion can be conducted using any suitable techniques, procedures or reagents. In some embodiments, bisulfite conversion can be conducted using any of the following kits and procedures provided in the kit: EpiMark Bisulfite Conversion Kit. New England Biosciences, E3318S, EZ DNA Methylation Kit, Zymo Research, D5001; MethylCode Bisulfite Conversion Kit, Thermo Fisher Scientific, MECOV50 EZ DNA Methylation Gold Kit. Zymo Research, D5005; EZ DNA Methylation Direct Kit, Zymo Research, D5020; EZ DNA Methylation Lightning Kit, Zymo Research, D5030T; EpiJET Bisulfite Conversion Kit, Thermo Fisher Scientific, K1461; or EpiTect Bisulfite Kit, Qiagen, 59104.

In some embodiments, DNA molecules can be prepared using the procedures illustrated in Example 4, including the steps for constructing single-stranded polynucleotide, conversion of single-stranded polynucleotide library to double-stranded polynucleotide library, semi-targeted amplification of double-stranded polynucleotide library, and construction of sequence library. Such DNA molecules can further be analyzed for methylation status using any suitable methods or procedures.

I. EXAMPLES

Example 1

In this example, the templates (e.g., polynucleotides to be sequenced) are short DNA fragments less than about 200 bp long. These DNA fragments can include extracted DNA from plasma, enzyme-treated (e.g., by a fragmentase) genomic DNA, or physically sheared DNA. The physically sheared DNA may be end repaired. In particular aspects, the template has a 3' hydroxyl group for ligation.

Typically, 10-30 ng of the properly prepared template DNA was dephosphorylated, for example, using 1 U FastAP Thermosensitive Alkaline Phosphatase (Thermo Scientific) in 100 mM MOPS (pH 7.5), 20 mM KCl, 10) mM $MgCl_2$, 2 mM DTT, and 5 mM $MnCl_2$ at 37° C., for 10 minutes. The DNA was then denatured, for example, at 95° C. for 2 minutes and put on ice for 1 minute.

A single-stranded adapter was synthesized from IDT with a 5' phosphate group and a 3' carbon spacer. The 5' end contains GA following by a 12-mer unique molecular identifier (UMI) sequence. A typical single-stranded adapter has the following sequence: /SPhos/GANNNNNNNNNNNN-NAGATCGGAAGACGTCGTTAGGGAAAGAGTG/ 3SpC3/ ("SPhos" represents a 5' phosphate group, "NNNNNNNNNNNN" represents a 12-mer UMI sequence, and "3SpC3'" represents a 3' carbon spacer.

A ligation reaction was then performed using the dephosphorylated, single-stranded DNA as template. The following final concentrations were used in the ligation reaction: 50 mM MOPS (pH 7.5), 10 mM KCl, 5 mM $MgCl_2$, 1 mM DTT, and 2.5 mM $MnCl_2$, 50% PEG 4000, 0.5 µM adapter, 125 µM ATP, and 200 U Epicentre Circligase™. The reaction was incubated at 60° C. for 2 hours, 80° C. for 10 minutes, 85° C. for 2 minutes, and held at 4° C.

The DNA was then double-stranded by adding the previous reaction volume to the following: 10 mM Tris-HCl (pH 8.3), 50 mM KCl, 1.5 mM $MgCl_2$, 1.25 U Taq DNA Polymerase (NEB), 1 µM reverse-complement primer (a primer that is reverse-complement to the adpator), and 200 µM dNTP mix. The reaction was incubated at 95° C. for 30 seconds, 62° C. for 2 minutes, 68° C. for 10 minutes, and held at 4° C. A typical reverse-complement primer comprises the sequence set forth in SEQ ID NO: 3: CACTCTTCCCTACACGACGC (5' to 3'). The following is an alignment between the adaptor and the reverse-complement primer.

performed with the following reagents: all purified DNA from previous reaction, 1×KAPA 2G multiplex master mix, 66 nM of each primer from pool, and 800 nM reverse-complement primer. The reaction under ent the following thermo-cycling program: 95° C. 3 minutes, (95° C. 15 seconds, 72° C. 90 seconds)×20, 72° C. 1 minute, and held at 4° C.

The reaction as then purified using 1.6 (bead ratio)× AmPure® XP beads. The beads were added and incubated for 10 minutes. The mixtures were then transferred to a magnet for 5 minutes. The supernatant was then removed. The beads were washed 2× with 150 µL 80% ethanol for 30 seconds each. All residual ethanol was then removed and the beads were dried for 3 minutes at room temperature off of the magnet. 20 µl of Low TE buffer (Thermo Fisher) was added to the beads and incubated for 2 minutes. The beads were then returned to the magnet for 1 minute. The supernatant is removed and stored for the next reaction. A bead ratio (such as 1.6) can be selected that removes molecules shorter than about 100 bp, including free adaptor molecules, free primer molecules, and/or adaptor/primer dimers.

Another PCR reaction was then completed to add full length sequencing adapters and sample specific barcodes. The PCR reaction contained the following: 2 µL purified DNA from previous reaction, 1×NEB ultra Q5 II master mix, 400 nM universal primer, and 400 nM barcode specific primer. The reaction underwent the following thermo-cycling program: 95° C. 3 minutes, (98° C. 10 seconds, 65° C. 75 seconds)×10, 65° C. 2 minute, and held at 4° C.

The reaction was then purified using 0.8 (bead ratio)× AmPure XP beads. The beads were added and incubated for 10 minutes. The mixtures were then transferred to a magnet for 5 minutes. The supernatant was then removed. The beads were washed 2× with 150 µL 80% ethanol for 30 seconds each. All residual ethanol % was then removed and the beads were dried for 3 minutes at room temperature off of the magnet. 25 µl of Low TE buffer (Thermo Fisher) is added to the beads and incubated for 2 minutes. The beads were then returned to the magnet for 1 minute. The supernatant is

```
Adaptor  /5Phos/GANNNNNNNNNNNNAGATCGGAAGAGCGTCGTGTAGGGAAAGAGTG/3SpC3/
                                  :::::::::::::::::::::
Primer                         CGCAGCACATCCCTTTCTCAC
```

The reaction was then purified using 1.6 (bead ratio)/ AmPure® XP beads. The beads % were added and incubated for 10 minutes. The mixtures were then transferred to a magnet for 5 minutes. The supernatant was then removed. The beads were washed 2× with 150 µL 80% ethanol for 30 seconds each. All residual ethanol was then removed and the beads were dried for 3 minutes at room temperature off of the magnet. 15 µl of Low TE buffer (Thermo Fisher) was added to the beads and incubated for 2 minutes. The beads were then returned to the magnet for 1 minute. The supernatant was removed and stored for the next reaction. In one aspect, the bead ratio causes size selectivity in the purification process, and a bead ratio (such as 1.6×) can be selected that removes molecules shorter than about 100 bp.

A set of PCR primers were designed to minimize primer-primer interactions and off-target annealing. The primers were further optimized to land within close proximity to specific variants. Once designed, the primers were synthesized by IDT. The primers were mixed in equal volume ratios into a primer pool. A semi-targeted PCR reaction was removed and is ready for sequencing. A bead ratio (such as 0.8) can be selected that removes a majority of molecules shorter than about 200 bp.

Example 2

In this example, both genomic DNA (gDNA) samples with known variants and plasma samples are tested, using 10 ng and 20 ng inputs. The gDNA samples contained single nucleotide variations (SNVs, used interchangeably with "single nucleotide changes," SNCs), indels, CNVs, and fusions. Each variant was called at various allele fractions: 5%, 1%, 0.5%, and 0.1%. The sensitivity and specificity at each allele fraction for each mutation type were measured. The primer pool used here is shown in Table 1. Each target-specific primer can be used at the same volume ratio for the entire pool, or at a different volume ratio. For example, for a primer with volume ratio 2, that primer is added at 2× volume of a primer with ratio 1.

TABLE 1

| Target Specific Primer | Volume Ratio | Sequence |
| --- | --- | --- |
| SEQ ID NO: 4 | 1 | GACTGGAGTTCAGACGTGTGCTCTTCCGATCTAAAACATCCCACGCCTAGTCCCTGG |
| SEQ ID NO: 5 | 1 | GACTGGAGTTCAGACGTGTGCTCTTCCGATCTAAACAGGTTTCCAGTGCCAGCT |
| SEQ ID NO: 6 | 1 | GACTGGAGTTCAGACGTGTGCTCTTCCGATCTAAACCCATAGAAGGGGTATTTGTTGGATTATTT |
| SEQ ID NO: 7 | 1 | GACTGGAGTTCAGACGTGTGCTCTTCCGATCTAAAGCCACCTCCTTACTTTGCCTCCT |
| SEQ ID NO: 8 | 1 | GACTGGAGTTCAGACGTGTGCTCTTCCGATCTAACAGATTGTGAACAGCCTTGGAAGCC |
| SEQ ID NO: 9 | 1 | GACTGGAGTTCAGACGTGTGCTCTTCCGATCTAACATGCAGAAGTCCAGGCTGAAAAGG |
| SEQ ID NO: 10 | 1 | GACTGGAGTTCAGACGTGTGCTCTTCCGATCTAACCATCATGATGTGTTACCCAGAATGTTTT |
| SEQ ID NO: 11 | 1 | GACTGGAGTTCAGACGTGTGCTCTTCCGATCTAACCGTAGTTCACATGCACTCCTGT |
| SEQ ID NO: 12 | 1 | GACTGGAGTTCAGACGTGTGCTCTTCCGATCTAACTAACAGGTTAAGTGCTCCCAGGGG |
| SEQ ID NO: 13 | 1 | GACTGGAGTTCAGACGTGTGCTCTTCCGATCTAACTTTGTGTCGCTACCTCAGTTTGCC |
| SEQ ID NO: 14 | 1 | GACTGGAGTTCAGACGTGTGCTCTTCCGATCTAAGAGTAATTCACACAAGCTCACCTGA |
| SEQ ID NO: 15 | 1 | GACTGGAGTTCAGACGTGTGCTCTTCCGATCTAAGCAGGATCTCAGGTCTCTCAAAGGG |
| SEQ ID NO: 16 | 1 | GACTGGAGTTCAGACGTGTGCTCTTCCGATCTAAGGCAAACACATCCACCCAAAGACTC |
| SEQ ID NO: 17 | 1 | GACTGGAGTTCAGACGTGTGCTCTTCCGATCTAAGTGAATTGCAGTCCTTCCCCTCTG |
| SEQ ID NO: 18 | 1 | GACTGGAGTTCAGACGTGTGCTCTTCCGATCTAATCTATTGTGGGCTCTGGGAATCCTG |
| SEQ ID NO: 19 | 1 | GACTGGAGTTCAGACGTGTGCTCTTCCGATCTAATTCTTAAGTAATACTAACCTTGAACCGACTGGT |
| SEQ ID NO: 20 | 1 | GACTGGAGTTCAGACGTGTGCTCTTCCGATCTACAAGAGCAGAAAGTCAGTCCCATGGA |
| SEQ ID NO: 21 | 1 | GACTGGAGTTCAGACGTGTGCTCTTCCGATCTACAAGTTGGAAATTTCTGGGCCATGAA |
| SEQ ID NO: 22 | 1 | GACTGGAGTTCAGACGTGTGCTCTTCCGATCTACACAGAAAGGGCCCAAATTCACCAAT |
| SEQ ID NO: 23 | 1 | GACTGGAGTTCAGACGTGTGCTCTTCCGATCTACAGAAGACCTCACATGCCACAAAGAA |
| SEQ ID NO: 24 | 1 | GACTGGAGTTCAGACGTGTGCTCTTCCGATCTACATGTGGAGTGAACGTTGTTGGACTC |
| SEQ ID NO: 25 | 1 | GACTGGAGTTCAGACGTGTGCTCTTCCGATCTACCAACTCCATAAACTAAACAGAAAGCGGT |
| SEQ ID NO: 26 | 1 | GACTGGAGTTCAGACGTGTGCTCTTCCGATCTACCGGGATTATGTCTCTTGTTTGGGA |
| SEQ ID NO: 27 | 1 | GACTGGAGTTCAGACGTGTGCTCTTCCGATCTACGGAATATAAGCTGGTGGTGGTGGG |
| SEQ ID NO: 28 | 1 | GACTGGAGTTCAGACGTGTGCTCTTCCGATCTACGGGAGAAAATAGCACCTCACTTCCA |

TABLE 1-continued

| Target Specific Primer | Volume Ratio | Sequence |
| --- | --- | --- |
| SEQ ID NO: 29 | 1 | GACTGGAGTTCAGACGTGTGCTCTTCCGATCTACTAGGTCAGCTGAAGATCCTGTGAGC |
| SEQ ID NO: 30 | 1 | GACTGGAGTTCAGACGTGTGCTCTTCCGATCTACTCCACACGCAAATTTCCTTCCACTC |
| SEQ ID NO: 31 | 1 | GACTGGAGTTCAGACGTGTGCTCTTCCGATCTACTGCTGGCTGATCTATGTCCCTGAAG |
| SEQ ID NO: 32 | 1 | GACTGGAGTTCAGACGTGTGCTCTTCCGATCTACTGGTTTCCAACAGGTTCTTGCTGGTGT |
| SEQ ID NO: 33 | 1 | GACTGGAGTTCAGACGTGTGCTCTTCCGATCTACTTACTGCAGCTGTTTTCACCTCTGT |
| SEQ ID NO: 34 | 1 | GACTGGAGTTCAGACGTGTGCTCTTCCGATCTAGAAAAAGTTTGCTGAGCTGGGTA |
| SEQ ID NO: 35 | 1 | GACTGGAGTTCAGACGTGTGCTCTTCCGATCTAGAAGGTGTGTCTTTAATTGAAGCATGA |
| SEQ ID NO: 36 | 1 | GACTGGAGTTCAGACGTGTGCTCTTCCGATCTAGACAATAAAAGGCAGCTTGGACACGG |
| SEQ ID NO: 37 | 1 | GACTGGAGTTCAGACGTGTGCTCTTCCGATCTAGACCATAACCCACCACAGCTAGAACT |
| SEQ ID NO: 38 | 1 | GACTGGAGTTCAGACGTGTGCTCTTCCGATCTAGACCCAACACAACTTCCTTATGATCACAA |
| SEQ ID NO: 39 | 1 | GACTGGAGTTCAGACGTGTGCTCTTCCGATCTAGAGTGCCAGCTGATGAAGACGGAG |
| SEQ ID NO: 40 | 1 | GACTGGAGTTCAGACGTGTGCTCTTCCGATCTAGATAATGACTCACCTGGGGCCACATT |
| SEQ ID NO: 41 | 1 | GACTGGAGTTCAGACGTGTGCTCTTCCGATCTAGATTGTCGTCGATTCTTGTGTGCTGT |
| SEQ ID NO: 42 | 1 | GACTGGAGTTCAGACGTGTGCTCTTCCGATCTAGCAAGTTCTTCATCAGCTGTACTCCT |
| SEQ ID NO: 43 | 1 | GACTGGAGTTCAGACGTGTGCTCTTCCGATCTAGCACTTACCTGTGACTCCATAGAAAATCT |
| SEQ ID NO: 44 | 1 | GACTGGAGTTCAGACGTGTGCTCTTCCGATCTAGCCACAAAACTTACAGATGCAGCAG |
| SEQ ID NO: 45 | 1 | GACTGGAGTTCAGACGTGTGCTCTTCCGATCTAGCCAGCCCGAAGTCTGTAATTTTGAC |
| SEQ ID NO: 46 | 1 | GACTGGAGTTCAGACGTGTGCTCTTCCGATCTAGCCCTCATGTCTGAACTCAAAGTCCT |
| SEQ ID NO: 47 | 1 | GACTGGAGTTCAGACGTGTGCTCTTCCGATCTAGCTGATTTGATGGAGTTGGACATGGC |
| SEQ ID NO: 48 | 1 | GACTGGAGTTCAGACGTGTGCTCTTCCGATCTAGGAAATCAAAGAACCTGTGGCCAAAC |
| SEQ ID NO: 49 | 1 | GACTGGAGTTCAGACGTGTGCTCTTCCGATCTAGGATCTTTTCTTCACGGTTGCCTACT |
| SEQ ID NO: 50 | 1 | GACTGGAGTTCAGACGTGTGCTCTTCCGATCTAGGATGAACAGGAAGAAGCCCACCC |
| SEQ ID NO: 51 | 1 | GACTGGAGTTCAGACGTGTGCTCTTCCGATCTAGGGAGGTCAAATAAGCAGCAGGAGAA |
| SEQ ID NO: 52 | 1 | GACTGGAGTTCAGACGTGTGCTCTTCCGATCTAGGTCACTGATGGAGGAGGTCTTGC |
| SEQ ID NO: 53 | 1 | GACTGGAGTTCAGACGTGTGCTCTTCCGATCTAGTACTTACCCACTGAAAAGCACTTCCTGA |

TABLE 1-continued

| Target Specific Primer | Volume Ratio | Sequence |
|---|---|---|
| SEQ ID NO: 54 | 1 | GACTGGAGTTCAGACGTGTGCTCTTCCGATCTAGTCAAGGTTGC TGATTTTGGTCTTG |
| SEQ ID NO: 55 | 1 | GACTGGAGTTCAGACGTGTGCTCTTCCGATCTAGTCCCTGATAG TTGCTAAGAACCGGT |
| SEQ ID NO: 56 | 1 | GACTGGAGTTCAGACGTGTGCTCTTCCGATCTAGTCCTCATGTA CTGGTCCCTCATTGC |
| SEQ ID NO: 57 | 1 | GACTGGAGTTCAGACGTGTGCTCTTCCGATCTAGTCTCTCTGCC TCAATAAGCCAACCA |
| SEQ ID NO: 58 | 1 | GACTGGAGTTCAGACGTGTGCTCTTCCGATCTAGTTGTCTCACT GCCTCATCTCTCACC |
| SEQ ID NO: 59 | 1 | GACTGGAGTTCAGACGTGTGCTCTTCCGATCTATCAGTCTGTCC AGCACTTCCATTGGG |
| SEQ ID NO: 60 | 1 | GACTGGAGTTCAGACGTGTGCTCTTCCGATCTATCCATGAACTC CACATTTGCCTTGGG |
| SEQ ID NO: 61 | 1 | GACTGGAGTTCAGACGTGTGCTCTTCCGATCTATCTCCTTGGTG ACCGCTCTGCATCTA |
| SEQ ID NO: 62 | 1 | GACTGGAGTTCAGACGTGTGCTCTTCCGATCTATTCCAGACGCA TTTCCACAGCTACAC |
| SEQ ID NO: 63 | 1 | GACTGGAGTTCAGACGTGTGCTCTTCCGATCTCAAAACAGCACA GTGAAAGCCAGCCAC |
| SEQ ID NO: 64 | 1 | GACTGGAGTTCAGACGTGTGCTCTTCCGATCTCAAAAGCCTCCA GTCGCCTCAGTAAAG |
| SEQ ID NO: 65 | 1 | GACTGGAGTTCAGACGTGTGCTCTTCCGATCTCAAACTTTATAA GATCCTGGCTATCCTGTGGA |
| SEQ ID NO: 66 | 1 | GACTGGAGTTCAGACGTGTGCTCTTCCGATCTCAACAAGTGTTA GCTCCTATTATCCTGTCCCT |
| SEQ ID NO: 67 | 1 | GACTGGAGTTCAGACGTGTGCTCTTCCGATCTCAACGGATGGGA GATTGAAGATTTCTGTTG |
| SEQ ID NO: 68 | 1 | GACTGGAGTTCAGACGTGTGCTCTTCCGATCTCAACTTGGAGGC CTTGCAGAAGAAGCT |
| SEQ ID NO: 69 | 1 | GACTGGAGTTCAGACGTGTGCTCTTCCGATCTCAAGGGGACTG TAGATGGGTGAAAAGAGCA |
| SEQ ID NO: 70 | 1 | GACTGGAGTTCAGACGTGTGCTCTTCCGATCTCACTCACCAATC ATGATGCCGGAGAAA |
| SEQ ID NO: 71 | 1 | GACTGGAGTTCAGACGTGTGCTCTTCCGATCTCAGAAGGTTGCA CTTGTCCACGCA |
| SEQ ID NO: 72 | 1 | GACTGGAGTTCAGACGTGTGCTCTTCCGATCTCAGACAGCAGCA CCGAGACGATGAAG |
| SEQ ID NO: 73 | 1 | GACTGGAGTTCAGACGTGTGCTCTTCCGATCTCAGACTCTCTCC TCCCCACTGCTG |
| SEQ ID NO: 74 | 1 | GACTGGAGTTCAGACGTGTGCTCTTCCGATCTCAGACTCTGGCC TACGTGTTTGTTTCC |
| SEQ ID NO: 75 | 1 | GACTGGAGTTCAGACGTGTGCTCTTCCGATCTCAGCGACATGTC TTTCCCCACAATCAT |
| SEQ ID NO: 76 | 1 | GACTGGAGTTCAGACGTGTGCTCTTCCGATCTCAGCTTTGCACC TGTTTTGTTGTGTAC |
| SEQ ID NO: 77 | 1 | GACTGGAGTTCAGACGTGTGCTCTTCCGATCTCAGGCCCTGGTA GCTCATCATCTGG |
| SEQ ID NO: 78 | 1 | GACTGGAGTTCAGACGTGTGCTCTTCCGATCTCAGGTCTCCGTG GATGCCTTCAAGATC |

TABLE 1-continued

| Target Specific Primer | Volume Ratio | Sequence |
|---|---|---|
| SEQ ID NO: 79 | 1 | GACTGGAGTTCAGACGTGTGCTCTTCCGATCTCAGTCTCTGGATCCCACACCTTTACCA |
| SEQ ID NO: 80 | 1 | GACTGGAGTTCAGACGTGTGCTCTTCCGATCTCAGTTTCTTCTTCTCATCGCGGGCTTG |
| SEQ ID NO: 81 | 1 | GACTGGAGTTCAGACGTGTGCTCTTCCGATCTCATACCCTCTCAGCGTACCCTTGTCC |
| SEQ ID NO: 82 | 1 | GACTGGAGTTCAGACGTGTGCTCTTCCGATCTCATATAGTTATCACCATAAAATTGTCATAGCTAGACATG |
| SEQ ID NO: 83 | 1 | GACTGGAGTTCAGACGTGTGCTCTTCCGATCTCATCGTGTACTTCCGGATCTTCTGCTG |
| SEQ ID NO: 84 | 1 | GACTGGAGTTCAGACGTGTGCTCTTCCGATCTCATGCCTTTCACGTTCCTTTCCCCAAA |
| SEQ ID NO: 85 | 1 | GACTGGAGTTCAGACGTGTGCTCTTCCGATCTCATTCTGGGAGCTTCATCTGGACCTGG |
| SEQ ID NO: 86 | 1 | GACTGGAGTTCAGACGTGTGCTCTTCCGATCTCCAATTGGCATGCTCTTCAATCACTGA |
| SEQ ID NO: 87 | 1 | GACTGGAGTTCAGACGTGTGCTCTTCCGATCTCCACACCTGTCATGTAGCAGCTTTCAG |
| SEQ ID NO: 88 | 1 | GACTGGAGTTCAGACGTGTGCTCTTCCGATCTCCACACGACGGGAAGACAAGTTCATG |
| SEQ ID NO: 89 | 1 | GACTGGAGTTCAGACGTGTGCTCTTCCGATCTCCACACTTCTCCATTCTTCACAAGGGT |
| SEQ ID NO: 90 | 1 | GACTGGAGTTCAGACGTGTGCTCTTCCGATCTCCACATGCTCCCAGGCTGTTTATTTGA |
| SEQ ID NO: 91 | 1 | GACTGGAGTTCAGACGTGTGCTCTTCCGATCTCCACTTCTCCAGGACCACGGACTG |
| SEQ ID NO: 92 | 1 | GACTGGAGTTCAGACGTGTGCTCTTCCGATCTCCAGGAGAGTTGCGGGGATTGAC |
| SEQ ID NO: 93 | 1 | GACTGGAGTTCAGACGTGTGCTCTTCCGATCTCCAGGGAATGTGGGGCCAGAC |
| SEQ ID NO: 94 | 1 | GACTGGAGTTCAGACGTGTGCTCTTCCGATCTCCAGTTGGTTACATACTTGGACTTGGT |
| SEQ ID NO: 95 | 1 | GACTGGAGTTCAGACGTGTGCTCTTCCGATCTCCATAGCTGACACCACGATACTTGACA |
| SEQ ID NO: 96 | 1 | GACTGGAGTTCAGACGTGTGCTCTTCCGATCTCCATGTAACAAACCTTCACGTCCTGCA |
| SEQ ID NO: 97 | 1 | GACTGGAGTTCAGACGTGTGCTCTTCCGATCTCCATTGGCATGGGGAAATATAAACTTGTTTGA |
| SEQ ID NO: 98 | 1 | GACTGGAGTTCAGACGTGTGCTCTTCCGATCTCCCAGTTTAAGATTTGCCCAGACTCAGC |
| SEQ ID NO: 99 | 1 | GACTGGAGTTCAGACGTGTGCTCTTCCGATCTCCCATCCTGCCAAAGTTTGTGATTCCA |
| SEQ ID NO: 100 | 1 | GACTGGAGTTCAGACGTGTGCTCTTCCGATCTCCCATGTCTTTGCAGCCGAGGAG |
| SEQ ID NO: 101 | 1 | GACTGGAGTTCAGACGTGTGCTCTTCCGATCTCCCCTCCTTCTGGCCACCATGCG |
| SEQ ID NO: 102 | 1 | GACTGGAGTTCAGACGTGTGCTCTTCCGATCTCCCTGTAAATTTCTCATGGGCAGCTCC |
| SEQ ID NO: 103 | 1 | GACTGGAGTTCAGACGTGTGCTCTTCCGATCTCCCTTGAAGCACTACACAGGCCACTT |

TABLE 1-continued

| Target Specific Primer | Volume Ratio | Sequence |
|---|---|---|
| SEQ ID NO: 104 | 1 | GACTGGAGTTCAGACGTGTGCTCTTCCGATCTCCGGAAGATGAT GTTCTCCAGGTCGAA |
| SEQ ID NO: 105 | 1 | GACTGGAGTTCAGACGTGTGCTCTTCCGATCTCCGTAGTAGGGG AAGATCATCTGCTGG |
| SEQ ID NO: 106 | 1 | GACTGGAGTTCAGACGTGTGCTCTTCCGATCTCCTCAAAAGACT TGGTGTTGTTGATGGC |
| SEQ ID NO: 107 | 1 | GACTGGAGTTCAGACGTGTGCTCTTCCGATCTCCTCATGGCAGG GCTCTAGGATGA |
| SEQ ID NO: 108 | 1 | GACTGGAGTTCAGACGTGTGCTCTTCCGATCTCCTCTGGTCAAG GTCACATTCTTCCA |
| SEQ ID NO: 109 | 1 | GACTGGAGTTCAGACGTGTGCTCTTCCGATCTCCTGCGTCATCA TCTTTGTCATCGTGT |
| SEQ ID NO: 110 | 1 | GACTGGAGTTCAGACGTGTGCTCTTCCGATCTCCTGTGCCCCTT AGCTGTGATTTCCTA |
| SEQ ID NO: 111 | 1 | GACTGGAGTTCAGACGTGTGCTCTTCCGATCTCCTGTGCTTCAA CTAAATTTAACTGTCAGCA |
| SEQ ID NO: 112 | 1 | GACTGGAGTTCAGACGTGTGCTCTTCCGATCTCCTTCGTCCTCC TTCCTCACTCTGC |
| SEQ ID NO: 113 | 1 | GACTGGAGTTCAGACGTGTGCTCTTCCGATCTCGATGTAGCTGT GCATGTCCTGGTG |
| SEQ ID NO: 114 | 1 | GACTGGAGTTCAGACGTGTGCTCTTCCGATCTCGCAGTGCTAAC CAAGTTCTTTCTTTTGC |
| SEQ ID NO: 115 | 1 | GACTGGAGTTCAGACGTGTGCTCTTCCGATCTCGCCAGTCTGTA TCACATCCACCTCAT |
| SEQ ID NO: 116 | 1 | GACTGGAGTTCAGACGTGTGCTCTTCCGATCTCGGACGCAACAG AGAAAGACTTGTCAG |
| SEQ ID NO: 117 | 1 | GACTGGAGTTCAGACGTGTGCTCTTCCGATCTCGGAGCAAACCC CTATGTCCACAAG |
| SEQ ID NO: 118 | 1 | GACTGGAGTTCAGACGTGTGCTCTTCCGATCTCGTCACTCTGGA TTGTGTACACTCTGTCAA |
| SEQ ID NO: 119 | 1 | GACTGGAGTTCAGACGTGTGCTCTTCCGATCTCGTGAGCGCTTC GAGATGTTCCGA |
| SEQ ID NO: 120 | 1 | GACTGGAGTTCAGACGTGTGCTCTTCCGATCTCTAAAGGAAATC ACGCTGTCCCCTGTG |
| SEQ ID NO: 121 | 1 | GACTGGAGTTCAGACGTGTGCTCTTCCGATCTCTAACCCCAGTC AGCTCCAGAGTCAC |
| SEQ ID NO: 122 | 1 | GACTGGAGTTCAGACGTGTGCTCTTCCGATCTCTAACTCTCTTT GACTGCAGAATCCAACTGTAA |
| SEQ ID NO: 123 | 1 | GACTGGAGTTCAGACGTGTGCTCTTCCGATCTCTAATCACCACC CCACCCAATTCCAGG |
| SEQ ID NO: 124 | 1 | GACTGGAGTTCAGACGTGTGCTCTTCCGATCTCTACGACAAGTG GGAGATGGAACGCA |
| SEQ ID NO: 125 | 1 | GACTGGAGTTCAGACGTGTGCTCTTCCGATCTCTAGGTGAGAGG CAGTGGTCAGGGTC |
| SEQ ID NO: 126 | 1 | GACTGGAGTTCAGACGTGTGCTCTTCCGATCTCTCAACGAGTGC TTCATCAAGGTGCC |
| SEQ ID NO: 127 | 1 | GACTGGAGTTCAGACGTGTGCTCTTCCGATCTCTCCACATTTCA GCAACAGCAGCATCT |
| SEQ ID NO: 128 | 1 | GACTGGAGTTCAGACGTGTGCTCTTCCGATCTCTCGATCTTGTA GGGGATGTTGAGGCT |

TABLE 1-continued

| Target Specific Primer | Volume Ratio | Sequence |
|---|---|---|
| SEQ ID NO: 129 | 1 | GACTGGAGTTCAGACGTGTGCTCTTCCGATCTCTCTACAACCCC ACCACGTACCAGATG |
| SEQ ID NO: 130 | 1 | GACTGGAGTTCAGACGTGTGCTCTTCCGATCTCTCTCCTTTTCC TCCTCTTCTCCTGGC |
| SEQ ID NO: 131 | 1 | GACTGGAGTTCAGACGTGTGCTCTTCCGATCTCTCTCTCAATGG CTTCTGTCCTGTGGA |
| SEQ ID NO: 132 | 1 | GACTGGAGTTCAGACGTGTGCTCTTCCGATCTCTCTGGAATCCA GTGTTTCTTTTAAATACCTGTTAAG |
| SEQ ID NO: 133 | 1 | GACTGGAGTTCAGACGTGTGCTCTTCCGATCTCTCTGGCATTCT GGGAGCTTCATCTGG |
| SEQ ID NO: 134 | 1 | GACTGGAGTTCAGACGTGTGCTCTTCCGATCTCTGAGCCTGTTC TTTCCAAGGGTGC |
| SEQ ID NO: 135 | 1 | GACTGGAGTTCAGACGTGTGCTCTTCCGATCTCTGAGGGAATGA AAGTGGGATCAGGGA |
| SEQ ID NO: 136 | 1 | GACTGGAGTTCAGACGTGTGCTCTTCCGATCTCTGATAAGGTTA AGGGCCCCAACGGTA |
| SEQ ID NO: 137 | 1 | GACTGGAGTTCAGACGTGTGCTCTTCCGATCTCTGGAAGTCGAT CACCTGCCTCACTAT |
| SEQ ID NO: 138 | 1 | GACTGGAGTTCAGACGTGTGCTCTTCCGATCTCTGGATGCTGCA CAGGTGTACAATCC |
| SEQ ID NO: 139 | 1 | GACTGGAGTTCAGACGTGTGCTCTTCCGATCTCTGGTGCTCATT TAGTCCTGGGGCAG |
| SEQ ID NO: 140 | 1 | GACTGGAGTTCAGACGTGTGCTCTTCCGATCTCTGGTTTGGGGA AGAGTGGGCTAGTG |
| SEQ ID NO: 141 | 1 | GACTGGAGTTCAGACGTGTGCTCTTCCGATCTCTGTAGACTACC GAGCTACTTTTCCAGAAGGTA |
| SEQ ID NO: 142 | 1 | GACTGGAGTTCAGACGTGTGCTCTTCCGATCTCTGTGCCGAGTA TCCTGGAGCCTC |
| SEQ ID NO: 143 | 1 | GACTGGAGTTCAGACGTGTGCTCTTCCGATCTCTGTGTGACTAT CTCCCTGGGTGTAGC |
| SEQ ID NO: 144 | 1 | GACTGGAGTTCAGACGTGTGCTCTTCCGATCTCTTCCACACTCT GAGGCGGAACATG |
| SEQ ID NO: 145 | 1 | GACTGGAGTTCAGACGTGTGCTCTTCCGATCTCTTCCCAGAGAC ATTGCTGCCAGAAAC |
| SEQ ID NO: 146 | 1 | GACTGGAGTTCAGACGTGTGCTCTTCCGATCTCTTCTTCACGCT CCTTCCCTATCCCTT |
| SEQ ID NO: 147 | 1 | GACTGGAGTTCAGACGTGTGCTCTTCCGATCTCTTGTCCTGCTT GCTTACCTCGCTTAG |
| SEQ ID NO: 148 | 1 | GACTGGAGTTCAGACGTGTGCTCTTCCGATCTCTTTATCTGTAT CAAAGAATGGTCCTGCACC |
| SEQ ID NO: 149 | 1 | GACTGGAGTTCAGACGTGTGCTCTTCCGATCTCTTTCTCGGTTC TCTGATTCCTGGCAG |
| SEQ ID NO: 150 | 1 | GACTGGAGTTCAGACGTGTGCTCTTCCGATCTGAAATGTGAGCC CTTGAGATCTGCGG |
| SEQ ID NO: 151 | 1 | GACTGGAGTTCAGACGTGTGCTCTTCCGATCTGAACAATGCCTC CACGACCATCATCAG |
| SEQ ID NO: 152 | 1 | GACTGGAGTTCAGACGTGTGCTCTTCCGATCTGAAGACCCAAGC TGCCTGACCC |
| SEQ ID NO: 153 | 1 | GACTGGAGTTCAGACGTGTGCTCTTCCGATCTGAAGCAACCCAC AGATGTTCCCGG |

TABLE 1-continued

| Target Specific Primer | Volume Ratio | Sequence |
|---|---|---|
| SEQ ID NO: 154 | 1 | GACTGGAGTTCAGACGTGTGCTCTTCCGATCTGAAGCCCCTTTCTTTGTTCAGCCCC |
| SEQ ID NO: 155 | 1 | GACTGGAGTTCAGACGTGTGCTCTTCCGATCTGAAGTGCCCTTGGTTCGGACAGACAAC |
| SEQ ID NO: 156 | 1 | GACTGGAGTTCAGACGTGTGCTCTTCCGATCTGAATCTCCTCCCAACTCAACTTCCCAG |
| SEQ ID NO: 157 | 1 | GACTGGAGTTCAGACGTGTGCTCTTCCGATCTGACACCTAGCTGTGATCCTGAAACTGAATTT |
| SEQ ID NO: 158 | 1 | GACTGGAGTTCAGACGTGTGCTCTTCCGATCTGACCCAAACAAAAGCGATCTCCTCCAG |
| SEQ ID NO: 159 | 1 | GACTGGAGTTCAGACGTGTGCTCTTCCGATCTGACTCACCGGTGGATGAAGTGGTTTTC |
| SEQ ID NO: 160 | 1 | GACTGGAGTTCAGACGTGTGCTCTTCCGATCTGACTTCTCCTCCACAAATCCAGAGCTG |
| SEQ ID NO: 161 | 1 | GACTGGAGTTCAGACGTGTGCTCTTCCGATCTGAGCCTTTCCCTCTGCCCTTTTCAAG |
| SEQ ID NO: 162 | 1 | GACTGGAGTTCAGACGTGTGCTCTTCCGATCTGAGCTCCCCACCCCCTGATCAG |
| SEQ ID NO: 163 | 1 | GACTGGAGTTCAGACGTGTGCTCTTCCGATCTGAGGAGGCCATCTTCCATCTTCTCACA |
| SEQ ID NO: 164 | 1 | GACTGGAGTTCAGACGTGTGCTCTTCCGATCTGAGTCTTCCCACAAGTTCGCTCTTTGG |
| SEQ ID NO: 165 | 1 | GACTGGAGTTCAGACGTGTGCTCTTCCGATCTGAGTGGGCATTGTATGGAAACTGAGGC |
| SEQ ID NO: 166 | 1 | GACTGGAGTTCAGACGTGTGCTCTTCCGATCTGATACGGCCAGGCATTGAAGTCTCATG |
| SEQ ID NO: 167 | 1 | GACTGGAGTTCAGACGTGTGCTCTTCCGATCTGATAGTTTCTGAAGGAATGCTATGGTATGAAACA |
| SEQ ID NO: 168 | 1 | GACTGGAGTTCAGACGTGTGCTCTTCCGATCTGATCCAGCCAGACCCAGCCAGTATTAT |
| SEQ ID NO: 169 | 1 | GACTGGAGTTCAGACGTGTGCTCTTCCGATCTGATCTTGAAGGCATCCACGGAGACC |
| SEQ ID NO: 170 | 1 | GACTGGAGTTCAGACGTGTGCTCTTCCGATCTGCAAAGGAGAAGACAAGAGGAGACAGAGTC |
| SEQ ID NO: 171 | 1 | GACTGGAGTTCAGACGTGTGCTCTTCCGATCTGCAACACCCAGCCCTCGGTAAG |
| SEQ ID NO: 172 | 1 | GACTGGAGTTCAGACGTGTGCTCTTCCGATCTGCAGCAACGGACATGAGTTTGTTTTCC |
| SEQ ID NO: 173 | 1 | GACTGGAGTTCAGACGTGTGCTCTTCCGATCTGCAGCACCGAGACGATGAAGGAGAAG |
| SEQ ID NO: 174 | 1 | GACTGGAGTTCAGACGTGTGCTCTTCCGATCTGCAGGACCCGACAAAACCTAAAGATGG |
| SEQ ID NO: 175 | 1 | GACTGGAGTTCAGACGTGTGCTCTTCCGATCTGCCCATCCCTGACTGTGAGATCAAGAA |
| SEQ ID NO: 176 | 1 | GACTGGAGTTCAGACGTGTGCTCTTCCGATCTGCCCCAATTGCAGGTAAAACAGTCAAG |
| SEQ ID NO: 177 | 1 | GACTGGAGTTCAGACGTGTGCTCTTCCGATCTGCCCGTATTTACTGCCGTTCTTTTCCA |
| SEQ ID NO: 178 | 1 | GACTGGAGTTCAGACGTGTGCTCTTCCGATCTGCCTCCCAGCAATTTCCTCCCTTGTT |

TABLE 1-continued

| Target Specific Primer | Volume Ratio | Sequence |
|---|---|---|
| SEQ ID NO: 179 | 1 | GACTGGAGTTCAGACGTGTGCTCTTCCGATCTGCCTGTGTTCTGCCCCCATTTC |
| SEQ ID NO: 180 | 1 | GACTGGAGTTCAGACGTGTGCTCTTCCGATCTGCGGAAGAATGTGTCAGCCTCAAAGAA |
| SEQ ID NO: 181 | 1 | GACTGGAGTTCAGACGTGTGCTCTTCCGATCTGCGTGCCTGCCAATGGTGATG |
| SEQ ID NO: 182 | 1 | GACTGGAGTTCAGACGTGTGCTCTTCCGATCTGCTAAGGGCACAGGGTAGGTAGT |
| SEQ ID NO: 183 | 1 | GACTGGAGTTCAGACGTGTGCTCTTCCGATCTGCTAATGTTAAGAATGTACTGATATTTATTACTGAACCTTTAGGT |
| SEQ ID NO: 184 | 1 | GACTGGAGTTCAGACGTGTGCTCTTCCGATCTGCTATTTAAGATTACGAAGGTATTGGTTTAGACAGAAAT |
| SEQ ID NO: 185 | 1 | GACTGGAGTTCAGACGTGTGCTCTTCCGATCTGCTCGGGTTGGCTCTAAAGTAGTCCT |
| SEQ ID NO: 186 | 1 | GACTGGAGTTCAGACGTGTGCTCTTCCGATCTGCTGCCACTTCTACGACTTCTTCAACC |
| SEQ ID NO: 187 | 1 | GACTGGAGTTCAGACGTGTGCTCTTCCGATCTGCTGGAAAGGGACGAACTGGTGTAATG |
| SEQ ID NO: 188 | 1 | GACTGGAGTTCAGACGTGTGCTCTTCCGATCTGCTTGCAAAAATCCAGTAGTAGCTAGCTCTGC |
| SEQ ID NO: 189 | 1 | GACTGGAGTTCAGACGTGTGCTCTTCCGATCTGCTTGGATCATATTGGCCTGTCTGCTC |
| SEQ ID NO: 190 | 1 | GACTGGAGTTCAGACGTGTGCTCTTCCGATCTGGAAATAGGTTTCATGGACTCAGTTACTACCTG |
| SEQ ID NO: 191 | 1 | GACTGGAGTTCAGACGTGTGCTCTTCCGATCTGGAAGCCAAGCCCAGTTCTGGAAG |
| SEQ ID NO: 192 | 1 | GACTGGAGTTCAGACGTGTGCTCTTCCGATCTGGACAGTTGATACAAAACAAGCCCACG |
| SEQ ID NO: 193 | 1 | GACTGGAGTTCAGACGTGTGCTCTTCCGATCTGGAGCAGATCAAACGGGTGAAGGACTC |
| SEQ ID NO: 194 | 1 | GACTGGAGTTCAGACGTGTGCTCTTCCGATCTGGAGTCCAGGAAATGATATCACATAAGT |
| SEQ ID NO: 195 | 1 | GACTGGAGTTCAGACGTGTGCTCTTCCGATCTGGATACTTACGCGCCACAGAGAAGTTG |
| SEQ ID NO: 196 | 1 | GACTGGAGTTCAGACGTGTGCTCTTCCGATCTGGATATATTCCAGTGGTTTGTTGCTCTCTG |
| SEQ ID NO: 197 | 1 | GACTGGAGTTCAGACGTGTGCTCTTCCGATCTGGATGCCTTATTGCGACAGATCCGGA |
| SEQ ID NO: 198 | 1 | GACTGGAGTTCAGACGTGTGCTCTTCCGATCTGGATGTTCTGGAAGGCAAACTCCATGG |
| SEQ ID NO: 199 | 1 | GACTGGAGTTCAGACGTGTGCTCTTCCGATCTGGCCTCTGATTCCTCACTGATTGCTCT |
| SEQ ID NO: 200 | 1 | GACTGGAGTTCAGACGTGTGCTCTTCCGATCTGGCCTGCTGAAAATGACTGAATATAAACTTGTGG |
| SEQ ID NO: 201 | 1 | GACTGGAGTTCAGACGTGTGCTCTTCCGATCTGGCTGGATCCTGAACTGGGCAAATTA |
| SEQ ID NO: 202 | 1 | GACTGGAGTTCAGACGTGTGCTCTTCCGATCTGGCTTCACAGACATCCTTGCACATCTC |

TABLE 1-continued

| Target Specific Primer | Volume Ratio | Sequence |
|---|---|---|
| SEQ ID NO: 203 | 1 | GACTGGAGTTCAGACGTGTGCTCTTCCGATCTGGGCTTGAACAT ACTAAATGCTCCAGT |
| SEQ ID NO: 204 | 1 | GACTGGAGTTCAGACGTGTGCTCTTCCGATCTGGGTTCAGCAAA TCTTCTAATCCATGAGG |
| SEQ ID NO: 205 | 1 | GACTGGAGTTCAGACGTGTGCTCTTCCGATCTGGTACTCTGTCT CGTCAATGTCCAGCA |
| SEQ ID NO: 206 | 1 | GACTGGAGTTCAGACGTGTGCTCTTCCGATCTGGTAGATTCCAG TTCTTGTGTGCGTGC |
| SEQ ID NO: 207 | 1 | GACTGGAGTTCAGACGTGTGCTCTTCCGATCTGGTCCCTCCCAC AGTTGCTTCAAGT |
| SEQ ID NO: 208 | 1 | GACTGGAGTTCAGACGTGTGCTCTTCCGATCTGGTGGGAAGAAC AGCCTAGACTTGGG |
| SEQ ID NO: 209 | 1 | GACTGGAGTTCAGACGTGTGCTCTTCCGATCTGGTTCCAGGCTT GCTGTAATTACCCAG |
| SEQ ID NO: 210 | 1 | GACTGGAGTTCAGACGTGTGCTCTTCCGATCTGTAATCCCCAAC CCAATAGACCCACCC |
| SEQ ID NO: 211 | 1 | GACTGGAGTTCAGACGTGTGCTCTTCCGATCTGTCAGAGTTCAA GTACTGGGGGCCA |
| SEQ ID NO: 212 | 1 | GACTGGAGTTCAGACGTGTGCTCTTCCGATCTGTCAGCAGAGAA CCAAGCCCTCCTAAG |
| SEQ ID NO: 213 | 1 | GACTGGAGTTCAGACGTGTGCTCTTCCGATCTGTCCTGAGCCTG TTTTGTGTCTACTGTTTC |
| SEQ ID NO: 214 | 1 | GACTGGAGTTCAGACGTGTGCTCTTCCGATCTGTCCTGGGATTG CAGATTGGGCCTTG |
| SEQ ID NO: 215 | 1 | GACTGGAGTTCAGACGTGTGCTCTTCCGATCTGTCTCCCATACC CTCTCAGCGTACC |
| SEQ ID NO: 216 | 1 | GACTGGAGTTCAGACGTGTGCTCTTCCGATCTGTGAAGGACCAA GGAGCAGAGGAGG |
| SEQ ID NO: 217 | 1 | GACTGGAGTTCAGACGTGTGCTCTTCCGATCTGTGACCGAGGAC AACGTGATGAAGATC |
| SEQ ID NO: 218 | 1 | GACTGGAGTTCAGACGTGTGCTCTTCCGATCTGTGAGCAGGTGG AAGTAGGAGGTCTTG |
| SEQ ID NO: 219 | 1 | GACTGGAGTTCAGACGTGTGCTCTTCCGATCTGTGATAGGAAGC TGTGGAGTGATGAGC |
| SEQ ID NO: 220 | 1 | GACTGGAGTTCAGACGTGTGCTCTTCCGATCTGTGCAATTCAGA CCCCAACAGTACGAA |
| SEQ ID NO: 221 | 1 | GACTGGAGTTCAGACGTGTGCTCTTCCGATCTGTTCAGAGTAGT AGCTGCAAATAATCTAGGGTTTGG |
| SEQ ID NO: 222 | 1 | GACTGGAGTTCAGACGTGTGCTCTTCCGATCTGTTCATCGGGAC TTGGCAGCCA |
| SEQ ID NO: 223 | 1 | GACTGGAGTTCAGACGTGTGCTCTTCCGATCTGTTGGGACCACA CTGAGTTCTCTGT |
| SEQ ID NO: 224 | 1 | GACTGGAGTTCAGACGTGTGCTCTTCCGATCTGTTGGTGCGGGA GTGAATAGGCC |
| SEQ ID NO: 225 | 1 | GACTGGAGTTCAGACGTGTGCTCTTCCGATCTGTTTACTTGAAG GCCTCCGGAATGCG |
| SEQ ID NO: 226 | 1 | GACTGGAGTTCAGACGTGTGCTCTTCCGATCTTACCTTTCCTCT GTGTTGGCGGATACC |
| SEQ ID NO: 227 | 1 | GACTGGAGTTCAGACGTGTGCTCTTCCGATCTTAGGCCTTGGTG TGCATTCTTCTCTCT |

TABLE 1-continued

| Target Specific Primer | Volume Ratio | Sequence |
|---|---|---|
| SEQ ID NO: 228 | 1 | GACTGGAGTTCAGACGTGTGCTCTTCCGATCTTAGTCGGTCATG<br>ATGGTCGAGGTGC |
| SEQ ID NO: 229 | 1 | GACTGGAGTTCAGACGTGTGCTCTTCCGATCTTCAAACTGCAGA<br>GTATTTGGGCGAATG |
| SEQ ID NO: 230 | 1 | GACTGGAGTTCAGACGTGTGCTCTTCCGATCTTCAAGGTTGGAA<br>TGAGCTGGATAAGGC |
| SEQ ID NO: 231 | 1 | GACTGGAGTTCAGACGTGTGCTCTTCCGATCTTCACATTTCTTT<br>GACCATTTGTTTTGCTGT |
| SEQ ID NO: 232 | 1 | GACTGGAGTTCAGACGTGTGCTCTTCCGATCTTCCCAAAGCAGA<br>AGTAAAACCAGATGC |
| SEQ ID NO: 233 | 1 | GACTGGAGTTCAGACGTGTGCTCTTCCGATCTTCCCTTACACAC<br>ACGCAAAATACTCCT |
| SEQ ID NO: 234 | 1 | GACTGGAGTTCAGACGTGTGCTCTTCCGATCTTCCTCCCCTGTC<br>ATCCTCACACTTTTC |
| SEQ ID NO: 235 | 1 | GACTGGAGTTCAGACGTGTGCTCTTCCGATCTTCGTCATAGTTG<br>TTGCAAGCCGAAGAG |
| SEQ ID NO: 236 | 1 | GACTGGAGTTCAGACGTGTGCTCTTCCGATCTTCGTGGAGAACA<br>AGTTTGGCAGCATC |
| SEQ ID NO: 237 | 1 | GACTGGAGTTCAGACGTGTGCTCTTCCGATCTTCTACCTTGTAG<br>CCTCCAATGCGATGC |
| SEQ ID NO: 238 | 1 | GACTGGAGTTCAGACGTGTGCTCTTCCGATCTTCTCAACTAAAA<br>GCTTCTGTCTGCAAG |
| SEQ ID NO: 239 | 1 | GACTGGAGTTCAGACGTGTGCTCTTCCGATCTTCTCCCCAATAA<br>TAATCAGCCACCCCC |
| SEQ ID NO: 240 | 1 | GACTGGAGTTCAGACGTGTGCTCTTCCGATCTTCTCTGGATGGA<br>ACTGATGTCTGGACG |
| SEQ ID NO: 241 | 1 | GACTGGAGTTCAGACGTGTGCTCTTCCGATCTTCTGCAGCAAAT<br>TCAACCACCAGAACA |
| SEQ ID NO: 242 | 1 | GACTGGAGTTCAGACGTGTGCTCTTCCGATCTTGAGCATTTGAA<br>GTTTTTATTAGTGATGGATTTG |
| SEQ ID NO: 243 | 1 | GACTGGAGTTCAGACGTGTGCTCTTCCGATCTTGAGTCTGAAGT<br>GAGAACTCCGTGTGG |
| SEQ ID NO: 244 | 1 | GACTGGAGTTCAGACGTGTGCTCTTCCGATCTTGATAACGACAC<br>AACACAAAATAGCCGT |
| SEQ ID NO: 245 | 1 | GACTGGAGTTCAGACGTGTGCTCTTCCGATCTTGCAAGAACCCA<br>GACCTCGAGTTTG |
| SEQ ID NO: 246 | 1 | GACTGGAGTTCAGACGTGTGCTCTTCCGATCTTGCATACATTCG<br>AAAGACCCTAGCCT |
| SEQ ID NO: 247 | 1 | GACTGGAGTTCAGACGTGTGCTCTTCCGATCTTGCCCGTGATGT<br>TCCATGTAATACTGG |
| SEQ ID NO: 248 | 1 | GACTGGAGTTCAGACGTGTGCTCTTCCGATCTTGCCTTCTAGAA<br>CAGTAGACACAAAACA |
| SEQ ID NO: 249 | 1 | GACTGGAGTTCAGACGTGTGCTCTTCCGATCTTGCTAGGAAAGA<br>GGCAAGGAAAGGTGA |
| SEQ ID NO: 250 | 1 | GACTGGAGTTCAGACGTGTGCTCTTCCGATCTTGCTCTTTTCAC<br>CCATCTACAGTCCCC |
| SEQ ID NO: 251 | 1 | GACTGGAGTTCAGACGTGTGCTCTTCCGATCTTGCTGAGGAAGT<br>GGATTTTGCAGGTTG |
| SEQ ID NO: 252 | 1 | GACTGGAGTTCAGACGTGTGCTCTTCCGATCTTGGAATATATCC<br>ACTCAATCTTCTACTTTAAAATGACTTAGG |

TABLE 1-continued

| Target Specific Primer | Volume Ratio | Sequence |
|---|---|---|
| SEQ ID NO: 253 | 1 | GACTGGAGTTCAGACGTGTGCTCTTCCGATCTTGGACATGAAGC AGGCTGATACTACACA |
| SEQ ID NO: 254 | 1 | GACTGGAGTTCAGACGTGTGCTCTTCCGATCTTGGCACATTCCA TTCTTACCAAACTCT |
| SEQ ID NO: 255 | 1 | GACTGGAGTTCAGACGTGTGCTCTTCCGATCTTGGCAGTTCCCA TCTCAGGCTGG |
| SEQ ID NO: 256 | 1 | GACTGGAGTTCAGACGTGTGCTCTTCCGATCTTGGCCCCGCCTC TGAATATTTCTTTAA |
| SEQ ID NO: 257 | 1 | GACTGGAGTTCAGACGTGTGCTCTTCCGATCTTGGGCTACAAGA ACTACCGATACCGTG |
| SEQ ID NO: 258 | 1 | GACTGGAGTTCAGACGTGTGCTCTTCCGATCTTGTACATGGCCA CTCAGATCTCGTCAG |
| SEQ ID NO: 259 | 1 | GACTGGAGTTCAGACGTGTGCTCTTCCGATCTTGTCACCACATT ACATACTTACCATGCC |
| SEQ ID NO: 260 | 1 | GACTGGAGTTCAGACGTGTGCTCTTCCGATCTTGTCAGTGGGGA ACAAGAAGTGGAGAA |
| SEQ ID NO: 261 | 1 | GACTGGAGTTCAGACGTGTGCTCTTCCGATCTTGTCCATCAGCC TCCAGTTCAGCAAG |
| SEQ ID NO: 262 | 1 | GACTGGAGTTCAGACGTGTGCTCTTCCGATCTTGTCTGAACACT TCTTCCAGGTCCAAG |
| SEQ ID NO: 263 | 1 | GACTGGAGTTCAGACGTGTGCTCTTCCGATCTTGTGATTTATTC TTTCAACAGCCACGG |
| SEQ ID NO: 264 | 1 | GACTGGAGTTCAGACGTGTGCTCTTCCGATCTTGTGCTCAGTTC CCTCCTCTATGCAAT |
| SEQ ID NO: 265 | 1 | GACTGGAGTTCAGACGTGTGCTCTTCCGATCTTGTGGTTGGTCA GAAAGATAAGCCAGT |
| SEQ ID NO: 266 | 1 | GACTGGAGTTCAGACGTGTGCTCTTCCGATCTTGTGTCACATTA TAAAGATTCAGGCAAT |
| SEQ ID NO: 267 | 1 | GACTGGAGTTCAGACGTGTGCTCTTCCGATCTTTATCACTGTCT GTCTCTCCTGCAGCC |
| SEQ ID NO: 268 | 1 | GACTGGAGTTCAGACGTGTGCTCTTCCGATCTTTATTTGAGCTA GAACCAGTGCCAGGC |
| SEQ ID NO: 269 | 1 | GACTGGAGTTCAGACGTGTGCTCTTCCGATCTTTCCCCAATCTA CCTGTGTCAGTTCCC |
| SEQ ID NO: 270 | 1 | GACTGGAGTTCAGACGTGTGCTCTTCCGATCTTTCTACCTGCAG TAAAACGATGTTTGC |
| SEQ ID NO: 271 | 1 | GACTGGAGTTCAGACGTGTGCTCTTCCGATCTTTCTCCAGGCGT TTCTTCCATCCTTCC |
| SEQ ID NO: 272 | 1 | GACTGGAGTTCAGACGTGTGCTCTTCCGATCTTTCTCTCTGGCA GGTCATGATGATGGG |
| SEQ ID NO: 273 | 1 | GACTGGAGTTCAGACGTGTGCTCTTCCGATCTTTCTTCATACCA GGACCAGAGGAAACC |
| SEQ ID NO: 274 | 1 | GACTGGAGTTCAGACGTGTGCTCTTCCGATCTTTCTTCCTTTTC CATGCAGTGTGTCCA |
| SEQ ID NO: 275 | 1 | GACTGGAGTTCAGACGTGTGCTCTTCCGATCTTTTAAACATGCA TTGATAACACCCCTACTGCT |
| SEQ ID NO: 276 | 1 | GACTGGAGTTCAGACGTGTGCTCTTCCGATCTTTTCTAATCACA TAGGCAGGAAATCTCAGTG |
| SEQ ID NO: 277 | 1 | GACTGGAGTTCAGACGTGTGCTCTTCCGATCTTTTCTTCCCTCC CCTCGAAATGAAGCT |

TABLE 1-continued

| Target Specific Primer | Volume Ratio | Sequence |
|---|---|---|
| SEQ ID NO: 278 | 1 | GACTGGAGTTCAGACGTGTGCTCTTCCGATCTTTTGTTTCTCCC ACACAGACACTATTGTG |
| SEQ ID NO: 279 | 1 | GACTGGAGTTCAGACGTGTGCTCTTCCGATCTTTTTGTGTGAGT GAATGTGTGCCAGGG |
| SEQ ID NO: 280 | 2 | GACTGGAGTTCAGACGTGTGCTCTTCCGATCTAAAGCTCTTCCT GTTTCAGTCCCCATT |
| SEQ ID NO: 281 | 2 | GACTGGAGTTCAGACGTGTGCTCTTCCGATCTACCTTTTCTTAT GTGCTTTTAGGGCCCA |
| SEQ ID NO: 282 | 2 | GACTGGAGTTCAGACGTGTGCTCTTCCGATCTAGCTTCTTCCCA TGATGATCTGTCCCT |
| SEQ ID NO: 283 | 2 | GACTGGAGTTCAGACGTGTGCTCTTCCGATCTAGTGGCTGTGAA GGTAAGAAGTGGCTC |
| SEQ ID NO: 284 | 2 | GACTGGAGTTCAGACGTGTGCTCTTCCGATCTCATCGCTGTAGA ACGCACCATAGAAGC |
| SEQ ID NO: 285 | 2 | GACTGGAGTTCAGACGTGTGCTCTTCCGATCTCATTCTGCTGGT CGTGGTCTTGGG |
| SEQ ID NO: 286 | 2 | GACTGGAGTTCAGACGTGTGCTCTTCCGATCTCCAAGAGAGCAA CACCCACACTTACAC |
| SEQ ID NO: 287 | 2 | GACTGGAGTTCAGACGTGTGCTCTTCCGATCTCCTGGTATGGTC ATGGAAGGGGCTT |
| SEQ ID NO: 288 | 2 | GACTGGAGTTCAGACGTGTGCTCTTCCGATCTCTGAGGAAGGTG AAGGTGCTTGGATCT |
| SEQ ID NO: 289 | 2 | GACTGGAGTTCAGACGTGTGCTCTTCCGATCTGGGATGTGATGA GAGGTGGATGGGTAG |
| SEQ ID NO: 290 | 2 | GACTGGAGTTCAGACGTGTGCTCTTCCGATCTGGTCAAGAGTCC CAACCATGTCAAAAT |
| SEQ ID NO: 291 | 2 | GACTGGAGTTCAGACGTGTGCTCTTCCGATCTGGTTCTTCTGAT ACGATCTGTGACCTGT |
| SEQ ID NO: 292 | 2 | GACTGGAGTTCAGACGTGTGCTCTTCCGATCTGTATGCGACACT TACAGCTGCCCAG |
| SEQ ID NO: 293 | 2 | GACTGGAGTTCAGACGTGTGCTCTTCCGATCTGTTTCTGATGTA CCAACCTCACCAACA |
| SEQ ID NO: 294 | 2 | GACTGGAGTTCAGACGTGTGCTCTTCCGATCTTAAGTGCCCGAA GTGTAAGCCCAACTA |
| SEQ ID NO: 295 | 2 | GACTGGAGTTCAGACGTGTGCTCTTCCGATCTTCCTTCCTCTTC CTACAGTACTCCCCT |
| SEQ ID NO: 296 | 2 | GACTGGAGTTCAGACGTGTGCTCTTCCGATCTTCGCCTGTCCTC ATGTATTGGTCTCTC |
| SEQ ID NO: 297 | 2 | GACTGGAGTTCAGACGTGTGCTCTTCCGATCTTCTAGTAACTCA GCAGCATCTCAGGGC |
| SEQ ID NO: 298 | 2 | GACTGGAGTTCAGACGTGTGCTCTTCCGATCTTGAAGCAATTTA GGTATGAAAGCCAGC |
| SEQ ID NO: 299 | 2 | GACTGGAGTTCAGACGTGTGCTCTTCCGATCTTGGCAGCCAGAA ATATCCTCCTTACTCA |
| SEQ ID NO: 300 | 2 | GACTGGAGTTCAGACGTGTGCTCTTCCGATCTTGTTCCATCCTC TGCTGTCACCTCTTG |
| SEQ ID NO: 301 | 2 | GACTGGAGTTCAGACGTGTGCTCTTCCGATCTTGTTTTCTTCCC TTTAGATGCTCTGCT |
| SEQ ID NO: 302 | 2 | GACTGGAGTTCAGACGTGTGCTCTTCCGATCTTTTAACCATGCA GATCCTCAGTTTGTG |

TABLE 1-continued

| Target Specific Primer | Volume Ratio | Sequence |
|---|---|---|
| SEQ ID NO: 303 | 3 | GACTGGAGTTCAGACGTGTGCTCTTCCGATCTACCCTTGTCTCT GTGTTCTTGTCCCC |
| SEQ ID NO: 304 | 3 | GACTGGAGTTCAGACGTGTGCTCTTCCGATCTAGCCAATATTGT CTTTGTGTTCCCGGA |
| SEQ ID NO: 305 | 3 | GACTGGAGTTCAGACGTGTGCTCTTCCGATCTCTCATATCCTCC TCTTTCTGCCCAGGG |
| SEQ ID NO: 306 | 3 | GACTGGAGTTCAGACGTGTGCTCTTCCGATCTGTTGAAGTCCTC GTTGTCTTGTTGGCA |
| SEQ ID NO: 307 | 4 | GACTGGAGTTCAGACGTGTGCTCTTCCGATCTGCACCATCTCAC AATTGCCAGTTAACG |

In one aspect, the present method can achieve increased sensitivity at certain loci. In Table 2 below, the present method is compared to the conventional hybrid capture method. The present method calls several loci missed by hybrid capture, which is directly related to the increased conversion rate of the present method.

TABLE 2

| Sample | Gene | Indel | Hybrid Capture Call | Call of the Present Method |
|---|---|---|---|---|
| Plasma 1 | EGFR | p.E746_A750delELREA | NOT CALLED | 0.235% |
| Plasma 2 | EGFR | p.E746_A750delELREA | NOT CALLED | 0.274% |
| Plasma 3 | EGFR | p.E746_A750delELREA | NOT CALLED | 0.324% |
| Plasma 4 | EGFR | p.E746_A750delELREA | NOT CALLED | 13.043% |
| Plasma 5 | EGFR | p.E746_A750delELREA | NOT CALLED | 16.195% |
| Plasma 6 | EGFR | p.E746_A750delELREA | NOT CALLED | 17.719% |
| Plasma 7 | EGFR | p.E746_A750delELREA | 0.44%; | 1.468% |

Extremely high ligation efficiencies of 80% were achieved, resulting in conversion rates of 60%, compared to 25% and 10% in standard libraries, respectively. Exemplary conversion rates of the present methods are shown in Table 3.

TABLE 3

| Chromosome | Target Position | UMI Depth (out of 6666 input molecules) of the present example | Conversion Rate of the present example | Hybridization Capture UMI Depth (out of 20000 input molecules) | Hybridization Capture Conversion Rate |
|---|---|---|---|---|---|
| chr10 | 43609975 | 5322 | 0.79837984 | 433 | 0.02165 |
| chr10 | 43609981 | 3184 | 0.47764777 | 435 | 0.02175 |
| chr6 | 117647309 | 307 | 0.04605461 | 521 | 0.02605 |
| chr6 | 117647319 | 400 | 0.060006 | 610 | 0.0305 |
| chr1 | 115258623 | 165 | 0.02475248 | 684 | 0.0342 |
| chr6 | 117657204 | 106 | 0.01590159 | 699 | 0.03495 |
| chr3 | 178917032 | 358 | 0.05370537 | 952 | 0.0476 |
| chr6 | 117658352 | 2071 | 0.31068107 | 1326 | 0.0663 |
| chr6 | 117647426 | 2820 | 0.4230423 | 1432 | 0.0716 |
| chr6 | 117657358 | 2353 | 0.3529853 | 1667 | 0.08335 |
| chr3 | 178936004 | 446 | 0.06690669 | 1895 | 0.09475 |
| chr6 | 117658053 | 1449 | 0.21737174 | 1921 | 0.09605 |
| chr12 | 25398153 | 105 | 0.01575158 | 1929 | 0.09645 |
| chr6 | 117658058 | 1584 | 0.23762376 | 1939 | 0.09695 |
| chr6 | 117645959 | 1603 | 0.24047405 | 2128 | 0.1064 |
| chr6 | 117658257 | 833 | 0.1249625 | 2204 | 0.1102 |
| chr7 | 55221932 | 4199 | 0.62991299 | 2260 | 0.113 |
| chr6 | 117647205 | 867 | 0.13006301 | 2271 | 0.11355 |
| chr3 | 178927985 | 849 | 0.12736274 | 2363 | 0.11815 |
| chr3 | 178927989 | 928 | 0.13921392 | 2377 | 0.11885 |
| chr7 | 55228037 | 2474 | 0.37113711 | 2573 | 0.12865 |
| chr12 | 25398295 | 2385 | 0.35778578 | 2575 | 0.12875 |
| chr12 | 25398280 | 2391 | 0.35868587 | 2804 | 0.1402 |
| chr6 | 117658112 | 3140 | 0.47104711 | 2815 | 0.14075 |
| chr6 | 117645611 | 1712 | 0.25682568 | 2852 | 0.1426 |
| chr6 | 117646015 | 2735 | 0.41029103 | 2912 | 0.1456 |
| chr12 | 25378604 | 2168 | 0.32523252 | 2962 | 0.1481 |
| chr1 | 115258783 | 3346 | 0.5019502 | 3025 | 0.15125 |
| chr6 | 117646362 | 1105 | 0.16576658 | 3090 | 0.1545 |
| chr6 | 117658134 | 379 | 0.05685569 | 3140 | 0.157 |
| chr12 | 25378610 | 2300 | 0.3450345 | 3178 | 0.1589 |

TABLE 3-continued

| Chromosome | Target Position | UMI Depth (out of 6666 input molecules) of the present example | Conversion Rate of the present example | Hybridization Capture UMI Depth (out of 20000 input molecules) | Hybridization Capture Conversion Rate |
|---|---|---|---|---|---|
| chr2 | 29436845 | 3089 | 0.46339634 | 3200 | 0.16 |
| chr3 | 178928065 | 3037 | 0.45559556 | 3244 | 0.1622 |
| chr3 | 178936100 | 1469 | 0.22037204 | 3284 | 0.1642 |
| chr7 | 55228009 | 4204 | 0.63066307 | 3776 | 0.1888 |
| chr17 | 7573999 | 3228 | 0.48424843 | 3789 | 0.18945 |
| chr17 | 7579588 | 2047 | 0.30708071 | 3804 | 0.1902 |
| chr17 | 7579584 | 4174 | 0.62616262 | 3969 | 0.19845 |
| chr1 | 115252244 | 3395 | 0.50930093 | 4080 | 0.204 |
| chr2 | 29443737 | 3636 | 0.54545455 | 4087 | 0.20435 |
| chr7 | 116412017 | 5521 | 0.82823282 | 4214 | 0.2107 |
| chr7 | 116423378 | 1939 | 0.29087909 | 4267 | 0.21335 |
| chr17 | 7578291 | 4943 | 0.74152415 | 4302 | 0.2151 |
| chr7 | 116412016 | 5560 | 0.83408341 | 4321 | 0.21605 |
| chr3 | 178928280 | 2069 | 0.31038104 | 4411 | 0.22055 |
| chr7 | 116423432 | 5859 | 0.87893789 | 4483 | 0.22415 |
| chr3 | 178916923 | 2200 | 0.330033 | 4634 | 0.2317 |
| chr17 | 7578238 | 1925 | 0.28877888 | 4636 | 0.2318 |
| chr2 | 29445367 | 4446 | 0.6669667 | 4650 | 0.2325 |
| chr6 | 117650705 | 2202 | 0.33033303 | 4735 | 0.23675 |
| chr6 | 117650651 | 1396 | 0.20942094 | 4907 | 0.24535 |
| chr6 | 117645786 | 2029 | 0.30438044 | 4965 | 0.24825 |
| chr7 | 55211154 | 4479 | 0.67191719 | 4972 | 0.2486 |
| chr7 | 116411968 | 148 | 0.02220222 | 5020 | 0.251 |
| chr3 | 178916829 | 710 | 0.10651065 | 5091 | 0.25455 |
| chr7 | 55229294 | 4929 | 0.73942394 | 5111 | 0.25555 |
| chr7 | 55259556 | 4813 | 0.7220222 | 5131 | 0.25655 |
| chr2 | 29432724 | 3421 | 0.51320132 | 5136 | 0.2568 |
| chr8 | 38274906 | 3087 | 0.46309631 | 5259 | 0.26295 |
| chr6 | 117647147 | 4329 | 0.64941494 | 5338 | 0.2669 |
| chr6 | 117645662 | 3116 | 0.46744675 | 5546 | 0.2773 |
| chr17 | 37881465 | 1101 | 0.16516652 | 5581 | 0.27905 |
| chr17 | 37881366 | 4657 | 0.69861986 | 5595 | 0.27975 |
| chr17 | 37879658 | 5429 | 0.81443144 | 5619 | 0.28095 |
| chr17 | 7576927 | 167 | 0.02505251 | 5665 | 0.28325 |
| chr7 | 55214422 | 5095 | 0.76432643 | 5682 | 0.2841 |
| chr6 | 117646459 | 1940 | 0.2910291 | 5693 | 0.28465 |
| chr17 | 37881381 | 4992 | 0.74887489 | 5717 | 0.28585 |
| chr17 | 37868235 | 3763 | 0.56450645 | 5729 | 0.28645 |
| chr6 | 117645719 | 879 | 0.13186319 | 5765 | 0.28825 |
| chr2 | 29443680 | 4606 | 0.6909691 | 5840 | 0.292 |
| chr7 | 55259490 | 3837 | 0.57560756 | 5920 | 0.296 |
| chr17 | 7578544 | 2217 | 0.33258326 | 5960 | 0.298 |
| chr7 | 55249105 | 4317 | 0.64761476 | 6011 | 0.30055 |
| chr2 | 29446552 | 1309 | 0.19636964 | 6025 | 0.30125 |
| chr6 | 117646632 | 408 | 0.06120612 | 6265 | 0.31325 |
| chr17 | 37879607 | 1530 | 0.22952295 | 6307 | 0.31535 |
| chr6 | 117647088 | 1238 | 0.18571857 | 6396 | 0.3198 |
| chr17 | 7577003 | 1285 | 0.19276928 | 6471 | 0.32355 |
| chr17 | 37881412 | 5115 | 0.76732673 | 6550 | 0.3275 |
| chr2 | 29447600 | 1022 | 0.15331533 | 6599 | 0.32995 |
| chr2 | 29447605 | 946 | 0.14191419 | 6645 | 0.33225 |
| chr6 | 117646875 | 1612 | 0.24182418 | 6684 | 0.3342 |
| chr6 | 117646910 | 1777 | 0.26657666 | 6985 | 0.34925 |
| chr2 | 29446439 | 898 | 0.13471347 | 7198 | 0.3599 |
| chr6 | 117646732 | 1343 | 0.20147015 | 7210 | 0.3605 |
| chr10 | 43611123 | 1142 | 0.17131713 | 7473 | 0.37365 |
| chr10 | 43611821 | 2212 | 0.33183318 | 7600 | 0.38 |
| chr10 | 43611334 | 1175 | 0.17626763 | 7786 | 0.3893 |
| chr10 | 43611728 | 978 | 0.14671467 | 7794 | 0.3897 |
| chr10 | 43610389 | 1202 | 0.18031803 | 7794 | 0.3897 |
| chr10 | 43611251 | 1313 | 0.1969697 | 7918 | 0.3959 |
| chr10 | 43611621 | 246 | 0.03690369 | 8053 | 0.40265 |
| chr2 | 29447805 | 2223 | 0.33348335 | 8183 | 0.40915 |
| chr2 | 29447732 | 728 | 0.10921092 | 8227 | 0.41135 |
| chr10 | 43611971 | 535 | 0.08025803 | 8235 | 0.41175 |
| chr10 | 43611006 | 1539 | 0.23087309 | 8241 | 0.41205 |
| chr10 | 43611452 | 1239 | 0.18586859 | 8446 | 0.4223 |
| chr10 | 43610636 | 1921 | 0.28817882 | 8476 | 0.4238 |
| chr2 | 29447492 | 977 | 0.14656466 | 8498 | 0.4249 |
| chr10 | 43610782 | 733 | 0.109961 | 8502 | 0.4251 |
| chr2 | 29448196 | 589 | 0.08835884 | 8570 | 0.4285 |
| chr2 | 29446294 | 2579 | 0.38688869 | 8956 | 0.4478 |
| chr2 | 29447924 | 618 | 0.09270927 | 8977 | 0.44885 |
| chr10 | 43610887 | 1922 | 0.28832883 | 9029 | 0.45145 |

TABLE 3-continued

| Chromosome | Target Position | UMI Depth (out of 6666 input molecules) of the present example | Conversion Rate of the present example | Hybridization Capture UMI Depth (out of 20000 input molecules) | Hybridization Capture Conversion Rate |
|---|---|---|---|---|---|
| chr2 | 29448061 | 591 | 0.08865887 | 9053 | 0.45265 |
| chr10 | 43610529 | 777 | 0.11656166 | 9120 | 0.456 |
| chr2 | 29448322 | 918 | 0.13771377 | 9435 | 0.47175 |

Figure 6:
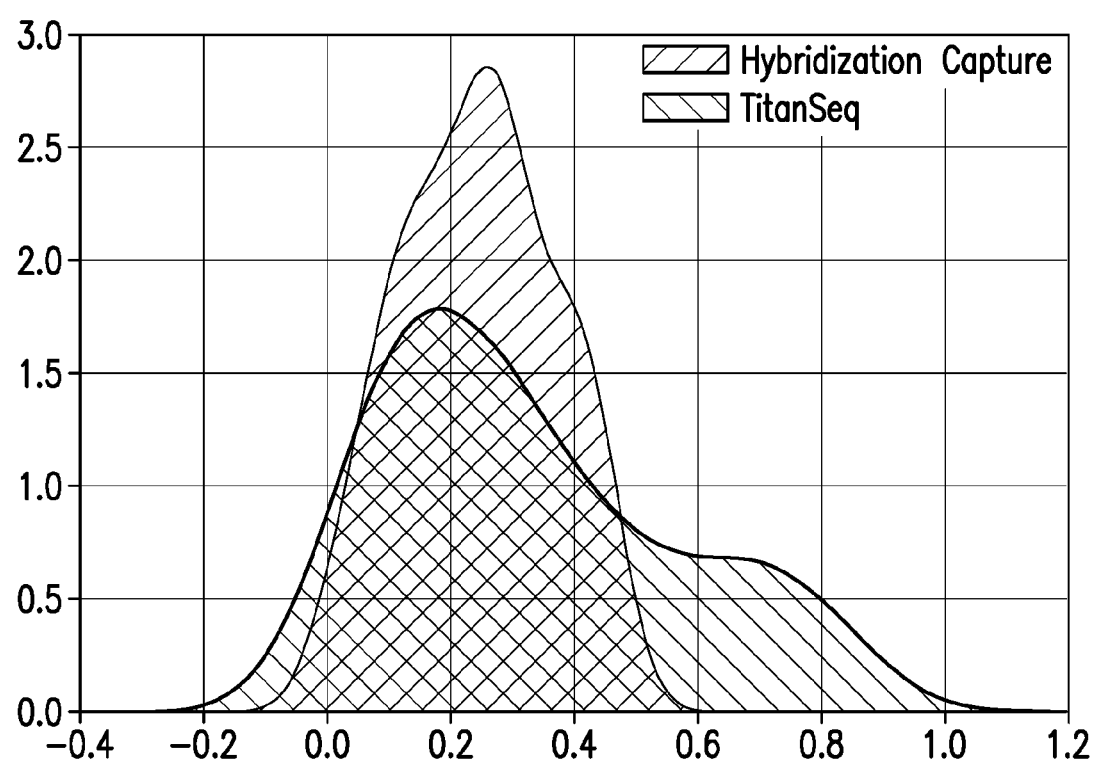
FIG. 6 compares the conversion rates of a method disclosed herein (TitanSeq) and the conventional hybridization capture method.

As shown in FIG. 6, the distribution displays that the conversion rate goes up significantly higher for the present method than for hybrid capture. While in this example, the conventional hybridization capture method may achieve a conversion rate of about 47%, the present method achieves a much higher conversion rate of about 88%. This significantly higher conversion rate, together with the ability to multiplex across hundreds of loci in a single reaction, makes the present method ideal for high throughput and high accuracy sequencing and analysis of polynucleotides, especially for samples with very low allele fractions, such as ctDNA carrying cancer-associated SNPs and/or mutations.

Additionally, the on-target rate is up to 70% for very small target regions (~30,000 bases) resulting in enrichment factors of >40,000×, compared to an enrichment factor of ~2000× for standard libraries. The improved efficiencies have resulted in greater sensitivities, allowing accurate calls down to 0.1% at many variants. SNVs, indels, CNVs, and fusions were accurately called. Furthermore, the procedure is very robust, with a failure rate of 0%.

Example 3

In this example, a method for constructing a library from extracted plasma DNA is described, for example, to interrogate single nucleotide changes (SNCs), indels, copy number variations (CNVs), and fusions, from circulating tumor DNA. As a principle in this example, extracted plasma DNA (e.g., from human) is dephosphorylated and denatured. A single stranded DNA ligation adds a universal adapter to the 3' end of each molecule. The DNA then undergoes semi-targeted PCR using a site-specific primer and a reverse-complement primer to the adapter. Libraries are made with a secondary PCR to add full length adapters and barcodes to each molecule.

Equipment, materials, and supplies used in this example include: Veriti Thermocycler, 96 well magnet, 96 well ice block, Vortexer, Plate mini centrifuge, Semi-skirted 96 well PCR plate, Plate seals, Pipettes, and Pipette tips.

Reagents and media used in this example include: Nuclease free water (Ambion/Thermo: AM9939), Low TE buffer (Thermo fisher: 12090015), Circligase Kit (Epicenter: CL4115K), FastAP (Thermo Fisher: EF0651), 50% PEG 4000 (Sigma: 95904-250g-F. Dilute 5 g in 10 mL in Nuclease free water Ambion/Thermo: AM9939), 10 µM N12 Adapter (IDT), Taq polymerasae (NEB: M0273 S), dNTP mix (NEB: N0447L), Standard Taq buffer (NEB: M0273S), Ampure XP beads (Agincourt/Beckman Coulter: A63881), 100 uM Reverse complement primer (IDT), Primer mix (IDT), KAPA 2G multiplex (KAPA: KK5802), NEBNext Ultra Q5 II (NEB: M0544L), and 10 µM NEBNext Multiplex Oligos (IDT).

Procedure

Dephosphorylation:
1. Creating the master mix below:

| Reagent | Volume (µL) |
|---|---|
| Water | To 22 µL |
| Circligase ™ buffer | 4 |
| MnCl$_2$ | 2 |
| FastAP | 1 |
| DNA | 20 ng |

2. Adding master mix and DNA to a 96 well plate.
3. Sealing the plate to briefly vortex it and spin down.
4. Running the following program: 37° C. 10 min, 95° C. 2 min.
5. Immediately after, placing the plate on a 96 well ice block for 1 min, then removing the plate to continue immediately with ligation below.

Ligation:
1. Creating the master mix below:

| Reagent | Volume (µL) |
|---|---|
| 50% PEG 4000 | 8 |
| Adapter | 2 |
| ATP | 2 |
| Water | 4 |
| Circligase ™ | 2 |

2. Adding 18 µl of the master mix directly to the products from dephosphorylation.
3. Sealing the plate to briefly vortex it and spin down.
4. Running the following program: 60° C. 2 hr, 80° C. 10 min, 85° C. 2 min, 4° C. on hold.
5. Proceeding immediately to second strand synthesis below.

Second Strand Synthesis:
1. Creating the master mix below:

| Reagent | Volume (µL) |
|---|---|
| Water | 3.25 |
| Primer | 0.5 |
| dNTP | 1 |
| Standard Taq buffer | 5 |
| Taq polymerase | 0.25 |

2. Adding 10 µl of master mix directly to the ligation products.
3. Sealing the plate to briefly vortex and spin down.
4. Running the following program: 95° C. 30 s, 62° C. 2 min, 68° C. 10 min, 4° C. on hold.
5. Proceeding immediately to AmPure® XP bead cleanup below.

AmPure® XP Bead Cleanup:
1. Vortexing the AmPure® beads until the solution is homogeneous.
2. Adding 80 µl of beads to the products from second strand synthesis, and pipetting up and down to homogenize beads.
3. Incubating at room temp for 10 min.
4. Transferring plate to a magnet and incubating on the magnet for 5 min or until all of the beads have moved towards the magnet.
5. Removing all supernatant.
6. Adding 150 µL of 80% EtOH and incubating for 30 s.
7. Removing the supernatant.
8. Repeating steps 6-7.
9. Ensuring that all residual ethanol is removed and removing plate from the magnet and incubating at room temperature for 3 min.
10. Adding 16 µl of Low TE buffer and pipetting up and down to homogenize beads.
11. Incubating at room temperature for 2 min.
12. Transferring plate to a magnet and incubating on magnet for 1 min or until all of the beads have move to the magnet.
13. Removing 15 µl of the supernatant and placing it in a clean plate.
14. Proceeding with the 1$^{st}$ PCR below or store at −20° C.

1$^{st}$ PCR:
1. Creating the master mix below:

| Reagent | Volume (µL) |
| --- | --- |
| KAPA 2G multiplex master mix | 25 |
| Primer pool | 10 |
| Reverse primer | 0.4 |
| DNA | 15 |

2. Adding 35 µl of master mix to 15 µl of purified DNA.
3. Sealing the plate to briefly vortex and spin it down.
4. Running the following program: 95° C. 3 min, (95° C. 15 s, 72° C. 90 s)×20, 72° C. 1 min, 4° C. on hold.
5. Proceeding immediately to AmPure® XP bead cleanup below.

AmPure® XP Bead Cleanup
1. Vortexing the AmPure® XP beads until the solution is homogeneous.
2. Adding 80 µl of beads to the products from second strand synthesis and pipetting up and down to homogenize beads.
3. Incubating at room temperature for 10 min.
4. Transferring plate to a magnet and incubating on the magnet for 5 min or until all of the beads have moved towards the magnet.
5. Removing all supernatant.
6. Adding 150 µL of 80% EtOH and incubating for 30 s.
7. Removing supernatant.
8. Repeating steps 6-7.
9. Ensuring that all residual EtOH is removed and removing plate from the magnet and incubating at room temperature for 3 min.
10. Adding 20 µl of low TE buffer and pipetting up and down to homogenize beads.
11. Incubating at room temperature for 2 min.
12. Transferring plate to a magnet and incubating on magnet for 1 min or until all of the beads have move to the magnet.
13. Removing 19 µl of the supernatant and place it in a clean plate.
14. Proceeding with the 2$^{nd}$ PCR below OR store at −20° C.

2$^{nd}$ PCR
1. Creating the master mix below, and note that the index primer and DNA are added separately, and the remaining DNA is stored at −20° C.:

| Reagent | Volume (µL) |
| --- | --- |
| NEBNext Q5 Ultra II master mix | 25 |
| Index primer | 2 |
| Universal primer | 2 |
| Water | 19 |
| DNA | 2 |

2. In a new plate, adding 46 µL master mix, 2 µL index primer, and 2 µL DNA.
3. Sealing the plate to briefly vortex and spin it down.
4. Running the following program: 95° C. 3 min, (98° C. 10 s, 65° C. 75 s)×10, 65° C. 2 min, 4° C. on hold.
5. Proceeding immediately to bead cleanup below.

AmPure XP Bead Cleanup
1. Vortexing the AmPure® beads until the solution is homogeneous.
2. Adding 40 µl of beads to the products from second strand synthesis and pipetting up and down to homogenize beads.
3. Incubating at room temperature for 10 min.
4. Transferring plate to a magnet and incubating on the magnet for 5 min or until all of the beads have moved towards the magnet.
5. Removing all supernatant.
6. Adding 150 µL of 80% EtOH and incubating for 30 s.
7. Removing supernatant.
8. Repeating steps 6-7.
9. Ensuring that all residual EtOH is removed and removing plate from the magnet and incubating at room temperature for 3 min.
10. Adding 25 µl of low TE buffer and pipetting up and down to homogenize beads.
11. Incubating at room temperature for 2 min.
12. Transferring plate to a magnet and incubating on magnet for 1 min or until all of the beads have move to the magnet.
13. Removing 24 µl of the supernatant and place in a clean plate to store at −20° C.

LabChip QC
For LabChip HS kit
1. Removing LabChip and reagents from 4° C. to equilibrate to RT (10 mins).
2. Preparing new gel-dye solution if necessary
3. Aspirating and rinsing each of the active chip well with molecular grade H$_2$O twice.
4. Preparing LabChip ladder by mixing 12 µL ladder solution with 108 µL H$_2$O in the ladder tube.
5. Preparing 750 µl H$_2$O in the buffer tube.
6. Using reverse pipetting technique to prepare LabChip.
7. In a BioRad Hardshell or Thermo Fisher Armadillo 96 well plate, diluting 1 µL of library in 19 µL water.
8. Running LabChip.

qPCR Quant
1. If needed, preparing qPCR master mix by adding 30 µl Illumina forward and reverse primers to new bottle of Kapa SYBR Fast qPCR MM 5 mL (KK4601).

2. Preparing 1:10,000 dilution of all libraries.
3. In a BioRad Hard-Shell plate or Thermo Fisher Armadillo plate, preparing the following reaction and leaving at least 12 wells empty.

| Reagent | Volume |
| --- | --- |
| Kapa SYBR Fast qPCR MM w/Illumina primers | 6 μL |
| 1:10,000 diluted library | 4 μL |

4. In the same 96 well plate, preparing duplicates of the 6 qPCR standards

| Reagent | Volume |
| --- | --- |
| Kapa SYBR Fast qPCR MM w/Illumina primers | 6 μL |
| Library Quantification DNA Standard (1-6 × 2) | 4 μL |

5. Editing the plate file to reflect plate layout and standard concentrations.
6. Running the following program on the BioRad C1000 thermal cycler: 95° C. 5 min>(95° C. 30 s>60° C. 45 s>Image step)×35.
7. Exporting the qPCR data as an excel sheet.
8. Multiplying starting concentration by (452/300) to adjust for the difference in size between the Kapa standards and the libraries.
9. Multiplying the concentration from step 8 by 10 to adjust for the dilution factor and to convert μM to nM.

Sequencing (NextSeq)
1. Thawing 300 cycle NextSeq reagent cartridge by placing in cold water and removing flow cell from 4° C. to equilibrate to room temperature.
2. Pooling libraries to be sequenced in a 1:1 molar ratio.
3. Using denature and dilute protocol to dilute library pool to a final concentration of 2.2 pM and a final volume of >1300 μL.
4. Loading 1300 μL in to well 10 of NextSeq reagent cartridge.
5. Emptying the NextSeq waste container and loading a new flow cell and buffer cartridge.
6. Loading the NextSeq reagent cartridge containing libraries in well 10, and settings for NextSeq read length are shown below:

| R1 | R2 | I1 | I2 |
| --- | --- | --- | --- |
| 150 | 150 | 6 | 12 |

7. Sequencing.

The invention claimed is:

1. A method, comprising ligating a set of adaptors to a library of single-stranded polynucleotides, wherein:
   - each single-stranded polynucleotide in the library of single-stranded polynucleotides comprises a target sequence;
   - the ligation is catalyzed by a single-stranded DNA (ssDNA) ligase;
   - each single-stranded polynucleotide is blocked at the 5' end to prevent ligation at the 5' end;
   - each adaptor comprises a unique molecular identifier (UMI) sequence that earmarks the single-stranded polynucleotide to which the adaptor is ligated, and is blocked at the 3' end to prevent ligation at the 3' end; and
   - the 5' end of the adaptor is ligated to the 3' end of the single-stranded polynucleotide by the ssDNA ligase to form a linear ligation product,
   - thereby obtaining a library of linear, single-stranded ligation products, wherein each linear, single-stranded ligation product comprises a single adaptor;
   - further comprising converting the library of linear, single-stranded ligation products into a library of linear, double-stranded ligation products;
   - further comprising amplifying the library of linear, double-stranded ligation products by a polymerase chain reaction (PCR), using a set of primers each comprising a sequence that is reverse-complement to the adaptor and/or hybridizable to the adaptor, and a primer hybridizable to the target sequence, thereby obtaining an amplified library of linear, double-stranded ligation products comprising sequence information of the target sequence; and
   - further comprising sequencing the amplified library of linear, double-stranded ligation products, wherein the conversion rate of the sequencing (percentage of single-stranded polynucleotides in the library that gives rise to sequencing reads) is at least 60%.

2. The method of claim 1, further comprising before the ligation step, a step of obtaining the library of single-stranded polynucleotides from a sample.

3. The method of claim 1, wherein the single-stranded polynucleotides are between 20 and 400 nucleic acid residues in length.

4. The method of claim 1, wherein the ssDNA ligase is a *Thermus* bacteriophage RNA ligase, an archaebacterium RNA ligase, T4 RNA ligase I, thermostable 5' App DNA/RNA ligase, T4 RNA ligase 2, truncated T4 RNA ligase 2, T4 RNA ligase2 Truncated K227Q, T4 RNA ligase2 Truncated KQ, or T4 DNA ligase.

5. The method of claim 1, wherein the blocking of each single-stranded polynucleotide comprises dephosphorylation to prevent ligation at its 5' end.

6. The method of claim 1, wherein the blocking of each adaptor comprises a carbon spacer, ddCTP, ddATP, ddTTP, ddGTP, hexanediol, triethylene glycol, and/or hexaethylene glycol, to prevent ligation at its 3' end.

7. The method of claim 1, wherein each adaptor comprises a dinucleotide sequence at the 5' end, which is 5' to the UMI sequence.

8. The method of claim 1, wherein the UMI sequence in each adaptor is between 6 and 15 nucleic acid residues in length.

9. The method of claim 1, wherein the ligation reaction is conducted in the presence of a crowding agent.

10. The method of claim 1, wherein the primer hybridizable to a target sequence comprises a plurality of sequences selected from the group consisting of SEQ ID NOs: 4-1529, or complementary sequence thereof.

11. The method of claim 10, wherein a plurality of primers are used, each comprising a sequence specific for the target sequence, wherein the primers have different target sequences.

12. The method of claim 10, further comprising purifying the amplified library of linear, double-stranded ligation products.

13. The method of claim 1, wherein the conversion rate of the sequencing (percentage of single-stranded polynucleotides in the library that give rise to sequencing reads) is at least 80%.

14. The method of claim 1, wherein the library of single-stranded polynucleotides comprises polynucleotides obtained from a sample of a subject that is treated for a disease or condition.

15. The method of claim 14, wherein the treatment is a cancer and/or neoplasia treatment.

16. The method of claim 1, wherein the library of single-stranded polynucleotides comprises polynucleotides obtained from a biological sample and the polynucleotides in the biological sample have been subject to partial or complete bisulfate conversion.

17. The method of claim 7, wherein each adaptor comprises a dinucleotide sequence that is GA (5' to 3'), GG (5' to 3'), AA (5' to 3'), or AG (5' to 3').

* * * * *